US011673947B2

(12) United States Patent
Igawa et al.

(10) Patent No.: US 11,673,947 B2
(45) Date of Patent: *Jun. 13, 2023

(54) TARGET TISSUE-SPECIFIC ANTIGEN-BINDING MOLECULE

(71) Applicant: Chugai Seiyaku Kabushiki Kaisha, Tokyo (JP)

(72) Inventors: Tomoyuki Igawa, Shizuoka (JP); Shigero Tamba, Shizuoka (JP); Kanako Tatsumi, Shizuoka (JP); Shun Shimizu, Shizuoka (JP); Shojiro Kadono, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 249 days.

This patent is subject to a terminal disclaimer.

(21) Appl. No.: 16/539,765

(22) Filed: Aug. 13, 2019

(65) Prior Publication Data
US 2019/0359704 A1 Nov. 28, 2019

Related U.S. Application Data

(62) Division of application No. 14/402,574, filed as application No. PCT/JP2013/064975 on May 30, 2013, now abandoned.

(30) Foreign Application Priority Data

May 30, 2012 (JP) ................................ 2012-123781
Aug. 9, 2012 (JP) ................................ 2012-177311

(51) Int. Cl.
C07K 16/00 (2006.01)
C07K 16/24 (2006.01)
C07K 16/18 (2006.01)
C07K 16/28 (2006.01)
C07K 16/30 (2006.01)
C07K 16/44 (2006.01)
G01N 33/68 (2006.01)
A61K 39/00 (2006.01)

(52) U.S. Cl.
CPC ............ C07K 16/248 (2013.01); C07K 16/00 (2013.01); C07K 16/005 (2013.01); C07K 16/18 (2013.01); C07K 16/2866 (2013.01); C07K 16/30 (2013.01); C07K 16/44 (2013.01); G01N 33/6845 (2013.01); G01N 33/6869 (2013.01); *A61K 2039/505* (2013.01); *C07K 2317/21* (2013.01); *C07K 2317/34* (2013.01); *C07K 2317/55* (2013.01); *C07K 2317/732* (2013.01); *C07K 2317/92* (2013.01); *G01N 2333/5412* (2013.01); *G01N 2500/00* (2013.01); *G01N 2500/20* (2013.01)

(58) Field of Classification Search
CPC .......... C07K 16/00–468; C07K 16/005; G01N 33/6845; G01N 33/6869; G01N 2500/00–20; G01N 2333/5412
See application file for complete search history.

(56) References Cited

U.S. PATENT DOCUMENTS

| 5,998,588 | A | 12/1999 | Hoffman et al. |
| 7,662,925 | B2 | 2/2010 | Lazar et al. |
| 8,388,955 | B2 | 3/2013 | Lazar et al. |
| 8,568,726 | B2 | 10/2013 | Beaumont et al. |
| 9,765,135 | B2 | 9/2017 | Ruike et al. |
| 10,000,560 | B2 | 6/2018 | Ruike et al. |
| 10,961,530 | B2 | 3/2021 | Igawa et al. |
| 2004/0110226 | A1 | 6/2004 | Lazar et al. |
| 2006/0141456 | A1 | 6/2006 | Edwards et al. |
| 2007/0009523 | A1 | 1/2007 | Presta |
| 2007/0148164 | A1 | 6/2007 | Farrington et al. |
| 2007/0224188 | A1 | 9/2007 | Allan et al. |
| 2008/0089892 | A1 | 4/2008 | Allan et al. |
| 2008/0292637 | A1 | 11/2008 | Fishman |
| 2009/0155255 | A1 | 6/2009 | Glaser et al. |
| 2010/0158909 | A1 | 6/2010 | Mcdonagh et al. |
| 2010/0172868 | A1 | 7/2010 | Morrison et al. |
| 2010/0183621 | A1 | 7/2010 | Jure-Kunkel et al. |
| 2011/0076284 | A1 | 3/2011 | Corbin et al. |
| 2011/0111406 | A1 | 5/2011 | Igawa et al. |
| 2011/0229489 | A1 | 9/2011 | Pons et al. |
| 2011/0236372 | A1 | 9/2011 | Villa et al. |
| 2011/0305714 | A1 | 12/2011 | Stavenhagen et al. |

(Continued)

FOREIGN PATENT DOCUMENTS

| CA | 2850041 | 4/2013 |
| CA | 2850322 | 4/2013 |

(Continued)

OTHER PUBLICATIONS

Mimoto et al., Protein Eng, Design & Selection 26(10):589-598 (Year: 2013).*
Forster et al., "Programming peptidomimetic syntheses by translating genetic codes designed de novo," Proc Natl Acad Sci USA, May 27, 2003, 100(11):6353-7. Epub May 16, 2003.
Kunkel et al., "Rapid and efficient site-specific mutagenesis without phenotypic selection," Proc Natl Acad Sci USA, Jan. 1985, 82(2):488-92.
Suzuki, "Research and Development of Antibody Pharmaceuticals," NIBS Letter, 2010, 56(4):45-51 (with English translation).
Wang et al., "Expanding the Genetic Code," Annu Rev Biophys Biomol Struct, Jun. 2006, 35:225-49.
USPTO Restriction Requirement in U.S. Appl. No. 14/402,574, dated Feb. 11, 2016, 10 pages.

(Continued)

Primary Examiner — Jessica H Roark
(74) Attorney, Agent, or Firm — Fish & Richardson P.C.

(57) ABSTRACT

The present inventors discovered that problems of existing antibody pharmaceuticals can be solved by producing antigen-binding molecules that contain an antigen-binding domain whose antigen-binding activity varies depending on the concentration of a target tissue-specific compound. Use of antigen-binding molecules of the present invention enables various diseases that originate from a target tissue to be treated in a manner specific to the target tissue.

51 Claims, 53 Drawing Sheets
Specification includes a Sequence Listing.

(56) References Cited

U.S. PATENT DOCUMENTS

| | | |
|---|---|---|
| 2012/0009188 A1 | 1/2012 | Behrens et al. |
| 2012/0237498 A1 | 9/2012 | Ahrens et al. |
| 2013/0203609 A1 | 8/2013 | Horn |
| 2014/0105889 A1 | 4/2014 | Igawa et al. |
| 2014/0255398 A1 | 9/2014 | Igawa et al. |
| 2014/0271617 A1 | 9/2014 | Igawa et al. |
| 2014/0335089 A1 | 11/2014 | Igawa et al. |
| 2014/0363428 A1 | 12/2014 | Igawa et al. |
| 2015/0056182 A1 | 2/2015 | Igawa et al. |
| 2015/0166654 A1 | 6/2015 | Igawa et al. |
| 2015/0203577 A1 | 7/2015 | Igawa et al. |
| 2015/0299296 A1 | 10/2015 | Ruike et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0229908 A1 | 8/2016 | Igawa et al. |
| 2016/0304862 A1 | 10/2016 | Igawa et al. |
| 2021/0122812 A1 | 4/2021 | Igawa et al. |
| 2021/0180049 A1* | 6/2021 | Igawa ............ C07K 16/4283 |
| 2021/0324099 A1* | 10/2021 | Igawa ............ A61K 47/6849 |
| 2022/0153875 A1 | 5/2022 | Mizuno et al. |
| 2023/0020377 A1 | 1/2023 | Katada et al. |

FOREIGN PATENT DOCUMENTS

| | | |
|---|---|---|
| CN | 101098890 | 1/2008 |
| CN | 102405278 | 4/2012 |
| CN | 104487457 | 4/2015 |
| EP | 2 275 443 | 1/2011 |
| EP | 2 305 710 | 4/2011 |
| EP | 2 409 990 | 1/2012 |
| EP | 2 552 955 | 2/2013 |
| EP | 2 679 681 A | 1/2014 |
| EP | 2 762 564 | 8/2014 |
| EP | 2 857 420 | 4/2015 |
| EP | 3 156 072 | 4/2017 |
| JP | 2007-531724 | 11/2007 |
| JP | 2007-532139 | 11/2007 |
| JP | 2010-110330 | 5/2010 |
| JP | 2011-097869 | 5/2011 |
| JP | 2011-137838 | 7/2011 |
| JP | 2011-184418 | 9/2011 |
| JP | 2012-518613 | 8/2012 |
| JP | 2013-521772 | 6/2013 |
| JP | 2018-517674 | 7/2018 |
| JP | 2018-537473 | 12/2018 |
| TW | 2014/00503 | 1/2014 |
| WO | WO 01/48480 | 7/2001 |
| WO | WO 02/081646 | 10/2002 |
| WO | WO 03/105757 | 12/2003 |
| WO | WO 2005/096706 | 10/2005 |
| WO | WO 2005/115452 | 12/2005 |
| WO | WO 2006/020114 | 2/2006 |
| WO | WO 2006/053301 | 5/2006 |
| WO | WO 2007/053718 | 5/2007 |
| WO | WO 2008/092117 | 7/2008 |
| WO | WO 2009/015284 | 1/2009 |
| WO | WO 2009/086320 | 7/2009 |
| WO | WO 2009/097017 | 8/2009 |
| WO | WO 2009/125825 | 10/2009 |
| WO | WO 2010/081173 | 7/2010 |
| WO | WO 2010/094698 | 8/2010 |
| WO | WO 2010/104821 | 9/2010 |
| WO | WO 2010/107109 | 9/2010 |
| WO | WO 2010/107110 | 9/2010 |
| WO | WO 2010/127284 | 11/2010 |
| WO | WO 2011/038302 | 3/2011 |
| WO | WO 2011/111007 | 9/2011 |
| WO | WO 2011/122011 | 10/2011 |
| WO | WO 2012/033953 | 3/2012 |
| WO | WO 2012/044831 | 4/2012 |
| WO | WO 2013/046722 | 4/2013 |
| WO | WO 2013/047729 | 4/2013 |
| WO | WO 2013/180200 | 12/2013 |
| WO | WO 2014/030750 | 2/2014 |
| WO | WO 2014/163101 | 10/2014 |
| WO | WO 2015/083764 | 6/2015 |
| WO | WO 2015/190538 | 12/2015 |
| WO | WO 2016/170176 | 10/2016 |
| WO | WO 2016/194992 | 12/2016 |
| WO | WO 2017/046994 | 3/2017 |
| WO | WO 2017/096165 | 6/2017 |
| WO | WO 2017/104783 | 6/2017 |
| WO | WO 2020/032230 | 2/2020 |
| WO | WO 2020/189748 | 9/2020 |
| WO | WO 2021/162020 | 8/2021 |

OTHER PUBLICATIONS

USPTO Non-Final Office Action in U.S. Appl. No. 14/402,574, dated May 6, 2016, 31 pages.

USPTO Final Office Action in U.S. Appl. No. 14/402,574, dated Oct. 31, 2016, 16 pages.

USPTO Advisory Action in U.S. Appl. No. 14/402,574, dated Feb. 16, 2017, 3 pages.

USPTO Non-Final Office Action in U.S. Appl. No. 14/402,574, dated Jan. 16, 2018, 24 pages.

USPTO Applicant-Initiated Interview Summary in U.S. Appl. No. 14/402,574, dated May 4, 2018, 27 pages.

USPTO Final Office Action in U.S. Appl. No. 14/402,574, dated Jul. 16, 2018, 10 pages.

USPTO Non-Final Office Action in U.S. Appl. No. 14/347,187, dated Sep. 4, 2018, 22 pages.

USPTO Final Office Action in U.S. Appl. No. 14/423,269, dated Aug. 15, 2018, 25 pages.

USPTO Non-Final Office Action in U.S. Appl. No. 15/100,934, dated Nov. 2, 2018, 40 pages.

USPTO Restriction Requirement in U.S. Appl. No. 14/781,069, dated Dec. 7, 2017, 7 pages.

USPTO Non-Final Office Action in U.S. Appl. No. 14/781,069, dated Aug. 27, 2018, 59 pages.

USPTO Final Office Action in U.S. Appl. No. 14/781,069, dated May 20, 2019, 29 pages.

Diamond et al., "Somatic mutation of the T15 heavy chain gives rise to an antibody with autoantibody specificity," Proc Natl Acad Sci USA, Sep. 1984, 81(18):5841-4.

Fanning et al., "A combinatorial approach to engineering a dual-specific metal switch antibody," Biochemistry, Jun. 14, 2011, 50(23):5093-5. doi: 10.1021/bi2003845. Epub May 18, 2011.

Fanning et al., "Structural basis of an engineered dual-specific antibody: conformational diversity leads to a hypervariable loop metal-binding site," Protein Eng Des Sel, Oct. 2014, 27(10):391-7.

Finkelstein et al., Protein physics: Lecture course with colored and stereoscope illustrations and tasks: study guide, 2012, p. 23 (with English translation).

Hasemann et al., "Mutational Analysis of Arsonate Binding by a $CRI_{A+}$ Antibody-$V_H$ and $V_L$ Junctional Diversity are Essential for Binding Activity," J Biol Chem, Apr. 25, 1991, 266(12):7626-32.

Ohno et al., "Antigen-binding specificities of antibodies are primarily determined by seven residues of $V_H$," Proc Natl Acad Sci USA, May 1985, 82(9):2945-9.

Roitt et al., Immunology, M:Mir, 2000, p. 110 (with English translation).

Stepanov, Chapter 6.12 "About a relationship between primary and spatial strutures of the protein," Molecular biology. Structure and Functions of Proteins, M:Nauka, 2005, pp. 144-146 (with English translation).

Yarilin, Fundamentals of Immunology, M:Medicina, 1999, pp. 172-174 (with English translation).

U.S. Appl. No. 17/182,331, filed Feb. 23, 2021, Igawa et al.

Ascierto et al., "Clinical Experiences With Anti-CD137 and Anti-PD1 Therapeutic Antibodies," Semin Oncol, Oct. 2010, 37(5):508-516. doi: 10.1053/j_seminoncol. 2010.09.008.

Clayton et al., "Cancer Exosomes Express CD39 and CD73, Which Suppress T Cells through Adenosine Production," J Immunol, 2011, 187(2):676-683, doi: 10.4049/jimmunol.1003884.

Dubrot et al., "Treatment with anti-CD137 mAbs causes intense accumulations of liver T cells without selective antitumor

(56) References Cited

OTHER PUBLICATIONS immunotherapeutic effects in this organ," Cancer Immunol Immunother. Aug. 2010, 59(8):1223-1233. doi: 10. 1007/s00262-010-0846-9. Epub Mar. 25, 2010.
Hamid et al., "Anti-programmed death-1 and anti-programmed death-ligand 1 antibodies in cancer therapy," Expert Opin Biol Ther, Jun. 2013, 13(6):847-61. doi:10.1517/14712598.2013.770836. Epub Feb. 19, 2013.
Hanahan et al., "Hallmarks of Cancer: The Next Generation," Cell, Mar. 4, 2011, 144(5):646-674. doi: 10.1016/j.oell.2011.02.013.
Houot et al., "Therapeutic effect of CD137 immunomodulation in lymphoma and its enhancement by $T_{reg}$ depletion," Blood, Oct. 15, 2009, 114(16):3431-3438. doi: 10.1182/blood-2009-05-223958. Epub Jul. 29, 2009.
Li et al., "Antitumor activities of agnostic anti-TNFR antibodies require differential FcγRIIB coengagement in vivo," Proc Natl Acad Sci USA, Nov. 26, 2013, 110(48): 19501-19506. doi: 10.1073/pnas.1319502110. Epub Nov. 11, 2013.
Mimoto et al., "Engineered antibody Fc variant with selectively enhanced FcγRIIb binding over both FcγRIIa$^{R131}$ and FcγRIIa$^{H131}$," Protein Eng Des Sel, Jun. 5, 2013, 26(10):589-598. doi: 10.1093/protein/gzt022.
Misawa et al., "Rapid and High-Sensitivity Cell-Based Assays of Protein—Protein Interactions Using Split Click Beetle Luciferase Complementation: An Approach to the Study of G-Protein-Coupled Receptors," Anal Chem, Mar. 15, 2010, 82(6):2552-2560. doi: 10.1021/ac100104Q.
Pace et al., "How to measure and predict the molar absorption coefficient of a protein," Protein Sci, Nov. 1995, 4(11):2411-2423.
Prieto et al., "CTLA-4 Blockade with Ipilimumab: Long-term Follow-up of 177 Patients with Metastatic Melanoma," Clin Cancer Res, Apr. 1, 2012, 18(7):2039-2047. doi: 10.1158/1078-0432.CCR-11-1823. Epub Jan. 23, 2012.
Schabowsky et al., "A Novel Form of 4-1BBL Has Better Immunomodulatory Activity than an Agonistic Anti-4-IBB Ab without A Associated Severe Toxicity," Vaccine, Dec. 11, 2009, 28(2):512-522. doi: 10.1016/j.vaccine.2009.09.127. Epub Oct. 29, 2009.
Summers et al., "Fine-tuning of dendritic cell biology by the TNF superfamily," Nat Rev Immunol, Apr. 10, 2012, 12(5):339-351. doi: 10.1038/nri3193.
Vinay et al., "4-1BB signaling beyond T cells," Cell Mol Immunol, Jul. 2011, 8(4):281-284. doi : 10.1038/cmi.2010.82.Epub Jan. 10, 2011.
Alley et al., "Antibody-drug conjugates: targeted drug delivery for cancer," Curr Opin Chem Biol, Aug. 2010 14(4):529-37. doi: 10.1016/j.cbpa.2010.06.170. Epub Jul. 17, 2010.
Baeuerle et al., "BiTE: Teaching antibodies to engage T-cells for cancer therapy," Curr Opin Mol Ther, Feb. 2009, 11(1):22-30.
Bergleson et al., "Integrin-Ligand Binding: Do integrins use a 'MIDAS touch' to grasp an Asp?" Current Biology 5.6, Jun. 1995, vol. 5, Issue 6, pp. 615-617.
Carreno et al., "2E8 binds to the high affinity I-domain in a metal ion-dependent manner: a second generation monoclonal antibody selectively targeting activated LFA-1," J Biol Chem, Oct. 22, 2010, 285(43):32860-8. doi: 10.1074/jbc.M110.111591. Epub Aug. 19, 2010.
Chen et al., "Kynurenine Pathway Metabolites in Humans: Disease and Healthy States," Int J Tryptophan Res, Jan. 2009, 2:1-19. Epub Jan. 8, 2009.
Chockalingam et al., "Design and application of stimulus-responsive peptide systems," Protein Eng Des Sel, Apr. 2007, 20(4):155-61. Epub Mar. 21, 2007.
Dall'Acqua et al., "Increasing the affinity of a human IgG1 for the neonatal Fc receptor: biological consequences," J Immunol, Nov. 1, 2002, 169(9):5171-80.
Dall'Acqua et al., "Properties of human IgG1s engineered for enhanced binding to the neonatal Fc receptor (FcRn)," J Biol Chem, Aug. 18, 2006, 281(33):23514-24. Epub Jun. 21, 2006.

De Bono et al., "ING-1, a monoclonal antibody targeting Ep-CAM in patients with advanced adenocarcinomas," Clin Cancer Res, Nov. 15, 2004, 10(22):7555-65.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Hardie et al., "Isolation of Specific Antibody Under Conditions of Low Ionic Strength," J Immunol Methods, May 1977, 15(4):305-14.
Hogenesch et al., "Challenges in pre-clinical testing of anti-cancer drugs in cell culture and in animal models", J Control Release, Dec. 10, 2012, 164(2):183-186.
Hu et al., "Combinatorial libraries against libraries for selecting neoepitope activation-specific antibodies," Proc Natl Acad Sci USA, Apr. 2010, 107(14):6252-57.
Igawa et al., "Antibody recycling by engineered pH-dependent antigen binding improves the duration of antigen neutralization," Nat Biotechnol, Nov. 2010, 28(11):1203-7. doi: 10.1038/nbt.1691. Epub Oct. 17, 2010.
Janeway et al., "Structure of the Antibody Molecule and Immunoglobulin Genes," Immunobiology, 3rd Edition, Garland Press, 1997, p. 3:1-3:11.
Juszczak et al., "Ipilimumab: a novel immunomodulating therapy causing autoimmune hypophysitis: a case report and review," Eur J Endocrinol, Jul. 2012, 167(1):1-5. doi: 10.1530/EJE-12-0167. Epub Apr. 10, 2012.
Kim et al., "Antibody Engineering for the Development of Therapeutic Antibodies," Mol Cells, Aug. 31, 2005, 20(1):17-29.
Klaasse et al., "Internalization and desensitization of adenosine receptors," Purinergic Signalling, Mar. 2008, 4(1):21-37.
Lewis et al., "Differential responses of human tumor cell lines to anti-p185HER2 monoclonal antibodies," Cancer Immunol Immunother, Sep. 1993, 37(4):255-63.
Lowder et al., "Monoclonal Antibodies—Therapeutic and Diagnostic Uses in Malignancy," West J Med, Dec. 1985, 143(6):810-8.
Lukashev et al., "Hypoxia-dependent anti-inflammatory pathways in protection of cancerous tissues", Cancer Metastasis Rev, Jun. 2007, 26(2):273-279.
Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-10. doi: 10.1073/pnas.1000976107. Epub Jun. 28, 2010.
Luttrell et al., "Reaction Coupling of Chelation and Antigen Binding in the Calcium Ion-dependent Antibody Binding of Cyclic AMP," J Biol Chem, Nov. 15, 1991, 266(32):21626-30.
Maurer et al., "Antigenicity of polypeptides (PolyαAmino acids): Calcium-Dependent and Independent Antibodies," J Immunol, Sep. 1970, 105(3):567-73.
Nam et al., "Current evidence for the management of rheumatoid arthritis with biological disease-modifying antirheumatic drugs: a systematic literature review informing the EULAR recommendations for the management of RA," Ann Rheum Dis, Jun. 2010, 69(6):976-86. doi: 10.1136/ard.2009.126573. Epub May 6, 2010.
Paul, Chapter 12 "Antigen-Antibody Interactions and Monoclonal Antibodies," Fundamental Immunology, Third Edition, 1984, pp. 421-424.
Paul, Fundamental Immunology, M.: Mir, 1987-1989, vol. 3, pp. 6-10 (in Russian, with corresponding pages from English language version provided as document Desig. ID 80).
Pavlou et al., "The therapeutic antibodies market to 2008," Eur J Pharm Biopharm, Apr. 2005, 59:389-96.
Pedroza et al., "Interleukin-6 Contributes to Inflammation and Remodeling in a Model of Adenosine Mediated Lung Injury", PLoS ONE, www.plosone.org, Jul. 2011, 6(7):e22667, pp. 1-13.
Petkova et al., "Enhanced half-life of genetically engineered human IgG1 antibodies in a humanized FcRn mouse model: potential application in humorally mediated autoimmune disease," Int Immunol, Dec. 2006, 18(12):1759-69. Epub Oct. 31, 2006.
Reichert et al., "Monoclonal antibody successes in the clinic," Nat. Biotechnol, Sep. 2005, 23(9):1073-78.
Reverberi et al., "Factors affecting the antigen-antibody reaction," Blood Transfus. Nov. 2007, 5(4):227-40. doi: 10.2450/2007.0047-07.

(56) References Cited

OTHER PUBLICATIONS

Richard et al., Adenosine upregulates CXCR4 and enhances the proliferative and migratory responses of human carcinoma cells to CXCL12/SDF-1α, Int J Cancer, Jul. 2006, 119:2044-2053.
Riechelmann et al., "Phase I trial with the CD44v6-targeting immunoconjugate bivatuzumab mertansine in head and neck squamous cell carcinoma," Oral Oncol, Sep. 2008, 44(9):823-9. doi: 10.1016/j.oraloncology.2007.10.009. Epub Jan. 18, 2008.
Roopenian et al., "FcRn: the neonatal Fc receptor comes of age," Nat Rev Immunol, Sep. 2007, 7(9):715-25. Epub Aug. 17, 2007.
Rudikoff et al., "Single amino acid substitution altering antigen-binding specificity," Proc Natl Acad Sci USA, Mar. 1982, 79(6):1979-83.
Satoh et al., "Non-fucosylated therapeutic antibodies as next-generation therapeutic antibodies," Expert Opin Biol Ther, Nov. 2006, 6(11):1161-73.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem, Mar. 2, 2001, 276(9):6591-604, Epub Nov. 28, 2000.
Takeuchi et al., "The Japanese experience with biologic therapies for rheumatoid arthritis," Nat Rev Rheumatol, Nov. 2010, 6(11):644-52. doi: 10.1038/nrrheum.2010.154. Epub Sep. 28, 2010.
Tang et al., "Immunotherapy and tumor microenvironment" Cancer Letters, Jan. 1, 2016, 370:85-90.
Trinh et al., "Ipilimumab in the treatment of melanoma," Expert Opin Biol Ther, Jun. 2012, 12(6):773-82. doi: 10.1517/14712598.2012.675325. Epub Apr. 14, 2012.
Vaccaro et al., "Engineering the Fc region of immunoglobulin G to modulate in vivo antibody levels," Nat Biotechnol, Oct. 2005, 23(10):1283-8. Epub Sep. 25, 2005.
Vengelen-Tyler et al., "Two Examples of Antibodies Dependent upon the Presence of Inosine," Transfusion, May-Jun. 1981,21(2):315-9.
Weiner et al., "Monoclonal antibodies: versatile platforms for cancer immunotherapy," Nat Rev Immunol, May 2010, 10(5):317-27. doi: 10.1038/nri2744.
Zalevsky et al., "Enhanced antibody half-life improves in vivo activity," Nat Biotechnol., Feb. 2010, 28(2):157-9. doi: 10.1038/nbt.1601. Epub Jan. 17, 2010.
USPTO Restriction Requirement in U.S. Appl. No. 14/347,187, dated Jan. 26, 2017, 9 pages.
Fish & Richardson P.C., Reply to Restriction Requirement dated Jan. 26, 2017 in U.S. Appl. No. 14/347,187, filed Mar. 27, 2017, 2 pages.
USPTO Non-Final Office Action in U.S. Appl. No. 14/347,187, dated Jun. 14, 2017, 23 pages.
Fish & Richardson P.C., Reply to Non-Final Office Action dated Jun. 14, 2017, in U.S. Appl. No. 14/347,187, filed Oct. 16, 2017, 36 pages.
USPTO Final Office Action in U.S. Appl. No. 14/347,187, dated Jan. 19, 2018, 24 pages.
USPTO Non-final Office Action in U.S. Appl. No. 14/423,269, dated Nov. 28, 2017, 58 pages.
USPTO Restriction Requirement in U.S. Appl. No. 14/423,269, dated May 4, 2017, 5 pages.
USPTO Restriction Requirement in U.S. Appl. No. 15/100,934, dated Apr. 20, 2018, 15 pages.
International Search Report for App. Ser. No. PCT/JP2013/064975, dated Aug. 6, 2013, 3 pages.
International Preliminary Report on Patentability for App. Ser. No. PCT/JP2013/064975, dated Dec. 2, 2014, 6 pages.
International Search Report for App. Ser. No. PCT/JP2014/082060, dated Mar. 10, 2015, 2 pages.
International Preliminary Report on Patentability for App. Ser. No. PCT/JP2014/082060, dated Jun. 7, 2016, 7 pages.
U.S. Appl. No. 14/402,574, Igawa et al., filed Nov. 20, 2014 (abandoned).
U.S. Appl. No. 17/182,331, Igawa et al., filed Feb. 23, 2021.
U.S. Appl. No. 17/438,993, Mizuno et al., filed Sep. 14, 2021.
U.S. Appl. No. 17/266,024, Igawa et al., filed Feb. 4, 2021.
U.S. Appl. No. 17/266,024, filed Feb. 4, 2021, Igawa et al.
U.S. Appl. No. 17/438,993, filed Sep. 14, 2021, Mizuno et al.
Enomoto et al., "Development of high-throughput spermidine synthase activity assay using homogeneous time-resolved fluorescence," Anal Biochem, Apr. 15, 2006, 351(2):229-240.
Limm et al., "The metabolite 5'-methylthioadenosine signals through the adenosine receptor A2B in melanoma," Eur J Cancer, Oct. 2014, 50(15):2714-2724.
Stevens et al., "Quantitative analysis of 5'-deoxy-5'methylthioadenosine in melanoma cells by liquid chromatography-stable isotope ratio tandem mass spectrometry," Chromatogr B Analyt Technol Biomed Life Sci, Dec. 1, 2008, 876(1):123-128.
USPTO Non-Final Office Action in U.S. Appl. No. 15/100,934, dated Apr. 2, 2020, 7 pages.
USPTO Restriction Requirement in U.S. Appl. No. 16/264,735, dated Nov. 16, 2020, 9 pages.
USPTO Non-Final Office Action in U.S. Appl. No. 16/264,735, dated Jun. 22, 2021, 21 pages.
USPTO Final Office Action in U.S. Appl. No. 16/264,735, dated Apr. 1, 2022, 18 pages.
Binyamin et al., "Probing ATP-dependent conformational changes in the multidrug resistance protein 1 (MRP1/ABCC1) in live tumor cells with a novel recombinant single-chain Fv antibody targeted to the extracellular N-terminus," Int J Cancer, Sep. 20, 2005, 116(5):703-709.
U.S. Appl. No. 17/788,998, Katada et al., filed Jun. 24, 2022.
U.S. Appl. No. 17/798,686, Sakurai et al., filed Aug. 10, 2022.
Fish & Richardson P.C., Reply to Restriction Requirement in U.S. Appl. No. 14/402,574 dated Feb. 11, 2016, filed on Apr. 11, 2016, 1 page.
Fish & Richardson P.C., Amendment and Reply to Non-Final Office Action in U.S. Appl. No. 14/402,574, filed on Oct. 6, 2016, 35 pages.
Fish & Richardson P.C., Amendment and Reply to Final Office Action in U.S. Appl. No. 14/402,574, filed on Jan. 30, 2017, 31 pages.
Fish & Richardson P.C., Amendment and Request for Continued Examination in U.S. Appl. No. 14/402,574, filed on Nov. 27, 2017, 32 pages.
Fish & Richardson P.C., Amendment and Reply to Non-Final Office action in U.S. Appl. No. 14/402,574, filed May 15, 2018, 29 pages.
U.S. Appl. No. 17/788,998, filed Jun. 24, 2022, Katada et al.
U.S. Appl. No. 17/798,686, filed Aug. 10, 2022, Sakurai et al.
U.S. Appl. No. 17/848,983, Katada et al., filed Jun. 24, 2022.
U.S. Appl. No. 17/848,983, filed Jun. 24, 2022, Katada et al.

* cited by examiner

SEQUENCE LISTING

```
<160> NUMBER OF SEQ ID NOS: 126

<210> SEQ ID NO 1
<211> LENGTH: 468
<212> TYPE: PRT
<213> ORGANISM: Homo sapiens

<400> SEQUENCE: 1

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125
```

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
            355                 360                 365

Val Ala Gly Gly Ser Leu Ala Phe Gly Thr Leu Leu Cys Ile Ala Ile
370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 2
<211> LENGTH: 1407
<212> TYPE: DNA
<213> ORGANISM: Homo sapiens

<400> SEQUENCE: 2
atgctggccg tcggctgcgc gctgctggct gccctgctgg ccgcgccggg agcggcgctg      60 gcccccaaggc gctgccctgc gcaggaggtg gcgagaggcg tgctgaccag tctgccagga     120
gacagcgtga ctctgaccctg cccgggggta gagccggaag acaatgccac tgttcactgg    180

```
gtgctcagga agccggctgc aggctcccac cccagcagat gggctggcat gggaaggagg    240
ctgctgctga ggtcggtgca gctccacgac tctggaaact attcatgcta ccgggccggc    300
cgcccagctg ggactgtgca cttgctggtg gatgttcccc ccgaggagcc ccagctctcc    360
tgcttccgga agagcccct cagcaatgtt gtttgtgagt ggggtcctcg gagcacccca    420
tccctgacga caaaggctgt gctcttggtg aggaagtttc agaacagtcc ggccgaagac    480
ttccaggagc cgtgccagta ttcccaggag tcccagaagt tctcctgcca gttagcagtc    540
ccggagggag acagctcttt ctacatagtg tccatgtgcg tcgccagtag tgtcgggagc    600
aagttcagca aaactcaaac ctttcagggt gtggaatct gcagcctga tccgcctgcc    660 aacatcacag tcactgccgt ggccagaaac ccccgctggc tcagtgtcac ctggcaagac    720
ccccactcct ggaactcatc tttctacaga ctacggtttg agctcagata tcgggctgaa    780
cggtcaaaga cattcacaac atggatggtc aaggacctcc agcatcactg tgtcatccac    840
gacgcctgga gcggcctgag gcacgtggtg cagcttcgtg cccaggagga gttcgggcaa    900
ggcgagtgga gcgagtggag cccggaggcc atgggcacgc cttggacaga atccaggagt    960
cctccagctg agaacgaggt gtccacccc atgcaggcac ttactactaa taaagacgat   1020
gataatattc tcttcagaga ttctgcaaat gcgacaagcc tcccagtgca agattcttct   1080
tcagtaccac tgcccacatt cctggttgct ggagggagcc tggccttcgg aacgctcctc   1140
tgcattgcca ttgttctgag gttcaagaag acgtggaagc tgcgggctct gaaggaaggc   1200
aagacaagca tgcatccgcc gtactctttg gggcagctgg tcccggagag gcctcgaccc   1260
accccagtgc ttgttcctct catctcccca ccggtgtccc ccagcagcct ggggtctgac   1320
aatacctcga ccacaaccg accagatgcc agggacccac ggagcccta tgacatcagc   1380 aatacagact acttcttccc cagatag                                       1407
```

<210> SEQ ID NO 3
<211> LENGTH: 19
<212> TYPE: PRT
<213> ORGANISM: Artificial sequence
<220> FEATURE:
<223> OTHER INFORMATION: an artificially synthesized sequence

<400> SEQUENCE: 3

Met Gly Trp Ser Cys Ile Ile Leu Phe Leu Val Ala Thr Ala Thr Gly
1               5                   10                  15

Val His Ser

<210> SEQ ID NO 4
<211> LENGTH: 21
<212> TYPE: PRT
<213> ORGANISM: Clostridium sp.

<400> SEQUENCE: 4

Phe Asn Asn Phe Thr Val Ser Phe Trp Leu Arg Val Pro Lys Val Ser
1               5                   10                  15

Ala Ser His Leu Glu
            20

<210> SEQ ID NO 5
<211> LENGTH: 330
<212> TYPE: PRT
<213> ORGANISM: Artificial sequence
<220> FEATURE:
<223> OTHER INFORMATION: an artificially synthesized sequence

```
<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 326
<212> TYPE: PRT
<213> ORGANISM: Artificial sequence
<220> FEATURE:
<223> OTHER INFORMATION: an artificially synthesized sequence

<400> SEQUENCE: 6

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 377
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60
```

```
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 8
<211> LENGTH: 327
<212> TYPE: PRT
<213> ORGANISM: Artificial sequence
<220> FEATURE:
<223> OTHER INFORMATION: an artificially synthesized sequence

<400> SEQUENCE: 8

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 1125
<212> TYPE: DNA
<213> ORGANISM: Homo sapiens
<220> FEATURE:
<221> NAME/KEY: CDS
<222> LOCATION: (1)..(1125)

<400> SEQUENCE: 9 atg tgg ttc ttg aca act ctg ctc ctt tgg gtt cca gtt gat ggg caa    48
Met Trp Phe Leu Thr Thr Leu Leu Leu Trp Val Pro Val Asp Gly Gln
1               5                   10                  15 gtg gac acc aca aag gca gtg atc act ttg cag cct cca tgg gtc agc    96
Val Asp Thr Thr Lys Ala Val Ile Thr Leu Gln Pro Pro Trp Val Ser
            20                  25                  30 gtg ttc caa gag gaa acc gta acc ttg cac tgt gag gtg ctc cat ctg   144
Val Phe Gln Glu Glu Thr Val Thr Leu His Cys Glu Val Leu His Leu
        35                  40                  45 cct ggg agc agc tct aca cag tgg ttt ctc aat ggc aca gcc act cag   192

```
                Pro Gly Ser Ser Ser Thr Gln Trp Phe Leu Asn Gly Thr Ala Thr Gln
                    50              55                  60 acc tcg acc ccc agc tac aga atc acc tct gcc agt gtc aat gac agt        240
Thr Ser Thr Pro Ser Tyr Arg Ile Thr Ser Ala Ser Val Asn Asp Ser
 65              70                  75                  80 ggt gaa tac agg tgc cag aga ggt ctc tca ggg cga agt gac ccc ata        288
Gly Glu Tyr Arg Cys Gln Arg Gly Leu Ser Gly Arg Ser Asp Pro Ile
                 85                  90                  95 cag ctg gaa atc cac aga ggc tgg cta cta ctg cag gtc tcc agc aga        336
Gln Leu Glu Ile His Arg Gly Trp Leu Leu Leu Gln Val Ser Ser Arg
                100                 105                 110 gtc ttc acg gaa gga gaa cct ctg gcc ttg agg tgt cat gcg tgg aag        384
Val Phe Thr Glu Gly Glu Pro Leu Ala Leu Arg Cys His Ala Trp Lys
            115                 120                 125 gat aag ctg gtg tac aat gtg ctt tac tat cga aat ggc aaa gcc ttt        432
Asp Lys Leu Val Tyr Asn Val Leu Tyr Tyr Arg Asn Gly Lys Ala Phe
        130                 135                 140 aag ttt ttc cac tgg aat tct aac ctc acc att ctg aaa acc aac ata        480
Lys Phe Phe His Trp Asn Ser Asn Leu Thr Ile Leu Lys Thr Asn Ile
145                 150                 155                 160 agt cac aat ggc acc tac cat tgc tca ggc atg gga aag cat cgc tac        528
Ser His Asn Gly Thr Tyr His Cys Ser Gly Met Gly Lys His Arg Tyr
                165                 170                 175 aca tca gca gga ata tct gtc act gtg aaa gag cta ttt cca gct cca        576
Thr Ser Ala Gly Ile Ser Val Thr Val Lys Glu Leu Phe Pro Ala Pro
                180                 185                 190 gtg ctg aat gca tct gtg aca tcc cca ctc ctg gag ggg aat ctg gtc        624
Val Leu Asn Ala Ser Val Thr Ser Pro Leu Leu Glu Gly Asn Leu Val
            195                 200                 205 acc ctg agc tgt gaa aca aag ttg ctc ttg cag agg cct ggt ttg cag        672
Thr Leu Ser Cys Glu Thr Lys Leu Leu Leu Gln Arg Pro Gly Leu Gln
        210                 215                 220 ctt tac ttc tcc ttc tac atg ggc agc aag acc ctg cga ggc agg aac        720
Leu Tyr Phe Ser Phe Tyr Met Gly Ser Lys Thr Leu Arg Gly Arg Asn
225                 230                 235                 240 aca tcc tct gaa tac caa ata cta act gct aga aga gaa gac tct ggg        768
Thr Ser Ser Glu Tyr Gln Ile Leu Thr Ala Arg Arg Glu Asp Ser Gly
                245                 250                 255 tta tac tgg tgc gag gct gcc aca gag gat gga aat gtc ctt aag cgc        816
Leu Tyr Trp Cys Glu Ala Ala Thr Glu Asp Gly Asn Val Leu Lys Arg
                260                 265                 270 agc cct gag ttg gag ctt caa gtg ctt ggc ctc cag tta cca act cct        864
Ser Pro Glu Leu Glu Leu Gln Val Leu Gly Leu Gln Leu Pro Thr Pro
            275                 280                 285 gtc tgg ttt cat gtc ctt ttc tat ctg gca gtg gga ata atg ttt tta        912
Val Trp Phe His Val Leu Phe Tyr Leu Ala Val Gly Ile Met Phe Leu
        290                 295                 300 gtg aac act gtt ctc tgg gtg aca ata cgt aaa gaa ctg aaa aga aag        960
Val Asn Thr Val Leu Trp Val Thr Ile Arg Lys Glu Leu Lys Arg Lys
305                 310                 315                 320 aaa aag tgg gat tta gaa atc tct ttg gat tct ggt cat gag aag aag       1008
Lys Lys Trp Asp Leu Glu Ile Ser Leu Asp Ser Gly His Glu Lys Lys
                325                 330                 335 gta att tcc agc ctt caa gaa gac aga cat tta gaa gaa gag ctg aaa       1056
Val Ile Ser Ser Leu Gln Glu Asp Arg His Leu Glu Glu Glu Leu Lys
                340                 345                 350 tgt cag gaa caa aaa gaa gaa cag ctg cag gaa ggg gtg cac cgg aag       1104
Cys Gln Glu Gln Lys Glu Glu Gln Leu Gln Glu Gly Val His Arg Lys
            355                 360                 365
```

```
gag ccc cag ggg gcc acg tag                                    1125
Glu Pro Gln Gly Ala Thr
    370
```

<210> SEQ ID NO 10
<211> LENGTH: 374
<212> TYPE: PRT
<213> ORGANISM: Homo sapiens

<400> SEQUENCE: 10

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
            340                 345                 350

Cys Gln Glu Gln Lys Glu Glu Gln Leu Gln Glu Gly Val His Arg Lys
```

355                 360                 365
Glu Pro Gln Gly Ala Thr
        370

<210> SEQ ID NO 11
<211> LENGTH: 951
<212> TYPE: DNA
<213> ORGANISM: Homo sapiens
<220> FEATURE:
<221> NAME/KEY: CDS
<222> LOCATION: (1)..(951)

<400> SEQUENCE: 11

```
atg act atg gag acc caa atg tct cag aat gta tgt ccc aga aac ctg      48
Met Thr Met Glu Thr Gln Met Ser Gln Asn Val Cys Pro Arg Asn Leu
1               5                   10                  15 tgg ctg ctt caa cca ttg aca gtt ttg ctg ctg gct tct gca gac          96
Trp Leu Leu Gln Pro Leu Thr Val Leu Leu Leu Ala Ser Ala Asp
            20                  25                  30 agt caa gct gct ccc cca aag gct gtg ctg aaa ctt gag ccc ccg tgg     144
Ser Gln Ala Ala Pro Pro Lys Ala Val Leu Lys Leu Glu Pro Pro Trp
        35                  40                  45 atc aac gtg ctc cag gag gac tct gtg act ctg aca tgc cag ggg gct    192
Ile Asn Val Leu Gln Glu Asp Ser Val Thr Leu Thr Cys Gln Gly Ala
50                  55                  60 cgc agc cct gag agc gac tcc att cag tgg ttc cac aat ggg aat ctc    240
Arg Ser Pro Glu Ser Asp Ser Ile Gln Trp Phe His Asn Gly Asn Leu
65                  70                  75                  80 att ccc acc cac acg cag ccc agc tac agg ttc aag gcc aac aac aat    288
Ile Pro Thr His Thr Gln Pro Ser Tyr Arg Phe Lys Ala Asn Asn Asn
                85                  90                  95 gac agc ggg gag tac acg tgc cag act ggc cag acc agc ctc agc gac    336
Asp Ser Gly Glu Tyr Thr Cys Gln Thr Gly Gln Thr Ser Leu Ser Asp
            100                 105                 110 cct gtg cat ctg act gtg ctt tcc gaa tgg ctg gtg ctc cag acc cct    384
Pro Val His Leu Thr Val Leu Ser Glu Trp Leu Val Leu Gln Thr Pro
        115                 120                 125 cac ctg gag ttc cag gag gga gaa acc atc atg ctg agg tgc cac agc    432
His Leu Glu Phe Gln Glu Gly Glu Thr Ile Met Leu Arg Cys His Ser
    130                 135                 140 tgg aag gac aag cct ctg gtc aag gtc aca ttc ttc cag aat gga aaa    480
Trp Lys Asp Lys Pro Leu Val Lys Val Thr Phe Phe Gln Asn Gly Lys
145                 150                 155                 160 tcc cag aaa ttc tcc cat ttg gat ccc acc ttc tcc atc cca caa gca    528
Ser Gln Lys Phe Ser His Leu Asp Pro Thr Phe Ser Ile Pro Gln Ala
                165                 170                 175 aac cac agt cac agt ggt gat tac cac tgc aca gga aac ata ggc tac    576
Asn His Ser His Ser Gly Asp Tyr His Cys Thr Gly Asn Ile Gly Tyr
            180                 185                 190 acg ctg ttc tca tcc aag cct gtg acc atc act gtc caa gtg ccc agc    624
Thr Leu Phe Ser Ser Lys Pro Val Thr Ile Thr Val Gln Val Pro Ser
        195                 200                 205 atg ggc agc tct tca cca atg ggg gtc att gtg gct gtg gtc att gcg    672
Met Gly Ser Ser Ser Pro Met Gly Val Ile Val Ala Val Val Ile Ala
    210                 215                 220 act gct gta gca gcc att gtt gct gct gta gtg gcc ttg atc tac tgc    720
Thr Ala Val Ala Ala Ile Val Ala Ala Val Val Ala Leu Ile Tyr Cys
225                 230                 235                 240 agg aaa aag cgg att tca gcc aat tcc act gat cct gtg aag gct gcc    768
Arg Lys Lys Arg Ile Ser Ala Asn Ser Thr Asp Pro Val Lys Ala Ala
                245                 250                 255
```

```
caa ttt gag cca cct gga cgt caa atg att gcc atc aga aag aga caa      816
Gln Phe Glu Pro Pro Gly Arg Gln Met Ile Ala Ile Arg Lys Arg Gln
            260                 265                 270 ctt gaa gaa acc aac aat gac tat gaa aca gct gac ggc ggc tac atg      864
Leu Glu Glu Thr Asn Asn Asp Tyr Glu Thr Ala Asp Gly Gly Tyr Met
        275                 280                 285 act ctg aac ccc agg gca cct act gac gat gat aaa aac atc tac ctg      912
Thr Leu Asn Pro Arg Ala Pro Thr Asp Asp Asp Lys Asn Ile Tyr Leu
    290                 295                 300 act ctt cct ccc aac gac cat gtc aac agt aat aac taa                  951
Thr Leu Pro Pro Asn Asp His Val Asn Ser Asn Asn
305                 310                 315

<210> SEQ ID NO 12
<211> LENGTH: 316
<212> TYPE: PRT
<213> ORGANISM: Homo sapiens

<400> SEQUENCE: 12

Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285
```

```
Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 13
<211> LENGTH: 876
<212> TYPE: DNA
<213> ORGANISM: Homo sapiens
<220> FEATURE:
<221> NAME/KEY: CDS
<222> LOCATION: (1)..(876)

<400> SEQUENCE: 13 atg gga atc ctg tca ttc tta cct gtc ctt gcc act gag agt gac tgg       48
Met Gly Ile Leu Ser Phe Leu Pro Val Leu Ala Thr Glu Ser Asp Trp
1               5                   10                  15 gct gac tgc aag tcc ccc cag cct tgg ggt cat atg ctt ctg tgg aca       96
Ala Asp Cys Lys Ser Pro Gln Pro Trp Gly His Met Leu Leu Trp Thr
                20                  25                  30 gct gtg cta ttc ctg gct cct gtt gct ggg aca cct gca gct ccc cca     144
Ala Val Leu Phe Leu Ala Pro Val Ala Gly Thr Pro Ala Ala Pro Pro
            35                  40                  45 aag gct gtg ctg aaa ctc gag ccc cag tgg atc aac gtg ctc cag gag     192
Lys Ala Val Leu Lys Leu Glu Pro Gln Trp Ile Asn Val Leu Gln Glu
        50                  55                  60 gac tct gtg act ctg aca tgc cgg ggg act cac agc cct gag agc gac     240
Asp Ser Val Thr Leu Thr Cys Arg Gly Thr His Ser Pro Glu Ser Asp
65                  70                  75                  80 tcc att cag tgg ttc cac aat ggg aat ctc att ccc acc cac acg cag     288
Ser Ile Gln Trp Phe His Asn Gly Asn Leu Ile Pro Thr His Thr Gln
                85                  90                  95 ccc agc tac agg ttc aag gcc aac aac aat gac agc ggg gag tac acg     336
Pro Ser Tyr Arg Phe Lys Ala Asn Asn Asn Asp Ser Gly Glu Tyr Thr
                100                 105                 110 tgc cag act ggc cag acc agc ctc agc gac cct gtg cat ctg act gtg     384
Cys Gln Thr Gly Gln Thr Ser Leu Ser Asp Pro Val His Leu Thr Val
            115                 120                 125 ctt tct gag tgg ctg gtg ctc cag acc cct cac ctg gag ttc cag gag     432
Leu Ser Glu Trp Leu Val Leu Gln Thr Pro His Leu Glu Phe Gln Glu
        130                 135                 140 gga gaa acc atc gtg ctg agg tgc cac agc tgg aag gac aag cct ctg     480
Gly Glu Thr Ile Val Leu Arg Cys His Ser Trp Lys Asp Lys Pro Leu
145                 150                 155                 160 gtc aag gtc aca ttc ttc cag aat gga aaa tcc aag aaa ttt tcc cgt     528
Val Lys Val Thr Phe Phe Gln Asn Gly Lys Ser Lys Lys Phe Ser Arg
                165                 170                 175 tcg gat ccc aac ttc tcc atc cca caa gca aac cac agt cac agt ggt     576
Ser Asp Pro Asn Phe Ser Ile Pro Gln Ala Asn His Ser His Ser Gly
                180                 185                 190 gat tac cac tgc aca gga aac ata ggc tac acg ctg tac tca tcc aag     624
Asp Tyr His Cys Thr Gly Asn Ile Gly Tyr Thr Leu Tyr Ser Ser Lys
            195                 200                 205 cct gtg acc atc act gtc caa gct ccc agc tct tca ccg atg ggg atc     672
Pro Val Thr Ile Thr Val Gln Ala Pro Ser Ser Ser Pro Met Gly Ile
        210                 215                 220 att gtg gct gtg gtc act ggg att gct gta gcg gcc att gtt gct gct     720
Ile Val Ala Val Val Thr Gly Ile Ala Val Ala Ala Ile Val Ala Ala
225                 230                 235                 240 gta gtg gcc ttg atc tac tgc agg aaa aag cgg att tca gcc aat ccc     768
Val Val Ala Leu Ile Tyr Cys Arg Lys Lys Arg Ile Ser Ala Asn Pro
```

```
act aat cct gat gag gct gac aaa gtt ggg gct gag aac aca atc acc    816
Thr Asn Pro Asp Glu Ala Asp Lys Val Gly Ala Glu Asn Thr Ile Thr
        260                 265                 270 tat tca ctt ctc atg cac ccg gat gct ctg gaa gag cct gat gac cag    864
Tyr Ser Leu Leu Met His Pro Asp Ala Leu Glu Glu Pro Asp Asp Gln
        275                 280                 285 aac cgt att tag                                                    876
Asn Arg Ile
    290

<210> SEQ ID NO 14
<211> LENGTH: 291
<212> TYPE: PRT
<213> ORGANISM: Homo sapiens

<400> SEQUENCE: 14

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290
```

<210> SEQ ID NO 15
<211> LENGTH: 765
<212> TYPE: DNA
<213> ORGANISM: Homo sapiens
<220> FEATURE:
<221> NAME/KEY: CDS
<222> LOCATION: (1)..(765)

<400> SEQUENCE: 15

```
atg tgg cag ctg ctc ctc cca act gct ctg cta ctt cta gtt tca gct      48
Met Trp Gln Leu Leu Leu Pro Thr Ala Leu Leu Leu Leu Val Ser Ala
1               5                   10                  15 ggc atg cgg act gaa gat ctc cca aag gct gtg gtg ttc ctg gag cct      96
Gly Met Arg Thr Glu Asp Leu Pro Lys Ala Val Val Phe Leu Glu Pro
            20                  25                  30 caa tgg tac agg gtg ctc gag aag gac agt gtg act ctg aag tgc cag     144
Gln Trp Tyr Arg Val Leu Glu Lys Asp Ser Val Thr Leu Lys Cys Gln
        35                  40                  45 gga gcc tac tcc cct gag gac aat tcc aca cag tgg ttt cac aat gag     192
Gly Ala Tyr Ser Pro Glu Asp Asn Ser Thr Gln Trp Phe His Asn Glu
    50                  55                  60 agc ctc atc tca agc cag gcc tcg agc tac ttc att gac gct gcc aca     240
Ser Leu Ile Ser Ser Gln Ala Ser Ser Tyr Phe Ile Asp Ala Ala Thr
65                  70                  75                  80 gtt gac gac agt gga gag tac agg tgc cag aca aac ctc tcc acc ctc     288
Val Asp Asp Ser Gly Glu Tyr Arg Cys Gln Thr Asn Leu Ser Thr Leu
                85                  90                  95 agt gac ccg gtg cag cta gaa gtc cat atc ggc tgg ctg ttg ctc cag     336
Ser Asp Pro Val Gln Leu Glu Val His Ile Gly Trp Leu Leu Leu Gln
            100                 105                 110 gcc cct cgg tgg gtg ttc aag gag gaa gac cct att cac ctg agg tgt     384
Ala Pro Arg Trp Val Phe Lys Glu Glu Asp Pro Ile His Leu Arg Cys
        115                 120                 125 cac agc tgg aag aac act gct ctg cat aag gtc aca tat tta cag aat     432
His Ser Trp Lys Asn Thr Ala Leu His Lys Val Thr Tyr Leu Gln Asn
    130                 135                 140 ggc aaa ggc agg aag tat ttt cat cat aat tct gac ttc tac att cca     480
Gly Lys Gly Arg Lys Tyr Phe His His Asn Ser Asp Phe Tyr Ile Pro
145                 150                 155                 160 aaa gcc aca ctc aaa gac agc ggc tcc tac ttc tgc agg ggg ctt gtt     528
Lys Ala Thr Leu Lys Asp Ser Gly Ser Tyr Phe Cys Arg Gly Leu Val
                165                 170                 175 ggg agt aaa aat gtg tct tca gag act gtg aac atc acc atc act caa     576
Gly Ser Lys Asn Val Ser Ser Glu Thr Val Asn Ile Thr Ile Thr Gln
            180                 185                 190 ggt ttg tca gtg tca acc atc tca ttc ttt cca cct ggg tac caa         624
Gly Leu Ser Val Ser Thr Ile Ser Ser Phe Phe Pro Pro Gly Tyr Gln
        195                 200                 205 gtc tct ttc tgc ttg gtg atg gta ctc ctt ttt gca gtg gac aca gga     672
Val Ser Phe Cys Leu Val Met Val Leu Leu Phe Ala Val Asp Thr Gly
    210                 215                 220 cta tat ttc tct gtg aag aca aac att cga agc tca aca aga gac tgg     720
Leu Tyr Phe Ser Val Lys Thr Asn Ile Arg Ser Ser Thr Arg Asp Trp
225                 230                 235                 240 aag gac cat aaa ttt aaa tgg aga aag gac cct caa gac aaa tga         765
Lys Asp His Lys Phe Lys Trp Arg Lys Asp Pro Gln Asp Lys
                245                 250
```

<210> SEQ ID NO 16
<211> LENGTH: 254
<212> TYPE: PRT

<213> ORGANISM: Homo sapiens

<400> SEQUENCE: 16

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 17
<211> LENGTH: 702
<212> TYPE: DNA
<213> ORGANISM: Homo sapiens
<220> FEATURE:
<221> NAME/KEY: CDS
<222> LOCATION: (1)..(702)

<400> SEQUENCE: 17

```
atg tgg cag ctg ctc ctc cca act gct ctg cta ctt cta gtt tca gct      48
Met Trp Gln Leu Leu Leu Pro Thr Ala Leu Leu Leu Val Ser Ala
1               5                   10                  15 ggc atg cgg act gaa gat ctc cca aag gct gtg gtg ttc ctg gag cct      96
Gly Met Arg Thr Glu Asp Leu Pro Lys Ala Val Val Phe Leu Glu Pro
            20                  25                  30 caa tgg tac agc gtg ctt gag aag gac agt gtg act ctg aag tgc cag     144
Gln Trp Tyr Ser Val Leu Glu Lys Asp Ser Val Thr Leu Lys Cys Gln
        35                  40                  45 gga gcc tac tcc cct gag gac aat tcc aca cag tgg ttt cac aat gag     192
Gly Ala Tyr Ser Pro Glu Asp Asn Ser Thr Gln Trp Phe His Asn Glu
    50                  55                  60
```

```
agc ctc atc tca agc cag gcc tcg agc tac ttc att gac gct gcc aca    240
Ser Leu Ile Ser Ser Gln Ala Ser Ser Tyr Phe Ile Asp Ala Ala Thr
 65                  70                  75                  80 gtc aac gac agt gga gag tac agg tgc cag aca aac ctc tcc acc ctc    288
Val Asn Asp Ser Gly Glu Tyr Arg Cys Gln Thr Asn Leu Ser Thr Leu
                 85                  90                  95 agt gac ccg gtg cag cta gaa gtc cat atc ggc tgg ctg ttg ctc cag    336
Ser Asp Pro Val Gln Leu Glu Val His Ile Gly Trp Leu Leu Leu Gln
            100                 105                 110 gcc cct cgg tgg gtg ttc aag gag gaa gac cct att cac ctg agg tgt    384
Ala Pro Arg Trp Val Phe Lys Glu Glu Asp Pro Ile His Leu Arg Cys
        115                 120                 125 cac agc tgg aag aac act gct ctg cat aag gtc aca tat tta cag aat    432
His Ser Trp Lys Asn Thr Ala Leu His Lys Val Thr Tyr Leu Gln Asn
    130                 135                 140 ggc aaa gac agg aag tat ttt cat cat aat tct gac ttc cac att cca    480
Gly Lys Asp Arg Lys Tyr Phe His His Asn Ser Asp Phe His Ile Pro
145                 150                 155                 160 aaa gcc aca ctc aaa gat agc ggc tcc tac ttc tgc agg ggg ctt gtt    528
Lys Ala Thr Leu Lys Asp Ser Gly Ser Tyr Phe Cys Arg Gly Leu Val
                165                 170                 175 ggg agt aaa aat gtg tct tca gag act gtg aac atc acc atc act caa    576
Gly Ser Lys Asn Val Ser Ser Glu Thr Val Asn Ile Thr Ile Thr Gln
            180                 185                 190 ggt ttg gca gtg tca acc atc tca tca ttc tct cca cct ggg tac caa    624
Gly Leu Ala Val Ser Thr Ile Ser Ser Phe Ser Pro Pro Gly Tyr Gln
        195                 200                 205 gtc tct ttc tgc ttg gtg atg gta ctc ctt ttt gca gtg gac aca gga    672
Val Ser Phe Cys Leu Val Met Val Leu Leu Phe Ala Val Asp Thr Gly
    210                 215                 220 cta tat ttc tct gtg aag aca aac att tga                            702
Leu Tyr Phe Ser Val Lys Thr Asn Ile
225                 230

<210> SEQ ID NO 18
<211> LENGTH: 233
<212> TYPE: PRT
<213> ORGANISM: Homo sapiens

<400> SEQUENCE: 18

Met Trp Gln Leu Leu Leu Pro Thr Ala Leu Leu Leu Leu Val Ser Ala
  1               5                  10                  15

Gly Met Arg Thr Glu Asp Leu Pro Lys Ala Val Val Phe Leu Glu Pro
             20                  25                  30

Gln Trp Tyr Ser Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
     50                  55                  60

Ser Leu Ile Ser Ser Gln Ala Ser Ser Tyr Phe Ile Asp Ala Ala Thr
 65                  70                  75                  80

Val Asn Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140
```

```
Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 19
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 19

Gly Gly Gly Ser
1

<210> SEQ ID NO 20
<211> LENGTH: 4
<212> TYPE: PRT
<213> ORGANISM: Artificial sequence
<220> FEATURE:
<223> OTHER INFORMATION: an artificially synthesized sequence

<400> SEQUENCE: 20

Ser Gly Gly Gly
1

<210> SEQ ID NO 21
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 21

Gly Gly Gly Gly Ser
1               5

<210> SEQ ID NO 22
<211> LENGTH: 5
<212> TYPE: PRT
<213> ORGANISM: Artificial sequence
<220> FEATURE:
<223> OTHER INFORMATION: an artificially synthesized sequence

<400> SEQUENCE: 22

Ser Gly Gly Gly Gly
1               5

<210> SEQ ID NO 23
<211> LENGTH: 6
<212> TYPE: PRT
<213> ORGANISM: Artificial sequence
<220> FEATURE:
<223> OTHER INFORMATION: an artificially synthesized sequence

<400> SEQUENCE: 23

```
Gly Gly Gly Gly Gly Ser
1               5

<210> SEQ ID NO 24
<211> LENGTH: 6
<212> TYPE: PRT
<213> ORGANISM: Artificial sequence
<220> FEATURE:
<223> OTHER INFORMATION: an artificially synthesized sequence

<400> SEQUENCE: 24

Ser Gly Gly Gly Gly Gly
1               5

<210> SEQ ID NO 25
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 25

Gly Gly Gly Gly Gly Gly Ser
1               5

<210> SEQ ID NO 26
<211> LENGTH: 7
<212> TYPE: PRT
<213> ORGANISM: Artificial sequence
<220> FEATURE:
<223> OTHER INFORMATION: an artificially synthesized sequence

<400> SEQUENCE: 26

Ser Gly Gly Gly Gly Gly Gly
1               5

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asn Thr Leu Pro Tyr
                85                  90                  95

Thr Phe Gly Gln Gly Thr Lys Val Glu Ile Lys
            100                 105

<210> SEQ ID NO 28
<211> LENGTH: 365
<212> TYPE: PRT
<213> ORGANISM: Homo sapiens

<400> SEQUENCE: 28
```

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 29
<211> LENGTH: 119
<212> TYPE: PRT
<213> ORGANISM: Homo sapiens

<400> SEQUENCE: 29

Met Ser Arg Ser Val Ala Leu Ala Val Leu Ala Leu Leu Ser Leu Ser

```
                1               5                   10                  15
            Gly Leu Glu Ala Ile Gln Arg Thr Pro Lys Ile Gln Val Tyr Ser Arg
                            20                  25                  30

His Pro Ala Glu Asn Gly Lys Ser Asn Phe Leu Asn Cys Tyr Val Ser
                            35                  40                  45

Gly Phe His Pro Ser Asp Ile Glu Val Asp Leu Leu Lys Asn Gly Glu
                        50                  55                  60

Arg Ile Glu Lys Val Glu His Ser Asp Leu Ser Phe Ser Lys Asp Trp
            65                  70                  75                  80

Ser Phe Tyr Leu Leu Tyr Tyr Thr Gly Phe Thr Pro Thr Glu Lys Asp
                            85                  90                  95

Glu Tyr Ala Cys Arg Val Asn His Val Thr Leu Ser Gln Pro Lys Ile
                        100                 105                 110

Val Lys Trp Asp Arg Asp Met
                        115

<210> SEQ ID NO 30
<211> LENGTH: 451
<212> TYPE: PRT
<213> ORGANISM: Homo sapiens

<400> SEQUENCE: 30

Gln Val Gln Leu Gln Glu Ser Gly Gly Gly Val Val Gln Pro Gly Arg
            1               5                   10                  15

Ser Leu Arg Leu Ser Cys Ala Ala Ser Gly Phe Thr Phe Ser Ser Tyr
                            20                  25                  30

Ala Met His Trp Val Arg Gln Ala Pro Gly Lys Gly Leu Glu Trp Val
                            35                  40                  45

Ala Val Ile Ser Tyr Asp Gly Ser Asn Lys Tyr Tyr Ala Asp Ser Val
                        50                  55                  60

Lys Gly Arg Phe Thr Ile Ser Arg Asp Asn Ser Lys Asn Thr Leu Tyr
            65                  70                  75                  80

Leu Gln Met Asn Ser Leu Arg Ala Glu Asp Thr Ala Val Tyr Tyr Cys
                            85                  90                  95

Ala Arg Asp Ala Val Thr Gly Asp Asp Trp Tyr Phe Asp Leu Trp Gly
                        100                 105                 110

Arg Gly Thr Leu Val Thr Val Ser Ser Ala Ser Thr Lys Gly Pro Ser
                        115                 120                 125

Val Phe Pro Leu Ala Pro Ser Ser Lys Ser Thr Ser Gly Gly Thr Ala
                        130                 135                 140

Ala Leu Gly Cys Leu Val Lys Asp Tyr Phe Pro Glu Pro Val Thr Val
            145                 150                 155                 160

Ser Trp Asn Ser Gly Ala Leu Thr Ser Gly Val His Thr Phe Pro Ala
                            165                 170                 175

Val Leu Gln Ser Ser Gly Leu Tyr Ser Leu Ser Ser Val Val Thr Val
                        180                 185                 190

Pro Ser Ser Ser Leu Gly Thr Gln Thr Tyr Ile Cys Asn Val Asn His
                        195                 200                 205

Lys Pro Ser Asn Thr Lys Val Asp Lys Lys Val Glu Pro Lys Ser Cys
                        210                 215                 220

Asp Lys Thr His Thr Cys Pro Pro Cys Pro Ala Pro Glu Leu Leu Gly
            225                 230                 235                 240

Gly Pro Ser Val Phe Leu Phe Pro Pro Lys Pro Lys Asp Thr Leu Met
                            245                 250                 255
```

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 31
<211> LENGTH: 214
<212> TYPE: PRT
<213> ORGANISM: Homo sapiens

<400> SEQUENCE: 31

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

```
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 32
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 32
```

```
Glu Val Gln Leu Val Glu Ser Gly Gly Lys Leu Leu Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Phe Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Gly Leu Trp Gly Tyr Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 33
<211> LENGTH: 213
<212> TYPE: PRT
<213> ORGANISM: Artificial sequence
<220> FEATURE:
<223> OTHER INFORMATION: an artificially synthesized sequence

<400> SEQUENCE: 33

Gln Ile Val Leu Ile Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Gly Tyr Pro Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 34
```

```
<211> LENGTH: 443
<212> TYPE: PRT
<213> ORGANISM: Artificial sequence
<220> FEATURE:
<223> OTHER INFORMATION: an artificially synthesized sequence

<400> SEQUENCE: 34
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Glu | Met | His | Trp | Ile | Arg | Gln | Pro | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Ala | Ile | Asp | Pro | Lys | Thr | Gly | Asp | Thr | Ala | Tyr | Ser | Gln | Lys | Phe |
|---|---|---|---|---|---|---|---|---|---|---|---|---|---|---|---|
| | 50 | | | | | 55 | | | | | 60 | | | | |

| Lys | Gly | Arg | Val | Thr | Leu | Thr | Ala | Asp | Lys | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Thr | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Arg | Phe | Tyr | Ser | Tyr | Thr | Tyr | Trp | Gly | Gln | Gly | Thr | Leu | Val | Thr |
|---|---|---|---|---|---|---|---|---|---|---|---|---|---|---|---|
| | | | | 100 | | | | | 105 | | | | | 110 | |

| Val | Ser | Ser | Ala | Ser | Thr | Lys | Gly | Pro | Ser | Val | Phe | Pro | Leu | Ala | Pro |
|---|---|---|---|---|---|---|---|---|---|---|---|---|---|---|---|
| | | 115 | | | | | 120 | | | | | 125 | | | |

| Ser | Ser | Lys | Ser | Thr | Ser | Gly | Gly | Thr | Ala | Ala | Leu | Gly | Cys | Leu | Val |
|---|---|---|---|---|---|---|---|---|---|---|---|---|---|---|---|
| | 130 | | | | | 135 | | | | | 140 | | | | |

| Lys | Asp | Tyr | Phe | Pro | Glu | Pro | Val | Thr | Val | Ser | Trp | Asn | Ser | Gly | Ala |
|---|---|---|---|---|---|---|---|---|---|---|---|---|---|---|---|
| 145 | | | | | 150 | | | | | 155 | | | | | 160 |

| Leu | Thr | Ser | Gly | Val | His | Thr | Phe | Pro | Ala | Val | Leu | Gln | Ser | Ser | Gly |
|---|---|---|---|---|---|---|---|---|---|---|---|---|---|---|---|
| | | | | 165 | | | | | 170 | | | | | 175 | |

| Leu | Tyr | Ser | Leu | Ser | Ser | Val | Val | Thr | Val | Pro | Ser | Ser | Ser | Leu | Gly |
|---|---|---|---|---|---|---|---|---|---|---|---|---|---|---|---|
| | | | 180 | | | | | 185 | | | | | 190 | | |

| Thr | Gln | Thr | Tyr | Ile | Cys | Asn | Val | Asn | His | Lys | Pro | Ser | Asn | Thr | Lys |
|---|---|---|---|---|---|---|---|---|---|---|---|---|---|---|---|
| | | 195 | | | | | 200 | | | | | 205 | | | |

| Val | Asp | Lys | Lys | Val | Glu | Pro | Lys | Ser | Cys | Asp | Lys | Thr | His | Thr | Cys |
|---|---|---|---|---|---|---|---|---|---|---|---|---|---|---|---|
| | 210 | | | | | 215 | | | | | 220 | | | | |

| Pro | Pro | Cys | Pro | Ala | Pro | Glu | Ala | Ala | Gly | Gly | Pro | Ser | Val | Phe | Leu |
|---|---|---|---|---|---|---|---|---|---|---|---|---|---|---|---|
| 225 | | | | | 230 | | | | | 235 | | | | | 240 |

| Phe | Pro | Pro | Lys | Pro | Lys | Asp | Thr | Leu | Met | Ile | Ser | Arg | Thr | Pro | Glu |
|---|---|---|---|---|---|---|---|---|---|---|---|---|---|---|---|
| | | | | 245 | | | | | 250 | | | | | 255 | |

| Val | Thr | Cys | Val | Val | Val | Asp | Val | Ser | His | Glu | Asp | Pro | Glu | Val | Lys |
|---|---|---|---|---|---|---|---|---|---|---|---|---|---|---|---|
| | | | | 260 | | | | | 265 | | | | | 270 | |

| Phe | Asn | Trp | Tyr | Val | Asp | Gly | Val | Glu | Val | His | Asn | Ala | Lys | Thr | Lys |
|---|---|---|---|---|---|---|---|---|---|---|---|---|---|---|---|
| | | 275 | | | | | 280 | | | | | 285 | | | |

| Pro | Arg | Glu | Glu | Gln | Tyr | Ala | Ser | Thr | Tyr | Arg | Val | Val | Ser | Val | Leu |
|---|---|---|---|---|---|---|---|---|---|---|---|---|---|---|---|
| | 290 | | | | | 295 | | | | | 300 | | | | |

| Thr | Val | Leu | His | Gln | Asp | Trp | Leu | Asn | Gly | Lys | Glu | Tyr | Lys | Cys | Lys |
|---|---|---|---|---|---|---|---|---|---|---|---|---|---|---|---|
| 305 | | | | | 310 | | | | | 315 | | | | | 320 |

| Val | Ser | Asn | Lys | Ala | Leu | Pro | Ala | Pro | Ile | Glu | Lys | Thr | Ile | Ser | Lys |
|---|---|---|---|---|---|---|---|---|---|---|---|---|---|---|---|
| | | | | 325 | | | | | 330 | | | | | 335 | |

| Ala | Lys | Gly | Gln | Pro | Arg | Glu | Pro | Gln | Val | Tyr | Thr | Leu | Pro | Pro | Ser |
|---|---|---|---|---|---|---|---|---|---|---|---|---|---|---|---|
| | | | 340 | | | | | 345 | | | | | 350 | | |

| Arg | Asp | Glu | Leu | Thr | Lys | Asn | Gln | Val | Ser | Leu | Thr | Cys | Leu | Val | Lys |
|---|---|---|---|---|---|---|---|---|---|---|---|---|---|---|---|
| | | 355 | | | | | 360 | | | | | 365 | | | |

| Gly | Phe | Tyr | Pro | Ser | Asp | Ile | Ala | Val | Glu | Trp | Glu | Ser | Asn | Gly | Gln |
|---|---|---|---|---|---|---|---|---|---|---|---|---|---|---|---|
| | 370 | | | | | 375 | | | | | 380 | | | | |

```
Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 35
<211> LENGTH: 219
<212> TYPE: PRT
<213> ORGANISM: Artificial sequence
<220> FEATURE:
<223> OTHER INFORMATION: an artificially synthesized sequence

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 36
<211> LENGTH: 453
<212> TYPE: PRT
<213> ORGANISM: Homo sapiens

<400> SEQUENCE: 36

Gln Val Gln Leu Val Leu Ser Gly Ala Glu Val Lys Lys Pro Gly Ala
1               5                   10                  15

Ser Val Met Val Ser Cys Lys Ala Ser Gly Tyr Thr Phe Thr Asp Tyr
            20                  25                  30
```

```
Tyr Met His Trp Val Arg Gln Ala Pro Gly Gln Gly Leu Glu Trp Met
         35                  40                  45
Gly Trp Ile Asn Pro Gln Ser Gly Asp Thr His Tyr Ala Gln Lys Phe
 50                  55                  60
Gln Gly Arg Val Thr Met Thr Arg Asp Thr Ser Val Ser Thr Gly Tyr
 65                  70                  75                  80
Met Gln Leu Ser Ser Leu Gly Ser Asp Asp Thr Ala Ile Tyr Tyr Cys
                 85                  90                  95
Ala Arg Gly Ser Leu Ile Thr Ala Ala Gly Pro Pro Phe Glu His
             100                 105                 110
Trp Gly Gln Gly Thr Met Val Thr Val Ser Ser Ala Ser Thr Lys Gly
             115                 120                 125
Pro Ser Val Phe Pro Leu Ala Pro Ser Ser Lys Ser Thr Ser Gly Gly
130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                 165                 170                 175
Pro Ala Val Leu Gln Ser Ser Gly Leu Tyr Ser Leu Ser Ser Val Val
             180                 185                 190
Thr Val Pro Ser Ser Ser Leu Gly Thr Gln Thr Tyr Ile Cys Asn Val
             195                 200                 205
Asn His Lys Pro Ser Asn Thr Lys Val Asp Lys Val Glu Pro Lys
         210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                 245                 250                 255
Leu Met Ile Ser Arg Thr Pro Glu Val Thr Cys Val Val Val Asp Val
             260                 265                 270
Ser His Glu Asp Pro Glu Val Lys Phe Asn Trp Tyr Val Asp Gly Val
         275                 280                 285
Glu Val His Asn Ala Lys Thr Lys Pro Arg Glu Glu Gln Tyr Asn Ser
         290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                 325                 330                 335
Pro Ile Glu Lys Thr Ile Ser Lys Ala Lys Gly Gln Pro Arg Glu Pro
             340                 345                 350
Gln Val Tyr Thr Leu Pro Pro Ser Arg Asp Glu Leu Thr Lys Asn Gln
         355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                 405                 410                 415
Thr Val Asp Lys Ser Arg Trp Gln Gln Gly Asn Val Phe Ser Cys Ser
             420                 425                 430
Val Met His Glu Ala Leu His Asn His Tyr Thr Gln Lys Ser Leu Ser
             435                 440                 445
Leu Ser Pro Gly Lys
```

```
<210> SEQ ID NO 37
<211> LENGTH: 213
<212> TYPE: PRT
<213> ORGANISM: Homo sapiens

<400> SEQUENCE: 37

Ser Tyr Glu Leu Thr Gln Pro Pro Ser Met Ser Val Ser Pro Gly Gln
1               5                   10                  15

Thr Ala Thr Met Pro Cys Ser Gly Asn Gly Leu Gly Asp Lys Phe Val
            20                  25                  30

Tyr Trp Tyr Gln Gln Lys Pro Gly His Ser Pro Val Ala Val Ile Tyr
        35                  40                  45

Gln Asp Ala Lys Arg Pro Ser Gly Val Pro Glu Arg Phe Ser Gly Ser
    50                  55                  60

Asn Ser Gly Gly Ser Thr Ala Thr Leu Thr Ile Ser Gly Ala Gln Ala
65                  70                  75                  80

Met Asp Glu Ala Asp Tyr Tyr Cys Gln Ala Trp Asp Ser Gly Thr Ala
                85                  90                  95

Val Phe Gly Thr Gly Thr Arg Leu Ser Ile Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 38
<211> LENGTH: 446
<212> TYPE: PRT
<213> ORGANISM: Oryctolagus cuniculus

<400> SEQUENCE: 38

Cys Gln Ser Val Glu Glu Ser Gly Gly Arg Leu Val Thr Pro Gly Thr
1               5                   10                  15

Pro Leu Thr Leu Thr Cys Thr Val Ser Gly Ile Asp Leu Ser Asn Tyr
            20                  25                  30

Ala Met Gly Trp Val Arg Gln Ala Pro Gly Lys Gly Leu Glu Trp Ile
        35                  40                  45

Gly Ile Ile Gly Ala Asp Ser Ser Thr Trp Tyr Pro Ser Trp Val Lys
    50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Arg Phe Val Gly Tyr Thr Asn Ala Phe Asp Pro Trp Gly Pro Gly Thr
```

```
            100                 105                 110
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro
        435                 440                 445

<210> SEQ ID NO 39
<211> LENGTH: 220
<212> TYPE: PRT
<213> ORGANISM: Oryctolagus cuniculus

<400> SEQUENCE: 39

Ala Gln Val Leu Thr Gln Thr Pro Ser Ser Val Ser Ala Ala Val Gly
1               5                   10                  15

Gly Thr Val Thr Ile Ser Cys Gln Ser Ser Gln Ser Val Trp Asn Asn
            20                  25                  30
```

Asn Tyr Leu Ser Trp Tyr Gln Gln Lys Pro Gly Gln Pro Lys Leu
                35                  40                  45

Leu Ile Phe Asp Ala Ser Thr Leu Ala Ser Gly Val Pro Ser Arg Phe
 50                  55                  60

Ser Gly Arg Gly Ser Gly Thr Gln Phe Thr Leu Thr Ile Ser Gly Val
 65                  70                  75                  80

Gln Cys Glu Asp Ala Ala Thr Tyr Tyr Cys His Gly Ser Tyr Ala Asn
                 85                  90                  95

Ser Gly Trp Tyr Asp Asn Ala Phe Gly Gly Thr Glu Val Val Val
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 40
<211> LENGTH: 452
<212> TYPE: PRT
<213> ORGANISM: Oryctolagus cuniculus

<400> SEQUENCE: 40

Cys Gln Ser Val Glu Glu Ser Gly Gly Arg Leu Val Thr Pro Gly Thr
1               5                   10                  15

Pro Leu Thr Leu Thr Cys Thr Val Ser Gly Phe Ser Leu Ser Ser Tyr
                20                  25                  30

Tyr Met Ser Trp Val Arg Gln Ala Pro Gly Glu Gly Leu Glu Tyr Ile
                35                  40                  45

Gly Phe Ile Asn Thr Gly Gly Ser Ser Tyr Tyr Ala Pro Trp Ala Ile
 50                  55                  60

Gly Arg Leu Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Arg Val
                 85                  90                  95

Lys Ser Tyr Val Asn Ser Asn Gly Tyr Phe Ile Phe Ser Arg Leu Asp
                100                 105                 110

Leu Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

```
Val Thr Val Pro Ser Ser Leu Gly Thr Gln Thr Tyr Ile Cys Asn
        195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 41
<211> LENGTH: 218
<212> TYPE: PRT
<213> ORGANISM: Oryctolagus cuniculus

<400> SEQUENCE: 41

Ala Gln Val Leu Thr Gln Thr Ala Ser Val Ser Ala Ala Val Gly
1               5                   10                  15

Gly Thr Val Thr Ile Ser Cys Gln Ser Ser Lys Ser Val Tyr Asn Asn
            20                  25                  30

Asn Phe Leu Ser Trp Tyr Gln Gln Lys Leu Gly Gln Pro Pro Lys Leu
        35                  40                  45

Leu Ile Tyr Tyr Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Gly
                85                  90                  95

Ile Pro Ile Asn Ala Phe Gly Gly Gly Thr Glu Val Val Val Lys Arg
```

```
                100             105             110
Thr Val Ala Ala Pro Ser Val Phe Ile Phe Pro Ser Asp Glu Gln
            115             120             125
Leu Lys Ser Gly Thr Ala Ser Val Val Cys Leu Leu Asn Asn Phe Tyr
        130             135             140
Pro Arg Glu Ala Lys Val Gln Trp Lys Val Asp Asn Ala Leu Gln Ser
145             150             155             160
Gly Asn Ser Gln Glu Ser Val Thr Glu Gln Asp Ser Lys Asp Ser Thr
                165             170             175
Tyr Ser Leu Ser Ser Thr Leu Thr Leu Ser Lys Ala Asp Tyr Glu Lys
            180             185             190
His Lys Val Tyr Ala Cys Glu Val Thr His Gln Gly Leu Ser Ser Pro
        195             200             205
Val Thr Lys Ser Phe Asn Arg Gly Glu Cys
210             215

<210> SEQ ID NO 42
<211> LENGTH: 446
<212> TYPE: PRT
<213> ORGANISM: Oryctolagus cuniculus

<400> SEQUENCE: 42

Cys Gln Ser Val Glu Glu Ser Gly Gly Arg Leu Val Thr Pro Gly Thr
1               5                   10                  15
Pro Leu Thr Leu Thr Cys Thr Val Ser Gly Ile Asp Leu Ser Ser Asn
            20                  25                  30
Ala Met Ser Trp Val Arg Gln Ala Pro Gly Lys Gly Leu Glu Trp Ile
        35                  40                  45
Gly Ala Ile Gly Gly Ser Gly Asp Thr Gly Tyr Ala Ser Trp Ala Asn
    50                  55                  60
Gly Arg Phe Thr Val Ser Lys Thr Ser Thr Thr Val Asp Leu Lys Met
65                  70                  75                  80
Thr Ser Leu Thr Ala Ala Asp Thr Ala Thr Tyr Phe Cys Val Arg His
                85                  90                  95
Ser Val Gly Ala Ser Trp Trp Val Phe Asn Ile Trp Gly Pro Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro
        435                 440                 445

<210> SEQ ID NO 43
<211> LENGTH: 219
<212> TYPE: PRT
<213> ORGANISM: Oryctolagus cuniculus

<400> SEQUENCE: 43

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Gly
            20                  25                  30

Asn Phe Phe Ala Trp Phe Gln Gln Lys Pro Gly Gln Pro Pro Lys Leu
        35                  40                  45

Leu Ile Tyr Asp Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Thr Tyr Tyr Asn
                85                  90                  95

Ser Gly Trp Ser Asn Val Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 44
<211> LENGTH: 443
<212> TYPE: PRT
<213> ORGANISM: Oryctolagus cuniculus

<400> SEQUENCE: 44

Cys Gln Ser Leu Glu Glu Ser Gly Gly Arg Leu Val Met Pro Gly Gly
1               5                   10                  15

Ser Leu Thr Leu Thr Cys Thr Val Ser Gly Phe Ser Leu Ser Asn Tyr
            20                  25                  30

Asn Ile Gln Trp Val Arg Gln Ala Pro Gly Lys Gly Leu Glu Tyr Ile
        35                  40                  45

Gly Phe Ile Asp Ser Gly Gly Ser Ala Tyr Tyr Ala Asn Trp Ala Lys
    50                  55                  60

Gly Arg Phe Thr Ile Ser Arg Thr Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Gly Val Asn Val Asp Tyr Tyr Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
```

```
                340                 345                 350
Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 45
<211> LENGTH: 217
<212> TYPE: PRT
<213> ORGANISM: Oryctolagus cuniculus

<400> SEQUENCE: 45

Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Ser Asn
            20                  25                  30

Asn Tyr Leu Ala Trp Phe Gln Gln Lys Pro Gly Gln Pro Pro Lys Leu
        35                  40                  45

Leu Ile Tyr Arg Ala Ser Asn Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Val Cys Asp Asp Ala Ala Ser Tyr Tyr Cys Gln Gly Tyr Tyr Tyr Gly
                85                  90                  95

Gly Ile Gly Pro Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 46
<211> LENGTH: 122
<212> TYPE: PRT
<213> ORGANISM: Homo sapiens

<400> SEQUENCE: 46

Gln Val Gln Leu Gln Glu Ser Gly Gly Asp Leu Val Lys Pro Gly Gly
```

```
                1               5                   10                  15
            Ser Leu Arg Leu Ser Cys Ala Ala Ser Gly Phe Thr Phe Asn Thr Tyr
                            20                  25                  30

Thr Met Asn Trp Val Arg Gln Ala Pro Gly Lys Gly Leu Glu Trp Leu
                            35                  40                  45

Ser Ser Ile Ser Ser Arg Ser Asn Tyr Ile Asn Tyr Ala Asp Ser Val
                            50                  55                  60

Lys Gly Arg Phe Thr Ile Ser Arg Asp Asn Ala Lys Asn Ser Leu Tyr
             65                 70                  75                  80

Leu Gln Met Asn Ser Leu Arg Ala Glu Asp Thr Ala Val Tyr Tyr Cys
                            85                  90                  95

Ala Arg Phe Gly Arg Lys Gly Asp Leu Asn Trp Val Phe Asp Tyr Trp
                            100                 105                 110

Gly Gln Gly Thr Leu Val Thr Val Ser Ser
                            115                 120
```

<210> SEQ ID NO 47
<211> LENGTH: 110
<212> TYPE: PRT
<213> ORGANISM: Homo sapiens

<400> SEQUENCE: 47

```
                1               5                   10                  15
            Gln Ser Ala Leu Thr Gln Pro Pro Ser Ala Ser Gly Ser Pro Gly Gln

Ser Val Thr Ile Ser Cys Thr Gly Thr Ser Ser Asp Val Gly Gly Tyr
                            20                  25                  30

Asn Tyr Val Ser Trp Tyr Gln Gln His Pro Gly Lys Ala Pro Lys Leu
                            35                  40                  45

Met Ile Tyr Glu Val Ser Lys Arg Pro Ser Gly Val Pro Asp Arg Phe
                            50                  55                  60

Ser Gly Ser Lys Ser Gly Asn Thr Ala Ser Leu Thr Val Ser Gly Leu
             65                 70                  75                  80

Gln Ala Glu Asp Glu Ala Asp Tyr Phe Cys Ser Ser Tyr Ala Gly Ser
                            85                  90                  95

Asn Asn Val Val Phe Gly Gly Gly Thr Lys Leu Thr Val Leu
                            100                 105                 110
```

<210> SEQ ID NO 48
<211> LENGTH: 119
<212> TYPE: PRT
<213> ORGANISM: Artificial sequence
<220> FEATURE:
<223> OTHER INFORMATION: an artificially synthesized sequence

<400> SEQUENCE: 48

```
                1               5                   10                  15
            Gln Val Gln Leu Gln Glu Ser Gly Pro Gly Leu Val Lys Pro Ser Glu

Thr Leu Ser Leu Thr Cys Ala Val Ser Gly Tyr Ser Ile Ser Asp Asp
                            20                  25                  30

His Ala Trp Ser Trp Val Arg Gln Pro Pro Gly Glu Gly Leu Glu Trp
                            35                  40                  45

Ile Gly Tyr Ile Ser Tyr Ser Gly Ile Thr Asn Tyr Asn Pro Ser Leu
                            50                  55                  60

Lys Gly Arg Val Thr Ile Ser Arg Asp Thr Ser Lys Asn Gln Phe Ser
             65                 70                  75                  80

Leu Lys Leu Ser Ser Val Thr Ala Ala Asp Thr Ala Ala Tyr Tyr Cys
                            85                  90                  95
```

```
Ala Arg Val Leu Ala Arg Ile Thr Ala Met Asp Tyr Trp Gly Glu Gly
            100                 105                 110

Thr Leu Val Thr Val Ser Ser
        115

<210> SEQ ID NO 49
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 49

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gly Asn Arg Leu Pro Tyr
                85                  90                  95

Thr Phe Gly Gln Gly Thr Lys Val Glu Ile Glu
            100                 105

<210> SEQ ID NO 50
<211> LENGTH: 449
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Leu Val Ser Asp Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 51
<211> LENGTH: 219
<212> TYPE: PRT
<213> ORGANISM: Homo sapiens

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Lys Ser Ser Leu Ser Leu Leu Asn Arg
            20                  25                  30

Asp Gly Lys Thr Phe Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Gln Ile
65                  70                  75                  80

Asn Arg Val Glu Ala Asp Asp Ala Gly Val Tyr Tyr Cys Met Gln Gly
                85                  90                  95
```

```
Leu His Leu Pro Arg Thr Phe Gly Leu Arg Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215
```

<210> SEQ ID NO 52
<211> LENGTH: 450
<212> TYPE: PRT
<213> ORGANISM: Homo sapiens

<400> SEQUENCE: 52

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Met Gly Gly Asp Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

-continued

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 53
<211> LENGTH: 216
<212> TYPE: PRT
<213> ORGANISM: Homo sapiens

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr His Cys Ala Ala Trp Asp Asp Ser Leu
                85                  90                  95

Asn Gly Pro Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

```
                165                 170                 175
Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 54
<211> LENGTH: 456
<212> TYPE: PRT
<213> ORGANISM: Homo sapiens

<400> SEQUENCE: 54

Glu Val Gln Leu Val Glu Ser Gly Gly Gly Val Val Gln Pro Gly Arg
1               5                   10                  15

Ser Leu Arg Leu Ser Cys Ala Ala Tyr Gly Phe Thr Phe Ser Arg Tyr
            20                  25                  30

Gly Met Gln Trp Val Arg Gln Ala Pro Gly Lys Gly Leu Glu Trp Val
        35                  40                  45

Ala Val Ile Trp Asn Asp Ala Ser Asn Gln Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asp Ser Leu Arg Ser Glu Asp Thr Gly Leu Tyr Tyr Cys
                85                  90                  95

Ala Lys Glu Gly Ser Ser Pro Lys Thr Pro Thr Ser Thr Trp Ser Ser
            100                 105                 110

Leu Glu Ser Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

```
Asp Trp Leu Asn Gly Lys Glu Tyr Lys Cys Lys Val Ser Asn Lys Ala
                325                 330                 335
Leu Pro Ala Pro Ile Glu Lys Thr Ile Ser Lys Ala Lys Gly Gln Pro
            340                 345                 350
Arg Glu Pro Gln Val Tyr Thr Leu Pro Pro Ser Arg Asp Glu Leu Thr
        355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Lys
    450                 455

<210> SEQ ID NO 55
<211> LENGTH: 217
<212> TYPE: PRT
<213> ORGANISM: Homo sapiens

<400> SEQUENCE: 55

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile His Asp Val Ser Asn Arg Pro Ser Gly Val Ser Asn Arg Phe
    50                  55                  60
Ser Gly Ser Lys Ser Gly Thr Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Thr Thr Pro Tyr Val Phe Gly Thr Gly Thr Lys Val Thr Val Leu Gly
            100                 105                 110
Gln Pro Lys Ala Ala Pro Ser Val Thr Leu Phe Pro Pro Ser Ser Glu
        115                 120                 125
Glu Leu Gln Ala Asn Lys Ala Thr Leu Val Cys Leu Ile Ser Asp Phe
    130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
        195                 200                 205
Lys Thr Val Ala Pro Thr Glu Cys Ser
    210                 215

<210> SEQ ID NO 56
```

-continued

```
<211> LENGTH: 30
<212> TYPE: PRT
<213> ORGANISM: Homo sapiens

<400> SEQUENCE: 56

Glu Val Gln Leu Val Glu Ser Gly Gly Gly Leu Val Lys Pro Gly Gly
1               5                   10                  15

Phe Leu Arg Leu Ser Cys Ala Ala Ser Gly Phe Thr Phe Ser
            20                  25                  30

<210> SEQ ID NO 57
<211> LENGTH: 14
<212> TYPE: PRT
<213> ORGANISM: Homo sapiens

<400> SEQUENCE: 57

Trp Val Arg Gln Ala Pro Gly Lys Gly Leu Glu Trp Val Ser
1               5                   10

<210> SEQ ID NO 58
<211> LENGTH: 32
<212> TYPE: PRT
<213> ORGANISM: Homo sapiens

<400> SEQUENCE: 58

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 59
<211> LENGTH: 11
<212> TYPE: PRT
<213> ORGANISM: Homo sapiens

<400> SEQUENCE: 59

Trp Gly Gln Gly Thr Leu Val Thr Val Ser Ser
1               5                   10

<210> SEQ ID NO 60
<211> LENGTH: 22
<212> TYPE: PRT
<213> ORGANISM: Homo sapiens

<400> SEQUENCE: 60

Gln Ser Ala Leu Thr Gln Pro Pro Ser Ala Ser Gly Ser Pro Gly Gln
1               5                   10                  15

Thr Val Thr Ile Ser Cys
            20

<210> SEQ ID NO 61
<211> LENGTH: 16
<212> TYPE: PRT
<213> ORGANISM: Homo sapiens

<400> SEQUENCE: 61

Ser Trp Tyr Gln Gln His Pro Gly Lys Ala Pro Lys Leu Met Ile Tyr
1               5                   10                  15

<210> SEQ ID NO 62
<211> LENGTH: 32
<212> TYPE: PRT
```

```
<400> SEQUENCE: 62

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Phe Cys
                20                  25                  30

<210> SEQ ID NO 63
<211> LENGTH: 10
<212> TYPE: PRT
<213> ORGANISM: Homo sapiens

<400> SEQUENCE: 63

Phe Gly Gly Gly Thr Lys Leu Thr Val Leu
1               5                   10

<210> SEQ ID NO 64
<211> LENGTH: 50
<212> TYPE: DNA
<213> ORGANISM: Artificial sequence
<220> FEATURE:
<223> OTHER INFORMATION: an artificially synthesized sequence
<220> FEATURE:
<221> NAME/KEY: misc_feature
<222> LOCATION: (38)..(38)
<223> OTHER INFORMATION: n is a, c, g, or t

<400> SEQUENCE: 64
tattactcgc ggcccagccg gccatggcag ccwtcganwt gacccagact         50

<210> SEQ ID NO 65
<211> LENGTH: 50
<212> TYPE: DNA
<213> ORGANISM: Artificial sequence
<220> FEATURE:
<223> OTHER INFORMATION: an artificially synthesized sequence
<220> FEATURE:
<221> NAME/KEY: misc_feature
<222> LOCATION: (39)..(39)
<223> OTHER INFORMATION: n is a, c, g, or t

<400> SEQUENCE: 65
tattactcgc ggcccagccg gccatggcag cctatgatnt gacccagact         50

<210> SEQ ID NO 66
<211> LENGTH: 50
<212> TYPE: DNA
<213> ORGANISM: Artificial sequence
<220> FEATURE:
<223> OTHER INFORMATION: an artificially synthesized sequence

<400> SEQUENCE: 66
tattactcgc ggcccagccg gccatggcag cbcaagtgct gacccagact         50

<210> SEQ ID NO 67
<211> LENGTH: 50
<212> TYPE: DNA
<213> ORGANISM: Artificial sequence
<220> FEATURE:
<223> OTHER INFORMATION: an artificially synthesized sequence

<400> SEQUENCE: 67
tattactcgc ggcccagccg gccatggcag ccmtygtgat gacccagact         50

<210> SEQ ID NO 68
<211> LENGTH: 50
<212> TYPE: DNA
```

```
<213> ORGANISM: Artificial sequence
<220> FEATURE:
<223> OTHER INFORMATION: an artificially synthesized sequence

<400> SEQUENCE: 68
tattactcgc ggcccagccg gccatggcag ccgccgtgct gacccagact              50

<210> SEQ ID NO 69
<211> LENGTH: 50
<212> TYPE: DNA
<213> ORGANISM: Artificial sequence
<220> FEATURE:
<223> OTHER INFORMATION: an artificially synthesized sequence

<400> SEQUENCE: 69
tattactcgc ggcccagccg gccatggcgg ctgacattgt gatgacccag              50

<210> SEQ ID NO 70
<211> LENGTH: 50
<212> TYPE: DNA
<213> ORGANISM: Artificial sequence
<220> FEATURE:
<223> OTHER INFORMATION: an artificially synthesized sequence

<400> SEQUENCE: 70
tattactcgc ggcccagccg gccatggccg ccgayrtygt gatgacccag              50

<210> SEQ ID NO 71
<211> LENGTH: 41
<212> TYPE: DNA
<213> ORGANISM: Artificial sequence
<220> FEATURE:
<223> OTHER INFORMATION: an artificially synthesized sequence

<400> SEQUENCE: 71
ctcttctaga acgcgtctaa gcgtcacccc tattgaagct c                       41

<210> SEQ ID NO 72
<211> LENGTH: 55
<212> TYPE: DNA
<213> ORGANISM: Artificial sequence
<220> FEATURE:
<223> OTHER INFORMATION: an artificially synthesized sequence

<400> SEQUENCE: 72
tattactcgc ggcccagccg gccatggcgc agcyygtgct gactcagtcg ccctc        55

<210> SEQ ID NO 73
<211> LENGTH: 44
<212> TYPE: DNA
<213> ORGANISM: Artificial sequence
<220> FEATURE:
<223> OTHER INFORMATION: an artificially synthesized sequence

<400> SEQUENCE: 73
ctcttctaga acgcgtctaa gcttctgcag gggccaggct cttc                    44

<210> SEQ ID NO 74
<211> LENGTH: 40
<212> TYPE: DNA
<213> ORGANISM: Artificial sequence
<220> FEATURE:
<223> OTHER INFORMATION: an artificially synthesized sequence

<400> SEQUENCE: 74
ttccgcctcg gcgctagccc aggagcagst ggwggagtcc                         40
```

<210> SEQ ID NO 75
<211> LENGTH: 40
<212> TYPE: DNA
<213> ORGANISM: Artificial sequence
<220> FEATURE:
<223> OTHER INFORMATION: an artificially synthesized sequence
<220> FEATURE:
<221> NAME/KEY: misc_feature
<222> LOCATION: (25)..(26)
<223> OTHER INFORMATION: n is a, c, g, or t

<400> SEQUENCE: 75
ttccgcctcg gcgctagccc agtcnntgga ggagtccggg         40

<210> SEQ ID NO 76
<211> LENGTH: 40
<212> TYPE: DNA
<213> ORGANISM: Artificial sequence
<220> FEATURE:
<223> OTHER INFORMATION: an artificially synthesized sequence
<220> FEATURE:
<221> NAME/KEY: misc_feature
<222> LOCATION: (26)..(27)
<223> OTHER INFORMATION: n is a, c, g, or t

<400> SEQUENCE: 76
ttccgcctcg gcgctagccc agtcgnngga ggagtccggg         40

<210> SEQ ID NO 77
<211> LENGTH: 40
<212> TYPE: DNA
<213> ORGANISM: Artificial sequence
<220> FEATURE:
<223> OTHER INFORMATION: an artificially synthesized sequence

<400> SEQUENCE: 77
ttccgcctcg gcgctagccc agcagcagct ggwggagtcc         40

<210> SEQ ID NO 78
<211> LENGTH: 122
<212> TYPE: PRT
<213> ORGANISM: Homo sapiens

<400> SEQUENCE: 78

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met His Trp Val Arg Gln Ala Pro Gly Lys Gly Leu Glu Trp Val
        35                  40                  45

Ser Ser Ile Ser Ser Arg Ser Thr His Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Arg Trp Ala Met Asn Trp Val Phe Asp Tyr Trp
            100                 105                 110

Gly Gln Gly Thr Leu Val Thr Val Ser Ser
        115                 120

<210> SEQ ID NO 79

```
<211> LENGTH: 110
<212> TYPE: PRT
<213> ORGANISM: Homo sapiens

<400> SEQUENCE: 79

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gly Gly Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Leu Lys Ser Tyr Ala
                85                  90                  95

Glu Gly Pro Met Phe Gly Gly Gly Thr Lys Leu Thr Val Leu
            100                 105                 110

<210> SEQ ID NO 80
<211> LENGTH: 122
<212> TYPE: PRT
<213> ORGANISM: Homo sapiens

<400> SEQUENCE: 80

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn His Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly His Arg Arg Asp Leu Asn Trp Val Phe Asp Tyr Trp
            100                 105                 110

Gly Gln Gly Thr Leu Val Thr Val Ser Ser
        115                 120

<210> SEQ ID NO 81
<211> LENGTH: 110
<212> TYPE: PRT
<213> ORGANISM: Homo sapiens

<400> SEQUENCE: 81

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Gly Gly Ser Lys Arg Pro Ser Gly Val Pro Asp Arg Phe
    50                  55                  60
```

```
Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Val Thr Tyr Ser Ile
                 85                  90                  95

Ala Asp Pro Leu Phe Gly Gly Gly Thr Lys Leu Thr Val Leu
            100                 105                 110

<210> SEQ ID NO 82
<211> LENGTH: 122
<212> TYPE: PRT
<213> ORGANISM: Homo sapiens

<400> SEQUENCE: 82

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Ala Leu Gly Gln Met Asn Trp Val Phe Asp Tyr Trp
            100                 105                 110

Gly Gln Gly Thr Leu Val Thr Val Ser Ser
            115                 120

<210> SEQ ID NO 83
<211> LENGTH: 110
<212> TYPE: PRT
<213> ORGANISM: Homo sapiens

<400> SEQUENCE: 83

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Ser Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Ser Arg Ser Ser Ser
                 85                  90                  95

Met Asn Val Leu Phe Gly Gly Gly Thr Lys Leu Thr Val Leu
            100                 105                 110

<210> SEQ ID NO 84
<211> LENGTH: 122
<212> TYPE: PRT
<213> ORGANISM: Homo sapiens

<400> SEQUENCE: 84

Glu Val Gln Leu Val Glu Ser Gly Gly Asp Leu Val Lys Pro Gly Gly
```

```
                1               5                  10                 15
            Gly Leu Arg Leu Ser Cys Ala Ala Ser Gly Phe Thr Phe Ser Gly Tyr
                            20                 25                 30

Thr Met Asn Trp Val Arg Gln Ala Pro Gly Lys Gly Leu Glu Trp Val
                            35                 40                 45

Ser Ser Ile Ser Ser Arg Ser Ser Tyr Ile Asp Tyr Ala Asp Ser Val
                            50                 55                 60

Lys Gly Arg Phe Thr Ile Ser Arg Asp Asn Ala Lys Asn Ser Leu Tyr
             65                 70                 75                 80

Leu Gln Met Asn Ser Leu Arg Ala Glu Asp Thr Ala Val Tyr Tyr Cys
                            85                 90                 95

Ala Arg Tyr Gly Ala Leu Gly Gln Arg Asn Trp Val Phe Asp Tyr Trp
                            100                105                110

Gly Gln Gly Thr Leu Val Thr Val Ser Ser
                            115                120
```

<210> SEQ ID NO 85
<211> LENGTH: 109
<212> TYPE: PRT
<213> ORGANISM: Homo sapiens

<400> SEQUENCE: 85

```
            Gln Ser Ala Leu Thr Gln Pro Pro Ser Ala Ser Gly Ser Pro Gly Gln
             1               5                  10                 15

Thr Val Thr Ile Ser Cys Thr Gly Thr Ser Thr Asp Val Gly Asp Tyr
                            20                 25                 30

Asn Tyr Val Ser Trp Tyr Gln Gln His Pro Gly Lys Ala Pro Lys Leu
                            35                 40                 45

Met Ile Tyr Gln Thr Ser Lys Arg Pro Ser Gly Val Pro Asp Arg Phe
                            50                 55                 60

Ser Gly Ser Lys Ser Gly Asn Thr Ala Ser Leu Thr Val Ser Gly Leu
             65                 70                 75                 80

Gln Ala Glu Asp Glu Ala Asp Tyr Phe Cys Ser Ser Arg Ser Ile Lys
                            85                 90                 95

His Pro Val Phe Gly Gly Gly Thr Lys Leu Thr Val Leu
                            100                105
```

<210> SEQ ID NO 86
<211> LENGTH: 123
<212> TYPE: PRT
<213> ORGANISM: Homo sapiens

<400> SEQUENCE: 86

```
            Gln Val Gln Leu Val Gln Ser Gly Ala Glu Val Lys Lys Pro Gly Ser
             1               5                  10                 15

Ser Val Lys Val Ser Cys Lys Ala Ser Gly Gly Thr Phe Ser Ser Tyr
                            20                 25                 30

Ala Ile Ser Trp Val Arg Gln Ala Pro Gly Gln Gly Leu Glu Trp Met
                            35                 40                 45

Gly Gly Ile Ile Pro Ile Phe Gly Thr Ala Asn Tyr Ala Gln Lys Phe
                            50                 55                 60

Gln Gly Arg Val Thr Ile Thr Ala Asp Glu Ser Thr Ser Thr Ala Tyr
             65                 70                 75                 80

Met Glu Leu Ser Ser Leu Arg Ser Glu Asp Thr Ala Val Tyr Tyr Cys
                            85                 90                 95

Ala Arg Asp Ala Pro Val Val Ala Arg Pro Arg Gly Ala Phe Asp Ile
```

```
                       100                 105                 110

Trp Gly Gln Gly Thr Met Val Thr Val Ser Ser
            115                 120

<210> SEQ ID NO 87
<211> LENGTH: 112
<212> TYPE: PRT
<213> ORGANISM: Homo sapiens

<400> SEQUENCE: 87

Asp Ile Val Met Thr Gln Thr Pro Leu Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile His Glu Ile Ser Asn Arg Phe Ser Gly Val Pro
    50                  55                  60

Asp Arg Phe Ser Gly Ser Gly Ala Gly Thr Asn Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Arg Thr Phe Gly Gln Gly Thr Lys Val Glu Ile Lys
            100                 105                 110

<210> SEQ ID NO 88
<211> LENGTH: 122
<212> TYPE: PRT
<213> ORGANISM: Homo sapiens

<400> SEQUENCE: 88

Glu Val Gln Leu Val Gln Ser Gly Gly Asp Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Val Pro Ser Ser Gly Tyr Pro Gly Arg Phe Asp Pro Trp
            100                 105                 110

Gly Gln Gly Thr Leu Val Thr Val Ser Ser
        115                 120

<210> SEQ ID NO 89
<211> LENGTH: 106
<212> TYPE: PRT
<213> ORGANISM: Homo sapiens

<400> SEQUENCE: 89

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ser
            20                  25                  30
```

Leu Asn Trp Tyr Gln Gln Ile Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Ser Ala Trp Thr
                85                  90                  95

Phe Gly Gln Gly Thr Lys Val Glu Ile Lys
            100                 105

<210> SEQ ID NO 90
<211> LENGTH: 328
<212> TYPE: PRT
<213> ORGANISM: Homo sapiens

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

```
                290                 295                 300
Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 91
<211> LENGTH: 107
<212> TYPE: PRT
<213> ORGANISM: Homo sapiens

<400> SEQUENCE: 91

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 92
<211> LENGTH: 119
<212> TYPE: PRT
<213> ORGANISM: Homo sapiens

<400> SEQUENCE: 92

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 93
<211> LENGTH: 107
<212> TYPE: PRT
<213> ORGANISM: Homo sapiens

<400> SEQUENCE: 93

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 94
<211> LENGTH: 328
<212> TYPE: PRT
<213> ORGANISM: Artificial sequence
<220> FEATURE:
<223> OTHER INFORMATION: an artificially synthesized sequence

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 95
<211> LENGTH: 122
<212> TYPE: PRT
<213> ORGANISM: Homo sapiens

<400> SEQUENCE: 95

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
            20                  25                  30

Thr Met His Trp Val Arg Gln Ala Pro Gly Lys Gly Leu Glu Trp Val
        35                  40                  45

Ser Ser Ile Ser Ser Arg Ser Ser His Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Arg Lys Tyr Arg Met Asn Trp Val Phe Asp Tyr Trp
            100                 105                 110

Gly Gln Gly Thr Leu Val Thr Val Ser Ser
        115                 120

<210> SEQ ID NO 96
<211> LENGTH: 110
<212> TYPE: PRT
<213> ORGANISM: Homo sapiens

<400> SEQUENCE: 96

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Asp Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Val Thr Gly Ile
                85                  90                  95

Trp Ser Val Gly Phe Gly Gly Gly Thr Lys Leu Thr Val Leu
            100                 105                 110

<210> SEQ ID NO 97
<211> LENGTH: 122
<212> TYPE: PRT
<213> ORGANISM: Homo sapiens
```

<400> SEQUENCE: 97

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn His Ala Thr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Lys Lys Gly Arg Tyr Leu Trp Val Phe Asp Tyr Trp
            100                 105                 110

Gly Gln Gly Thr Leu Val Thr Val Ser Ser
            115                 120

<210> SEQ ID NO 98
<211> LENGTH: 110
<212> TYPE: PRT
<213> ORGANISM: Homo sapiens

<400> SEQUENCE: 98

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Tyr Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Leu Thr Thr Asp Ser
                85                  90                  95

Leu Asn Pro Val Phe Gly Gly Thr Lys Leu Thr Val Leu
            100                 105                 110

<210> SEQ ID NO 99
<211> LENGTH: 233
<212> TYPE: PRT
<213> ORGANISM: Homo sapiens

<400> SEQUENCE: 99

Cys His Pro Arg Leu Ser Leu His Arg Pro Ala Leu Glu Asp Leu Leu
1               5                   10                  15

Leu Gly Ser Glu Ala Asn Leu Thr Cys Thr Leu Thr Gly Leu Arg Asp
            20                  25                  30

Ala Ser Gly Val Thr Phe Thr Trp Thr Pro Ser Ser Gly Lys Ser Ala
        35                  40                  45

Val Gln Gly Pro Pro Glu Arg Asp Leu Cys Gly Cys Tyr Ser Val Ser
50                  55                  60

Ser Val Leu Pro Gly Cys Ala Glu Pro Trp Asn His Gly Lys Thr Phe
65                  70                  75                  80

```
Thr Cys Thr Ala Ala Tyr Pro Glu Ser Lys Thr Pro Leu Thr Ala Thr
                85                  90                  95

Leu Ser Lys Ser Gly Asn Thr Phe Arg Pro Glu Val His Leu Leu Pro
            100                 105                 110

Pro Pro Ser Glu Glu Leu Ala Leu Asn Glu Leu Val Thr Leu Thr Cys
            115                 120                 125

Leu Ala Arg Gly Phe Ser Pro Lys Asp Val Leu Val Arg Trp Leu Gln
        130                 135                 140

Gly Ser Gln Glu Leu Pro Arg Glu Lys Tyr Leu Thr Trp Ala Ser Arg
145                 150                 155                 160

Gln Glu Pro Ser Gln Gly Thr Thr Thr Phe Ala Val Thr Ser Ile Leu
                165                 170                 175

Arg Val Ala Ala Glu Asp Trp Lys Lys Gly Asp Thr Phe Ser Cys Met
            180                 185                 190

Val Gly His Glu Ala Leu Pro Leu Ala Phe Thr Gln Lys Thr Ile Asp
            195                 200                 205

Arg Leu Ala Gly Lys Gly Gly Gly Ser Gly Leu Asn Asp Ile Phe
        210                 215                 220

Glu Ala Gln Lys Ile Glu Trp His Glu
225                 230

<210> SEQ ID NO 100
<211> LENGTH: 122
<212> TYPE: PRT
<213> ORGANISM: Homo sapiens

<400> SEQUENCE: 100

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn His Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Lys Phe Met Met Asn Trp Val Phe Asp Tyr Trp
            100                 105                 110

Gly Gln Gly Thr Leu Val Thr Val Ser Ser
        115                 120

<210> SEQ ID NO 101
<211> LENGTH: 110
<212> TYPE: PRT
<213> ORGANISM: Homo sapiens

<400> SEQUENCE: 101

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45
```

```
Met Ile Tyr Gln Asn Ser Lys Arg Pro Ser Gly Val Pro Asp Arg Phe
 50                  55                  60
Ser Gly Ser Lys Ser Gly Asn Thr Ala Ser Leu Thr Val Ser Gly Leu
 65                  70                  75                  80
Gln Ala Glu Asp Glu Ala Asp Tyr Phe Cys Ser Leu Arg Ser Ser Asn
                 85                  90                  95
Leu Ser Pro Gly Phe Gly Gly Gly Thr Lys Leu Thr Val Leu
            100                 105                 110

<210> SEQ ID NO 102
<211> LENGTH: 25
<212> TYPE: DNA
<213> ORGANISM: Artificial sequence
<220> FEATURE:
<223> OTHER INFORMATION: an artificially synthesized sequence

<400> SEQUENCE: 102
actcgcggcc cagccggcca tggcg                                   25

<210> SEQ ID NO 103
<211> LENGTH: 27
<212> TYPE: DNA
<213> ORGANISM: Artificial sequence
<220> FEATURE:
<223> OTHER INFORMATION: an artificially synthesized sequence

<400> SEQUENCE: 103
taggacggtc agcttggtac ctccgcc                                 27

<210> SEQ ID NO 104
<211> LENGTH: 18
<212> TYPE: DNA
<213> ORGANISM: Artificial sequence
<220> FEATURE:
<223> OTHER INFORMATION: an artificially synthesized sequence

<400> SEQUENCE: 104
gcgcagccgg cgctagcc                                           18

<210> SEQ ID NO 105
<211> LENGTH: 18
<212> TYPE: DNA
<213> ORGANISM: Artificial sequence
<220> FEATURE:
<223> OTHER INFORMATION: an artificially synthesized sequence

<400> SEQUENCE: 105
tgggcccttg gtcgacgc                                           18

<210> SEQ ID NO 106
<211> LENGTH: 122
<212> TYPE: PRT
<213> ORGANISM: Homo sapiens

<400> SEQUENCE: 106

Glu Val Gln Leu Val Glu Ser Gly Gly Asp Leu Val Lys Pro Gly Gly
  1               5                  10                  15
Gly Leu Arg Leu Ser Cys Ala Ala Ser Gly Phe Thr Phe Ser Thr Tyr
                 20                  25                  30
Thr Met His Trp Val Arg Gln Ala Pro Gly Lys Gly Leu Glu Trp Val
             35                  40                  45
Ser Ser Ile Ser Ser Arg Ser Gly His Arg His Tyr Ala Asp Ser Val
 50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Lys Lys Gly Asn Arg Asn Trp Val Phe Asp Tyr Trp
            100                 105                 110

Gly Gln Gly Thr Leu Val Thr Val Ser Ser
        115                 120
```

<210> SEQ ID NO 107
<211> LENGTH: 110
<212> TYPE: PRT
<213> ORGANISM: Homo sapiens

<400> SEQUENCE: 107

```
Gln Ser Ala Leu Thr Gln Pro Pro Ser Ala Ser Gly Ser Pro Gly Gln
  1               5                  10                  15

Thr Val Thr Ile Ser Cys Thr Gly Thr Ser Thr Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Ser Thr Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Thr Thr Thr Tyr Ala
                 85                  90                  95

Lys Asn Pro Val Phe Gly Gly Gly Thr Lys Leu Thr Val Leu
            100                 105                 110
```

<210> SEQ ID NO 108
<211> LENGTH: 122
<212> TYPE: PRT
<213> ORGANISM: Homo sapiens

<400> SEQUENCE: 108

```
Glu Val Gln Leu Val Glu Ser Gly Gly Asp Leu Val Lys Pro Gly Gly
  1               5                  10                  15

Gly Leu Arg Leu Ser Cys Ala Ala Ser Gly Phe Thr Phe Ser Gly Tyr
                 20                  25                  30

Thr Met His Trp Val Arg Gln Ala Pro Gly Lys Gly Leu Glu Trp Val
             35                  40                  45

Ser Ser Ile Ser Ser Arg Ser Asn His Arg Ser Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Phe Gly Lys Arg Phe Asp Arg Asn Trp Val Phe Asp Tyr Trp
            100                 105                 110

Gly Gln Gly Thr Leu Val Thr Val Ser Ser
        115                 120
```

<210> SEQ ID NO 109
<211> LENGTH: 110
<212> TYPE: PRT
<213> ORGANISM: Homo sapiens

<400> SEQUENCE: 109

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Thr Tyr
            20                  25                  30

Asn Tyr Val Ser Trp Tyr Gln Gln His Pro Gly Lys Ala Pro Lys Leu
        35                  40                  45

Met Ile Tyr Lys Thr Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Arg Arg Tyr Arg
                85                  90                  95

Arg Ser Leu Ser Phe Gly Gly Gly Thr Lys Leu Thr Val Leu
            100                 105                 110

<210> SEQ ID NO 110
<211> LENGTH: 20
<212> TYPE: DNA
<213> ORGANISM: Artificial sequence
<220> FEATURE:
<223> OTHER INFORMATION: an artificially synthesized sequence

<400> SEQUENCE: 110
cgcaacgcaa ttaatgtgag                                           20

<210> SEQ ID NO 111
<211> LENGTH: 18
<212> TYPE: DNA
<213> ORGANISM: Artificial sequence
<220> FEATURE:
<223> OTHER INFORMATION: an artificially synthesized sequence

<400> SEQUENCE: 111
gcgtcacact ttgctatg                                             18

<210> SEQ ID NO 112
<211> LENGTH: 21
<212> TYPE: DNA
<213> ORGANISM: Artificial sequence
<220> FEATURE:
<223> OTHER INFORMATION: an artificially synthesized sequence

<400> SEQUENCE: 112
tgagttccac gacaccgtca c                                         21

<210> SEQ ID NO 113
<211> LENGTH: 122
<212> TYPE: PRT
<213> ORGANISM: Homo sapiens

<400> SEQUENCE: 113

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Tyr Tyr Ala Asp Ser Val
50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Tyr Gly Arg Leu His Asp Arg Asn Trp Val Phe Asp Tyr Trp
        100                 105                 110

Gly Gln Gly Thr Leu Val Thr Val Ser Ser
        115                 120
```

<210> SEQ ID NO 114
<211> LENGTH: 110
<212> TYPE: PRT
<213> ORGANISM: Homo sapiens

<400> SEQUENCE: 114

```
Gln Ser Ala Leu Thr Gln Pro Pro Ser Ala Ser Gly Ser Pro Gly Gln
 1               5                  10                  15

Thr Val Thr Ile Ser Cys Thr Gly Thr Ser Thr Asp Val Gly Asp Tyr
             20                  25                  30

Asn Tyr Val Ser Trp Tyr Gln Gln His Pro Gly Lys Ala Pro Lys Leu
         35                  40                  45

Met Ile Tyr Gln Val Ser Lys Lys Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Phe Cys Ser Ser Arg Ser Tyr Gly
             85                  90                  95

Ala Gly Val Val Phe Gly Gly Gly Thr Lys Leu Thr Val Leu
        100                 105                 110
```

<210> SEQ ID NO 115
<211> LENGTH: 122
<212> TYPE: PRT
<213> ORGANISM: Homo sapiens

<400> SEQUENCE: 115

```
Glu Val Gln Leu Val Glu Ser Gly Gly Asp Leu Val Lys Pro Gly Gly
 1               5                  10                  15

Gly Leu Arg Leu Ser Cys Ala Ala Ser Gly Phe Thr Phe Ser Thr His
             20                  25                  30

Thr Met Asn Trp Val Arg Gln Ala Pro Gly Lys Gly Leu Glu Trp Val
         35                  40                  45

Ser Ser Ile Ser Ser Arg Ser Ser Tyr Ile His Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Phe Gly Lys Leu Gly Glu Arg Asn Trp Val Phe Asp Tyr Trp
        100                 105                 110

Gly Gln Gly Thr Leu Val Thr Val Ser Ser
        115                 120
```

<210> SEQ ID NO 116
<211> LENGTH: 110
<212> TYPE: PRT
<213> ORGANISM: Homo sapiens

<400> SEQUENCE: 116

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Val Arg Ser Asp Gly
                85                  90                  95

His Gly Pro Met Phe Gly Gly Gly Thr Lys Leu Thr Val Leu
            100                 105                 110

<210> SEQ ID NO 117
<211> LENGTH: 122
<212> TYPE: PRT
<213> ORGANISM: Homo sapiens

<400> SEQUENCE: 117

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ala His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Leu Gly Asp Arg Asn Trp Val Phe Asp Tyr Trp
            100                 105                 110

Gly Gln Gly Thr Leu Val Thr Val Ser Ser
        115                 120

<210> SEQ ID NO 118
<211> LENGTH: 110
<212> TYPE: PRT
<213> ORGANISM: Homo sapiens

<400> SEQUENCE: 118

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Lys Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

```
Gln Ala Glu Asp Glu Ala Asp Tyr Phe Cys Ser Leu Arg Ala Ala Thr
                85                  90                  95

Thr Gly Val Leu Phe Gly Gly Gly Thr Lys Leu Thr Val Leu
        100                 105                 110
```

<210> SEQ ID NO 119
<211> LENGTH: 122
<212> TYPE: PRT
<213> ORGANISM: Homo sapiens

<400> SEQUENCE: 119

```
Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Gly Tyr Ala Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ala Leu Asn Thr Leu Asn Trp Val Phe Asp Tyr Trp
            100                 105                 110

Gly Gln Gly Thr Leu Val Thr Val Ser Ser
            115                 120
```

<210> SEQ ID NO 120
<211> LENGTH: 110
<212> TYPE: PRT
<213> ORGANISM: Homo sapiens

<400> SEQUENCE: 120

```
Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Arg Thr Ala Asn
                85                  90                  95

Ala Gly Val Leu Phe Gly Gly Gly Thr Lys Leu Thr Val Leu
            100                 105                 110
```

<210> SEQ ID NO 121
<211> LENGTH: 122
<212> TYPE: PRT
<213> ORGANISM: Homo sapiens

<400> SEQUENCE: 121

```
Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
```

```
                    20                  25                  30

Thr Met Asn Trp Val Arg Gln Ala Pro Gly Lys Gly Leu Glu Trp Val
            35                  40                  45

Ser Ser Ile Ser Ser Arg Ser Ser Tyr Ala Ser Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Leu Asn Ser His Asn Trp Val Phe Asp Tyr Trp
            100                 105                 110

Gly Gln Gly Thr Leu Val Thr Val Ser Ser
            115                 120

<210> SEQ ID NO 122
<211> LENGTH: 110
<212> TYPE: PRT
<213> ORGANISM: Homo sapiens

<400> SEQUENCE: 122

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Gln Gly Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Arg Ala Thr Thr
                85                  90                  95

Lys Gly Val Leu Phe Gly Gly Gly Thr Lys Leu Thr Val Leu
            100                 105                 110

<210> SEQ ID NO 123
<211> LENGTH: 122
<212> TYPE: PRT
<213> ORGANISM: Homo sapiens

<400> SEQUENCE: 123

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Leu His Asp Arg Asn Trp Val Phe Asp Tyr Trp
            100                 105                 110

Gly Gln Gly Thr Leu Val Thr Val Ser Ser
```

115                 120

<210> SEQ ID NO 124
<211> LENGTH: 110
<212> TYPE: PRT
<213> ORGANISM: Homo sapiens

<400> SEQUENCE: 124

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Gln Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Arg Ser Tyr Gly
                85                  90                  95

Ala Gly Val Val Phe Gly Gly Gly Thr Lys Leu Thr Val Leu
            100                 105                 110

<210> SEQ ID NO 125
<211> LENGTH: 122
<212> TYPE: PRT
<213> ORGANISM: Homo sapiens

<400> SEQUENCE: 125

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser His
            20                  25                  30

Thr Met Asn Trp Val Arg Gln Ala Pro Gly Lys Gly Leu Glu Trp Val
        35                  40                  45

Ser Ser Ile Ser Ser Arg Ser Gly Tyr Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Lys Leu Asn His Met Asn Trp Val Phe Asp Tyr Trp
            100                 105                 110

Gly Gln Gly Thr Leu Val Thr Val Ser Ser
        115                 120

<210> SEQ ID NO 126
<211> LENGTH: 110
<212> TYPE: PRT
<213> ORGANISM: Homo sapiens

<400> SEQUENCE: 126

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Thr Tyr
            20                  25                  30

Asn Tyr Val Ser Trp Tyr Gln Gln His Pro Gly Lys Ala Pro Lys Leu
        35                  40                  45

```
Met Ile Tyr Gln Val Ser Lys Arg Pro Ser Gly Val Pro Asp Arg Phe
    50              55              60

Ser Gly Ser Lys Ser Gly Asn Thr Ala Ser Leu Thr Val Ser Gly Leu
65              70                  75                      80

Gln Ala Glu Asp Glu Ala Asp Tyr Phe Cys Ser Thr Arg Ala Ile Thr
            85                  90                      95

Arg Gly Val Ala Phe Gly Gly Gly Thr Lys Leu Thr Val Leu
            100             105             110
```

TARGET TISSUE-SPECIFIC ANTIGEN-BINDING MOLECULE

CROSS-REFERENCE TO RELATED APPLICATIONS

This application is a divisional of U.S. application Ser. No. 14/402,574, filed on Nov. 20, 2014, which is the National Stage of International Application No. PCT/JP2013/064975, filed on May 30, 2013, which claims the benefit of Japanese Application Serial Nos. 2012-123781, filed on May 30, 2012, and 2012-177311, filed on Aug. 9, 2012.

SEQUENCE LISTING

This application contains a Sequence Listing that has been submitted electronically as an ASCII text file named SequenceListing.txt. The ASCII text file, created on Aug. 13, 2019, is 180 kilobytes in size. The material in the ASCII text file is hereby incorporated by reference in its entirety.

TECHNICAL FIELD

The present invention provides antigen-binding molecules comprising an antigen-binding domain whose antigen-binding activity varies depending on the concentration of a target tissue-specific compound; production methods and screening methods for the antigen-binding molecules; and pharmaceutical compositions containing the antigen-binding molecules.

BACKGROUND ART

Antibodies are drawing attention as pharmaceuticals as they are highly stable in plasma and have few side effects. In particular, a number of IgG-type antibody pharmaceuticals are available on the market, and many antibody pharmaceuticals are currently under development (Non-Patent Documents 1 and 2).

As cancer therapeutic agents using antibody pharmaceuticals, Rituxan against a CD20 antigen, cetuximab against an EGFR antigen, herceptin against a HER2 antigen, and such have been approved so far (Non-Patent Document 3). These antibody molecules bind to antigens expressed on cancer cells, and exhibit cytotoxic activity against cancer cells by ADCC and such. Such cytotoxic activity by ADCC and etc. are known to depend on the number of antigens expressed on cells targeted by the therapeutic antibodies (Non-Patent Document 4); therefore, high expression level of the target antigen is preferable from the stand point of the effects of the therapeutic antibodies. However, even if the antigen expression level is high, when antigens are expressed in normal tissues, cytotoxic activity mediated by ADCC etc will be exerted against normal cells, and therefore side-effects will become a major problem. Therefore, antigens targeted by therapeutic antibodies used as therapeutic agents for cancer are preferably antigens specifically expressed in cancer cells. For example, antibody molecules against the EpCAM antigen which is known as a cancer antigen have been considered to be promising as therapeutic agents for cancer. However, the EpCAM antigen is known to be expressed in the pancreas as well, and in practice, administration of anti-EpCAM antibodies in clinical trials has been reported to cause pancreatitis as a side-effect due to cytotoxic activity towards the pancreas (Non-Patent Document 5).

Following the success of antibody pharmaceuticals that exert cytotoxic activity by ADCC activity, a second generation of improved antibody molecules that exert strong cytotoxic activity through enhancement of ADCC activity by removing fucose of N-type sugar chains in the native human IgG1 Fc region (Non-Patent Document 6), enhancement of ADCC activity by enhancing the binding toward FcγRIIIa by substitution of amino acids in the native human IgG1 Fc region (Non-Patent Document 7), and such have been reported. As antibody pharmaceuticals that exert cytotoxic activity against cancer cells through a mechanism other than the above-mentioned ADCC activity mediated by NK cells, improved antibody molecules that exert a stronger cytotoxic activity, such as an antibody-drug conjugate (ADC) in which an antibody is conjugated with a drug having potent cytotoxic activity (Non-Patent Document 8), and a low molecular weight antibody that exerts toxic activity against cancer cells by recruiting T cells to cancer cells, have been reported as well.

Such antibody molecules exerting a stronger cytotoxic activity can exert cytotoxic activity against cancer cells that do not have much antigen expression, but on the other hand, they will exert similar cytotoxic activity against normal tissues with low antigen expression. In fact, in comparison to cetuximab which is a natural human IgG1 against an EGFR antigen, EGFR-BiTE, which is a bispecific antibody against CD3 and EGFR, can exert a potent cytotoxic activity against cancer cells by recruiting T cells to cancer cells and exert antitumor effects. On the other hand, since EGFR is expressed also in normal tissues, when EGFR-BiTE is administered to cynomolgus monkeys, serious side effects have appeared (Non-Patent Document 10). Furthermore, bivatuzumab mertansine, an ADC formed by linking mertansine to an antibody against CD44v6 which is highly expressed in cancer cells, has been shown to cause severe skin toxicity and liver toxicity in clinical practice because CD44v6 is expressed also in normal tissues (Non-Patent Document 11).

When antibodies that can exert a potent cytotoxic activity against cancer cells having low antigen expression are used as such, the target antigen needs to be expressed in a highly cancer-specific manner. However, since HER2 and EGFR, which are target antigens of herceptin and cetuximab, respectively, are also expressed in normal tissues, the number of cancer antigens expressed in a highly cancer-specific manner is thought to be limited. Therefore, while it is possible to strengthen the cytotoxic activity against cancer, the side effects occurring due to cytotoxic actions against normal tissues may become problematic.

Furthermore, recently, ipilimumab which enhances tumor immunity by inhibiting CTLA4 which contributes to immunosuppression in cancer was shown to prolong overall survival of metastatic melanoma (Non-Patent Document 12). However, since ipulimumab inhibits CTLA4 systemically, while tumor immunity is enhanced, the emergence of autoimmune disease-like severe side effects due to systemic activation of the immune system is becoming a problem (Non-Patent Document 13).

On the other hand, as antibody pharmaceuticals against diseases besides cancer, antibody pharmaceuticals that exert therapeutic effects by inhibiting inflammatory cytokines in inflammatory/autoimmune diseases are known (Non-Patent Document 14). For example, Remicade and Humira which target TNF, and Actemra which targets IL-6R exhibit high therapeutic effects against rheumatoid arthritis, but on the other hand, systemic neutralization of these cytokines has led to the observation of infection as side effects (Non-Patent Document 15).

Various techniques have been developed as techniques that can be applied to second-generation antibody pharmaceuticals. While techniques for improving effector functions, antigen-binding ability, pharmacokinetics, and stability, or techniques for reducing immunogenic risks have been reported (Non-Patent Document 16), there are hardly any reports on techniques that enable target tissue-specific action of antibody pharmaceuticals to overcome such side effects. For example, regarding lesions such as cancer tissues and inflammatory tissues, pH-dependent antibodies that make use of the acidic pH condition at these target tissues have been reported (Patent Documents 1 and 2). However, the decrease of pH (that is, increase in hydrogen ion concentration) in cancer tissues and inflammatory tissues as compared to normal tissues is slight, and since it is difficult to produce antibodies that act by detecting a slight increase in the concentration of hydrogen ions which have an extremely small molecular weight, and also because acidic pH conditions may be found in normal tissues such as osteoclastic bone resorption region or in tissues other than the lesion of interest, use of pH conditions as a lesion-specific environmental factor was considered to face many challenges. On the other hand, methods for producing antibodies that exert antigen-binding activity only after they are cleaved by a protease expressed at lesion sites such as cancer tissues and inflammatory tissues have been reported (Patent Document 3). However, since cleavage of antibodies by proteases is irreversible, when the antibodies that have been cleaved at the lesion site enter the blood stream and return to normal tissues, they can bind to the antigens in normal tissues as well, and this is considered to be a problem. Furthermore, cancer specificity of such proteases is also thought to have problems that need to be addressed. Therefore, techniques that enable reversible action at sites of inflammation or cancer (lesion sites) without systemic action in normal tissues and blood for exerting drug efficacy while avoiding side effects are not known.

PRIOR ART DOCUMENTS

Patent Documents

[Patent document 1] WO 2003/105757
[Patent document 2] WO 2012/033953
[Patent document 3] WO 2010/081173

Non-Patent Documents

[Non-patent document 1] Monoclonal antibody successes in the clinic. Janice M Reichert, Clark J Rosensweig, Laura B Faden & Matthew C Dewitz, Nat. Biotechnol. (2005) 23, 1073-1078
[Non-patent document 2] The therapeutic antibodies market to 2008. Pavlou A K, Belsey M J., Eur. J. Pharm. Biopharm. (2005) 59 (3), 389-396
[Non-patent document 3] Monoclonal antibodies: versatile platforms for cancer immunotherapy. Weiner L M, Surana R, Wang S., Nat. Rev. Immunol. (2010) 10 (5), 317-327
[Non-patent document 4] Differential responses of human tumor cell lines to anti-p185HER2 monoclonal antibodies. Lewis G D, Figari I, Fendly B, Wong W L, Carter P, Gorman C, Shepard H M, Cancer Immunol. Immunotherapy (1993) 37, 255-263
[Non-patent document 5] ING-1, a monoclonal antibody targeting Ep-CAM in patients with advanced adenocarcinomas. de Bono J S, Tolcher A W, Forero A, Vanhove G F, Takimoto C, Bauer R J, Hammond L A, Patnaik A, White M L, Shen S, Khazaeli M B, Rowinsky E K, LoBuglio A F, Clin. Cancer Res. (2004) 10 (22), 7555-7565
[Non-patent document 6] Non-fucosylated therapeutic antibodies as next-generation therapeutic antibodies. Satoh M, Iida S, Shitara K., Expert Opin. Biol. Ther. (2006) 6 (11), 1161-1173
[Non-patent document 7] Optimizing engagement of the immune system by anti-tumor antibodies: an engineer's perspective. Desjarlais J R, Lazar G A, Zhukovsky E A, Chu S Y, Drug Discov. Today (2007) 12 (21-22), 898-910
[Non-patent document 8] Antibody-drug conjugates: targeted drug delivery for cancer. Alley S C, Okeley N M, Senter P D., Curr. Opin. Chem. Biol. (2010) 14 (4), 529-537
[Non-patent document 9] BiTE: Teaching antibodies to engage T-cells for cancer therapy. Baeuerle P A, Kufer P, Bargou R., Curr. Opin. Mol. Ther. (2009) 11 (1), 22-30
[Non-patent document 10] T cell-engaging BiTE antibodies specific for EGFR potently eliminate KRAS- and BRAF-mutated colorectal cancer cells. Lutterbuese R, Raum T, Kischel R, Hoffmann P, Mangold S, Rattel B, Friedrich M, Thomas O, Lorenczewski G, Rau D, Schaller E, Herrmann I, Wolf A, Urbig T, Baeuerle P A, Kufer P., Proc. Natl. Acad. Sci. U.S.A. (2010) 107 (28), 12605-12610
[Non-patent document 11] Phase I trial with the CD44v6-targeting immunoconjugate bivatuzumab mertansine in head and neck squamous cell carcinoma. Riechelmann H, Sauter A, Golze W, Hanft G, Schroen C, Hoermann K, Erhardt T, Gronau S., Oral Oncol. (2008) 44 (9), 823-829
[Non-patent document 12] Ipilimumab in the treatment of melanoma. Trinh V A, Hwu W J., Expert Opin. Biol. Ther., 2012 Apr. 14 (doi: 10.1517/14712598.2012.675325)
[Non-patent document 13] IPILIMUMAB—A NOVEL IMMUNOMODULATING THERAPY CAUSING AUTOIMMUNE HYPOPHYSITIS: A CASE REPORT AND REVIEW. Juszczak A, Gupta A, Karavitaki N, Middleton M R, Grossman A., Eur. J. Endocrinol. 2012 Apr. 10 (doi: 10.1530/EJE-12-0167)
[Non-patent document 14] The Japanese experience with biologic therapies for rheumatoid arthritis. Takeuchi T, Kameda H., Nat. Rev. Rheumatol. (2010) 6 (11), 644-652
[Non-patent document 15] Current evidence for the management of rheumatoid arthritis with biological disease-modifying antirheumatic drugs: a systematic literature review informing the EULAR recommendations for the management of RA. Nam J L, Winthrop K L, van Vollenhoven R F, Pavelka K, Valesini G, Hensor E M, Worthy G, Landewe R, Smolen J S, Emery P, Buch M H., Ann. Rheum. Dis. (2010) 69 (6), 976-986
[Non-patent document 16] Antibody engineering for the development of therapeutic antibodies. Kim S J, Park Y, Hong H J., Mol. Cells. (2005) 20 (1), 17-29

SUMMARY OF THE INVENTION

Problems to be Solved by the Invention

The present invention was achieved in view of the above circumstances. An objective of the present invention is to provide pharmaceutical compositions that are useful for treating diseases originating from target tissues, and active ingredients thereof. Another objective is to provide methods of screening for the pharmaceutical compositions and active ingredients, as well as their production methods.

Means for Solving the Problems

The present inventors conducted dedicated studies to achieve the above-described objectives. As a result, they generated antigen-binding molecules comprising an antigen-binding domain whose antigen-binding activity varies depending on the concentration of the target tissue-specific compound. Furthermore, the present inventors discovered that the antigen-binding molecules or pharmaceutical compositions comprising the antigen-binding molecules are useful for treating diseases that originate from a target tissue, and that they are also useful for treatment of diseases originating from target tissues that includes administering the antigen-binding molecules. They also discovered that the antigen-binding molecules are useful in the production of pharmaceuticals for treating diseases that originate from target tissues. Furthermore, the present inventors produced screening methods and production methods for the antigen-binding molecules, and thereby completed the present invention.

More specifically, the present invention provides the following:

[1] An antigen-binding molecule comprising an antigen-binding domain whose antigen-binding activity varies depending on the concentration of a target tissue-specific compound.
[2] The antigen-binding molecule of [1], wherein the target tissue is a cancer tissue.
[3] The antigen-binding molecule of [2], wherein the compound specific to a cancer tissue is a metabolite specific to a cancer cell, a metabolite specific to an immune cell that has infiltrated into a cancer tissue, or a metabolite specific to a stromal cell in a cancer tissue.
[4] The antigen-binding molecule of [1], wherein the target tissue is an inflamed tissue.
[5] The antigen-binding molecule of [4], wherein the compound specific to an inflamed tissue is a metabolite specific to an immune cell that has infiltrated into an inflamed tissue or a metabolite specific to a normal cell that has been damaged in an inflamed tissue.
[6] The antigen-binding molecule of [1], wherein the compound is at least one compound selected from a nucleoside having a purine ring structure, an amino acid and its metabolite, a lipid and its metabolite, a primary metabolite of glycometabolism, and nicotinamide and its metabolite.
[7] The antigen-binding molecule of [6], wherein the compound is at least one compound selected from adenosine, adenosine triphosphate, inosine, alanine, glutamic acid, aspartic acid, kynurenine, prostaglandin E2, succinic acid, citric acid, and 1-methylnicotinamide.
[8] The antigen-binding molecule of any one of [1] to [7], wherein the antigen is a membrane-type molecule.
[9] The antigen-binding molecule of any one of [1] to [8], which is an antigen-binding molecule that has a neutralizing activity.
[10] The antigen-binding molecule of any one of [1] to [9], which is an antigen-binding molecule that has a cytotoxic activity.
[11] The antigen-binding molecule of any one of [1] to [10], which comprises an Fc region.

[12] The antigen-binding molecule of [11], wherein the Fc region is an Fc region contained in the constant region of SEQ ID NOs: 5, 6, 7, or 8.
[13] The antigen-binding molecule of [11], wherein the Fc region comprises an altered FcγR-binding Fc region that has a higher Fcγ receptor-binding activity than the Fcγ receptor-binding activity of a native human IgG Fc region.
[14] The antigen-binding molecule of [13], wherein at least one or more amino acids selected from the group consisting of amino acids at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 according to EU numbering, in the amino acid sequence of the altered FcγR-binding Fc region are different from the amino acids of the native human IgG Fc region.
[15] The antigen-binding molecule of [14], which comprises at least one or more amino acids selected from the group consisting of:
Lys or Tyr for the amino acid at position 221;
Phe, Trp, Glu, or Tyr for the amino acid at position 222;
Phe, Trp, Glu, or Lys for the amino acid at position 223;
Phe, Trp, Glu, or Tyr for the amino acid at position 224;
Glu, Lys, or Trp for the amino acid at position 225;
Glu, Gly, Lys, or Tyr for the amino acid at position 227;
Glu, Gly, Lys, or Tyr for the amino acid at position 228;
Ala, Glu, Gly, or Tyr for the amino acid at position 230;
Glu, Gly, Lys, Pro, or Tyr for the amino acid at position 231;
Glu, Gly, Lys, or Tyr for the amino acid at position 232;
Ala, Asp, Phe, Gly, His, Ile, Lys, Leu, Met, Asn, Gln, Arg, Ser, Thr, Val, Trp, or Tyr for the amino acid at position 233;
Ala, Asp, Glu, Phe, Gly, His, Ile, Lys, Met, Asn, Pro, Gln, Arg, Ser, Thr, Val, Trp, or Tyr for the amino acid at position 234;
Ala, Asp, Glu, Phe, Gly, His, Ile, Lys, Met, Asn, Pro, Gln, Arg, Ser, Thr, Val, Trp, or Tyr for the amino acid at position 235;
Ala, Asp, Glu, Phe, His, Ile, Lys, Leu, Met, Asn, Pro, Gln, Arg, Ser, Thr, Val, Trp, or Tyr for the amino acid at position 236;
Asp, Glu, Phe, His, Ile, Lys, Leu, Met, Asn, Pro, Gln, Arg, Ser, Thr, Val, Trp, or Tyr for the amino acid at position 237;
Asp, Glu, Phe, Gly, His, Ile, Lys, Leu, Met, Asn, Gln, Arg, Ser, Thr, Val, Trp, or Tyr for the amino acid at position 238;
Asp, Glu, Phe, Gly, His, Ile, Lys, Leu, Met, Asn, Pro, Gln, Arg, Thr, Val, Trp, or Tyr for the amino acid at position 239;
Ala, Ile, Met, or Thr for the amino acid at position 240;
Asp, Glu, Leu, Arg, Trp, or Tyr for the amino acid at position 241;
Leu, Glu, Leu, Gln, Arg, Trp, or Tyr for the amino acid at position 243;
His for the amino acid at position 244;
Ala for the amino acid at position 245;
Asp, Glu, His, or Tyr for the amino acid at position 246;
Ala, Phe, Gly, His, Ile, Leu, Met, Thr, Val, or Tyr for the amino acid at position 247;
Glu, His, Gln, or Tyr for the amino acid at position 249;
Glu or Gln for the amino acid at position 250;
Phe for the amino acid at position 251;
Phe, Met, or Tyr for the amino acid at position 254;
Glu, Leu, or Tyr for the amino acid at position 255;

Ala, Met, or Pro for the amino acid at position 256;
Asp, Glu, His, Ser, or Tyr for the amino acid at position 258;
Asp, Glu, His, or Tyr for the amino acid at position 260;
Ala, Glu, Phe, Ile, or Thr for the amino acid at position 262;
Ala, Ile, Met, or Thr for the amino acid at position 263;
Asp, Glu, Phe, Gly, His, Ile, Lys, Leu, Met, Asn, Pro, Gln, Arg, Ser, Thr, Trp, or Tyr for the amino acid at position 264;
Ala, Leu, Phe, Gly, His, Ile, Lys, Leu, Met, Asn, Pro, Gln, Arg, Ser, Thr, Val, Trp, or Tyr for the amino acid at position 265;
Ala, Ile, Met, or Thr for the amino acid at position 266;
Asp, Glu, Phe, His, Ile, Lys, Leu, Met, Asn, Pro, Gln, Arg, Thr, Val, Trp, or Tyr for the amino acid at position 267;
Asp, Glu, Phe, Gly, Ile, Lys, Leu, Met, Pro, Gln, Arg, Thr, Val, or Trp for the amino acid at position 268;
Phe, Gly, His, Ile, Lys, Leu, Met, Asn, Pro, Arg, Ser, Thr, Val, Trp, or Tyr for the amino acid at position 269;
Glu, Phe, Gly, His, Ile, Leu, Met, Pro, Gln, Arg, Ser, Thr, Trp, or Tyr for the amino acid at position 270;
Ala, Asp, Glu, Phe, Gly, His, Ile, Lys, Leu, Met, Asn, Gln, Arg, Ser, Thr, Val, Trp, or Tyr for the amino acid at position 271;
Asp, Phe, Gly, His, Ile, Lys, Leu, Met, Pro, Arg, Ser, Thr, Val, Trp, or Tyr for the amino acid at position 272;
Phe or Ile for the amino acid at position 273;
Asp, Glu, Phe, Gly, His, Ile, Leu, Met, Asn, Pro, Arg, Ser, Thr, Val, Trp, or Tyr for the amino acid at position 274;
Leu or Trp for the amino acid at position 275;
Asp, Glu, Phe, Gly, His, Ile, Leu, Met, Pro, Arg, Ser, Thr, Val, Trp, or Tyr for the amino acid at position 276;
Asp, Glu, Gly, His, Ile, Lys, Leu, Met, Asn, Pro, Gln, Arg, Ser, Thr, Val, or Trp for the amino acid at position 278;
Ala for the amino acid at position 279;
Ala, Gly, His, Lys, Leu, Pro, Gln, Trp, or Tyr for the amino acid at position 280;
Asp, Lys, Pro, or Tyr for the amino acid at position 281;
Glu, Gly, Lys, Pro, or Tyr for the amino acid at position 282;
Ala, Gly, His, Ile, Lys, Leu, Met, Pro, Arg, or Tyr for the amino acid at position 283;
Asp, Glu, Leu, Asn, Thr, or Tyr for the amino acid at position 284;
Asp, Glu, Lys, Gln, Trp, or Tyr for the amino acid at position 285;
Glu, Gly, Pro, or Tyr for the amino acid at position 286;
Asn, Asp, Glu, or Tyr for the amino acid at position 288;
Asp, Gly, His, Leu, Asn, Ser, Thr, Trp, or Tyr for the amino acid at position 290;
Asp, Glu, Gly, His, Ile, Gln, or Thr for the amino acid at position 291;
Ala, Asp, Glu, Pro, Thr, or Tyr for the amino acid at position 292;
Phe, Gly, His, Ile, Leu, Met, Asn, Pro, Arg, Ser, Thr, Val, Trp, or Tyr for the amino acid at position 293;
Phe, Gly, His, Ile, Lys, Leu, Met, Asn, Pro, Arg, Ser, Thr, Val, Trp, or Tyr for the amino acid at position 294;
Asp, Glu, Phe, Gly, His, Ile, Lys, Met, Asn, Pro, Arg, Ser, Thr, Val, Trp, or Tyr for the amino acid at position 295;
Ala, Asp, Glu, Gly, His, Ile, Lys, Leu, Met, Asn, Gln, Arg, Ser, Thr, or Val for the amino acid at position 296;
Asp, Glu, Phe, Gly, His, Ile, Lys, Leu, Met, Pro, Gln, Arg, Ser, Thr, Val, Trp, or Tyr for the amino acid at position 297;
Ala, Asp, Glu, Phe, His, Ile, Lys, Met, Asn, Gln, Arg, Thr, Val, Trp, or Tyr for the amino acid at position 298;
Ala, Asp, Glu, Phe, Gly, His, Ile, Lys, Leu, Met, Pro, Gln, Arg, Ser, Val, Trp, or Tyr for the amino acid at position 299;
Ala, Asp, Glu, Gly, His, Ile, Lys, Leu, Met, Asn, Pro, Gln, Arg, Ser, Thr, Val, or Trp for the amino acid at position 300;
Asp, Glu, His, or Tyr for the amino acid at position 301;
Ile for the amino acid at position 302;
Asp, Gly, or Tyr for the amino acid at position 303;
Asp, His, Leu, Asn, or Thr for the amino acid at position 304;
Glu, Ile, Thr, or Tyr for the amino acid at position 305;
Ala, Asp, Asn, Thr, Val, or Tyr for the amino acid at position 311;
Phe for the amino acid at position 313;
Leu for the amino acid at position 315;
Glu, or Gln for the amino acid at position 317;
His, Leu, Asn, Pro, Gln, Arg, Thr, Val, or Tyr for the amino acid at position 318;
Asp, Phe, Gly, His, Ile, Leu, Asn, Pro, Ser, Thr, Val, Trp, or Tyr for the amino acid at position 320;
Ala, Asp, Phe, Gly, His, Ile, Pro, Ser, Thr, Val, Trp, or Tyr for the amino acid at position 322;
Ile for the amino acid at position 323;
Asp, Phe, Gly, His, Ile, Leu, Met, Pro, Arg, Thr, Val, Trp, or Tyr for the amino acid at position 324;
Ala, Asp, Glu, Phe, Gly, His, Ile, Lys, Leu, Met, Pro, Gln, Arg, Ser, Thr, Val, Trp, or Tyr for the amino acid at position 325;
Ala, Asp, Glu, Gly, Ile, Leu, Met, Asn, Pro, Gln, Ser, Thr, Val, Trp, or Tyr for the amino acid at position 326;
Ala, Asp, Glu, Phe, Gly, His, Ile, Lys, Leu, Met, Asn, Pro, Arg, Thr, Val, Trp, or Tyr for the amino acid at position 327;
Ala, Asp, Glu, Phe, Gly, His, Ile, Lys, Met, Asn, Pro, Gln, Arg, Ser, Thr, Val, Trp, or Tyr for the amino acid at position 328;
Asp, Glu, Phe, Gly, His, Ile, Lys, Leu, Met, Asn, Gln, Arg, Ser, Thr, Val, Trp, or Tyr for the amino acid at position 329;
Cys, Glu, Phe, Gly, His, Ile, Lys, Leu, Met, Asn, Pro, Arg, Ser, Thr, Val, Trp, or Tyr for the amino acid at position 330;
Asp, Phe, His, Ile, Leu, Met, Gln, Arg, Thr, Val, Trp, or Tyr for the amino acid at position 331;
Ala, Asp, Glu, Phe, Gly, His, Lys, Leu, Met, Asn, Pro, Gln, Arg, Ser, Thr, Val, Trp, or Tyr for the amino acid at position 332;
Ala, Asp, Glu, Phe, Gly, His, Ile, Leu, Met, Pro, Ser, Thr, Val, or Tyr for the amino acid at position 333;
Ala, Glu, Phe, Ile, Leu, Pro, or Thr for the amino acid at position 334;
Asp, Phe, Gly, His, Ile, Leu, Met, Asn, Pro, Arg, Ser, Val, Trp, or Tyr for the amino acid at position 335;
Glu, Lys, or Tyr for the amino acid at position 336;
Glu, His, or Asn for the amino acid at position 337;
Asp, Phe, Gly, Ile, Lys, Met, Asn, Gln, Arg, Ser, or Thr for the amino acid at position 339;
Ala or Val for the amino acid at position 376;
Gly or Lys for the amino acid at position 377;
Asp for the amino acid at position 378;
Asn for the amino acid at position 379;
Ala, Asn, or Ser for the amino acid at position 380;
Ala, or Ile for the amino acid at position 382;
Glu for the amino acid at position 385;
Thr for the amino acid at position 392;
Leu for the amino acid at position 396;
Lys for the amino acid at position 421;
Asn for the amino acid at position 427;
Phe, or Leu for the amino acid at position 428;
Met for the amino acid at position 429;
Trp for the amino acid at position 434;
Ile for the amino acid at position 436; and Gly, His, Ile, Leu, or Tyr for the amino acid at position 440 according to EU numbering in the amino acid sequence of the altered FcγR-binding Fc region.

[16] The antigen-binding molecule of [11], wherein the Fc region is modified so that there is a higher proportion of Fc region bound by a fucose-deficient sugar chain in a composition of sugar chain bound at position 297, according to EU numbering, of the Fc region, or so that there is a higher proportion of Fc region with an added bisecting N-acetylglucosamine.

[17] The antigen-binding molecule of any one of [11] and [13] to [16], wherein the FcRn-binding activity of the Fc region under an acidic pH range condition is enhanced compared to the FcRn-binding activity of the Fc region of SEQ ID NO: 5, 6, 7, or 8.

[18] The antigen-binding molecule of [17], wherein the Fc region is an Fc region with substitution of at least one or more amino acids selected from the group consisting of amino acids at positions 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447, according to EU numbering, in the amino acid sequence of the Fc region comprised in the constant region of SEQ ID NO: 5, 6, 7, or 8.

[19] The antigen-binding molecule of [18], wherein the Fc region comprises at least one or more amino acids selected from the group consisting of:
Leu for the amino acid at position 238;
Leu for the amino acid at position 244;
Arg for the amino acid at position 245;
Pro for the amino acid at position 249;
Gln or Glu for the amino acid at position 250;
Arg, Asp, Glu, or Leu for the amino acid at position 251;
Phe, Ser, Thr, or Tyr for the amino acid at position 252;
Ser or Thr for the amino acid at position 254;
Arg, Gly, Ile, or Leu for the amino acid at position 255;
Ala, Arg, Asn, Asp, Gln, Glu, Pro, or Thr for the amino acid at position 256;
Ala, Ile, Met, Asn, Ser, or Val for the amino acid at position 257;
Asp for the amino acid at position 258;
Ser for the amino acid at position 260;
Leu for the amino acid at position 262;
Lys for the amino acid at position 270;
Leu, or Arg for the amino acid at position 272;
Ala, Asp, Gly, His, Met, Asn, Gln, Arg, Ser, Thr, Trp, or Tyr for the amino acid at position 279;
Ala, Asp, Phe, Gly, His, Ile, Lys, Leu, Asn, Pro, Gln, Arg, Ser, Thr, Trp, or Tyr for the amino acid at position 283;
Asn for the amino acid at position 285;
Phe for the amino acid at position 286;
Asn or Pro for the amino acid at position 288;
Val for the amino acid at position 293,
Ala, Glu, Gln, or Met for the amino acid at position 307;
Ala, Glu, Ile, Lys, Leu, Met, Ser, Val, or Trp for the amino acid at position 311;
Pro for the amino acid at position 309;
Ala, Asp, or Pro for the amino acid at position 312;
Ala or Leu for the amino acid at position 314;
Lys for the amino acid at position 316;
Pro for the amino acid at position 317;
Asn or Thr for the amino acid at position 318;
Phe, His, Lys, Leu, Met, Arg, Ser, or Trp for the amino acid at position 332;
Asn, Thr, or Trp for the amino acid at position 339;
Pro for the amino acid at position 341;
Glu, His, Lys, Gln, Arg, Thr, or Tyr for the amino acid at position 343;
Arg for the amino acid at position 375;
Gly, Ile, Met, Pro, Thr, or Val for the amino acid at position 376;
Lys for the amino acid at position 377;
Asp, Asn, or Val for the amino acid at position 378;
Ala, Asn, Ser, or Thr for the amino acid at position 380;
Phe, His, Ile, Lys, Leu, Met, Asn, Gln, Arg, Ser, Thr, Val, Trp, or Tyr for the amino acid at position 382;
Ala, Arg, Asp, Gly, His, Lys, Ser, or Thr for the amino acid at position 385;
Arg, Asp, Ile, Lys, Met, Pro, Ser, or Thr for the amino acid at position 386;
Ala, Arg, His, Pro, Ser, or Thr for the amino acid at position 387;
Asn, Pro, or Ser for the amino acid at position 389;
Asn for the amino acid at position 423;
Asn for the amino acid at position 427;
Leu, Met, Phe, Ser, or Thr for the amino acid at position 428;
Ala, Phe, Gly, His, Ile, Lys, Leu, Met, Asn, Gln, Arg, Ser, Thr, Val, or Tyr for the amino acid at position 430;
His or Asn for the amino acid at position 431;
Arg, Gln, His, Ile, Lys, Pro, or Ser for the amino acid at position 433;
Ala, Gly, His, Phe, Ser, Trp, or Tyr for the amino acid at position 434;
Arg, Asn, His, Ile, Leu, Lys, Met, or Thr for the amino acid at position 436;
Lys, Leu, Thr, or Trp for the amino acid at position 438;
Lys for the amino acid at position 440;
Lys for the amino acid at position 442; and
Ile, Pro, or Thr for the amino acid at position 308;
as indicated by EU numbering, in the amino acid sequence of the Fc region comprised in the constant region of SEQ ID NO: 5, 6, 7, or 8.

[20] The antigen-binding molecule of any one of [1] to [19], wherein the antigen-binding domain is a multispecific or a multiparatopic antigen-binding domain.

[21] The antigen-binding molecule of [20], wherein an antigen bound by at least one of the antigen-binding domains is a membrane-type molecule expressed on a cancer cell membrane, and an antigen bound by at least one of the antigen-binding domains is a membrane-type molecule expressed on an effector cell membrane.

[22] The antigen-binding molecule of [21], wherein the effector cell is an NK cell, a macrophage, or a T cell.

[23] The antigen-binding molecule of [21] or [22], wherein the membrane-type molecule expressed on an effector cell membrane is a TCR-constituting polypeptide, CD2, CD3, CD28, CD44, CD16, CD32, CD64, or NKG2D.

[24] The antigen-binding molecule of [20], wherein an antigen bound by at least one of the antigen-binding domains is a membrane-type molecule expressed on a cancer cell membrane, and an antigen bound by at least one of the antigen-binding domains is a cytotoxic substance.

[25] The antigen-binding molecule of any one of [20] to [24], wherein the antigen-binding molecule is an antibody fragment.

[26] The antigen-binding molecule of any one of [1] to [24], wherein the antigen-binding molecule is an antibody.

[27] The antigen-binding molecule of any one of [1] to [7], wherein the antigen is a soluble molecule.

[28] The antigen-binding molecule of [27], which is an antigen-binding molecule having a neutralizing activity.

[29] The antigen-binding molecule of [27] or [28], which comprises an Fc region.

[30] The antigen-binding molecule of [29], wherein the Fc region is an Fc region comprised in the constant region of SEQ ID NO: 5, 6, 7, or 8.

[31] The antigen-binding molecule of [29], wherein the FcRn-binding activity of the Fc region under an acidic pH range condition is enhanced compared to the FcRn-binding activity of the Fc region comprised in the constant region of SEQ ID NO: 5, 6, 7, or 8.

[32] The antigen-binding molecule of [31], wherein the Fc region is an Fc region with substitution of at least one or more amino acids selected from the group consisting of amino acids at positions 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447, according to EU numbering, in the amino acid sequence of the Fc region comprised in the constant region of SEQ ID NO: 5, 6, 7, or 8.

[33] The antigen-binding molecule of [32], wherein the Fc region comprises at least one or more amino acids selected from the group consisting of:
Leu for the amino acid at position 238;
Leu for the amino acid at position 244;
Arg for the amino acid at position 245;
Pro for the amino acid at position 249;
Gln or Glu for the amino acid at position 250;
Arg, Asp, Glu, or Leu for the amino acid at position 251;
Phe, Ser, Thr, or Tyr for the amino acid at position 252;
Ser or Thr for the amino acid at position 254;
Arg, Gly, Ile, or Leu for the amino acid at position 255;
Ala, Arg, Asn, Asp, Gln, Glu, Pro, or Thr for the amino acid at position 256;
Ala, Ile, Met, Asn, Ser, or Val for the amino acid at position 257;
Asp for the amino acid at position 258;
Ser for the amino acid at position 260;
Leu for the amino acid at position 262;
Lys for the amino acid at position 270;
Leu, or Arg for the amino acid at position 272;
Ala, Asp, Gly, His, Met, Asn, Gln, Arg, Ser, Thr, Trp, or Tyr for the amino acid at position 279;
Ala, Asp, Phe, Gly, His, Ile, Lys, Leu, Asn, Pro, Gln, Arg, Ser, Thr, Trp, or Tyr for the amino acid at position 283;
Asn for the amino acid at position 285;
Phe for the amino acid at position 286;
Asn or Pro for the amino acid at position 288;
Val for the amino acid at position 293,
Ala, Glu, Gln, or Met for the amino acid at position 307;
Ala, Glu, Ile, Lys, Leu, Met, Ser, Val, or Trp for the amino acid at position 311;
Pro for the amino acid at position 309;
Ala, Asp, or Pro for the amino acid at position 312;
Ala or Leu for the amino acid at position 314;
Lys for the amino acid at position 316;
Pro for the amino acid at position 317;
Asn or Thr for the amino acid at position 318;
Phe, His, Lys, Leu, Met, Arg, Ser, or Trp for the amino acid at position 332;
Asn, Thr, or Trp for the amino acid at position 339;
Pro for the amino acid at position 341;
Glu, His, Lys, Gln, Arg, Thr, or Tyr for the amino acid at position 343;
Arg for the amino acid at position 375;
Gly, Ile, Met, Pro, Thr, or Val for the amino acid at position 376;
Lys for the amino acid at position 377;
Asp, Asn, or Val for the amino acid at position 378;
Ala, Asn, Ser, or Thr for the amino acid at position 380;
Phe, His, Ile, Lys, Leu, Met, Asn, Gln, Arg, Ser, Thr, Val, Trp, or Tyr for the amino acid at position 382;
Ala, Arg, Asp, Gly, His, Lys, Ser, or Thr for the amino acid at position 385;
Arg, Asp, Ile, Lys, Met, Pro, Ser, or Thr for the amino acid at position 386;
Ala, Arg, His, Pro, Ser, or Thr for the amino acid at position 387;
Asn, Pro, or Ser for the amino acid at position 389;
Asn for the amino acid at position 423;
Asn for the amino acid at position 427;
Leu, Met, Phe, Ser, or Thr for the amino acid at position 428;
Ala, Phe, Gly, His, Ile, Lys, Leu, Met, Asn, Gln, Arg, Ser, Thr, Val, or Tyr for the amino acid at position 430;
His or Asn for the amino acid at position 431;
Arg, Gln, His, Ile, Lys, Pro, or Ser for the amino acid at position 433;
Ala, Gly, His, Phe, Ser, Trp, or Tyr for the amino acid at position 434;
Arg, Asn, His, Ile, Leu, Lys, Met, or Thr for the amino acid at position 436;
Lys, Leu, Thr, or Trp for the amino acid at position 438;
Lys for the amino acid at position 440;
Lys for the amino acid at position 442; and
Ile, Pro, or Thr for the amino acid at position 308;
as indicated by EU numbering, in the amino acid sequence of the Fc region comprised in the constant region of SEQ ID NO: 5, 6, 7, or 8.

[34] The antigen-binding molecule of [29], wherein the FcRn-binding activity of the Fc region under a neutral pH range condition is enhanced compared to the FcRn-binding activity of the Fc region comprised in the constant region of SEQ ID NO: 5, 6, 7, or 8.

[35] The antigen-binding molecule of [34], wherein the Fc region is an Fc region with substitution of at least one or more amino acids selected from the group consisting of amino acids at positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 according to EU numbering, in the amino acid sequence of the Fc region comprised in the constant region of SEQ ID NO: 5, 6, 7, or 8.

[36] The antigen-binding molecule of [35], wherein the Fc region comprises at least one or more amino acids selected from the group consisting of:
Met for the amino acid at position 237;
Ile for the amino acid at position 248;
Ala, Phe, Ile, Met, Gln, Ser, Val, Trp, or Tyr for the amino acid at position 250;
Phe, Trp, or Tyr for the amino acid at position 252;
Thr for the amino acid at position 254;
Glu for the amino acid at position 255;
Asp, Asn, Glu, or Gln for the amino acid at position 256;
Ala, Gly, Ile, Leu, Met, Asn, Ser, Thr, or Val for the amino acid at position 257;
His for the amino acid at position 258;
Ala for the amino acid at position 265;
Ala or Glu for the amino acid at position 286;
His for the amino acid at position 289;
Ala for the amino acid at position 297;
Ala for the amino acid at position 303;

Ala for the amino acid at position 305;
Ala, Asp, Phe, Gly, His, Ile, Lys, Leu, Met, Asn, Pro, Gln, Arg, Ser, Val, Trp, or Tyr for the amino acid at position 307;
Ala, Phe, Ile, Leu, Met, Pro, Gln, or Thr for the amino acid at position 308;
Ala, Asp, Glu, Pro, or Arg for the amino acid at position 309;
Ala, His, or Ile for the amino acid at position 311;
Ala or His for the amino acid at position 312;
Lys or Arg for the amino acid at position 314;
Ala, Asp, or His for the amino acid at position 315;
Ala for the amino acid at position 317;
Val for the amino acid at position 332;
Leu for the amino acid at position 334;
His for the amino acid at position 360;
Ala for the amino acid at position 376;
Ala for the amino acid at position 380;
Ala for the amino acid at position 382;
Ala for the amino acid at position 384;
Asp or His for the amino acid at position 385;
Pro for the amino acid at position 386;
Glu for the amino acid at position 387;
Ala or Ser for the amino acid at position 389;
Ala for the amino acid at position 424;
Ala, Asp, Phe, Gly, His, Ile, Lys, Leu, Asn, Pro, Gln, Ser, Thr, Val, Trp, or Tyr for the amino acid at position 428;
Lys for the amino acid at position 433;
Ala, Phe, His, Ser, Trp, or Tyr for the amino acid at position 434; and
His, Ile, Leu, Phe, Thr, or Val for the amino acid at position 436 as indicated by EU numbering, in the amino acid sequence of the Fc region of SEQ ID NO: 5, 6, 7, or 8.
[37] The antigen-binding molecule of any one of [29] and [31] to [36], wherein the Fc region has a higher binding activity to an inhibitory Fcγ receptor than to an activating Fcγ receptor.
[38] The antigen-binding molecule of [37], wherein the inhibitory Fcγ receptor is human FcγRIIb.
[39] The antigen-binding molecule of [37] or [38], wherein the activating Fcγ receptor is human FcγRIa, human FcγRIIa (R), human FcγRIIa (H), human FcγRIIIa (V), or human FcγRIIIa (F).
[40] The antigen-binding molecule of any one of [37] to [39], wherein the amino acid at position 238 or 328 (EU numbering) of the Fc region includes an amino acid that is different from the amino acid of the native human IgG Fc region.
[41] The antigen-binding molecule of [40], wherein the amino acid at position 238 indicated by EU numbering in the Fc region is Asp or the amino acid at position 328 is Glu.
[42] The antigen-binding molecule of [40] or [41], which comprises at least one or more amino acids selected from the group consisting of:
Asp for the amino acid at position 233;
Trp or Tyr for the amino acid at position 234;
Ala, Asp, Glu, Leu, Met, Phe, Trp, or Tyr for the amino acid at position 237;
Asp for the amino acid at position 239;
Ala, Gln, or Val for the amino acid at position 267;
Asn, Asp, or Glu for the amino acid at position 268;
Gly for the amino acid at position 271;
Ala, Asn, Asp, Gln, Glu, Leu, Met, Ser, or Thr for the amino acid at position 326;
Arg, Lys, or Met for the amino acid at position 330;
Ile, Leu, or Met for the amino acid at position 323; and
Asp for the amino acid at position 296 according to EU numbering, in the amino acid sequence of the Fc region.

[43] The antigen-binding molecule of any one of [27] to [42], wherein the antigen-binding molecule is an antibody.
[44] A method for producing the antigen-binding molecule of any one of [1] to [43], which comprises selecting an antigen-binding domain whose antigen-binding activity varies depending on the concentration of a target tissue-specific compound.
[45] A method of screening for the antigen-binding molecule of any one of [1] to [43], which comprises selecting an antigen-binding domain whose antigen-binding activity varies depending on the concentration of a target tissue-specific compound.
[46] A pharmaceutical composition comprising the antigen-binding molecule of any one of [1] to [43].

MODE FOR CARRYING OUT THE INVENTION

Figure 1:
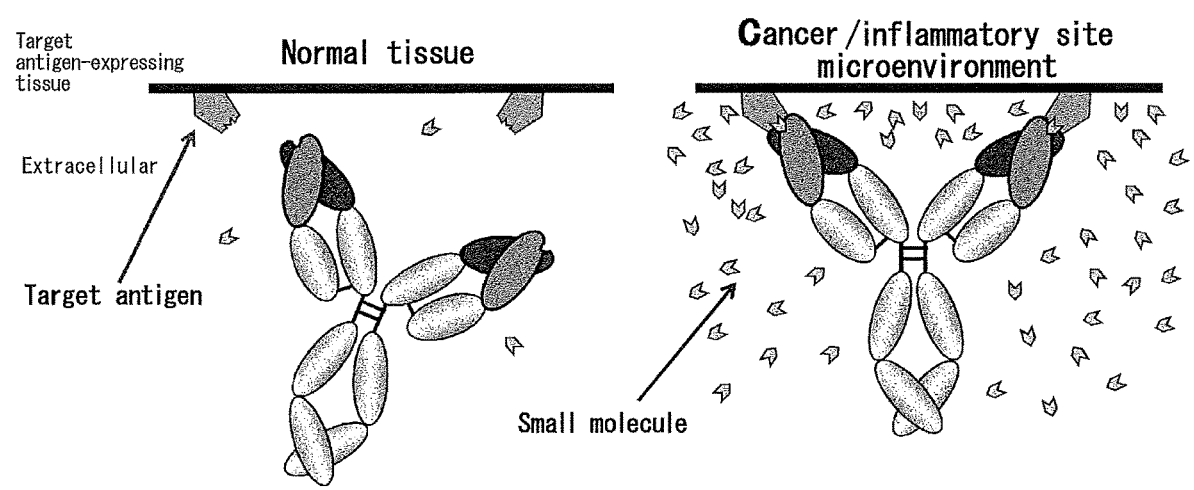
FIG. 1 shows that a small-molecule-switch antibody does not bind to antigens in a normal environment where the small molecules are not present, but binds to the antigens in the target tissue where the small molecules are present at a high concentration.

The definitions and detailed description below are provided to facilitate understanding of the present invention illustrated herein.

Amino Acids

Herein, amino acids are described by one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acids

For amino acid alteration in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Furthermore, several known methods may also be employed as amino acid alteration methods for substitution to non-natural amino acids (Annu. Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA which has a non-natural amino acid bound to a complementary amber suppressor tRNA of one of the stop codons, the UAG codon (amber codon).

In the present specification, the meaning of the term "and/or" when describing the site of amino acid alteration includes every combination where "and" and "or" are suitably combined. Specifically, for example, "the amino acids at positions 33, 55, and/or 96 are substituted" includes the following variation of amino acid alterations:

amino acid(s) at (a) position 33, (b) position 55, (c) position 96, (d) positions 33 and 55, (e) positions 33 and 96, (f) positions 55 and 96, and (g) positions 33, 55, and 96.

Furthermore, herein, as an expression showing alteration of amino acids, an expression that shows before and after a number indicating a specific position, one-letter or three-letter codes for amino acids before and after alteration, respectively, may be used appropriately. For example, the alteration N100bL or Asn100bLeu used when substituting an amino acid contained in an antibody variable region indicates substitution of Asn at position 100b (according to Kabat numbering) with Leu. That is, the number shows the amino acid position according to Kabat numbering, the one-letter or three-letter amino-acid code written before the number shows the amino acid before substitution, and the one-letter or three-letter amino-acid code written after the number shows the amino acid after substitution. Similarly the alteration P238D or Pro238Asp used when substituting an amino acid of the Fc region contained in an antibody constant region indicates substitution of Pro at position 238 (according to EU numbering) with Asp. That is, the number shows the amino acid position according to EU numbering, the one-letter or three-letter amino-acid code written before the number shows the amino acid before substitution, and the one-letter or three-letter amino-acid code written after the number shows the amino acid after substitution.

Antigens

Herein, "antigens" are not particularly limited in their structure, as long as they comprise epitopes to which antigen-binding domains bind. In other words, antigens can be inorganic or organic substances. Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Axl, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, PD1, PDL1, LAG3, TIM3, galectin-9, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-21, IL-23, IL-27, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), PlGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEMS, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alpha-beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-$\alpha$ Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TLR1 (Toll-like receptor 1), TLR2, TLR3, TLR4, TLR5, TLR6, TLR7, TLR8, TLR9, TLR10, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and S1P; and receptors for hormone and growth factors. Preferred antigens are antigens that are expressed in cancer cells, immune cells, stromal cells, or such present in cancer tissues or inflammatory tissues.

While receptors are recited as examples of the above-mentioned antigens, when these receptors exist in soluble forms in biological fluids, they may be used as antigens that bind to the antigen-binding molecule of the present invention, which contains an antigen-binding domain whose antigen-binding activity varies depending on the concentration of the target tissue-specific compound. An example of a non-limiting embodiment of such a soluble receptor is the soluble IL-6R, which is a protein consisting of the amino acids at positions 1 to 357 in the IL-6R polypeptide sequence of SEQ ID NO: 1 as described in Mullberg et al. (J. Immunol. (1994) 152 (10), 4958-4968).

Membrane-type molecules expressed on cell membranes and soluble molecules secreted from cells to the outside of the cells are included in the examples of the above-mentioned antigens. When the antigen-binding molecule of the present invention, which contains an antigen-binding domain whose antigen-binding activity varies depending on the concentration of the target tissue-specific compound, binds to a soluble molecule secreted from cells, it is preferable that the antigen-binding molecule has neutralizing activity as described later.

The fluids in which the soluble molecules exist are not limited, and the soluble molecules may exist in biological fluids, or more specifically in all fluids filling the space between tissues and cells or vessels in organisms. In a non-limiting embodiment, the soluble molecules to which antigen-binding molecules of the present invention bind may be present in the extracellular fluid. In vertebrates, extracellular fluid is a general term for plasma, interstitial fluid, lymph, compact connective tissue, cerebrospinal fluid, spinal fluid, puncture fluid, synovial fluid, or such components in the bone and cartilage, alveolar fluid (bronchoalveolar lavage fluid), peritoneal fluid, pleural fluid, pericardial effusion, cyst fluid, aqueous humor (hydatoid), or such transcellular fluids (various fluids in the glandular cavities and fluids in the digestive tract cavity and other body cavity fluids produced as a result of active transport/secretory activities of cells).

When an antigen-binding molecule of the present invention comprising an antigen-binding domain whose antigen-binding activity varies depending on the concentration of a target tissue-specific compound binds to a membrane-type molecule expressed on a cell membrane, suitable examples of the antigen-binding molecule include antigen-binding molecules which have cytotoxic activity, bind to a cytotoxic substance, or have the ability to bind to a cytotoxic substance, as described later. Furthermore, antigen-binding molecules having a neutralizing activity instead of the properties of having a cytotoxic activity, binding to a cytotoxic substance, or having the ability to bind to a cytotoxic substance; or in addition to these properties are also suitable examples of a non-limiting embodiment.

Epitopes

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence has been recognized. Such a linear epitope typically contains at least three and most commonly at least five, for example, about 8 to about 10 or 6 to 20 amino acids in a specific sequence.

In contrast to the linear epitope, a "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

The structure of the antigen-binding domain which binds to an epitope is called a paratope. An epitope and a paratope bind with stability through the action of hydrogen bonds, electrostatic force, van der Waals force, hydrophobic bonds, and such between the epitope and the paratope. This strength of binding between the epitope and paratope is called affinity. The total sum of binding strength when a plurality of antigens and a plurality of antigen-binding molecules bind is referred to as avidity. When an antibody comprising a plurality of antigen-binding domains (i.e., multivalent antibody) or such binds to a plurality of epitopes, the affinity acts synergistically, and therefore avidity becomes higher than affinity.

Binding Activity

Examples of a method for assessing the epitope binding by a test antigen-binding molecule containing an IL-6R antigen-binding domain are described below. According to the examples below, methods for assessing the epitope binding by a test antigen-binding molecule containing an antigen-binding domain for an antigen other than IL-6R, can also be appropriately conducted.

For example, whether a test antigen-binding molecule containing an IL-6R antigen-binding domain recognizes a linear epitope in the IL-6R molecule can be confirmed for example as mentioned below. A linear peptide comprising an amino acid sequence forming the extracellular domain of IL-6R is synthesized for the above purpose. The peptide can be synthesized chemically, or obtained by genetic engineering techniques using a region encoding the amino acid sequence corresponding to the extracellular domain in an IL-6R cDNA. Then, a test antigen-binding molecule containing an IL-6R antigen-binding domain is assessed for its binding activity towards a linear peptide comprising the amino acid sequence forming the extracellular domain. For example, an immobilized linear peptide can be used as an antigen by ELISA to evaluate the binding activity of the antigen-binding molecule towards the peptide. Alternatively, the binding activity towards a linear peptide can be assessed based on the level that the linear peptide inhibits the binding of the antigen-binding molecule to IL-6R-expressing cells. These tests can demonstrate the binding activity of the antigen-binding molecule towards the linear peptide.

Whether a test antigen-binding molecule containing an IL-6R antigen-binding domain recognizes a conformational epitope can be assessed as follows. IL-6R-expressing cells are prepared for the above purpose. A test antigen-binding molecule containing an IL-6R antigen-binding domain can be determined to recognize a conformational epitope when it strongly binds to IL-6R-expressing cells upon contact, but does not substantially bind to an immobilized linear peptide comprising an amino acid sequence forming the extracellular domain of IL-6R. Herein, "not substantially bind" means that the binding activity is 80% or less, generally 50% or less, preferably 30% or less, and particularly preferably 15% or less compared to the binding activity towards cells expressing human IL-6R.

Methods for assaying the binding activity of a test antigen-binding molecule containing an IL-6R antigen-binding domain towards IL-6R-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using IL-6R-expressing cells as antigen.

In the ELISA format, the binding activity of a test antigen-binding molecule containing an IL-6R antigen-binding domain towards IL-6R-expressing cells can be assessed quantitatively by comparing the levels of signal generated by enzymatic reaction. Specifically, a test polypeptide complex is added to an ELISA plate onto which IL-6R-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody binding titer for IL-6R-expressing cells can be determined to compare the binding activity of the test antigen-binding molecule towards IL-6R-expressing cells.

The binding of a test antigen-binding molecule towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of a test antigen-binding molecule containing an IL-6R antigen-binding domain towards an antigen include, for example, the following method. First, IL-6R-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IL-6R antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IL-6R protein immobilized to the wells of a microtiter plate is pre-incubated in the presence or absence of a candidate competitor antigen-binding molecule, and then a test antigen-binding molecule is added thereto. The quantity of test antigen-binding molecule bound to the IL-6R protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IL-6R protein-coated wells.

The quantity of the test antigen-binding molecule bound to the wells via the IL-6R protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IL-6R antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or compete for the binding to the same epitope.

When the structure of an epitope bound by a test antigen-binding molecule containing an IL-6R antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, IL-6R-expressing cells and cells expressing IL-6R with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 μg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IL-6R" can be assessed, for example, by the following method. First, the test and control antigen-binding molecules bound to cells expressing mutant IL-6R are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value ($\Delta$Geo-Mean) can be calculated according to Formula 1 below to determine the ratio of increase in fluorescence intensity as a result of the binding by the antigen-binding molecule.

$$\Delta\text{Geo-Mean}=\text{Geo-Mean (in the presence of the polypeptide complex)}/\text{Geo-Mean (in the absence of the polypeptide complex)} \quad \text{Formula 1:}$$

The Geometric Mean comparison value ($\Delta$Geo-Mean value for the mutant IL-6R molecule) determined by the above analysis, which reflects the quantity of a test antigen-binding molecule bound to cells expressing mutant IL-6R, is compared to the $\Delta$Geo-Mean comparison value that reflects the quantity of the test antigen-binding molecule bound to IL-6R-expressing cells. In this case, the concentrations of the test antigen-binding molecule used to determine the $\Delta$Geo-Mean comparison values for IL-6R-expressing cells and cells expressing mutant IL-6R are particularly preferably adjusted to be equal or substantially equal. An antigen-binding molecule that has been confirmed to recognize an epitope in IL-6R is used as a control antigen-binding molecule.

If the $\Delta$Geo-Mean comparison value of a test antigen-binding molecule for cells expressing mutant IL-6R is smaller than the $\Delta$Geo-Mean comparison value of the test antigen-binding molecule for IL-6R-expressing cells by at least 80%, preferably 50%, more preferably 30%, and particularly preferably 15%, then the test antigen-binding molecule "does not substantially bind to cells expressing mutant IL-6R". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Target Tissue

The term "target tissue" as used herein refers to a tissue containing cells carrying antigens to which the antigen-binding molecules of the present invention bind in a manner dependent on compounds. It is a tissue that yields positive pharmacological effects for the organism carrying the tissue, when the antigen-binding molecules bind to a membrane-type molecule expressed on the cells or bind to a soluble molecule present in the tissue. In this case, the phrase "positive pharmacological effects" refers to effects that relieve, alleviate, ameliorate, or cure symptoms brought about by pathological sites containing the target tissue for the organism carrying the tissue. When the symptoms are brought about by malignant tumors such as cancer, a non-limiting embodiment of a mechanism that yields such a pharmacological effect is, for example, cytotoxic activity and growth inhibition against cancer cells, and immunostimulation in cancer tissues. In the case of inflammatory diseases, examples of such a non-limiting embodiment of the mechanism include immunosuppression and activity to block actions of inflammatory cytokines in inflammatory tissues.

Cancer Tissue-Specific Compounds

The term "compound specific to a cancer tissue (cancer tissue-specific compound)" as used herein refers to a compound differentially present in cancer tissues as compared to non-cancerous tissues. Herein, the term "cancer" is generally used to describe malignant neoplasms, which may be metastatic or non-metastatic. Non-limiting examples of carcinomas developed from epithelial tissues such as skin or digestive tract include brain tumor, skin cancer, head and neck cancer, esophageal cancer, lung cancer, stomach cancer, duodenal cancer, breast cancer, prostate cancer, cervical cancer, endometrial cancer, pancreatic cancer, liver cancer, colorectal cancer, colon cancer, bladder cancer, and ovarian cancer. Non-limiting examples of sarcomas developed from non-epithelial (interstitial) tissues such as muscles include osteosarcoma, chondrosarcoma, rhabdomyosarcoma, leiomyosarcoma, liposarcoma, and angiosarcoma. Non-limiting examples of hematological cancer derived from hematopoietic organs include malignant lymphomas including Hodgkin's lymphoma and non Hodgkin's lymphoma; leukemia including acute myelocytic leukemia or chronic myelocytic leukemia, and acute lymphatic leukemia or chronic lymphatic leukemia; and multiple myeloma. The term "neoplasm" widely used herein refers to any newly formed diseased tissue tumor. In the present invention, neoplasms cause formation of tumors, which are partly characterized by angiogenesis. Neoplasms may be benign such as hemangioma, glioma, or teratoma, or malignant such as carcinoma, sarcoma, glioma, astrocytoma, neuroblastoma, or retinoblastoma.

The term "cancer tissue" refers to a tissue containing at least one cancer cell. Therefore, as cancer tissues contain cancer cells and blood vessels, it refers to all cell types contributing to the formation of a tumor mass containing cancer cells and endothelial cells. Herein, "tumor mass" refers to a foci of tumor tissue. The term "tumor" is generally used to mean a benign neoplasm or a malignant neoplasm.

For example, in several embodiments, cancer tissue-specific compounds may be compounds defined by qualitative properties of cancer tissues such as being present in cancer tissues but absent in non-cancer tissues, or being absent in cancer tissues but present in non-cancer tissues. In other embodiments, cancer tissue-specific compounds may be compounds defined by quantitative properties of cancer tissues such as being present in cancer tissues at a concentration different (for example, higher concentration or lower concentration) from that in non-cancer tissues. For example, cancer tissue-specific compounds are present differentially at arbitrary concentrations. Generally, cancer tissue-specific compounds can be present at a concentration increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 2-fold, at least 5-fold, at least 10-fold, at least 50-fold, at least 100-fold, at least $10^3$-fold, at least $10^4$-fold, at least $10^5$-fold, at least $10^6$-fold, or more, or up to infinity (i.e., when the compound is absent in non-cancerous tissues). Alternatively, they can generally be present at a concentration decreased by at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, or at least 100% (i.e., absent). Preferably, cancer tissue-specific compounds are differentially present at statistically significant concentrations (that is, as determined using either Welch's t-test or Wilcoxon rank sum test, the p value is less than 0.05 and/or the q value is less than 0.10). Examples of a non-limiting embodiment of a cancer tissue-specific compound include compounds which are cancer tissue-specific metabolites produced by metabolic activities characteristic of cancer cells, immune cells, or stromal cells contained in cancer tissues, such as those described below (cancer tissue-specific metabolites, cancer cell-specific metabolites, metabolites specific to immune cells that infiltrated into cancer tissues, and cancer stromal cell-specific metabolites).

Cancer Tissue-Specific Metabolites

The term "metabolism" refers to chemical changes that take place in biological tissues and includes "anabolism" and "catabolism". Anabolism refers to biosynthesis or accumulation of molecules, and catabolism refers to degradation of molecules. "Metabolites" are intermediates or products that arise from metabolism. "Primary metabolites" refers to metabolites directly involved in the process of growth or proliferation of cells or organisms. "Secondary metabolites" refer to products that are not directly involved in such process of growth or proliferation, and are products such as pigments or antibiotics that are produced as a result of metabolism which biosynthesizs substances that are not directly involved in biological phenomena common to cells and organisms. The metabolites may be metabolites of "biopolymers", or they may be metabolites of "small molecules". "Biopolymers" are polymers comprising one or more types of repeating units. Biopolymers are generally found in biological systems, and examples include cells forming the organism and intercellular matrices that adhere to them, molecules having a molecular weight of approximately 5000 or more which form structures such as interstitial matrices, particularly polysaccharides (carbohydrates and such), peptides (this term is used so as to include polypeptides and proteins), and polynucleotides, and similarly their analogs such as compounds composed of or including amino acid analogs or non-amino acid groups. "Small molecules" refers to natural chemical substances other than "biopolymers" that exist in vivo. Suitable examples of a non-limiting embodiment of a cancer tissue-specific metabolite described herein include cancer cell-specific small-molecule metabolites (Eva Gottfried, Katrin Peter and Marina P. Kreutz, From Molecular to Modular Tumor Therapy (2010) 3 (2), 111-132). In addition, metabolites that are highly produced by immune cells that infiltrate into cancer tissues, and metabolites that are highly produced by stromal cells that support the survival and/or growth of cancer cells (cancer stromal cells or cancer associated stromal fibroblasts (CAF)) are also included. Infiltrating immune cells are, for example, dendritic cells, inhibitory dendritic cells, inhibitory T cells, exhausted T cells, and myeloma derived suppressor cells (MDSC). Furthermore, metabolites of the present invention include compounds released from inside the cells to outside the cells when cells present in cancer tissues (cancer cells, immune cells, or stromal cells) die due to apoptosis, necrosis, or such.

To identify cancer cell-specific metabolites, metabolomic analyses focused on metabolic profiling can be suitably used, in addition to transcriptome-level analyses (for example, Dhanasekaran et al. (Nature (2001) 412, 822-826), Lapointe et al. (Proc. Natl. Acad. Sci. U.S.A. (2004) 101, 811-816) or Perou et al. (Nature (2000) 406, 747-752)) and proteome-level analyses (for example, Ahram et al. (Mol. Carcinog. (2002) 33, 9-15), Hood et al. (Mol. Cell. Proteomics (2005) 4, 1741-1753)). More specifically, to identify metabolites in test samples, metabolic profiling that uses high-pressure liquid chromatography (HPLC), nuclear magnetic resonance (NMR) (Brindle et al. (J. Mol. Recognit. (1997) 10, 182-187), mass spectrometry (Gates and Sweeley (Clin. Chem. (1978) 24, 1663-1673) (GC/MS and LC/MS)), and ELISA or such individually and/or in combination may be used appropriately.

These studies elucidated heterogeneity within the constituted tumors which results from changing the concentration gradient of growth factors and metabolites (glucose, oxygen, or such) that enable cancer cell growth under low oxygen pressure conditions (Dang and Semenza (Trends Biochem. Sci. (1999) 24, 68-72)). In these studies, cell line models are also used to understand the change in energy utilization pathway depending on the different malignancy levels of tumors (Vizan et al. (Cancer Res. (2005) 65, 5512-5515)). Examples of a non-limiting embodiment of the technical components of the metabolomics platform include sample extraction, separation, detection, spectroscopic analysis, data normalization, description of class-specific metabolites, pathway mapping, confirmation, and functional characterization of candidate metabolites described by Lawton et al. (Pharmacogenomics (2008) 9, 383). These methods enable identification of cancer cell-specific metabolites in desired cancer tissues.

Examples of a non-limiting embodiment of cancer tissue-specific compounds or cancer tissue-specific metabolites used in the present invention preferably include at least one compound selected from the compounds below. At least one compound means that in addition to cases where the antigen-binding activity of a same antigen-binding domain described below depends on one type of cancer tissue-specific compound or metabolite, cases where it depends on several types of cancer tissue-specific compounds or metabolites are included.

(1) Primary Metabolites of the Krebs Cycle or of the Glycolytic System Such as Lactic Acid, Succinic Acid, and Citric Acid Preferable examples of a non-limiting embodiment of a cancer tissue-specific compound, particularly a cancer cell-specific metabolite, used in the present invention include primary metabolites such as lactic acid, succinic acid, and citric acid, which are produced as a result of glucose metabolism, and are present at higher concentrations in cancer tissues as compared to in the surrounding non-cancerous tissues. The glycolytic system phenotype, which is characterized as an up-regulation of enzymes of the glycolytic system (Embden-Meyerhof pathway) such as pyruvate kinase, hexokinase, and lactic acid dehydrogenase (LDH), has been conventionally known to be a characteristic of solid tumors as Warburg effect.

That is, in tumor cells, high expression of the pyruvate kinase isoform M2 which is necessary for anaerobic glycolysis, and not isoform M1, is considered to be working advantageously for the growth of tumor cells in vivo (Christofk et al. (Nature (2008) 452, 230-233). Pyruvic acid produced by pyruvate kinase is subjected to feedback inhibition by lactic acid produced as a result of equilibrium reaction by lactic acid dehydrogenase (LDH) under anaerobic conditions. Since the feedback inhibition causes promotion of respiration in mitochondria (Krebs cycle) and cell growth inhibition, up regulation of LDH, hexokinase, and glucose transporter (GLUT) is said to play an important role in the proliferation of cancer cells (Fantin et al. (Cancer Cell (2006) 9, 425-434)). Glucose is metabolized by the glycolytic system, and the final metabolite lactic acid is transported together with protons to the tumor surrounding, and as a result, the pH of the tissues surrounding the tumor is said to become acidic. Lactic acid, which is the final product of the glycolytic pathway, as well as succinic acid and citric acid produced by promotion of respiration in mitochondria are known to be accumulated in cancer tissues (Teresa et al. (Mol. Cancer (2009) 8, 41-59)). Examples of a non-limiting embodiment of cancer tissue-specific compounds, particularly cancer cell-specific metabolites, used in the present invention preferably include such primary metabolites such as lactic acid, succinic acid, and citric acid produced by metabolism by the glycolytic pathway. Furthermore, succinic acid which is present at high concentration in cells is known to leak out to the outside of the cells upon cell death (Nature Immunology, (2008) 9, 1261-1269). Therefore, succinic acid concentration is thought to be increased in cancer tissues in which cell death occurs frequently.

(2) Amino Acids Such as Alanine, Glutamic Acid, and Aspartic Acid

Besides the above-mentioned glucose metabolism, the amino acid metabolism is also known to be altered in tumor cells which require continuous supply of essential amino acids and non-essential amino acids that are necessary for the biosynthesis of biopolymers under anaerobic conditions. Glutamine which contains two nitrogens in its side chain acts as a nitrogen transporter, and is an amino acid that is most widely distributed in an organism. Tumor cells, in which the rate of glutamine uptake into cells is increased, is said to be functioning as a glutamine trap. Such increase in the uptake of glutamine and activity of converting into glutamic acid and lactic acid is called "glutaminolysis", and is considered to be a characteristic of transformed (tumor) cells (Mazurek and Eigenbrodt (Anticancer Res. (2003) 23, 1149-1154); and Mazurek et al. (J. Cell. Physiol. (1999) 181, 136-146)). As a result, cancer patients show an increase in glutamic acid concentration while showing a decrease in plasma glutamine level (Droge et al. (Immunobiology (1987) 174, 473-479)). Furthermore, correlation was observed between concentrations of $^{13}$C-labeled succinic acid, $^{13}$C-labeled alanine, $^{13}$C-labeled glutamic acid, and $^{13}$C-labeled citric acid in studies on $^{13}$C-radiolabeled glucose metabolism in lung cancer tissues. Suitable examples of a non-limiting embodiment of cancer tissue-specific compounds used in this invention include alanine, glutamic acid, and aspartic acid which accumulate at high concentrations in cancer tissues through such glutaminolysis and the like.

(3) Amino Acid Metabolite Such as Kynurenine

Indolamine 2,3-dioxygenase (IDO) is a tryptophan-metabolizing enzyme which is highly expressed in many cancers such as melanoma, colon cancer, and kidney cancer (Uyttenhove et al. (Nat. Med. (2003) 9, 1269-127)); and it is known to have two isoforms (Lob et al. (Cancer Immunol. Immunother. (2009) 58, 153-157)). IDO catalyzes the conversion of tryptophan to kynurenine (shown as Compound 1), and is the first enzyme in the nicotinamide nucleotide (NAD) de novo pathway. Furthermore, in glioma which does not express IDO, kynurenine is produced from tryptophan by tryptophan 2,3-dioxygenase (TDO) in the liver (Opitz et al. (Nature (2011) 478, 7368, 197-203)). IDO is also expressed in dendritic cells infiltrated into cancer tissues, and dendritic cells also produce kynurenine (J. Immunol. (2008) 181, 5396-5404). IDO is also expressed in myeloid-derived suppressor cells (MDSC) in cancer tissues, and MDSC also produces kynurenine (Yu et al. (J. Immunol. (2013) 190, 3783-3797)).

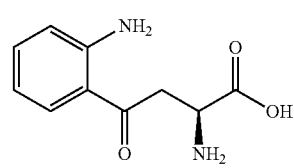

[Compound 1]

Kynurenine is known to suppress the same type of T cell response (Frumento et al. (J. Exp. Med. (2002) 196, 459-

468); and a mechanism has been suggested, in which tumor cells evade antitumor immune responses through such inhibition, and proliferation of glioma cells is promoted through an autocrine proliferation mechanism in which kynurenine acts as an endogenous ligand for the aryl hydrocarbon receptor expressed on gliomas (Optiz et al. (mentioned above)). Kynurenine is converted to anthranilic acid (shown as Compound 2) by kynurenidase, and to 3-hydroxykynurenine (shown as Compound 3) by kynurenine 3-hydroxylase. Anthranilic acid and 3-hydroxykynurenine are both converted to 3-hydroxyanthranilic acid, the precursor of NAD.

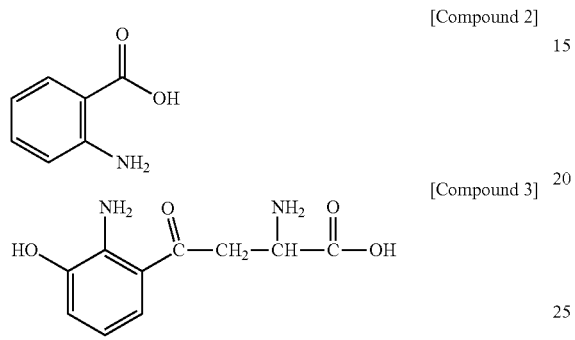

[Compound 2]

[Compound 3]

Kynurenine is converted to kynurenic acid (shown as Compound 4) by kynurenine aminotransferase. Examples of a non-limiting embodiment of cancer tissue-specific compounds, particularly cancer cell-specific metabolites, used in the present invention preferably include such amino acid metabolites such as kynurenine and its metabolites such as anthranilic acid, 3-hydroxykynurenine, and kynurenic acid.

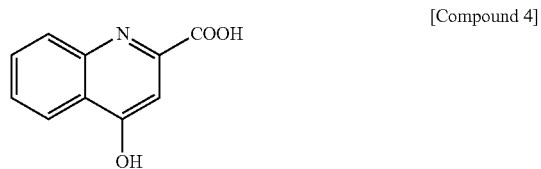 [SMILES: O=C(O)c1cc(O)c2ccccc2n1]

[Compound 4]

(4) Arachidonic Acid Metabolites Such as Prostaglandin E2

Prostaglandin E2 (PGE2) (Compound 5) is an arachidonic acid metabolite called a prostanoid, which includes thromboxane and prostaglandin synthesized by cyclooxygenase (COX)-1/2 (Warner and Mitchell (FASEB J. (2004) 18, 790-804)). PGE2 promotes the proliferation of colon cancer cells and suppresses their apoptosis (Sheng et al. (Cancer Res. (1998) 58, 362-366)). Cyclooxygenase expression is known to be altered in many cancer cells. More specifically, while COX-1 is expressed constitutively in almost all tissues, COX-2 has been found to be mainly induced by certain types of inflammatory cytokines and cancer genes in tumors (Warner and Mitchell (mentioned above)). In addition, COX-2 overexpression has been reported to be related to bad prognosis for breast cancer (Denkert et al. (Clin. Breast Cancer (2004) 4, 428-433)), and rapid disease progression for ovarian cancer (Denker et al. (Mod. Pathol. (2006) 19, 1261-1269)). Inhibitory T cells that have infiltrated into cancer tissues also produce prostaglandin E2 (Curr. Med. Chem. (2011) 18, 5217-5223). Small molecules such as the arachidonic acid metabolites prostaglandin and leukotriene are known to act as a stimulating factor that regulates autocrine and/or paracrine growth of cancer (Nat. Rev. Cancer (2012) 12 (11) 782-792). Examples of a non-limiting embodiment of cancer tissue-specific compounds used in the present invention, particularly cancer cell-specific metabolites and immune cell-specific metabolites that have infiltrated into cancer tissues, preferably include such arachidonic acid metabolites such as prostaglandin E2. Besides prostaglandin E2, production of thromboxane A2 (TXA2) is enhanced in cancer tissues such as colorectal cancer tissues (J. Lab. Clin. Med. (1993) 122, 518-523), and thromboxane A2 can be suitably presented as a non-limiting embodiment of an arachidonic acid metabolite of the present invention.

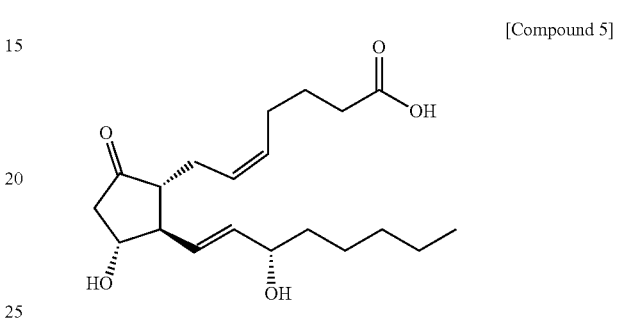

[Compound 5]

(5) Nucleosides Carrying a Purine Ring Structure Such as Adenosine, Adenosine Triphosphate (ATP), Adenosine Diphosphate (ADP), and Adenosine Monophosphate (AMP)

When cancer cells undergo cell death, a large amount of ATP in the cell is known to leak out to the outside of the cells. Therefore, the ATP concentration is remarkably higher in cancer tissues than in normal tissues (PLoS One. (2008) 3, e2599). Multiple types of cells release adenine nucleotides in the form of ATP, ADP, and AMP. Metabolism takes place through an extracellular enzyme on the cell surface such as extracellular 5'-nucleotidase (ecto-5'-nucleotidase) (CD73) (Resta and Thompson (Immunol. Rev. (1998) 161, 95-109) and Sadej et al. (Melanoma Res. (2006) 16, 213-222)). Adenosine is a purine nucleoside that exists constitutively at low concentration in the extracellular environment, but in hypoxic tissues found in solid cancers, a remarkable increase in the extracellular adenosine concentration has been reported (Blay and Hoskin (Cancer Res. (1997) 57, 2602-2605). CD73 is expressed on the surface of immune cells and tumors (Kobie et al. (J. Immunol. (2006) 177, 6780-6786)), and its activity has been found to be increased in breast cancer (Canbolat et al. (Breast Cancer Res. Treat. (1996) 37, 189-193)), stomach cancer (Durak et al. (Cancer Lett. (1994) 84, 199-202)), pancreatic cancer (Flocke and Mannherz (Biochim. Biophys. Acta (1991) 1076, 273-281), and glioblastoma (Bardot et al. (Br. J. Cancer (1994) 70, 212-218)). It has been proposed that the accumulation of adenosine in cancer tissues may be caused by an increase in the intracellular adenosine production through dephosphorylation of AMP by 5'-nucleotidase in the cytoplasm (Headrick and Willis (Biochem. J. (1989) 261, 541-550)). Furthermore, inhibitory T cells and such that have infiltrated into cancer tissues also express ATPase and produce adenosine (Proc. Natl. Acad. Sci. (2006) 103 (35), 13132-13137; Curr. Med. Chem. (2011) 18, 5217-5223). The produced adenosine is considered to be rendering the cancer tissue an immunosuppressive environment through adenosine receptors such as the A2A receptor (Curr. Med. Chem. (2011), 18, 5217-23). Examples of a non-limiting embodiment of the cancer tissue-specific compound used in the present invention preferably include ATP, ADP, AMP, and adenosine which accumulate at high concentration in cancer tissues through such metabolism of purine nucleotides such as ATP. Furthermore, since adenosine is degraded to inosine by adenosine deaminase, inosine accumulates at high concentration.

(6) Uric Acid

Uric acid is a product of the metabolic pathway of purine nucleosides in vivo, and is released to the outside of cells such as the interstitial space and blood. In recent years, it has been found to be released from dead cells that are present at sites of lesions such as cancer tissues (Nat. Med. (2007) 13, 851-856). Examples of a non-limiting embodiment of cancer tissue-specific compounds used in the present invention preferably include such uric acid which accumulates at high concentration in cancer tissues due to metabolism of purine nucleotides such as ATP.

(7) 1-Methyl Nicotinamide

The enzyme nicotinamide N-methyl transferase is known to be highly expressed in several human cancer tissues. When this enzyme produces the stable metabolite 1-methylnicotinamide from nicotinamide, the methyl group of S-adenosylmethionine (SAM) which serves as a methyl donor is consumed; therefore, the high expression of nicotinamide N-methyltransferase has been suggested to contribute to tumorigenesis through a mechanism that impairs the DNA methylation ability accompanying a decrease in the SAM concentration in cancer cells (Ulanovskaya et al. (Nat. Chem. Biol. (2013) 9 (5) 300-306)). The stable metabolite of this enzyme, 1-methylnicotinamide is known to be secreted to the outside of cancer cells (Yamada et al. (J. Nutr. Sci. Vitaminol. (2010) 56, 83-86)), and preferable examples of a non-limiting embodiment of cancer tissue-specific compounds used in the present invention include 1-methylnicotinamide and such which accumulate at high concentration in cancer tissues through nicotinamide metabolism.

Inflammatory Tissue-Specific Compounds

The term "compound specific to inflammatory tissue (inflammatory tissue-specific compound)" as used herein refers to a compound that is present differentially in inflammatory tissues as compared to non-inflammatory tissues. Herein, suitable examples of "inflammatory tissues" include:
joints with rheumatoid arthritis or osteoarthritis;
lungs (alveoli) with bronchial asthma or COPD;
digestive organs of inflammatory bowel disease, Crohn's disease, or ulcerative colitis;
fibrotic tissues of fibrosis of the liver, kidney, or lung;
tissues undergoing rejection reaction in organ transplantation;
blood vessels and heart (myocardium) in arteriosclerosis or heart failure;
visceral fat in metabolic syndrome;
skin tissues in atopic detrmatitis or other dermatitis; and
spinal nerves in disk hemiation or chronic low back pain.

Inflammatory Tissue-Specific Metabolites

"Inflammatory tissue-specific metabolite" refers to metabolites highly produced by immune cells that have infiltrated into inflammatory tissues, and metabolites highly produced by specifically normal cells that have been damaged in inflammatory tissues. Examples of infiltrating immune cells include effector T cells, mature dendritic cells, neutrophils, granule cells (mast cells), and basophils. Furthermore, metabolites in the present invention include compounds that are released from inside the cells to the outside of the cells when the cells that are present in inflammatory tissues (immune cells and normal cells) die by apoptosis, necrosis, or such.

Examples of a non-limiting embodiment of the inflammatory tissue-specific compounds or inflammatory tissue-specific metabolites used in the present invention preferably include at least one compound selected from the compounds below. At least one compound means including cases where the antigen-binding activity of a same antigen-binding domain described below depends on one type of inflammatory tissue-specific compound or metabolite, as well as cases where it depends on several types of inflammatory tissue-specific compounds or metabolites.

(1) Arachidonic Acid Metabolites Such as Prostaglandin E2

The PGE2 concentration has been known to be high in rheumatoid arthritis and osteoarthritis (Eur. J. Clin. Pharmacol. (1994) 46, 3-7.; Clin. Exp. Rheumatol. (1999) 17, 151-160; Am. J. Vet. Res. (2004) 65, 1269-1275). Examples of a non-limiting embodiment of inflamatory tissue-specific compounds, particularly inflammatory tissue-specific metabolites and metabolites specific to immune cells that infiltrate into inflammatory tissues used in the present invention preferably include such arachidonic acid metabolites such as prostaglandin E2.

(2) Nucleosides Carrying a Purine Ring Structure Such as Adenosine, Adenosine Triphosphate (ATP), Adenosine Diphosphate (ADP), and Adenosine Monophosphate (AMP)

ATP concentration is known to be high in pulmonary alveoli where inflammation caused by bronchial asthma is taking place (Nat. Med. (2007) 13, 913-919). ATP concentration is also known to be high in pulmonary alveoli where inflammation caused by COPD is taking place (Am. J. Respir. Crit. Care Med. (2010) 181, 928-934). Furthermore, adenosine concentration has been observed to be high in the joint fluid of rheumatoid arthritis patients (Journal of Pharmaceutical and Biomedical Analysis (2004) 36, 877-882). Furthermore, ATP concentration is known to be high in tissues where a rejection reaction is taking place due to GVHD (Nat. Med. (2010) 16, 1434-1438). Adenosine concentration is known to be enhanced in fibrotic tissues of the liver, kidney, and lung (FASEB J. (2008) 22, 2263-2272; J. Immunol. (2006) 176, 4449-4458; J. Am. Soc. Nephrol. (2011) 22 (5), 890-901; PLoS ONE J. (2010) 5 (2), e9242). Furthermore, ATP concentration has been observed to be increased in fibrotic tissues of pulmonary fibrosis patients (Am. J. Respir. Crit. Care Med. (2010) 182, 774-783). Examples of a non-limiting embodiment of an inflammatory tissue-specific compound used in the present invention suitably include ATP, ADP, AMP, adenosine and such which accumulate at high concentration in inflammatory tissues by metabolism of such purine nucleotides such as ATP. In addition, inosine accumulates at a high concentration due to degradation of adenosine by adenosine deaminase to produce inosine.

(3) Uric Acid

Uric acid is a product of the metabolic pathway of purine nucleosides in vivo, and is released to the outside of cells such as the interstitial space and blood. In recent years, uric acid released from cells undergoing necrosis has been found to promote inflammatory response (J. Clin. Invest. (2010) 120 (6), 1939-1949). Examples of a non-limiting embodiment of inflammatory tissue-specific compounds to be used in the present invention suitably include such uric acid which accumulates at high concentration in inflammatory tissues due to metabolism of purine nucleotides such as ATP.

Antigen-Binding Domain

Herein, an "antigen-binding domain" may be of any structure as long as it binds to an antigen of interest. Such domains preferably include, for example:
antibody heavy-chain and light-chain variable regions;
a module of about 35 amino acids called A domain which is contained in the in vivo cell membrane protein Avimer (International Publication No. WO 2004/044011, International Publication No. WO 2005/040229);

Adnectin containing the 10Fn3 domain which binds to the protein moiety of fibronectin, a glycoprotein expressed on cell membrane (International Publication No. WO 2002/032925);

Affibody which is composed of a 58-amino acid three-helix bundle based on the scaffold of the IgG-binding domain of Protein A (International Publication No. WO 1995/001937);

Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (International Publication No. WO 2002/020565);

Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (International Publication No. WO 2003/029462); and the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (International Publication No. WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')2".

The antigen-binding domains of antigen-binding molecules of the present invention can bind to an identical epitope. Such identical epitope can be present, for example, in a protein comprising the amino acid sequence of SEQ ID NO: 1. Alternatively, each of the antigen-binding domains of antigen-binding molecules of the present invention can bind to a different epitope. Herein, the different epitope can be present in, for example, a protein comprising the amino acid sequence of SEQ ID NO: 1.

Specificity

"Specific" means that one of the molecules that specifically bind does not substantially bind to molecules other than the single or plurality of partner molecules it binds to. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope. Here, "does not substantially bind" is determined according to the method described in the above-mentioned section on binding activity, and refers to the binding activity of a molecule that specifically binds to a molecule other than the partner molecule, where the binding activity is not more than 80%, normally not more than 50%, preferably not more than 30%, or particularly preferably not more than 15% of the binding activity to its partner molecule.

Cytotoxic Activity

In a non-limiting embodiment, the present invention provides antigen-binding molecules that comprise an antigen-binding domain whose antigen-binding activity varies depending on the concentration of a cancer-tissue specific compound, and which have cytotoxic activity against cells expressing a membrane-type molecule on their cell membrane; and pharmaceutical compositions comprising these antigen-binding molecules as an active ingredient. In the present invention, cytotoxic activity includes, for example, antibody-dependent cell-mediated cytotoxicity (ADCC) activity, complement-dependent cytotoxicity (CDC) activity, and cytotoxic activity by T cells. In the present invention, CDC activity refers to cytotoxic activity by the complement system. On the other hand, ADCC activity refers to the activity of immune cells to damage target cells when the immune cells and such bind to the Fc region of antigen-binding molecules comprising an antigen-binding domain that binds to a membrane-type molecule expressed on the cell membrane of target cells via an Fcγ receptor expressed on the immune cells. Whether an antigen-binding molecule of interest has an ADCC activity or whether it has a CDC activity can be determined using known methods (for example, Current Protocols in Immunology, Chapter 7. Immunologic studies in humans, Editor, Coligan et al., (1993)).

Specifically, effector cells, complement solution, and target cells are first prepared.

(1) Preparation of Effector Cells

Spleen is removed from a CBA/N mouse or the like, and spleen cells are dispersed in an RPMI1640 medium (Invitrogen). After the cells are washed in the same medium containing 10% fetal bovine serum (FBS, HyClone), effector cells are prepared by adjusting the spleen cell concentration to $5 \times 10^6$/mL.

(2) Preparation of Complement Solution

Baby Rabbit Complement (CEDARLANE) is diluted 10-fold in a culture medium (Invitrogen) containing 10% FBS to prepare a complement solution.

(3) Preparation of Target Cells

The target cells can be radioactively labeled by culturing cells expressing the antigen with 0.2 mCi of $^{51}$Cr-sodium chromate—(GE Healthcare Bio-Sciences) in a DMEM medium containing 10% FBS for one hour at 37° C. After radioactive labeling, cells are washed three times in an RPMI1640 medium containing 10% FBS, and the target cells can be prepared by adjusting the cell concentration to $2 \times 10^5$/mL.

ADCC activity or CDC activity can be measured by the method described below. In the case of ADCC activity measurement, 50 µL each of the target cell and antigen-binding molecule are added to a 96-well U-bottom plate (Becton Dickinson), and allowed to react for 15 minutes at room temperature. Then, 100 µL of effector cells are added to the plate and this plate is placed in a carbon dioxide incubator for four hours. The final concentration of the antigen-binding molecule may be set, for example, to 0 µg/mL or 10 µg/mL. After incubation, 100 µL of the supernatant is collected from each well, and the radioactivity is measured with a gamma counter (COBRAII AUTO-GAMMA, MODEL D5005, Packard Instrument Company). The cytotoxic activity (%) can be calculated using the measured values according to the equation: $(A-C)/(B-C) \times 100$. A represents the radioactivity (cpm) in each sample, B represents the radioactivity (cpm) in a sample to which 1% NP-40 (Nacalai Tesque) has been added, and C represents the radioactivity (cpm) of a sample containing the target cells alone.

Meanwhile, in the case of CDC activity measurement, 50 µL of target cell and 50 µL of an antigen-binding molecule are added to a 96-well flat-bottomed plate (Becton Dickinson), and allowed to react for 15 minutes on ice. Then, 100 µL of a complement solution is added to the plate, and this plate is placed in a carbon dioxide incubator for four hours. The final concentration of the antigen-binding molecule may be set, for example, to 0 µg/mL or 3 µg/mL. After incubation, 100 µL of supernatant is collected from each well, and the radioactivity is measured with a gamma counter. The cytotoxic activity can be calculated in the same way as in the determination of ADCC activity.

The later-described modified antigen-binding molecules to which cytotoxic substances such as chemotherapeutic agents, toxic peptides, or radioactive chemical substances have been ligated can also be suitably used as the antigen-binding molecules of the present invention having cytotoxic activity. Such modified antigen-binding molecules (hereinafter referred to as "antigen-binding molecule-drug conjugate") can be obtained by chemically modifying the obtained antigen-binding molecules. Methods that have been already established in the field of antibody-drug conjugates and such may be used appropriately as a method for modifying antigen-binding molecules. Furthermore, a modified antigen-binding molecule with a linked toxic peptide can be obtained by expressing in an appropriate host cell a fusion gene produced by linking a gene encoding the toxic peptide in frame with a gene encoding an antigen-binding molecule of the present invention, and then isolating the molecule from the culture solution of the cells.

Neutralizing Activity

The present invention provides in a non-limiting embodiment a pharmaceutical composition that induces an immune response, comprising as an active ingredient an antigen-binding molecule that contains an antigen-binding domain whose antigen-binding activity varies depending on the concentration of a cancer tissue-specific compound and has a neutralizing activity against a membrane-type molecule. In another non-limiting embodiment, the present invention provides a pharmaceutical composition that induces an immune response, comprising as an active ingredient an antigen-binding molecule that contains an antigen-binding domain whose antigen-binding activity varies depending on the concentration of a cancer tissue-specific compound and has a neutralizing activity against a membrane-type molecule in addition to a cytotoxic activity against cells expressing the membrane-type molecule on their cell membrane. Generally, a neutralizing activity refers to an activity of inhibiting the biological activity of a ligand which has a biological activity towards cells, such as viruses and toxins. Thus, a substance having a neutralizing activity refers to a substance that binds to a ligand or a receptor to which the ligand binds and inhibits the binding between the ligand and the receptor. A receptor whose binding to the ligand has been blocked by the neutralizing activity will not be able to exhibit the biological activity through the receptor. When the antigen-binding molecule is an antibody, the antibody having such a neutralizing activity is generally called a neutralizing antibody. The neutralizing activity of a test substance may be measured by comparing the biological activities in the presence of a ligand between conditions when the test substance is present or absent.

A suitable example of a major ligand for the IL-6 receptor is IL-6, which is shown in SEQ ID NO: 27. The IL-6 receptor, which is an I-type membrane protein whose amino terminus forms the extracellular domain, forms a heterotetramer with the gp130 receptor which was induced by IL-6 to dimerize (Heinrich et al. (Biochem. J. (1998) 334, 297-314)). Formation of the heterotetramer activates Jak associated with the gp130 receptor. Jak carries out autophosphorylation and receptor phosphorylation. The phosphorylation sites of the receptor and of Jak serve as binding sites for molecules belonging to the Stat family having SH2 such as Stat3, and for the MAP kinases, PI3/Akt, and other proteins and adapters having SH2. Next, Stat that bound to the gp130 receptor is phosphorylated by Jak. The phosphorylated Stat dimerizes and translocates to the nucleus, and regulates transcription of target genes. Jak and Stat can also be involved in the signaling cascade through receptors of other classes. A deregulated IL-6 signaling cascade is observed in inflammation and pathological conditions of autoimmune diseases, and cancers such as prostate cancer and multiple myeloma. Stat3 which may act as an oncogene is constitutively activated in many cancers. In prostate cancer and multiple myeloma, there is a crosstalk between the signaling cascade from the IL-6 receptor and the signaling cascade from members of the epidermal growth factor receptor (EGFR) family (Ishikawa et al. (J. Clin. Exp. Hematopathol. (2006) 46 (2), 55-66)).

Such intracellular signaling cascades are different for each cell type; therefore, an appropriate target molecule can be set according to each of the target cells of interest, and the target molecule is not limited to the above-mentioned factors. The neutralization activity can be evaluated by measuring the in vivo signal activation. Furthermore, activation of in vivo signals can also be detected by using as an indicator the transcription-inducing action on a target gene that exists downstream of the in vivo signaling cascade. A change in the transcription activity of a target gene can be detected by the principle of a reporter assay. Specifically, a reporter gene such as the green fluorescence protein (GFP) or luciferase is placed downstream of a transcription factor or a promoter region of the target gene; and a change in transcription activity can be measured in terms of reporter activity by measuring the reporter activity. Commercially available kits for measuring in vivo signal activation can be suitably used (for example, the Mercury Pathway Profiling Luciferase System (Clontech)).

Furthermore, as a method for measuring the neutralization activity on a receptor ligand in the EGF receptor family and such which acts on a signaling cascade that typically works toward enhancing cell proliferation, neutralization activity of an antigen-binding molecule can be evaluated by measuring the proliferation activity of the target cells. For example, the following method is suitably used as a method for measuring or evaluating inhibitory effects based on the neutralization activity of an anti-HB-EGF antibody against the proliferation of cells whose proliferation is promoted by EGF family growth factors such as HB-EGF. As a method for evaluating or measuring the activity of inhibiting cell proliferation in a test tube, a method that measures the incorporation by living cells of [$^3$H]-labeled thymidine added to the culture medium as an index of the DNA replication ability is used. As a more convenient method, a dye exclusion method that measures under a microscope the ability of a cell to release a dye such as trypan blue to the outside of the cell, or the MTT method is used. The latter makes use of the ability of living cells to convert 3-(4,5-dimethylthiazol-2-yl)-2,5-diphenyl tetrazolium bromide (MTT), which is a tetrazolium salt, to a blue formazan product. More specifically, a test antibody is added along with a ligand to the culture solution of a test cell; and after a certain period of time has elapsed, an MTT solution is added to the culture, and this is left to stand for a certain amount of time to let the cell incorporate MTT. As a result, MTT which is a yellow compound is converted to a blue compound by succinate dehydrogenase in the mitochondria of the cell. After this blue product is dissolved for coloration, its absorbance is measured and used as an indicator of the number of viable cells. Besides MTT, reagents such as MTS, XTT, WST-1, and WST-8 are also commercially available (Nacalai Tesque, and such), and can be suitably used. For measurement of the activity, a binding antibody that has the same isotype as the anti-HB-EGF antibody but does not have the cell proliferation-inhibiting activity can be used as a control antibody in the same manner as the anti-HB-EGF antibody, and the anti-HB-EGF antibody is judged to have the activity when it shows a stronger cell proliferation-inhibiting activity than the control antibody.

As cells for evaluating activity, for example, cells showing HB-EGF-promoted proliferation such as the RMG-1 cell line which is an ovarian cancer cell line may be suitably used; and mouse Ba/F3 cells transformed with a vector in which a gene encoding hEGFR/mG-CSFR, which is a fusion protein of the extracellular domain of human EGFR fused in frame with the intracellular domain of the mouse G-CSF receptor, is linked so as to allow expression, may also be suitably used. This way, those skilled in the art may appropriately select cells for evaluating activity to measure the cell proliferation activity mentioned above.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4. A number of allotype sequences of human IgG1, human IgG2, human IgG3, and human IgG4 constant regions due to gene polymorphisms are described in "Sequences of proteins of immunological interest", NIH Publication No. 91-3242. Any of such sequences may be used in the present invention. In particular, for the human IgG1 sequence, the amino acid sequence at positions 356 to 358 as indicated by EU numbering may be DEL or EEM. Several allotype sequences due to genetic polymorphisms have been described in "Sequences of proteins of immunological interest", NIH Publication No. 91-3242 for the human Igκ (Kappa) constant region and human Igλ (Lambda) constant region, and any of the sequences may be used in the present invention.

Methods for producing an antibody with desired binding activity are known to those skilled in the art. Below is an example that describes a method for producing an antibody that binds to IL-6R (anti-IL-6R antibody). Antibodies that bind to an antigen other than IL-6R can also be produced according to the example described below.

Anti-IL-6R antibodies can be obtained as polyclonal or monoclonal antibodies using known methods. The anti-IL-6R antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IL-6R protein as a sensitizing antigen. Resulting immune cells are fused with known parental cells by conventional cell fusion methods. Then, hybridomas producing an anti-IL-6R antibody can be selected by screening for monoclonal antibody-producing cells using conventional screening methods.

Specifically, monoclonal antibodies are prepared as mentioned below. First, the IL-6R gene whose nucleotide sequence is disclosed in SEQ ID NO: 2 can be expressed to produce an IL-6R protein shown in SEQ ID NO: 1, which will be used as a sensitizing antigen for antibody preparation. That is, a gene sequence encoding IL-6R is inserted into a known expression vector, and appropriate host cells are transformed with this vector. The desired human IL-6R protein is purified from the host cells or their culture supernatants by known methods. In order to obtain soluble IL-6R from culture supernatants, for example, a protein consisting of the amino acids at positions 1 to 357 in the IL-6R polypeptide sequence of SEQ ID NO: 1, such as described in Mullberg et al. (J. Immunol. (1994) 152 (10), 4958-4968), is expressed as a soluble IL-6R, instead of the IL-6R protein of SEQ ID NO: 1. Purified natural IL-6R protein can also be used as a sensitizing antigen.

The purified IL-6R protein can be used as a sensitizing antigen for immunization of mammals. A partial IL-6R peptide may also be used as a sensitizing antigen. In this case, a partial peptide can be prepared by chemical synthesis based on the amino acid sequence of human IL-6R, or by inserting a partial IL-6R gene into an expression vector for expression. Alternatively, a partial peptide can be produced by degrading an IL-6R protein with a protease. The length and region of the partial IL-6R peptide are not limited to particular embodiments. A preferred region can be arbitrarily selected from the amino acid sequence at amino acid positions 20 to 357 in the amino acid sequence of SEQ ID NO: 1. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IL-6R protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IL-6R to be used as a sensitizing antigen, and immunization methods using IL-6R are specifically described in WO 2003/000883, WO 2004/022754, WO 2006/006693, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection administration of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as IL-6R; and
there is no need to purify the antigen for immunization.

In order to prepare a monoclonal antibody of the present invention using DNA immunization, first, a DNA expressing an IL-6R protein is administered to an animal to be immunized. The IL-6R-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized IL-6R can also be produced by the methods described in WO 2003/104453.

After immunizing a mammal as described above, an increase in the titer of an IL-6R-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:
P3(P3x63Ag8.653) (J. Immunol. (1979) 123 (4), 1548-1550);
P3x63Ag8U.1 (Current Topics in Microbiology and Immunology (1978) 81, 1-7);
NS-1 (C. Eur. J. Immunol. (1976) 6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);
S194/5.XX0.BU.1 (J. Exp. Med. (1978) 148 (1), 313-323);
R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an IL-6R-binding monoclonal antibody can bind to IL-6R expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, IL-6R-expressing cells are first prepared. Cells preferably used for screening are mammalian cells in which IL-6R is forcedly expressed. As control, the activity of an antibody to bind to cell-surface IL-6R can be selectively detected using non-transformed mammalian cells as host cells. Specifically, hybridomas producing an anti-IL-6R monoclonal antibody can be isolated by selecting hybridomas that produce an antibody which binds to cells forced to express IL-6R, but not to host cells.

Alternatively, the activity of an antibody to bind to immobilized IL-6R-expressing cells can be assessed based on the principle of ELISA. For example, IL-6R-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IL-6R antibody is prepared from hybridoma cells expressing the anti-IL-6R antibody. For this purpose, total RNA is first extracted from hybridomas. Methods used for extracting mRNAs from cells include, for example:
the guanidine ultracentrifugation method (Biochemistry (1979) 18(24), 5294-5299), and
the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. U.S.A. (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into *E. coli* or such. After colony selection, the desired recombinant vector can be prepared from the colony-forming *E. coli*. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding 1γ1, γ2a, γ2b, and γ3 heavy chains and K and X light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

PCR products thus amplified are used to reshape immunoglobulins composed of a combination of heavy and light chains. A desired antibody can be selected using the IL-6R-binding activity of a reshaped immunoglobulin as an indicator. For example, when the objective is to isolate an antibody against IL-6R, it is more preferred that the binding of the antibody to IL-6R is specific. An IL-6R-binding antibody can be screened, for example, by the following steps:

(1) contacting an IL-6R-expressing cell with an antibody comprising the V region encoded by a cDNA isolated from a hybridoma;

(2) detecting the binding of the antibody to the IL-6R-expressing cell; and (3) selecting an antibody that binds to the IL-6R-expressing cell.

Methods for detecting the binding of an antibody to IL-6R-expressing cells are known. Specifically, the binding of an antibody to IL-6R-expressing cells can be detected by the above-described techniques such as FACS. Immobilized samples of IL-6R-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IL-6R antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IL-6R antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region. A chimeric antibody expression vector is constructed by fusing in frame the two genes digested with the same combination of restriction enzymes.

To produce an anti-IL-6R monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples below, a peptide having the amino acid sequence MGWSCI-ILFLVATATGVHS (SEQ ID NO: 3) is used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IL-6R antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994/011523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.

(1) mammalian cells: CHO (Chinese hamster ovary cell line), COS (Monkey kidney cell line), myeloma (Sp2/0, NS0, etc.), BHK (baby hamster kidney cell line), HeLa, Vero, HEK293 (human embryonic kidney cell line with sheared adenovirus (Ad)5 DNA), PER.C6 cell (human embryonic retinal cell line transformed with the Adenovirus Type 5 (Ad5) E1A and E1B genes) and such (Current Protocols in Protein Science (May, 2001, Unit 5.9, Table 5.9.1));

(2) amphibian cells: *Xenopus* oocytes, or such; and (3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces serevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat 3-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When an antigen-binding molecule described herein is administered to human, an antigen-binding domain derived from a genetically recombinant antibody that has been artificially altered to reduce the heterologous antigenicity against human and such, can be appropriately used as the antigen-binding domain of the antigen-binding molecule. Such genetically recombinant antibodies include, for example, humanized antibodies. These altered antibodies are appropriately produced by known methods.

An antibody variable region used to produce the antigen-binding domain of an antigen-binding molecule described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

EU Numbering and Kabat Numbering

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated by Kabat numbering, while constant region amino acids are indicated by EU numbering based on Kabat's amino acid positions.

Antigen-Binding Domains Dependent on a Target Tissue-Specific Compound

To obtain an antigen-binding domain (or an antigen-binding molecule containing the domain) whose antigen-binding activity varies depending on the concentration of a target tissue-specific compound, or more specifically, an antigen-binding domain (or an antigen-binding molecule containing the domain) dependent on a target tissue-specific compound, the methods indicated in the above section on binding activity may be appropriately applied. As a non-limiting embodiment, some specific examples of the methods are presented below. For example, to confirm that the antigen-binding activity of an antigen-binding domain (or an antigen-binding molecule containing the domain) in the presence of a target tissue-specific compound becomes higher than the antigen-binding activity of an antigen-binding domain (or an antigen-binding molecule containing the domain) in the absence of the compound, the antigen-binding activities of the antigen-binding domain (or the antigen-binding molecule containing the domain) in the presence and absence of the target tissue-specific compound or in the presence of high and low concentrations of the compound are compared. In another non-limiting embodiment, for example, to confirm that the antigen-binding activity of an antigen-binding domain (or an antigen-binding molecule containing the domain) in the presence of a high concentration of a target tissue-specific compound becomes higher than the antigen-binding activity of an antigen-binding domain (or an antigen-binding molecule containing the domain) in the presence of a low concentration of the compound, the antigen-binding activities of the antigen-binding domain (or the antigen-binding molecule containing the domain) in the presence of high and low concentrations of the target tissue-specific compound are compared.

Furthermore, in the present invention, the phrase "the antigen-binding activity in the presence of a target tissue-specific compound is higher than the antigen-binding activity in the absence of the compound" can be alternatively expressed as "the antigen-binding activity of an antigen-binding domain (or an antigen-binding molecule containing the domain) in the absence of a target tissue-specific compound is lower than the antigen-binding activity in the presence of the compound". Furthermore, in the present invention, "the antigen-binding activity of an antigen-binding domain (or an antigen-binding molecule containing the domain) in the absence of a target tissue-specific compound is lower than the antigen-binding activity in the presence of the compound" may be alternatively described as "the antigen-binding activity of an antigen-binding domain (or an antigen-binding molecule containing the domain) in the absence of a target tissue-specific compound is weaker than the antigen-binding activity in the presence of the compound".

Furthermore, in the present invention, the phrase "the antigen-binding activity in the presence of a high concentration of a target tissue-specific compound is higher than the antigen-binding activity in the presence of a low concentration of the compound" can be alternatively expressed as "the antigen-binding activity of an antigen-binding domain (or an antigen-binding molecule containing the domain) in the presence of a low concentration of a target tissue-specific compound is lower than the antigen-binding activity in the presence of a high concentration of the compound". In the present invention, "the antigen-binding activity of an antigen-binding domain (or an antigen-binding molecule containing the domain) in the presence of a low concentration of a target tissue-specific compound is lower than the antigen-binding activity in the presence of a high concentration of the compound" may be alternatively described as "the antigen-binding activity of an antigen-binding domain (or an antigen-binding molecule containing the domain) in the presence of a low concentration of a target tissue-specific compound is weaker than the antigen-binding activity in the presence of a high concentration of the compound".

Conditions when measuring antigen-binding activity other than the concentration of a target tissue-specific compound are not particularly limited, and can be selected appropriately by those skilled in the art. For example, it is possible to measure under conditions of HEPES buffer and 37° C. For example, Biacore (GE Healthcare) or such can be used for measurement. When the antigen is a soluble molecule, the activity of an antigen-binding domain (or an antigen-binding molecule containing the domain) to bind to the soluble molecule can be determined by loading the antigen as an analyte onto a chip immobilized with the antigen-binding domain (or an antigen-binding molecule containing the domain). Alternatively, when the antigen is a membrane-type molecule, the binding activity towards the membrane-type molecule can be determined by loading the antigen-binding domain (or an antigen-binding molecule containing the domain) as an analyte onto a chip immobilized with the antigen.

As long as the antigen-binding activity of an antigen-binding domain (or an antigen-binding molecule containing the domain) contained in antigen-binding molecules of the present invention in the absence of a target tissue-specific compound is weaker than the antigen-binding activity in the presence of the target tissue-specific compound, the ratio between the antigen-binding activity in the absence of the compound and the antigen-binding activity in the presence of the compound is not particularly limited. However, the value of KD (in the absence of the compound)/KD (in the presence of the compound), which is a ratio of dissociation constant (KD) against an antigen in the absence of the target tissue-specific compound to KD in the presence of the compound, is preferably 2 or greater, more preferably 10 or greater, and still more preferably 40 or greater. The upper limit of the value of KD (in the absence of the compound)/KD (in the presence of the compound) is not particularly limited, and may be any value, for example, 400, 1,000, or 10,000, as long as it can be provided by the technologies of those skilled in the art. When antigen-binding activity is not observed in the absence of the target tissue-specific compound, the value of the upper limit is infinity.

As long as the antigen-binding activity of an antigen-binding domain (or an antigen-binding molecule containing the domain) contained in antigen-binding molecules of the present invention in the presence of a low concentration of a target tissue-specific is weaker than the antigen-binding activity in the presence of a high concentration of the target tissue-specific compound, the ratio between the antigen-binding activity in the presence of a low concentration of the compound and the antigen-binding activity in the presence of a high concentration of the compound is not particularly limited. However, the value of KD (in the presence of a low concentration of the compound)/KD (in the presence of a high concentration of the compound), which is a ratio of dissociation constant (KD) against an antigen in the presence of a low concentration of the target tissue-specific compound to KD in the presence of a high concentration of the compound, is preferably 2 or greater, more preferably 10 or greater, and still more preferably 40 or greater. The upper limit of the value of KD (in the presence of a low concentration of the compound)/KD (in the presence of a high concentration of the compound) is not particularly limited, and may be any value, for example, 400, 1,000, or 10,000, as long as it can be provided by the technologies of those skilled in the art. When antigen-binding activity is not observed in the presence of a low concentration of the target tissue-specific compound, the value of the upper limit is infinity.

For the value of antigen-binding activity, if the antigen is a soluble molecule, dissociation constant (KD) can be used; and if the antigen is a membrane-type molecule, apparent dissociation constant (apparent KD) can be used. The dissociation constant (KD) and apparent dissociation constant (apparent KD) can be determined by methods known to those skilled in the art, for example, using Biacore (GE Healthcare), a Scatchard plot, a flow cytometer, or such.

As another indicator that shows the ratio between the antigen-binding activity of an antigen-binding domain (or an antigen-binding molecule containing the domain) of the present invention in the absence of a target tissue-specific compound and the antigen-binding activity in the presence of the compound, for example, dissociation rate constant kd can be suitably used. When the dissociation rate constant (kd) is used instead of the dissociation constant (KD) as an indicator that shows the binding activity ratio, the value of kd (in the absence of the compound)/kd (in the presence of the compound), which is a ratio between kd (dissociation rate constant) for an antigen in the absence of a target tissue-specific compound and kd in the presence of the compound, is preferably 2 or greater, more preferably 5 or greater, even more preferably 10 or greater, and still more preferably 30 or greater. The upper limit of the value of kd (in the absence of the compound)/kd (in the presence of the compound) is not particularly limited, and may be any value, for example, 50, 100, or 200, as long as it can be provided by the common technical knowledge of those skilled in the art. When antigen-binding activity is not observed in the absence of the tissue-specific compound, there is no dissociation and the value of the upper limit becomes infinity.

As another indicator that shows the ratio between the antigen-binding activity of an antigen-binding domain (or an antigen-binding molecule containing the domain) of the present invention in the presence of a low concentration of a target tissue-specific compound and the antigen-binding activity in the presence of a high concentration of the compound, for example, dissociation rate constant kd can be suitably used. When the dissociation rate constant (kd) is used instead of the dissociation constant (KD) as an indicator showing the binding activity ratio, the value of kd (in the presence of a low concentration of the compound)/kd (in the presence of a high concentration of the compound), which is a ratio between kd (dissociation rate constant) for an antigen in the presence of a low concentration of a target tissue-specific compound and kd in the presence of a high concentration of the compound, is preferably 2 or greater, more preferably 5 or greater, even more preferably 10 or greater, and still more preferably 30 or greater. The upper limit of the value of kd (in the presence of a low concentration of the compound)/kd (in the presence of a high concentration of the compound) is not particularly limited, and may be any value, for example, 50, 100, or 200, as long as it can be provided by the common technical knowledge of those skilled in the art. When antigen-binding activity is not observed in the presence of a low concentration of the target tissue-specific compound, there is no dissociation and the value of the upper limit becomes infinity.

For the value of antigen-binding activity, if the antigen is a soluble molecule, dissociation rate constant (kd) can be used; and if the antigen is a membrane-type molecule, apparent dissociation rate constant (apparent kd) can be used. The dissociation rate constant (kd) and apparent dissociation rate constant (apparent kd) can be determined by methods known to those skilled in the art, for example, using Biacore (GE Healthcare), a flow cytometer, or such. In the present invention, when measuring the antigen-binding activity of an antigen-binding domain (or an antigen-binding molecule containing the domain) at a certain concentration of the target tissue-specific compound, conditions other than the concentration of the compound concentration are preferably the same.

For example, in an embodiment provided by the present invention, an antigen-binding domain (or an antigen-binding molecule containing the domain) with lower antigen-binding activity in the absence of a target tissue-specific compound than in the presence of the compound, may be obtained by screening of antigen-binding domains (or antigen-binding molecules) that comprises the steps of:

(a) determining antigen-binding activity of antigen-binding domains (or antigen-binding molecules) in the absence of a target tissue-specific compound;

(b) determining antigen-binding activity of the antigen-binding domains (or antigen-binding molecules) in the presence of the target tissue-specific compound; and (c) selecting an antigen-binding domain (or an antigen-binding molecule) with lower antigen-binding activity in the absence of the target tissue-specific compound than in the presence of the compound.

For example, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by screening of antigen-binding domains (or antigen-binding molecules) that comprises the steps of:

(a) determining antigen-binding activity of antigen-binding domains (or antigen-binding molecules) in the presence of a low concentration of a target tissue-specific compound;

(b) determining antigen-binding activity of the antigen-binding domains (or antigen-binding molecules) in the presence of a high concentration of the target tissue-specific compound; and (c) selecting an antigen-binding domain (or an antigen-binding molecule) with lower antigen-binding activity in the presence of a low concentration of the target tissue-specific compound than in the presence of a high concentration of the compound.

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by screening of antigen-binding domains (or antigen-binding molecules) or a library thereof that comprises the steps of:

(a) contacting antigen-binding domains (or antigen-binding molecules) or a library thereof with an antigen in the presence of a target tissue-specific compound;

(b) placing antigen-binding domains (or antigen-binding molecules) that bind to the antigen in said step (a) in the absence of the compound;

(c) isolating an antigen-binding domain (or an antigen-binding molecule) that dissociated in said step (b).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by screening of antigen-binding domains (or antigen-binding molecules) or a library thereof that comprises the steps of:

(a) contacting antigen-binding domains (or antigen-binding molecules) or a library thereof with an antigen in the presence of a high concentration of a target tissue-specific compound;

(b) placing antigen-binding domains (or antigen-binding molecules) that bind to the antigen in said step (a) in the presence of a low concentration of the compound;

(c) isolating an antigen-binding domain (or an antigen-binding molecule) that dissociates in said step (b).

Alternatively, in an embodiment provided by the present invention, an antigen-binding domain (or an antigen-binding molecule containing the domain) with lower antigen-binding activity in the absence of a target tissue-specific compound than in the presence of the compound, may be obtained by screening of antigen-binding domains (or antigen-binding molecules) or a library thereof that comprises the steps of:

(a) contacting a library of antigen-binding domains (or antigen-binding molecules) with an antigen in the absence of a target tissue-specific compound;

(b) selecting antigen-binding domains (or antigen-binding molecules) that do not bind to the antigen in said step (a);

(c) allowing the antigen-binding domains (or antigen-binding molecules) selected in said step (b) to bind to the antigen in the presence of the compound; and (d) isolating an antigen-binding domain (or an antigen-binding molecule) that binds to the antigen in said step (c).

Alternatively, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by screening of antigen-binding domains (or antigen-binding molecules) or a library thereof that comprises the steps of:

(a) contacting a library of antigen-binding domains (or antigen-binding molecules) with an antigen in the presence of a low concentration of a target tissue-specific compound;

(b) selecting antigen-binding domains (or antigen-binding molecules) that do not bind to the antigen in said step (a);

(c) allowing the antigen-binding domains (or antigen-binding molecules) selected in said step (b) to bind to the antigen in the presence of a high concentration the compound; and (d) isolating an antigen-binding domain (or an antigen-binding molecule) that binds to the antigen in said step (c).

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by a screening method comprising the steps of:

(a) contacting a library of antigen-binding domains (or antigen-binding molecules) with an antigen-immobilized column in the presence of a target tissue-specific compound;

(b) eluting an antigen-binding domain (or antigen-binding molecule) that binds to the column in said step (a) from the column in the absence of the compound; and (c) isolating the antigen-binding domain (or antigen-binding molecule) eluted in said step (b).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by a screening method comprising the steps of:

(a) contacting a library of antigen-binding domains (or antigen-binding molecules) with an antigen-immobilized column in the presence of a high concentration of a target tissue-specific compound;

(b) eluting an antigen-binding domain (or antigen-binding molecule) that binds to the column in said step (a) from the column in the presence of a low concentration of the compound; and (c) isolating the antigen-binding domain (or antigen-binding molecule) eluted in said step (b).

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by a screening method comprising the steps of:

(a) allowing a library of antigen-binding domains (or antigen-binding molecules) to pass through an antigen-immobilized column in the absence of a target tissue-specific compound;

(b) collecting an antigen-binding domain (or antigen-binding molecule) eluted without binding to the column in said step (a);

(c) allowing the antigen-binding domain (or antigen-binding molecule) collected in said step (b) to bind to the antigen in the presence of the compound; and (d) isolating an antigen-binding domain (or antigen-binding molecule) that binds to the antigen in said step (c).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by a screening method comprising the steps of:

(a) allowing a library of antigen-binding domains (or antigen-binding molecules) to pass through an antigen-immobilized column in the presence of a low concentration of a target tissue-specific compound;

(b) collecting an antigen-binding domain (or antigen-binding molecule) eluted without binding to the column in said step (a);

(c) allowing the antigen-binding domain (or antigen-binding molecule) collected in said step (b) to bind to the antigen in the presence of a high concentration of the compound; and (d) isolating an antigen-binding domain (or antigen-binding molecule) that binds to the antigen in said step (c).

Furthermore, in an embodiment provided by the present invention, an antigen-binding domain (or an antigen-binding molecule containing the domain) with lower antigen-binding activity in the absence of a target tissue-specific compound than in the presence of the compound, may be obtained by a screening method comprising the steps of:

(a) contacting an antigen with a library of antigen-binding domains (or antigen-binding molecules) in the presence of a target tissue-specific compound;

(b) obtaining an antigen-binding domain (or antigen-binding molecule) that binds to the antigen in said step (a);

(c) placing the antigen-binding domain (or antigen-binding molecule) obtained in said step (b) in the absence of the compound; and (d) isolating an antigen-binding domain (or antigen-binding molecule) whose antigen-binding activity in said step (c) is weaker than that of the reference selected in said step (b).

Furthermore, in an embodiment provided by the present invention, an antigen-binding domain (or an antigen-binding molecule containing the domain) with lower antigen-binding activity in the presence of a low concentration of a target tissue-specific compound than in the presence of a high concentration of the compound, may be obtained by a screening method comprising the steps of:

(a) contacting an antigen with a library of antigen-binding domains (or antigen-binding molecules) in the presence of a high concentration of a target tissue-specific compound;
(b) obtaining an antigen-binding domain (or antigen-binding molecule) that binds to the antigen in said step (a);
(c) placing the antigen-binding domain (or antigen-binding molecule) obtained in said step (b) in the presence of a low concentration of the compound; and
(d) isolating an antigen-binding domain (or antigen-binding molecule) whose antigen-binding activity in said step (c) is weaker than that of the reference selected in said step (b).

The above-mentioned steps may be repeated two or more times. Thus, the present invention provides an antigen-binding domain (or an antigen-binding molecule containing the domain) with lower antigen-binding activity in the absence of a target tissue-specific compound than in the presence of the compound, or an antigen-binding domain (or an antigen-binding molecule containing the domain) with lower antigen-binding activity in the presence of a low concentration of a target tissue-specific compound than in the presence of a high concentration of the compound, obtained by screening methods that further comprise the step of repeating steps (a) to (c) or (a) to (d) two or more times in the above-mentioned screening methods. The number of repeats of steps (a) to (c) or (a) to (d) is not particularly limited, and it is generally ten or less.

In the screening methods of the present invention, a target tissue-specific compound may be a compound defined by quantitative target tissue specificity such as presence in the target tissue at a concentration (for example, high concentration or low concentration) different from the concentration in non-target tissues. For example, a target tissue-specific compound is differentially present at any concentrations. However, generally, a target tissue-specific compound can be present at a concentration increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 2-fold, at least 5-fold, at least 10-fold, at least 50-fold, at least 100-fold, at least $10^3$-fold, at least $10^4$-fold, at least $10^5$-fold, at least $10^6$-fold, or more, or up to infinity (when the compound is absent in non-target tissues).

The threshold differentiating low and high concentrations can be set appropriately according to the compound. For example, in a non-limiting embodiment of the threshold of ATP or adenosine, the threshold for a low-concentration condition may be selected appropriately from the values of 10 nM, 1 nM, 100 pM, 10 pM, 1 pM, and 0 M. Depending on the predetermined threshold, the high-concentration condition may be set appropriately at a value selected from at least 110%, at least 120%, at least 130%, at least 140%, at least 150%, at least twice, at least five-fold, at least 10-fold, at least 50-fold, at least 100-fold, at least $10^3$-fold, at least $10^4$-fold, at least $10^5$-fold, and at least $10^6$-fold the value of each threshold. Furthermore, in a non-limiting embodiment of PGE2, the threshold for a low-concentration condition may be selected appropriately from the values of 10 pM, 1 pM, 100 fM, 10 fM, 1 fM, and 0 M. Depending on the predetermined threshold, the high-concentration condition may be set appropriately at a value selected from at least 110%, at least 120%, at least 130%, at least 140%, at least 150%, at least twofold, at least five-fold, at least 10-fold, at least 50-fold, at least 100-fold, at least $10^3$-fold, at least $10^4$-fold, at least $10^5$-fold, and at least $10^6$-fold the value of each threshold. Furthermore, in a non-limiting embodiment of Kynurenine, the threshold for a low-concentration condition may be selected appropriately from the values of 10 μM, 1 μM, 100 nM, 10 nM, and 1 nM, and 0 M. Depending on the predetermined threshold, the high-concentration condition may be set appropriately at a value selected from at least 110%, at least 120%, at least 130%, at least 140%, at least 150%, at least twofold, at least five-fold, at least 10-fold, at least 50-fold, at least 100-fold, at least $10^3$-fold, at least $10^4$-fold, at least $10^5$-fold, and at least $10^6$-fold the value of each threshold.

The antigen-binding activity of an antigen-binding domain (or an antigen-binding molecule) may be measured by a method known to those skilled in the art, and conditions other than the concentration of a target tissue-specific compound can be set appropriately by one skilled in the art. The antigen-binding activity of an antigen-binding domain (or an antigen-binding molecule) can be assessed as dissociation constant (KD), apparent dissociation constant (apparent KD), dissociation rate constant (kd), apparent dissociation rate constant (apparent kd), etc. They can be determined by methods known to those skilled in the art, for example, using Biacore (GE Healthcare), the Scatchard plot, FACS, or such.

In the present invention, the step of selecting an antibody or an antigen-binding domain with higher antigen-binding activity in the presence of a target tissue-specific compound than in the absence of the compound has the same meaning as the step of selecting an antibody or an antigen-binding domain with lower antigen-binding activity in the absence of a target tissue-specific compound than in the presence of the compound.

In the present invention, the step of selecting an antibody or an antigen-binding domain with higher antigen-binding activity in the presence of a high concentration of a target tissue-specific compound than in the presence of a low concentration of the compound has the same meaning as the step of selecting an antibody or an antigen-binding domain with lower antigen-binding activity in the absence of a target tissue-specific compound than in the presence of the compound.

As long as antigen-binding activity in the absence of a target tissue-specific compound is lower than the antigen-binding activity in the presence of the compound, the difference between antigen-binding activity in the presence of the compound and antigen-binding activity in the absence of the compound is not particularly limited, but preferably, the antigen-binding activity in the presence of the compound relative to the antigen-binding activity in the absence of the compound is twofold or more, more preferably 10-fold or more, and even more preferably 40-fold or more. The upper limit of the difference between the antigen-binding activities is not particularly limited, and as long as it can be produced by the techniques of those skilled in the art, any value such as 400-fold, 1000-fold, or 10000-fold is possible. In the absence of a target tissue-specific compound, when antigen-binding activity is not observed, this upper limit becomes infinity.

The antigen-binding domains (or antigen-binding molecules containing the domains) of the present invention which are to be screened by the aforementioned screening methods may be any antigen-binding domains (or antigen-binding molecules); and for example, the above-mentioned antigen-binding domains (or antigen-binding molecules) can be screened. For example, antigen-binding domains (or antigen-binding molecules) having naturally-occurring sequences can be screened, and antigen-binding domains (or antigen-binding molecules) with substituted amino acid sequences may be screened.

Library

According to a certain embodiment, the antigen-binding domain (or an antigen-binding molecule containing this domain) of the present invention can be obtained from a library mainly comprising a plurality of antigen-binding molecules having different sequences from one another, in which at least one amino acid residue that changes the binding activity of the antigen-binding molecule toward an antigen dependent on a target tissue-specific compound is contained in the antigen-binding domain. Examples of the compound include (1) primary metabolites of the Krebs cycle or the glycolytic pathway such as lactose, succinic acid, or citric acid, (2) amino acids such as alanine, glutamic acid, or asparagine, (3) kynurenine and amino acid metabolites thereof such as anthranilic acid, 3-hudroxykynurenine, and kynurenic acid, (4) arachidonic acid metabolites such as prostaglandin E2, and (5) nucleosides carrying a purine ring structure such as adenosine, adenosine triphosphate (ATP), adenosine diphosphate (ADP), and adenosine monophosphate (AMP). Below are examples of such a library mainly comprising a plurality of antigen-binding molecules having different sequences from one another, in which at least one amino acid residue that changes the binding activity of the antigen-binding molecule toward adenosine- and/or ATP-dependent antigens which are target tissue-specific compounds is contained in the antigen-binding domain.

Herein, a "library" refers to a plurality of antigen-binding molecules or a plurality of fusion polypeptides containing antigen-binding molecules, or nucleic acids or polynucleotides encoding their sequences. The sequences of a plurality of antigen-binding molecules or a plurality of fusion polypeptides containing antigen-binding molecules in a library are not identical, but are different from one another.

Herein, the phrase "sequences are different from one another" in the expression "a plurality of antigen-binding molecules whose sequences are different from one another" means that the sequences of antigen-binding molecules in a library are different from one another. Specifically, in a library, the number of sequences different from one another reflects the number of independent clones with different sequences, and may also be referred to as "library size". The library size of a conventional phage display library ranges from $10^6$ to $10^{12}$. The library size can be increased up to $10^{14}$ by the use of known techniques such as ribosome display. However, the actual number of phage particles used in panning selection of a phage library is in general 10 to 10,000 times greater than the library size. This excess multiplicity is also referred to as "the number of library equivalents", and means that there are 10 to 10,000 individual clones that have the same amino acid sequence. Thus, in the present invention, the phrase "sequences are different from one another" means that the sequences of independent antigen-binding molecules in a library, excluding library equivalents, are different from one another. More specifically, the above means that there are $10^6$ to $10^{14}$ antigen-binding molecules whose sequences are different from one another, preferably $10^7$ to $10^{12}$ molecules, more preferably $10^8$ to $10^{11}$ molecules, and particularly preferably $10^8$ to $10^{10}$ molecules whose sequences are different from one another.

Herein, the phrase "a plurality of" in the expression "a library mainly composed of a plurality of antigen-binding molecules" generally refers to, in the case of, for example, antigen-binding molecules, fusion polypeptides, polynucleotide molecules, vectors, or viruses of the present invention, a group of two or more types of the substance. For example, when two or more substances are different from one another in a particular characteristic, this means that there are two or more types of the substance. Such examples may include, for example, mutant amino acids observed at specific amino acid positions in an amino acid sequence. For example, when there are two or more antigen-binding molecules of the present invention whose sequences are substantially the same or preferably the same except for flexible residues or except for particular mutant amino acids at hypervariable positions exposed on the surface, there are a plurality of antigen-binding molecules of the present invention. In another example, when there are two or more polynucleotide molecules whose sequences are substantially the same or preferably the same except for nucleotides encoding flexible residues or nucleotides encoding mutant amino acids of hypervariable positions exposed on the surface, there are a plurality of polynucleotide molecules of the present invention.

In addition, herein, the phrase "mainly composed of" in the expression "a library mainly composed of a plurality of antigen-binding molecules" reflects the number of antigen-binding molecules whose antigen-binding activity varies depending on the concentration of a target tissue-specific compound, among independent clones with different sequences in a library. Specifically, it is preferable that there are at least $10^4$ antigen-binding molecules having such binding activity in a library. More preferably, antigen-binding domains of the present invention can be obtained from a library containing at least $10^5$ antigen-binding molecules having such binding activity. Still more preferably, antigen-binding domains of the present invention can be obtained from a library containing at least $10^6$ antigen-binding molecules having such binding activity. Particularly preferably, antigen-binding domains of the present invention can be obtained from a library containing at least $10^7$ antigen-binding molecules having such binding activity. Yet more preferably, antigen-binding domains of the present invention can be obtained from a library containing at least $10^8$ antigen-binding molecules having such binding activity. Alternatively, this may also be preferably expressed as the ratio of the number of antigen-binding molecules in which antigen-binding activity of the antigen-binding domain varies depending on the presence or absence of adenosine and/or ATP with respect to the number of independent clones having different sequences in a library. Specifically, antigen-binding domains of the present invention can be obtained from a library in which antigen-binding molecules having such binding activity account for 0.1% to 80%, preferably 0.5% to 60%, more preferably 1% to 40%, still more preferably 2% to 20%, and particularly preferably 4% to 10% of independent clones with different sequences in the library. In the case of fusion polypeptides, polynucleotide molecules, or vectors, similar expressions may be possible using the number of molecules or the ratio to the total number of molecules. In the case of viruses, similar expressions may also be possible using the number of virions or the ratio to total number of virions.

Amino Acids that Change the Antigen-Binding Activity of the Antigen-Binding Domain Depending on the Presence or Absence of Adenosine and/or ATP Antigen-binding domains or antibodies of the present invention screened by the above-described screening methods may be prepared in any manner. It is possible to use preexisting antibodies, preexisting libraries (phage libraries, etc.), antibodies or libraries prepared from hybridomas obtained by immunizing animals or from B cells of immunized animals, and antibodies or libraries prepared from immune cells such as B cells of animals immunized by a conjugate in which adenosine or ATP is suitably linked to an adjuvant agent such as a highly immunogenic T cell epitope peptide. A non-limiting example of the T cell epitope peptide suitably includes Tetanus toxin-derived p30 helper peptide (shown in SEQ ID NO: 4, and also referred to as Fragment C (FrC)).

Examples of amino acids that change the antigen-binding activity of the antigen-binding molecule depending on the presence or absence of adenosine and/or ATP as described above include amino acids that form an adenosine- and/or ATP-binding motif. The amino acid positions where the above-mentioned amino acids are contained in the antigen-binding domain are not limited to any specific position. As long as the antigen-binding activity of the antigen-binding domain is changed depending on the presence or absence of adenosine and/or ATP, any position in the heavy chain variable region or light chain variable region forming the antigen-binding domain is possible. More specifically, the antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in the antigen-binding domain of the heavy chain. In a non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in CDR1, CDR2, and/or CDR3 of the heavy chain. In another non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in FR1, FR2, FR3 and/or FR4 of the heavy chain.

Furthermore, in an embodiment of the present invention, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in the antigen-binding domain of the heavy chain and/or light chain. In a non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in CDR1, CDR2, and/or CDR3 of the heavy chain and/or light chain.

In another non-limiting embodiment, antigen-binding domains of the present invention may be obtained from a library mainly comprising antigen-binding molecules having different sequences from one another, in which the amino acids that change the antigen-binding activity of the antigen-binding molecule depending on the presence or absence of adenosine and/or ATP are contained in FR1, FR2, FR3 and/or FR4 of the heavy chain and/or light chain.

In a non-limiting embodiment, examples of such amino acids include any one or more amino acids selected from amino acids at positions 52, 52a, 53, 96, 100a, and 100c contained in the heavy chain variable region. Also, in a non-limiting embodiment, examples of such amino acids include one or more amino acids selected from amino acids including Ser at position 52, Ser at position 52a, Arg at position 53, Gly at position 96, Leu at position 100a, and Trp at position 100c contained in the heavy chain variable region.

Any framework sequence can be used as the framework sequence of the light-chain and/or heavy-chain variable regions of an antigen-binding molecule as long as the amino acids that change the antigen-binding activity of the antigen-binding molecule depending on the presence or absence of adenosine and/or ATP are contained in the antigen-binding domain of the heavy chain and/or light chain. The origin of the framework sequences is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In a particularly preferred embodiment, the framework sequences of the light chain and/or heavy chain variable region of an antigen-binding molecule preferably have human germ-line framework sequences. Thus, in an embodiment of the present invention, if the entire framework sequences are human sequences, it is thought that an antigen-binding molecule of the present invention induces little or no immunogenic response when it is administered to humans (for example, to treat diseases). In the above sense, the phrase "containing a germ line sequence" in the present invention means that a part of the framework sequences of the present invention is identical to a part of any human germ line framework sequences. For example, when the heavy chain FR2 sequence of an antigen-binding molecule of the present invention is a combination of heavy chain FR2 sequences of different human germ line framework sequences, such a molecule is also an antigen-binding molecule "containing a germ line sequence" in the present invention. Even when the framework sequences of antigen-binding molecules of the present invention are sequences with substitutions, they are antigen-binding molecules "containing a germ line sequence" of the present invention. Examples of such sequences with substitutions include, in particular, sequences in which amino acids of part of human germ line framework sequences have been substituted with amino acids that change the antigen-binding activity of the antigen-binding molecule depending on the presence or absence of adenosine and/or ATP.

Preferred examples of the frameworks include, for example, fully human framework region sequences currently known, which are included in the website of V-Base (vbase.mrc-cpe.cam.ac.uk) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J.

Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of:
subgroup VH1 (for example, VH1-2, VH1-3, VH1-8, VH1-18, VH1-24, VH1-45, VH1-46, VH1-58, and VH1-69);
subgroup VH2 (for example, VH2-5, VH2-26, and VH2-70);
subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
subgroup VH4 (VH4-4, VH4-28, VH4-31, VH4-34, VH4-39, VH4-59, and VH4-61);
subgroup VH5 (VH5-51);
subgroup VH6 (VH6-1); and
subgroup VH7 (VH7-4 and VH7-81).

These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.

Fully human Vκ sequences preferably include, but are not limited to, for example:
A20, A30, L1, L4, L5, L8, L9, L11, L12, L14, L15, L18, L19, L22, L23, L24, O2, O4, O8, O12, O14, and O18 grouped into subgroup Vk1;
A1, A2, A3, A5, A7, A17, A18, A19, A23, O1, and O11, grouped into subgroup Vk2;
A11, A27, L2, L6, L10, L16, L20, and L25, grouped into subgroup Vk3;
B3, grouped into subgroup Vk4;
B2 (herein also referred to as Vk5-2), grouped into subgroup Vk5; and
A10, A14, and A26, grouped into subgroup Vk6 (Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human Vλ sequences preferably include, but are not limited to, for example:
V1-2, V1-3, V1-4, V1-5, V1-7, V1-9, V1-11, V1-13, V1-16, V1-17, V1-18, V1-19, V1-20, and V1-22, grouped into subgroup VL1;
V2-1, V2-6, V2-7, V2-8, V2-11, V2-13, V2-14, V2-15, V2-17, and V2-19, grouped into subgroup VL1;
V3-2, V3-3, and V3-4, grouped into subgroup VL3;
V4-1, V4-2, V4-3, V4-4, and V4-6, grouped into subgroup VL4; and
V5-1, V5-2, V5-4, and V5-6, grouped into subgroup VL5 (Kawasaki et al. (Genome Res. (1997) 7, 250-261)).

Normally, these framework sequences are different from one another at one or more amino acid residues. These framework sequences can be used in combination with "at least one amino acid residue that alters the antigen-binding activity of an antigen-binding domain depending on the presence or absence of adenosine and/or ATP" of the present invention. Other examples of the fully human frameworks used in combination with "at least one amino acid residue that alters the antigen-binding activity of an antigen-binding domain depending on the presence or absence of adenosine and/or ATP" of the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce the antigen-binding molecules of the present invention in which the above-described variable region sequences, heavy or light chain variable region sequences, CDR sequences, or framework sequences contain amino acids that alter the antigen-binding activity of the antigen-binding domain depending on the presence or absence of adenosine and/or ATP.

For example, a library which contains a plurality of antigen-binding molecules of the present invention whose sequences are different from one another can be constructed by combining heavy chain variable regions prepared as a randomized variable region sequence library with a light chain variable region selected as a CDR sequence and/or framework sequence originally containing at least one amino acid residue that alters the antigen-binding activity of the antigen-binding domain depending on the presence or absence of adenosine and/or ATP.

Alternatively, a heavy chain and/or light chain variable region sequence selected as a CDR sequence and/or a framework sequence originally containing at least one amino acid residue that changes the antigen-binding activity of an antigen-binding domain depending on the presence or absence of adenosine and/or ATP as mentioned above, can be designed to contain various amino acid residues other than the above amino acid residue(s). Herein, such residues are referred to as "flexible residues". The number and position of flexible residues are not particularly limited as long as the antigen-binding activity of the antigen-binding molecule of the present invention varies depending on the concentration of a tissue-specific compound. Specifically, the CDR sequences and/or FR sequences of the heavy chain and/or light chain may contain one or more flexible residues. One can identify the flexible residues and those residues that can be substituted into other amino acids for library production by introducing mutations or by crystal structure analysis of complexes formed between an antibody and adenosine and/or ATP. For example, from crystal structure analysis of complexes formed between an antibody and adenosine and/or ATP, one can identify residues in the antibody that are not involved in binding to adenosine and/or ATP. One can select amino acids that can maintain binding to the compounds at an appropriate level even when the residues that have been identified as not being involved in binding to adenosine and/or ATP are substituted into other amino acids. Accordingly, it is possible to design a library that has the selected amino acids for the selected residues. In this case, one can design a library mainly comprising multiple antigen-binding molecules to be an assembly of antigen-binding molecules in which residues identified as not being involved in binding to adenosine and/or ATP have been substituted with amino acids that are different from one another. That is, the combination of individual flexible residues substituted with amino acids that are different from one another can provide sequence diversity in antigen-binding molecules containing the flexible residues.

Antigen-binding molecules can be designed to include residues wherein at least one of the residues identified to be involved in binding to adenosine and/or ATP binding becomes any residue selected from the residue and other residues that are different from the residue. In a non-limiting embodiment, examples of amino acids identified as being involved in binding to adenosine and/or ATP may include one or more amino acids selected from amino acids at positions 52, 52a, 53, 96, 100a, and 100c in the heavy chain variable region. In a non-limiting embodiment, examples of such amino acids include one or more amino acids selected from amino acids including Ser at position 52, Ser at position 52a, Arg at position 53, Gly at position 96, Leu at position 100a, and Trp at position 100c contained in the heavy chain variable region. For example, when Leu at position 100a mentioned above is identified to be involved in binding to adenosine and/or ATP, the amino acid residue at position 100a in the antigen-binding molecules included in the library may be any amino acid residue selected from the flexible residues of His, Met, Leu, Arg, Trp, or Tyr, in addition to Leu.

In a non-limiting embodiment, examples of the flexible residues may include amino acids at positions 31, 32, 33, 35, 50, 55, 56, 57, 58, 59, 95, 96, 97, 98, 99, 100, 100a, and 100b contained in the heavy chain variable region. In another non-limiting embodiment, examples of such amino acids may include amino acids at positions 26, 27, 27a, 27b, 27c, 28, 29, 31, 32, 50, 51, 52, 53, 54, 55, 89, 90, 91, 92, 93, 94, 95a, 96, and 97 contained in the light chain variable region.

In a non-limiting embodiment, examples of the aforementioned flexible residues may include the following amino acids contained in the heavy chain variable region:
Asp, Gly, Asn, Ser, Arg, or Thr for the amino acid at position 31;
Ala, Phe, His, Asn, Ser, or Tyr for the amino acid at position 32;
Ala, Glu, Asp, Gly, Phe, Ile, His, Lys, Met, Leu, Asn, Gln, Pro, Ser, Arg, Trp, Val, Tyr, or Thr for the amino acid at position 33;
His, Ser, Thr, Tyr, or Asn for the amino acid at position 35;
Ala, Glu, Asp, Gly, Phe, Ile, His, Lys, Met, Leu, Asn, Gln, Pro, Arg, Thr, Trp, Val, Tyr, or Ser for the amino acid at position 50;
Ala, Glu, Asp, Gly, Leu, Thr, Ser, Arg, or Asn for the amino acid at position 55;
Ala, Glu, Asp, Gly, Phe, Ile, His, Lys, Met, Leu, Gln, Pro, Ser, Thr, Trp, Val, or Tyr for the amino acid at position 56;
Ala, Lys, Arg, Thr, or Ile for the amino acid at position 57;
Asp, Gly, Phe, His, Ser, Thr, Tyr, or Asn for the amino acid at position 58;
Leu, or Tyr for the amino acid at position 59;
Ala, Ile, Lys, Met, Leu, Arg, Trp, Val, Tyr, or Phe for the amino acid at position 95;
Ala, Asp, Asn, or Ser for the amino acid at position 96;
Ala, Asp, Gly, Ile, His, Lys, Met, Leu, Asn, Ser, Val, Tyr, or Arg for the amino acid at position 97;
Ala, Glu, Asp, Gly, Phe, Ile, His, Met, Leu, Asn, Gln, Pro, Ser, Arg, Thr, Trp, Val, Tyr, or Lys for the amino acid at position 98;
Ala, Glu, Asp, Phe, His, Lys, Asn, Gln, Ser, Arg, Trp, Val, Tyr, or Gly for the amino acid at position 99;
Ala, Glu, Gly, Phe, Ile, His, Lys, Met, Leu, Asn, Gln, Pro, Ser, Arg, Thr, Trp, Val, Tyr, or Asp for the amino acid at position 100;
Ala, Phe, Ile, His, Lys, Met, Arg, Trp, Val, or Tyr for the amino acid at position 100a; or
Ala, Glu, Asp, Gly, Phe, Ile, His, Lys, Met, Leu, Gln, Pro, Ser, Arg, Thr, Trp, Val, Tyr, or Asn for the amino acid at position 100b.

In a non-limiting embodiment, examples of the aforementioned flexible residues may include the following amino acids contained in the light chain variable region:
Ala, Ser, or Thr for the amino acid at position 26;
Thr or Ser for the amino acid at position 27;
Gly, Asn, Thr, or Ser for the amino acid at position 27a;
Asn or Asp for the amino acid at position 27b;
Ile or Val for the amino acid at position 27c;
Asp or Gly for the amino acid at position 28;
Ala, Asp, Phe, Ser, Arg, Thr, Tyr, or Gly for the amino acid at position 29;
Glu, Asp, Lys, or Asn for the amino acid at position 31;
Ala, Asp, Ser, Thr, or Tyr for the amino acid at position 32;
Asp, Gly, Lys, Asn, Gln, Ser, Arg, Tyr, or Glu for the amino acid at position 50;
Asp, Gly, Lys, Asn, Thr, or Val for the amino acid at position 51;
Ala, Asp, Asn, Thr, or Ser for the amino acid at position 52;
Glu, Asp, His, Asn, Gln, Ser, Tyr, or Lys for the amino acid at position 53;
Lys or Arg for the amino acid at position 54;
Leu or Pro for the amino acid at position 55;
Ala, Gly, Phe, Leu, Asn, Gln, Thr, Val, Tyr, or Ser for the amino acid at position 89;
Ala, Leu, Thr, Val, or Ser for the amino acid at position 90;
Ala, Asp, Phe, His, Lys, Asn, Ser, Arg, Thr, Trp, Val, or Tyr for the amino acid at position 91;
Glu, Asp, Ser, Arg, Thr, Val, Tyr, or Ala for the amino acid at position 92;
Ala, Asp, Ile, Asn, Ser, Arg, Thr, Val, Tyr, or Gly for the amino acid at position 93;
Ala, Asp, Gly, Ile, Asn, Arg, Thr, or Ser for the amino acid at position 94;
Ala, Glu, Asp, Gly, Phe, Ile, His, Lys, Met, Leu, Gln, Pro, Ser, Arg, Thr, Trp, Val, Tyr, or Asn for the amino acid at position 95;
Ala, Glu, Asp, Gly, Ile, His, Lys, Leu, Gln, Pro, Ser, Arg, Thr, Tyr, or Asn for the amino acid at position 95a;
Ala, Asp, Gly, Phe, His, Lys, Leu, Asn, Gln, Pro, Ser, Thr, Trp, Tyr, or Val for the amino acid at position 96; or
Ala, Gly, Ile, Met, Leu, Ser, or Val for the amino acid at position 97.

Herein, "flexible residue" refers to amino acid residue variations present at hypervariable amino acid positions of light-chain and heavy-chain variable regions at which several different amino acids exist, when the amino acid sequences of known and/or native antibodies or antigen-binding domains are compared. The hypervariable positions are generally located in the CDR regions. In an embodiment, the data provided by Kabat, Sequences of Proteins of Immunological Interest (National Institute of Health Bethesda Md., 1987 and 1991) is useful for determining the hypervariable positions in known and/or native antibodies. Furthermore, databases on the Internet (vbase.mrc-cpe.cam.ac.uk, and www.bioinf.org.uk/abs/index.html) provide many collected sequences of human light chains and heavy chains, and their locations. The information on the sequences and locations is useful for determining the hypervariable positions in the present invention. According to the present invention, when a certain amino acid position has preferably about 2 to about 20, preferably about 3 to about 19, preferably about 4 to about 18, preferably 5 to 17, preferably 6 to 16, preferably 7 to 15, preferably 8 to 14, preferably 9 to 13, and preferably 10 to 12 possible amino acid residue variations, the position can be said to be hypervariable. In some embodiments, a certain amino acid position may have preferably at least about 2, preferably at least about 4, preferably at least about 6, preferably at least about 8, preferably about 10, and preferably about 12 possible amino acid residue variations.

A library of the present invention that contains a plurality of antigen-binding molecules having different sequences from one another can be constructed by combining heavy chain variable regions produced as a randomized variable region sequence library with the aforementioned light chain variable regions introduced with at least one amino acid residue that changes the antigen-binding activity of the antigen-binding domains depending on the presence or absence of adenosine and/or ATP. Similarly, a library of the present invention that contains a plurality of antigen-binding molecules having different sequences from one another can also be produced by combining the heavy-chain variable regions introduced with at least one amino acid residue that changes the antigen-binding activity of the antigen-binding domains depending on the presence or absence of adenosine and/or ATP, and having the other amino acid residues designed as flexible residues.

When heavy chain variable regions produced as a randomized variable region sequence library and light chain variable regions into which at least one amino acid residue that alters the antigen-binding activity of an antigen-binding molecule depending on the concentration of the target tissue-specific compound has been introduced are combined as described above, the sequences of the light chain variable regions can be designed to contain flexible residues in the same manner as described above. The number and position of such flexible residues are not particularly limited to particular embodiments as long as the antigen-binding activity of antigen-binding molecules of the present invention varies depending on the presence or absence of adenosine and/or ATP. Specifically, the CDR sequences and/or FR sequences of heavy chain and/or light chain can contain one or more flexible residues.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

Furthermore, in a non-limiting embodiment of the present invention, amino acids of the variable region including the CDR region and/or the framework region may be altered appropriately to improve antibody stability. In a non-limiting embodiment, examples of such amino acids may include the amino acids of positions 1, 5, 10, 30, 48, and 58. More specifically, examples may include Gln at position 1, Gln at position 5, Asp at position 10, Asn at position 30, Leu at position 48, and Asn at position 58. For the improvement of antibody stability, these amino acids can be substituted for corresponding amino acids contained in a germ-line sequence. In a non-limiting embodiment, an example of such a germ line sequence may be the VH3-21 sequence. In this case, Gln of position 1 may be substituted with Glu, Gln of position 5 may be substituted with Val, Asp of position 10 may be substituted with Gly, Asn of position 30 may be substituted with Ser, Leu of position 48 may be substituted with Val, and Asn of position 58 may be substituted with Tyr.

In another non-limiting embodiment of the present invention, a naive library which is constructed from antibody genes derived from lymphocytes of healthy individuals and consists of naive sequences which are antibody sequences that do not have bias in their repertoire, can also be particularly preferably used as a randomized variable region library (Gejima et al. (Human Antibodies (2002) 11, 121-129); Cardoso et al. (Scand. J. Immunol. (2000) 51, 337-344)). Herein, "an amino acid sequence comprising a naive sequence" refers to an amino acid sequence obtained from such a naive library.

Fc Region

An Fc region contains an amino acid sequence derived from the heavy chain constant region of an antibody. An Fc region is a portion of the antibody heavy chain constant region that includes the N terminal end of the hinge region, which is the papain cleavage site, at an amino acid around position 216 (indicated by EU numbering), and the hinge, CH2, and CH3 domains. Fc regions can be obtained from human IgG1; however, they are not limited to any specific IgG subclass. Preferred examples of the Fc regions include Fc regions having FcRn-binding activity in an acidic pH range as described below. Preferred examples of the Fc regions include Fc regions having Fcγ receptor-binding activity as described below. In a non-limiting embodiment, examples of such Fc regions include the Fc regions of human IgG1 (SEQ ID NO: 5), IgG2 (SEQ ID NO: 6), IgG3 (SEQ ID NO: 7), or IgG4 (SEQ ID NO: 8).

Fcγ Receptor (FcγR)

"Fcγ receptor" (also called "FcγR") refers to a receptor capable of binding to the Fc region of monoclonal IgG1, IgG2, IgG3, or IgG4 antibodies; and means all members belonging to the family of proteins substantially encoded by Fcγ receptor genes. In humans, the family includes FcγRI (CD64) including isoforms FcγRIa, FcγRIb, and FcγRIc; FcγRII (CD32) including isoforms FcγRIIa (including allotype H131 and R131, i.e., FcγRIIa(H) and FcγRIIa(R)), FcγRIIb (including FcγRIIb-1 and FcγRIIb-2), and FcγRIIc; and FcγRIII (CD16) including isoform FcγRIIIa (including allotype V158 and F158, i.e., FcγRIIIa(V) and FcγRIIIa(F)) and FcγRIIIb (including allotype FcγRIIIb-NA1 and FcγRIIIb-NA2); as well as all unidentified human FcγRs, FcγR isoforms, and allotypes thereof; but the family is not limited to these examples. Without being limited thereto, FcγRs include those derived from humans, mice, rats, rabbits, and monkeys. FcγRs may be derived from any organism. Mouse FcγRs include FcγRI (CD64), FcγRII (CD32), FcγRIII (CD16), and FcγRIII-2 (FcγRIV, CD16-2), as well as all unidentified mouse FcγRs, FcγR isoforms, and allotypes thereof, but they are not limited to these examples. Preferred examples of such Fcγ receptors include, human FcγRI (CD64), FcγRIIa (CD32), FcγRIIb (CD32), FcγRIIIa (CD16), and/or FcγRIIIb (CD16). The polynucleotide sequence and amino acid sequence of human FcγRI are shown in SEQ ID NOs: 9 (NM_000566.3) and 10 (NP_000557.1), respectively; the polynucleotide sequence and amino acid sequence of human FcγRIIa (allotype H131) are shown in SEQ ID NOs: 11 (BC020823.1) and 12 (AAH20823.1), respectively (allotype R131 is a sequence in which the amino acid at position 166 of SEQ ID NO: 12 is substituted with Arg); the polynucleotide sequence and amino acid sequence of FcγIIb are shown in SEQ ID NOs: 13 (BC146678.1) and 14 (AAI46679.1), respectively; the polynucleotide sequence and amino acid sequence of FcγRIIIa are shown in SEQ ID NOs: 15 (BC033678.1) and 16 (AAH33678.1), respectively; and the polynucleotide sequence and amino acid sequence of FcγRIIIb are shown in SEQ ID NOs: 17 (BC128562.1) and 18 (AAI28563.1), respectively (RefSeq accession number or such is shown in parentheses). Whether an Fcγ receptor has binding activity to the Fc region of a monoclonal IgG1, IgG2, IgG3, or IgG4 antibody can be assessed by ALPHA (Amplified Luminescent Proximity Homogeneous Assay) screen, surface plasmon resonance (SPR)-based BIACORE methods, and others (Proc. Natl. Acad. Sci. USA (2006) 103(11), 4005-4010), in addition to the above-described FACS and ELISA formats.

In FcγRI (CD64) including FcγRIa, FcγRIb, and FcγRIc, and FcγRIII (CD16) including isoforms FcγRIIIa (including allotypes V158 and F158) and FcγRIIIb (including allotypes FcγRIIIb-NA1 and FcγRIIIb-NA2), at chain that binds to the Fc region of IgG is associated with common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc region of IgG results in enhancement of the phagocytic activity of macrophages, inflammatory cytokine production, mast cell degranulation, and the enhanced function of antigen-presenting cells. Fcγ receptors having the ability to transduce the activation signal as described above are herein referred to as activating Fcγ receptors.

Meanwhile, the intracytoplasmic domain of FcγRIIb (including FcγRIIb-1 and FcγRIIb-2) contains ITIM responsible for transduction of inhibitory signals. The crosslinking between FcγRIIb and B cell receptor (BCR) on B cells suppresses the activation signal from BCR, which results in suppression of antibody production via BCR. The crosslinking of FcγRIII and FcγRIIb on macrophages suppresses the phagocytic activity and inflammatory cytokine production. Fcγ receptors having the ability to transduce the inhibitory signal as described above are herein referred to as inhibitory Fcγ receptor.

FcγR-Binding Activity of Fc Region

As mentioned above, Fc regions having an Fcγ receptor-binding activity are examples of Fc regions comprised in the antigen-binding molecules of the present invention. A non-limiting embodiment of such an Fc region includes the Fc region of human IgG1 (SEQ ID NO: 5), IgG2 (SEQ ID NO: 6), IgG3 (SEQ ID NO: 7), or IgG4 (SEQ ID NO: 8). Whether an Fcγ receptor has binding activity to the Fc region of a monoclonal IgG1, IgG2, IgG3, or IgG4 antibody can be assessed by ALPHA screen (Amplified Luminescent Proximity Homogeneous Assay), surface plasmon resonance (SPR)-based BIACORE method, and others (Proc. Natl. Acad. Sci. U.S.A. (2006) 103(11), 4005-4010), in addition to the above-described FACS and ELISA formats.

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule comprising Fc region is immobilized to the donor beads and glutathione S-transferase (GST)-tagged Fcγ receptor is immobilized to the acceptor beads. In the absence of an antigen-binding molecule comprising a competitive Fc region variant, Fcγ receptor interacts with an antigen-binding molecule comprising a native Fc region, inducing a signal of 520 to 620 nm as a result. The antigen-binding molecule having a non-tagged Fc region variant competes with the antigen-binding molecule comprising a native Fc region for the interaction with Fcγ receptor. The relative binding affinity can be determined by quantifying the reduction of fluorescence as a result of competition. Methods for biotinylating the antigen-binding molecules such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector to which the gene is operably linked, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these constants. Inhibition assay is preferably used in the BIACORE methods. Examples of such inhibition assay are described in Proc. Natl. Acad. Sci. U.S.A. (2006) 103(11), 4005-4010.

Fc Regions with Altered Fcγ Receptor (FcγR) Binding

In addition to the Fc region of human IgG1 (SEQ ID NO: 5), IgG2 (SEQ ID NO: 6), IgG3 (SEQ ID NO: 7), or IgG4 (SEQ ID NO: 8), an Fc region with altered FcγR binding, which has a higher Fcγ receptor-binding activity than an Fc region of a native human IgG may be appropriately used as an Fc region included in the present invention. Herein, "Fc region of a native human IgG" refers to an Fc region in which the sugar chain bonded to position 297 (EU numbering) of the Fc region of human IgG1, IgG2, IgG3, or IgG4 shown in SEQ ID NOs: 5, 6, 7, or 8 is a fucose-containing sugar chain. Such Fc regions with altered FcγR binding may be produced by altering amino acids of the Fc region of a native human IgG. Whether the FcγR-binding activity of an Fc region with altered FcγR binding is higher than that of an Fc region of a native human IgG can be determined appropriately using methods described in the abovementioned section on binding activity.

In the present invention, "alteration of amino acids" or "amino acid alteration" of an Fc region includes alteration into an amino acid sequence which is different from that of the starting Fc region. The starting Fc region may be any Fc region, as long as a variant modified from the starting Fc region can bind to human Fcγ receptor in a neutral pH range. Furthermore, an Fc region altered from a starting Fc region which had been already altered can also be used preferably as an Fc region of the present invention. The "starting Fc region" can refer to the polypeptide itself, a composition comprising the starting Fc region, or an amino acid sequence encoding the starting Fc region. Starting Fc regions can comprise known Fc regions produced via recombination described briefly in the section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG class. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of native IgG variants or altered forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between an FcγR-binding altered Fc region of the present invention and its starting Fc region. Amino acid difference between an FcγR-binding altered Fc region of the present invention and its starting Fc region can also be preferably specified based on the specific amino acid differences at the above-described specific amino acid positions by EU numbering. Examples of methods of preparing such variants are shown in the section "Alteration of amino acids".

Included in the antigen-binding molecules of the present invention, an Fc region with altered FcγR binding, which has a higher Fcγ receptor-binding activity than that of an Fc region of a native human IgG, (an FcγR binding-altered Fc region) may be obtained by any method. Specifically, the Fc region with altered FcγR binding may be obtained by altering amino acids of an IgG-type human immunoglobulin used as a starting Fc region. Preferred Fc regions of the IgG-type immunoglobulins for alteration include, for example, those of human IgGs shown in SEQ ID NOs: 5, 6, 7, or 8 (IgG1, IgG2, IgG3, or IgG4, respectively, and variants thereof).

Amino acids of any positions may be altered into other amino acids, as long as the binding activity toward the Fcγ receptor is higher than that of the Fc region of a native human IgG. When the antigen-binding molecule contains a human IgG1 Fc region as the human Fc region, it preferably contains an alteration that yields the effect of a higher Fcγ receptor-binding activity than that of the Fc region of a native human IgG, in which the sugar chain bound at position 297 (EU numbering) is a fucose-containing sugar chain. Such amino acid alterations have been reported, for example, in international publications such as WO2007/

024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Examples of such amino acids that may be altered include at least one or more amino acids selected from the group consisting of positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 (EU numbering). An Fc region (Fc region with altered FcγR binding) having a higher Fcγ receptor-binding activity than that of an Fc region of a native human IgG can be obtained by altering these amino acids.

Examples of particularly preferable alterations for use in the present invention include at least one or more amino acid alterations selected from the group consisting of:
Lys or Tyr for the amino acid of position 221;
Phe, Trp, Glu, or Tyr for the amino acid of position 222;
Phe, Trp, Glu, or Lys for the amino acid of position 223;
Phe, Trp, Glu, or Tyr for the amino acid of position 224;
Glu, Lys, or Trp for the amino acid of position 225;
Glu, Gly, Lys, or Tyr for the amino acid of position 227;
Glu, Gly, Lys, or Tyr for the amino acid of position 228;
Ala, Glu, Gly, or Tyr for the amino acid of position 230;
Glu, Gly, Lys, Pro, or Tyr for the amino acid of position 231;
Glu, Gly, Lys, or Tyr for the amino acid of position 232;
Ala, Asp, Phe, Gly, His, Ile, Lys, Leu, Met, Asn, Gln, Arg, Ser, Thr, Val, Trp, or Tyr for the amino acid of position 233;
Ala, Asp, Glu, Phe, Gly, His, Ile, Lys, Met, Asn, Pro, Gln, Arg, Ser, Thr, Val, Trp, or Tyr for the amino acid of position 234;
Ala, Asp, Glu, Phe, Gly, His, Ile, Lys, Met, Asn, Pro, Gln, Arg, Ser, Thr, Val, Trp, or Tyr for the amino acid of position 235;
Ala, Asp, Glu, Phe, His, Ile, Lys, Leu, Met, Asn, Pro, Gln, Arg, Ser, Thr, Val, Trp, or Tyr for the amino acid of position 236;
Asp, Glu, Phe, His, Ile, Lys, Leu, Met, Asn, Pro, Gln, Arg, Ser, Thr, Val, Trp, or Tyr for the amino acid of position 237;
Asp, Glu, Phe, Gly, His, Ile, Lys, Leu, Met, Asn, Gln, Arg, Ser, Thr, Val, Trp, or Tyr for the amino acid of position 238;
Asp, Glu, Phe, Gly, His, Ile, Lys, Leu, Met, Asn, Pro, Gln, Arg, Thr, Val, Trp, or Tyr for the amino acid of position 239;
Ala, Ile, Met, or Thr for the amino acid of position 240;
Asp, Glu, Leu, Arg, Trp, or Tyr for the amino acid of position 241;
Leu, Glu, Leu, Gln, Arg, Trp, or Tyr for the amino acid of position 243;
His for the amino acid of position 244;
Ala for the amino acid of position 245;
Asp, Glu, His, or Tyr for the amino acid of position 246;
Ala, Phe, Gly, His, Ile, Leu, Met, Thr, Val, or Tyr for the amino acid of position 247;
Glu, His, Gln, or Tyr for the amino acid of position 249;
Glu or Gln for the amino acid of position 250;
Phe for the amino acid of position 251;
Phe, Met, or Tyr for the amino acid of position 254;
Glu, Leu, or Tyr for the amino acid of position 255;
Ala, Met, or Pro for the amino acid of position 256;
Asp, Glu, His, Ser, or Tyr for the amino acid of position 258;
Asp, Glu, His, or Tyr for the amino acid of position 260;
Ala, Glu, Phe, Ile, or Thr for the amino acid of position 262;
Ala, Ile, Met, or Thr for the amino acid of position 263;
Asp, Glu, Phe, Gly, His, Ile, Lys, Leu, Met, Asn, Pro, Gln, Arg, Ser, Thr, Trp, or Tyr for the amino acid of position 264;
Ala, Leu, Phe, Gly, His, Ile, Lys, Leu, Met, Asn, Pro, Gln, Arg, Ser, Thr, Val, Trp, or Tyr for the amino acid of position 265;
Ala, Ile, Met, or Thr for the amino acid of position 266;
Asp, Glu, Phe, His, Ile, Lys, Leu, Met, Asn, Pro, Gln, Arg, Thr, Val, Trp, or Tyr for the amino acid of position 267;
Asp, Glu, Phe, Gly, Ile, Lys, Leu, Met, Pro, Gln, Arg, Thr, Val, or Trp for the amino acid of position 268;
Phe, Gly, His, Ile, Lys, Leu, Met, Asn, Pro, Arg, Ser, Thr, Val, Trp, or Tyr for the amino acid of position 269;
Glu, Phe, Gly, His, Ile, Leu, Met, Pro, Gln, Arg, Ser, Thr, Trp, or Tyr for the amino acid of position 270;
Ala, Asp, Glu, Phe, Gly, His, Ile, Lys, Leu, Met, Asn, Gln, Arg, Ser, Thr, Val, Trp, or Tyr for the amino acid of position 271;
Asp, Phe, Gly, His, Ile, Lys, Leu, Met, Pro, Arg, Ser, Thr, Val, Trp, or Tyr for the amino acid of position 272;
Phe or Ile for the amino acid of position 273;
Asp, Glu, Phe, Gly, His, Ile, Leu, Met, Asn, Pro, Arg, Ser, Thr, Val, Trp, or Tyr for the amino acid of position 274;
Leu or Trp for the amino acid of position 275;
Asp, Glu, Phe, Gly, His, Ile, Leu, Met, Pro, Arg, Ser, Thr, Val, Trp, or Tyr for the amino acid of position 276;
Asp, Glu, Gly, His, Ile, Lys, Leu, Met, Asn, Pro, Gln, Arg, Ser, Thr, Val, or Trp for the amino acid of position 278;
Ala for the amino acid of position 279;
Ala, Gly, His, Lys, Leu, Pro, Gln, Trp, or Tyr for the amino acid of position 280;
Asp, Lys, Pro, or Tyr for the amino acid of position 281;
Glu, Gly, Lys, Pro, or Tyr for the amino acid of position 282;
Ala, Gly, His, Ile, Lys, Leu, Met, Pro, Arg, or Tyr for the amino acid of position 283;
Asp, Glu, Leu, Asn, Thr, or Tyr for the amino acid of position 284;
Asp, Glu, Lys, Gln, Trp, or Tyr for the amino acid of position 285;
Glu, Gly, Pro, or Tyr for the amino acid of position 286;
Asn, Asp, Glu, or Tyr for the amino acid of position 288;
Asp, Gly, His, Leu, Asn, Ser, Thr, Trp, or Tyr for the amino acid of position 290;
Asp, Glu, Gly, His, Ile, Gln, or Thr for the amino acid of position 291;
Ala, Asp, Glu, Pro, Thr, or Tyr for the amino acid of position 292;
Phe, Gly, His, Ile, Leu, Met, Asn, Pro, Arg, Ser, Thr, Val, Trp, or Tyr for the amino acid of position 293;
Phe, Gly, His, Ile, Lys, Leu, Met, Asn, Pro, Arg, Ser, Thr, Val, Trp, or Tyr for the amino acid of position 294;
Asp, Glu, Phe, Gly, His, Ile, Lys, Met, Asn, Pro, Arg, Ser, Thr, Val, Trp, or Tyr for the amino acid of position 295;
Ala, Asp, Glu, Gly, His, Ile, Lys, Leu, Met, Asn, Gln, Arg, Ser, Thr, or Val for the amino acid of position 296;
Asp, Glu, Phe, Gly, His, Ile, Lys, Leu, Met, Pro, Gln, Arg, Ser, Thr, Val, Trp, or Tyr for the amino acid of position 297;
Ala, Asp, Glu, Phe, His, Ile, Lys, Met, Asn, Gln, Arg, Thr, Val, Trp, or Tyr for the amino acid of position 298;
Ala, Asp, Glu, Phe, Gly, His, Ile, Lys, Leu, Met, Asn, Pro, Gln, Arg, Ser, Val, Trp, or Tyr for the amino acid of position 299;
Ala, Asp, Glu, Gly, His, Ile, Lys, Leu, Met, Asn, Pro, Gln, Arg, Ser, Thr, Val, or Trp for the amino acid of position 300;

Asp, Glu, His, or Tyr for the amino acid of position 301;
Ile for the amino acid of position 302;
Asp, Gly, or Tyr for the amino acid of position 303;
Asp, His, Leu, Asn, or Thr for the amino acid of position 304;
Glu, Ile, Thr, or Tyr for the amino acid of position 305;
Ala, Asp, Asn, Thr, Val, or Tyr for the amino acid of position 311;
Phe for the amino acid of position 313;
Leu for the amino acid of position 315;
Glu or Gln for the amino acid of position 317;
His, Leu, Asn, Pro, Gln, Arg, Thr, Val, or Tyr for the amino acid of position 318;
Asp, Phe, Gly, His, Ile, Leu, Asn, Pro, Ser, Thr, Val, Trp, or Tyr for the amino acid of position 320;
Ala, Asp, Phe, Gly, His, Ile, Pro, Ser, Thr, Val, Trp, or Tyr for the amino acid of position 322;
Ile for the amino acid of position 323;
Asp, Phe, Gly, His, Ile, Leu, Met, Pro, Arg, Thr, Val, Trp, or Tyr for the amino acid of position 324;
Ala, Asp, Glu, Phe, Gly, His, Ile, Lys, Leu, Met, Pro, Gln, Arg, Ser, Thr, Val, Trp, or Tyr for the amino acid of position 325;
Ala, Asp, Glu, Gly, Ile, Leu, Met, Asn, Pro, Gln, Ser, Thr, Val, Trp, or Tyr for the amino acid of position 326;
Ala, Asp, Glu, Phe, Gly, His, Ile, Lys, Leu, Met, Asn, Pro, Arg, Thr, Val, Trp, or Tyr for the amino acid of position 327;
Ala, Asp, Glu, Phe, Gly, His, Ile, Lys, Met, Asn, Pro, Gln, Arg, Ser, Thr, Val, Trp, or Tyr for the amino acid of position 328;
Asp, Glu, Phe, Gly, His, Ile, Lys, Leu, Met, Asn, Gln, Arg, Ser, Thr, Val, Trp, or Tyr for the amino acid of position 329;
Cys, Glu, Phe, Gly, His, Ile, Lys, Leu, Met, Asn, Pro, Arg, Ser, Thr, Val, Trp, or Tyr for the amino acid of position 330;
Asp, Phe, His, Ile, Leu, Met, Gln, Arg, Thr, Val, Trp, or Tyr for the amino acid of position 331;
Ala, Asp, Glu, Phe, Gly, His, Lys, Leu, Met, Asn, Pro, Gln, Arg, Ser, Thr, Val, Trp, or Tyr for the amino acid of position 332;
Ala, Asp, Glu, Phe, Gly, His, Ile, Leu, Met, Pro, Ser, Thr, Val, or Tyr for the amino acid of position 333;
Ala, Glu, Phe, Ile, Leu, Pro, or Thr for the amino acid of position 334;
Asp, Phe, Gly, His, Ile, Leu, Met, Asn, Pro, Arg, Ser, Val, Trp, or Tyr for the amino acid of position 335;
Glu, Lys, or Tyr for the amino acid of position 336;
Glu, His, or Asn for the amino acid of position 337;
Asp, Phe, Gly, Ile, Lys, Met, Asn, Gln, Arg, Ser, or Thr for the amino acid of position 339;
Ala or Val for the amino acid of position 376;
Gly or Lys for the amino acid of position 377;
Asp for the amino acid of position 378;
Asn for the amino acid of position 379;
Ala, Asn, or Ser for the amino acid of position 380;
Ala or Ile for the amino acid of position 382;
Glu for the amino acid of position 385;
Thr for the amino acid of position 392;
Leu for the amino acid of position 396;
Lys for the amino acid of position 421;
Asn for the amino acid of position 427;
Phe or Leu for the amino acid of position 428;
Met for the amino acid of position 429;
Trp for the amino acid of position 434;
Ile for the amino acid of position 436; and
Gly, His, Ile, Leu, or Tyr for the amino acid of position 440; as indicated by EU numbering in the Fc region. The number of amino acids to be altered is not particularly limited; and amino acid may be altered at only one site or amino acids may be altered at two or more sites. Examples of combinations for amino acid alterations at two or more sites include those described in Table 1 (Tables 1-1 to 1-3).

TABLE 1-1

| Combination of amino acids | Combination of amino acids |
|---|---|
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |

TABLE 1-2

| | |
|---|---|
| F243L/V264I | S239D/N297D/I332E |
| H268D/A330Y | S239D/S298A/I332E |
| H268E/A330Y | S239D/V264I/I332E |
| K246H/I332E | S239D/N297D/I332E |
| L234D/I332E | S239E/V264I/I332E |
| L234E/I332E | S239N/A330L/I332E |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262T/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |

TABLE 1-2-continued

| | |
|---|---|
| L328V/I332E | S239D/A330Y/I332E/L234I |
| L328Y/I332D | S239D/A330Y/I332E/L235D |

Table 1-2 is a continuation of Table 1-1.
Table 1-3 is a continuation of Table 1-2.

TABLE 1-3

| | |
|---|---|
| L328Y/I332E | S239D/A330Y/I332E/V240I |
| N297D/I332E | S239D/A330Y/I332E/V264T |
| N297E/I332E | S239D/A330Y/I332E/V266I |
| N297S/I322E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239D/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |
| S267E/L328F | G236D/S267E |
| S239D/S267E | |

For the pH conditions to measure the binding activity of the Fcγ receptor binding domain and the Fcγ receptor contained in the antigen-binding molecule of the present invention, conditions in an acidic pH range or in a neutral pH range may be suitably used. The acidic pH range or neutral pH range, as a condition to measure the binding activity of the Fcγ receptor binding domain and the Fcγ receptor contained in the antigen-binding molecule of the present invention, generally indicates pH 5.8 to pH 8.0. Preferably, it is a range indicated with arbitrary pH values between pH 6.0 and pH 7.4; and preferably, it is selected from pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, and pH 7.4; and particularly preferably, it is pH 6.15 to 7.4, which is close to the pH of cancer tissues (Vaupel et al., Cancer Res. (1989) 49, 6449-6665). With regard to the temperature used as a measurement condition, the binding affinity between an Fcγ receptor binding domain and a human Fcγ receptor can be evaluated at any temperature between 10° C. and 50° C. Preferably, a temperature between 15° C. and 40° C. is used to determine the binding affinity between a human Fcγ receptor binding domain and Fcγ receptor. More preferably, any temperature between 20° C. and 35° C., such as any single temperature from 20° C., 21° C., 22° C., 23° C., 24° C., 25° C., 26° C., 27° C., 28° C., 29° C., 30° C., 31° C., 32° C., 33° C., 34° C., and 35° C., can be similarly used to determine the binding affinity between an Fcγ receptor binding domain and an Fcγ receptor. A temperature of 25° C. is a non-limiting example in an embodiment of the present invention.

Herein, "Fc region with altered FcγR binding has a higher Fcγ receptor-binding activity than the native Fc region" means that the human Fcγ receptor-binding activity of the Fc region with altered FcγR binding toward any of the human Fcγ receptors of FcγRI, FcγRIIa, FcγRIIb, FcγRIIIa, and/or FcγRIIIb is higher than the binding activity of the native Fc region toward these human Fcγ receptors. For example, it means that based on an above-described analytical method, in comparison to the binding activity of an antigen-binding molecule containing a native human IgG Fc region as a control, the binding activity of the antigen-binding molecule comprising an Fc region with altered FcγR binding is 105% or more, preferably 110% or more, 115% or more, 120% or more, 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2-fold or more, 2.5-fold or more, 3-fold or more, 3.5-fold or more, 4-fold or more, 4.5-fold or more, 5-fold or more, 7.5-fold or more, 10-fold or more, 20-fold or more, 30-fold or more, 40-fold or more, 50-fold or more, 60-fold or more, 70-fold or more, 80-fold or more, 90-fold or more, or 100-fold or more. The starting Fc region may be used as a native Fc region, and native Fc regions of antibodies of the same subclass may also be used.

In the present invention, an Fc region of a native human IgG in which the sugar chain bonded to the amino acid at position 297 (EU numbering) is a fucose-containing sugar chain, is suitably used as a native Fc region of human IgG to be used as a control. Whether or not the sugar chain bonded to the amino acid at position 297 (EU numbering) is a fucose-containing sugar chain can be determined using the technique described in Non-Patent Document 6. For example, it is possible to determine whether or not the sugar chain bonded to the native human IgG Fc region is a fucose-containing sugar chain by a method such as the one below. Sugar chain is dissociated from a native human IgG to be tested, by reacting the test native human IgG with N-Glycosidase F (Roche diagnostics) (Weitzhandler et al. (J. Pharma. Sciences (1994) 83, 12, 1670-1675)). Next, a dried concentrate of a reaction solution from which protein has been removed by reaction with ethanol (Schenk et al. (J. Clin. Investigation (2001) 108 (11) 1687-1695)) is fluorescently labeled with 2-aminopyridine (Bigge et al. (Anal. Biochem. (1995) 230 (2) 229-238)). Reagents are removed by solid extraction using a cellulose cartridge, and the fluorescently labeled 2-AB-modified sugar chain is analyzed by normal-phase chromatography. It is possible to determine whether or not the sugar chain bonded to the native Fc region of a human IgG is a fucose-containing sugar chain by observing the detected chromatogram peaks.

As an antigen-binding molecule containing a native Fc region of an antibody of the same subclass, which is to be used as a control, an antigen-binding molecule having an Fc region of a monoclonal IgG antibody may be suitably used. The structures of the Fc regions are described in SEQ ID NO: 5 (A is added to the N terminus of Database Accession No. AAC82527.1), SEQ ID NO: 6 (A is added to the N terminus of Database Accession No. AAB59393.1), SEQ ID NO: 7 (Database Accession No. CAA27268.1), and SEQ ID NO: 8 (A is added to the N terminus of Database Accession No. AAB59394.1). Further, when an antigen-binding molecule containing an Fc region of a particular antibody isotype is used as the test substance, the effect of the antigen-binding molecule containing the test Fc region on Fcγ receptor-binding activity is tested by using as a control an antigen-binding molecule having an Fc region of a monoclonal IgG antibody of that particular isotype. In this way, antigen-binding molecules containing an Fc region of which Fcγ receptor-binding activity is demonstrated to be high are suitably selected.

Fc Regions Having a Selective Binding Activity Toward an Fcγ Receptor

Examples of Fcγ receptor binding domains suitable for use in the present invention include Fcγ receptor binding domains having a higher binding activity to a particular Fcγ receptor than to other Fcγ receptors (Fcγ receptor binding domains having a selective binding activity to an Fcγ receptor). When an antibody is used as the antigen-binding molecule (when an Fc region is used as the Fcγ receptor binding domain), a single antibody molecule can only bind to a single Fcγ receptor molecule. Therefore, a single antigen-binding molecule cannot bind to other activating FcγRs in an inhibitory Fcγ receptor-bound state, and cannot bind to other activating Fcγ receptors or inhibitory Fcγ receptors in an activating Fcγ receptor-bound state.

Fc Regions with a Higher Binding Activity Toward an Activating Fcγ Receptor than the Binding Activity Toward an Inhibitory Fcγ Receptor As described above, preferable activating Fcγ receptors include FcγRI (CD64) including FcγRIa, FcγRIb, and FcγRIc; FcγRIIa; and FcγRIII (CD16) including FcγRIIIa (including allotypes V158 and F158) and FcγRIIIb (including allotypes FcγRIIIb-NA1 and FcγRIIIb-NA2). Meanwhile, preferred examples of inhibitory Fcγ receptors include FcγRIIb (including FcγRIIb-1 and FcγRIIb-2).

Herein, an example of a case where the binding activity toward a certain Fcγ receptor is higher than the binding activity toward another Fcγ receptor is the case where the binding activity toward an activating Fcγ receptor is higher than the binding activity toward an inhibitory Fcγ receptor. In this case, the binding activity of the Fc region toward any of the human Fcγ receptors of FcγRIa, FcγRIIa, FcγRIIIa, and/or FcγRIIIb is said to be higher than the binding activity toward FcγRIIb. For example, this means that, based on an above-described analytical method, the binding activity of an antigen-binding molecule containing the Fc region toward any of the human Fcγ receptors, FcγRIa, FcγRIIa, FcγRIIIa, and/or FcγRIIIb, is 105% or more, preferably 110% or more, 120% or more, 130% or more, 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10-fold or more, 20-fold or more, 30-fold or more, 40-fold or more, 50-fold or more, 60-fold, 70-fold, 80-fold, 90-fold, or 100-fold or more as compared with the binding activity toward FcγRIIb. The Fc region with a higher binding activity toward activating Fcγ receptors than to inhibitory Fcγ receptors may be favorably included in antigen-binding molecules of the present invention whose antigen-binding domain binds to a membrane-type molecule. IgG1 antibodies containing such Fc regions are known to enhance the ADCC activity mentioned below. Therefore, antigen-binding molecules containing the Fc-region are also useful as antigen-binding molecules to be included in the pharmaceutical compositions of the present invention.

In a non-limiting embodiment of the present invention, examples of the Fc region with a higher binding activity toward activating Fcγ receptors than to inhibitory Fcγ receptors (or having a selective binding activity toward inhibitory Fcγ receptors) preferably include Fc regions in which at least one or more amino acids selected from the group consisting of amino acids at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440 indicated by EU numbering mentioned above, have been altered to amino acids different from those of the native Fc region.

In a non-limiting embodiment of the present invention, examples of the Fc region with a higher binding activity toward activating Fcγ receptors than to inhibitory Fcγ receptors (or having a selective binding activity toward inhibitory Fcγ receptors) preferably include Fc regions in which multiple amino acids indicated in Tables 1-1 to 1-3 have been altered to amino acids different from those of the native Fc region.

Fc Regions Whose Binding Activity Toward an Inhibitory Fcγ Receptor is Higher than the Binding Activity Toward an Activating Fcγ Receptor Herein, an example of a case where the binding activity toward a certain Fcγ receptor is higher than the binding activity toward another Fcγ receptor is the case where the binding activity toward an inhibitory Fcγ receptor is higher than the binding activity toward an activating Fcγ receptor. In this case, the binding activity of the Fc region toward FcγRIIb is said to be higher than the binding activity toward any of the human Fcγ receptors of FcγRIa, FcγRIIa, FcγRIIIa, and/or FcγRIIIb. For example, this means that, based on an above-described analytical method, the binding activity of an antigen-binding molecule containing the Fc region toward FcγRIIb is 105% or more, preferably 110% or more, 120% or more, 130% or more, 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10-fold or more, 20-fold or more, 30-fold or more, 40-fold or more, 50-fold, 60-fold, 70-fold, 80-fold, 90-fold, or 100-fold or more as compared with the binding activity toward any of the human Fcγ receptors of FcγRIa, FcγRIIa, FcγRIIIa, and/or FcγRIIIb. The Fc region with a higher binding activity toward inhibitory Fcγ receptors than to activating Fcγ receptors may be favorably included in antigen-binding molecules of the present invention whose antigen-binding domain binds to a soluble molecule.

In a non-limiting embodiment of the present invention, examples of the Fc region with a higher binding activity toward inhibitory Fcγ receptors than to activating Fcγ receptors (or having a selective binding activity toward inhibitory Fcγ receptors) preferably include Fc regions in which, of the amino acids of the above Fc region, the amino acids at 238 and 328 indicated by EU numbering are altered to amino acids different from those of the native Fc region.

In a non-limiting embodiment of the present invention, examples of the Fc region with a higher binding activity toward inhibitory Fcγ receptors than to activating Fcγ receptors (or having a selective binding activity toward inhibitory Fcγ receptors) preferably include Fc regions altered at any one or more of the amino acids in the above Fc region as indicated by EU numbering: the amino acid at position 238 (indicated by EU numbering) is altered into Asp; and the amino acid at position 328 (indicated by EU numbering) is altered into Glu. Furthermore, as the Fc regions having a selective binding activity toward inhibitory Fcγ receptors, the Fc regions or alterations described in US 2009/0136485 can be suitably selected.

In another non-limiting embodiment of the present invention, preferred examples include Fc regions altered at any one or more of the amino acids in the above Fc region as indicated by EU numbering: the amino acid at position 238 (indicated by EU numbering) to Asp; and the amino acid at position 328 (indicated by EU numbering) to Glu.

In still another non-limiting embodiment of the present invention, preferred examples include Fc regions that have one or more of the alterations exemplified in PCT/JP2012/054624: substitution of Pro at position 238 (indicated by EU numbering) with Asp; alteration of the amino acid at position 237 (indicated by EU numbering) to Trp; alteration of the amino acid at position 237 (indicated by EU numbering) to Phe; alteration of the amino acid at position 267 (indicated by EU numbering) to Val; alteration of the amino acid at position 267 (indicated by EU numbering) to Gln; alteration of the amino acid at position 268 (indicated by EU numbering) to Asn; alteration of the amino acid at position 271 (indicated by EU numbering) to Gly; alteration of the amino acid at position 326 (indicated by EU numbering) to Leu; alteration of the amino acid at position 326 (indicated by EU numbering) to Gln; alteration of the amino acid at position 326 (indicated by EU numbering) to Glu; alteration of the amino acid at position 326 (indicated by EU numbering) to Met; alteration of the amino acid at position 239 (indicated by EU numbering) to Asp; alteration of the amino acid at position 267 (indicated by EU numbering) to Ala; alteration of the amino acid at position 234 (indicated by EU numbering) to Trp; alteration of the amino acid at position 234 (indicated by EU numbering) to Tyr; alteration of the amino acid at position 237 (indicated by EU numbering) to Ala; alteration of the amino acid at position 237 (indicated by EU numbering) to Asp; alteration of the amino acid at position 237 (indicated by EU numbering) to Glu; alteration of the amino acid at position 237 (indicated by EU numbering) to Leu; alteration of the amino acid at position 237 (indicated by EU numbering) to Met; alteration of the amino acid at position 237 (indicated by EU numbering) to Tyr; alteration of the amino acid at position 330 (indicated by EU numbering) to Lys; alteration of the amino acid at position 330 (indicated by EU numbering) to Arg, alteration of the amino acid at position 233 (indicated by EU numbering) to Asp, alteration of the amino acid at position 268 (indicated by EU numbering) to Asp, alteration of the amino acid at position 268 (indicated by EU numbering) to Glu, alteration of the amino acid at position 326 (indicated by EU numbering) to Asp, alteration of the amino acid at position 326 (indicated by EU numbering) to Ser, alteration of the amino acid at position 326 (indicated by EU numbering) to Thr, alteration of the amino acid at position 323 (indicated by EU numbering) to Ile, alteration of the amino acid at position 323 (indicated by EU numbering) to Leu, alteration of the amino acid at position 323 (indicated by EU numbering) to Met, alteration of the amino acid at position 296 (indicated by EU numbering) to Asp, alteration of the amino acid at position 326 (indicated by EU numbering) to Ala, alteration of the amino acid at position 326 (indicated by EU numbering) to Asn, and alteration of the amino acid at position 330 (indicated by EU numbering) to Met.

Fc Regions with Modified Sugar Chains

Fc regions contained in the antigen-binding molecules provided by the present invention may include Fc regions that have been modified so that the composition of the sugar-chain-attached Fc regions has a high percentage of fucose-deficient sugar-chain-attached Fc regions, or a high percentage of bisecting N-acetylglucosamine-added Fc regions. Removal of fucose residue from N-acetylglucosamine at the reducing end of N-glycoside linkage complex sugar chains bonded to the antibody Fc region is known to enhance the affinity to FcγRIIIa (Non-Patent Document 6). It is known that for IgG1 antibodies containing such Fc regions, the ADCC activity mentioned below is enhanced; therefore, antigen-binding molecules containing such Fc regions are also useful as antigen-binding molecules to be contained in pharmaceutical compositions of the present invention. Examples of antibodies with fucose residue removed from N-acetylglucosamine at the reducing end of N-glycoside linkage complex sugar chains bonded to the antibody Fc regions are antibodies such as:

antibodies modified by glycosylation (for example, WO 1999/054342); and antibodies deficient in fucose attached to sugar chains (for example, WO 2000/061739, WO 2002/031140, and WO 2006/067913).

More specifically, to produce antibodies deficient in fucose attached to sugar chains (for example, WO 2000/061739, WO 2002/031140, and WO 2006/067913) as another non-limiting embodiment of antibodies with fucose residue removed from N-acetylglucosamine at the reducing end of N-glycoside linkage complex sugar chains bonded to the antibody Fc regions, host cells having a low ability to add fucose to sugar chains are produced by altering the activity of forming the sugar chain structure of the polypeptide to be glycosylated. Antibodies that lack fucose in their sugar chains can be collected from culture of the host cells by expressing a desired antibody gene in the host cells. Non-limiting suitable examples of the activity to form the sugar chain structure of a polypeptide include the activity of a transporter or an enzyme selected from the group consisting of fucosyltransferase (EC 2.4.1.152), fucose transporter (SLC35C1), GMD (GDP-mannose-4,6-dehydratase) (EC 4.2.1.47), Fx (GDP-keto-6-deoxymannose-3,5-epimerase, 4-reductase) (EC 1.1.1.271), and GFPP (GDP-β-L-fucose pyrophosphorylase (EC 2.7.7.30). As long as these enzymes or transporters can exhibit their activities, their structures are not necessarily specified. Herein, proteins that can exhibit these activities are referred to as "functional proteins". In a non-limiting embodiment, methods for altering these activities include deletion of these activities. To produce host cells deficient in these activities, known methods such as a method for destroying the genes of these functional proteins to make them unable to function may be appropriately employed (for example, WO2000/061739, WO2002/031140, and WO2006/067913). Host cells deficient in such activities can be produced, for example, by a method that destroys the genes of these functional proteins endogenous to CHO cells, BHK cells, NS0 cells, SP2/0 cells, YO myeloma cells, P3X63 mouse myeloma cells, PER cells, PER.C6 cells, HEK293 cells, hybridoma cells, or such, so that the genes are unable to function.

Antibodies that have a sugar chain containing bisecting GlcNAc (WO2002/079255, etc.) are known. In a non-limiting embodiment, host cells for expressing a gene that encodes a functional protein having GnTIII (β-1,4-mannosyl-glycoprotein 4-β-N-acetylglucosaminyltransferase) (EC 2.4.1.144) activity or GalT (β-1,4-galactosyltransferase) (EC 2.4.1.38) activity are produced to prepare antibodies that have bisecting GlcNAc-containing sugar chains. In another suitable non-limiting embodiment, host cells that co-express, in addition to the aforementioned functional proteins, a gene encoding a functional protein having human ManII (manosidase II) (3.2.1.114) activity, a gene encoding a functional protein having GnTI (β-1,2-acetylglucosaminyltransferase I) (EC 2.4.1.94) activity, a gene encoding a functional protein having GnTII (β-1,2-acetylglucosaminyl-transferase II) (EC 2.4.1.143) activity, a gene encoding a functional protein having ManI (mannosidase) (EC 3.2.1.113) activity, and α-1,6-fucosyl transferase (EC 2.4.1.68), are produced (WO2004/065540).

Antibodies with fucose residue removed from N-acetylglucosamine at the reducing end of N-glycoside linkage complex sugar chains bonded to the antibody Fc regions and antibodies having sugar chains containing bisecting GlcNAc can be produced, respectively, by transfecting an expression vector containing the antibody gene into host cells with a low ability to add fucose to sugar chains, and into host cells having the activity to form bisecting GlcNAc structure-containing sugar chains. Methods for producing these antibodies can be applied to methods for producing antigen-binding molecules containing altered Fc regions that have been modified so that the composition of the sugar-chain-attached Fc regions of the present invention has a high percentage of fucose-deficient sugar chain-attached Fc regions or a high percentage of bisecting N-acetylglucosamine-added Fc regions. The composition of the sugar-chain-attached Fc regions contained in the antigen-binding molecules of the present invention produced by such production methods can be assessed by the method described in "Fc regions with altered Fcγ receptor (FcγR) binding" above.

Multispecific Antigen-Binding Molecules or Multiparatopic Antigen-Binding Molecules An antigen-binding molecule comprising at least two antigen-binding domains in which at least one of the antigen-binding domains binds to a first epitope in an antigen molecule, and at least another one of the antigen-binding domains binds to a second epitope in the antigen molecule, is called "multispecific antigen-binding molecule" from the viewpoint of its reaction specificity. When two types of antigen-binding domains contained in a single antigen-binding molecule allow binding to two different epitopes by the antigen-binding molecule, this molecule is called "bispecific antigen-binding molecule". When three types of antigen-binding domains contained in a single antigen-binding molecule allow binding to three different epitopes by the antigen-binding molecule, this antigen-binding molecule is called "trispecific antigen-binding molecule".

A paratope in the antigen-binding domain that binds to the first epitope in the antigen molecule and a paratope in the antigen-binding domain that binds to the second epitope which is structurally different from the first epitope have different structures. Therefore, an antigen-binding molecule comprising at least two antigen-binding domains in which at least one of the antigen-binding domains binds to a first epitope in an antigen molecule, and at least another one of the antigen-binding domains binds to a second epitope in the antigen molecule, is called "multiparatopic antigen-binding molecule" from the viewpoint of the specificity of its structure. When two types of antigen-binding domains contained in a single antigen-binding molecule allow binding to two different epitopes by the antigen-binding molecule, this molecule is called "biparatopic antigen-binding molecule". When three types of antigen-binding domains contained in a single antigen-binding molecule allow binding to three different epitopes by the antigen-binding molecule, this molecule is called "triparatopic antigen-binding molecule".

Multivalent multispecific or multiparatopic antigen-binding molecules comprising one or more antigen-binding domains and methods for preparing them are described in non-patent documents such as Conrath et al., (J. Biol. Chem. (2001) 276 (10) 7346-7350), Muyldermans (Rev. Mol. Biotech. (2001) 74, 277-302), and Kontermann R. E. (2011) Bispecific Antibodies (Springer-Verlag), and in patent documents such as WO1996/034103 and WO 1999/023221. Antigen-binding molecules of the present invention can be produced using multispecific or multiparatopic antigen-binding molecules, and their preparation methods described in these documents.

Bispecific Antibodies and Methods for Producing them

In an embodiment, bispecific antibodies and methods for producing them are mentioned below as examples of the aforementioned multispecific or multiparatopic antigen-binding molecules and methods for preparing them. Bispecific antibodies are antibodies comprising two types of variable regions that bind specifically to different epitopes. IgG-type bispecific antibodies can be secreted from a hybrid hybridoma (quadroma) produced by fusing two types of hybridomas that produce IgG antibodies (Milstein et al., Nature (1983) 305, 537-540).

When a bispecific antibody is produced by using recombination techniques such as those described in the above-mentioned section on antibodies, one may adopt a method that introduces genes encoding heavy chains containing the two types of variable regions of interest into cells to co-express them. However, even when only the heavy-chain combination is considered, such a co-expression method will produce a mixture of (i) a combination of a pair of heavy chains in which one of the heavy chains contains a variable region that binds to a first epitope and the other heavy chain contains a variable region that binds to a second epitope, (ii) a combination of a pair of heavy chains which include only heavy chains containing a variable region that binds to the first epitope, and (iii) a combination of a pair of heavy chains which include only heavy chains containing a variable region that binds to the second epitope, which are present at a molecular ratio of 2:1:1. It is difficult to purify antigen-binding molecules containing the desired combination of heavy chains from the mixture of three types of heavy chain combinations.

When producing bispecific antibodies using such recombination techniques, bispecific antibodies containing a heteromeric combination of heavy chains can be preferentially secreted by adding appropriate amino acid substitutions in the CH3 domains constituting the heavy chains. Specifically, this method is conducted by substituting an amino acid having a larger side chain (knob (which means "bulge")) for an amino acid in the CH3 domain of one of the heavy chains, and substituting an amino acid having a smaller side chain (hole (which means "void")) for an amino acid in the CH3 domain of the other heavy chain so that the knob is placed in the hole. This promotes heteromeric heavy chain formation and simultaneously inhibits homomeric heavy chain formation (International Publication No. WO 1996027011; Ridgway et al., Protein Engineering (1996) 9, 617-621; Merchant et al., Nature Biotechnology (1998) 16, 677-681).

Furthermore, there are also known techniques for producing a bispecific antibody by applying methods for controlling polypeptide association, or association of polypeptide-formed heteromeric multimers to the association between heavy chains. Specifically, methods for controlling heavy chain formation may be employed to produce a bispecific antibody (International Publication No. WO 2006/106905), in which amino acid residues forming the interface between the heavy chains are altered to inhibit the association between the heavy chains having the same sequence and to allow the formation of heavy chains of different sequences. Such methods can be used for generating bispecific antibodies.

In a non-limiting embodiment of the present invention, two polypeptides constituting an Fc region derived from a bispecific antibody described above can be suitably used as an Fc region to be included in the antigen-binding molecule. More specifically, it is preferable to use two polypeptides that constitute an Fc region, and which comprise Cys for the amino acid at position 349 and Trp for the amino acid at position 366 according to EU numbering in the amino acid sequence of one of the polypeptides; and Cys for the amino acid at position 356, Ser for the amino acid at position 366, Ala for the amino acid at position 368, and Val for the amino acid at position 407 as indicated by EU numbering in the amino acid sequence of the other polypeptide.

In another non-limiting embodiment of the present invention, two polypeptides that constitute an Fc region and which comprise Asp for the amino acid at position 409 according to EU numbering in the amino acid sequence of one of the polypeptides, and Lys for the amino acid at position 399 according to EU numbering in the amino acid sequence of the other polypeptide, may be suitably used as the Fc region. In the above embodiment, the amino acid at position 409 may be Glu instead of Asp, and the amino acid at position 399 may be Arg instead of Lys. Moreover, in addition to the amino acid Lys at position 399, Asp may be suitably be added as the amino acid at position 360 or Asp may suitably be added as the amino acid at position 392.

In still another non-limiting embodiment of the present invention, two polypeptides that constitute an Fc region, and which comprise Glu for the amino acid at position 370 according to EU numbering in the amino acid sequence of one of the polypeptides, and Lys for the amino acid at position 357 according to EU numbering in the amino acid sequence of the other polypeptide, may be suitably used as the Fc region.

In yet another non-limiting embodiment of the present invention, two polypeptides that constitute an Fc region, and which comprise Glu for the amino acid at position 439 according to EU numbering in the amino acid sequence of one of the polypeptides, and Lys for the amino acid at position 356 according to EU numbering in the amino acid sequence of the other polypeptide, may be suitably used as the Fc region.

In still yet another non-limiting embodiment of the present invention, any of the embodiments indicated below of combinations from the above may be suitably used as the Fc region:

(i) two polypeptides that constitute an Fc region, and which comprise Asp for the amino acid at position 409 and Glu for the amino acid at position 370 according to EU numbering in the amino acid sequence of one of the polypeptides, and Lys for the amino acid at position 399 and Lys for the amino acid at position 357 according to EU numbering in the amino acid sequence of the other polypeptide (in this embodiment, the amino acid at position 370 according to EU numbering may be Asp instead of Glu, and the amino acid Asp at position 392 may be used instead of the amino acid Glu at position 370 according to EU numbering);

(ii) two polypeptides that constitute an Fc region, and which comprise Asp for the amino acid at position 409 and Glu for the amino acid at position 439 according to EU numbering of the amino acid sequence of one of the polypeptides; and Lys for the amino acid at position 399 and Lys for the amino acid at position 356 according to EU numbering in the amino acid sequence of the other polypeptide (in this embodiment, the amino acid Asp at position 360, the amino acid Asp at position 392, or the amino acid Asp at position 439 may be used instead of the amino acid Glu at position 439 according to EU numbering);

(iii) two polypeptides that constitute an Fc region, and which comprise Glu for the amino acid at position 370 and Glu for the amino acid at position 439 according to EU numbering in the amino acid sequence of one of the polypeptides, and Lys for the amino acid at position 357 and Lys for the amino acid at position 356 according to EU numbering in the amino acid sequence of the other polypeptide; or two polypeptides that constitute an Fc region, and which comprise Asp the amino acid at position 409, Glu for the amino acid at position 370, and Glu for the amino acid at position 439 according to EU numbering in the amino acid sequence of one of the polypeptides; and Lys for the amino acid at position 399, Lys for the amino acid at position 357, and Lys for the amino acid at position 356 according to EU numbering in the amino acid sequence of the other polypeptide (in this embodiment, the amino acid at position 370 may not be substituted with Glu, and furthermore, when the amino acid at position 370 is not substituted with Glu, the amino acid at position 439 may be Asp instead of Glu, or the amino acid Asp at position 392 may be used instead of the amino acid Glu at position 439, according to EU numbering).

Further, in another non-limiting embodiment of the present invention, it may also be suitable to use two polypeptides that constitute an Fc region, and which comprise Lys for the amino acid at position 356 according to EU numbering in the amino acid sequence of one of the polypeptides, and Arg for the amino acid at position 435 and Glu for the amino acid at position 439 according to EU numbering in the amino acid sequence of the other polypeptide.

In still another non-limiting embodiment of the present invention, it may also be suitable to use two polypeptides that constitute an Fc region and which comprise Lys for the amino acid at position 356 and Lys for the amino acid at position 357 according to EU numbering in the amino acid sequence of one of the polypeptides, and Glu for the amino acid at position 370, Arg for the amino acid at position 435, and Glu for the amino acid at position 439 according to EU numbering in the amino acid sequence of the other polypeptide.

Furthermore, in addition to the above-mentioned technologies of associating heterologous heavy chains, CrossMab technology which is known as a technology for associating heterologous light chains, in which a light chain forming a variable region that binds to a first epitope and a light chain forming a variable region that binds to a second epitope are respectively associated with a heavy chain forming a variable region that binds to the first epitope and a heavy chain forming a variable region that binds to the second epitope (Scaefer et al. (Proc. Natl. Acad. Sci. U.S.A. (2011) 108, 11187-11192)), may also be used to produce the multispecific or multiparatopic antigen-binding molecules provided by the present invention. Furthermore, Fab-Arm Exchange which is known as a technology for associating heterologous heavy chains, in which a heavy chain forming a variable region that binds to a first epitope and a heavy chain forming a variable region that binds to a second epitope by utilizing that heterologous IgG4 heavy chains exchange each other (Labrijn et al. (Proc. Natl. Acad. Sci. U.S.A. (2013) 110, 5145-5150), WO2008119353), may also be used to produce the multispecific or multiparatopic antigen-binding molecules provided by the present invention.

Effector Cells

In the present invention, the term "effector cells" may be used in the broadest sense including T cells (CD4$^+$ (helper lymphocyte) T cells and/or CD8$^+$ (cytotoxic) T cells), multinuclear leucocytes (neutrophils, eosinophils, basophils, mast cells), monocytes, macrophages, histiocytes, or leukocytes such as natural killer cells (NK cells), NK-like T cells, Kupffer cells, Langerhans cells, or lymphokine-activated killer cells (LAK cells), B-lymphocytes, or antigen-presenting cells such as dendritic cells or macrophages. Preferred examples of effector cells include CD8$^+$ (cytotoxic) T cells, NK cells, or macrophages. Membrane-type molecules expressed on the cell membrane of effector cells may be used as antigens to which at least one antigen-binding domain contained in the antigen-binding molecule of the present invention binds. Non-limiting examples of a preferred membrane-type molecule may be CD3, CD2, CD28, CD44, CD16, CD32, CD64, or NKG2D, NK cell-activating ligands, or polypeptides constituting TCR.

Cytotoxic Substances

In order for antigen-binding molecules of the present invention to bind to cancer cells and exhibit cytotoxic activity, cytotoxic substances may be linked to antigen-binding molecules. The cytotoxic substances may be chemotherapeutic agents exemplified below, or compounds disclosed in Curr Opin Chem Biol (2010) 14, 529-37 and WO 2009/140242; and these compounds are linked to antigen-binding molecules by appropriate linkers and such. When antigen-binding molecules of the present invention are used as pharmaceutical compositions, these cytotoxic substances may be linked to the antigen-binding molecules prior to administration, or they may be administered before, after, or at the same time when the antigen-binding molecules are administered to subjects (test individuals, patients, and such).

The later-described modified antigen-binding molecules to which cytotoxic substances such as chemotherapeutic agents, toxic peptides, or radioactive chemical substances have been linked may also be used preferably as antigen-binding molecules of the present invention having cytotoxic activity. Such modified antigen-binding molecules (hereinafter referred to as antigen-binding molecule-drug conjugate) can be obtained by chemically modifying the obtained antigen-binding molecules. Methods that have been already established in the field of antibody-drug conjugates and such may be used appropriately as methods for modifying antigen-binding molecules. Furthermore, a modified antigen-binding molecule to which a toxic peptide is linked can be obtained by expressing in appropriate host cells a fused gene produced by linking a gene encoding the toxic peptide in frame with a gene encoding an antigen-binding molecule of the present invention, and then isolating it from the cell culture.

Examples of chemotherapeutic agents linked to the antigen-binding molecules of the present invention may include: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, and vincristine.

In the present invention, preferred chemotherapeutic agents are low-molecular-weight chemotherapeutic agents. Low-molecular-weight chemotherapeutic agents are unlikely to interfere with the function of antigen-binding molecules even after they bind to antigen-binding molecules of the present invention. In the present invention, low-molecular-weight chemotherapeutic agents usually have a molecular weight of 100 to 2000, preferably 200 to 1000. The chemotherapeutic agents exemplified herein are all low-molecular-weight chemotherapeutic agents. The chemotherapeutic agents of the present invention include prodrugs that are converted into active chemotherapeutic agents in vivo. Prodrug activation may be enzymatic conversion or non-enzymatic conversion.

Moreover, cytotoxic substances that are linked to antigen-binding molecules of the present invention include, for example, toxic peptides (toxins) such as *Pseudomonas* exotoxin A, Saporin-s6, Diphtheria toxin, Cnidarian toxin; radioiodine; and photosensitizers. Suitable examples of the toxic peptides include the following:

Diphtheria toxin A Chain (Langone et al. (Methods in Enzymology (1983) 93, 307-308));

*Pseudomonas* Exotoxin (Nature Medicine (1996) 2, 350-353);

Ricin Chain (Ricin A Chain) (Fulton et al. (J. Biol. Chem. (1986) 261, 5314-5319), Sivam et al. (Cancer Res. (1987) 47, 3169-3173), Cumber et al. (J. Immunol. Methods (1990) 135, 15-24), Wawrzynczak et al. (Cancer Res. (1990) 50, 7519-7562), and Gheeite et al. (J. Immunol. Methods (1991) 142, 223-230));

Deglicosylated Ricin A Chain (Thorpe et al. (Cancer Res. (1987) 47, 5924-5931));

Abrin A Chain (Wawrzynczak et al. (Br. J. Cancer (1992) 66, 361-366), Wawrzynczak et al. (Cancer Res. (1990) 50, 7519-7562), Sivam et al. (Cancer Res. (1987) 47, 3169-3173), and Thorpe et al. (Cancer Res. (1987) 47, 5924-5931));

Gelonin (Sivam et al. (Cancer Res. (1987) 47, 3169-3173), Cumber et al. (J. Immunol. Methods (1990) 135, 15-24), Wawrzynczak et al. (Cancer Res., (1990) 50, 7519-7562), and Bolognesi et al. (Clin. exp. Immunol. (1992) 89, 341-346));

PAP-s; Pokeweed anti-viral protein from seeds (Bolognesi et al. (Clin. exp. Immunol. (1992) 89, 341-346));

Briodin (Bolognesi et al. (Clin. exp. Immunol. (1992) 89, 341-346));

Saporin (Bolognesi et al. (Clin. exp. Immunol. (1992) 89, 341-346));

Momordin (Cumber et al. (J. Immunol. Methods (1990) 135, 15-24); Wawrzynczak et al. (Cancer Res. (1990) 50, 7519-7562); and Bolognesi et al. (Clin. exp. Immunol. (1992) 89, 341-346));

Momorcochin (Bolognesi et al. (Clin. exp. Immunol. (1992) 89, 341-346));

Dianthin 32 (Bolognesi et al. (Clin. exp. Immunol. (1992) 89, 341-346));

Dianthin 30 (Stirpe F., Barbieri L. (FEBS letter (1986) 195, 1-8));

Modeccin (Stirpe F., Barbieri L. (FEBS letter (1986) 195, 1-8));

Viscumin (Stirpe F., Barbieri L. (FEBS letter (1986) 195, 1-8));
Volkesin (Stirpe F., Barbieri L. (FEBS letter (1986) 195, 1-8));
Dodecandrin (Stirpe F., Barbieri L. (FEBS letter (1986) 195, 1-8));
Tritin (Stirpe F., Barbieri L. (FEBS letter (1986) 195, 1-8));
Luffin (Stirpe F., Barbieri L. (FEBS letter (1986) 195, 1-8)); and
Trichokirin (Casellas et al. (Eur. J. Biochem. (1988) 176, 581-588), and Bolognesi et al. (Clin. exp. Immunol., (1992) 89, 341-346)).

Antigen-Binding Molecule

In the present invention, "an antigen-binding molecule comprising an antigen-binding domain whose antigen-binding activity in the presence of a target tissue-specific compound is higher than in the absence of the target tissue-specific compound" is used in the broadest sense; and specifically, it includes various types of molecules as long as they show antigen-binding activity. Molecules in which an antigen-binding domain is linked to an Fc region include, for example, antibodies. Antibodies may include single monoclonal antibodies (including agonistic antibodies and antagonistic antibodies), human antibodies, humanized antibodies, chimeric antibodies, and such. Alternatively, when used as antibody fragments, they preferably include antigen-binding domains and antigen-binding fragments (for example, Fab, F(ab')2, scFv, and Fv). Scaffold molecules where three dimensional structures, such as already-known stable at/3 barrel protein structure, are used as a scaffold (base) and only some portions of the structures are made into libraries to construct antigen-binding domains are also included in antigen-binding molecules of the present invention.

An antigen-binding molecule of the present invention may contain at least some portions of an Fc region that mediates the binding to Fcγ receptor and/or FcRn. In a non-limiting embodiment, the antigen-binding molecule includes, for example, antibodies and Fc fusion proteins. A fusion protein refers to a chimeric polypeptide comprising a polypeptide having a first amino acid sequence that is linked to a polypeptide having a second amino acid sequence that would not naturally link in nature. For example, a fusion protein may comprise a polypeptide comprising the amino acid sequence of at least a portion of an Fc region (for example, a portion of an Fc region responsible for the binding to Fcγ receptor, and/or a portion of an Fc region responsible for the binding to FcRn). The amino acid sequences may be present in separate proteins that are transported together to a fusion protein, or generally may be present in a single protein; however, they are included in a new rearrangement in a fusion polypeptide. Fusion proteins can be produced, for example, by chemical synthesis, or by genetic recombination techniques to express a polynucleotide encoding peptide regions in a desired arrangement.

Respective domains of the present invention can be linked together via linkers or directly via polypeptide binding. The linkers comprise arbitrary peptide linkers that can be introduced by genetic engineering, synthetic linkers, and linkers disclosed in, for example, Holliger et al., Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:

Ser

Gly · Ser

Gly · Gly · Ser

Ser · Gly · Gly

Gly · Gly · Gly · Ser (SEQ ID NO: 19)

Ser · Gly · Gly · Gly (SEQ ID NO: 20)

Gly · Gly · Gly · Gly · Ser (SEQ ID NO: 21)

Ser · Gly · Gly · Gly · Gly (SEQ ID NO: 22)

Gly · Gly · Gly · Gly · Gly · Ser (SEQ ID NO: 23)

Ser · Gly · Gly · Gly · Gly · Gly (SEQ ID NO: 24)

Gly · Gly · Gly · Gly · Gly · Gly · Ser (SEQ ID NO: 25)

Ser · Gly · Gly · Gly · Gly · Gly · Gly (SEQ ID NO: 26)

(Gly · Gly · Gly · Gly · Ser (SEQ ID NO: 21))n (Ser · Gly · Gly · Gly · Gly (SEQ ID NO: 22))n where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate (BS$^3$),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES). These crosslinking agents are commercially available.

When multiple linkers for linking the respective domains are used, they may all be of the same type, or may be of different types. In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link respective domains via peptide linkage, polynucleotides encoding the domains are linked together in frame. Known methods for linking polynucleotides in frame include techniques such as ligation of restriction fragments, fusion PCR, and overlapping PCR. Such methods can be appropriately used alone or in combination to construct antigen-binding molecules of the present invention. In the present invention, the terms "linked" and "fused", or "linkage" and "fusion" are used interchangeably. These terms mean that two or more elements or components such as polypeptides are linked together to form a single structure by any means including the above-described chemical linking means and genetic recombination techniques. Fusing in frame means, when two or more elements or components are polypeptides, linking two or more units of reading frames to form a continuous longer reading frame while maintaining the correct reading frames of the polypeptides. When two molecules of Fab are used as an antigen-binding domain, an antibody, which is an antigen-binding molecule of the present invention where the antigen-binding domain is linked in frame to a constant region including an Fc region via peptide bond without linker, can be used as a preferred antigen-binding molecule of the present invention.

Low-Molecular-Weight Antibody

The antibodies used in the present invention are not limited to full-length antibody molecules, and can be low-molecular-weight antibodies (minibodies) and modified products thereof. A low-molecular-weight antibody includes an antibody fragment that lacks a portion of a full-length antibody (for example, whole antibody such as whole IgG); and is not particularly limited as long as it has an antigen-binding activity. The low-molecular-weight antibody of the present invention is not particularly limited as long as it is a portion of a full-length antibody, but preferably comprises a heavy-chain variable region (VH) and/or a light-chain variable region (VL). The amino acid sequence of VH or VL may have substitution(s), deletion(s), addition(s), and/or insertion(s). Furthermore, as long as it has an antigen-binding activity, VH and/or VL can be partially deleted. The variable region may be chimerized or humanized. Specific examples of antibody fragments include Fab, Fab', F(ab')2, and Fv. Specific examples of low-molecular-weight antibodies include Fab, Fab', F(ab')2, Fv, scFv (single chain Fv), diabody, and sc(Fv)2 (single chain (Fv)2). Multimers of these antibodies (for example, dimers, trimers, tetramers, and polymers) are also included in the low-molecular-weight antibodies of the present invention.

Antibody fragments can be produced by treating an antibody with an enzyme such as papain and pepsin. Alternatively, genes encoding these antibody fragments can be constructed, inserted into expression vectors, and then expressed in appropriate host cells (see, for example, Co et al., (J. Immunol. (1994) 152, 2968-2976); Better and Horwitz (Methods in Enzymology (1989) 178, 476-496), Plueckthun and Skerra (Methods in Enzymology (1989) 178, 476-496); Lamoyi (Methods in Enzymology (1989) 121, 652-663); Rousseaux (Methods in Enzymology (1989) 121, 663-669); and Bird, et al., TIBTECH (1991) 9, 132-137).

A diabody refers to a bivalent low-molecular-weight antibody constructed by gene fusion (Hollinger et al., (Proc. Natl. Acad. Sci. USA 90, 6444-6448 (1993)); EP 404,097; WO 1993/11161; and such). A diabody is a dimer composed of two polypeptide chains. Generally, in each polypeptide chain constituting the dimer, VL and VH are linked by a linker within the same chain. The linker in a diabody is generally short enough to prevent binding between VL and VH. Specifically, the amino acid residues constituting the linker are, for example, about five residues. A linker between VL and VH that are encoded by the same polypeptide chain is too short to form a single-chain variable region fragment, and a dimer is formed between the polypeptide chains. As a result, diabodies have two antigen binding sites.

scFv can be obtained by linking the H-chain V region and L-chain V region of an antibody. In scFv, the H-chain V region and L-chain V region are ligated via a linker, preferably a peptide linker (Huston, et al., Proc. Natl. Acad. Sci. U.S.A. (1988) 85, 5879-5883). The H-chain V region and L-chain V region of scFv may be derived from any of the antibodies described herein. The peptide linker for ligating the V regions is not particularly limited; and for example, any single-chain peptide consisting of 3 to 25 residues or so, or peptide linkers described later or such can be used as the linker. PCR methods such as those described above can be used for ligating the V regions. DNA encoding scFv can be amplified by a PCR method using as a template either whole DNA or a partial DNA encoding a desired amino acid sequence, which is selected from a DNA sequence encoding the H chain or the H chain V region of the above-mentioned antibody, and a DNA encoding the L chain or the L chain V region of the above-mentioned antibody; and using a pair of primers having sequences corresponding to the sequences of the two ends. Next, a DNA having the desired sequence can be obtained by performing a PCR reaction using a combination of a DNA encoding the peptide linker portion, and a pair of primers having sequences designed so that both ends of the DNA will be ligated to the H chain and the L chain, respectively. Once the scFv-encoding DNA is constructed, expression vectors having the DNA, and recombinant cells transformed with the expression vector can be obtained according to conventional methods. Furthermore, the scFvs can be obtained by culturing the resulting recombinant cells to express the scFv-encoding DNA.

sc(Fv)2 is a low-molecular-weight antibody prepared by linking two VHs and two VLs with linkers or such to form a single chain (Hudson et al. (J. Immunol. Methods 1999; 231: 177-189)). sc(Fv)2 can be produced, for example, by linking scFvs with a linker.

Moreover, antibodies in which two VHs and two VLs are arranged in the order of VH, VL, VH, and VL starting from the N-terminal side of a single chain polypeptide ([VH]-linker-[VL]-linker-[VH]-linker-[VL]) are preferred. The order of the two VHs and the two VLs is not particularly limited to the above-mentioned arrangement, and they may be arranged in any order. Examples include the following arrangements:

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

A linker similar to the linker described in the section "Antigen-binding molecules" above may be used as the linker for linking the antibody variable regions. A particularly preferred embodiment of sc(Fv)2 in the present invention includes, for example, the following sc(Fv)2:

[VH]-peptide linker (15 amino acids)-[VL]-peptide linker (15 amino acids)-[VH]-peptide linker (15 amino acids)-[VL]

Typically, three linkers are required to link four antibody variable regions. The linkers to be used may be of the same type or different types. Examples of a non-limiting embodiment of a low-molecular-weight antibody in the present invention include a diabody or sc(Fv)2, wherein the paratopes are different from each other; one of the paratopes binds to an epitope in a membrane-type molecule which binds to a cancer cell membrane; and the other paratope binds to an epitope in the membrane-type molecule expressed on the cell membrane of effector cells. In the above-mentioned diabody or sc(Fv)2, the binding activity of one paratope that binds to an epitope in a membrane-type molecule which binds to a cancer cell membrane may depend on a cancer tissue-specific compound, the binding activity of one of the paratopes toward an epitope in a membrane-type molecule which binds to an effector cell membrane may depend on a cancer tissue-specific compound, or the binding activities of both paratopes may depend on a cancer tissue-specific compound.

A non-limiting embodiment of a low-molecular-weight antibody in the present invention includes, for example, a diabody or sc(Fv)2, wherein the paratopes are different from each other; one of the paratopes binds to an epitope in a membrane-type molecule which binds to a cancer cell membrane; and the other paratope binds to an epitope in a cytotoxic substance. In the diabody or sc(Fv)2 mentioned above, the binding activity of one of the paratopes that binds to an epitope in a membrane-type molecule which binds to a cancer cell membrane may depend on a cancer tissue-specific compound, the binding activity of the other paratope that binds to an epitope in a cytotoxic substance may depend on a cancer tissue-specific compound, or the binding activities of both paratopes may depend on a cancer tissue-specific compound.

Such low-molecular-weight antibody can be obtained by treating an antibody with an enzyme such as papain or pepsin to generate antibody fragments, or by constructing DNAs that encode these antibody fragments or low-molecular-weight antibodies, inserting them into expression vectors, and then expressing them in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

FcRn

Unlike Fcγ receptor belonging to the immunoglobulin superfamily, human FcRn is structurally similar to polypeptides of major histocompatibility complex (MHC) class I, exhibiting 22% to 29% sequence identity to class I MHC molecules (Ghetie el al., Immunol. Today (1997) 18 (12): 592-598). FcRn is expressed as a heterodimer consisting of soluble β light chain (β2 microglobulin) complexed with transmembrane α or heavy chain. Like MHC, FcRn α chain comprises three extracellular domains ($\alpha 1$, $\alpha 2$, and $\alpha 3$) and its short cytoplasmic domain anchors the protein onto the cell surface. $\alpha 1$ and $\alpha 2$ domains interact with the FcRn-binding domain of the antibody Fc region (Raghavan et al., Immunity (1994) 1: 303-315).

FcRn is expressed in maternal placenta and york sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG.

Typically, binding of FcRn to IgG molecules is strictly pH dependent. The optimal binding is observed in an acidic pH range below 7.0.

Human FcRn whose precursor is a polypeptide having the signal sequence of SEQ ID NO: 28 (the polypeptide with the signal sequence is shown in SEQ ID NO: 29) forms a complex with human β2-microglobulin in vivo. Soluble human FcRn complexed with β2-microglobulin is produced by using conventional recombinant expression techniques. Fc regions of the present invention can be assessed for their binding activity to such a soluble human FcRn complexed with β2-microglobulin. Herein, unless otherwise specified, human FcRn refers to a form capable of binding to an Fc region of the present invention. Examples include a complex between human FcRn and human β2-microglobulin.

Binding Activity of the Fc Region to FcRn, in Particular, Human FcRn

The binding activity of an Fc region of the present invention to FcRn, human FcRn in particular, can be measured by methods known to those skilled in the art, as described in the section "Binding Activity" above. Those skilled in the art can appropriately determine the conditions other than pH. The antigen-binding activity and human FcRn-binding activity of an antigen-binding molecule can be assessed based on the dissociation constant (KD), apparent dissociation constant (KD), dissociation rate (kd), apparent dissociation rate (kd), and such. These can be measured by methods known to those skilled in the art. For example, Biacore (GE healthcare), Scatchard plot, or flow cytometer may be used.

When the human FcRn-binding activity of an Fc region of the present invention is measured, conditions other than the pH are not particularly limited, and can be appropriately selected by those skilled in the art. Measurements can be carried out, for example, at 37° C. using MES buffer, as described in International Publication No. WO 2009125825. Alternatively, the human FcRn-binding activity of an Fc region of the present invention can be measured by methods known to those skilled in the art, and may be measured by using, for example, Biacore (GE Healthcare) or such. The binding activity of an Fc region of the present invention to human FcRn can be assessed by pouring, as an analyte, human FcRn, an Fc region, or an antigen-binding molecule of the present invention containing the Fc region into a chip immobilized with an Fc region, an antigen-binding molecule of the present invention containing the Fc region, or human FcRn.

A neutral pH range as the condition where the Fc region contained in an antigen-binding molecule of the present invention has the FcRn-binding activity means pH6.7 to pH10.0 in general. Preferably, the neutral pH range is a range indicated with arbitrary pH values between pH7.0 and pH8.0, and is preferably selected from pH7.0, 7.1, 7.2, 7.3, 7.4, 7.5, 7.6, 7.7, 7.8, 7.9, and 8.0, and is particularly preferably pH7.4 that is close to the pH of plasma (blood) in vivo. When the binding affinity between the human FcRn-binding domain and human FcRn at pH7.4 is too low to assess, pH7.0 may be used instead of pH7.4. Herein, an acidic pH range as the condition where the Fc region contained in an antigen-binding molecule of the present invention has the FcRn-binding activity means pH4.0 to pH6.5 in general. Preferably, the acidic pH range means pH5.5 to pH6.5, particularly preferably pH5.8 to pH6.0 which is close to the pH in the early endosome in vivo. Regarding the temperature used as the measurement condition, the binding affinity between the human FcRn-binding domain and human FcRn may be assessed at any temperature between 10° C. and 50° C. Preferably, the binding affinity between the human FcRn-binding domain and human FcRn can be determined at 15° C. to 40° C. More preferably, the binding affinity between the human FcRn-binding domain and human FcRn can be determined in the same manner at an arbitrary temperature between 20° C. and 35° C., such as any one temperature of 20, 21, 22, 23, 24, 25, 26, 27, 28, 29, 30, 31, 32, 33, 34, and 35° C. In an embodiment of the present invention, the temperature includes, but is not limited to, for example, 25° C.

According to the Journal of Immunology (2009) 182, 7663-7671, the human FcRn-binding activity of native human IgG1 in an acidic pH range (pH 6.0) is 1.7 µM (KD), and the activity is almost undetectable in a neutral pH range. Thus, in a preferred embodiment, antigen-binding molecules comprising an Fc region of which human FcRn-binding activity in an acidic pH range is 20 µM (KD) or stronger may be screened. In a more preferred embodiment, the antigen-binding molecules comprising an Fc region of which human FcRn-binding activity in an acidic pH range is 2.0 µM (KD) or stronger may be screened. In a still more preferred embodiment, the antigen-binding molecules comprising an Fc region of which human FcRn-binding activity in an acidic pH range is 0.5 µM (KD) or stronger may be screened. The above-mentioned KD values are determined by the method described in the Journal of Immunology (2009) 182: 7663-7671 (by immobilizing the antigen-binding molecule onto a chip and loading human FcRn as an analyte).

Fc Region Having FcRn-Binding Activity Under an Acidic pH Range Condition

An Fc region having FcRn-binding activity under an acidic pH range condition may also be preferably used as the Fc region contained in an antigen-binding molecule provided by the present invention. Generally, IgG antibodies are known to have long plasma retention through binding to FcRn. Binding between IgG and FcRn is observed only under acidic conditions (pH 6.0), and the binding is hardly observed under neutral conditions (pH 7.4). IgG antibodies are non-specifically incorporated into cells, but they return to the cell surface by binding to FcRn in the endosome under endosomal acidic conditions, and then dissociate from FcRn under neutral conditions in plasma. When mutations are introduced into the Fc region of IgG to eliminate the FcRn-binding under an acidic pH range condition, the antibodies are not recycled from inside the endosome into plasma. Therefore, plasma retention of the antibody is remarkably impaired. A method for improving FcRn-binding under an acidic pH range condition has been reported as a method for improving plasma retention of IgG antibodies. Improving FcRn-binding under an acidic pH range condition by introducing amino acid substitutions into the IgG antibody Fc region can increase the efficiency of recycling from inside the endosome into plasma, and as a result, plasma retention is improved.

The present invention is not restricted to a particular theory, but for example, when an antigen-binding molecule provided by the present invention binds to a membrane-type antigen expressed on cancer cells contained in cancer tissues, it may be possible to continuously suppress cancer cell proliferation as described below. Even after cancer cells expressing a membrane-type molecule, to which an antigen-binding molecule of the present invention is bound in the presence of a high concentration of a cancer tissue-specific compound, are damaged by cytotoxic activity mediated by the antigen-binding molecule, the antigen may still be bound to the antigen-binding domain in the antigen-binding molecule. From the antigen-binding molecules non-specifically incorporated into cells, those that release the antigen in the presence of a low concentration of the cancer tissue-specific compound return to the cell surface by binding to FcRn in the endosome under acidic conditions inside the endosome, and then dissociate from FcRn under neutral conditions in plasma. In the presence of a high concentration of a cancer tissue-specific compound, the antigen-binding molecules of the present invention recycled in this manner can bind again to their antigens which are membrane-type molecules expressed on cancer cells.

The present invention is not restricted to a particular theory, but for example, when a soluble antigen bound by antigen-binding molecules provided by the present invention is a ligand that positively regulates activation of inflammatory cells or proliferation of target cells contained in a target tissue, it may be possible to suppress proliferation of target cells or activation of inflammatory cells as described below. Antigen-binding molecules of the present invention bound to the soluble molecule, i.e., its antigen, are non-specifically incorporated into cells in the presence of a high concentration of target tissue-specific compounds. This is followed by release of the antigen in the presence of a low concentration of target tissue-specific compounds, the antigen-binding molecules return to the cell surface by binding to FcRn in the endosome under acidic conditions inside the endosome, and then the antigen-binding molecules dissociate from FcRn under neutral conditions in plasma. The antigen-binding molecules of the present invention recycled in this manner can bind again to soluble molecules, i.e., their antigen, in the presence of a high concentration of target tissue-specific compounds. On the other hand, the antigens that dissociated from the antigen-binding molecules in the presence of a low concentration of the target tissue-specific compounds are degraded in the lysosome. The concentration of the soluble antigen decreases as it passes through the recycling stage. Therefore, it is considered that cancer cell proliferation or inflammatory cell activation can be suppressed.

In the present invention, preferred Fc regions have an FcRn-binding activity in an acidic pH range condition. When an Fc region originally has an FcRn-binding activity under an acidic pH range condition, the domain can be used as it is. When the domain has a weak or no FcRn-binding activity under an acidic pH range condition, an Fc region having a desired FcRn-binding activity can be obtained by altering amino acids of an antigen-binding molecule. Fc regions having a desired or enhanced FcRn-binding activity under an acidic pH range condition can also be suitably obtained by altering the amino acids of an Fc region. Amino acid alterations of an Fc region that result in such a desired binding activity can be found by comparing the FcRn-binding activity under an acidic pH range condition before and after amino acid alteration. Those skilled in the art can appropriately alter the amino acids using known techniques similar to the aforementioned techniques used to modify the Fcγ-receptor-binding activity.

Fc regions comprised in the antigen-binding molecules of the present invention, which have an FcRn-binding activity under an acidic pH range condition, can be obtained by any method. Specifically, FcRn-binding domains having an FcRn-binding activity or an enhanced FcRn-binding activity under an acidic pH range condition can be obtained by altering the amino acids of an IgG-type human immunoglobulin used as a starting Fc region. Preferred Fc regions of an IgG-type immunoglobulin for alteration include, for example, those of human IgGs (IgG1, IgG2, IgG3, and IgG4, and variants thereof). As long as the Fc region has an FcRn-binding activity under an acidic pH range condition or can increase the human FcRn-binding activity under an acidic pH range condition, amino acids at any position may be altered into other amino acids. When the antigen-binding molecule contains the Fc region of human IgG1 as the Fc region, it is preferable that the resulting Fc region contains an alteration that results in the effect of enhancing FcRn binding under an acidic pH range condition as compared to the binding activity of the starting human IgG1 Fc region. Amino acids that allow such alteration include, for example, amino acids of positions 252, 254, 256, 309, 311, 315, 433, and/or 434 according to EU numbering, and their combination amino acids at positions 253, 310, 435, and/or 426 as described in WO 1997/034631. Favorable examples include amino acids of positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 as indicated by EU numbering as described in WO 2000/042072. Similarly, favorable examples of amino acids that allow such alteration include, amino acids of positions 251, 252, 254, 255, 256, 308, 309, 311, 312, 385, 386, 387, 389, 428, 433, 434, and/or 436 according to EU numbering as described in WO 2002/060919. Furthermore, amino acids that allow such alteration include, for example, amino acids of positions 250, 314, and 428 according to EU numbering as described in WO2004/092219. In addition, favorable examples of amino acids that allow such alteration include amino acids of positions 238, 244, 245, 249, 252, 256, 257, 258, 260, 262, 270, 272, 279, 283, 285, 286, 288, 293, 307, 311, 312, 316, 317, 318, 332, 339, 341, 343, 375, 376, 377, 378, 380, 382, 423, 427, 430, 431, 434, 436, 438, 440, and/or 442 as described in WO 2006/020114. Furthermore, favorable examples of amino acids that allow such alteration include amino acids of positions 251, 252, 307, 308, 378, 428, 430, 434, and/or 436 according to EU numbering as described in WO 2010/045193. Alteration of these amino acids enhances FcRn binding of the Fc region of an IgG-type immunoglobulin under an acidic pH range condition.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 includes at least one or more amino acid alterations selected from the group consisting of:
Arg or Leu for the amino acid of position 251;
Phe, Ser, Thr, or Tyr for the amino acid of position 252;
Ser or Thr for the amino acid of position 254;
Arg, Gly, Ile, or Leu for the amino acid of position 255;
Ala, Arg, Asn, Asp, Gln, Glu, or Thr for the amino acid of position 256;
Ile or Thr for the amino acid of position 308;
Pro for the amino acid of position 309;
Glu, Leu, or Ser for the amino acid of position 311;
Ala or Asp for the amino acid of position 312;
Ala or Leu for the amino acid of position 314;
Ala, Arg, Asp, Gly, His, Lys, Ser, or Thr for the amino acid of position 385;
Arg, Asp, Ile, Lys, Met, Pro, Ser, or Thr for the amino acid of position 386;
Ala, Arg, His, Pro, Ser, or Thr for the amino acid of position 387;
Asn, Pro, or Ser for the amino acid of position 389;
Leu, Met, Phe, Ser, or Thr for the amino acid of position 428;
Arg, Gln, His, Ile, Lys, Pro, or Ser for the amino acid of position 433;
His, Phe, or Tyr for the amino acid of position 434; and
Arg, Asn, His, Lys, Met, or Thr for the amino acid of position 436, as indicated by EU numbering. Meanwhile, the number of amino acids to be altered is not particularly limited; and
amino acid may be altered at only one site or amino acids may be altered at two or more sites.

When the Fc region of human IgG1 is comprised as the Fc region, a non-limiting embodiment of the alteration that results in the effect of enhancing FcRn binding in an acidic pH range condition as compared to the binding activity of the starting Fc region of human IgG1 may be alterations including Ile for the amino acid of position 308, Pro for the amino acid of position 309, and/or Glu for the amino acid of position 311 according to EU numbering. Another non-limiting embodiment of this alteration may include Thr for the amino acid of position 308, Pro for the amino acid of position 309, Leu for the amino acid of position 311, Ala for the amino acid of position 312, and/or Ala for the amino acid of position 314. Furthermore, another non-limiting embodiment of this alteration may include Ile or Thr for the amino acid of position 308, Pro for the amino acid of position 309, Glu, Leu, or Ser for the amino acid of position 311, Ala for the amino acid of position 312, and/or Ala or Leu for the amino acid of position 314. Another non-limiting embodiment of this alteration may include Thr for the amino acid of position 308, Pro for the amino acid of position 309, Ser for the amino acid of position 311, Asp for the amino acid of position 312, and/or Leu for the amino acid of position 314.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including Leu for the amino acid of position 251, Tyr for the amino acid of position 252, Ser or Thr for the amino acid of position 254, Arg for the amino acid of position 255, and/or Glu for the amino acid of position 256 according to EU numbering.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including Leu, Met, Phe, Ser, or Thr for the amino acid of position 428, Arg, Gln, His, Ile, Lys, Pro, or Ser for the amino acid of position 433, His, Phe, or Tyr for the amino acid of position 434, and/or Arg, Asn, His, Lys, Met, or Thr for the amino acid of position 436 according to EU numbering. Another non-limiting embodiment of this alteration may include His or Met for the amino acid of position 428, and/or His or Met for the amino acid of position 434.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including Arg for the amino acid of position 385, Thr for the amino acid of position 386, Arg for the amino acid of position 387, and/or Pro for the amino acid of position 389 according to EU numbering. Another non-limiting embodiment of this alteration may include Asp for the amino acid of position 385, Pro for the amino acid of position 386, and/or Ser for the amino acid of position 389.

Furthermore, when the Fc region of human IgG1 is comprised as the Fc region, a non-limiting embodiment of the alteration that results in the effect of enhancing FcRn binding under an acidic pH range condition as compared to the binding activity of the starting Fc region of human IgG1 include at least one or more amino acid alterations selected from the group consisting of:

Gln or Glu for the amino acid of position 250; and
Leu or Phe for the amino acid of position 428 according to EU numbering. The number of amino acids to be altered is not particularly limited; and amino acid may be altered at only one site or amino acids may be altered at two sites.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including Gln for the amino acid of position 250, and/or Leu or Phe for the amino acid of position 428 according to EU numbering. Another non-limiting embodiment of this alteration may include Glu for the amino acid of position 250, and/or Leu or Phe for the amino acid of position 428.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 include at least two or more amino acid alterations selected from the group consisting of:

Asp or Glu for the amino acid of position 251;
Tyr for the amino acid of position 252;
Gln for the amino acid of position 307;
Pro for the amino acid of position 308;
Val for the amino acid of position 378;
Ala for the amino acid of position 380;
Leu for the amino acid of position 428;
Ala or Lys for the amino acid of position 430;
Ala, His, Ser, or Tyr for the amino acid of position 434; and
Ile for the amino acid of position 436, as indicated by EU numbering. The number of amino acids to be altered is not particularly limited; and amino acid may be altered at only two sites or amino acids may be altered at three or more sites.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including Gln for the amino acid of position 307, and Ala or Ser for the amino acid of position 434 according to EU numbering. Another non-limiting embodiment of this alteration may include Pro for the amino acid of position 308, and Ala for the amino acid of position 434. Furthermore, another non-limiting embodiment of this alteration may include Tyr for the amino acid of position 252, and Ala for the amino acid of position 434. A different non-limiting embodiment of this alteration may include Val for the amino acid of position 378, and Ala for the amino acid of position 434. Another different non-limiting embodiment of this alteration may include Leu for the amino acid of position 428, and Ala for the amino acid of position 434. Another different non-limiting embodiment of this alteration may include Ala for the amino acid of position 434, and Ile for the amino acid of position 436. Furthermore, another non-limiting embodiment of this alteration may include Pro for the amino acid of position 308, and Tyr for the amino acid of position 434. In addition, another non-limiting embodiment of this alteration may include Gln for the amino acid of position 307, and Ile for the amino acid of position 436.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including any one of Gln for the amino acid of position 307, Ala for the amino acid of position 380, and Ser for the amino acid of position 434 according to EU numbering. Another non-limiting embodiment of this alteration may include Gln for the amino acid of position 307, Ala for the amino acid of position 380, and Ala for the amino acid of position 434. Furthermore, another non-limiting embodiment of this alteration may include Tyr for the amino acid of position 252, Pro for the amino acid of position 308, and Tyr for the amino acid of position 434. A different non-limiting embodiment of this alteration may include Asp for the amino acid of position 251, Gln for the amino acid of position 307, and His for the amino acid of position 434.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 include alteration of at least two or more amino acids selected from the group consisting of:

Leu for the amino acid of position 238;
Leu for the amino acid of position 244;
Arg for the amino acid of position 245;
Pro for the amino acid of position 249;
Tyr for the amino acid of position 252;
Pro for the amino acid of position 256;
Ala, Ile, Met, Asn, Ser, or Val for the amino acid of position 257;
Asp for the amino acid of position 258;
Ser for the amino acid of position 260;
Leu for the amino acid of position 262;
Lys for the amino acid of position 270;
Leu or Arg for the amino acid of position 272;
Ala, Asp, Gly, His, Met, Asn, Gln, Arg, Ser, Thr, Trp, or Tyr for the amino acid of position 279;
Ala, Asp, Phe, Gly, His, Ile, Lys, Leu, Asn, Pro, Gln, Arg, Ser, Thr, Trp, or Tyr for the amino acid of position 283;
Asn for the amino acid of position 285;
Phe for the amino acid of position 286;
Asn or Pro for the amino acid of position 288;
Val for the amino acid of position 293;
Ala, Glu, or Met for the amino acid of position 307;
Ala, Ile, Lys, Leu, Met, Val, or Trp for the amino acid of position 311;
Pro for the amino acid of position 312;
Lys for the amino acid of position 316;
Pro for the amino acid of position 317;
Asn or Thr for the amino acid of position 318;
Phe, His, Lys, Leu, Met, Arg, Ser, or Trp for the amino acid of position 332;
Asn, Thr, or Trp for the amino acid of position 339;
Pro for the amino acid of position 341;
Glu, His, Lys, Gln, Arg, Thr, or Tyr for the amino acid of position 343;
Arg for the amino acid of position 375;
Gly, Ile, Met, Pro, Thr, or Val for the amino acid of position 376;
Lys for the amino acid of position 377;
Asp or Asn for the amino acid of position 378;

Asn, Ser, or Thr for the amino acid of position 380;
Phe, His, Ile, Lys, Leu, Met, Asn, Gln, Arg, Ser, Thr, Val, Trp, or Tyr for the amino acid of position 382;
Asn for the amino acid of position 423;
Asn for the amino acid of position 427;
Ala, Phe, Gly, His, Ile, Lys, Leu, Met, Asn, Gln, Arg, Ser, Thr, Val, or Tyr for the amino acid of position 430;
His or Asn for the amino acid of position 431;
Phe, Gly, His, Trp, or Tyr for the amino acid of position 434;
Ile, Leu, or Thr for the amino acid of position 436;
Lys, Leu, Thr, or Trp for the amino acid of position 438;
Lys for the amino acid of position 440; and
Lys for the amino acid of position 442 according to EU numbering. The number of amino acids to be altered is not particularly limited and amino acid at only two sites may be altered and amino acids at three or more sites may be altered.

When the Fc region of human IgG1 is comprised as the Fc region, a non-limiting embodiment of the alteration that results in the effect of enhancing FcRn binding under an acidic pH range condition as compared to the binding activity of the starting Fc region of human IgG1 may be alterations including Ile for the amino acid of position 257, and Ile for the amino acid of position 311 according to EU numbering. Another non-limiting embodiment of this alteration may include Ile for the amino acid of position 257, and His for the amino acid of position 434. Another non-limiting embodiment of this alteration may include Val for the amino acid of position 376, and His for the amino acid of position 434.

Fc Regions Having FcRn-Binding Activity Under Neutral pH Range Conditions

Furthermore, in another non-limiting embodiment, one may screen for antigen-binding molecules comprising an Fc region with the characteristic of having a human FcRn-binding activity in the neutral pH range instead of the above-described characteristic of having a human FcRn-binding activity in the acidic pH range. In a preferred embodiment, one may screen for antigen-binding molecules comprising an Fc region whose human FcRn-binding activity in the neutral pH range is 40 µM (KD) or stronger. In a more preferred embodiment, one may screen for antigen-binding molecules comprising an Fc region whose human FcRn-binding activity in the neutral pH range is 15 µM (KD) or stronger.

Furthermore, in another non-limiting embodiment, one may screen for antigen-binding molecules comprising an Fc region with the characteristic of having a human FcRn-binding activity in the neutral pH range in addition to the above-described characteristic of having a human FcRn-binding activity in the acidic pH range. In a preferred embodiment, one may screen for antigen-binding molecules comprising an Fc region whose human FcRn-binding activity in the neutral pH range is 40 µM (KD) or stronger. In a more preferred embodiment, one may screen for antigen-binding molecules comprising an Fc region whose human FcRn-binding activity in the neutral pH range is 15 µM (KD) or stronger.

In the present invention, preferred Fc regions have a human FcRn-binding activity in the acidic pH range and/or neutral pH range. When an Fc region originally has a human FcRn-binding activity in the acidic pH range and/or neutral pH range, it can be used as it is. When an Fc region has a weak or no human FcRn-binding activity in the acidic pH range and/or neutral pH range, antigen-binding molecules comprising an Fc region having a desired human FcRn-binding activity can be obtained by altering amino acids of the Fc region comprised in the antigen-binding molecules. Fc regions having a desired human FcRn-binding activity in the acidic pH range and/or neutral pH range can also be suitably obtained by altering amino acids of a human Fc region. Alternatively, antigen-binding molecules comprising an Fc region having a desired human FcRn-binding activity can be obtained by altering amino acids of an Fc region that originally has a human FcRn-binding activity in the acidic pH range and/or neutral pH range. Amino acid alterations of a human Fc region that result in such a desired binding activity can be found by comparing the human FcRn-binding activity in the acidic pH range and/or neutral pH range before and after amino acid alteration. Those skilled in the art can appropriately alter amino acids using known methods.

In the present invention, "alteration of amino acids" or "amino acid alteration" of an Fc region includes alteration into an amino acid sequence which is different from that of the starting Fc region. The starting Fc region may be any Fc region, as long as a variant modified from the starting Fc region can bind to human FcRn in an acidic pH range (i.e., the starting Fc region does not necessarily need to have an activity to bind to human FcRn in a neutral pH range). Examples of starting Fc regions preferably include Fc regions of IgG antibodies, i.e., native Fc regions. Furthermore, an altered Fc region modified from a starting Fc region which has been already modified can also be used preferably as an altered Fc region of the present invention. The "starting Fc region" can refer to the polypeptide itself, a composition comprising the starting Fc region, or an amino acid sequence encoding the starting Fc region. Starting Fc regions can comprise a known IgG antibody Fc region produced via recombination described briefly in section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG subclass. This means that an Fc region represented by human IgG1 (SEQ ID NO: 5), IgG2 (SEQ ID NO: 6), IgG3 (SEQ ID NO: 7), or IgG4 (SEQ ID NO: 8) can be used appropriately as a starting Fc region, and herein also means that an Fc region of an arbitrary IgG class or subclass derived from any organisms described above can be preferably used as a starting Fc region. Examples of naturally-occurring IgG variants or altered forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; International Publication Nos. WO 2009/086320, WO 2008/092117, WO 2007/041635, and WO 2006/105338); however, they are not limited to the examples.

Examples of alterations include those with one or more mutations, for example, mutations by substitution of different amino acid residues for amino acids of starting Fc regions, by insertion of one or more amino acid residues into amino acids of starting Fc regions, or by deletion of one or more amino acids from amino acids of starting Fc regions. Preferably, the amino acid sequences of altered Fc regions comprise at least a part of the amino acid sequence of a non-native Fc region. Such variants must have sequence identity or similarity of less than 100% to their starting Fc region. In a preferred embodiment, the variants have amino acid sequence identity or similarity of about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between an altered Fc region of the present invention and its starting Fc region. Amino acid difference between an altered Fc region and its starting Fc region can also be preferably specified based on amino acid differences at the above-described particular amino acid residue positions as indicated by EU numbering. Methods for producing such variants are exemplified in the section "Amino acid alterations".

Fc regions comprised in the antigen-binding molecules of the present invention that have a human FcRn-binding activity in the neutral pH range can be obtained by any method. Specifically, one can screen for antigen-binding molecules comprising an Fc region of which human FcRn-binding activity in the neutral pH range is 20 µM (KD) or stronger; in a more favorable embodiment, an Fc region of which human FcRn-binding activity in the neutral pH range is 2.0 µM (KD) or stronger; and in an even more favorable embodiment, an Fc region of which human FcRn-binding activity in the neutral pH range is 0.5 µM (KD) or stronger as a result of altering amino acids of an IgG-type human immunoglobulin used as a starting Fc region. Preferred Fc regions of IgG-type immunoglobulins for alteration include, for example, those of human IgGs such as IgG1, IgG2, IgG3, and IgG4 shown in SEQ ID NOs: 5, 6, 7, and 8, respectively, and variants thereof.

When an antigen-binding molecule comprises the Fc region of human IgG1 as the Fc region, suitable examples of amino acids that may be altered to achieve the above-mentioned desired effects on FcRn binding under a neutral pH range condition by altering amino acids of an IgG-type human immunoglobulin as a starting Fc region, include amino acids of positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 according to EU numbering as described in WO 2000/042072. Similarly, favorable examples of amino acids that allow such alteration include amino acids of positions 251, 252, 254, 255, 256, 308, 309, 311, 312, 385, 386, 387, 389, 428, 433, 434, and/or 436 according to EU numbering as described in WO 2002/060919. Furthermore, amino acids that allow such alteration include, for example, amino acids of positions 250, 314, and 428 according to EU numbering as described in WO2004/092219. Furthermore, favorable examples of amino acids that allow such alteration include amino acids of positions 251, 252, 307, 308, 378, 428, 430, 434, and/or 436 according to EU numbering as described in WO 2010/045193. Alteration of these amino acids enhances FcRn binding of the Fc region of an IgG-type immunoglobulin under a neutral pH range condition.

Fc regions having human FcRn-binding activity in the neutral pH range can also be obtained by altering amino acids of human immunoglobulin of IgG type used as the starting Fc region. The Fc regions of IgG type immunoglobulins adequate for alteration include, for example, those of human IgGs such as IgG1, IgG2, IgG3, and IgG4 respectively represented by SEQ ID NOs: 5, 6, 7, and 8, and altered forms thereof. Amino acids of any positions may be altered into other amino acids, as long as the Fc regions have the human FcRn-binding activity in the neutral pH range or can increase the human FcRn-binding activity in the neutral range. When the antigen-binding molecule contains the Fc region of human IgG1 as the human Fc region, it is preferable that the resulting Fc region contains a alteration that results in the effect of enhancing the human FcRn binding in the neutral pH range as compared to the binding activity of the starting Fc region of human IgG1. Amino acids that allow such alteration include, for example, amino acids of the following positions: 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 according to EU numbering. Alteration of these amino acids augments the human FcRn binding of the Fc region of IgG-type immunoglobulin in the neutral pH range.

From those described above, alterations that augment the human FcRn binding in the neutral pH range are appropriately selected for use in the present invention. Particularly preferred amino acids of the altered Fc regions include, for example, amino acids of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 according to the EU numbering system. The human FcRn-binding activity in the neutral pH range of the Fc region contained in an antigen-binding molecule can be increased by substituting at least one amino acid selected from the above amino acids into a different amino acid.

Particularly preferred alterations include, for example:
Met for the amino acid at position 237;
Ile for the amino acid at position 248;
Ala, Phe, Ile, Met, Gln, Ser, Val, Trp, or Tyr for the amino acid at position 250;
Phe, Trp, or Tyr for the amino acid at position 252;
Thr for the amino acid at position 254;
Glu for the amino acid at position 255;
Asp, Asn, Glu, or Gln for the amino acid at position 256;
Ala, Gly, Ile, Leu, Met, Asn, Ser, Thr, or Val for the amino acid at position 257;
His for the amino acid at position 258:
Ala for the amino acid at position 265;
Ala or Glu for the amino acid at position 286;
His for the amino acid at position 289;
Ala for the amino acid at position 297;
Ala for the amino acid at position 303;
Ala for the amino acid at position 305;
Ala, Asp, Phe, Gly, His, Ile, Lys, Leu, Met, Asn, Pro, Gln, Arg, Ser, Val, Trp, or Tyr for the amino acid at position 307;
Ala, Phe, Ile, Leu, Met, Pro, Gln, or Thr for the amino acid at position 308; Ala, Asp, Glu, Pro, or Arg for the amino acid at position 309;
Ala, His, or Ile for the amino acid at position 311;
Ala or His for the amino acid at position 312;
Lys or Arg for the amino acid at position 314;
Ala, Asp, or His for the amino acid at position 315;
Ala for the amino acid at position 317;
Val for the amino acid at position 332;
Leu for the amino acid at position 334;
His for the amino acid at position 360;
Ala for the amino acid at position 376;
Ala for the amino acid at position 380;
Ala for the amino acid at position 382;
Ala for the amino acid at position 384;
Asp or His for the amino acid at position 385;
Pro for the amino acid at position 386;
Glu for the amino acid at position 387;

Ala or Ser for the amino acid at position 389;
Ala for the amino acid at position 424;
Ala, Asp, Phe, Gly, His, Ile, Lys, Leu, Asn, Pro, Gln, Ser, Thr, Val, Trp, or Tyr for the amino acid at position 428;
Lys for the amino acid at position 433;
Ala, Phe, His, Ser, Trp, or Tyr for the amino acid at position 434; and
His, Ile, Leu, Phe, Thr, or Val for the amino acid at position 436 of the Fc region according to EU numbering. Meanwhile, the number of amino acids to be altered is not particularly limited and an amino acid at only one site may be altered, and amino acids at two or more sites may be altered. These combinations of amino acid alterations include, for example, those described in Tables 2-1 to 2-33.

TABLE 2-1

| Variant | KD (M) | Amino acid alteration site |
|---|---|---|
| F1 | 8.10E−07 | N434W |
| F2 | 3.20E−06 | M252Y/S254T/T256E |
| F3 | 2.50E−06 | N434Y |
| F4 | 5.80E−06 | N434S |
| F5 | 6.80E−06 | N434A |
| F7 | 5.60E−06 | M252Y |
| F8 | 4.20E−06 | M252W |
| F9 | 1.40E−07 | M252Y/S254T/T256E/N434Y |
| F10 | 6.90E−08 | M252Y/S254T/T256E/N434W |
| F11 | 3.10E−07 | M252Y/N434Y |
| F12 | 1.70E−07 | M252Y/N434W |
| F13 | 3.20E−07 | M252W/N434Y |
| F14 | 1.80E−07 | M252W/N434W |
| F19 | 4.60E−07 | P257L/N434Y |
| F20 | 4.60E−07 | V308F/N434Y |
| F21 | 3.00E−08 | M252Y/V308P/N434Y |
| F22 | 2.00E−06 | M428L/N434S |
| F25 | 9.20E−09 | M252Y/S254T/T256E/V308P/N434W |
| F26 | 1.00E−06 | I332V |
| F27 | 7.40E−06 | G237M |
| F29 | 1.40E−06 | I332V/N434Y |
| F31 | 2.80E−06 | G237M/V308F |
| F32 | 8.00E−07 | S254T/N434W |
| F33 | 2.30E−06 | S254T/N434Y |
| F34 | 2.80E−07 | T256E/N434W |
| F35 | 8.40E−07 | T256E/N434Y |
| F36 | 3.60E−07 | S254T/T256E/N434W |
| F37 | 1.10E−07 | S254T/T256E/N434Y |
| F38 | 1.00E−07 | M252Y/S254T/N434W |
| F39 | 3.00E−07 | M252Y/S254T/N434Y |
| F40 | 8.20E−08 | M252Y/T256E/N434W |
| F41 | 1.50E−07 | M252Y/T256E/N434Y |

Table 2-2 is a continuation of Table 2-1.

TABLE 2-2

| F42 | 1.00E−06 | M252Y/S254T/T256E/N434A |
|---|---|---|
| F43 | 1.70E−06 | M252Y/N434A |
| F44 | 1.10E−06 | M252W/N434A |
| F47 | 2.40E−07 | M252Y/T256Q/N434W |
| F48 | 3.20E−07 | M252Y/T256Q/N434Y |
| F49 | 5.10E−07 | M252F/T256D/N434W |
| F50 | 1.20E−06 | M252F/T256D/N434Y |
| F51 | 8.10E−06 | N434F/Y436H |
| F52 | 3.10E−06 | H433K/N434F/Y436H |
| F53 | 1.00E−06 | I332V/N434W |
| F54 | 8.40E−08 | V308P/N434W |
| F56 | 9.40E−07 | I332V/M428L/N434Y |
| F57 | 1.10E−05 | G385D/Q386P/N389S |
| F58 | 7.70E−07 | G385D/Q386P/N389S/N434W |
| F59 | 2.40E−06 | G385D/Q386P/N389S/N434Y |
| F60 | 1.10E−05 | G385H |
| F61 | 9.70E−07 | G385H/N434W |
| F62 | 1.90E−06 | G385H/N434Y |
| F63 | 2.50E−06 | N434F |
| F64 | 5.30E−06 | N434H |
| F65 | 2.90E−07 | M252Y/S254T/T256E/N434F |

TABLE 2-2-continued

| F66 | 4.30E−07 | M252Y/S254T/T256E/N434H |
|---|---|---|
| F67 | 6.30E−07 | M252Y/N434F |
| F68 | 9.30E−07 | M252Y/N434H |
| F69 | 5.10E−07 | M428L/N434W |
| F70 | 1.50E−06 | M428L/N434Y |
| F71 | 8.30E−08 | M252Y/S254T/T256E/M428L/N434W |
| F72 | 2.00E−07 | M252Y/S254T/T256E/M428L/N434Y |
| F73 | 1.70E−07 | M252Y/M428L/N434W |
| F74 | 4.60E−07 | M252Y/M428L/N434Y |
| F75 | 1.40E−06 | M252Y/M428L/N434A |
| F76 | 1.00E−06 | M252Y/S254T/T256E/M428L/N434A |
| F77 | 9.90E−07 | T256E/M428L/N434Y |
| F78 | 7.80E−07 | S254T/M428L/N434W |

Table 2-3 is a continuation of Table 2-2.

TABLE 2-3

| F79 | 5.90E−06 | S254T/T256E/N434A |
|---|---|---|
| F80 | 2.70E−06 | M252Y/T256Q/N434A |
| F81 | 1.60E−06 | M252Y/T256E/N434A |
| F82 | 1.10E−06 | T256Q/N434W |
| F83 | 2.60E−06 | T256Q/N434Y |
| F84 | 2.80E−07 | M252W/T256Q/N434W |
| F85 | 5.50E−07 | M252W/T256Q/N434Y |
| F86 | 1.50E−06 | S254T/T256Q/N434W |
| F87 | 4.30E−06 | S254T/T256Q/N434Y |
| F88 | 1.90E−07 | M252Y/S254T/T256Q/N434W |
| F89 | 3.60E−07 | M252Y/S254T/T256Q/N434Y |
| F90 | 1.90E−08 | M252Y/T256E/V308P/N434W |
| F91 | 4.80E−08 | M252Y/V308P/M428L/N434Y |
| F92 | 1.10E−08 | M252Y/S254T/T256E/V308P/M428L/N434W |
| F93 | 7.40E−07 | M252W/M428L/N434W |
| F94 | 3.70E−07 | P257L/M428L/N434Y |
| F95 | 2.60E−07 | M252Y/S254T/T256E/M428L/N434F |
| F99 | 6.20E−07 | M252Y/T256E/N434H |
| F101 | 1.10E−07 | M252W/T256Q/P257L/N434Y |
| F103 | 4.40E−08 | P238A/M252Y/V308P/N434Y |
| F104 | 3.70E−08 | M252Y/D265A/V308P/N434Y |
| F105 | 7.50E−08 | M252Y/T307A/V308P/N434Y |
| F106 | 3.70E−08 | M252Y/V303A/V308P/N434Y |
| F107 | 3.40E−08 | M252Y/V308P/D376A/N434Y |
| F108 | 4.10E−08 | M252Y/V305A/V308P/N434Y |
| F109 | 3.20E−08 | M252Y/V308P/Q311A/N434Y |
| F111 | 3.20E−08 | M252Y/V308P/K317A/N434Y |
| F112 | 6.40E−08 | M252Y/V308P/E380A/N434Y |
| F113 | 3.20E−08 | M252Y/V308P/E382A/N434Y |
| F114 | 3.80E−08 | M252Y/V308P/S424A/N434Y |
| F115 | 6.60E−06 | T307A/N434A |
| F116 | 8.70E−06 | E380A/N434A |
| F118 | 1.40E−05 | M428L |
| F119 | 5.40E−06 | T250Q/M428L |

Table 2-4 is a continuation of Table 2-3.

TABLE 2-4

| F120 | 6.30E−08 | P257L/V308P/M428L/N434Y |
|---|---|---|
| F121 | 1.50E−08 | M252Y/T256E/V308P/M428L/N434W |
| F122 | 1.20E−07 | M252Y/T256E/M428L/N434W |
| F123 | 3.00E−08 | M252Y/T256E/V308P/N434Y |
| F124 | 2.90E−07 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| F131 | 3.00E−06 | P257G/M428L/N434Y |
| F132 | 2.10E−07 | P257I/M428L/N434Y |
| F133 | 4.10E−07 | P257M/M428L/N434Y |
| F134 | 2.70E−07 | P257N/M428L/N434Y |
| F135 | 7.50E−07 | P257S/M428L/N434Y |
| F136 | 3.80E−07 | P257T/M428L/N434Y |
| F137 | 4.60E−07 | P257V/M428L/N434Y |
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |

TABLE 2-4-continued

| | | |
|---|---|---|
| F145 | 5.30E−08 | M252Y/V308F/N434Y |
| F147 | 2.40E−07 | M252Y/V308I/N434Y |
| F149 | 1.90E−07 | M252Y/V308L/N434Y |
| F150 | 2.00E−07 | M252Y/V308M/N434Y |
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−07 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |

Table 2-5 is a continuation of Table 2-4.

TABLE 2-5

| | | |
|---|---|---|
| F166 | 1.50E−07 | M252W/T307Q/N434Y |
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M252W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |
| F178 | 2.70E−07 | M252W/D270F/N434Y |
| F179 | 3.10E−07 | M252W/N325G/N434Y |
| F182 | 6.60E−08 | P257A/M428L/N434W |
| F183 | 2.20E−07 | P257T/M428L/N434W |
| F184 | 2.70E−07 | P257V/M428L/N434W |
| F185 | 2.60E−07 | M252W/I332V/N434Y |
| F188 | 3.00E−06 | P257I/Q311I |
| F189 | 1.90E−07 | M252Y/T307A/N434Y |
| F190 | 1.10E−07 | M252Y/T307Q/N434Y |
| F191 | 1.60E−07 | P257L/T307A/M428L/N434Y |
| F192 | 1.10E−07 | P257A/T307A/M428L/N434Y |
| F193 | 8.50E−08 | P257T/T307A/M428L/N434Y |
| F194 | 1.20E−07 | P257V/T307A/M428L/N434Y |
| F195 | 5.60E−08 | P257L/T307Q/M428L/N434Y |
| F196 | 3.50E−08 | P257A/T307Q/M428L/N434Y |
| F197 | 3.30E−08 | P257T/T307Q/M428L/N434Y |
| F198 | 4.80E−08 | P257V/T307Q/M428L/N434Y |
| F201 | 2.10E−07 | M252Y/T307D/N434Y |
| F203 | 2.40E−07 | M252Y/T307F/N434Y |
| F204 | 2.10E−07 | M252Y/T307G/N434Y |
| F205 | 2.00E−07 | M252Y/T307H/N434Y |
| F206 | 2.30E−07 | M252Y/T307I/N434Y |

Table 2-6 is a continuation of Table 2-5.

TABLE 2-6

| | | |
|---|---|---|
| F207 | 9.40E−07 | M252Y/T307K/N434Y |
| F208 | 3.90E−07 | M252Y/T307L/N434Y |
| F209 | 1.30E−07 | M252Y/T307M/N434Y |
| F210 | 2.90E−07 | M252Y/T307N/N434Y |
| F211 | 2.40E−07 | M252Y/T307P/N434Y |
| F212 | 6.80E−07 | M252Y/T307R/N434Y |
| F213 | 2.30E−07 | M252Y/T307S/N434Y |
| F214 | 1.70E−07 | M252Y/T307V/N434Y |
| F215 | 9.60E−08 | M252Y/T307W/N434Y |
| F216 | 2.30E−07 | M252Y/T307Y/N434Y |
| F217 | 2.30E−07 | M252Y/K334L/N434Y |
| F218 | 2.60E−07 | M252Y/G385H/N434Y |
| F219 | 2.50E−07 | M252Y/T289H/N434Y |
| F220 | 2.50E−07 | M252Y/Q311H/N434Y |
| F221 | 3.10E−07 | M252Y/D312H/N434Y |
| F222 | 3.40E−07 | M252Y/N315H/N434Y |
| F223 | 2.70E−07 | M252Y/K360H/N434Y |
| F225 | 1.50E−06 | M252Y/L314R/N434Y |
| F226 | 5.40E−07 | M252Y/L314K/N434Y |

TABLE 2-6-continued

| | | |
|---|---|---|
| F227 | 1.20E−07 | M252Y/N286E/N434Y |
| F228 | 2.30E−07 | M252Y/L309E/N434Y |
| F229 | 5.10E−07 | M252Y/R255E/N434Y |
| F230 | 2.50E−07 | M252Y/P387E/N434Y |
| F236 | 8.90E−07 | K248I/M428L/N434Y |
| F237 | 2.30E−07 | M252Y/M428A/N434Y |
| F238 | 7.40E−07 | M252Y/M428D/N434Y |
| F240 | 7.20E−07 | M252Y/M428F/N434Y |
| F241 | 1.50E−06 | M252Y/M428G/N434Y |
| F242 | 8.50E−07 | M252Y/M428H/N434Y |
| F243 | 1.80E−07 | M252Y/M428I/N434Y |
| F244 | 1.30E−06 | M252Y/M428K/N434Y |
| F245 | 4.70E−07 | M252Y/M428N/N434Y |
| F246 | 1.10E−06 | M252Y/M428P/N434Y |
| F247 | 4.40E−07 | M252Y/M428Q/N434Y |

Table 2-7 is a continuation of Table 2-6.

TABLE 2-7

| | | |
|---|---|---|
| F249 | 6.40E−07 | M252Y/M428S/N434Y |
| F250 | 2.90E−07 | M252Y/M428T/N434Y |
| F251 | 1.90E−07 | M252Y/M428V/N434Y |
| F252 | 1.00E−06 | M252Y/M428W/N434Y |
| F253 | 7.10E−07 | M252Y/M428Y/N434Y |
| F254 | 7.50E−08 | M252W/T307Q/M428Y/N434Y |
| F255 | 1.10E−07 | M252W/Q311A/M428Y/N434Y |
| F256 | 5.40E−08 | M252W/T307Q/Q311A/M428Y/N434Y |
| F257 | 5.00E−07 | M252Y/T307A/M428Y/N434Y |
| F258 | 3.20E−07 | M252Y/T307Q/M428Y/N434Y |
| F259 | 2.80E−07 | M252Y/D270F/N434Y |
| F260 | 1.30E−07 | M252Y/T307A/Q311A/N434Y |
| F261 | 8.40E−08 | M252Y/T307Q/Q311A/N434Y |
| F262 | 1.90E−07 | M252Y/T307A/Q311H/N434Y |
| F263 | 1.10E−07 | M252Y/T307Q/Q311H/N434Y |
| F264 | 2.80E−07 | M252Y/E382A/N434Y |
| F265 | 6.80E−07 | M252Y/E382A/M428Y/N434Y |
| F266 | 4.70E−07 | M252Y/T307A/E382A/M428Y/N434Y |
| F267 | 3.20E−07 | M252Y/T307Q/E382A/M428Y/N434Y |
| F268 | 6.30E−07 | P238A/M252Y/M428F/N434Y |
| F269 | 5.20E−07 | M252Y/V305A/M428F/N434Y |
| F270 | 6.60E−07 | M252Y/N325G/M428/N434Y |
| F271 | 6.90E−07 | M252Y/D376A/M428F/N434Y |
| F272 | 6.80E−07 | M252Y/E380A/M428F/N434Y |
| F273 | 6.50E−07 | M252Y/E382A/M428F/N434Y |
| F274 | 7.60E−07 | M252Y/E380A/E382A/M428F/N434Y |
| F275 | 4.20E−08 | S239K/M252Y/V308P/E382A/N434Y |
| F276 | 4.10E−08 | M252Y/D270F/V308P/E382A/N434Y |
| F277 | 1.30E−07 | S239K/M252Y/V308P/M428Y/N434Y |
| F278 | 3.00E−08 | M252Y/T307Q/V308P/E382A/N434Y |
| F279 | 6.10E−08 | M252Y/V308P/Q311H/E382A/N434Y |
| F280 | 4.10E−08 | S239K/M252Y/D270F/V308P/N434Y |
| F281 | 9.20E−08 | M252Y/V308P/E382A/M428F/N434Y |
| F282 | 2.90E−08 | M252Y/V308P/E382A/M428L/N434Y |

Table 2-8 is a continuation of Table 2-7.

TABLE 2-8

| | | |
|---|---|---|
| F283 | 1.00E−07 | M252Y/V308P/E382A/M428Y/N434Y |
| F284 | 1.00E−07 | M252Y/V308P/M428Y/N434Y |
| F285 | 9.90E−08 | M252Y/V308P/M428F/N434Y |
| F286 | 1.20E−07 | S239K/M252Y/V308P/E382A/M428Y/N434Y |
| F287 | 1.00E−07 | M252Y/V308P/E380A/E382A/M428F/N434Y |
| F288 | 1.90E−07 | M252Y/T256E/E382A/N434Y |
| F289 | 4.80E−07 | M252Y/T256E/M428Y/N434Y |
| F290 | 4.60E−07 | M252Y/T256E/E382A/M428Y/N434Y |
| F292 | 2.30E−08 | S239K/M252Y/V308P/E382A/M428I/N434Y |
| F293 | 5.30E−08 | M252Y/V308P/E380A/E382A/M428I/N434Y |
| F294 | 1.10E−07 | S239K/M252Y/V308P/M428F/N434Y |
| F295 | 6.80E−07 | S239K/M252Y/E380A/E382A/M428P/N434Y |
| F296 | 4.90E−07 | M252Y/Q311A/M428Y/N434Y |
| F297 | 5.10E−07 | M252Y/D312A/M428Y/N434Y |
| F298 | 4.80E−07 | M252Y/Q311A/D312A/M428Y/N434Y |
| F299 | 9.40E−08 | S239K/M252Y/V308P/Q311A/M428Y/N434Y |
| F300 | 8.30E−08 | S239K/M252Y/V308P/D312A/M428Y/N434Y |
| F301 | 7.20E−08 | S239K/M252Y/V308P/Q311A/D312A/M428Y/N434Y |

TABLE 2-8-continued

| | | |
|---|---|---|
| F302 | 1.90E−07 | M252Y/T256E/T307P/N434Y |
| F303 | 6.70E−08 | M252Y/T307P/M428Y/N434Y |
| F304 | 1.60E−08 | M252W/V308P/M428Y/N434Y |
| F305 | 2.70E−08 | M252Y/T256E/V308P/E382A/N434Y |
| F306 | 3.60E−08 | M252W/V308P/E382A/N434Y |
| F307 | 3.60E−08 | S239K/M252W/V308P/E382A/N434Y |
| F308 | 1.90E−08 | S239K/M252W/V308P/E382A/M428Y/N434Y |
| F310 | 9.40E−08 | S239K/M252W/V308P/E382A/M428I/N434Y |
| F311 | 2.80E−08 | S239K/M252W/V308P/M428F/N434Y |
| F312 | 4.50E−07 | S239K/M252W/E380A/E382A/M428F/N434Y |
| F313 | 6.50E−08 | S239K/M252Y/T307P/M428Y/N434Y |
| F314 | 3.20E−07 | M252Y/T256E/Q311A/D312A/M428Y/N434Y |
| F315 | 6.80E−07 | S239K/M252Y/M428Y/N434Y |
| F316 | 7.00E−08 | S239K/M252Y/D270F/M428Y/N434Y |
| F317 | 1.10E−07 | S239K/M252Y/D270F/V308P/M428Y/N434Y |
| F318 | 1.80E−08 | S239K/M252Y/V308P/M428I/N434Y |

Table 2-9 is a continuation of Table 2-8.

TABLE 2-9

| | | |
|---|---|---|
| F320 | 2.00E−08 | S239K/M252Y/V308P/N325G/E382A/M428I/N434Y |
| F321 | 3.20E−08 | S239K/M252Y/D270F/V308P/N325G/N434Y |
| F322 | 9.20E−08 | S239K/M252Y/D270F/T307P/V308P/N434Y |
| F323 | 2.70E−08 | S239K/M252Y/T256E/D270F/V308P/N434Y |
| F324 | 2.80E−08 | S239K/M252Y/D270F/T307Q/V308P/N434Y |
| F325 | 2.10E−08 | S239K/M252Y/D270F/T307Q/V308P/Q311A/N434Y |
| F326 | 7.50E−08 | S239K/M252Y/D270F/T307Q/Q311A/N434Y |
| F327 | 6.50E−08 | S239K/M252Y/T256E/D270F/T307Q/Q311A/N434Y |
| F328 | 1.90E−08 | S239K/M252Y/D270F/V308P/M428I/N434Y |
| F329 | 1.20E−08 | S239K/M252Y/D270F/N286E/V308P/N434Y |
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/M428I/N434Y |
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−07 | S239K/M252Y/V308P/L309P/M428L/N434Y |
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/M428I/N434Y |
| F358 | 1.00E−07 | S239K/M252Y/T307Q/N434Y |
| F359 | 4.20E−07 | P257V/T307Q/M428I/N434Y |
| F360 | 1.30E−06 | P257V/T307Q/M428V/N434Y |
| F362 | 5.40E−08 | P257V/T307Q/N325G/M428L/N434Y |
| F363 | 4.10E−08 | P257V/T307Q/Q311A/M428L/N434Y |
| F364 | 3.50E−08 | P257V/T307Q/Q311A/N325G/M428L/N434Y |

Table 2-10 is a continuation of Table 2-9.

TABLE 2-10

| | | |
|---|---|---|
| F365 | 5.10E−08 | P257V/V305A/T307Q/M428L/N434Y |
| F367 | 1.50E−08 | S239K/M252Y/E258H/D270F/T307Q/V308P/Q311A/N434Y |
| F368 | 2.00E−08 | S239K/M252Y/D270F/V308P/N325G/E382A/M428I/N434Y |
| F369 | 7.50E−08 | M252Y/P257V/T307Q/M428I/N434Y |
| F372 | 1.30E−08 | S239K/M252W/V308P/M428Y/N434Y |
| F373 | 1.10E−08 | S239K/M252W/V308P/Q311A/M428Y/N434Y |
| F374 | 1.20E−08 | S239K/M252W/T256E/V308P/M428Y/N434Y |
| F375 | 5.50E−09 | S239K/M252W/N286E/V308P/M428Y/N434Y |
| F376 | 9.60E−08 | S239K/M252Y/T256E/D270F/N286E/V308P/N434Y |
| F377 | 1.30E−07 | S239K/M252W/T307P/M428Y/N434Y |
| F379 | 9.00E−09 | S239K/M252W/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |

TABLE 2-10-continued

| | | |
|---|---|---|
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252W/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428I/N434Y |
| F393 | 1.20E−08 | S239K/M252Y/N286E/V308P/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/N434Y |
| F397 | 4.50E−08 | S239K/M252Y/D270F/T307Q/Q311A/P387E/M428I/N434Y |
| F398 | 4.40E−09 | S239K/M252Y/D270F/N286E/T307Q/V308P/Q311A/M428I/N434Y |
| F399 | 6.50E−09 | S239K/M252Y/D270F/N286E/T307Q/V308P/M428I/N434Y |
| F400 | 6.10E−09 | S239K/M252Y/D270F/N286E/V308P/Q311A/M428I/N434Y |
| F401 | 6.90E−09 | S239K/M252Y/D270F/N286E/V308P/P387E/M428I/N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257V/T307Q/L309P/M428L/N434Y |

Table 2-11 is a continuation of Table 2-10.

TABLE 2-11

| | | |
|---|---|---|
| F406 | 1.50E−07 | P257A/T307Q/L309R/M428L/N434Y |
| F407 | 1.60E−07 | P257V/T307Q/L309R/M428L/N434Y |
| F408 | 2.50E−08 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |
| F412 | 8.80E−08 | P257V/T307G/M428L/N434Y |
| F413 | 1.20E−07 | P257V/T307P/M428L/N434Y |
| F414 | 1.10E−07 | P257V/T307S/M428L/N434Y |
| F415 | 5.60E−08 | P257V/N286E/T307A/M428L/N434Y |
| F416 | 9.40E−08 | P257V/T307A/P287E/M428L/N434Y |
| F418 | 6.20E−07 | S239K/M252Y/T307P/N325G/M428Y/N434Y |
| F419 | 1.60E−07 | M252Y/T307A/Q311H/K360H/N434Y |
| F420 | 1.50E−07 | M252Y/T307A/Q311H/P387E/N434Y |
| F421 | 1.30E−07 | M252Y/T307A/Q311H/M428A/N434Y |
| F422 | 1.80E−07 | M252Y/T307A/Q311H/E382A/N434Y |
| F423 | 8.40E−08 | M252Y/T307W/Q311H/N434Y |
| F424 | 9.40E−08 | S239K/P257A/V308P/M428L/N434Y |
| F425 | 8.00E−08 | P257A/V308P/L309E/M428L/N434Y |
| F426 | 8.40E−08 | P257V/T307Q/N434Y |
| F427 | 1.10E−07 | M252Y/P257V/T307Q/M428V/N434Y |
| F428 | 8.00E−08 | M252Y/P257V/T307Q/M428L/N434Y |
| F429 | 3.70E−08 | M252Y/P257V/T307Q/N434Y |
| F430 | 8.10E−08 | M252Y/P257V/T307Q/M428Y/N434Y |
| F431 | 6.50E−08 | M252Y/P257V/T307Q/M428F/N434Y |
| F432 | 9.20E−07 | P257V/T307Q/Q311A/N325G/M428V/N434Y |
| F433 | 6.00E−08 | P257V/T307Q/Q311A/N325G/N434Y |
| F434 | 2.00E−08 | P257V/T307Q/Q311A/N325G/M428Y/N434Y |
| F435 | 2.50E−08 | P257V/T307Q/Q311A/N325G/M428F/N434Y |
| F436 | 2.50E−07 | P257A/T307Q/M428V/N434Y |
| F437 | 5.70E−08 | P257A/T307Q/N434Y |
| F438 | 3.60E−08 | P257A/T307Q/M428Y/N434Y |
| F439 | 4.00E−08 | P257A/T307Q/M428F/N434Y |
| F440 | 1.50E−08 | P257V/N286E/T307Q/Q311A/N325G/M428L/N434Y |

Table 2-12 is a continuation of Table 2-11.

TABLE 2-12

| | | |
|---|---|---|
| F441 | 1.80E−07 | P257A/Q311A/M428L/N434Y |
| F442 | 2.00E−07 | P257A/Q311H/M428L/N434Y |
| F443 | 5.50E−08 | P257A/T307Q/Q311A/M428L/N434Y |
| F444 | 1.40E−07 | P257A/T307A/Q311A/M428L/N434Y |
| F445 | 6.20E−08 | P257A/T307Q/Q311H/M428L/N434Y |
| F446 | 1.10E−07 | P257A/T307A/Q311H/M428L/N434Y |

TABLE 2-12-continued

| | | |
|---|---|---|
| F447 | 1.40E−08 | P257A/N286E/T307Q/M428L/N434Y |
| F448 | 5.30E−08 | P257A/N286E/T307A/M428L/N434Y |
| F449 | 5.70E−07 | S239K/M252Y/D270F/T307P/N325G/M428Y/N434Y |
| F450 | 5.20E−07 | S239K/M252Y/T307P/L309E/N325G/M428Y/N434Y |
| F451 | 1.00E−07 | P257S/T307A/M428L/N434Y |
| F452 | 1.40E−07 | P257M/T307A/M428L/N434Y |
| F453 | 7.80E−08 | P257N/T307A/M428L/N434Y |
| F454 | 9.60E−08 | P257I/T307A/M428L/N434Y |
| F455 | 2.70E−08 | P257V/T307Q/M428Y/N434Y |
| F456 | 3.40E−08 | P257V/T307Q/M428F/N434Y |
| F457 | 4.00E−08 | S239K/P257V/V308P/M428L/N434Y |
| F458 | 1.50E−08 | P257V/T307Q/V308P/N325G/M428L/N434Y |
| F459 | 1.30E−08 | P257V/T307Q/V308P/Q311A/N325G/M428L/N434Y |
| F460 | 4.70E−08 | P257V/T307A/V308P/N325G/M428L/N434Y |
| F462 | 8.50E−08 | P257A/V308P/N325G/M428L/N434Y |
| F463 | 1.30E−07 | P257A/T307A/V308P/M428L/N434Y |
| F464 | 5.50E−08 | P257V/T307Q/V308P/M428L/N434Y |
| F465 | 2.10E−08 | P257V/N286E/T307Q/N325G/M428L/N434Y |
| F466 | 3.50E−07 | T256E/P257V/N434Y |
| F467 | 5.70E−07 | T256E/P257T/N434Y |
| F468 | 5.70E−08 | S239K/P257V/V308P/M428L/N434Y |
| F469 | 5.60E−08 | P257T/V308P/N325G/M428L/N434Y |
| F470 | 5.40E−08 | T256E/P257T/V308P/N325G/M428L/N434Y |
| F471 | 6.60E−08 | P257T/V308P/N325G/E382A/M428L/N434Y |
| F472 | 5.40E−08 | P257T/V308P/P387E/M428L/N434Y |
| F473 | 4.50E−07 | P257T/V308P/L309P/N325G/M428L/N434Y |
| F474 | 3.50E−08 | P257T/V308P/L309R/N325G/M428L/N434Y |
| F475 | 4.30E−08 | T256E/P257V/T307Q/M428L/N434Y |

Table 2-13 is a continuation of Table 2-12.

TABLE 2-13

| | | |
|---|---|---|
| F476 | 5.50E−08 | P257V/T307Q/E382A/M428L/N434Y |
| F477 | 4.30E−08 | P257V/T307Q/P387E/M428L/N434Y |
| F480 | 3.90E−08 | P257L/V308P/N434Y |
| F481 | 5.60E−08 | P257T/T307Q/N434Y |
| F482 | 7.00E−08 | P257V/T307Q/N325G/N434Y |
| F483 | 5.70E−08 | P257V/T307Q/Q311A/N434Y |
| F484 | 6.20E−08 | P257V/V305A/T307Q/N434Y |
| F485 | 9.70E−08 | P257V/N286E/T307A/N434Y |
| F486 | 3.40E−07 | P257V/T307Q/L309R/Q311H/M428L/N434Y |
| F488 | 3.50E−08 | P257V/V308P/N325G/M428L/N434Y |
| F490 | 7.50E−08 | S239K/P257V/V308P/Q311H/M428L/N434Y |
| F492 | 9.80E−08 | P257V/V305A/T307A/N325G/M428L/N434Y |
| F493 | 4.90E−07 | S239K/D270F/T307P/N325G/M428Y/N434Y |
| F497 | 3.10E−06 | P257T/T307A/M428V/N434Y |
| F498 | 1.30E−06 | P257A/M428V/N434Y |
| F499 | 5.20E−07 | P257A/T307A/M428V/N434Y |
| F500 | 4.30E−08 | P257S/T307Q/M428L/N434Y |
| F506 | 1.90E−07 | P257V/N297A/T307Q/M428L/N434Y |
| F507 | 5.10E−08 | P257V/N286A/T307Q/M428L/N434Y |
| F508 | 1.10E−08 | P257V/T307Q/N315A/M428L/N434Y |
| F509 | 5.80E−08 | P257V/T307Q/N384A/M428L/N434Y |
| F510 | 5.30E−08 | P257V/T307Q/N389A/M428L/N434Y |
| F511 | 4.20E−07 | P257V/N434Y |
| F512 | 5.80E−07 | P257T/N434Y |
| F517 | 3.10E−07 | P257V/N286E/N434Y |
| F518 | 4.20E−07 | P257T/N286E/N434Y |
| F519 | 2.60E−08 | P257V/N286E/T307Q/N434Y |
| F521 | 1.10E−08 | P257V/N286E/T307Q/M428Y/N434Y |
| F523 | 2.60E−08 | P257V/V305A/T307Q/M428Y/N434Y |
| F526 | 1.90E−08 | P257V/M428Y/N434Y |
| F527 | 9.40E−09 | P257V/T307Q/V308P/N325G/M428Y/N434Y |
| F529 | 2.50E−08 | P257T/T307Q/M428F/N434Y |
| F533 | 1.20E−08 | P257A/N286E/T307Q/M428F/N434Y |
| F534 | 1.20E−08 | P257A/N286E/T307Q/M428Y/N434Y |

Table 2-14 is a continuation of Table 2-13.

TABLE 2-14

| | | |
|---|---|---|
| F535 | 3.90E−08 | T250A/P257V/T307Q/M428L/N434Y |
| F538 | 9.90E−08 | T250F/P257V/T307Q/M428L/N434Y |
| F541 | 6.00E−08 | T250I/P257V/T307Q/M428L/N434Y |
| F544 | 3.10E−08 | T250M/P257V/T307Q/M428L/N434Y |
| F549 | 5.40E−08 | T250S/P257V/T307Q/M428L/N434Y |

TABLE 2-14-continued

| | | |
|---|---|---|
| F550 | 5.90E−08 | T250V/P257V/T307Q/M428L/N434Y |
| F551 | 1.20E−07 | T250W/P257V/T307Q/M428L/N434Y |
| F552 | 1.10E−07 | T250Y/P257V/T307Q/M428L/N434Y |
| F553 | 1.70E−07 | M252Y/Q311A/N434Y |
| F554 | 2.80E−08 | S239K/M252Y/S254T/V308P/N434Y |
| F556 | 1.50E−06 | M252Y/T307Q/Q311A |
| F559 | 8.00E−08 | M252Y/S254T/N286E/N434Y |
| F560 | 2.80E−08 | M252Y/S254T/V308P/N434Y |
| F561 | 1.40E−07 | M252Y/S254T/T307A/N434Y |
| F562 | 8.30E−08 | M252Y/S254T/T307Q/N434Y |
| F563 | 1.30E−07 | M252Y/S254T/Q311A/N434Y |
| F564 | 1.90E−07 | M252Y/S254T/Q311H/N434Y |
| F565 | 9.20E−08 | M252Y/S254T/T307A/Q311A/N434Y |
| F566 | 6.10E−08 | M252Y/S254T/T307Q/Q311A/N434Y |
| F567 | 2.20E−07 | M252Y/S254T/M428I/N434Y |
| F568 | 1.10E−07 | M252Y/T256E/T307A/Q311H/N434Y |
| F569 | 2.00E−07 | M252Y/T256Q/T307A/Q311H/N434Y |
| F570 | 1.30E−07 | M252Y/S254T/T307A/Q311H/N434Y |
| F571 | 8.10E−08 | M252Y/N286E/T307A/Q311H/N434Y |
| F572 | 1.00E−07 | M252Y/T307A/Q311H/M428I/N434Y |
| F576 | 1.60E−06 | M252Y/T256E/T307Q/Q311H |
| F577 | 1.30E−06 | M252Y/N286E/T307A/Q311A |
| F578 | 5.70E−07 | M252Y/N286E/T307Q/Q311A |
| F580 | 8.60E−07 | M252Y/N286E/T307Q/Q311H |
| F581 | 7.20E−08 | M252Y/T256E/N286E/N434Y |
| F582 | 7.50E−08 | S239K/M252Y/V308P |
| F583 | 7.80E−07 | S239K/M252Y/V308P/E382A |
| F584 | 6.30E−07 | S239K/M252Y/T256E/V308P |
| F585 | 2.90E−07 | S239K/M252Y/N286E/V308P |

Table 2-15 is a continuation of Table 2-14.

TABLE 2-15

| | | |
|---|---|---|
| F586 | 1.40E−07 | S239K/M252Y/N286E/V308P/M428I |
| F587 | 1.90E−07 | M252Y/N286E/M428L/N434Y |
| F592 | 2.00E−07 | M252Y/S254T/E382A/N434Y |
| F593 | 3.10E−08 | S239K/M252Y/S254T/V308P/M428I/N434Y |
| F594 | 1.60E−08 | S239K/M252Y/T256E/V308P/M428I/N434Y |
| F595 | 1.80E−07 | S239K/M252Y/M428I/N434Y |
| F596 | 4.00E−07 | M252Y/D312A/E382A/M428Y/N434Y |
| F597 | 2.20E−07 | M252Y/E382A/P387E/N434Y |
| F598 | 1.40E−07 | M252Y/D312A/P387E/N434Y |
| F599 | 5.20E−07 | M252Y/P387E/M428Y/N434Y |
| F600 | 2.80E−07 | M252Y/T256Q/E382A/N434Y |
| F601 | 9.60E−09 | M252Y/N286E/V308P/N434Y |
| F608 | | G236A/S239D/I332E |
| F611 | 2.80E−07 | M252Y/V305T/T307P/V308I/L309A/N434Y |
| F612 | 3.60E−07 | M252Y/T307P/V308I/L309A/N434Y |
| F613 | | S239D/A330L/I332E |
| F616 | | S239D/K326D/L328Y |
| F617 | 7.40E−07 | S239K/N434W |
| F618 | 6.40E−07 | S239K/V308F/N434Y |
| F619 | 3.10E−07 | s239K/M252Y/N434Y |
| F620 | 2.10E−07 | S239K/M252Y/S254T/N434Y |
| F621 | 1.50E−07 | S239K/M252Y/T307A/Q311H/N434Y |
| F622 | 3.50E−07 | S239K/M252Y/T256Q/N434Y |
| F623 | 1.80E−07 | S239K/M252W/N434W |
| F624 | 1.40E−08 | S239K/P257A/N286E/T307Q/M428L/N434Y |
| F625 | 7.60E−08 | S239K/P257A/T307Q/M428L/N434Y |
| F626 | 1.30E−06 | V308P |
| F629 | 3.90E−08 | M252Y/V279L/V308P/N434Y |
| F630 | 3.70E−08 | S239K/M252Y/V279L/V308P/N434Y |
| F633 | 2.40E−07 | M252Y/V282D/V308P/N434Y |
| F634 | 3.20E−06 | S239K/M252Y/V282D/V308P/N434Y |
| F635 | 4.50E−08 | M252Y/V284K/V308P/N434Y |
| F636 | 4.80E−08 | S239K/M252Y/V284K/V308P/N434Y |
| F637 | 1.50E−07 | M252Y/K288S/V308P/N434Y |

Table 2-16 is a continuation of Table 2-15.

TABLE 2-16

| | | |
|---|---|---|
| F638 | 1.40E−07 | S239K/M252Y/K288S/V308P/N434Y |
| F639 | 2.70E−08 | M252Y/V308P/G385R/N434Y |
| F640 | 3.60E−08 | S239K/M252Y/V308P/G385R/N434Y |
| F641 | 3.00E−08 | M252Y/V308P/Q386K/N434Y |

TABLE 2-16-continued

| | | |
|---|---|---|
| F642 | 3.00E−08 | S239K/M252Y/V308P/Q386K/N434Y |
| F643 | 3.20E−08 | L235G/G236R/S239K/M252Y/V308P/N434Y |
| F644 | 3.00E−08 | G236R/S239K/M252Y/V308P/N434Y |
| F645 | 3.30E−08 | S239K/M252Y/V308P/L328R/N434Y |
| F646 | 3.80E−08 | S239K/M252Y/N297A/V308P/N434Y |
| F647 | 2.90E−08 | P238D/M252Y/V308P/N434Y |
| F648 | | P238D |
| F649 | 1.20E−07 | S239K/M252Y/N286E/N434Y |
| F650 | 1.70E−07 | S239K/M252Y/T256E/N434Y |
| F651 | 1.80E−07 | S239K/M252Y/Q311A/N434Y |
| F652 | 2.40E−07 | P238D/M252Y/N434Y |
| F654 | 3.20E−08 | L235K/S239K/M252Y/V308P/N434Y |
| F655 | 3.40E−08 | L235R/S239K/M252Y/V308P/N434Y |
| F656 | 3.30E−08 | G237K/S239K/M252Y/V308P/N434Y |
| F657 | 3.20E−08 | G237R/S239K/M252Y/V308P/N434Y |
| F658 | 3.20E−08 | P238K/S239K/M252Y/V308P/N434Y |
| F659 | 3.00E−08 | P238R/S239K/M252Y/V308P/N434Y |
| F660 | 3.10E−08 | S239K/M252Y/V308P/P329K/N434Y |
| F661 | 3.40E−08 | S239K/M252Y/V308P/P329R/N434Y |
| F663 | 6.40E−09 | S239K/M252Y/N286E/T307Q/V308P/Q311A/N434Y |
| F664 | 3.90E−08 | M252Y/N286A/V308P/N434Y |
| F665 | 2.00E−08 | M252Y/N286D/V308P/N434Y |
| F666 | 2.10E−08 | M252Y/N286F/V308P/N434Y |
| F667 | 3.00E−08 | M252Y/N286G/V308P/N434Y |
| F668 | 4.00E−08 | M252Y/N286B/V308P/N434Y |
| F669 | 3.50E−08 | M252Y/N286I/V308P/N434Y |
| F670 | 2.10E−07 | M252Y/N286E/V308P/N434Y |
| F671 | 2.20E−08 | M252Y/N286L/V308P/N434Y |
| F672 | 2.40E−08 | M252Y/N286M/V308P/N434Y |
| F673 | 2.30E−08 | M252Y/N286P/V308P/N434Y |

Table 2-17 is a continuation of Table 2-16.

TABLE 2-17

| | | |
|---|---|---|
| F674 | 3.20E−08 | M252Y/N286Q/V308P/N434Y |
| F675 | 5.10E−08 | M252Y/N286R/V308P/N434Y |
| F676 | 3.20E−08 | M252Y/N286S/V308P/N434Y |
| F677 | 4.70E−08 | M252Y/N286T/V308P/N434Y |
| F678 | 3.30E−08 | M252Y/N286V/V308P/N434Y |
| F679 | 1.70E−08 | M252Y/N286W/V308P/N434Y |
| F680 | 1.50E−08 | M252Y/N286Y/V308P/N434Y |
| F681 | 4.90E−08 | M252Y/K288A/V308P/N434Y |
| F682 | 8.20E−08 | M252Y/K288D/V308P/N434Y |
| F683 | 5.00E−08 | M252Y/K288E/V308P/N434Y |
| F684 | 5.10E−08 | M252Y/K288F/V308P/N434Y |
| F685 | 5.30E−08 | M252Y/K288G/V308P/N434Y |
| F686 | 4.60E−08 | M252Y/K288H/V308P/N434Y |
| F687 | 4.90E−08 | M252Y/K288I/V308P/N434Y |
| F688 | 2.80E−08 | M252Y/K288L/V308P/N434Y |
| F689 | 4.10E−08 | M252Y/K288M/V308P/N434Y |
| F690 | 1.00E−07 | M252Y/K288N/V308P/N434Y |
| F691 | 3.20E−07 | M252Y/K288P/V308P/N434Y |
| F692 | 3.90E−08 | M252Y/K288Q/V308P/N434Y |
| F693 | 3.60E−08 | M252Y/K288R/V308P/N434Y |
| F694 | 4.70E−08 | M252Y/K288V/V308P/N434Y |
| F695 | 4.00E−08 | M252Y/K288W/V308P/N434Y |
| F696 | 4.40E−08 | M252Y/K288Y/V308P/N434Y |
| F697 | 3.10E−08 | S239K/M252Y/V308P/N325G/N434Y |
| F698 | 2.20E−08 | M252Y/N286E/T307Q/Q311A/N434Y |
| F699 | 2.30E−08 | S239K/M252Y/N286E/T307Q/Q311A/N434Y |
| F700 | 5.20E−08 | M252Y/V308P/L328E/N434Y |
| F705 | 7.10E−09 | M252Y/N286E/V308P/M428I/N434Y |
| F706 | 1.80E−08 | M252Y/N286E/T307Q/Q311A/M428I/N434Y |
| F707 | 5.90E−09 | M252Y/N286E/T307Q/V308P/Q311A/N434Y |
| F708 | 4.10E−09 | M252Y/N286E/T307Q/V308P/Q311A/M428I/N434Y |
| F709 | 2.00E−08 | S239K/M252Y/N286E/T307Q/Q311A/M428I/N434Y |
| F710 | 1.50E−08 | P238D/M252Y/N286E/T307Q/Q311A/M428I/N434Y |
| F711 | 6.50E−08 | S239K/M252Y/T307Q/Q311A/N434Y |

Table 2-18 is a continuation of Table 2-17.

TABLE 2-18

| | | |
|---|---|---|
| F712 | 6.00E−08 | P238D/M252Y/T307Q/Q311A/N434Y |
| F713 | 2.00E−08 | P238D/M252Y/N286E/T307Q/Q311A/N434Y |
| F714 | 2.30E−07 | P238D/M252Y/N325S/N434Y |
| F715 | 2.30E−07 | P238D/M252Y/N325M/N434Y |
| F716 | 2.70E−07 | P238D/M252Y/N325L/N434Y |
| F717 | 2.60E−07 | P238D/M252Y/N325I/N434Y |
| F718 | 2.80E−07 | P238D/M252Y/Q295M/N434Y |
| F719 | 7.40E−08 | P238D/M252Y/N325G/N434Y |
| F720 | 2.40E−08 | M252Y/T307Q/V308P/Q311A/N434Y |
| F721 | 1.50E−08 | M252Y/T307Q/V308P/Q311A/M428I/N434Y |
| F722 | 2.70E−07 | P238D/M252Y/A327G/N434Y |
| F723 | 2.80E−07 | P238D/M252Y/L328D/N434Y |
| F724 | 2.50E−07 | P238D/M252Y/L328E/N434Y |
| F725 | 4.20E−08 | L235K/G237R/S239K/M252Y/V308P/N434Y |
| F726 | 3.70E−08 | L235K/P238K/S239K/M252Y/V308P/N434Y |
| F729 | 9.20E−07 | T307A/Q311A/N434Y |
| F730 | 6.00E−07 | T307Q/Q311A/N434Y |
| F731 | 8.50E−07 | T307A/Q311H/N434Y |
| F732 | 6.80E−07 | T307Q/Q311H/N434Y |
| F733 | 3.20E−07 | M252Y/L328E/N434Y |
| F734 | 3.10E−07 | G236D/M252Y/L328E/N434Y |
| F736 | 3.10E−07 | M252Y/S267M/L328E/N434Y |
| F737 | 3.10E−07 | M252Y/S267L/L328E/N434Y |
| F738 | 3.50E−07 | P238D/M252Y/T307P/N434Y |
| F739 | 2.20E−07 | M252Y/T307P/Q311A/N434Y |
| F740 | 2.90E−07 | M252Y/T307P/Q311H/N434Y |
| F741 | 3.10E−07 | P238D/T250A/M252Y/N434Y |
| F744 | 9.90E−07 | P238D/T250F/M252Y/N434Y |
| F745 | 6.60E−07 | P238D/T250G/M252Y/N434Y |
| F746 | 6.00E−07 | P238D/T250H/M252Y/N434Y |
| F747 | 2.80E−07 | P238D/T250I/M252Y/N434Y |
| F749 | 5.10E−07 | P238D/T250L/M252Y/N434Y |
| F750 | 3.00E−07 | P238D/T250M/M252Y/N434Y |
| F751 | 5.30E−07 | P238D/T250N/M252Y/N434Y |

Table 2-19 is a continuation of Table 2-18.

TABLE 2-19

| | | |
|---|---|---|
| F753 | 1.80E−07 | P238D/T250Q/M252Y/N434Y |
| F755 | 3.50E−07 | P238D/T250S/M252Y/N434Y |
| F756 | 3.70E−07 | P238D/T250V/M252Y/N434Y |
| F757 | 1.20E−06 | P238D/T250W/M252Y/N434Y |
| F758 | 1.40E−06 | P238D/T250Y/M252Y/N434Y |
| F759 | | L235K/S239K |
| F760 | | L235K/S239K |
| F761 | 1.10E−06 | P238D/N434Y |
| F762 | 3.60E−08 | L235K/S239K/M252Y/N286E/T307Q/Q311A/N434Y |
| F763 | 3.50E−08 | L235K/S239K/M252Y/N286E/T307Q/Q311A/N434Y |
| F764 | 6.30E−07 | P238D/T307Q/Q311A/N434Y |
| F765 | 8.50E−08 | P238D/M252V/T307Q/L309E/Q311A/N434Y |
| F766 | 6.00E−07 | T307A/L309E/Q311A/N434Y |
| F767 | 4.30E−07 | T307Q/L309E/Q311A/N434Y |
| F768 | 6.40E−07 | T307A/L309E/Q311H/N434Y |
| F769 | 4.60E−07 | T307Q/L309E/Q311H/N434Y |
| F770 | 3.00E−07 | M252Y/T256A/N434Y |
| F771 | 4.00E−07 | M252Y/E272A/N434Y |
| F772 | 3.80E−07 | M252Y/K274A/N434Y |
| F773 | 3.90E−07 | M252Y/V282A/N434Y |
| F774 | 4.00E−07 | M252Y/N286A/N434Y |
| F775 | 6.20E−07 | M252Y/K338A/N434Y |
| F776 | 3.90E−07 | M252Y/K340A/N434Y |
| F777 | 3.90E−07 | M252Y/E345A/N434Y |
| F779 | 3.90E−07 | M252Y/N361A/N434Y |
| F780 | 3.90E−07 | M252Y/Q362A/N434Y |
| F781 | 3.70E−07 | M252Y/S375A/N434Y |
| F782 | 3.50E−07 | M252Y/Y391A/N434Y |
| F783 | 4.00E−07 | M252Y/D413A/N434Y |
| F784 | 5.00E−07 | M252Y/L309A/N434Y |
| F785 | 7.40E−07 | M252Y/L309H/N434Y |
| F786 | 2.80E−08 | M252Y/S254T/N286E/T307Q/Q311A/N434Y |
| F787 | 8.80E−08 | M252Y/S254T/T307Q/L309E/Q311A/N434Y |
| F788 | 4.10E−07 | M252Y/N315A/M434Y |

Table 2-20 is a continuation of Table 2-19.

TABLE 2-20

| | | |
|---|---|---|
| F789 | 1.50E−07 | M252Y/N315D/N434Y |
| F790 | 2.70E−07 | M252Y/N315E/N434Y |

TABLE 2-20-continued

| | | |
|---|---|---|
| F791 | 4.40E−07 | M252Y/N315F/N434Y |
| F792 | 4.40E−07 | M252Y/N315G/N434Y |
| F793 | 3.30E−07 | M252Y/N315I/N434Y |
| F794 | 4.10E−07 | M252Y/N315K/N434Y |
| F795 | 3.10E−07 | M252Y/N315L/N434Y |
| F796 | 3.40E−07 | M252Y/N315M/N434Y |
| F798 | 3.50E−07 | M252Y/N315Q/N434Y |
| F799 | 4.10E−07 | M252Y/N315R/N434Y |
| F800 | 3.80E−07 | M252Y/N315S/N434Y |
| F801 | 4.40E−07 | M252Y/N315T/N434Y |
| F802 | 3.30E−07 | M252Y/N315V/N434Y |
| F803 | 3.60E−07 | M252Y/N315W/N434Y |
| F804 | 4.00E−07 | M252Y/N315Y/N434Y |
| F805 | 3.00E−07 | M252Y/N325A/N434Y |
| F806 | 3.10E−07 | M252Y/N384A/N434Y |
| F807 | 3.20E−07 | M252Y/N389A/N434Y |
| F808 | 3.20E−07 | M252Y/N389A/N390A/N434Y |
| F809 | 2.20E−07 | M252Y/S254T/T256S/N434Y |
| F810 | 2.20E−07 | M252Y/A378V/N434Y |
| F811 | 4.90E−07 | M252Y/E380S/N434Y |
| F812 | 2.70E−07 | M252Y/E382V/N434Y |
| F813 | 2.80E−07 | M252Y/S424E/N434Y |
| F814 | 1.20E−07 | M252Y/N434Y/Y436I |
| F815 | 5.50E−07 | M252Y/N434Y/T437R |
| F816 | 3.60E−07 | P238D/T250V/M252Y/T307P/N434Y |
| F817 | 9.80E−08 | P238D/T250V/M252Y/T307Q/Q311A/N434Y |
| F819 | 1.40E−07 | P238D/M252Y/N286E/N434Y |
| F820 | 3.40E−07 | L235K/S239K/M252Y/N434Y |
| F821 | 3.10E−07 | L235K/S239K/M252Y/N434Y |
| F822 | 1.10E−06 | P238D/T250Y/M252Y/W313Y/N434Y |
| F823 | 1.10E−06 | P238D/T250Y/M252Y/W313F/N434Y |
| F828 | 2.50E−06 | P238D/T250V/M252Y/I253V/N434Y |

Table 2-21 is a continuation of Table 2-20.

TABLE 2-21

| | | |
|---|---|---|
| F831 | 1.60E−06 | P238D/T250V/M252Y/R255A/N434Y |
| F832 | 2.60E−06 | P238D/T250V/M252Y/R255D/N434Y |
| F833 | 8.00E−07 | P238D/T250V/M252Y/R255E/N434Y |
| F834 | 8.10E−07 | P238D/T250V/M252Y/R255F/N434Y |
| F836 | 5.00E−07 | P238D/T250V/M252Y/R255H/N434Y |
| F837 | 5.60E−07 | P238D/T250V/M252Y/R255I/N434Y |
| F838 | 4.30E−07 | P238D/T250V/M252Y/R255K/N434Y |
| F839 | 3.40E−07 | P238D/T250V/M252Y/R255L/N434Y |
| F840 | 4.20E−07 | P238D/T250V/M252Y/R255M/N434Y |
| F841 | 1.10E−06 | P238D/T250V/M252Y/R255N/N434Y |
| F843 | 6.60E−07 | P238D/T250V/M252Y/R255Q/N434Y |
| F844 | 1.30E−06 | P238D/T250V/M252Y/R255S/N434Y |
| F847 | 3.40E−07 | P238D/T250V/M252Y/R255W/N434Y |
| F848 | 8.30E−07 | P238D/T250V/M252Y/R255Y/N434Y |
| F849 | 3.30E−07 | M252Y/D280A/N434Y |
| F850 | 2.90E−07 | M252Y/D280E/N434Y |
| F852 | 3.30E−07 | M252Y/D280G/N434Y |
| F853 | 3.20E−07 | M252Y/D280H/N434Y |
| F855 | 3.20E−07 | M252Y/D280K/N434Y |
| F858 | 3.20E−07 | M252Y/D280N/N434Y |
| F860 | 3.30E−07 | M252Y/D280Q/N434Y |
| F861 | 3.20E−07 | M252Y/D280R/N434Y |
| F862 | 3.00E−07 | M252Y/D280S/N434Y |
| F863 | 2.70E−07 | M252Y/D280T/N434Y |
| F867 | 2.80E−07 | M252Y/N384A/N389A/N434Y |
| F868 | 2.00E−08 | G236A/S239D/M252Y/N286E/T307Q/Q311A/N434Y |
| F869 | | G236A/S239D |
| F870 | 7.30E−08 | L235K/S239K/M252Y/T307Q/Q311A/N434Y |
| F871 | 7.10E−08 | L235K/S239K/M252Y/T307Q/Q311A/N434Y |
| F872 | 1.30E−07 | L235K/S239K/M252Y/N286E/N434Y |
| F873 | 1.20E−07 | L235K/S239K/M252Y/N286E/N434Y |
| F875 | 4.80E−07 | M252Y/N434Y/Y436A |
| F877 | 8.30E−07 | M252Y/N434Y/Y436E |
| F878 | 1.90E−07 | M252Y/N434Y/Y436F |

Table 2-22 is a continuation of Table 2-21.

TABLE 2-22

| | | |
|---|---|---|
| F879 | 9.20E−07 | M252Y/N434Y/Y436G |
| F880 | 3.90E−07 | M252Y/N434Y/Y436H |
| F881 | 3.10E−07 | M252Y/N434Y/Y436K |
| F882 | 1.30E−07 | M252Y/N434Y/Y436L |
| F883 | 2.10E−07 | M252Y/N434Y/Y436M |
| F884 | 4.00E−07 | M252Y/N434Y/Y436N |
| F888 | 4.80E−07 | M252Y/N434Y/Y436S |
| F889 | 2.20E−07 | M252Y/N434Y/Y436T |
| F890 | 1.10E−07 | M252Y/N434Y/Y436V |
| F891 | 1.70E−07 | M252Y/N434Y/Y436W |
| F892 | 7.10E−08 | M252Y/S254T/N434Y/Y436I |
| F893 | 9.80E−08 | L235K/S239K/M252Y/N434Y/Y436I |
| F894 | 9.20E−08 | L235R/S239K/M252Y/N434Y/Y436I |
| F895 | 2.10E−08 | L235K/S239K/M252Y/N286E/T307Q/Q311A/N315E/N434Y |
| F896 | 2.00E−08 | L235R/S239K/M252Y/N286E/T307Q/Q311A/N315E/N434Y |
| F897 | 9.70E−08 | M252Y/N315D/N384A/N389A/N434Y |
| F898 | 1.70E−07 | M252Y/N315E/N384A/N389A/N434Y |
| F899 | 1.10E−07 | M252Y/N315D/G316A/N434Y |
| F900 | 1.70E−07 | M252Y/N315D/G316D/N434Y |
| F901 | 1.30E−07 | M252Y/N315D/G316E/N434Y |
| F902 | 2.20E−07 | M252Y/N315D/G316F/N434Y |
| F903 | 2.30E−07 | M252Y/N315D/G316H/N434Y |
| F904 | 1.00E−07 | M252Y/N315D/G316I/N434Y |
| F905 | 1.30E−07 | M252Y/N315D/G316K/N434Y |
| F906 | 1.50E−07 | M252Y/N315D/G316L/N434Y |
| F907 | 1.30E−07 | M252Y/N315D/G316M/N434Y |
| F908 | 1.50E−07 | M252Y/N315D/G316N/N434Y |
| F909 | 1.30E−07 | M252Y/N315D/G316P/N434Y |
| F910 | 1.40E−07 | M252Y/N315D/G316Q/N434Y |
| F911 | 1.30E−07 | M252Y/N315D/G316R/N434Y |
| F912 | 1.20E−07 | M252Y/N315D/G316S/N434Y |
| F913 | 1.10E−07 | M252Y/N315D/G316T/N434Y |
| F914 | 1.50E−07 | M252Y/N315D/G316V/N434Y |
| F915 | 2.30E−07 | M252Y/N315D/G316W/N434Y |

Table 2-23 is a continuation of Table 2-22.

TABLE 2-23

| | | |
|---|---|---|
| F917 | 2.50E−07 | M252Y/N286S/N434Y |
| F918 | 2.80E−07 | M252Y/D280E/N384A/N389A/N434Y |
| F919 | 3.30E−07 | M252Y/D280G/N384A/N389A/N434Y |
| F920 | 2.50E−07 | M252Y/N286S/N384A/N389A/N434Y |
| F921 | 1.20E−07 | M252Y/N286E/N384A/N389A/N434Y |
| F922 | 5.90E−08 | L235K/S239K/M252Y/N286E/N434Y/Y436I |
| F923 | 6.00E−08 | L235R/S239K/M252Y/N286E/N434Y/Y436I |
| F924 | 3.40E−08 | L235K/S239K/M252Y/T307Q/Q311A/N434Y/Y436I |
| F925 | 3.20E−08 | L235R/S239K/M252Y/T307Q/Q311A/N434Y/Y436I |
| F926 | 1.10E−07 | L235K/S239K/M252Y/S254T/N434Y/Y436I |
| F927 | 1.00E−07 | L235R/S239K/M252Y/S254T/N434Y/Y436I |
| F928 | 2.90E−08 | M252Y/T307Q/Q311A/N434Y/Y436I |
| F929 | 2.90E−08 | M252Y/S254T/T307Q/Q311A/N434Y/Y436I |
| F930 | 1.40E−07 | P238D/T250V/M252Y/N286E/N434Y |
| F931 | 1.20E−07 | P238D/T250V/M252Y/N434Y/Y436I |
| F932 | 3.20E−07 | T250V/M252Y/N434Y |
| F933 | 3.00E−07 | L234R/P238D/T250V/M252Y/N434Y |
| F934 | 3.10E−07 | G236K/P238D/T250V/M252Y/N434Y |
| F935 | 3.20E−07 | G237K/P238D/T250V/M252Y/N434Y |
| F936 | 3.20E−07 | G237R/P238D/T250V/M252Y/N434Y |
| F937 | 3.10E−07 | P238D/S239K/T250V/M252Y/N434Y |
| F938 | 1.60E−07 | L235K/S239K/M252Y/N434Y/Y436V |
| F939 | 1.50E−07 | L235R/S239K/M252Y/N434Y/Y436V |
| F940 | 1.50E−07 | P238D/T250V/M252Y/N434Y/Y436V |
| F941 | 1.20E−08 | M252Y/N286E/T307Q/Q311A/N434Y/Y436V |
| F942 | 4.20E−08 | L235K/S239K/M252Y/T307Q/Q311A/N434Y/Y436V |
| F943 | 4.00E−08 | L235R/S239K/M252Y/T307Q/Q311A/N434Y/Y436V |
| F944 | 1.70E−07 | T250V/M252Y/N434Y/Y436V |
| F945 | 1.70E−08 | T250V/M252Y/V308P/N434Y/Y436V |
| F946 | 4.30E−08 | T250V/M252Y/T307Q/Q311A/N434Y/Y436V |
| F947 | 1.10E−08 | T250V/M252Y/T307Q/V308P/Q311A/N434Y/Y436V |
| F954 | 5.30E−07 | M252Y/N434Y/H435K/Y436V |
| F957 | 7.70E−07 | M252Y/N434Y/H435N/Y436V |
| F960 | 8.00E−07 | M252Y/N434Y/H435R/Y436V |

Table 2-24 is a continuation of Table 2-23.

TABLE 2-24

| | | |
|---|---|---|
| F966 | 3.10E−07 | M252Y/S254A/N434Y |
| F970 | 2.50E−06 | M252Y/S254G/N434Y |
| F971 | 2.60E−06 | M252Y/S254H/N434Y |
| F972 | 2.60E−07 | M252Y/S254I/N434Y |
| F978 | 1.30E−06 | M252Y/S254Q/N434Y |
| F980 | 1.80E−07 | M252Y/S254V/N434Y |
| F987 | 4.00E−08 | P238D/T250V/M252Y/T307Q/Q311A/N434Y/Y436V |
| F988 | 6.90E−08 | P238D/T250V/M252Y/N286E/N434Y/Y436V |
| F989 | 1.40E−08 | L235R/S239K/M252Y/V308P/N434Y/Y436V |
| F990 | 9.40E−09 | L235R/S239K/M252Y/T307Q/V308P/Q311A/N434Y/Y436V |
| F991 | 1.30E−08 | L235R/S239K/M252Y/N286E/T307Q/Q311A/N434Y/Y436V |
| F992 | 5.10E−08 | L235R/S239K/M252Y/T307Q/Q311A/M428I/N434Y/Y436V |
| F993 | 3.80E−08 | M252Y/T307Q/Q311A/N434Y/Y436V |
| F994 | 2.80E−07 | M252Y/N325G/N434Y |
| F995 | 2.90E−07 | L235R/P238D/S239K/M252Y/N434Y |
| F996 | 1.30E−07 | L235R/P238D/S239K/M252Y/N434Y/Y436V |
| F997 | 3.80E−07 | K248I/T250V/M252Y/N434Y/Y436V |
| F998 | 8.50E−07 | K248Y/T250V/M252Y/N434Y/Y436V |
| F999 | 2.10E−07 | T250V/M252Y/E258H/N434Y/Y436V |
| F1005 | | N325G |
| F1008 | 1.70E−07 | L235R/S239K/T250V/M252Y/N434Y/Y436V |
| F1009 | 1.20E−08 | L235R/S239K/T250V/M252Y/T307Q/V308P/Q311A/N434Y/Y436V |
| F1010 | 1.90E−07 | L235R/S239K/M252Y/T307A/Q311H/N434Y |
| F1011 | 4.50E−08 | T250V/M252Y/V308P/N434Y |
| F1012 | 4.70E−08 | L235R/S239K/T250V/M252Y/V308P/N434Y |
| F1013 | 3.00E−08 | T250V/M252Y/T307Q/V308P/Q311A/N434Y |
| F1014 | 3.20E−08 | L235R/S239K/T250V/M252Y/T307Q/V308P/Q311A/N434Y |
| F1015 | 2.20E−08 | L235R/S239K/M252Y/T307Q/V308P/Q311A/N434Y |
| F1016 | 3.80E−09 | T250V/M252Y/N286E/T307Q/V308P/Q311A/N434Y/Y436V |
| F1017 | 4.20E−09 | L235R/S239K/T250V/M252Y/N286E/T307Q/V308P/Q311A/N434Y/Y436V |
| F1018 | 3.20E−09 | L235R/S239K/M252Y/N286E/T307Q/V308P/Q311A/N434Y/Y436V |
| F1019 | 3.40E−07 | P238D/T250V/M252Y/N325G/N434Y |
| F1020 | 8.50E−08 | P238D/T250V/M252Y/T307Q/Q311A/N325G/N434Y |

Table 2-25 is a continuation of Table 2-24.

TABLE 2-25

| | | |
|---|---|---|
| F1021 | 3.30E−07 | P238D/T250V/M252Y/N325A/N434Y |
| F1022 | | K326D/L328Y |
| F1023 | 4.40E−08 | S239D/T250V/M252Y/T307Q/Q311A/N434Y/Y436V |
| F1024 | 4.00E−08 | T250V/M252Y/T307Q/Q311A/K326D/L328Y/N434Y/Y436V |
| F1025 | 3.60E−08 | S239D/T250V/M252Y/T307Q/Q311A/K326D/L328Y/N434Y/Y436V |
| F1026 | 8.40E−08 | M252Y/T307A/Q311H/N434Y/Y436V |
| F1027 | 8.60E−08 | L235R/S239K/M252Y/T307A/Q311H/N434Y/Y436V |
| F1028 | 4.60E−08 | G236A/S239D/T250V/M252Y/T307Q/Q311A/N434Y/Y436V |
| F1029 | 5.10E−08 | T250V/M252Y/T307Q/Q311A/I332E/N434Y/Y436V |
| F1030 | | I332E |
| F1031 | 5.30E−08 | G236A/S239D/T250V/M252Y/T307Q/Q311A/I332E/N434Y/Y436V |
| F1032 | 4.30E−08 | P238D/T250V/M252Y/T307Q/Q311A/N325G/Y436V |
| F1033 | 1.00E−06 | P238D/N434W |
| F1034 | 1.50E−08 | L235K/S239K/M252Y/V308P/N434Y/Y436V |
| F1035 | 1.00E−08 | L235K/S239K/M252Y/T307Q/V308P/Q311A/N434Y/Y436V |
| F1036 | 1.40E−08 | L235K/S239K/M252Y/N286E/T307Q/Q311A/N434Y/Y436V |
| F1037 | 6.10E−08 | L235K/S239K/M252Y/T307Q/Q311A/M428I/N434Y/Y436V |
| F1038 | 2.80E−07 | L235K/P238D/S239K/M252Y/N434Y |
| F1039 | 1.30E−07 | L235K/P238D/S239K/M252Y/N434Y/Y436V |
| F1040 | 2.00E−07 | L235K/S239K/T250V/M252Y/N434Y/Y436V |
| F1041 | 1.40E−08 | L235K/S239K/T250V/M252Y/T307Q/V308P/Q311A/N434Y/Y436V |
| F1042 | 2.00E−07 | L235K/S239K/M252Y/T307A/Q311H/N434Y |
| F1043 | 5.20E−08 | L235K/S239K/T250V/M252Y/V308P/N434Y |
| F1044 | 3.50E−08 | L235K/S239K/T250V/M252Y/T307Q/V308P/Q311A/N434Y |
| F1045 | 2.50E−08 | L235K/S239K/M252Y/T307Q/V308P/Q311A/N434Y |
| F1046 | 4.50E−09 | L235K/S239K/T250V/M252Y/N286E/T307Q/V308P/Q311A/N434Y/Y436V |
| F1047 | 3.40E−09 | L235K/S239K/M252Y/N286E/T307Q/V308P/Q311A/N434Y/Y436V |
| F1048 | 9.90E−08 | L235K/S239K/M252Y/T307A/Q311H/N434Y/Y436V |
| F1050 | 3.50E−09 | T250V/M252Y/N286E/T307Q/V308P/Q311A/M428I/N434Y/Y436V |
| F1051 | 3.90E−09 | L235R/S239K/T250V/M252Y/N286E/T307Q/V308P/Q311A/M428I/N434Y/Y436V |
| F1052 | 3.20E−09 | L235R/S239K/M252Y/N286E/T307Q/V308P/Q311A/M428I/N434Y/Y436V |

Table 2-26 is a continuation of Table 2-25.

TABLE 2-26

| | | |
|---|---|---|
| F1053 | 4.23E−08 | L235R/S239K/T250V/M252Y/T307Q/Q311A/N434Y/Y436V |
| F1058 | 1.31E−07 | M252Y/Q386E/N434Y/Y436V |
| F1059 | 1.39E−07 | M252Y/Q386R/N434Y/Y436V |
| F1060 | 1.43E−07 | M252Y/Q386S/N434Y/Y436V |
| F1061 | 1.19E−07 | M252Y/P387E/N434Y/Y436V |
| F1062 | 1.2E−07 | M252Y/P387R/N434Y/Y436V |
| F1063 | 1.43E−07 | M252Y/P387S/N434Y/Y436V |
| F1064 | 1.32E−07 | M252Y/V422E/N434Y/Y436V |
| F1065 | 1.38E−07 | M252Y/V422R/N434Y/Y436V |
| F1066 | 1.45E−07 | M252Y/V422S/N434Y/Y436V |
| F1067 | 1.26E−07 | M252Y/S424E/N434Y/Y436V |
| F1068 | 1.69E−07 | M252Y/S424R/N434Y/Y436V |
| F1069 | 1.39E−07 | M252Y/N434Y/Y436V/Q438E |
| F1070 | 1.73E−07 | M252Y/N434Y/Y436V/Q438R |
| F1071 | 1.24E−07 | M252Y/N434Y/Y436V/Q438S |
| F1072 | 1.35E−07 | M252Y/N434Y/Y436V/S440E |
| F1073 | 1.34E−07 | M252Y/N434Y/Y436V/S440R |
| F1074 | 1.32E−07 | S239D/M252Y/N434Y/Y436V |
| F1075 | 1.4E−07 | M252Y/K326D/L328Y/N434Y/Y436V |
| F1076 | 1.27E−07 | S239D/M252Y/K326D/L328Y/N434Y/Y436V |

TABLE 2-26-continued

| | | |
|---|---|---|
| F1077 | 2.03E−06 | K248N/M252Y/N434Y |
| F1078 | 4.7E−07 | M252Y/E380N/E382S/N434Y |
| F1079 | 3.44E−07 | M252Y/E382N/N384S/N434Y |
| F1080 | 3.19E−07 | M252Y/S424N/N434Y |
| F1081 | 6.2E−07 | M252Y/N434Y/Y436N/Q438T |
| F1082 | 2.76E−07 | M252Y/N434Y/Q438N |
| F1083 | 3.45E−07 | M252Y/N434Y/S440N |
| F1094 | 2.6E−07 | M252Y/N434Y/S442N |
| F1095 | 2.86E−07 | M252Y/S383N/G385S/N434Y |
| F1096 | 2.72E−07 | M252Y/Q386T/N434Y |
| F1097 | 2.82E−07 | M252Y/Q385N/P387S/N434Y |
| F1098 | 2.58E−07 | S239D/M252Y/N434Y |
| F1099 | 2.57E−07 | M252Y/K326D/L328Y/N434Y |
| F1100 | 2.41E−07 | S239D/M252Y/K326D/L328Y/N434Y |
| F1101 | 6.59E−08 | S239D/M252Y/T307Q/Q311A/N434Y |
| F1102 | 6.46E−08 | M252Y/T307Q/Q311A/K326D/L328Y/N434Y |
| F1103 | 6.11E−08 | S239D/M252Y/T307Q/Q311A/K326D/L328Y/N434Y |
| F1104 | 1.77E−07 | M252Y/V422E/S424R/N434Y/Y436V |
| F1105 | 1.54E−07 | M252Y/V422S/S424R/N434Y/Y436V |
| F1106 | 1.42E−07 | M252Y/N434Y/Y436V/Q438R/S440E |
| F1107 | 1.23E−07 | M252Y/V422D/N434Y/Y436V |

Table 2-27 is a continuation of Table 2-26.

TABLE 2-27

| | | |
|---|---|---|
| F1108 | 1.26E−07 | M252Y/V422K/N434Y/Y436V |
| F1109 | 1.27E−07 | M252Y/V422T/N434Y/Y436V |
| F1110 | 1.33E−07 | M252Y/V422Q/N434Y/Y436V |
| F1111 | 1.65E−07 | M252Y/S424K/N434Y/Y436V |
| F1112 | 1.23E−07 | M252Y/N434Y/Y436V/Q438K |
| F1113 | 1.18E−07 | M252Y/N434Y/Y436V/S440D |
| F1114 | 1.31E−07 | M252Y/N434Y/Y436V/S440Q |
| F1115 | 1.35E−07 | M252Y/S424N/N434Y/Y436V |
| F1116 | 7.44E−08 | M252Y/T307Q/Q311A/S424N/N434Y |
| F1117 | 4.87E−08 | T250V/M252Y/T307Q/Q311A/S424N/N434Y/Y436V |
| F1118 | 1.32E−08 | T250V/M252Y/T307Q/Q311A/V308P/S424N/N434Y/Y436V |
| F1119 | 1.03E−08 | T250V/M252Y/T307Q/V308P/Q311A/V422E/N434Y/Y436V |
| F1120 | 1.04E−08 | T250V/M252Y/T307Q/V308P/Q311A/S424R/N434Y/Y436V |
| F1121 | 1.04E−08 | T250V/M252Y/T307Q/V308P/Q311A/V422E/S424R/N434Y/Y436V |
| F1122 | 1.37E−08 | T250V/M252Y/T307Q/V308P/Q311A/N434Y/Y436V/Q438R |
| F1123 | 9.55E−09 | T250V/M252Y/T307Q/V308P/Q311A/N434Y/Y436V/S440E |
| F1124 | 1.22E−08 | T250V/M252Y/T307Q/V308P/Q311A/N434Y/Y436V/Q438R/S440E |
| F1125 | 5.18E−08 | M252Y/T307Q/N434Y/Y436V |
| F1126 | 8.95E−08 | M252Y/T307A/N434Y/Y436V |
| F1127 | 7.94E−08 | M252Y/Q311A/N434Y/Y436V |
| F1128 | 1.17E−07 | M252Y/Q311H/N434Y/Y436V |
| F1129 | 4.48E−08 | M252Y/T307Q/Q311H/N434Y/Y436V |
| F1130 | 5.54E−08 | M252Y/T307A/Q311A/N434Y/Y436V |
| F1131 | 1.29E−07 | L235R/S239K/M252Y/V422E/N434Y/Y436V |
| F1132 | 1.4E−07 | L235R/S239K/M252Y/V422S/N434Y/Y436V |
| F1133 | 1.58E−07 | L235R/S239K/M252Y/S424R/N434Y/Y436V |
| F1134 | 1.66E−07 | L235R/S239K/M252Y/N434Y/Y436V/Q438R |
| F1135 | 1.26E−07 | L235R/S239K/M252Y/N434Y/Y436V/S440E |
| F1136 | 1.63E−07 | L235R/S239K/M252Y/V422E/S424R/N434Y/Y436V |
| F1137 | 1.58E−07 | L235R/S239K/M252Y/V422S/S242R/N434Y/Y436V |
| F1138 | 1.65E−07 | L235R/S239K/M252Y/N434Y/Y436V/Q438R/S440E |
| F1139 | 1.52E−07 | L235R/S239K/M252Y/S424N/N434Y/Y436V |
| F1140 | 1.62E−07 | M252Y/V422E/S424R/N434Y/Y436V/Q438R/S440E |
| F1141 | 1.77E−07 | M252Y/V422S/S424R/N434Y/Y436V/Q438R/S440E |
| F1142 | 1.87E−07 | L235R/S239K/M252Y/V422E/S424R/N434Y/Y436V/Q438R/S440E |
| F1143 | 1.98E−07 | L235R/S239K/M252Y/V422S/S424R/N434Y/Y436V/Q438R/S440E |
| F1144 | 1.44E−08 | L235R/S239K/T250V/M252Y/T307Q/V308P/Q311A/N434Y/Y436V/Q438R/S440E |
| F1145 | 5.23E−08 | T250V/M252Y/T307Q/Q311A/N434Y/Y436V/Q438R/S440E |
| F1146 | 6.24E−08 | L235R/S239K/T250V/M252Y/T307Q/Q311A/N434Y/Y436V/Q438R/S440E |
| F1147 | 7.19E−08 | M252Y/T307Q/Q311A/N434Y/Q438R/S440E |

Table 2-28 is a continuation of Table 2-27.

TABLE 2-28

| | | |
|---|---|---|
| F1148 | 7.63E−08 | L235R/S239K/M252Y/T307Q/Q311A/N434Y/Q438R/S440E |
| F1151 | 2.51E−07 | L235R/S239K/M252Y/S424N/N434Y |
| F1152 | 7.38E−08 | L235R/S239K/M252Y/T307Q/Q311A/S424N/N434Y |
| F1153 | 4.85E−08 | L235R/S239K/T250V/M252Y/T307Q/Q311A/S424N/N434Y/Y436V |
| F1154 | 1.34E−08 | L235R/S239K/T250V/M252Y/T307Q/V308P/Q311A/S424N/N434Y/Y436V |

TABLE 2-28-continued

| | | |
|---|---|---|
| F1157 | 2.09E−07 | M252Y/N434Y/Q438R/S440E |
| F1158 | 2.44E−07 | L235R/S239K/M252Y/N434Y/Q438R/S440E |
| F1159 | 4.79E−07 | S424N/N434W |
| F1160 | 2.88E−07 | V308F/S424N/N434Y |
| F1161 | 1.07E−06 | I332V/S424N/N434Y |
| F1162 | 3.43E−07 | P238D/T250Y/M252Y/N434Y/Y436V |
| F1163 | 1.54E−07 | P238D/T250Y/M252Y/T307Q/Q311A/N434Y |
| F1164 | 6.96E−08 | P238D/T250Y/M252Y/T307Q/Q311A/N434Y/Y436V |
| F1165 | 1.63E−08 | P238D/T250Y/M252Y/T307Q/V308P/Q311A/N434Y/Y436V |
| F1174 | 4.9E−07 | P257I/N434H |
| F1176 | 1.98E−06 | V308F |
| F1178 | 8.72E−07 | V259I/V308F/M428L |
| F1183 | 1.28E−06 | E380A/M428L/N434S |
| F1184 | 1E−06 | T307A/M428L/N434S |
| F1185 | 9.17E−07 | T307A/E380A/M428L/N434S |
| F1188 | 1.72E−06 | T307A/E380A/N434H |
| F1189 | 1.57E−07 | M252Y/H433D/N434Y/Y436V/Q438R/S440E |
| F1190 | 2.4E−07 | M252Y/H433E/N434Y/Y436V/Q438R/S440E |
| F1191 | 2.11E−07 | M252Y/N434Y/Y436V/T437A/Q438R/S440E |
| F1192 | 1.27E−07 | M252Y/N434Y/Y436V/T437G/Q438R/S440E |
| F1194 | 1.55E−07 | M252Y/N434Y/Q438R/K439D/S440E |
| F1195 | 1.76E−07 | M252Y/N434Y/Y436V/Q438R/S440E/L441A |
| F1196 | 1.51E−07 | M252Y/N434Y/Y436V/Q438R/S440E/L441E |
| F1197 | 9.46E−08 | M252Y/S254T/N434Y/Y436V/Q438R/S440E |
| F1198 | 7.83E−08 | M252Y/T256E/N434Y/Y436V/Q438R/S440E |
| F1199 | 6.25E−08 | M252Y/S254T/T256E/N434Y/Y436V/Q438R/S440E |
| F1200 | 1.26E−07 | T250V/M252Y/S254T/N434Y/Y436V/Q438R/S440E |
| F1201 | 1.07E−07 | T250V/M252Y/T256E/N434Y/Y436V/Q438R/S440E |
| F1202 | 8.81E−08 | T250V/M252Y/S254T/T256E/N434Y/Y436V/Q438R/S440E |
| F1203 | 1.52E−07 | M252Y/T256Q/N434Y/Y436V/Q438R/S440E |
| F1204 | 1.18E−07 | M252Y/S254T/T256Q/N434Y/Y436V/Q438R/S440E |
| F1205 | 1.98E−07 | T250V/M252Y/T256Q/N434Y/Y436V/Q438R/S440E |
| F1206 | 1.69E−07 | T250V/M252Y/S254T/T256Q/N434Y/Y436V/Q438R/S440E |
| F1207 | 1.11E−06 | I332E/M428L/N434S |
| F1208 | 5.71E−07 | L251A/M252Y/N434Y/Y436V |
| F1211 | 1.23E−06 | L251H/M252Y/N434Y/Y436V |

Table 2-29 is a continuation of Table 2-28.

TABLE 2-29

| | | |
|---|---|---|
| F1213 | 6.33E−07 | L251N/M252Y/N434Y/Y436V |
| F1216 | 1.16E−06 | L251S/M252Y/N434Y/Y436V |
| F1217 | 1.14E−06 | L251T/M252Y/N434Y/Y436V |
| F1218 | 2.51E−07 | L251V/M252Y/N434Y/Y436V |
| F1229 | 2.81E−06 | M252Y/I253V/N434Y/Y436V |
| F1230 | 1.12E−07 | M252Y/N434Y/Y436V/Q438R/S440D |
| F1231 | 9.73E−08 | M252Y/N434Y/Y436V/Q438K/S440E |
| F1232 | 9.79E−08 | M252Y/N434Y/Y436V/Q438K/S440D |
| F1243 | 1.25E−07 | L235R/S239K/M252Y/S254T/N434Y/Y436V/Q438R/S440E |
| F1244 | 1.02E−07 | L235R/S239K/M252Y/T256E/N434Y/Y436V/Q438R/S440E |
| F1245 | 8.2E−08 | L235R/S239K/M252Y/S254T/T256E/N434Y/Y436V/Q438R/S440E |
| F1246 | 1.73E−07 | L235R/S239K/T250V/M252Y/S254T/N434Y/Y436V/Q438R/S440E |
| F1247 | 1.45E−07 | L235R/S239K/T250V/M252Y/T256E/N434Y/Y436V/Q438R/S440E |
| F1248 | 1.2E−07 | L235R/S239K/T250V/M252Y/S254T/T256E/N434Y/Y436V/Q438R/S440E |
| F1249 | 2.06E−07 | L235R/S239K/M252Y/T256Q/N434Y/Y436V/Q438R/S440E |
| F1250 | 1.66E−07 | L235R/S239K/M252Y/S254T/T256Q/N434Y/Y436V/Q438R/S440E |
| F1251 | 2.77E−07 | L235R/S239K/T250V/M252Y/T256Q/N434Y/Y436V/Q438R/S440E |
| F1252 | 2.33E−07 | L235R/S239K/T250V/M252Y/S254T/T256Q/N434Y/Y436V/Q438R/S440E |
| F1253 | 1.12E−07 | L235R/S239K/M252Y/T307A/N434Y/Y436V/Q438R/S440E |
| F1254 | 6.42E−08 | L235R/S239K/M252Y/T307Q/N434Y/Y436V/Q438R/S440E |
| F1255 | 1.11E−07 | L235R/S239K/M252Y/Q311A/N434Y/Y436V/Q438R/S440E |
| F1256 | 1.56E−07 | L235R/S239K/M252Y/Q311H/N434Y/Y436V/Q438R/S440E |
| F1257 | 7.81E−08 | L235R/S239K/M252Y/T307A/Q311A/N434Y/Y436V/Q438R/S440E |
| F1258 | 1.05E−07 | L235R/S239K/M252Y/T307A/Q311H/N434Y/Y436V/Q438R/S440E |
| F1259 | 4.46E−08 | L235R/S239K/M252Y/T307Q/Q311A/N434Y/Y436V/Q438R/S440E |
| F1260 | 6.53E−08 | L235R/S239K/M252Y/T307Q/Q311H/N434Y/Y436V/Q438R/S440E |
| F1261 | 1.35E−07 | L235R/S239K/M252Y/N434Y/Y436V/Q438R/S440E |
| F1262 | 1.26E−07 | L235R/S239K/M252Y/N434Y/Y436V/Q438R/S440E |
| F1263 | 1.24E−07 | L235R/S239K/M252Y/N434Y/Y436V/Q438R/S440E |
| F1264 | 1.27E−07 | L235R/S239K/M252Y/T256A/N434Y/Y436V/Q438R/S440E |
| F1265 | 1.57E−07 | L235R/S239K/M252Y/T256G/N434Y/Y436V/Q438R/S440E |
| F1266 | 9.99E−08 | L235R/S239K/M252Y/T256N/N434Y/Y436V/Q438R/S440E |
| F1267 | 1.5E−07 | L235R/S239K/M252Y/S254A/N434Y/Y436V/Q438R/S440E |
| F1268 | 2E−07 | L235R/S239K/M252Y/H433D/N434Y/Y436V/Q438R/S440E |
| F1269 | 1.69E−07 | L235R/S239K/M252Y/H433D/N434Y/Y436V/Q438K/S440D |
| F1270 | 1.18E−07 | L235R/S239K/M252Y/S254A/N434Y/Y436V/Q438K/S440D |
| F1271 | 2.05E−07 | L235R/S239K/M252Y/S254A/H433D/N434Y/Y436V/Q438R/S440E |

TABLE 2-29-continued

| | | |
|---|---|---|
| F1272 | 1.71E−07 | L235R/S239K/M252Y/S254A/H433D/N434Y/Y436V/Q438K/S440D |
| F1273 | 1.53E−07 | L235R/S239K/M252Y/T256Q/N434Y/Y436V/Q438K/S440D |
| F1274 | 2.48E−07 | L235R/S239K/M252Y/T256Q/H433D/N434Y/Y436V/Q438R/S440E |
| F1275 | 2.09E−07 | L235R/S239K/M252Y/T256Q/H433D/N434Y/Y436V/Q438K/S440D |

Table 2-30 is a continuation of Table 2-29.

TABLE 2-30

| | | |
|---|---|---|
| F1276 | 1.02E−07 | L235R/S239K/M252Y/T256A/N434Y/Y436V/Q438K/S440D |
| F1277 | 1.69E−07 | L235R/S239K/M252Y/T256A/H433D/N434Y/Y436V/Q438K/S440E |
| F1278 | 1.4E−07 | L235R/S239K/M252Y/T256A/H433D/N434Y/Y436V/Q438K/S440D |
| F1279 | 1.23E−07 | L235R/S239K/M252Y/T256G/N434Y/Y436V/Q438K/S440D |
| F1280 | 2.09E−07 | L235R/S239K/M252Y/T256G/H433D/N434Y/Y436V/Q438R/S440E |
| F1281 | 1.74E−07 | L235R/S239K/M252Y/T256G/H433D/N434Y/Y436V/Q438K/S440E |
| F1282 | 7.69E−08 | L235R/S239K/M252Y/T256N/N434V/Y436V/Q438K/S440D |
| F1283 | 1.34E−07 | L235R/S239K/M252Y/T256N/H433D/N434Y/Y436V/Q438R/S440E |
| F1284 | 1.12E−07 | L235R/S239K/M252Y/T256N/H433D/N434Y/Y436V/Q438K/S440D |
| F1285 | 9.36E−08 | L235R/S239K/M252Y/S254T/N434Y/Y436V/Q438K/S440D |
| F1286 | 1.57E−07 | L235R/S239K/M252Y/S254T/H433D/N434Y/Y436V/Q438R/S440E |
| F1287 | 1.5E−07 | L235R/S239K/M252Y/S254T/H433D/N434Y/Y436V/Q438K/S440D |
| F1288 | 7.95E−08 | L235R/S239K/M252Y/T256E/N434Y/Y436V/Q438K/S440D |
| F1289 | 1.33E−07 | L235R/S239K/M252Y/T256E/H433D/N434Y/Y436V/Q438R/S440E |
| F1290 | 1.11E−07 | L235R/S239K/M252Y/T256E/H433D/N434Y/Y436V/Q438K/S440D |
| F1291 | 1.51E−07 | L235R/S239K/M252Y/H433D/N434Y/Y436V |
| F1292 | 4.24E−07 | L235R/S239K/H433D/N434W/Y436V/Q438R/S440E |
| F1293 | 1.61E−07 | L235R/S239K/M252Y/T256E/N434Y/Q438R/S440E |
| F1294 | 2E−07 | L235R/S239K/M252Y/T256E/N434Y/Y436T/Q438R/S440E |
| F1295 | 9.84E−08 | L235R/S239K/M252Y/T256E/N434Y/Y436F/Q438R/S440E |
| F1296 | 2.27E−07 | L235R/S239K/M252Y/T256E/H433D/N434Y/Q438R/S440E |
| F1297 | 2.5E−07 | L235R/S239K/M252Y/T256E/H433D/N434Y/Y436T/Q438R/S440E |
| F1298 | 1.47E−07 | L235R/S239K/M252Y/T256E/H433D/N434Y/Y436F/Q438R/S440E |
| F1299 | 1.5E−07 | L235R/S239K/M252Y/T256E/N434Y/Q438K/S440D |
| F1300 | 1.63E−07 | L235R/S239K/M252Y/T256E/N434Y/Y436T/Q438K/S440D |
| F1301 | 8.3E−08 | L235R/S239K/M252Y/T256E/N434Y/Y436F/Q438K/S440D |
| F1302 | 2.15E−07 | L235R/S239K/M252Y/T256E/H433D/N434Y/Q438K/S440D |
| F1303 | 2.1E−07 | L235R/S239K/M252Y/T256E/H433D/N434Y/Y436T/Q438K/S440D |
| F1304 | 1.24E−07 | L235R/S239K/M252Y/T256E/H433D/N434Y/Y436F/Q438K/S440D |
| F1305 | 2.05E−07 | L235R/S239K/M252Y/H433D/M434Y/Y436V/Q438R/S440D |
| F1306 | 1.92E−07 | L235R/S239K/M252Y/H433D/N434Y/Y436V/Q438K/S440E |
| F1307 | 1.44E−07 | L235R/S239K/M252Y/V422A/S424A/N434Y/Y436V |
| F1308 | 2.06E−07 | L235R/S239K/M252Y/V422L/S424L/N434Y/Y436V |
| F1309 | 1.26E−07 | L235R/S239K/M252Y/N434Y/Y436V/Q438A/S440A |
| F1310 | 2.28E−07 | L235R/S239K/M252Y/N434Y/Y436V/Q438L/S440L |
| F1311 | 1.69E−07 | L235R/S239K/M252Y/V422A/S424A/H433D/N434Y/Y436V |
| F1312 | 1.79E−07 | L235R/S239K/M252Y/V422L/S424L/H433D/N434Y/Y436V |
| F1313 | 1.77E−07 | L235R/S239K/M252Y/H433D/N434Y/Y436V/Q438A/S440A |
| F1314 | 2.27E−07 | L235R/S239K/M252Y/H433D/N434Y/Y436V/Q438L/S440L |
| F1315 | 1.52E−07 | G237R/S239K/M252Y/N434Y/Y436V |
| F1316 | 1.49E−07 | G237R/S239K/M252Y/N434Y/Y436V |

Table 2-31 is a continuation of Table 2-30.

TABLE 2-31

| | | |
|---|---|---|
| F1317 | 1.38E−07 | S239K/M252Y/P329K/H434Y/Y436V |
| F1318 | 1.43E−07 | S239K/M252Y/P329R/N434Y/Y436V |
| F1319 | 2.67E−07 | M252Y/L328Y/N434Y |
| F1320 | 1.22E−07 | L235R/S239K/M252Y/S254T/N434Y/Y436V/Q438R/S440D |
| F1321 | 1.03E−07 | L235R/S239K/M252Y/S254T/N434Y/Y436V/Q438K/S440E |
| F1322 | 1.6E−07 | L235R/S239K/M252Y/S254T/H433D/N434Y/Y436V/Q438R/S440D |
| F1323 | 1.49E−07 | L235R/S239K/M252Y/S254T/H433D/N434Y/Y436V/Q438K/S440E |
| F1324 | 1.32E−07 | L234A/L235A/M252Y/N434Y/Y436V |
| F1325 | 2.13E−07 | L234A/L235A/M252Y/N297A/N434Y/Y436V |
| F1326 | 1.09E−08 | L234A/L235A/T250V/M252Y/T307Q/V308P/Q311A/N434Y/Y436V |
| F1327 | 1.41E−08 | L234A/L235A/T250V/M252Y/N297A/T307Q/V308P/Q311A/N434Y/Y436V |
| F1328 | 1.52E−07 | L235R/G236R/S239K/M252Y/N434Y/Y436V/Q438R/S440E |
| F1329 | 1.29E−07 | L235R/G236R/S239K/M252Y/S254T/N434Y/Y436V/Q438R/S440E |
| F1330 | 1.03E−07 | L235R/G236R/S239K/M252Y/T256E/N434Y/T436V/Q438R/S440E |
| F1331 | 7.75E−08 | L235R/G236R/S239K/M252Y/S254T/T256E/N434Y/Y436V/Q438R/S440E |
| F1333 | 1.23E−07 | L235R/G236R/S239K/M252Y/N434Y/Y436V |
| F1334 | 1.04E−07 | L235R/G236R/S239K/M252Y/N434Y/Y436V/Q438K/S440D |
| F1335 | 8.78E−08 | L235R/G236R/S239K/M252Y/S254T/N434Y/Y436V/Q438K/S440D |
| F1336 | 7.18E−08 | L235R/G236R/S239K/M252Y/T256E/N434Y/Y436V/Q438K/S440D |
| F1337 | 7.41E−08 | L235R/S239K/M252Y/T256E/N434Y/Y436V/Q438K/S440E |

TABLE 2-31-continued

| | | |
|---|---|---|
| F1338 | 1.04E−07 | L235R/S239K/M252Y/T256E/H433D/N434Y/Y436V/Q438K/S440E |
| F1339 | 2.51E−07 | L235R/S239K/M252Y/S254T/T256E/H433D/N434Y/Y436V/Q438K/S440E |
| F1340 | 5.58E−08 | L235R/S239K/M252Y/S254T/T256E/N434Y/Y436V/Q438K/S440E |
| F1341 | 3.32E−07 | L235R/S239K/M252Y/S254T/N434Y/Y436T/Q438K/S440E |
| F1342 | 2.51E−07 | L235R/S239K/M252Y/T256E/N434Y/Y436T/Q438K/S440E |
| F1343 | 2.01E−07 | L235R/S239K/M252Y/S254T/T256E/N434Y/Y436T/Q438K/S440E |
| F1344 | 3.96E−07 | L235R/S239K/M252Y/N434Y/Y436T/Q438K/S440E |
| F1345 | 1.05E−07 | L235R/G236R/S239K/M252Y/N434Y/Y436V/Q438K/S440E |
| F1346 | 8.59E−08 | L235R/G236R/S239K/M252Y/S254T/N434Y/Y436V/Q438K/S440E |
| F1347 | 7.14E−08 | L235R/G236R/S239K/M252Y/T256E/N434Y/Y436V/Q438K/S440E |
| F1348 | 5.52E−08 | L235R/G236R/S239K/M252Y/S254T/T256E/N434Y/Y436V/Q438K/S440E |
| F1349 | 3.36E−07 | L235R/S239K/M252Y/N434Y/Y436T/Q438R/S440E |
| F1350 | 1.18E−07 | L335R/S239K/M252Y/N434Y/Y436F/Q438K/S440E |
| F1351 | 1.62E−07 | L235R/S239K/M252Y/N434Y/Y436F/Q438K/S440E |
| F1352 | 3.93E−07 | L235R/S239K/M252Y/H433D/N434Y/Y436T/Q438K/S440E |
| F1353 | 4.33E−07 | L235R/S239K/M252Y/K433D/N434Y/Y436T/Q438R/S440E |
| F1354 | 2.29E−07 | L235R/S239K/M252Y/H433D/N434Y/Y436F/Q438K/S440E |
| F1355 | 2.47E−07 | L235R/S239K/M252V/H433D/N434Y/Y436F/Q438R/S440E |
| F1356 | 1.58E−07 | G236R/M252Y/L328R/N434Y/Y436V |
| F1357 | 2.81E−07 | L235R/S239K/M252Y/S254T/N434Y/Y436T/Q438R/S440E |
| F1358 | 9.07E−08 | L235R/S239K/M252Y/S254T/N434Y/Y436F/Q438K/S440E |

Table 2-32 is a continuation of Table 2-31.

TABLE 2-32

| | | |
|---|---|---|
| F1359 | 1.28E−07 | L235R/S239K/M252Y/S254T/N434Y/Y436F/Q438R/S440E |
| F1360 | 3.12E−07 | L235R/S239K/M252Y/S254T/H433D/N434Y/Y436T/Q438K/S440E |
| F1361 | 3.52E−07 | L235R/S239K/M252Y/S254T/H433D/N434Y/Y436T/Q438R/S440E |
| F1362 | 1.41E−07 | L235R/S239K/M252Y/S254T/H433D/N434Y/Y436F/Q438K/S440E |
| F1363 | 1.9E−07 | L235R/S239K/M252Y/S254T/H433D/N434Y/Y436F/Q438R/S440E |
| F1364 | 7.49E−08 | L235R/S239K/M252Y/T256E/N434Y/Y436F/Q438K/S440E |
| F1365 | 3.14E−07 | L235R/S239K/M252Y/T256E/H433D/N434Y/Y436T/Q438K/S440E |
| F1366 | 1.17E−07 | L235R/S239K/M252Y/T256E/H433D/N434Y/Y436F/Q438K/S440E |
| F1367 | 1.79E−07 | L235R/S239K/M252Y/S254T/T256E/N434Y/Y436T/Q438R/S440E |
| F1368 | 5.49E−08 | L235R/S239K/M252Y/S254T/T256E/N434Y/Y436F/Q438K/S440E |
| F1369 | 7.6E−08 | L235R/S239K/M252Y/S254T/T256E/N434Y/Y436F/Q438R/S440E |
| F1370 | 9.14E−08 | L235R/S239K/M252Y/S254T/T256E/H433D/N434Y/Y436V/Q438K/S440E |
| F1371 | 1.09E−07 | L235R/S239K/M252Y/S254T/T256E/H433D/N434Y/Y436V/Q438R/S440E |
| F1372 | 2.28E−07 | L235R/S239K/M252Y/S254T/T256E/H433D/N434Y/Y436T/Q438R/S440E |
| F1373 | 8.67E−08 | L235R/S239K/M252Y/S254T/T256E/H433D/N434Y/Y436F/Q438K/S440E |
| F1374 | 1.2E−07 | L235R/S239K/M252Y/S254T/T256E/H433D/N434Y/Y436F/Q438R/S440E |
| F1375 | 1.03E−07 | L235R/S239K/M252Y/S254T/N434Y/Y436V |
| F1376 | 9.09E−08 | L235R/S239K/M252Y/S254T/T256E/N434Y/Y436V |
| F1377 | 8.27E−08 | L235R/S239K/M252Y/T256E/N434Y/Y436V |
| F1378 | 3.61E−07 | L235R/S239K/M252Y/N434Y/Y436T |
| F1379 | 2.85E−07 | L235R/S239K/M252Y/N434Y/Y436F |
| F1410 | 1.90E−06 | V308P/I332V |
| F1411 | 1.70E−07 | V308P/I332V/M428L/N434S |
| F1413 | 3.70E−08 | L235R/S239K/M252Y/S254T/T256E/T307Q/Q311A/H433D/N434Y/Y436V/Q438K/S440E |
| F1414 | 5.60E−08 | L235R/S239K/M252Y/S254T/T256E/T307Q/H433D/N434Y/Y436V/Q438K/S440E |
| F1415 | 5.90E−08 | L235R/S239K/M252Y/S254T/T256E/Q311A/H433D/N434Y/Y436V/Q438K/S440E |
| F1416 | 1.30E−08 | L235R/S239K/M252Y/S254T/T256E/V308P/H433D/N434Y/Y436V/Q438K/S440E |
| F1417 | 5.90E−08 | L235R/S239K/M252Y/S254T/T256E/H433D/N434W/Y436V/Q438K/S440E |
| F1418 | 7.50E−08 | L235R/S239K/M252Y/S254T/T256E/H433D/N434W/Y436V/Q438R/S440E |
| F1419 | 1.50E−07 | L235R/S239K/M252Y/H433D/N434W/Y436V/Q438K/S440E |
| F1420 | 1.30E−07 | L235R/S239K/M252Y/H433D/N434W/Y436V/Q438K/S440E |
| F1421 | 3.20E−08 | V308P/M428L/N434W |
| F1422 | 1.90E−08 | L235R/S239K/M252Y/T256E/V308P/H433D/N434Y/Y436V/Q438R/S440E |
| F1423 | 1.60E−08 | L235R/S239K/M252Y/T256E/V302D/V308P/H433D/N434Y/Y436V/Q438R/S440E |
| F1424 | 1.60E−08 | L235R/S239K/M252Y/T256E/V302E/V308P/H433D/N434Y/Y436V/Q438R/S440E |

Table 2-33 is a continuation of Table 2-32.

TABLE 2-33

| | | |
|---|---|---|
| F1425 | 1.90E−08 | L235R/S239K/M252Y/T256E/V303D/V308P/H433D/N434Y/Y436V/Q438R/S440E |
| F1426 | 1.80E−08 | L235R/S239K/M252Y/T256E/V303E/V308P/H433D/N434Y/Y436V/Q438R/S440E |
| F1428 | 1.50E−08 | L235R/S239K/M252Y/T256E/S304E/V308P/H433D/N434Y/Y436V/Q438R/S440E |
| F1430 | 3.10E−08 | L235R/S239K/M252Y/T256E/V305E/V308P/H433D/N434Y/Y436V/Q438R/S440E |
| F1433 | 4.50E−08 | L235R/S239K/M252Y/T256E/T307D/V308P/H433D/N434Y/Y436V/Q438R/S440E |
| F1434 | 3.60E−08 | L235R/S239K/M252Y/T256E/T307E/V308P/H433D/N434Y/Y436V/Q438R/S440E |

Heterocomplex Comprising the Four Molecules Including Two Molecules of FcRn and One Molecule of Activating Fcγ Receptor Crystallographic studies on FcRn with IgG antibodies demonstrated that an FcRn-IgG complex is composed of one molecule of IgG for two molecules of FcRn, and the two molecules are thought to bind around the interface of the CH2 and CH3 domains located on both sides of the IgG Fc region (Burmeister et al. (Nature (1994) 372, 336-343)). Meanwhile, as demonstrated in Example 3 of PCT/JP2012/058603, the antibody Fc region was demonstrated to be able to form a complex comprising the four molecules including two molecules of FcRn and one molecule of activating Fcγ receptor (PCT/JP2012/058603). This heterocomplex formation is a phenomenon which was revealed as a result of analyzing the properties of antigen-binding molecules containing an Fc region having an FcRn-binding activity under a neutral pH range condition.

While the present invention is not bound to a particular principle, it can be considered that antigen-binding molecules administered in vivo produce the effects described below on the in vivo pharmacokinetics (plasma retention) of the antigen-binding molecules and an immune response (immunogenicity) to the administered antigen-binding molecules, as a result of the formation of heterocomplexes containing the four molecules including the Fc region contained in the antigen-binding molecules, two molecules of FcRn, and one molecule of activating Fcγ receptor. In addition to the various types of activating Fcγ receptors, FcRn is expressed on immune cells. It is suggested that the formation of such tetrameric complexes on immune cells by antigen-binding molecules promotes incorporation of antigen-binding molecules into immune cells by increasing affinity toward immune cells and by causing association of intracellular domains to enhance the internalization signal. The same also applies to antigen-presenting cells and the possibility that antigen binding-molecules are likely to be incorporated into antigen-presenting cells by formation of tetrameric complexes on the cell membrane of antigen-presenting cells. In general, antigen-binding molecules incorporated into antigen-presenting cells are degraded in the lysosomes of the antigen-presenting cells and are presented to T cells. As a result, plasma retention of antigen-binding molecules may be worsened because incorporation of antigen-binding molecules into antigen-presenting cells is promoted by the formation of the above-described tetrameric complexes on the cell membrane of the antigen-presenting cells. Similarly, an immune response may be induced (aggravated).

For this reason, it is conceivable that when an antigen-binding molecule having lowered ability to form such tetrameric complexes is administered in vivo, plasma retention of the antigen-binding molecules would improve, and induction of in vivo immune response would be suppressed. Preferred embodiments of such antigen-binding molecules which inhibit the formation of these complexes on immune cells including antigen-presenting cells are, for example, the three embodiments described below.

Antigen-Binding Molecules which Inhibit the Formation of Heterocomplexes (Embodiment 1) An Antigen-Binding Molecule Containing an Fc Region Having FcRn-Binding Activity Under a Neutral pH Range Condition and Whose Binding Activity Toward Activating FcγR is Lower than the Binding Activity of a Native Fc Region Toward Activating FcγR The antigen-binding molecule of Embodiment 1 forms a trimeric complex by binding to two molecules of FcRn; however, it does not form any complex containing activating FcγR. An Fc region whose binding activity toward activating FcγR is lower than the binding activity of a native Fc region toward activating FcγR can be prepared by altering the amino acids of the native Fc region as described above. Whether the binding activity toward activating FcγR of the altered Fc region is lower than the binding activity toward activating FcγR of the native Fc region can be appropriately tested using the methods described in the section "Binding Activity" above.

Preferred activating Fcγ receptors include FcγRI (CD64) which includes FcγRIa, FcγRIb, and FcγRIc; FcγRIIa (including allotypes R131 and H131); and FcγRIII (CD16) which includes isoforms FcγRIIIa (including allotypes V158 and F158) and FcγRIIIb (including allotypes FcγRIIIb-NA1 and FcγRIIIb-NA2).

Herein, "a binding activity of the Fc region variant toward an activating Fcγ receptor is lower than the binding activity of the native Fc region toward an activating Fcγ receptor" means that the binding activity of the Fc region variant toward any of the human Fcγ receptors (FcγRI, FcγRIIa, FcγRIIIa, and/or FcγRIIIb) is lower than the binding activity of the native Fc region toward these human Fcγ receptors. For example, it means that based on an above-described analytical method, the binding activity of the antigen-binding molecule containing an Fc region variant as compared to the binding activity of an antigen-binding molecule containing a native Fc region as a control is 95% or less, preferably 90% or less, 85% or less, 80% or less, 75% or less, and particularly preferably 70% or less, 65% or less, 60% or less, 55% or less, 50% or less, 45% or less, 40% or less, 35% or less, 30% or less, 25% or less, 20% or less, 15% or less, 10% or less, 9% or less, 8% or less, 7% or less, 6% or less, 5% or less, 4% or less, 3% or less, 2% or less, or 1% or less. As a native Fc region, a starting Fc region may be used, and Fc regions of wild-type antibodies of different isotypes may also be used.

Meanwhile, the binding activity of the native form toward an activating FcγR is preferably a binding activity toward the Fcγ receptor for human IgG1. Other than performing the above-described alterations, binding activity toward the Fcγ receptor can be lowered by changing the isotype to human IgG2, human IgG3, or human IgG4. Alternatively, besides by performing the above-described alterations, the binding activity toward an Fcγ receptor can also be lowered by expressing the antigen-binding molecule containing an Fc region having a binding activity toward the Fcγ receptor in hosts that do not add sugar chains such as *Escherichia coli*.

For the antigen-binding molecule containing a control Fc region, an antigen-binding molecule having an Fc region of a monoclonal IgG antibody may be appropriately used. The structures of such Fc regions are shown in SEQ ID NO: 5 (A is added to the N terminus of RefSeq Accession No. AAC82527.1), SEQ ID NO: 6 (A is added to the N terminus of RefSeq Accession No. AAB59393.1), SEQ ID NO: 7 (RefSeq Accession No. CAA27268.1), and SEQ ID NO: 8 (A is added to the N terminus of RefSeq Accession No. AAB59394.1). Further, when an antigen-binding molecule containing an Fc region of a particular antibody isotype is used as the test substance, effect on the binding activity of the antigen-binding molecule containing the Fc region toward an Fcγ receptor is tested by using the antigen-binding molecule having an Fc region of a monoclonal IgG antibody of a particular isotype as a control. In this way, antigen-binding molecules containing an Fc region whose binding activity toward the Fcγ receptor was demonstrated to be high are suitably selected.

In a non-limiting embodiment of the present invention, preferred examples of Fc regions whose binding activity toward an activating FcγR is lower than the binding activity of the native Fc region toward an activating FcγR include Fc regions with alteration of one or more amino acids at any of positions 234, 235, 236, 237, 238, 239, 270, 297, 298, 325, 328, and 329 as indicated by EU numbering in the amino acids of an above-described Fc region to be different from those of the native Fc region. The alterations in the Fc region are not limited to the above example, and they may be, for example, modifications such as deglycosylation (N297A and N297Q), IgG1-L234A/L235A, IgG1-A325A/A330S/P331S, IgG1-C226S/C229S, IgG1-C226S/C229S/E233P/L234V/L235A, IgG1-L234F/L235E/P331 S, IgG1-S267E/L328F, IgG2-V234A/G237A, IgG2-H268Q/V309L/A330S/A331S, IgG4-L235A/G237A/E318A, and IgG4-L236E described in Cur. Opin. in Biotech. (2009) 20 (6), 685-691; alterations such as G236R/L328R, L235G/G236R, N325A/L328R, and N325L/L328R described in WO 2008/092117; amino acid insertions at positions 233, 234, 235, and 237 according to EU numbering; and alterations at the positions described in WO 2000/042072.

In a non-limiting embodiment of the present invention, examples of a preferred Fc region include Fc regions having one or more of the following alterations as indicated by EU numbering in an aforementioned Fc region:
Ala, Arg, Asn, Asp, Gln, Glu, Gly, His, Lys, Met, Phe, Pro, Ser, Thr, or Trp for the amino acid at position 234;
Ala, Asn, Asp, Gln, Glu, Gly, His, Ile, Lys, Met, Pro, Ser, Thr, Val, or Arg for the amino acid at position 235;
Arg, Asn, Gln, His, Leu, Lys, Met, Phe, Pro, or Tyr for the amino acid at position 236;
Ala, Asn, Asp, Gln, Glu, His, Ile, Leu, Lys, Met, Pro, Ser, Thr, Val, Tyr, or Arg for the amino acid at position 237;
Ala, Asn, Gln, Glu, Gly, His, Ile, Lys, Thr, Trp, or Arg for the amino acid at position 238;
Gln, His, Lys, Phe, Pro, Trp, Tyr, or Arg for the amino acid at position 239;
Ala, Arg, Asn, Gln, Gly, His, Ile, Leu, Lys, Met, Phe, Ser, Thr, Trp, Tyr, or Val for the amino acid at position 265;
Ala, Arg, Asn, Asp, Gln, Glu, Gly, His, Lys, Phe, Pro, Ser, Thr, Trp, or Tyr for the amino acid at position 266;
Arg, His, Lys, Phe, Pro, Trp, or Tyr for the amino acid at position 267;
Ala, Arg, Asn, Gln, Gly, His, Ile, Leu, Lys, Met, Phe, Pro, Ser, Thr, Trp, Tyr, or Val for the amino acid at position 269;
Ala, Arg, Asn, Gln, Gly, His, Ile, Leu, Lys, Met, Phe, Pro, Ser, Thr, Trp, Tyr, or Val for the amino acid at position 270;
Arg, His, Phe, Ser, Thr, Trp, or Tyr for the amino acid at position 271;
Arg, Asn, Asp, Gly, His, Phe, Ser, Trp, or Tyr for the amino acid at position 295;
Arg, Gly, Lys, or Pro for the amino acid at position 296;
Ala for the amino acid at position 297;
Arg, Gly, Lys, Pro, Trp, or Tyr for the amino acid at position 298;
Arg, Lys, or Pro for the amino acid at position 300;
Lys or Pro for the amino acid at position 324;
Ala, Arg, Gly, His, Ile, Lys, Phe, Pro, Thr, Trp, Tyr, or Val for the amino acid at position 325;
Arg, Gln, His, Ile, Leu, Lys, Met, Phe, Pro, Ser, Thr, Trp, Tyr, or Val for the amino acid at position 327;
Arg, Asn, Gly, His, Lys, or Pro for the amino acid at position 328;
Asn, Asp, Gln, Glu, Gly, His, Ile, Leu, Lys, Met, Phe, Ser, Thr, Trp, Tyr, Val, or Arg for the amino acid at position 329;
Pro or Ser for the amino acid at position 330;
Arg, Gly, or Lys for the amino acid at position 331; or
Arg, Lys, or Pro for the amino acid at position 332.

(Embodiment 2) An Antigen-Binding Molecule Containing an Fc Region Having FcRn-Binding Activity Under a Neutral pH Range Condition and Whose Binding Activity Toward an Inhibitory FcγR is Higher than the Binding Activity Toward an Activating Fcγ Receptor By binding to two molecules of FcRn and one molecule of inhibitory FcγR, the antigen-binding molecule of Embodiment 2 can form a complex comprising these four molecules. However, since a single antigen-binding molecule can bind with only one molecule of FcγR, the single antigen-binding molecule in a state bound to an inhibitory FcγR cannot bind to other activating FcγRs. Furthermore, it has been reported that an antigen-binding molecule that is incorporated into cells in a state bound to an inhibitory FcγR is recycled onto the cell membrane, and thus escapes from degradation inside the cells (Immunity (2005) 23, 503-514). More specifically, it is considered that antigen-binding molecules having selective binding activity toward an inhibitory FcγR cannot form heterocomplexes containing an activating FcγR and two molecules of FcRn, which cause an immune response.

Preferred activating Fcγ receptors include FcγRI (CD64) which includes FcγRIa, FcγRIb, and FcγRIc; FcγRIIa (including allotypes R131 and H131); and FcγRIII (CD16) which includes isoforms FcγRIIIa (including allotypes V158 and F158) and FcγRIIIb (including allotypes FcγRIIIb-NA1 and FcγRIIIb-NA2). Meanwhile, examples of preferred inhibitory Fcγ receptors include FcγRIIb (including FcγRIIb-1 and FcγRIIb-2).

Herein, "a binding activity toward an inhibitory FcγR is higher than the binding activity toward an activating Fcγ receptor" means that the binding activity of the Fc region variant toward FcγRIIb is higher than the binding activity toward any of the human Fcγ receptors, FcγRI, FcγRIIa, FcγRIIIa, and/or FcγRIIIb. For example, it means that based on an above-described analytical method, the binding activity toward FcγRIIb of the antigen-binding molecule containing an Fc region variant as compared with the binding activity toward any of the human Fcγ receptors, FcγRI, FcγRIIa, FcγRIIIa, and/or FcγRIIIb is 105% or more, preferably 110% or more, 120% or more, 130% or more, 140% or more, and particularly preferably 150% or more, 160% or more, 170% or more, 180% or more, 190% or more, 200% or more, 250% or more, 300% or more, 350% or more, 400% or more, 450% or more, 500% or more, 750% or more, 10 times or more, 20 times or more, 30 times or more, 40 times or more, 50 times or more.

Most preferably, the binding activity toward FcγRIIb is higher than each of the binding activities toward FcγRIa, FcγRIIa (including allotypes R131 and H131), and FcγRIIIa (including allotypes V158 and F158). FcγRIa shows a markedly high affinity toward native IgG1; thus, the binding is thought to be saturated in vivo due to the presence of a large amount of endogenous IgG1. For this reason, inhibition of complex formation may be possible even if the binding activity toward FcγRIIb is greater than the binding activities toward FcγRIIa and FcγRIIIa, and lower than the binding activity toward FcγRIa.

As a control antigen-binding molecule containing an Fc region, antigen-binding molecules having an Fc region of a monoclonal IgG antibody may be appropriately used. The structures of such Fc regions are shown in SEQ ID NO: 5 (A is added to the N terminus of RefSeq Accession No. AAC82527.1), SEQ ID NO: 6 (A is added to the N terminus of RefSeq Accession No. AAB59393.1), SEQ ID NO: 7

(RefSeq Accession No. CAA27268.1), and SEQ ID NO: 8 (A is added to the N terminus of RefSeq Accession No. AAB59394.1). Further, when an antigen-binding molecule containing an Fc region of a particular antibody isotype is used as the test substance, effect on the binding activity of the Fc region-containing antigen-binding molecule toward an Fcγ receptor is tested by using an antigen-binding molecule having the Fc region of a monoclonal IgG antibody of a particular isotype as a control. In this way, antigen-binding molecules containing an Fc region whose binding activity toward the Fcγ receptor was demonstrated to be high are appropriately selected.

In a non-limiting embodiment of the present invention, preferred examples of Fc regions having a selective binding activity toward an inhibitory FcγR include Fc regions in which among the amino acids of an above-described Fc region, the amino acid at 238 or 328 as indicated by EU numbering is altered to an amino acid different from that of the native Fc region. Furthermore, as an Fc region having a selective binding activity toward an inhibitory Fcγ receptor, the Fc regions or alterations described in US 2009/0136485 can be appropriately selected.

In a non-limiting embodiment of the present invention, a preferred example is an Fc region having one or more of the following alterations as indicated by EU numbering in an aforementioned Fc region: the amino acid at position 238 is Asp; or the amino acid at position 328 is Glu.

In still another non-limiting embodiment of the present invention, examples of a preferred Fc region include Fc regions having a substitution of Pro at position 238 according to EU numbering with Asp and having one or more of the alterations:
alteration of the amino acid at position 237 according to EU numbering to Trp, the amino acid at position 237 according to EU numbering is Phe, the amino acid at position 267 according to EU numbering is Val, the amino acid at position 267 according to EU numbering is Gln, the amino acid at position 268 according to EU numbering is Asn, the amino acid at position 271 according to EU numbering is Gly, the amino acid at position 326 according to EU numbering is Leu, the amino acid at position 326 according to EU numbering is Gln, the amino acid at position 326 according to EU numbering is Glu, the amino acid at position 326 according to EU numbering is Met, the amino acid at position 239 according to EU numbering is Asp, the amino acid at position 267 according to EU numbering is Ala, the amino acid at position 234 according to EU numbering is Trp, the amino acid at position 234 according to EU numbering is Tyr, the amino acid at position 237 according to EU numbering is Ala, the amino acid at position 237 according to EU numbering is Asp, the amino acid at position 237 according to EU numbering is Glu, the amino acid at position 237 according to EU numbering is Leu, the amino acid at position 237 according to EU numbering is Met, the amino acid at position 237 according to EU numbering is Tyr, the amino acid at position 330 according to EU numbering is Lys, the amino acid at position 330 according to EU numbering is Arg, the amino acid at position 233 according to EU numbering is Asp, the amino acid at position 268 according to EU numbering is Asp, the amino acid at position 268 according to EU numbering is Glu, the amino acid at position 326 according to EU numbering is Asp, the amino acid at position 326 according to EU numbering is Ser, the amino acid at position 326 according to EU numbering is Thr, the amino acid at position 323 according to EU numbering is Ile, the amino acid at position 323 according to EU numbering is Leu, the amino acid at position 323 according to EU numbering is Met, the amino acid at position 296 according to EU numbering is Asp, the amino acid at position 326 according to EU numbering is Ala, the amino acid at position 326 according to EU numbering is Asn, and the amino acid at position 330 according to EU numbering is Met.

(Embodiment 3) An Antigen-Binding Molecule Containing an Fc Region, in which One of the Two Polypeptides Constituting the Fc Region has an FcRn-Binding Activity Under a Neutral pH Range Condition and the Other Polypeptide does not have FcRn-Binding Activity Under a Neutral pH Range Condition By binding to one molecule of FcRn and one molecule of FcγR, the antigen-binding molecule of Embodiment 3 can form a trimeric complex; however, it does not form any heterocomplex comprising four molecules including two molecules of FcRn and one molecule of FcγR. As an Fc region in which one of the two polypeptides constituting the Fc region has an FcRn-binding activity under a neutral pH range condition and the other does not have any FcRn-binding activity under a neutral pH range condition contained in the antigen-binding molecule of Embodiment 3, Fc regions derived from bispecific antibodies may be suitably used. Bispecific antibodies are two types of antibodies having specificities toward different antigens. Bispecific antibodies of an IgG type can be secreted from hybrid hybridomas (quadromas) resulting from fusion of two types of hybridomas producing IgG antibodies (Milstein et al. (Nature (1983) 305, 537-540).

When an antigen-binding molecule of Embodiment 3 described above is produced by using recombination techniques such as those described in the section "Antibodies" above, one can use a method in which genes encoding the polypeptides that constitute the two types of Fc regions of interest are transfected into cells to co-express them. However, the produced Fc regions will be a mixture in which the following will exist at a molecular ratio of 2:1:1: an Fc region in which one of the two polypeptides constituting the Fc region has an FcRn-binding activity under a neutral pH range condition and the other polypeptide does not have any FcRn-binding activity under a neutral pH range condition; an Fc region in which the two polypeptides constituting the Fc region both have an FcRn-binding activity under a neutral pH range condition; and an Fc region in which both of the two polypeptides constituting the Fc region do not have FcRn-binding activity under a neutral pH range condition. It is difficult to purify antigen-binding molecules containing the desired combination of Fc regions from the three types of IgGs.

When producing the antigen-binding molecules of Embodiment 3 using such recombination techniques, antigen-binding molecules comprising a heteromeric combination of Fc regions can be preferentially secreted by adding appropriate amino acid substitutions to the CH3 domains constituting the Fc regions. Specifically, this method is conducted by substituting an amino acid having a larger side chain (knob (which means "bulge")) for an amino acid in the CH3 domain of one of the heavy chains, and substituting an amino acid having a smaller side chain (hole (which means "void")) for an amino acid in the CH3 domain of the other heavy chain so that the knob is arranged in the hole. This promotes heteromeric H chain formation and simultaneously inhibits homomeric H chain formation (WO 1996027011; Ridgway et al., (Protein Engineering (1996) 9, 617-621); Merchant et al., (Nature Biotechnology (1998) 16, 677-681)).

Furthermore, there are also known techniques for producing a bispecific antibody by applying methods for controlling polypeptide association or association of polypeptide-formed heteromeric multimers to the association between two polypeptides that constitute an Fc region. Specifically, methods for controlling polypeptide association may be employed to produce a bispecific antibody (WO 2006/106905), in which amino acid residues forming the interface between two polypeptides that constitute the Fc region are altered to inhibit the association between Fc regions having the same sequence, and to allow the formation of polypeptide complexes formed by two Fc regions of different sequences. Specifically, the methods in the above-described section on bispecific antibodies and methods for producing them can be used as a non-limiting embodiment for preparing the antigen-binding molecule of Embodiment 3 of the present invention.

These antigen-binding molecules of Embodiments 1 to 3 are all expected to be able to reduce immunogenicity and improve plasma retention as compared to antigen-binding molecules capable of forming tetrameric complexes.

Methods for Producing Antigen-Binding Domains

The present invention provides methods for producing antigen-binding domains whose antigen-binding activity in the presence of a target tissue-specific compound is higher than the antigen-binding activity in the absence of the compound.

More specifically, the present invention provides a method for producing an antigen-binding domain, which comprises steps (a) to (e) below:
(a) determining the antigen-binding activity of an antigen-binding domain in the absence of a target tissue-specific compound;
(b) determining the antigen-binding activity of an antigen-binding domain in the presence of the target tissue-specific compound;
(c) selecting an antigen-binding domain whose antigen-binding activity in the absence of a target tissue-specific compound is lower than in the presence of the compound;
(d) culturing cells transfected with a vector to which a polynucleotide encoding the antigen-binding domain selected in (c) is operably linked; and
(e) collecting an antigen-binding domain from a culture medium of the cells cultured in (d).

The present invention also provides a method for producing an antigen-binding domain, which comprises steps (a) to (e) below:
(a) determining the antigen-binding activity of an antigen-binding domain in the presence of a low concentration of a target tissue-specific compound;
(b) determining the antigen-binding activity of an antigen-binding domain in the presence of a high concentration of the target tissue-specific compound;
(c) selecting an antigen-binding domain whose antigen-binding activity in the presence of a low concentration of the target tissue-specific compound is lower than in the presence of a high concentration of the compound;
(d) culturing cells transfected with a vector to which a polynucleotide encoding the antigen-binding domain selected in (c) is operably linked; and
(e) collecting an antigen-binding domain from a culture medium of the cells cultured in (d).

Furthermore, the present invention provides a method for producing an antigen-binding domain, which comprises steps (a) to (e) below:
(a) contacting antigen-binding domains or a library thereof with an antigen in the presence of a target tissue-specific compound;
(b) placing the antigen-binding domains that bound to the antigen in said step (a) in the absence of the compound;
(c) isolating an antigen-binding domain that was dissociated in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

In addition, the present invention provides a method for producing an antigen-binding domain, which comprises steps (a) to (e) below:
(a) contacting antigen-binding domains or a library thereof to an antigen in the presence of a high concentration of a target tissue-specific compound;
(b) placing the antigen-binding domains that bind to the antigen in said step (a) in the presence of a low concentration of the compound;
(c) isolating an antigen-binding domain that dissociates in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

The present invention provides a method for producing an antigen-binding domain, which comprises steps of (a) to (f) below:
(a) contacting a library of antigen-binding domains with an antigen in the absence of a target tissue-specific compound;
(b) selecting antigen-binding domains that do not bind to the antigen in said step (a);
(c) allowing the antigen-binding domains selected in said step (b) to bind to the antigen in the presence of the compound;
(d) isolating an antigen-binding domain that bind to the antigen in said step (c);
(e) culturing cells transfected with a vector to which a polynucleotide encoding the antigen-binding domain selected in (d) is operably linked; and
(f) collecting an antigen-binding domain from a culture medium of the cells cultured in (e).

The present invention provides a method for producing an antigen-binding domain, which comprises steps (a) to (f) below:
(a) contacting a library of antigen-binding domains with an antigen in the presence of a low concentration of a target tissue-specific compound;
(b) selecting antigen-binding domains that do not bind to the antigen in said step (a);
(c) allowing the antigen-binding domains selected in said step (b) to bind to the antigen in the presence of a high concentration of the compound;
(d) isolating an antigen-binding domain that bind to the antigen in said step (c);
(e) culturing cells transfected with a vector to which a polynucleotide encoding the antigen-binding domain selected in (d) is operably linked; and
(f) collecting an antigen-binding domain from a culture medium of the cells cultured in (e).

The present invention provides a method for producing an antigen-binding domain, which comprises steps (a) to (e) below:
(a) contacting a library of antigen-binding domains with an antigen-immobilized column in the presence of a target tissue-specific compound;
(b) eluting antigen-binding domains that bind to the column in said step (a) from the column in the absence of the compound;
(c) isolating the antigen-binding domain eluted in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

The present invention provides a method for producing an antigen-binding domain, which comprises steps (a) to (e) below:
(a) contacting a library of antigen-binding domains with an antigen-immobilized column in the presence of a high concentration of a target tissue-specific compound;
(b) eluting antigen-binding domains that bind to the column in said step (a) from the column in the presence of a low concentration of the compound;
(c) isolating an antigen-binding domain eluted in said step (b);
(d) culturing cells transfected with a vector to which a polynucleotide encoding the antigen-binding domain selected in (c) is operably linked; and
(e) collecting an antigen-binding domain from a culture medium of the cells cultured in (d).

The present invention provides a method for producing an antigen-binding domain, which comprises steps (a) to (f) below:
(a) allowing a library of antigen-binding domains to pass through an antigen-immobilized column in the absence of a target tissue-specific compound;
(b) collecting antigen-binding domains that are eluted without binding to the column in step (a);
(c) allowing the antigen-binding domains collected in step (b) to bind to the antigen in the presence of the compound;
(d) isolating an antigen-binding domain that bind to the antigen in step (c);
(e) culturing cells transfected with a vector to which a polynucleotide encoding the antigen-binding domain selected in (d) is operably linked; and
(f) collecting an antigen-binding domain from a culture medium of the cells cultured in (e).

The present invention provides a method for producing an antigen-binding domain, which comprises steps (a) to (f) below:
(a) allowing a library of antigen-binding domains to pass through an antigen-immobilized column in the presence of a low concentration of a target tissue-specific compound;
(b) collecting antigen-binding domains that are eluted without binding to the column in said step (a);
(c) allowing the antigen-binding domains collected in said step (b) to bind to the antigen in the presence of a high concentration of the compound;
(d) isolating an antigen-binding domain that binds to the antigen in said step (c);
(e) culturing cells transfected with a vector to which a polynucleotide encoding the antigen-binding domain selected in (d) is operably linked; and
(f) collecting an antigen-binding domain from a culture medium of the cells cultured in (e).

Furthermore, the present invention provides a method for producing an antigen-binding domain, which comprises steps (a) to (f) below:
(a) contacting an antigen with a library of antigen-binding domains in the presence of a target tissue-specific compound;
(b) obtaining antigen-binding domains that bind to the antigen in step (a);
(c) placing the antigen-binding domain obtained in step (b) in the absence of the compound;
(d) isolating an antigen-binding domain whose antigen-binding activity in step (c) is weaker than the reference selected in step (b);
(e) culturing cells transfected with a vector to which a polynucleotide encoding the antigen-binding domain selected in (d) is operably linked; and
(f) collecting an antigen-binding domain from a culture medium of the cells cultured in (e).

The present invention provides a method for producing an antigen-binding domain, which comprises steps (a) to (f) below:
(a) contacting an antigen with a library of antigen-binding domains in the presence of a high concentration of a target tissue-specific compound;
(b) obtaining antigen-binding domains that bind to the antigen in step (a);
(c) placing the antigen-binding domains obtained in step (b) in the presence of a low concentration of the compound;
(d) isolating an antigen-binding domain whose antigen-binding activity in step (c) is weaker than the reference selected in step (b);
(e) culturing cells transfected with a vector to which a polynucleotide encoding the antigen-binding domain selected in (d) is operably linked; and
(f) collecting an antigen-binding domain from a culture medium of the cells cultured in (e).

The terms "cells", "cell line", and "cell culture" are used synonymously herein, and such naming may include all progenies of the cells or cell line. This way, for example, the terms "transformant" and "transformed cells" include cultures and primary target cells derived from them regardless of the number of passages. Furthermore, it is understood that due to intentional or accidental mutations, the DNA content is not always exactly the same in all progenies. Progenies of mutants having substantially the same function or biological activity such as those screened for in the initially transformed cells may also be included. When the description is intended to refer to a different naming, that intention may become obvious from the context of the description. Cells that are appropriate for use are suitably selected from cells described in the section "Antibodies" above.

When referring to the expression of a coding sequence, the term "control sequences" refers to DNA nucleotide sequences necessary for the expression of an operably linked coding sequence in a particular host organism. The control sequences that are suitable for prokaryotes include, for example, a promoter, optionally an operator sequence, a ribosome binding site, and possibly, other as yet poorly understood sequences. Eukaryotic cells are known to utilize promoters, polyadenylation signals, and enhancers for the expression of a coding sequence.

For a nucleic acid, the term "operably linked" means that the nucleic acid is placed into a functional relationship with another nucleic acid sequence. For example, DNA for a presequence or secretory leader is operably linked to DNA for a polypeptide if it is expressed as a precursor protein that participates in the secretion of the polypeptide. A promoter or enhancer is operably linked to a coding sequence if it affects the transcription of the sequence. A ribosome binding site is operably linked to a coding sequence if it is positioned so as to facilitate translation. Generally, "operably linked" means that the DNA sequences being linked are contiguous and, in the case of a secretory leader, contiguous and in reading frame. However, enhancers do not have to be contiguous. Linking is accomplished by ligation at suitable restriction sites. If such sites do not exist, the synthetic oligonucleotide adaptors or linkers are used in accordance with conventional practice. Furthermore, linked nucleic acids may be produced by the above-mentioned overlap extension PCR technique.

"Ligation" refers to the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation, or by silica purification. The DNA fragments that are to be ligated together are put in solution in equimolar amounts. The solution will contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation of the fragment during the ligation step.

In the production methods of the present invention, an antigen-binding domain which has a higher antigen-binding activity in the presence of a target tissue-specific compound than in its absence, which has been selected by the method described in the above section "Antigen-binding domain dependent on a compound specific to a target tissue" is isolated. For example, when an antigen-binding domain isolated in this manner has been selected from a library, the polynucleotide encoding the antigen-binding domain is isolated by general gene amplification from a virus such as a phage, as described in the Examples below. Furthermore, when an antigen-binding domain or an antibody isolated in this manner has been selected from culture media of cells such as hybridomas, the antibody gene or such can be isolated by general gene amplification from the cells as shown in the section "Antibodies" above.

Methods for Producing Antigen-Binding Molecules

The present invention provides methods for producing antigen-binding molecules whose antigen-binding activity in the presence of a target tissue-specific compound is higher than the antigen-binding activity in the absence of the compound.

More specifically, the present invention provides a method for producing antigen-binding molecules, which comprises the steps of:

(a) determining the antigen-binding activity of an antigen-binding domain in the absence of a target tissue-specific compound;

(b) determining the antigen-binding activity of the antigen-binding domain in the presence of the target tissue-specific compound;

(c) selecting an antigen-binding domain with lower antigen-binding activity in the absence of the target tissue-specific compound than in the presence of the compound;

(d) linking a polynucleotide encoding the antigen-binding domain selected in (c) to a polynucleotide encoding a polypeptide containing an Fc region;

(e) culturing cells introduced with a vector to which the polynucleotide obtained in (d) is operably linked; and (f) collecting antigen-binding molecules from a culture medium of the cells cultured in (e).

The present invention also provides a method for producing an antigen-binding molecule, which comprises the steps of:

(a) determining the antigen-binding activity of an antigen-binding domain in the presence of a low concentration of a target tissue-specific compound;

(b) determining the antigen-binding activity of the antigen-binding domain in the presence of a high concentration of the target tissue-specific compound;

(c) selecting an antigen-binding domain with lower antigen-binding activity in the presence of a low concentration of the target tissue-specific compound than in the presence of a high concentration of the compound;

(d) linking a polynucleotide encoding the antigen-binding domain selected in (c) to a polynucleotide encoding a polypeptide containing an Fc region;

(e) culturing cells introduced with a vector to which the polynucleotide obtained in (d) is operably linked; and (f) collecting antigen-binding molecules from a culture medium of the cells cultured in (e).

Furthermore, the present invention provides a method for producing an antigen-binding molecule, which comprises the steps of:

(a) contacting antigen-binding domains or a library thereof with an antigen in the presence of a target tissue-specific compound;

(b) placing the antigen-binding domains that bind to the antigen in said step (a) in the absence of the compound;

(c) isolating an antigen-binding domain that dissociates in said step (b);

(d) linking a polynucleotide encoding the antigen-binding domain selected in (c) to a polynucleotide encoding a polypeptide containing an Fc region;

(e) culturing cells introduced with a vector to which the polynucleotide obtained in (d) is operably linked; and (f) collecting an antigen-binding molecule from a culture medium of the cells cultured in (e).

In addition, the present invention provides a method for producing an antigen-binding molecule, which comprises the steps of:

(a) contacting antigen-binding domains or a library thereof with an antigen in the presence of a high concentration of a target tissue-specific compound;

(b) placing the antigen-binding domains that bind to the antigen in said step (a) in the presence of a low concentration of the compound;

(c) isolating an antigen-binding domain that dissociates in said step (b);

(d) linking a polynucleotide encoding the antigen-binding domain selected in (c) to a polynucleotide encoding a polypeptide containing an Fc region;

(e) culturing cells introduced with a vector to which the polynucleotide obtained in (d) is operably linked; and (f) collecting antigen-binding molecules from a culture medium of the cells cultured in (e).

The present invention provides a method for producing an antigen-binding molecule, which comprises the steps of:
(a) contacting a library of antigen-binding domains with an antigen in the absence of a target tissue-specific compound;
(b) selecting antigen-binding domains that do not bind to the antigen in said step (a);
(c) allowing the antigen-binding domains selected in said step (b) to bind to the antigen in the presence of the compound;
(d) isolating an antigen-binding domain that binds to the antigen in said step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) contacting a library of antigen-binding domains with an antigen in the presence of a low concentration of a target tissue-specific compound;
(b) selecting antigen-binding domains that do not bind to the antigen in said step (a);
(c) allowing the antigen-binding domains selected in said step (b) to bind to the antigen in the presence of a high concentration of the compound;
(d) isolating an antigen-binding domain that binds to the antigen in said step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) contacting a library of antigen-binding domains with an antigen-immobilized column in the presence of a target tissue-specific compound;
(b) eluting antigen-binding domains that bind to the column in said step (a) from the column in the absence of the compound;
(c) isolating an antigen-binding domain eluted in said step (b);
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

The present invention provides a method for producing an antigen-binding molecule, which comprises the steps of:
(a) contacting a library of antigen-binding domains with an antigen-immobilized column in the presence of a high concentration of a target tissue-specific compound;
(b) eluting antigen-binding domains that bind to the column in said step (a) from the column in the presence of a low concentration of the compound;
(c) isolating an antigen-binding domain eluted in said step (b);
(d) linking a polynucleotide encoding the antigen-binding domain selected in (c) to a polynucleotide encoding a polypeptide containing an Fc region;
(e) culturing cells introduced with a vector to which the polynucleotide obtained in (d) is operably linked; and
(f) collecting antigen-binding molecules from a culture medium of the cells cultured in (e).

The present invention provides a method for producing an antigen-binding molecule, which comprises the steps of:
(a) allowing a library of antigen-binding domains to pass through an antigen-immobilized column in the absence of a target tissue-specific compound;
(b) collecting antigen-binding domains that are eluted without binding to the column in said step (a);
(c) allowing the antigen-binding domains collected in step (b) to bind to the antigen in the presence of the compound;
(d) isolating an antigen-binding domain that binds to the antigen in step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:
(a) allowing a library of antigen-binding domains to pass through an antigen-immobilized column in the presence of a low concentration of a target tissue-specific compound;
(b) collecting antigen-binding domains that are eluted without binding to the column in said step (a);
(c) allowing the antigen-binding domains collected in said step (b) to bind to the antigen in the presence of a high concentration of the compound;
(d) isolating an antigen-binding domain that binds to the antigen in said step (c);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

Furthermore, the present invention provides a method for producing an antigen-binding molecule, which comprises the steps of:
(a) contacting a library of antigen-binding domains with an antigen in the presence of a target tissue-specific compound;
(b) obtaining antigen-binding domains that bind to the antigen in said step (a);
(c) placing the antigen-binding domains obtained in said step (b) in the absence of the compound;
(d) isolating an antigen-binding domain whose antigen-binding activity in said step (c) is weaker than the reference selected in step (b);
(e) linking a polynucleotide encoding the antigen-binding domain selected in (d) to a polynucleotide encoding a polypeptide containing an Fc region;
(f) culturing cells introduced with a vector to which the polynucleotide obtained in (e) is operably linked; and
(g) collecting antigen-binding molecules from a culture medium of the cells cultured in (f).

The present invention provides a method for producing an antigen-binding molecule, which comprises the steps of:

(a) contacting a library of antigen-binding domains with an antigen in the presence of a high concentration of a target tissue-specific compound;

(b) obtaining antigen-binding domains that bind to the antigen in said step (a);

(c) placing the antigen-binding domains obtained in step (b) in the presence of a low concentration of the compound;

(d) isolating an antigen-binding domain whose antigen-binding activity in step (c) is weaker than the reference selected in step (b);

(e) linking a polynucleotide encoding the antigen-binding domain selected in (d) to a polynucleotide encoding a polypeptide containing an Fc region;

(f) culturing cells introduced with a vector to which the polynucleotide obtained in (e) is operably linked; and (g) collecting antigen-binding molecules from a culture medium of the cells cultured in (f).

A non-limiting embodiment of the Fc region whose polynucleotide sequence is linked to a polynucleotide encoding an antigen-binding domain is, for example, the Fc region contained in the constant region of a human IgG1 (SEQ ID NO: 5), IgG2 (SEQ ID NO: 6), IgG3 (SEQ ID NO: 7), or IgG4 (SEQ ID NO: 8) antibody. An Fc region is a portion of the heavy chain constant region of an antibody, starting from the N terminal end of the hinge region, which corresponds to the papain cleavage site at an amino acid around position 216 according to EU numbering, and contains the hinge, CH2, and CH3 domains. The Fc region may be obtained from human IgG1, but it is not limited to any particular subclass of IgG.

A non-limiting embodiment of the Fc region whose polynucleotide sequence is linked to a polynucleotide encoding an antigen-binding domain includes, for example, Fc regions whose Fcγ receptor-binding activity is higher than the Fcγ receptor-binding activity of the Fc region of a native human IgG. Examples of such Fc regions include Fc regions in which at least one or more amino acids selected from the group consisting of amino acids at positions 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, and 440, according to EU numbering, are different from the corresponding amino acid residues according to EU numbering in the Fc region contained in the antibody constant region of SEQ ID NO: 5, 6, 7, or 8.

Furthermore, a non-limiting embodiment of the above-mentioned Fc region includes, for example, Fc regions comprising at least one or more amino acid alterations selected from the group consisting of:

alteration of the amino acid at position 221 to Lys or Tyr;
alteration of the amino acid at position 222 to Phe, Trp, Glu, or Tyr;
alteration of the amino acid at position 223 to Phe, Trp, Glu, or Lys;
alteration of the amino acid at position 224 to Phe, Trp, Glu, or Tyr;
alteration of the amino acid at position 225 to Glu, Lys, or Trp;
alteration of the amino acid at position 227 to Glu, Gly, Lys, or Tyr;
alteration of the amino acid at position 228 to Glu, Gly, Lys, or Tyr;
alteration of the amino acid at position 230 to Ala, Glu, Gly, or Tyr;
alteration of the amino acid at position 231 to Glu, Gly, Lys, Pro, or Tyr;
alteration of the amino acid at position 232 to Glu, Gly, Lys, or Tyr;
alteration of the amino acid at position 233 to Ala, Asp, Phe, Gly, His, Ile, Lys, Leu, Met, Asn, Gln, Arg, Ser, Thr, Val, Trp, or Tyr;
alteration of the amino acid at position 234 to Ala, Asp, Glu, Phe, Gly, His, Ile, Lys, Met, Asn, Pro, Gln, Arg, Ser, Thr, Val, Trp, or Tyr;
alteration of the amino acid at position 235 to Ala, Asp, Glu, Phe, Gly, His, Ile, Lys, Met, Asn, Pro, Gln, Arg, Ser, Thr, Val, Trp, or Tyr; alteration of the amino acid at position 236 to Ala, Asp, Glu, Phe, His, Ile, Lys, Leu, Met, Asn, Pro, Gln, Arg, Ser, Thr, Val, Trp, or Tyr;
alteration of the amino acid at position 237 to Asp, Glu, Phe, His, Ile, Lys, Leu, Met, Asn, Pro, Gln, Arg, Ser, Thr, Val, Trp, or Tyr;
alteration of the amino acid at position 238 to Asp, Glu, Phe, Gly, His, Ile, Lys, Leu, Met, Asn, Gln, Arg, Ser, Thr, Val, Trp, or Tyr;
alteration of the amino acid at position 239 to Asp, Glu, Phe, Gly, His, Ile, Lys, Leu, Met, Asn, Pro, Gln, Arg, Thr, Val, Trp, or Tyr;
alteration of the amino acid at position 240 to Ala, Ile, Met, or Thr;
alteration of the amino acid at position 241 to Asp, Glu, Leu, Arg, Trp, or Tyr;
alteration of the amino acid at position 243 to Leu, Glu, Leu, Gln, Arg, Trp, or Tyr;
alteration of the amino acid at position 244 to His;
alteration of the amino acid at position 245 to Ala;
alteration of the amino acid at position 246 to Asp, Glu, His, or Tyr;
alteration of the amino acid at position 247 to Ala, Phe, Gly, His, Ile, Leu, Met, Thr, Val, or Tyr;
alteration of the amino acid at position 249 to Glu, His, Gln, or Tyr;
alteration of the amino acid at position 250 to Glu, or Gln;
alteration of the amino acid at position 251 to Phe;
alteration of the amino acid at position 254 to Phe, Met, or Tyr;
alteration of the amino acid at position 255 to Glu, Leu, or Tyr;
alteration of the amino acid at position 256 to Ala, Met, or Pro;
alteration of the amino acid at position 258 to Asp, Glu, His, Ser, or Tyr;
alteration of the amino acid at position 260 to Asp, Glu, His, or Tyr;
alteration of the amino acid at position 262 to Ala, Glu, Phe, Ile, or Thr;
alteration of the amino acid at position 263 to Ala, Ile, Met, or Thr;
alteration of the amino acid at position 264 to Asp, Glu, Phe, Gly, His, Ile, Lys, Leu, Met, Asn, Pro, Gln, Arg, Ser, Thr, Trp, or Tyr;
alteration of the amino acid at position 265 to Ala, Leu, Phe, Gly, His, Ile, Lys, Leu, Met, Asn, Pro, Gln, Arg, Ser, Thr, Val, Trp, or Tyr;
alteration of the amino acid at position 266 to Ala, Ile, Met, or Thr;

alteration of the amino acid at position 267 to Asp, Glu, Phe, His, Ile, Lys, Leu, Met, Asn, Pro, Gln, Arg, Thr, Val, Trp, or Tyr;
alteration of the amino acid at position 268 to Asp, Glu, Phe, Gly, Ile, Lys, Leu, Met, Pro, Gln, Arg, Thr, Val, or Trp;
alteration of the amino acid at position 269 to Phe, Gly, His, Ile, Lys, Leu, Met, Asn, Pro, Arg, Ser, Thr, Val, Trp, or Tyr;
alteration of the amino acid at position 270 to Glu, Phe, Gly, His, Ile, Leu, Met, Pro, Gln, Arg, Ser, Thr, Trp, or Tyr;
alteration of the amino acid at position 271 to Ala, Asp, Glu, Phe, Gly, His, Ile, Lys, Leu, Met, Asn, Gln, Arg, Ser, Thr, Val, Trp, or Tyr;
alteration of the amino acid at position 272 to Asp, Phe, Gly, His, Ile, Lys, Leu, Met, Pro, Arg, Ser, Thr, Val, Trp, or Tyr;
alteration of the amino acid at position 273 to Phe or Ile;
alteration of the amino acid at position 274 to Asp, Glu, Phe, Gly, His, Ile, Leu, Met, Asn, Pro, Arg, Ser, Thr, Val, Trp, or Tyr;
alteration of the amino acid at position 275 to Leu or Trp;
alteration of the amino acid at position 276 to Asp, Glu, Phe, Gly, His, Ile, Leu, Met, Pro, Arg, Ser, Thr, Val, Trp, or Tyr;
alteration of the amino acid at position 278 to Asp, Glu, Gly, His, Ile, Lys, Leu, Met, Asn, Pro, Gln, Arg, Ser, Thr, Val, or Trp;
alteration of the amino acid at position 279 to Ala;
alteration of the amino acid at position 280 to Ala, Gly, His, Lys, Leu, Pro, Gln, Trp, or Tyr;
alteration of the amino acid at position 281 to Asp, Lys, Pro, or Tyr;
alteration of the amino acid at position 282 to Glu, Gly, Lys, Pro, or Tyr;
alteration of the amino acid at position 283 to Ala, Gly, His, Ile, Lys, Leu, Met, Pro, Arg, or Tyr;
alteration of the amino acid at position 284 to Asp, Glu, Leu, Asn, Thr, or Tyr;
alteration of the amino acid at position 285 to Asp, Glu, Lys, Gln, Trp, or Tyr;
alteration of the amino acid at position 286 to Glu, Gly, Pro, or Tyr;
alteration of the amino acid at position 288 to Asn, Asp, Glu, or Tyr;
alteration of the amino acid at position 290 to Asp, Gly, His, Leu, Asn, Ser, Thr, Trp, or Tyr;
alteration of the amino acid at position 291 to Asp, Glu, Gly, His, Ile, Gln, or Thr;
alteration of the amino acid at position 292 to Ala, Asp, Glu, Pro, Thr, or Tyr;
alteration of the amino acid at position 293 to Phe, Gly, His, Ile, Leu, Met, Asn, Pro, Arg, Ser, Thr, Val, Trp, or Tyr;
alteration of the amino acid at position 294 to Phe, Gly, His, Ile, Lys, Leu, Met, Asn, Pro, Arg, Ser, Thr, Val, Trp, or Tyr;
alteration of the amino acid at position 295 to Asp, Glu, Phe, Gly, His, Ile, Lys, Met, Asn, Pro, Arg, Ser, Thr, Val, Trp, or Tyr;
alteration of the amino acid at position 296 to Ala, Asp, Glu, Gly, His, Ile, Lys, Leu, Met, Asn, Gln, Arg, Ser, Thr, or Val;
alteration of the amino acid at position 297 to Asp, Glu, Phe, Gly, His, Ile, Lys, Leu, Met, Pro, Gln, Arg, Ser, Thr, Val, Trp, or Tyr;
alteration of the amino acid at position 298 to Ala, Asp, Glu, Phe, His, Ile, Lys, Met, Asn, Gln, Arg, Thr, Val, Trp, or Tyr;
alteration of the amino acid at position 299 to Ala, Asp, Glu, Phe, Gly, His, Ile, Lys, Leu, Met, Asn, Pro, Gln, Arg, Ser, Val, Trp, or Tyr;
alteration of the amino acid at position 300 to Ala, Asp, Glu, Gly, His, Ile, Lys, Leu, Met, Asn, Pro, Gln, Arg, Ser, Thr, Val, or Trp;
alteration of the amino acid at position 301 to Asp, Glu, His, or Tyr;
alteration of the amino acid at position 302 to Ile;
alteration of the amino acid at position 303 to Asp, Gly, or Tyr;
alteration of the amino acid at position 304 to Asp, His, Leu, Asn, or Thr;
alteration of the amino acid at position 305 to Glu, Ile, Thr, or Tyr;
alteration of the amino acid at position 311 to Ala, Asp, Asn, Thr, Val, or Tyr;
alteration of the amino acid at position 313 to Phe;
alteration of the amino acid at position 315 to Leu;
alteration of the amino acid at position 317 to Glu or Gln;
alteration of the amino acid at position 318 to His, Leu, Asn, Pro, Gln, Arg, Thr, Val, or Tyr;
alteration of the amino acid at position 320 to Asp, Phe, Gly, His, Ile, Leu, Asn, Pro, Ser, Thr, Val, Trp, or Tyr;
alteration of the amino acid at position 322 to Ala, Asp, Phe, Gly, His, Ile, Pro, Ser, Thr, Val, Trp, or Tyr;
alteration of the amino acid at position 323 to Ile;
alteration of the amino acid at position 324 to Asp, Phe, Gly, His, Ile, Leu, Met, Pro, Arg, Thr, Val, Trp, or Tyr;
alteration of the amino acid at position 325 to Ala, Asp, Glu, Phe, Gly, His, Ile, Lys, Leu, Met, Pro, Gln, Arg, Ser, Thr, Val, Trp, or Tyr;
alteration of the amino acid at position 326 to Ala, Asp, Glu, Gly, Ile, Leu, Met, Asn, Pro, Gln, Ser, Thr, Val, Trp, or Tyr;
alteration of the amino acid at position 327 to Ala, Asp, Glu, Phe, Gly, His, Ile, Lys, Leu, Met, Asn, Pro, Arg, Thr, Val, Trp, or Tyr;
alteration of the amino acid at position 328 to Ala, Asp, Glu, Phe, Gly, His, Ile, Lys, Met, Asn, Pro, Gln, Arg, Ser, Thr, Val, Trp, or Tyr;
alteration of the amino acid at position 329 to Asp, Glu, Phe, Gly, His, Ile, Lys, Leu, Met, Asn, Gln, Arg, Ser, Thr, Val, Trp, or Tyr;
alteration of the amino acid at position 330 to Cys, Glu, Phe, Gly, His, Ile, Lys, Leu, Met, Asn, Pro, Arg, Ser, Thr, Val, Trp, or Tyr;
alteration of the amino acid at position 331 to Asp, Phe, His, Ile, Leu, Met, Gln, Arg, Thr, Val, Trp, or Tyr;
alteration of the amino acid at position 332 to Ala, Asp, Glu, Phe, Gly, His, Lys, Leu, Met, Asn, Pro, Gln, Arg, Ser, Thr, Val, Trp, or Tyr;
alteration of the amino acid at position 333 to Ala, Asp, Glu, Phe, Gly, His, Ile, Leu, Met, Pro, Ser, Thr, Val, or Tyr;
alteration of the amino acid at position 334 to Ala, Glu, Phe, Ile, Leu, Pro, or Thr;
alteration of the amino acid at position 335 to Asp, Phe, Gly, His, Ile, Leu, Met, Asn, Pro, Arg, Ser, Val, Trp, or Tyr;
alteration of the amino acid at position 336 to Glu, Lys, or Tyr;
alteration of the amino acid at position 337 to Glu, His, or Asn;
alteration of the amino acid at position 339 to Asp, Phe, Gly, Ile, Lys, Met, Asn, Gln, Arg, Ser, or Thr;
alteration of the amino acid at position 376 to Ala or Val;
alteration of the amino acid at position 377 to Gly or Lys;
alteration of the amino acid at position 378 to Asp;
alteration of the amino acid at position 379 to Asn;
alteration of the amino acid at position 380 to Ala, Asn, or Ser;
alteration of the amino acid at position 382 to Ala or Ile;
alteration of the amino acid at position 385 to Glu;
alteration of the amino acid at position 392 to Thr;
alteration of the amino acid at position 396 to Leu;

alteration of the amino acid at position 421 to Lys;
alteration of the amino acid at position 427 to Asn;
alteration of the amino acid at position 428 to Phe or Leu;
alteration of the amino acid at position 429 to Met;
alteration of the amino acid at position 434 to Trp;
alteration of the amino acid at position 436 to Ile; and
alteration of the amino acid at position 440 to Gly, His, Ile, Leu, or Tyr;
according to EU numbering, in the amino acid residues of the Fc region contained in the antibody constant region of SEQ ID NO: 5, 6, 7, or 8. The number of altered amino acids is not particularly limited; an amino acid at only one site may be altered, or amino acids at two or more sites may be altered. Combinations of amino acid alterations at two or more sites include, for example, those described in Table 1 (Table 1-1 to Table 1-3).

A non-limiting embodiment of the Fc region whose polynucleotide sequence is linked to a polynucleotide encoding an antigen-binding domain is, for example, an Fc region having binding activity toward an inhibitory Fcγ receptor that is higher than the binding activity toward an activating Fcγ receptor. Specifically, a non-limiting embodiment of such Fc regions is an Fc region whose binding activity to FcγRIIb is higher than the binding activity toward any of the human Fcγ receptors FcγRIa, FcγRIIa, FcγRIIIa, and/or FcγRIIIb.

A non-limiting embodiment of the above-mentioned Fc region preferably includes, for example, an Fc region in which the amino acid at 238 or 328 according to EU numbering in the Fc region contained in the antibody constant region of SEQ ID NO: 5, 6, 7, or 8, is altered to an amino acid different from that of the native Fc region. A preferred example of such Fc regions is an Fc region having one or more of the following alterations: alteration of the amino acid at position 238 to Asp, and alteration of the amino acid at position 328 to Glu, according to EU numbering, in the aforementioned Fc region.

In still another non-limiting embodiment of the above-mentioned Fc region, preferred examples include Fc regions having one or more of the alterations exemplified in PCT/JP2012/054624: substitution of Pro at position 238 according to EU numbering with Asp, alteration of the amino acid at position 237 according to EU numbering to Trp, alteration of the amino acid at position 237 according to EU numbering to Phe, alteration of the amino acid at position 267 according to EU numbering to Val, alteration of the amino acid at position 267 according to EU numbering to Gln, alteration of the amino acid at position 268 according to EU numbering to Asn, alteration of the amino acid at position 271 according to EU numbering to Gly, alteration of the amino acid at position 326 according to EU numbering to Leu, alteration of the amino acid at position 326 according to EU numbering to Gln, alteration of the amino acid at position 326 according to EU numbering to Glu, alteration of the amino acid at position 326 according to EU numbering to Met, alteration of the amino acid at position 239 according to EU numbering to Asp, alteration of the amino acid at position 267 according to EU numbering to Ala, alteration of the amino acid at position 234 according to EU numbering to Trp, alteration of the amino acid at position 234 according to EU numbering to Tyr, alteration of the amino acid at position 237 according to EU numbering to Ala, alteration of the amino acid at position 237 according to EU numbering to Asp, alteration of the amino acid at position 237 according to EU numbering to Glu, alteration of the amino acid at position 237 according to EU numbering to Leu, alteration of the amino acid at position 237 according to EU numbering to Met, alteration of the amino acid at position 237 according to EU numbering to Tyr, alteration of the amino acid at position 330 according to EU numbering to Lys, alteration of the amino acid at position 330 according to EU numbering to Arg, alteration of the amino acid at position 233 according to EU numbering to Asp, alteration of the amino acid at position 268 according to EU numbering to Asp, alteration of the amino acid at position 268 according to EU numbering to Glu, alteration of the amino acid at position 326 according to EU numbering to Asp, alteration of the amino acid at position 326 according to EU numbering to Ser, alteration of the amino acid at position 326 according to EU numbering to Thr, alteration of the amino acid at position 323 according to EU numbering to Ile, alteration of the amino acid at position 323 according to EU numbering to Leu, alteration of the amino acid at position 323 according to EU numbering to Met, alteration of the amino acid at position 296 according to EU numbering to Asp, alteration of the amino acid at position 326 according to EU numbering to Ala, alteration of the amino acid at position 326 according to EU numbering to Asn, and alteration of the amino acid at position 330 according to EU numbering to Met.

A non-limiting embodiment of the Fc region whose polynucleotide sequence is linked to a polynucleotide encoding an antigen-binding domain includes Fc regions having binding activity to FcRn in the acidic pH range. Amino acids that can undergo such alteration include, for example, amino acids at positions 252, 254, 256, 309, 311, 315, 433, and/or 434 according to EU numbering, and amino acids at positions 253, 310, 435, and/or 426 which are combined with the above amino acids, as described in WO 1997/034631. Preferred examples include amino acids at positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 (EU numbering) as described in WO 2000/042072. Similarly, preferred examples of amino acids that can undergo such alteration include amino acids at positions 251, 252, 254, 255, 256, 308, 309, 311, 312, 385, 386, 387, 389, 428, 433, 434, and/or 436 according to EU numbering as described in WO 2002/060919. Furthermore, amino acids that can undergo such alteration are, for example, amino acids at positions 250, 314, and 428 according to EU numbering as described in WO2004/092219. In addition, preferred examples of amino acids that can undergo such alteration include amino acids at positions 238, 244, 245, 249, 252, 256, 257, 258, 260, 262, 270, 272, 279, 283, 285, 286, 288, 293, 307, 311, 312, 316, 317, 318, 332, 339, 341, 343, 375, 376, 377, 378, 380, 382, 423, 427, 430, 431, 434, 436, 438, 440, and/or 442 as described in WO 2006/020114. Furthermore, preferred examples of amino acids that can undergo such alteration include amino acids at positions 251, 252, 307, 308, 378, 428, 430, 434, and/or 436 according to EU numbering as described in WO 2010/045193.

A non-limiting embodiment of the above-mentioned Fc region includes, for example, Fc regions having at least one or more amino acid alterations selected from the group consisting of:
alteration of the amino acid of position 251 to Arg or Leu;
alteration of the amino acid of position 252 to Phe, Ser, Thr, or Tyr;
alteration of the amino acid of position 254 to Ser or Thr;
alteration of the amino acid of position 255 to Arg, Gly, Ile, or Leu;

alteration of the amino acid of position 256 to Ala, Arg, Asn, Asp, Gln, Glu, or Thr;
alteration of the amino acid of position 308 to Ile or Thr;
alteration of the amino acid of position 309 to Pro;
alteration of the amino acid of position 311 to Glu, Leu, or Ser;
alteration of the amino acid of position 312 to Ala or Asp;
alteration of the amino acid of position 314 to Ala or Leu;
alteration of the amino acid of position 385 to Ala, Arg, Asp, Gly, His, Lys, Ser, or Thr;
alteration of the amino acid of position 386 to Arg, Asp, Ile, Lys, Met, Pro, Ser, or Thr;
alteration of the amino acid of position 387 to Ala, Arg, His, Pro, Ser, or Thr;
alteration of the amino acid of position 389 to Asn, Pro, or Ser;
alteration of the amino acid of position 428 to Leu, Met, Phe, Ser, or Thr;
alteration of the amino acid of position 433 to Arg, Gln, His, Ile, Lys, Pro, or Ser;
alteration of the amino acid of position 434 to His, Phe, or Tyr; and
alteration of the amino acid of position 436 to Arg, Asn, His, Lys, Met, or Thr, according to EU numbering, in the amino acid residues of the Fc region contained in the antibody constant region of SEQ ID NO: 5, 6, 7, or 8. The number of amino acids to be altered is not particularly limited; an amino acid at only one site may be altered or amino acids at two or more sites may be altered.

Another non-limiting embodiment of the Fc region whose binding activity to FcRn in the acidic pH range is stronger than the binding activity of the starting Fc region of human IgG1 includes Fc regions in which the amino acid at position 308 is Ile, the amino acid at position 309 is Pro, and/or the amino acid at position 311 is Glu, according to EU numbering, in the amino acid residues of the Fc region contained in the antibody constant region of SEQ ID NO: 5, 6, 7, or 8. Another non-limiting embodiment of this Fc region may include Fc regions containing Thr for the amino acid of position 308, Pro for the amino acid of position 309, Leu for the amino acid of position 311, Ala for the amino acid of position 312, and/or Ala for the amino acid of position 314. Furthermore, yet another non-limiting embodiment of this alteration may include Fc regions containing Ile or Thr for the amino acid of position 308, Pro for the amino acid of position 309, Glu, Leu, or Ser for the amino acid of position 311, Ala for the amino acid of position 312, and/or Ala or Leu for the amino acid of position 314. A different non-limiting embodiment of this alteration may include Fc regions containing Thr for the amino acid of position 308, Pro for the amino acid of position 309, Ser for the amino acid of position 311, Asp for the amino acid of position 312, and/or Leu for the amino acid of position 314.

Another non-limiting embodiment of the Fc region whose binding activity to FcRn in the acidic pH range is stronger than the binding activity of the starting Fc region of human IgG1 includes, for example, Fc regions containing Leu for the amino acid of position 251, Tyr for the amino acid of position 252, Ser or Thr for the amino acid of position 254, Arg for the amino acid of position 255, and/or Glu for the amino acid of position 256, according to EU numbering, in the amino acid residues of the Fc region included in the antibody constant region of SEQ ID NO: 5, 6, 7, or 8.

A different non-limiting embodiment of the Fc region whose binding activity to FcRn in the acidic pH range is stronger than the binding activity of the starting Fc region of human IgG1 includes, for example, Fc regions containing Leu, Met, Phe, Ser, or Thr for the amino acid of position 428, Arg, Gln, His, Ile, Lys, Pro, or Ser for the amino acid of position 433, His, Phe, or Tyr for the amino acid of position 434, and/or Arg, Asn, His, Lys, Met, or Thr for the amino acid of position 436, according to EU numbering, in the amino acid residues of the Fc region included in the antibody constant region of SEQ ID NO: 5, 6, 7, or 8. Moreover, another non-limiting embodiment of this alteration includes Fc regions containing His or Met for the amino acid of position 428 and/or His or Met for the amino acid of position 434.

Another different non-limiting embodiment of the Fc region whose binding activity to FcRn in the acidic pH range is stronger than the binding activity of the starting Fc region of human IgG1 may be, for example, alterations including Arg for the amino acid of position 385, Thr for the amino acid of position 386, Arg for the amino acid of position 387, and/or Pro for the amino acid of position 389, according to EU numbering, in the amino acid residues of the Fc region included in the antibody constant region of SEQ ID NO: 5, 6, 7, or 8. Another non-limiting embodiment of this alteration include Fc regions containing Asp for the amino acid of position 385, Pro for the amino acid of position 386, and/or Ser for the amino acid of position 389.

Another non-limiting embodiment of the Fc region whose binding activity to FcRn in the acidic pH range is stronger than the binding activity of the starting Fc region of human IgG1 includes Fc regions containing at least one or more amino acids selected from the group consisting of
Gln or Glu for the amino acid of position 250; and
Leu or Phe for the amino acid of position 428, according to EU numbering,
in the amino acid residues of the Fc region contained in the antibody constant region of SEQ ID NO: 5, 6, 7, or 8.

Another non-limiting embodiment of the Fc region whose binding activity to FcRn in the acidic pH range is stronger than the binding activity of the starting Fc region of human IgG1 includes, for example, Fc regions containing Gln for the amino acid of position 250, and/or Leu or Phe for the amino acid of position 428, according to EU numbering, in the amino acid residues of the Fc region contained in the antibody constant region of SEQ ID NO: 5, 6, 7, or 8. Another non-limiting embodiment of this alteration may include Glu for the amino acid of position 250, and/or Leu or Phe for the amino acid of position 428.

Another non-limiting embodiment of the Fc region whose binding activity to FcRn in the acidic pH range is stronger than the binding activity of the starting Fc region of human IgG1 includes Fc regions containing at least two or more amino acids selected from the group consisting of:
Asp or Glu for the amino acid of position 251;
Tyr for the amino acid of position 252;
Gln for the amino acid of position 307;
Pro for the amino acid of position 308;
Val for the amino acid of position 378;
Ala for the amino acid of position 380;
Leu for the amino acid of position 428;
Ala or Lys for the amino acid of position 430;
Ala, His, Ser, or Tyr for the amino acid of position 434; and
Ile for the amino acid of position 436;
according to EU numbering, in the amino acid residues of the Fc region contained in the antibody constant region of SEQ ID NO: 5, 6, 7, or 8.

Another non-limiting embodiment of the Fc region whose binding activity to FcRn in the acidic pH range is stronger than the binding activity of the starting Fc region of human IgG1 includes, for example, Fc regions containing Gln for the amino acid of position 307, and Ala or Ser for the amino acid of position 434, according to EU numbering, in the amino acid residues of the Fc region contained in the antibody constant region of SEQ ID NO: 5, 6, 7, or 8. Another non-limiting embodiment of this Fc region includes Fc regions containing Pro for the amino acid of position 308, and Ala for the amino acid of position 434. Furthermore, another non-limiting embodiment of this Fc region includes Fc regions containing Tyr for the amino acid of position 252, and Ala for the amino acid of position 434. A different non-limiting embodiment of this Fc region includes Fc regions containing Val for the amino acid of position 378, and Ala for the amino acid of position 434. Another different non-limiting embodiment of this Fc region includes alterations including Leu for the amino acid of position 428, and Ala for the amino acid of position 434. Another different non-limiting embodiment of this Fc region includes Fc regions containing Ala for the amino acid of position 434, and Ile for the amino acid of position 436. Furthermore, another non-limiting embodiment of this alteration includes Fc regions containing Pro for the amino acid of position 308, and Tyr for the amino acid of position 434. In addition, another non-limiting embodiment of this alteration includes Fc regions containing Gln for the amino acid of position 307, and Ile for the amino acid of position 436.

Another non-limiting embodiment of the Fc region whose binding activity to FcRn in the acidic pH range is stronger than the binding activity of the starting Fc region of human IgG1 includes Fc regions containing any one of Gln for the amino acid of position 307, Ala for the amino acid of position 380, and Ser for the amino acid of position 434, according to EU numbering, in the amino acid residues of the Fc region contained in the antibody constant region of SEQ ID NO: 5, 6, 7, or 8. Another non-limiting embodiment of this Fc region includes Fc regions containing Gln for the amino acid of position 307, Ala for the amino acid of position 380, and Ala for the amino acid of position 434. Furthermore, another non-limiting embodiment of this Fc region includes Fc regions containing Tyr for the amino acid of position 252, Pro for the amino acid of position 308, and Tyr for the amino acid of position 434. A different non-limiting embodiment of this Fc region includes Fc regions containing Asp for the amino acid of position 251, Gln for the amino acid of position 307, and His for the amino acid of position 434.

Another non-limiting embodiment of the Fc region whose binding activity to FcRn in the acidic pH range is stronger than the binding activity of the starting Fc region of human IgG1 includes at least one or more amino acid alterations selected from the group consisting of:
alteration of the amino acid of position 238 to Leu;
alteration of the amino acid of position 244 to Leu;
alteration of the amino acid of position 245 to Arg;
alteration of the amino acid of position 249 to Pro;
alteration of the amino acid of position 252 to Tyr;
alteration of the amino acid of position 256 to Pro;
alteration of the amino acid of position 257 to Ala, Ile, Met, Asn, Ser, or Val;
alteration of the amino acid of position 258 to Asp;
alteration of the amino acid of position 260 to Ser;
alteration of the amino acid of position 262 to Leu;
alteration of the amino acid of position 270 to Lys;
alteration of the amino acid of position 272 to Leu or Arg;
alteration of the amino acid of position 279 to Ala, Asp, Gly, His, Met, Asn, Gln, Arg, Ser, Thr, Trp, or Tyr;
alteration of the amino acid of position 283 to Ala, Asp, Phe, Gly, His, Ile, Lys, Leu, Asn, Pro, Gln, Arg, Ser, Thr, Trp, or Tyr;
alteration of the amino acid of position 285 to Asn;
alteration of the amino acid of position 286 to Phe;
alteration of the amino acid of position 288 to Asn or Pro;
alteration of the amino acid of position 293 to Val;
alteration of the amino acid of position 307 to Ala, Glu, or Met;
alteration of the amino acid of position 311 to Ala, Ile, Lys, Leu, Met, Val, or Trp;
alteration of the amino acid of position 312 to Pro;
alteration of the amino acid of position 316 to Lys;
alteration of the amino acid of position 317 to Pro;
alteration of the amino acid of position 318 to Asn or Thr;
alteration of the amino acid of position 332 to Phe, His, Lys, Leu, Met, Arg, Ser, or Trp;
alteration of the amino acid of position 339 to Asn, Thr, or Trp;
alteration of the amino acid of position 341 to Pro;
alteration of the amino acid of position 343 to Glu, His, Lys, Gln, Arg, Thr, or Tyr;
alteration of the amino acid of position 375 to Arg;
alteration of the amino acid of position 376 to Gly, Ile, Met, Pro, Thr, or Val;
alteration of the amino acid of position 377 to Lys;
alteration of the amino acid of position 378 to Asp or Asn;
alteration of the amino acid of position 380 to Asn, Ser, or Thr;
alteration of the amino acid of position 382 to Phe, His, Ile, Lys, Leu, Met, Asn, Gln, Arg, Ser, Thr, Val, Trp, or Tyr;
alteration of the amino acid of position 423 to Asn;
alteration of the amino acid of position 427 to Asn;
alteration of the amino acid of position 430 to Ala, Phe, Gly, His, Ile, Lys, Leu, Met, Asn, Gln, Arg, Ser, Thr, Val, or Tyr;
alteration of the amino acid of position 431 to His or Asn;
alteration of the amino acid of position 434 to Phe, Gly, His, Trp, or Tyr;
alteration of the amino acid of position 436 to Ile, Leu, or Thr;
alteration of the amino acid of position 438 to Lys, Leu, Thr, or Trp;
alteration of the amino acid of position 440 to Lys; and
alteration of the amino acid of position 442 to Lys;
according to EU numbering, in the amino acid residues of the Fc region contained in the antibody constant region of SEQ ID NO: 5, 6, 7, or 8. The number of amino acids to be altered is not particularly limited and amino acids at only two sites may be altered and amino acids at three or more sites may be altered.

Another non-limiting embodiment of the Fc region whose binding activity to FcRn in the acidic pH range is stronger than the binding activity of the starting Fc region of human IgG1 include Fc regions containing Ile for the amino acid of position 257, and Ile for the amino acid of position 311, according to EU numbering, in the amino acid residues of the Fc region contained in the antibody constant region of SEQ ID NO: 5, 6, 7, or 8. Another non-limiting embodiment of this Fc region includes Fc regions containing Ile for the amino acid of position 257 and His for the amino acid of position 434. Another non-limiting embodiment of this Fc region includes Fc regions containing Val for the amino acid of position 376 and His for the amino acid of position 434.

A non-limiting embodiment of the Fc region whose polynucleotide sequence is linked to a polynucleotide encoding an antigen-binding domain includes, for example, Fc regions having binding activity to human FcRn in the neutral pH range. Examples of Fc regions having binding activity to human FcRn in the neutral pH range include Fc regions in which at least one or more amino acids at positions selected from the group consisting of positions 221-225, 227, 228, 230, 232, 233-241, 243-252, 254-260, 262-272, 274, 276, 278-289, 291-312, 315-320, 324, 325, 327-339, 341, 343, 345, 360, 362, 370, 375-378, 380, 382, 385-387, 389, 396, 414, 416, 423, 424, 426-438, 440, and 442, according to EU numbering, are substituted in the amino acid residues of the Fc region included in the antibody constant region of SEQ ID NO: 5, 6, 7, or 8.

Another non-limiting embodiment of the aforementioned Fc region having binding activity to FcRn in the neutral pH range includes Fc regions in which amino acids at positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436, according to EU numbering, are substituted in the amino acid residues of the Fc region contained in the antibody constant region of SEQ ID NO: 5, 6, 7, or 8. By substituting at least one amino acid selected from these amino acids with a different amino acid, the Fc region included in the antigen-binding molecule can bind to human FcRn in the neutral pH range.

Another non-limiting embodiment of the aforementioned Fc region having binding activity to FcRn in the neutral pH range includes Fc regions containing at least one or more amino acids selected from the group consisting of:
Met for the amino acid of position 237;
Ile for the amino acid of position 248;
Ala, Phe, Ile, Met, Gln, Ser, Val, Trp, or Tyr for the amino acid of position 250;
Phe, Trp, or Tyr for the amino acid of position 252;
Thr for the amino acid of position 254;
Glu for the amino acid of position 255;
Asp, Asn, Glu, or Gln for the amino acid of position 256;
Ala, Gly, Ile, Leu, Met, Asn, Ser, Thr, or Val for the amino acid of position 257;
His for the amino acid of position 258:
Ala for the amino acid of position 265;
Ala or Glu for the amino acid of position 286;
His for the amino acid of position 289;
Ala for the amino acid of position 297;
Ala for the amino acid of position 303;
Ala for the amino acid of position 305;
Ala, Asp, Phe, Gly, His, Ile, Lys, Leu, Met, Asn, Pro, Gln, Arg, Ser, Val, Trp, or Tyr for the amino acid of position 307;
Ala, Phe, Ile, Leu, Met, Pro, Gln, or Thr for the amino acid of position 308;
Ala, Asp, Glu, Pro, or Arg for the amino acid of position 309;
Ala, His, or Ile for the amino acid of position 311;
Ala or His for the amino acid of position 312;
Lys or Arg for the amino acid of position 314;
Ala, Asp, or His for the amino acid of position 315;
Ala for the amino acid of position 317;
Val for the amino acid of position 332;
Leu for the amino acid of position 334;
His for the amino acid of position 360;
Ala for the amino acid of position 376;
Ala for the amino acid of position 380;
Ala for the amino acid of position 382;
Ala for the amino acid of position 384;
Asp or His for the amino acid of position 385;
Pro for the amino acid of position 386;
Glu for the amino acid of position 387;
Ala or Ser for the amino acid of position 389;
Ala for the amino acid of position 424;

Ala, Asp, Phe, Gly, His, Ile, Lys, Leu, Asn, Pro, Gln, Ser, Thr, Val, Trp, or Tyr for the amino acid of position 428;
Lys for the amino acid of position 433;
Ala, Phe, His, Ser, Trp, or Tyr for the amino acid of position 434; and
His, Ile, Leu, Phe, Thr, or Val for the amino acid of position 436;
according to EU numbering. The number of amino acids to be altered is not particularly limited and an amino acid at only one site may be altered or amino acids at two or more sites may be altered. Combinations of these amino acid alterations include, for example, those described in Table 2-1 to 2-33.

A non-limiting embodiment of the Fc region whose polynucleotide sequence is linked to a polynucleotide encoding an antigen-binding domain includes, for example, Fc regions whose binding activity toward an activating FcγR is lower than that of the native Fc region toward an activating FcγR. Another non-limiting embodiment of the Fc region preferably includes, for example, Fc regions in which one or more amino acids at positions 234, 235, 236, 237, 238, 239, 270, 297, 298, 325, 328, and 329 according to EU numbering are altered to amino acids that are different from those of the native Fc region of SEQ ID NO: 5, 6, 7, or 8. The alterations in the Fc region are not limited to the above example, and they may be, for example, alterations such as deglycosylation (N297A and N297Q), IgG1-L234A/L235A, IgG1-A325A/A330S/P331 S, IgG1-C226S/C229S, IgG1-C226S/C229S/E233P/L234V/L235A, IgG1-L234F/L235E/P331S, IgG1-S267E/L328F, IgG2-V234A/G237A, IgG2-H268Q/V309L/A330S/A331 S, IgG4-L235A/G237A/E318A, and IgG4-L236E described in Cur. Opin. in Biotech. (2009) 20 (6), 685-691; alterations such as G236R/L328R, L235G/G236R, N325A/L328R, and N325L/L328R described in WO 2008/092117; amino acid insertions at positions 233, 234, 235, and 237 according to EU numbering; and alterations at the positions described in WO 2000/042072.

Another non-limiting embodiment of the aforementioned Fc region whose binding activity toward activating FcγR is lower than the binding activity of the native Fc region toward activating FcγR includes Fc regions comprising at least one or more amino acids selected from the group consisting of: Ala, Arg, Asn, Asp, Gln, Glu, Gly, His, Lys, Met, Phe, Pro, Ser, Thr, or Trp for the amino acid at position 234;
Ala, Asn, Asp, Gln, Glu, Gly, His, Ile, Lys, Met, Pro, Ser, Thr, Val, or Arg for the amino acid at position 235;
Arg, Asn, Gln, His, Leu, Lys, Met, Phe, Pro, or Tyr for the amino acid at position 236;
Ala, Asn, Asp, Gln, Glu, His, Ile, Leu, Lys, Met, Pro, Ser, Thr, Val, Tyr, or Arg for the amino acid at position 237;
Ala, Asn, Gln, Glu, Gly, His, Ile, Lys, Thr, Trp, or Arg for the amino acid at position 238;
Gln, His, Lys, Phe, Pro, Trp, Tyr, or Arg for the amino acid at position 239;
Ala, Arg, Asn, Gln, Gly, His, Ile, Leu, Lys, Met, Phe, Ser, Thr, Trp, Tyr, or Val for the amino acid at position 265;
Ala, Arg, Asn, Asp, Gln, Glu, Gly, His, Lys, Phe, Pro, Ser, Thr, Trp, or Tyr for the amino acid at position 266;
Arg, His, Lys, Phe, Pro, Trp, or Tyr for the amino acid at position 267;
Ala, Arg, Asn, Gln, Gly, His, Ile, Leu, Lys, Met, Phe, Pro, Ser, Thr, Trp, Tyr, or Val for the amino acid at position 269;
Ala, Arg, Asn, Gln, Gly, His, Ile, Leu, Lys, Met, Phe, Pro, Ser, Thr, Trp, Tyr, or Val for the amino acid at position 270;

Arg, His, Phe, Ser, Thr, Trp, or Tyr for the amino acid at position 271;
Arg, Asn, Asp, Gly, His, Phe, Ser, Trp, or Tyr for the amino acid at position 295;
Arg, Gly, Lys, or Pro for the amino acid at position 296;
Ala for the amino acid at position 297;
Arg, Gly, Lys, Pro, Trp, or Tyr for the amino acid at position 298;
Arg, Lys, or Pro for the amino acid at position 300;
Lys or Pro for the amino acid at position 324;
Ala, Arg, Gly, His, Ile, Lys, Phe, Pro, Thr, Trp, Tyr, or Val for the amino acid at position 325;
Arg, Gln, His, Ile, Leu, Lys, Met, Phe, Pro, Ser, Thr, Trp, Tyr, or Val for the amino acid at position 327;
Arg, Asn, Gly, His, Lys, or Pro for the amino acid at position 328;
Asn, Asp, Gln, Glu, Gly, His, Ile, Leu, Lys, Met, Phe, Ser, Thr, Trp, Tyr, Val, or Arg for the amino acid at position 329;
Pro or Ser for the amino acid at position 330;
Arg, Gly, or Lys for the amino acid at position 331; or
Arg, Lys, or Pro for the amino acid at position 332;
according to EU numbering. The number of amino acids to be altered is not particularly limited, and an amino acid at only one site may be altered or amino acids at two or more sites may be altered.

In a non-limiting embodiment of the present invention, two polypeptides forming an Fc region that are derived from a bispecific antibody as described above can be suitably used as the Fc region to be included in an antigen-binding molecule. More specifically, it is preferable to use two polypeptides that constitute an Fc region, and which comprise Cys for the amino acid at position 349 and Trp for the amino acid at position 366 according to EU numbering in the amino acid sequence of one of the polypeptides; and Cys for the amino acid at position 356, Ser for the amino acid at position 366, Ala for the amino acid at position 368, and Val for the amino acid at position 407 as indicated by EU numbering in the amino acid sequence of the other polypeptide.

In another non-limiting embodiment of the present invention, two polypeptides that constitute an Fc region and which comprises Asp for the amino acid at position 409 according to EU numbering in the amino acid sequence of one of the polypeptides, and Lys for the amino acid at position 399 according to EU numbering in the amino acid sequence of the other polypeptide, may be suitably used as the Fc region. In the above embodiment, the amino acid at position 409 may be Glu instead of Asp, and the amino acid at position 399 may be Arg instead of Lys. Moreover, in addition to the amino acid Lys at position 399, Asp may suitably be added as the amino acid at position 360 or Asp may suitably be added as the amino acid at position 392.

In still another non-limiting embodiment of the present invention, two polypeptides that constitute an Fc region and which comprise Glu for the amino acid at position 370 according to EU numbering in the amino acid sequence of one of the polypeptides, and Lys for the amino acid at position 357 according to EU numbering in the amino acid sequence of the other polypeptide, may be suitably used as the Fc region.

In yet another non-limiting embodiment of the present invention, two polypeptides that constitute an Fc region and which comprise Glu for the amino acid at position 439 according to EU numbering in the amino acid sequence of one of the polypeptides, and Lys for the amino acid at position 356 according to EU numbering in the amino acid sequence of the other polypeptide, may be suitably used as the Fc region.

In still yet another non-limiting embodiment of the present invention, any of combinations of the above-mentioned embodiments, as shown below, may be suitably used as the Fc region:

(i) two polypeptides that constitute an Fc region and which comprise Asp for the amino acid at position 409 and Glu for the amino acid at position 370 according to EU numbering in the amino acid sequence of one of the polypeptides, and Lys for the amino acid at position 399 and Lys for the amino acid at position 357 according to EU numbering in the amino acid sequence of the other polypeptide (in this embodiment, the amino acid at position 370 according to EU numbering may be Asp instead of Glu, and the amino acid Asp at position 392 according to EU numbering may be used instead of the amino acid Glu at position 370 according to EU numbering);

(ii) two polypeptides that constitute an Fc region, and which comprise Asp for the amino acid at position 409 and Glu for the amino acid at position 439 according to EU numbering of the amino acid sequence of one of the polypeptides; and Lys for the amino acid at position 399 and Lys for the amino acid at position 356 according to EU numbering in the amino acid sequence of the other polypeptide (in this embodiment, the amino acid Asp at position 360 according to EU numbering, the amino acid Asp at position 392 according to EU numbering, or the amino acid Asp at position 439 according to EU numbering may be used instead of the amino acid Glu at position 439 according to EU numbering);

(iii) two polypeptides that constitute an Fc region, and which comprise Glu for the amino acid at position 370 and Glu for the amino acid at position 439 according to EU numbering in the amino acid sequence of one of the polypeptides, and Ly for the amino acid at position 357 and Lys for the amino acid at position 356 according to EU numbering in the amino acid sequence of the other polypeptide; or two polypeptides that constitute an Fc region, and which comprise Asp the amino acid at position 409, Glu for the amino acid at position 370, and Glu for the amino acid at position 439 according to EU numbering in the amino acid sequence of one of the polypeptides; and Lys for the amino acid at position 399, Lys for the amino acid at position 357, and Lys for the amino acid at position 356 according to EU numbering in the amino acid sequence of the other polypeptide (in this embodiment, the amino acid at position 370 according to EU numbering may not be substituted with Glu, and furthermore, when the amino acid at position 370 is not substituted with Glu, the amino acid at position 439 may be Asp instead of Glu, or the amino acid Asp at position 392 may be used instead of the amino acid Glu at position 439).

Further, in another non-limiting embodiment of the present invention, two polypeptides that constitute an Fc region and which comprise Lys for the amino acid at position 356 according to EU numbering in the amino acid sequence of one of the polypeptides, and Arg for the amino acid at position 435 and Glu for the amino acid at position 439 according to EU numbering in the amino acid sequence of the other polypeptide may also be suitably used.

In still another non-limiting embodiment of the present invention, two polypeptides that constitute an Fc region and which comprise Lys for the amino acid at position 356 and Lys for the amino acid at position 357 according to EU numbering in the amino acid sequence of one of the polypeptides, and Glu for the amino acid at position 370, Arg for the amino acid at position 435, and Glu for the amino acid at position 439 according to EU numbering in the amino acid sequence of the other polypeptide may also be suitably used.

Antigen-binding molecules of the present invention are isolated from culture media of cells transformed with a desired expression vector in which a polynucleotide encoding an antigen-binding domain and a polynucleotide encoding a polypeptide containing an Fc region, which have been linked in the above-described manner, are operably linked. When the Fc region contained in the antigen-binding molecule of the present invention is an Fc region that has been modified so that the percentage of the Fc region to which a fucose-deficient sugar chain has been attached, or bisecting N-acetylglucosamine has been attached, will become higher, the above-mentioned transformed host cells that are suitably used are host cells that have low ability to add fucose to a sugar chain as a result of modification of the activity to form the sugar chain structure of a polypeptide to be modified with a sugar chain (for example, WO 2000/061739, WO 2002/031140, and WO 2006/067913). In a non-limiting embodiment of such host cells, host cells deficient in the activity of an enzyme or transporter selected from the group consisting of fucosyltransferase (EC 2.4.1.152), fucose transporter (SLC35C1), GMD (GDP-mannose-4,6-dehydratase) (EC 4.2.1.47), Fx (GDP-keto-6-deoxymannose-3,5-epimerase, 4-reductase) (EC 1.1.1.271), and GFPP (GDP-β-L-fucose pyrophosphorylase (EC 2.7.7.30), may be suitably used (for example, WO 2000/061739, WO 2002/031140, and WO 2006/067913). Host cells deficient in such activity can be produced, for example, by a method that destroys the genes of these functional proteins endogenous to CHO cells, BHK cells, NS0 cells, SP2/0 cells, YO myeloma cells, P3X63 mouse myeloma cells, PER cells, PER.C6 cells, HEK293 cells, hybridoma cells, or such so that they are unable to function.

When the Fc region contained in the antigen-binding molecule of the present invention is an Fc region having a sugar chain containing a bisecting GlcNAc, the above-described transformed cells that are suitably used are host cells expressing a gene encoding a functional protein having GnTIII (β-1,4-mannosyl-glycoprotein 4-β-N-acetylglucosaminyltransferase) (EC2.4.1.144) activity or GaT (β-1, 4-galactosyltransferase) (EC 2.4.1.38) activity to produce antibodies which have bisecting GlcNAc-containing sugar chains (WO2002/079255 and such). In another suitable non-limiting embodiment, host cells that co-express, in addition to the aforementioned functional proteins, a gene encoding a functional protein having human ManII (manosidase II) (3.2.1.114) activity, a gene encoding a functional protein having GnTI (β-1,2-acetylglucosaminyltransferase I) (EC 2.4.1.94) activity, a gene encoding a functional protein having GnTII (β-1,2-acetylglucosaminyltransferase II) (EC 2.4.1.143) activity, a gene encoding a functional protein having ManI (mannosidase) (EC 3.2.1.113) activity, and α-1,6-fucosyl transferase (EC 2.4.1.68), are suitably used (WO2004/065540).

Antigen-binding molecules of the present invention are produced using methods that follow the methods for producing antibodies, such as isolation from culture media of the above-mentioned cells, which are described in the section "Antibodies" above. A non-limiting embodiment of the aforementioned polypeptides containing an Fc region includes, for example, the antibody constant region of SEQ ID NO: 5, 6, 7, or 8. A non-limiting embodiment of the antigen-binding molecules of the present invention is for example, a full-length antibody molecule.

Pharmaceutical Compositions

The present invention provides pharmaceutical compositions comprising an antigen-binding molecule that does not act systemically in the blood or normal tissues, but acts on lesions such as cancer and inflamed sites, to exhibit drug efficacy while avoiding side effects. The antigen-binding molecule contained in the pharmaceutical composition of the present invention binds to an antigen expressed in cancer cells, immune cells, stromal cells, or such in cancer tissues; an antigen secreted in cancer tissues; or an antigen expressed by immune cells or such in inflammatory tissues; and an antigen secreted in inflammatory tissues; and cannot bind to antigens expressed in normal tissues; therefore, side effects due to cytotoxic activity, neutralizing activity, or such against normal tissues are avoided; and at the same time, potent cytotoxic effects, growth suppressing effects, and immunity-enhancing action on cancers, or immunosuppressive effects against inflammatory cells in inflammatory tissues, are exhibited. For example, a bispecific or biparatopic antigen-binding molecule containing an antigen-binding domain that binds to EGFR expressed on cancer cells and an antigen-binding domain that binds to CD3 expressed on T cells in a manner dependent on a cancer tissue-specific compound, does not bind to EGFR expressed on normal tissues but bind to EGFR expressed on cancer cells; thereby exhibiting potent antitumor effects while avoiding side effects. Specifically, while the antigen-binding molecule binds to CD3 expressed on T cells in the vicinity of cancer cells in a manner dependent on a cancer tissue-specific compound, the molecule does not bind to CD3 expressed on T cells that are not in the vicinity of cancer cells. Therefore, the molecule activates T cells in the vicinity of cancer cells, exhibiting potent antitumor effects while avoiding side effects.

Such antigen-binding molecules that bind to an antigen in target tissues but not in other normal tissues and blood exhibit drug efficacy while avoiding side effects. Antigen-binding molecules provided by the present invention, which bind to an antigen by using a small molecule present at high concentrations in target tissues in vivo as a switch, namely, small molecule switch antigen-binding molecules, do not bind to the antigen in a normal environment where the small molecule is not present, but can bind to the antigen in target tissues where the small molecule is present at high concentrations.

A non-limiting embodiment of such small molecule switch antigen-binding molecules includes cancer tissue-specific, or inflammatory tissue-specific, compound-dependent antigen-binding molecules; and a cancer tissue-specific or inflammatory tissue-specific compound such as adenosine, adenosine 5'-triphosphate (ATP), inosine, kynurenine, prostaglandin E2 (PGE2), succinic acid, and lactic acid, which are present at a high concentration in cancer tissues or inflammatory tissues and capable of functioning as a switch, provides a switch function by being sandwiched between the antigen-binding molecule of the present invention (the paratope contained therein) and the antigen (the epitope contained therein). In the absence of the compound, the interaction between the paratope in the antigen-binding molecule of the present invention and the epitope in the antigen is not sufficient for the antigen-binding molecule of the present invention to be able to bind to the antigen. In the presence of the compound, the compound interposes between the paratope in the antigen-binding molecule of the present invention and the epitope in the antigen; and the antigen-binding molecule that has bound to the antigen in a target tissue such as cancer tissue or inflammatory tissue, where the compound is present at a high concentration, can exhibit drug efficacy on cells expressing the antigen. Moreover, since this binding of the switch compound is reversible, the binding of an antigen-binding molecule of the present invention to an antigen by means of these switch compounds may be controlled in a reversible manner. Thus, antigen-binding molecules of the present invention which can exhibit drug efficacy in a lesion site such as cancer tissue or inflammatory tissue by binding to pathogenic cells such as cancer cells or immune cells in a cancer tissue or inflammatory tissue or by binding to an antigen secreted in a cancer tissue or inflammatory tissue are useful as pharmaceutical compositions. The pharmaceutical compositions of the present invention may comprise a pharmaceutically acceptable carrier.

In the present invention, pharmaceutical compositions generally refer to pharmaceutical agents for treating or preventing, or testing and diagnosing diseases. Furthermore, in the present invention, the phrase "pharmaceutical composition containing an antigen-binding molecule whose antigen-binding activity varies depending on the concentration of a target tissue-specific compound" can be rephrased as "method for treating a disease which comprises administering to a subject to be treated an antigen-binding molecule whose antigen-binding activity varies depending on the concentration of a target tissue-specific compound", or rephrased as "use of an antigen-binding molecule whose antigen-binding activity varies depending on the concentration of a target tissue-specific compound in the production of a pharmaceutical for treating a disease". Furthermore, the phrase "pharmaceutical composition containing an antigen-binding molecule whose antigen-binding activity varies depending on the concentration of a target tissue-specific compound" can be rephrased as "use of an antigen-binding molecule whose antigen-binding activity varies depending on the concentration of a target tissue-specific compound, for treating a disease".

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions can be formulated by mixing in the form of unit dose required in the generally approved medicine manufacturing practice, by appropriately combining with pharmacologically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice. Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions in the dosage form for injections, transnasal administration, transpulmonary administration, or transdermal administration are administered. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule can be, for example, from 0.0001 to 1,000 mg/kg for each administration. Alternatively, the dose can be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in this specification are incorporated herein by reference.

Herein below, the present invention will be specifically described with the Examples; however, the present invention should not be limited thereto.

EXAMPLES

[Example 1] Concept of Antibodies that Bind to Antigens Via Small Molecules Serving as a Switch, which are Present at High Concentrations in Target Tissues In order to exert drug efficacy while avoiding adverse effects, there is a need for drug discovery technology that works in lesions such as cancer or inflammatory sites without acting systemically in normal tissues or blood. Antibody molecules that can bind to antigens expressed on cancer cells but are incapable of binding to the antigens expressed on normal tissues after administration can exert strong cytotoxic effects against cancer while avoiding adverse effects on normal tissues as a result of cytotoxic action. For example, antigen-binding molecules that have been altered from the above-described EGFR-BiTE (Non-patent Document 9), which cannot bind to EGFR expressed on normal tissues but are capable of binding to EGFR expressed on cancer cells, can exert strong an antitumor effect while avoiding adverse effects. Meanwhile, BiTE exerts an antitumor effect by recruiting and activating T cells via CD3 (Non-patent Document 8); and if it is possible to confer EGFR-BiTE with the property of binding to CD3 expressed on T cells in the vicinity of cancer cells but not to CD3 expressed on T cells outside the vicinity of cancer cells, EGFR-BiTE altered to have the property can activate T cells in cancer and thus can exert strong antitumor effects while avoiding adverse effects.

However, this is not limited to only antibody pharmaceuticals against cancer. When an antibody molecule binds and inhibits cytokines in the synovial fluid of inflamed joints in rheumatoid arthritis but does not systemically inhibit the cytokines, the molecule can exert potent therapeutic effects against inflammatory/autoimmune diseases such as rheumatoid arthritis while avoiding increased risks of infection due to systemic neutralization of cytokines.

As described above, antibodies that bind to antigens in cancer tissues but not to antigens in other tissues such as normal tissues and blood can exert drug efficacy while avoiding adverse effects. However, ideal antibodies having such properties have not been reported so far. Meanwhile, as shown in FIG. 1, antibody molecules that bind to antigens via small molecules, as a switch, that are present at high concentrations in cancer tissues in vivo (i.e., small molecule switch antibodies), do not bind to antigens in environments in the absence of such small molecules; and they can bind to antigens in target tissues where the small molecules are present at high concentrations.

Figure 2:
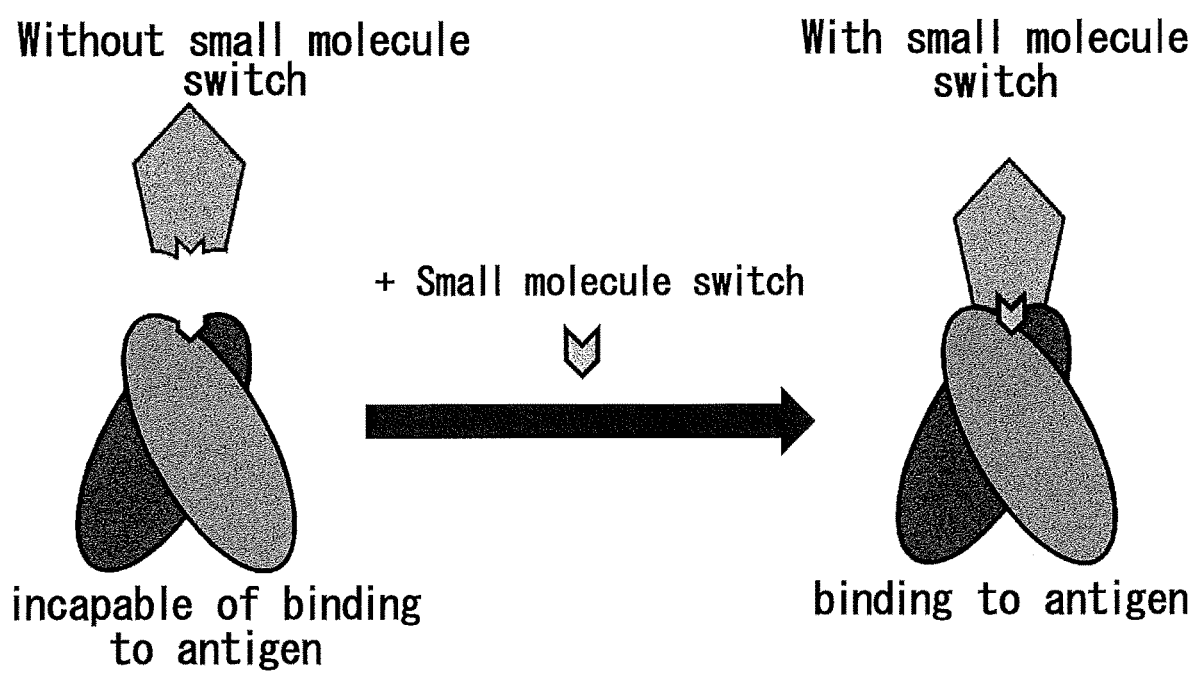
FIG. 2 shows that the small molecule functions as a switch by fitting between the anti-small-molecule antibody and the antigen. If the small molecule is absent, the antibody-antigen interaction is insufficient and the antibody cannot bind to the antigen, but if the small molecule is present, the antibody can bind to the antigen by having the small molecule placed between the antibody and the antigen.

In developing such small-molecule switch antibodies, first it was to search for small molecules that are present at high concentration in cancer tissues and are considered to be usable as a switch. The result suggested that adenosine, adenosine triphosphate (adenosine 5'-triphosphate (ATP)), inosine, kynurenine, prostaglandin E2 (PGE2), succinic acid, and lactic acid were promising as a switch. Each of these small molecules is either produced by cancer cells, or released from cancer cells after cell death, or produced by immune cells etc infiltrating cancer tissues, and thus they are present at high concentrations in cancer tissues; however, they are present at lower concentrations in normal tissues and blood in comparison to cancer tissues. If these small molecules can be sandwiched in a complex between an antibody and an antigen in such a way as shown in FIG. 2, the small molecules can achieve the switch function. Specifically, in the absence of small molecules, the antigen-antibody interaction is insufficient and the antibody cannot bind to its antigen. Meanwhile, in the presence of a small molecule, the antibody can bind to its antigen via the small molecule sandwiched between the antibody and antigen. In other words, in the presence of a low concentration of small molecules, the antigen-antibody interaction is insufficient and the antibody cannot bind to its antigen, while in the presence of a high concentration of small molecules, the antibody can bind to its antigen via a small molecule sandwiched between the antibody and antigen. Furthermore, the binding of small molecules as a switch is reversible, and the regulation of antigen binding by the small molecule switch is also reversible.

In this context, first, the present inventors attempted to isolate small molecule switch antibodies against IL-6 (Br. J. Haematol. (2011) 152 (5), 579-92) which is reported to be involved in cancer cell growth.

[Example 2] Acquisition of Antibodies that Bind to Human IL-6 in the Presence of Small Molecules from a Human Antibody Library Using Phage-Display Techniques (2-1) Construction of a Phage-Display Library of Naïve Human Antibodies A phage-display library of human antibodies consisting of multiple phages that present the Fab domains of human antibodies whose sequences were different from one another was constructed using as a template, polyA RNA prepared from human PBMC, commercially available human polyA RNA, or such according to a method known to those skilled in the art.

(2-2) Acquirement of Antibodies that Bind to Human IL-6 in the Presence of Small Molecules from the Library by Bead Panning The phage-display library of naïve human antibodies constructed as described in (2-1) was screened for antibodies that exhibit antigen-binding activity in the presence of small molecules, specifically, by collecting phages displaying antibodies that in the presence of small molecules exhibit antigen-binding activity to antigens captured by beads. Phages were collected from a phage suspension eluted from the beads in the absence of small molecules. In this preparation method, the antigen used was biotin-labeled human IL-6.

Phages produced in *E. coli* containing the phagemid vector constructed for phage display were purified by a conventional method. Then, a phage library suspension was prepared by dialyzing the phages against TBS. Next, BSA was added at a final concentration of 4% to the phage library suspension. Panning was performed using antigen-immobilized magnetic beads. The magnetic beads used were NeutrAvidin coated beads (Sera-Mag SpeedBeads NeutrAvidin-coated) or Streptavidin coated beads (Dynabeads M-280 Streptavidin).

To efficiently isolate small molecule switch antibodies which depend on small molecules which can serve as a switch in cancer tissues, panning was carried out to enrich antibodies that bind to antigens in the presence of a mixed solution of small molecules (adenosine, adenosine triphosphate (adenosine 5'-triphosphate (ATP)), inosine, kynurenine, prostaglandin E2 (PGE2), succinic acid, and lactic acid (hereinafter referred to as small molecule cocktail (SC)) but not in the absence of SC.

Specifically, together with 250 pmol of biotin-labeled antigen, SC containing adenosine triphosphate sodium salt (ATP-Na), adenosine, inosine, succinic acid, and lactic acid at a final concentration of 1 mM, prostaglandin E2 (PGE2) at a final concentration of 1 µM, and kynurenine at a final concentration of 100 µM, which had been adjusted to be pH 7.4 with NaOH, was contacted with the prepared phage library suspension for 60 minutes at room temperature. Then, BSA-blocked magnetic beads were added to the phage library suspension, and the antigen-phage complex was allowed to bind to the magnetic beads at room temperature for 15 minutes. After washing once with SC/TBS (TBS containing SC), the beads were combined with 0.5 ml of 1 mg/ml trypsin solution. Immediately after suspending the beads at room temperature for 15 minutes, the phage suspension was collected from the isolated beads using a magnetic stand. The collected phage suspension was added to 10 ml of *E. coli* cells of strain ER2738 at the logarithmic growth phase (OD600=0.4 to 0.7). The *E. coli* was infected with the phage by incubating the above *E. coli* with gently stirring at 37° C. for one hour. The infected *E. coli* was seeded in a 225 mm×225 mm plate. Then, phages were collected from the culture medium of the seeded *E. coli* to prepare a liquid stock of phage library.

The first round of panning was carried out to collect phages that are capable of binding in the presence of small molecules, while the second and subsequent rounds of panning were performed to enrich phages that are capable of binding to antigens in the presence of SC. Specifically, the prepared phage library suspension was mixed with 40 pmol biotin-labeled antigen, SC, and NaOH, and contacted with the small molecules and antigens for 60 minutes at room temperature. BSA-blocked magnetic beads were added and allowed to bind to the antigen-phage complex for 15 minutes at room temperature. The beads were washed with 1 ml of SC/TBST and SC/TBS. Then, immediately after 0.5 ml of TBS was added to suspend the beads at room temperature, a phage suspension was collected from the isolated beads using a magnetic stand. After this treatment was repeated, the two separately eluted phage suspensions were mixed together. Then, the resultant beads were combined with 0.5 ml of TBS and stirred at room temperature for five minutes. A phage suspension was collected from the isolated beads using a magnetic stand. By addition of 5 μl of 100 mg/ml trypsin to the collected phage suspension, the pIII protein (helper phage-derived protein pIII) that does not display Fab was cleaved off from phages, and the ability of phages that do not display Fab to infect E. coli was eliminated. The phages collected from the trypsinized phage suspension were added to 10 ml of E. coli strain ER2738 at the logarithmic growth phase (OD600=0.4 to 0.7). The E. coli was incubated at 37° C. for one hour under gentle stirring to infect phage. The infected E. coli was seeded in a 225 mm×225 mm plate. The two types of infected E. coli obtained through the second round of panning were mixed in equal amounts at this time point. Then, phages were collected from the culture medium of the seeded E. coli to prepare a phage library suspension. Panning was performed three times to isolate antibodies that have antigen-binding activity in the presence of SC.

(2-3) Acquisition of Antibodies that Bind to Human IL-6 in the Presence of Small Molecules from the Library Using a Negative Selection Method The constructed phage-display library of naïve human antibodies was screened for antibodies that exhibit antigen-binding activity in the presence of small molecules. As a first step of screening, the phage-display library of naïve human antibodies was contacted with biotin-labeled antigen-streptavidin in the absence of small molecules to eliminate phages displaying antibodies that have antigen-binding activity even in the absence of small molecules. Then, panning was performed in the presence of small molecules in the same manner. Thus, screening was carried out for antibodies that have antigen-binding activity in the presence of small molecules. Biotin-labeled IL-6 was used as the antigen.

Phages were produced in E. coli retaining the constructed phage-display phagemid. The produced phages were purified by a conventional method, and then a phage library suspension was prepared by dialyzing the phages against TBS. Then, BSA was added to the phage library suspension at a final concentration of 4%. The magnetic beads used were NeutrAvidin coated beads (Sera-Mag SpeedBeads NeutrAvidin-coated) or Streptavidin coated beads (Dynabeads M-280 Streptavidin). Panning was performed using antigen-immobilized magnetic beads.

Together with 250 pmol of biotin-labeled antigen, SC containing ATP-Na, adenosine, inosine, succinic acid, and lactic acid at a final concentration of 1 mM, PGE2 at a final concentration of 1 μM, and kynurenine at a final concentration of 100 μM, whose pH was adjusted to 7.4 with NaOH, was added and contacted with the prepared phage library suspension for 60 minutes at room temperature. Then, BSA-blocked magnetic beads were added to the phage library suspension, and the antigen-phage complex was allowed to bind to the magnetic beads at room temperature for 15 minutes. After washing once with SC/TBS, the beads were combined with 0.5 ml of 1 mg/ml trypsin solution. Immediately after suspending the beads at room temperature for 15 minutes, the phage suspension was collected from the isolated beads using a magnetic stand. The collected phage suspension was added to 10 ml of E. coli cells of strain ER2738 at the logarithmic growth phase (OD600=0.4 to 0.7). The E. coli was incubated at 37° C. for one hour with gentle stirring to be infected by phage. The infected E. coli was seeded in a 225 mm×225 mm plate. Then, phages were collected from the culture medium of the seeded E. coli to prepare a liquid stock of phage library.

The first round of panning was carried out to collect phages that are capable of binding in the presence of SC, while the second and subsequent rounds of panning were performed to enrich phages that are capable of binding to antigens in the presence of SC. Specifically, 250 pmol of biotinylated antigen was added to BSA-blocked Sera-Mag NeutrAvidin beads for binding at room temperature for 15 minutes. The beads were washed three times with TBS. The phage library suspension subjected to BSA blocking was added to the beads, and allowed to bind thereto at room temperature for one hour. Phages that did not bind to the antigens or beads were collected by isolating the beads using a magnetic stand. 40 pmol of biotin-labeled antigen, SC, and NaOH were added to the collected phages. Thus, the phage library was contacted with the small molecules in SC at room temperature for 60 minutes. Then, BSA-blocked magnetic beads were added to the mixture of labeled antigen, SC, and phage library, and allowed to bind to the antigen-phage complex for 15 minutes at room temperature. The beads were washed with 1 ml of SC/TBST and SC/TBS. Then, 0.5 ml of 1 mg/ml trypsin solution was added to the mixture. After the mixed suspension was stirred at room temperature for 20 minutes, phages were collected from the beads that had been separated using a magnetic stand. The collected phages were added to 10 ml of E. coli strain ER2738 at the logarithmic growth phase (OD600=0.4 to 0.7). The E. coli was incubated at 37° C. for one hour under gentle stirring to be infected by phage. The infected E. coli was seeded in a 225 mm×225 mm plate. Panning was performed three times to isolate antibodies that have antigen-binding activity in the presence of SC.

(2-4) Assessment of Binding Activity in the Presence of Small Molecules by Phage ELISA Culture supernatants containing phages were collected according to a conventional method (Methods Mol. Biol. (2002) 178, 133-145) from single colonies of E. coli obtained by the method described above. The collected culture supernatants were treated by ultrafiltration using NucleoFast 96 (MACHEREY-NAGEL). 100 μl of the collected culture supernatants were added to each well of NucleoFas96 and centrifuged (4500 g for 45 minutes) to remove the flow-through portion. 100 μl of H₂O was added to each well, and again the NucleoFast 96 was centrifuged (4500 g for 30 minutes) for washing. After 100 μl of TBS was added, the NucleoFast 96 was allowed to stand for five minutes at room temperature. Finally, a phage suspension was collected from the supernatant in each well.

After addition of TBS or SC/TBS, the purified phages were subjected to ELISA by the following procedure. A StreptaWell 96 microtiter plate (Roche) was coated overnight with 100 μl of TBS containing the biotin-labeled antigen. After the antigen was removed by washing each well of the plate with TBST, the wells were blocked with 250 μl of 2% skim milk-TBS for one hour or more. 2% skim milk-TBS was removed, and then the prepared, purified phages were added to each well. The plate was allowed to stand at 37° C. for one hour to allow binding of antibody-displaying phages to the antigen in the presence or absence of SC in each well. After each well was washed with TBST or SC/TBST, the HRP-conjugated anti-M13 antibody (Amersham Pharmacia Biotech) diluted with TBS or SC/TBS was added thereto, and the plate was incubated for one hour. Following washing with TBST or SC/TBST, the TMB single solution (ZYMED) was added to each well, and the chromogenic reaction in the solution was terminated by adding sulfuric acid. Then, the developed color was assessed by measuring absorbance at 450 nm.

Phage ELISA of isolated 96 clones revealed a clone "I6NMSC1-3_A11", which has binding activity to human IL-6 as an antigen in the presence of a small molecule cocktail.

[Example 3] Assessment of Antibodies that Bind to Antigens in the Presence of Small Molecules (3-1) Expression and Purification of Antibodies that Bind to Human IL-6

Genes were amplified from clone I6NMSC1-3_A11 which had been assessed to have antigen-binding activity in the presence of SC using specific primers (SEQ ID NOs: 110 and 112) by phage ELISA as described in Example 2. The nucleotide sequences of the genes were analyzed (the heavy chain and light chain sequences are shown in SEQ ID NOs: 30 and 31, respectively). The gene encoding the variable region of I6NMSC1-3_A11 was inserted into an animal expression plasmid for human IgG1/Lambda, while each of the genes encoding the variable regions of known anti-human IL-6 antibody CLB8-F1 (the heavy chain and light chain are SEQ ID NOs: 32 and 33, respectively) and the variable regions of anti-human glypican 3 antibody GC413 (the heavy chain and light chain are SEQ ID NOs: 34 and 35, respectively) as a negative control were inserted into an animal expression plasmid for human IgG1/kappa. Antibodies were expressed using the method described below. FreeStyle 293-F (Invitrogen) which is derived from human fetal kidney cells were suspended at a cell density of $1.33 \times 10^6$ cells/ml in FreeStyle 293 Expression Medium (Invitrogen) and aliquoted at 3 ml into each well of a 6-well plate. The plasmid DNA was transfected into the cells by lipofection. From the culture supernatants after four days of culture in a $CO_2$ incubator (37° C., 8% $CO_2$, 90 rpm), antibodies were purified by a method known to those skilled in the art using rProtein A Sepharose™ Fast Flow (Amersham Biosciences). Absorbance of solutions of purified antibodies was measured at 280 nm using a spectrophotometer. From the values obtained by measurement, the concentrations of purified antibodies were calculated using an extinction coefficient determined by the PACE method (Protein Science (1995) 4, 2411-2423).

(3-2) Identification of Small Molecules Necessary for Human IL-6 Binding of the Obtained Antibodies Three types of antibodies: isolated I6NMSC1-3_A11 (hereinafter abbreviated as A11), and CLB8-F1 and GC413 as controls were subjected to ELISA under the nine conditions described in Table 3. Meanwhile, each small molecule was appropriately prepared at the concentrations shown in Table 3 using the buffers indicated in Table 4. Biotin-labeled human IL-6 was used as the antigen.

TABLE 3

| Condition | Small molecule | Concentration |
|---|---|---|
| 1 | ATP-Na | 1 mM |
| 2 | Adenosine | 1 mM |

TABLE 3-continued

| Condition | Small molecule | Concentration |
|---|---|---|
| 3 | Inosine | 1 mM |
| 4 | PGE2 | 1 µM |
| 5 | Succinic acid | 1 mM |
| 6 | Lactic acid | 1 mM |
| 7 | Kynurenine | 100 µM |
| 8 | ATP 1 mM, Adenosine 1 mM, Inosine 1 mM, PGE2 1 µM, Succinic acid 1 mM, Lactic acid 1 mM, Kynurenine 100 µM | |
| 9 | — | — |

TABLE 4

| | |
|---|---|
| Wash buffer | 10 mM ACES, 150 mM NaCl, 0.05% Tween20, pH 7.4 |
| Blocking Buffer | 10 mM ACES, 150 mM NaCl, 2% BSA, pH 7.4 |
| Sample Buffer | 10 mM ACES, 150 mM NaCl, Each small molecule, pH 7.4 |

First, a StreptaWell 96 microtiter plate (Roche) was coated at room temperature for one hour or more with 100 µl of PBS containing the biotin-labeled antigen. After washing with the Wash buffer to remove unbound antigen from the plate, each well was blocked for one hour or more with 250 µl of the Blocking Buffer. The Blocking Buffer was removed from each well. The purified IgGs were prepared to 2.5 µg/ml in a Sample Buffer containing small molecules at the final concentrations shown in Table 3, and each was aliquoted at 100 µl to each well of the plate. The plate was allowed to stand at room temperature for one hour to allow binding of each IgG to the antigen in each well. After washing with a Wash Buffer containing the small molecules at the final concentrations shown in Table 3, an HRP-conjugated anti-human IgG antibody (BIOSOURCE) diluted with a Sample Buffer containing the same small molecules was added to each well. The plate was incubated for one hour. Following wash with a Wash Buffer containing each small molecule, the TMB single solution (ZYMED) was added to each well. The chromogenic reaction in the solution of each well was terminated by adding sulfuric acid. Then, the developed color was assessed by measuring absorbance at 450 nm.

Figure 3:
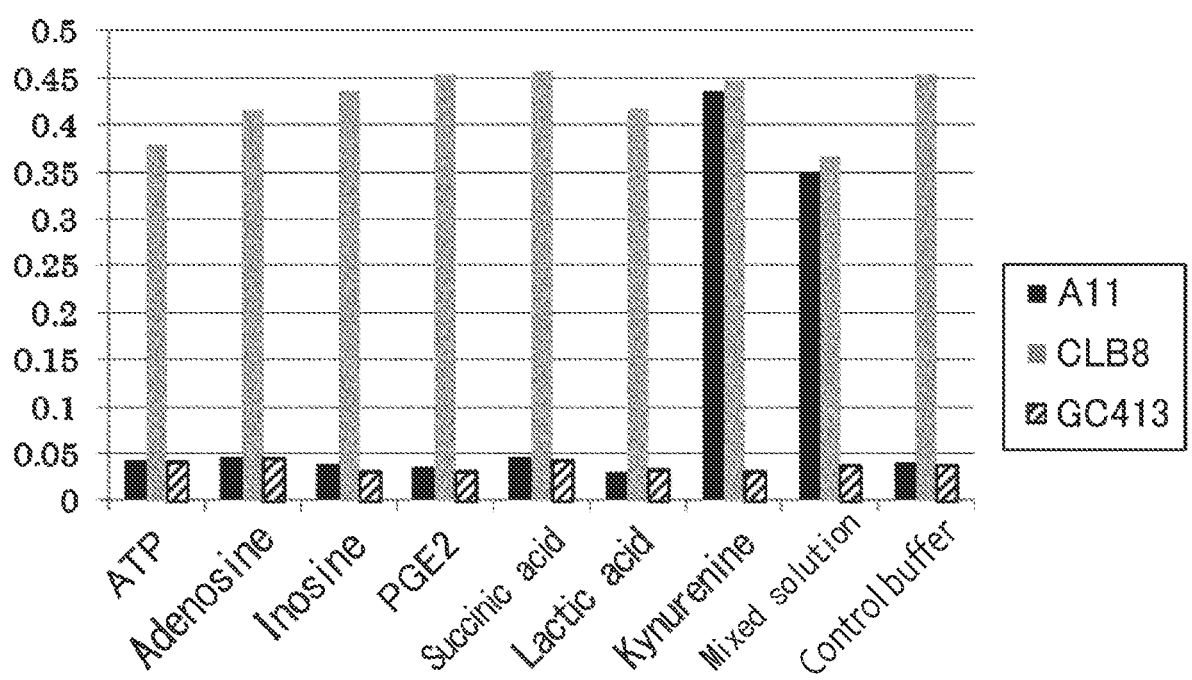
FIG. 3 is a figure showing the result of ELISA for the binding of the antibody to human IL-6. The vertical axis shows the absorbance values which assess the binding activity to human IL-6 of each of the antibodies in the presence or absence of each of the small molecules.

The measurement result is shown in FIG. 3. The result showed that the absorbance of CLB8-F1 was constant regardless of the type or presence of small molecule, whereas the absorbance of I6NMSC1-3_A11 was markedly lower under condition 9 (without small molecules) as compared to under condition 8 (the complete small molecule cocktail solution). Similar to phage ELISA, this result showed that I6NMSC1-3_A11 had the property that its antigen binding is altered depending on the presence of small molecules. Meanwhile, I6NMSC1-3_A11 showed equivalent absorbance under condition 7 (in the presence of 100 µM kynurenine) to that under condition 8; however, the absorbance was markedly lower under other conditions. This result demonstrates that I6NMSC1-3_A11 is an antibody that binds to human IL-6 as an antigen in the presence of kynurenine but not in the absence of kynurenine.

[Example 4] Assessment of the Effect of Kynurenine on Human IL6 Binding by Surface Plasmon Resonance (4-1) Assessment of Kynurenine for its Switch Function in Human IL-6 Binding Using Biacore T200 (GE Healthcare), A11 was analyzed for its interaction with human IL-6 (Kamakura Techno-Science, Inc.) in antigen-antibody reaction. Sensor chip CM5 (GE Healthcare) was immobilized with an appropriate amount of protein A/G (Invitrogen) by amine coupling. Antibodies of interest were captured by the chip to allow interaction to IL-6 as an antigen. The two types of running buffers used were 10 mmol/l ACES, 150 mmol/l NaCl, 0.05% (w/v) Tween20, 100 µmol/l kynurenine, pH 7.4, and 10 mmol/l ACES, 150 mmol/l NaCl, 0.05% (w/v) Tween20, pH 7.4. The interaction with IL-6 as an antigen was assessed at 37° C. The buffer used to dilute IL-6 was the same running buffer as described above.

A diluted solution of human IL-6 and a running buffer as a blank were injected at a flow rate of 5 µl/min for three minutes to allow interaction of human IL-6 with A11 captured on the sensor chip. Then, the running buffer was injected at a flow rate of 5 µl/min for three minutes. After observation of human IL-6 dissociation from the antibody, 10 mmol/l glycine-HCl (pH 1.5) was injected at a flow rate of 30 µl/min for 30 seconds to regenerate the sensor chip. The dissociation constant $K_D$ (M) of A11 was calculated for human IL-6 based on the association rate constant ka (1/Ms) and dissociation rate constant kd (1/s), both of which are kinetic parameters calculated from the sensorgram obtained by the measurement. Each parameter was calculated using the Biacore T200 Evaluation Software (GE Healthcare).

Figure 4:
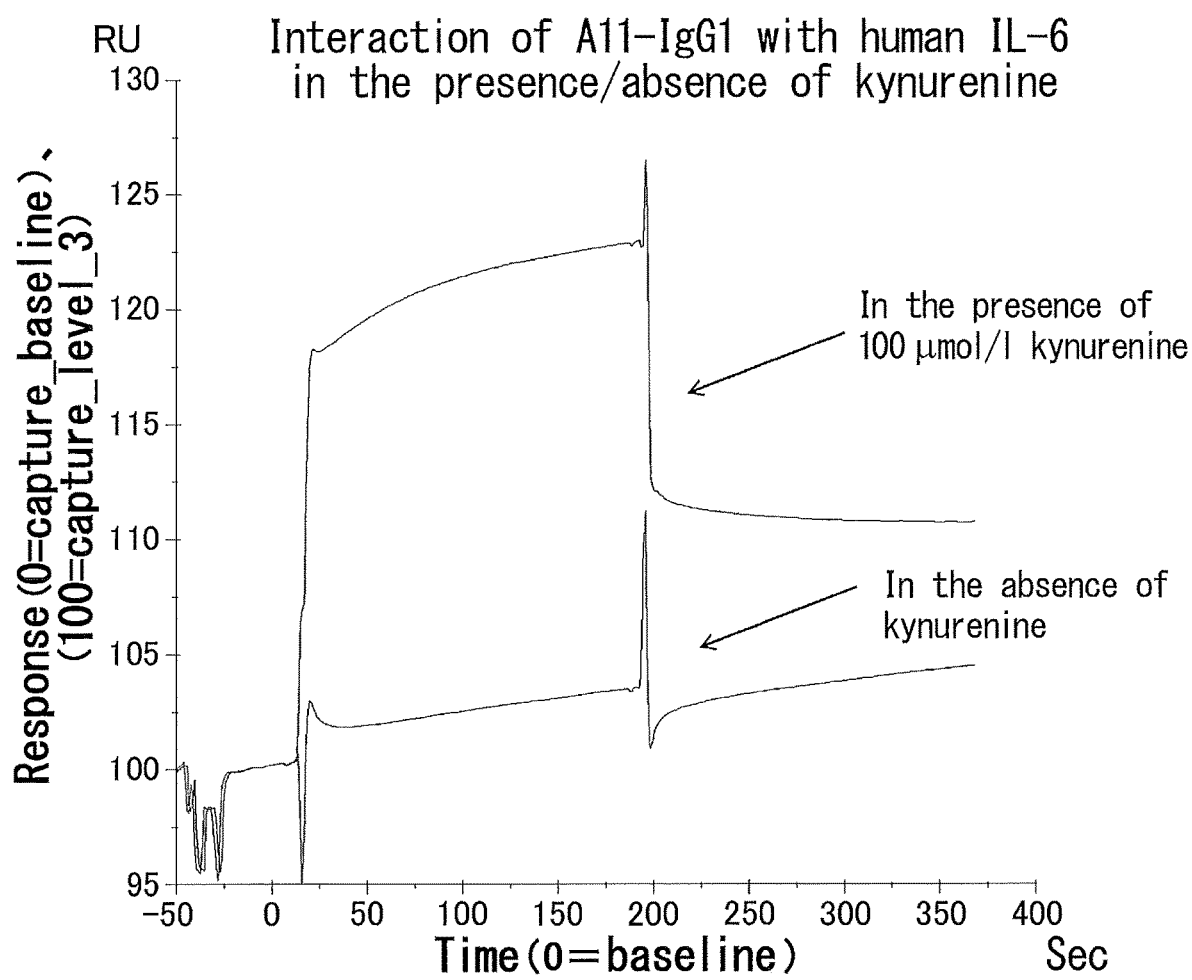
FIG. 4 is a sensorgram showing the interaction between 4 µmol/L of human IL-6 and A11 in the presence or absence of 100 µmol/L kynurenine.

The sensorgrams for the interaction between A11 and 4 µmol/l human IL-6 obtained by the measurement in the presence or absence of 100 µmol/l kynurenine are shown in FIG. 4. As shown in FIG. 4, A11 bound to IL-6 in the presence of 100 µmol/l kynurenine; however, in the absence of kynurenine, the IL-6 binding was undetectable. This demonstrates that A11 has the property that it binds to IL-6 via kynurenine as a switch. Meanwhile, the dissociation constant $K_D$ of A11 was $1.0E^{-6}$ mol/l in the presence of 100 µmol/l kynurenine.

Figure 5:
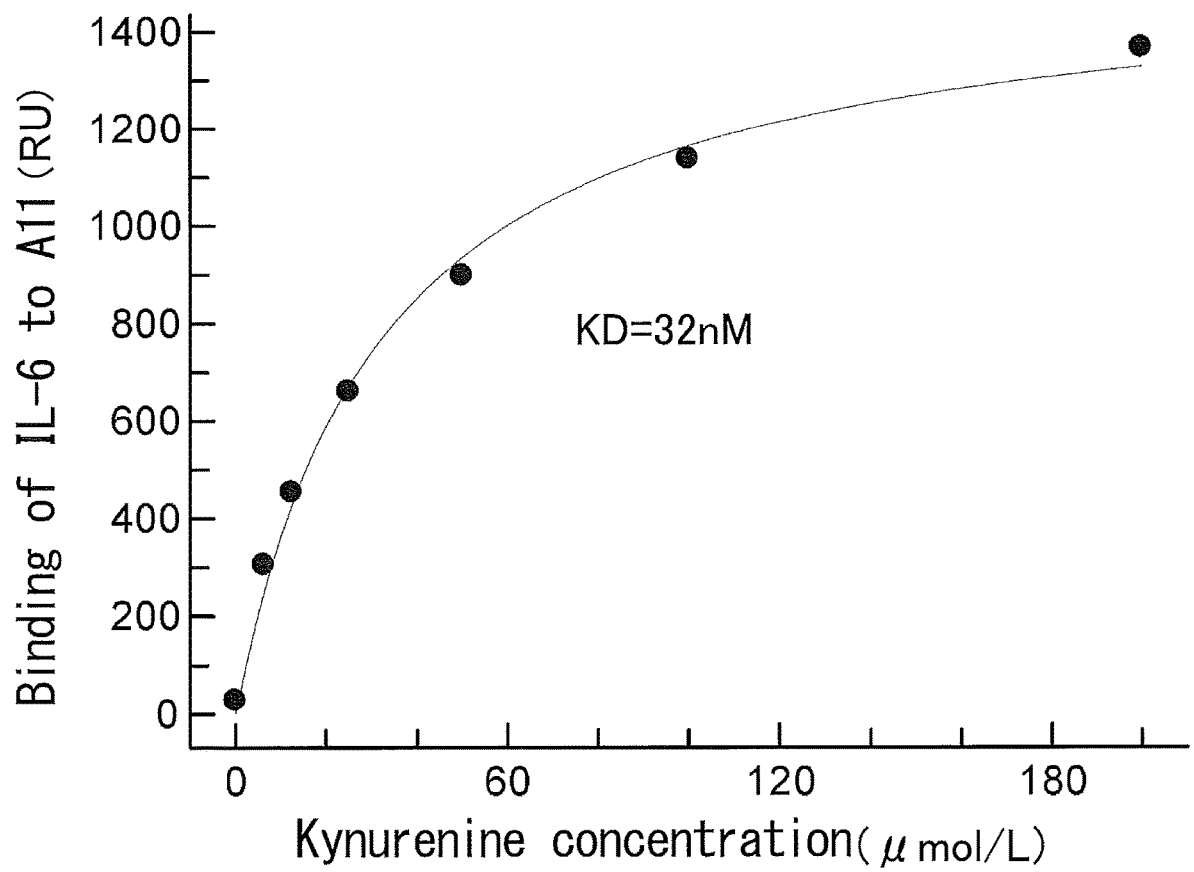
FIG. 5 shows a graph that evaluates change in the response of binding to A11 immobilized onto Sensorchip CM5, when interaction is allowed to take place for 60 seconds with 1 µmol/L of IL-6 as the analyte. The vertical axis shows change in the response (RU) before and after IL-6 interaction, and the horizontal axis shows the concentration of kynurenine (µmol/L) contained in the solution at that time.

(4-2) Assessment for the Effect of Kynurenine Concentration on Human IL-6 Binding Then, the effect of kynurenine concentration on antigen-antibody reaction between A11 and human IL-6 was assessed using Biacore T200 (GE Healthcare). The running buffer used was 10 mmol/l ACES, 150 mmol/l NaCl, 0.05% (w/v) Tween20, pH 7.4. Antigen-antibody reaction between A11 and human IL-6 was assessed at 25° C. A11 was immobilized onto sensor chip CM5 by amine coupling, and as an analyte IL-6 was diluted to 1 µmol/l with 10 mmol/l ACES, 150 mmol/l NaCl, 0.05% (w/v) Tween20, pH 7.4 containing kynurenine at various concentrations, and allowed to interact for 60 seconds to observe changes in the amount of binding. The result is shown in FIG. 5. This result demonstrated that the higher the concentration of kynurenine as a switch, the more IL-6 binds to A11.

Figure 6:
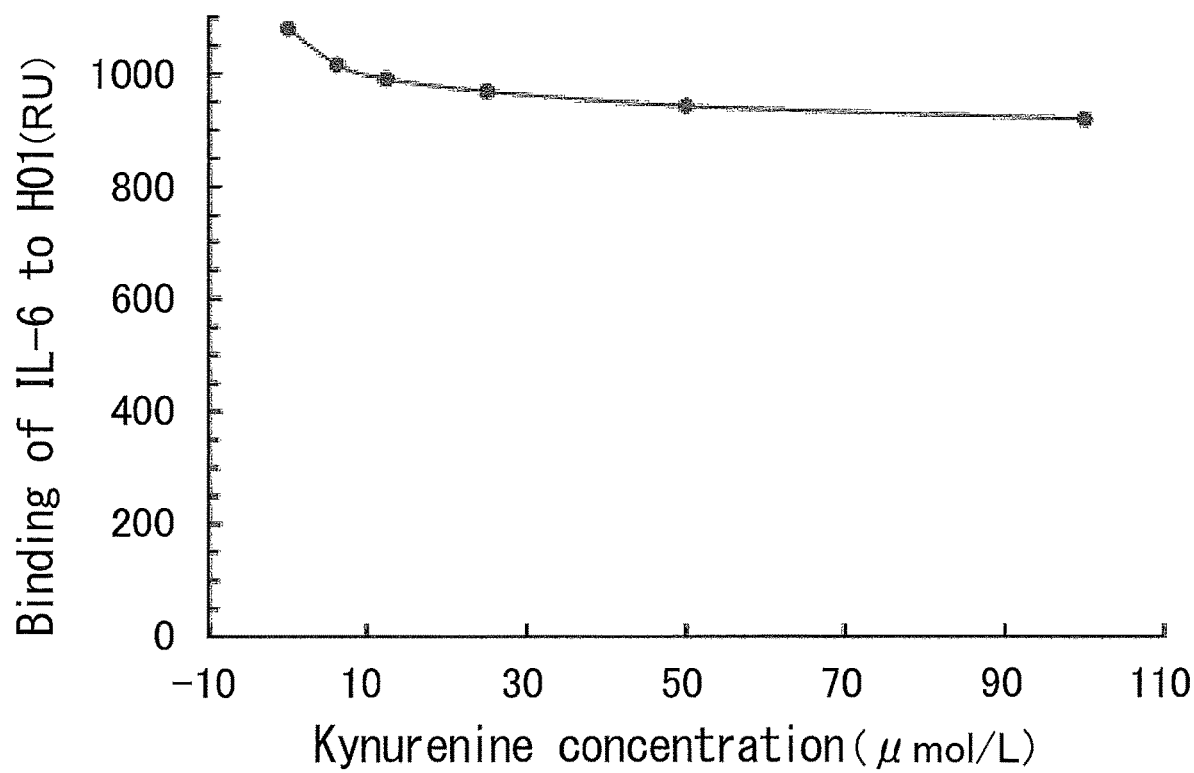
FIG. 6 shows a graph that evaluates the response to H01 which has been immobilized onto Sensorchip CM5, when interaction is allowed to take place for 60 seconds with 1 µmol/L of IL-6 as the analyte. The vertical axis shows change in the response (RU) before and after IL-6 interaction, and the horizontal axis shows the concentration of kynurenine contained in the solution (µmol/L) at that time.

Next, the same experiment as described above was carried out to assess the effect of kynurenine concentration on antigen-antibody reaction between human IL-6 and the human IL-6-binding antibody H01 (the heavy chain and light chain are SEQ ID NOs: 36 and 37, respectively) immobilized on sensor chip CM5, which was derived from a library and served as a control for the switch function of kynurenine in A11. The result is shown in FIG. 6. This result confirmed that for the control anti-IL-6 antibody H01 derived from a library, its binding to IL-6 is not altered even if the kynurenine concentration changes.

Figure 7:
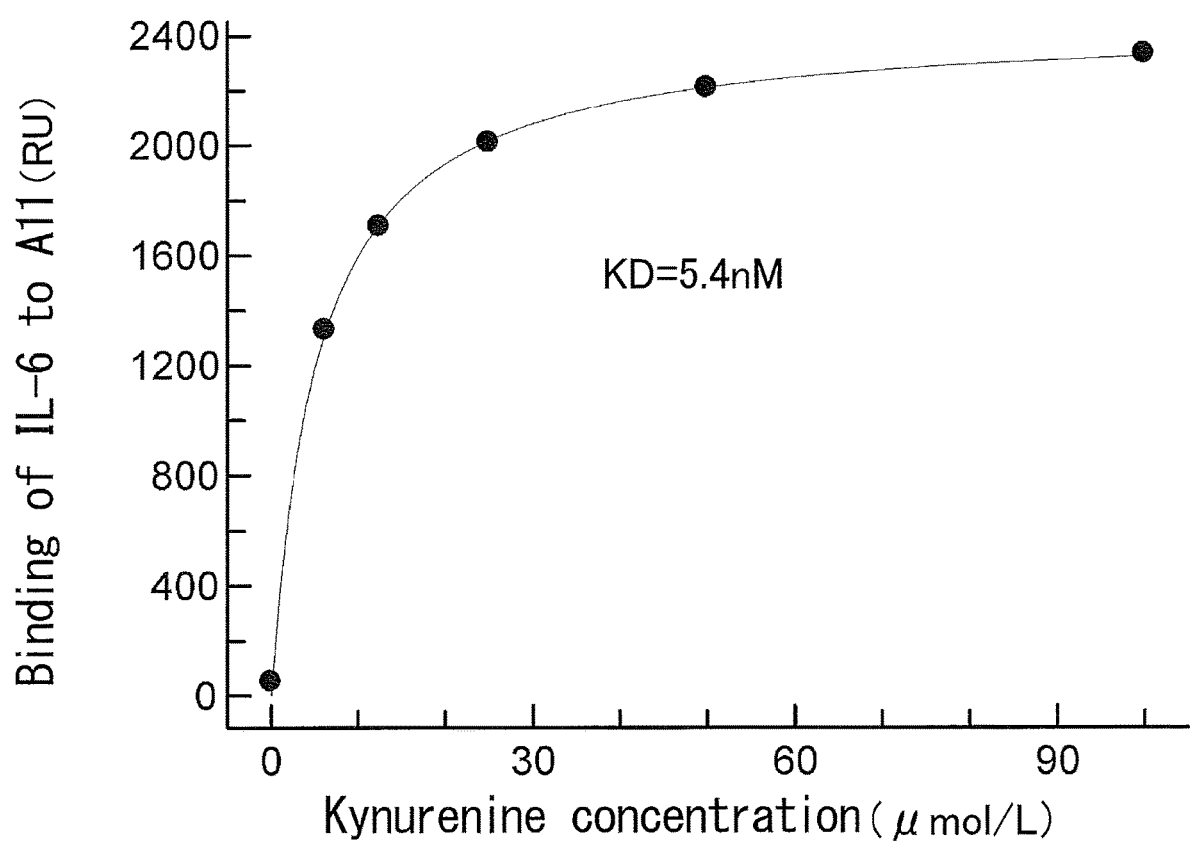
FIG. 7 shows a graph that evaluates the response to IL-6 which has been immobilized onto Sensorchip CM5, when interaction is allowed to take place for 60 seconds with 0.1 µmol/L of A11 as the analyte. The vertical axis shows change in the response (RU) before and after A11 interaction, and the horizontal axis shows the concentration of kynurenine contained in the solution (µmol/L).

Then, the effect of the concentration of kynurenine as a switch in the divalent binding of A11 to IL-6 was assessed using Biacore T200 (GE Healthcare). The running buffer used was 10 mmol/l ACES, 150 mmol/l NaCl, 0.05% (w/v) Tween20, pH 7.4. Antigen-antibody reaction between A11 and human IL-6 was assessed at 25° C. IL-6 was immobilized onto sensor chip CM5 by amine coupling, and as an analyte A11 was diluted to 0.1 µmol/l with 10 mmol/l ACES, 150 mmol/l NaCl, 0.05% (w/v) Tween20, pH 7.4 containing various concentrations of kynurenine, and allowed to interact for 60 seconds to observe changes in the amount of divalent binding of A11 to IL-6. The result is shown in FIG. 7. In this assay system, A11 is expected to bind in a divalent manner since IL-6 is immobilized on a sensor chip. With such an assay system where A11 recognizes IL-6 in a divalent manner, the amount of A11 bound to IL-6 was also observed to increase with a higher kynurenine concentration. This result demonstrated that A11 has the property that in its divalent binding, it also binds to IL-6 via kynurenine as a switch.

(4-3) Effect of Kynurenine as a Switch on the Dissociation of Antibodies from Human IL-6

Figure 8:
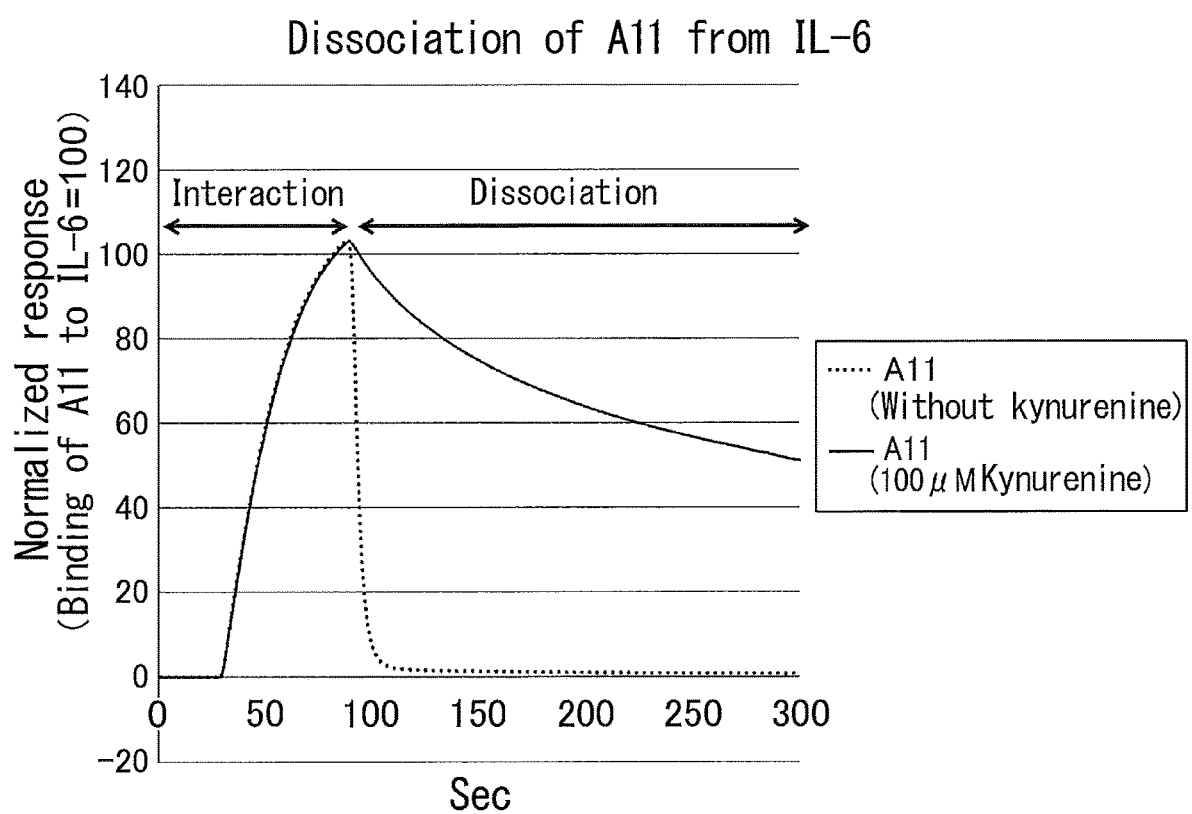
FIG. 8 shows a graph obtained by allowing A11 to interact with IL-6 immobilized on Sensorchip CM5 in the presence of 100 µmol/L kynurenine, and then observing the dissociation of A11 from IL6 in the presence of a buffer containing 100 µmol/L kynurenine or in the presence of a buffer that does not contain kynurenine. In the figure, the vertical axis shows values normalized by defining the amount of A11 bound in the presence of 100 µmol/L kynurenine as 100, and the horizontal axis shows the passage of time (in seconds) from the start of the interaction.

Using Biacore T200 (GE Healthcare), A11 bound to IL-6 in the presence of kynurenine was tested to assess whether in the absence of kynurenine, it dissociates in a kynurenine concentration-dependent manner. The running buffer used was 10 mmol/l ACES, 150 mmol/l NaCl, 0.05% (w/v) Tween20, pH 7.4, and 10 mmol/l ACES, 150 mmol/l NaCl, 0.05% (w/v) Tween20, pH 7.4, 100 µmol/l kynurenine. Assay was carried out at 25° C. IL-6 was immobilized onto sensor chip CM5 by amine coupling, and as an analyte A11 was diluted to 0.1 µmol/l with 10 mmol/l ACES, 150 mmol/l NaCl, 0.05% (w/v) Tween20, pH 7.4, containing 100 µmol/l kynurenine, and allowed to interact for 60 seconds. Then, the dissociation of IL-6 was monitored with each type of running buffer. In order to compare the degree of dissociation between respective running buffer conditions, the amounts of IL-6 bound to A11 were normalized and compared by taking the value in the presence of 100 µmol/l kynurenine as 100. A sensorgram representing the interaction between A11 and IL-6 after normalization is shown in FIG. 8. The result shown in FIG. 8 demonstrates that A11 has the property that it binds to IL-6 in the presence of kynurenine and then rapidly dissociates from IL-6 in the absence of kynurenine. Specifically, the kynurenine-mediated regulation of the antibody binding to human IL-6 by kynurenine was demonstrated to be completely reversible.

These results demonstrated that A11 is an antibody that binds to IL-6 in the presence of kynurenine via kynurenine as a switch, but is dissociated from IL-6 in the absence of kynurenine. It was also confirmed that it is possible to have full ON/OFF regulation of A11 so that it has no human IL-6-binding activity in the absence of kynurenine. The switch function was expected to be achieved in the manner such as shown in FIG. 2.

(4-4) Assessment of Kynurenine for its Binding to Human IL-6

The interaction between IL-6 (Kamakura Techno-Science, Inc.) and kynurenine was analyzed using Biacore T200 (GE Healthcare). Sensor chip CM5 (GE Healthcare) was immobilized with about 5000 RU of IL-6 by amine coupling, and 800, 400, 200, 100, 50, or 25 nmol/l kynurenine was allowed to interact with IL-6. The running buffer used was 10 mmol/l ACES, 150 mmol/l NaCl, 0.05% (w/v)

Figure 9:
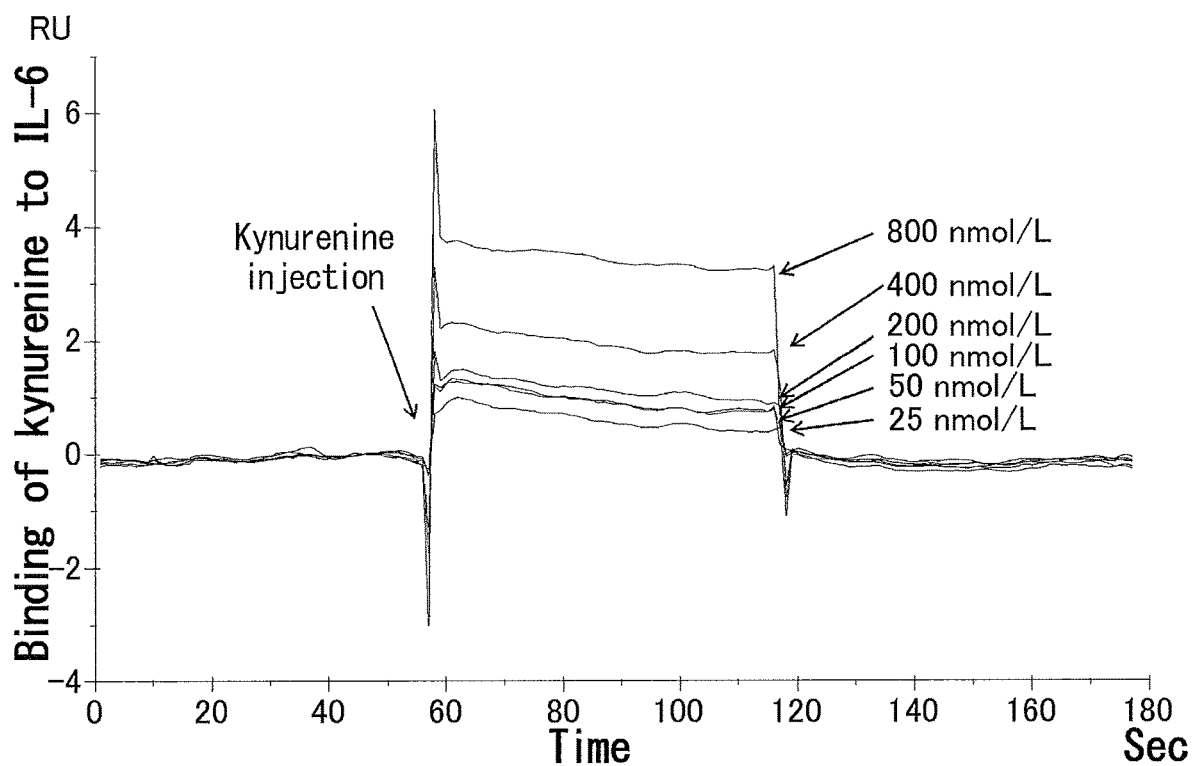
FIG. 9 shows a sensorgram obtained by allowing 800, 400, 200, 100, 50, or 25 nmol/L of kynurenine to interact with IL-6 immobilized on a sensorchip. The vertical axis shows change in the amount of IL-6 bound by kynurenine (RU) (the response at the start of the interaction experiment was defined as 0), and the horizontal axis shows the passage of time from the start of the interaction experiment.

Tween20, pH 7.4. All measurements for the interaction described above were carried out at 25° C. Kynurenine was diluted using the running buffer. The obtained sensorgram showing the interaction between IL-6 and kynurenine is shown in FIG. 9.

About 5000 RU of IL-6 was immobilized in the above-described experiment. The molecular weights of IL-6 and kynurenine were about 20000 g/mol and about 200 g/mol, respectively. Thus, at maximum about 50 RU of kynurenine was expected to interact. Under the measurement condition described above, however, obvious interaction with IL-6 was not detectable even when kynurenine was allowed to interact at a maximal concentration of 800 nmol/l.

Based on the result of the Example described above, the KD of kynurenine for formation of the complex consisting of A11, IL-6, and kynurenine is estimated to be several tens nM to several nM. This also suggests that if hypothetically kynurenine interacts directly with IL-6, the interaction would be observed unambiguously when kynurenine was allowed to interact at 800 nmol/l. The result described above implies the possibility that kynurenine does not interact directly with IL-6 but interacts with A11 or the A11-IL-6 complex at several tens nM.

Figure 10:
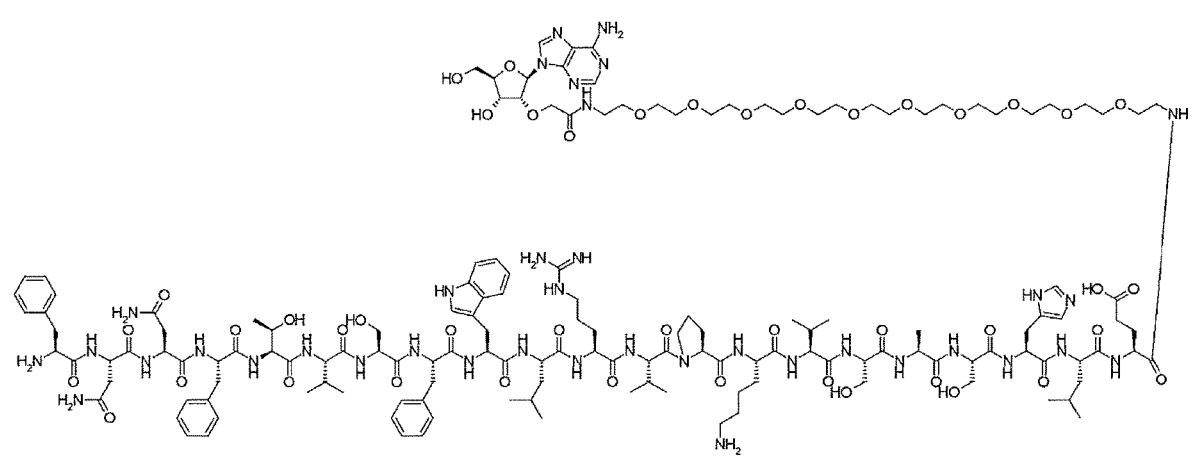
FIG. 10 shows the structure of 2'-Adenosine-PEG-peptide which is an adenosine analog used for immunization of rabbits.
Figure 11:
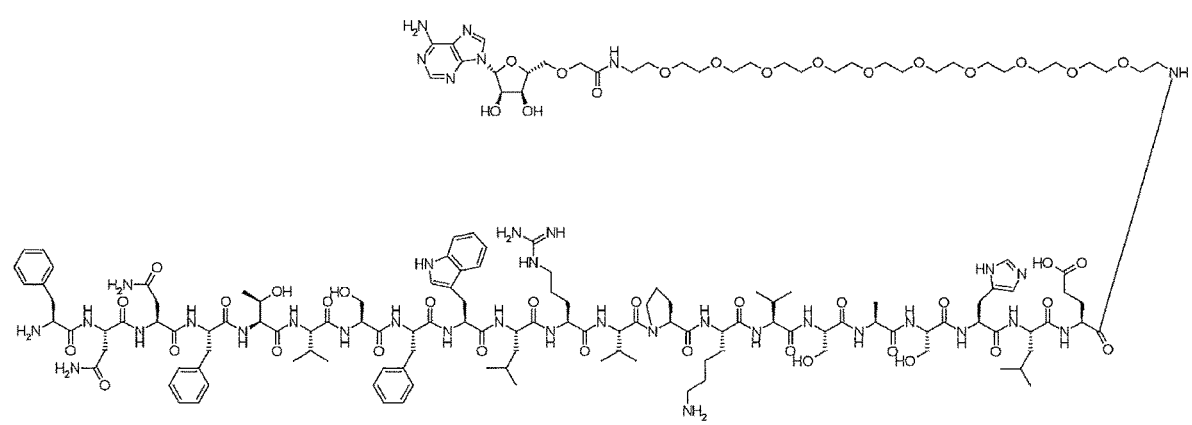
FIG. 11 shows the structure of 5'-Adenosine-PEG-peptide which is an adenosine analog used for immunization of rabbits.

[Example 5] Acquisition of Anti-Adenosine Antibodies by Rabbit B Cell Cloning (5-1) Design of Immunogen to Construct Adenosine-Binding Library The immunogens used in immunizing rabbits were 2'-Adenosine-PEG-Tetanus toxin p30 helper peptide (2'-Adenosine-PEG-peptide) shown in FIG. 10 and 5'-Adenosine-PEG-Tetanus toxin p30 helper peptide (5'-Adenosine-PEG-peptide) shown in FIG. 11. The Tetanus toxin p30 helper peptide consists of the amino acid sequence FNNFTVSFWLRVPKVSASHLE (SEQ ID NO: 4), and is a peptide identified as an epitope of T cell receptor expressed on helper T cells (Eur. J. Immunol. (1989) 19, 2237-2242). The peptide is known to activate antibody production (J. Immunol. (1992) 149, 717-721). When linked to adenosine, the peptide serves as an adjuvant and thus is expected to enhance the production of antibodies against adenosine. The linkage between adenosine and the Tetanus toxin p30 helper peptide was designed to be through PEG so that epitopes of antibodies against adenosine can hardly contain the Tetanus toxin p30 helper peptide. Adenosine is an ATP metabolite, and since the phosphate groups of ATP are attached to the 5' hydroxyl group of adenosine, antibodies that do not recognize the 5' hydroxyl group of adenosine as an epitope may also bind to ATP in addition to adenosine. That is, it would be easier to obtain antibodies that can bind to both adenosine and ATP by using as an immunogen the 5'-Adenosine-PEG-Tetanus toxin p30 helper peptide, while it would be easier to obtain antibodies that bind to adenosine but not to ATP by using as an immunogen the 2'-Adenosine-PEG-Tetanus toxin p30 helper peptide. For this reason, the two types of immunogens which contain the Tetanus toxin p30 helper peptide linked to the 2' or 5' position of adenosine were prepared in the manner described in (5-2).

Figure 12:
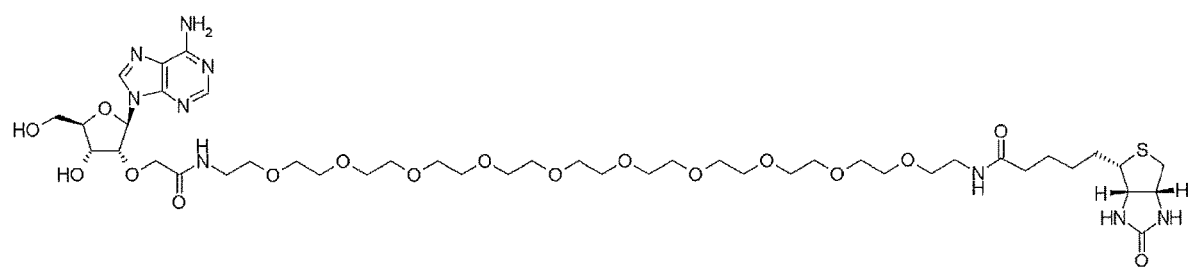
FIG. 12 shows the structure of 2'-Adenosine-PEG-biotin produced by substituting biotin for the peptide portion of the adenosine analog used for immunization of rabbits.
Figure 13:
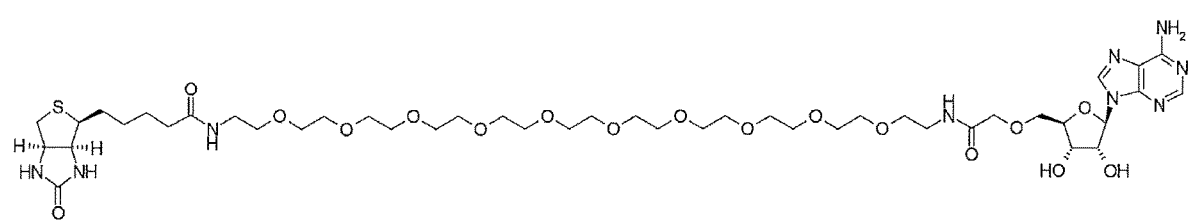
FIG. 13 shows the structure of 5'-Adenosine-PEG-biotin produced by substituting biotin for the peptide portion of the adenosine analog used for immunization of rabbits.

In addition, 2'-Adenosine-PEG-biotin (FIG. 12) and 5'-Adenosine-PEG-biotin (FIG. 13), in which biotin is conjugated instead of the Tetanus toxin p30 helper peptide, were produced as described below. By assessing the binding to these two types of Adenosine-PEG-biotin, antibodies can be tested to demonstrate that their epitopes do not contain the Tetanus toxin p30 helper peptide.

(5-2) Synthesis of Immunogens to Prepare Adenosine-Binding Library

2'-Adenosine-PEG-peptide (adenosine 2'-PEG-peptide conjugate or 2'-(PEG-peptide)adenosine) and 2'-Adenosine-PEG-biotin (adenosine 2'-PEG-biotin conjugate or 2'-(PEG-biotin)adenosine) were synthesized in the manner described below. The synthesized 2'-Adenosine-PEG-peptide and 2'-Adenosine-PEG-biotin were analyzed or fractionated under the conditions below.

The conditions of LCMS analysis are noted as below.

TABLE 5

| Analysis condition | Apparatus | Column (length, mm) | Mobile phase | Gradient (A/B) | Flow rate (ml/min) | Column temperature (° C.) | Wavelength |
| --- | --- | --- | --- | --- | --- | --- | --- |
| SQDAA05 | Acquity UPLC/SQD | Aldrich Ascentis Express C18 (2.1 × 50) | A) 10 mM AcONH4, H2O B) MeOH | 95/5 => 0/100 (1.0 min) => 0/100 (0.4 min) | 1.0 | 35 | 210-400 nm PDA total |
| SQDAA50 | Acquity UPLC/SQD | Aldrich Ascentis Express C18 (2.1 × 50) | A) 10 mM AcONH4, H2O B) MeOH | 50/50 => 0/100 (0.7 min) => 0/100 (0.7 min) | 1.0 | 35 | 210-400 nm PDA total |
| SQDFA05 | Acquity UPLC/SQD | Aldrich Ascentis Express C18 (2.1 × 50) | A) 0.1% FA, H2O B) 0.1% FA CH3CN | 95/5 => 0/100 (1.0 min) => 0/100 (0.4 min) | 1.0 | 35 | 210-400 nm PDA total |
| SQDFA50 | Acquity UPLC/SQD | Aldrich Ascentis Express C18 (2.1 × 50) | A) 0.1% FA, H2O B) 0.1% FA CH3CN | 50/50 => 0/100 (0.7 min) => 0/100 (0.7 min) | 1.0 | 35 | 210-400 nm PDA total |

The conditions of preparative HPLC are described as below.

TABLE 6

| Preparative condition | Apparatus | Column (length, mm) | Mobile phase | Gradient(A/B) | Flow rate (ml/min) | Column temperature (° C.) | Wavelength |
| --- | --- | --- | --- | --- | --- | --- | --- |
| A | Preparative HPLC system with injection/ fractionation (Gilson, Inc.) | Aldrich Ascentis RP-Amide (21.2 × 150 mm 5 μm) | A) 0.1% FA H2O B) 0.1% FA MeCN | isocratic (A/B): 15/85 | 20.0 | 40 | 254, 258 nm |

TABLE 6-continued

| Preparative condition | Apparatus | Column (length, mm) | Mobile phase | Gradient(A/B) | Flow rate (ml/min) | Column temperature (° C.) | Wavelength |
|---|---|---|---|---|---|---|---|
| B | Preparative HPLC system with injection/ fractionation (Gilson, Inc.) | YMC Actus ODS-A (20 × 100 mm 5 μm) | A) 20 mM AcONH4 H2O B) 20 mM AcONH4 MeOH/MeCN(1/1) | isocratic (A/B): 47/53 | 20.0 | 40 | 254, 258 nm |

(5-2-1) Synthesis of Compound 006 (Boc-Phe-Asn-Asn-Phe-Thr (tBu)-Val-Ser (tBu)-Phe-Trp (Boc)-Lue-Arg (Pbf)-Val-Pro-Lys (Boc)-Val-Ser (tBu)-Ala-Ser (tBu)-his (Trt)-Leu-Glu (tBu)-OH)

Peptide synthesis was performed by the Fmoc method using a peptide synthesizer (Multipep RS; Intavis). All Fmoc amino acids were purchased from WATANABE CHEMICAL INDUSTRIES, LTD. The detailed procedure of the treatment was in the manual attached to the synthesizer.

Fmoc-Glu(tBu)-OH linked at its C terminus to 2-chlorotrityl resin (250 mg/column, 30 columns, 11.7 mmol), an N,N-dimethylformamide solution containing various Fmoc amino acids (0.6 mol/l) and 1-hydroxy-7-azabenzotriazole (0.375 mol/l), and an N,N-dimethylformamide solution (10% v/v) of diisopropylcarbodiimide were loaded in the synthesizer. The synthesis reaction was performed using as an Fmoc-deprotection solution, an N,N-dimethylformamide

[Compound 6]

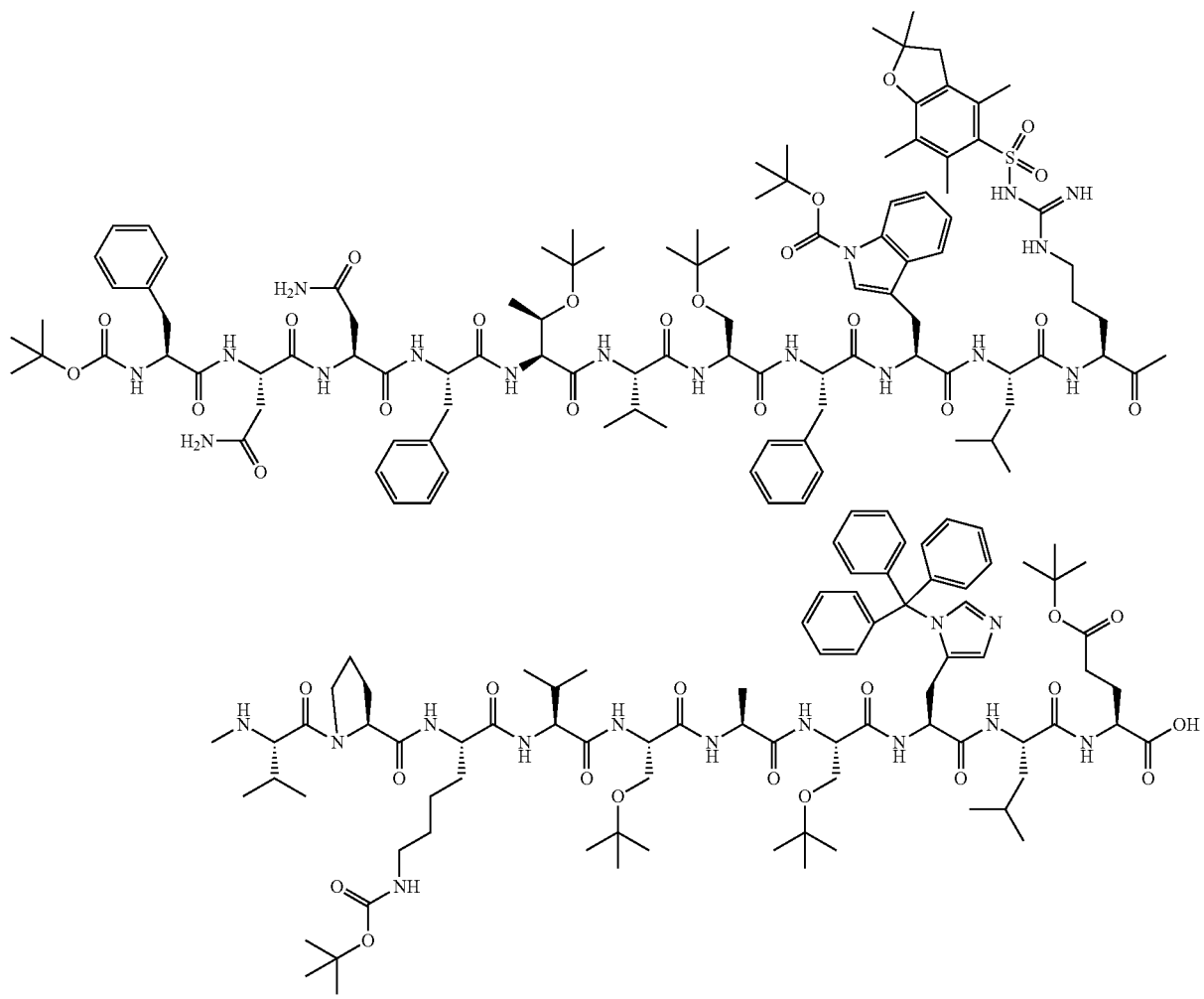

solution (200 v/v) containing piperidine and 50 (wt/v) urea. After the resin was washed with N,N-dimethylformamide, Fmoc deprotection was carried out, followed by one cycle of Fmoc amino acid condensation reaction. This cycle was repeated to elongate peptides on the resin surface. After elongation, the resin was washed with trifluoroethanol. Peptides were cleaved off from the resin by adding trifluoroethanol/dichloromethane (=1/1). Thus, compound 006 (7.2 g) was obtained as a crude product.

LCMS (ESI) m/z=1185 (M+3H)3+

(5-2-2) Synthesis of Compound 007

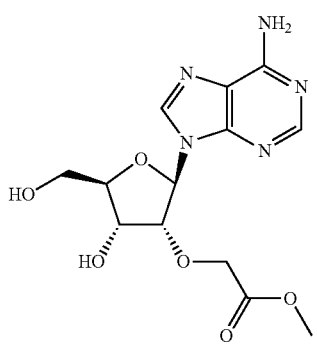
[Compound 7]

A suspension of adenosine (2.00 g, 7.48 mmol) in N,N-dimethylformamide (40 ml) was cooled down to 0° C., and 60% sodium hydride (0.42 g, 10.48 mol) was added thereto. The reaction mixture was stirred for one hour at 0° C. After adding methyl bromoacetate (0.76 ml, 8.01 mmol), the resulting reaction mixture was stirred for five hours at room temperature, and acetic acid (1 ml) and methanol (3 ml) were added thereto. The reaction mixture was concentrated under reduced pressure. The resulting residue was purified by normal phase silica gel column chromatography (dichloromethane/methanol). Thus, compound 007 (0.93 g, 37%) was obtained.

LCMS (ESI) m/z=340 (M+H)+

Retention time: 0.27 minute (Analysis condition, SQDFA05)

(5-2-3) Synthesis of Compound 008

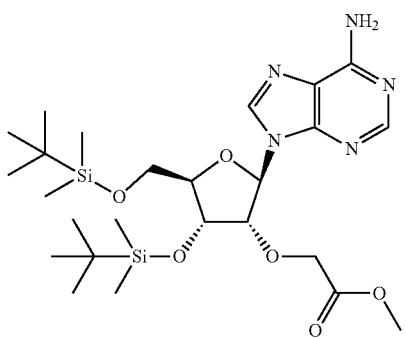
[Compound 8]

t-Butyldimethylsilyl chloride (999 mg, 6.63 mol) and imidazole (722 mg, 10.61 mol) were added to a pyridine solution (8 ml) of compound 007 (900 mg, 2.65 mmol). The reaction mixture was stirred for four hours at room temperature, and extracted with ethyl acetate/water. The extracted organic layer was washed with a saturated sodium chloride solution, and dried over anhydrous sodium sulfate. After filtration, the organic layer was concentrated under reduced pressure. The resulting residue was purified by normal phase silica gel column chromatography (dichloromethane/methanol). Thus, compound 008 (1.17 g, 78%) was obtained.

LCMS (ESI) m/z=568 (M+H)+

Retention time: 1.10 minute (Analysis condition, SQDFA05)

(5-2-4) Synthesis of Compound 009

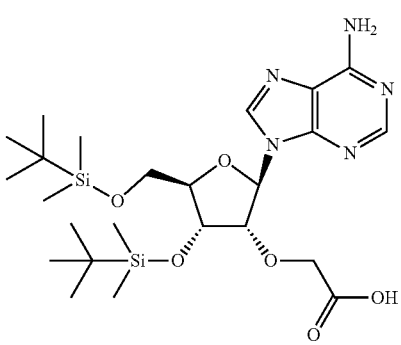
[Compound 9]

Lithium hydroxide (61 mg, 2.55 mol) dissolved in water (0.17 ml) was added to a solution of compound 008 (290 mg, 0.511 mmol) in methanol (0.34 ml)/tetrahydrofuran (0.34 ml). The reaction mixture was stirred for 30 minutes at room temperature. The mixture was neutralized with 1 M hydrochloric acid, and concentrated under reduced pressure. The concentrated residue was extracted with ethyl acetate/water. The resulting organic layer was washed with a saturated sodium chloride solution, and dried over anhydrous sodium sulfate. After filtration, the organic layer was concentrated under a reduced pressure. Thus, compound 009 (319 mg, 90%) was obtained.

LCMS (ESI) m/z=552(M−H)−

Retention time: 0.97 minute (Analysis condition, SQDFA05)

(5-2-5) Synthesis of Compounds 010 and 011

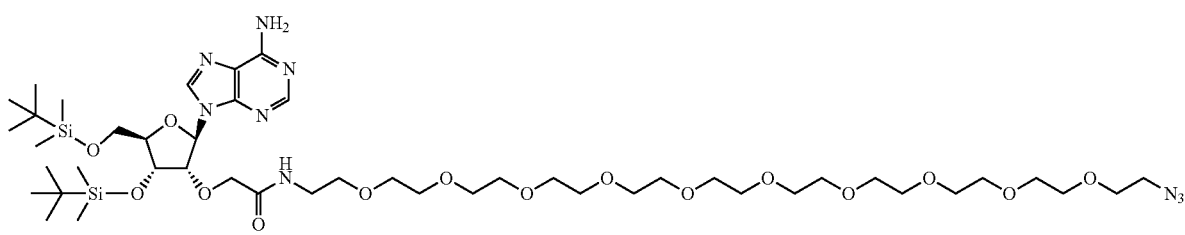
[Compound 10]

Retention time: 1.24 minute (Analysis condition, SQDAA05)

[Compound 11]

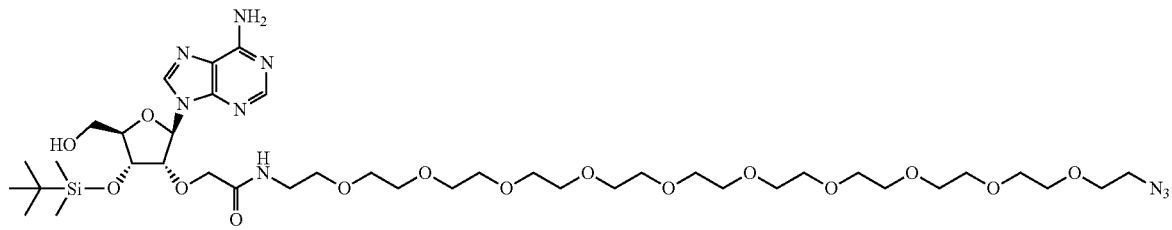

1-Hydroxybenzotriazole (75 mg, 0.553 mol) and 1-ethyl-3-(3-dimethylaminopropyl) carbodiimide hydrochloride (106 mg, 0.553 mol) were added to an N,N-dimethylformamide (1.5 ml) solution of compound 009 (255 mg, 0.460 mmol), and it was stirred for three minutes at room temperature. O-(2-aminoethyl)-O'-2-azidoethyl) nonaethylene glycol (291 mg, 0.553 mmol) was added to the reaction mixture, and it was stirred for three hours at room temperature. The reaction mixture was concentrated under a reduced pressure, and the resulting residue was purified by reverse phase silica gel column chromatography (aqueous 10 mM ammonium acetate solution/methanol. Compounds 010 (177 mg, 4%) and 011 (72 mg, 19%) were obtained.

Compound 010
LCMS (ESI) m/z=1063 (M+H)+
Retention time: 0.98 minute (Analysis condition, SQDFA05)

Compound 011
LCMS (ESI) m/z=949 (M+H)+
Retention time: 0.67 minute (Analysis condition, SQDFA05)

(5-2-6) Synthesis of compound 012

[Compound 12]

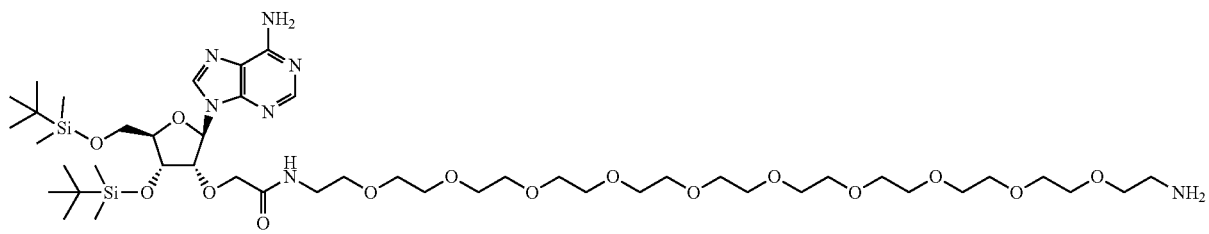

10% palladium carbon (34 mg) was added to a solution of compound 010 (170 mg, 0.160 mmol) in ethanol (1 ml). The reaction mixture was stirred for two hours under hydrogen atmosphere, and again 10% palladium carbon (34 mg) was added thereto. The reaction mixture was stirred for two hours under a hydrogen atmosphere to complete the reaction. The filtrate of the reaction solution was concentrated under a reduced pressure. Compound 012 (34 mg, 95%) was obtained.

LCMS (ESI) m/z=1037 (M+H)+
Retention time: 0.70 minute (Analysis condition, SQDFA05)

(5-2-7) Synthesis of Compounds 013 and 014

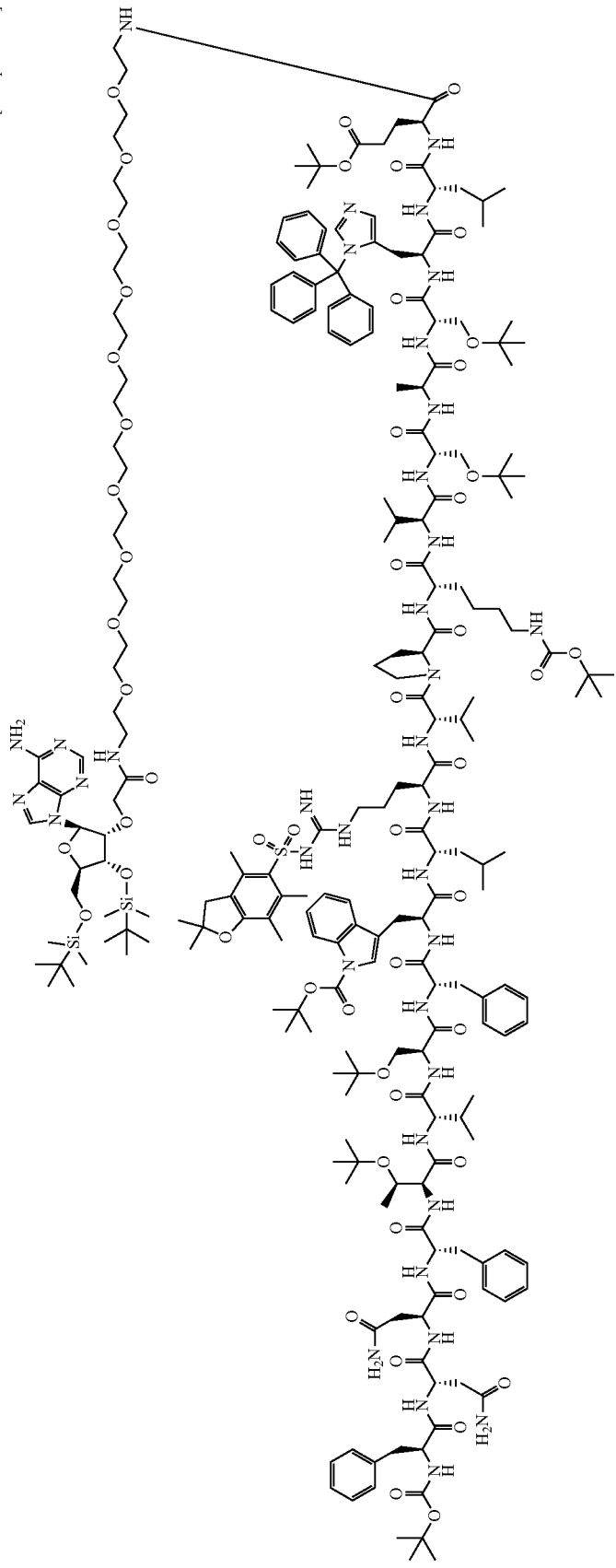
[Compound 13]

-continued
[Compound 14]
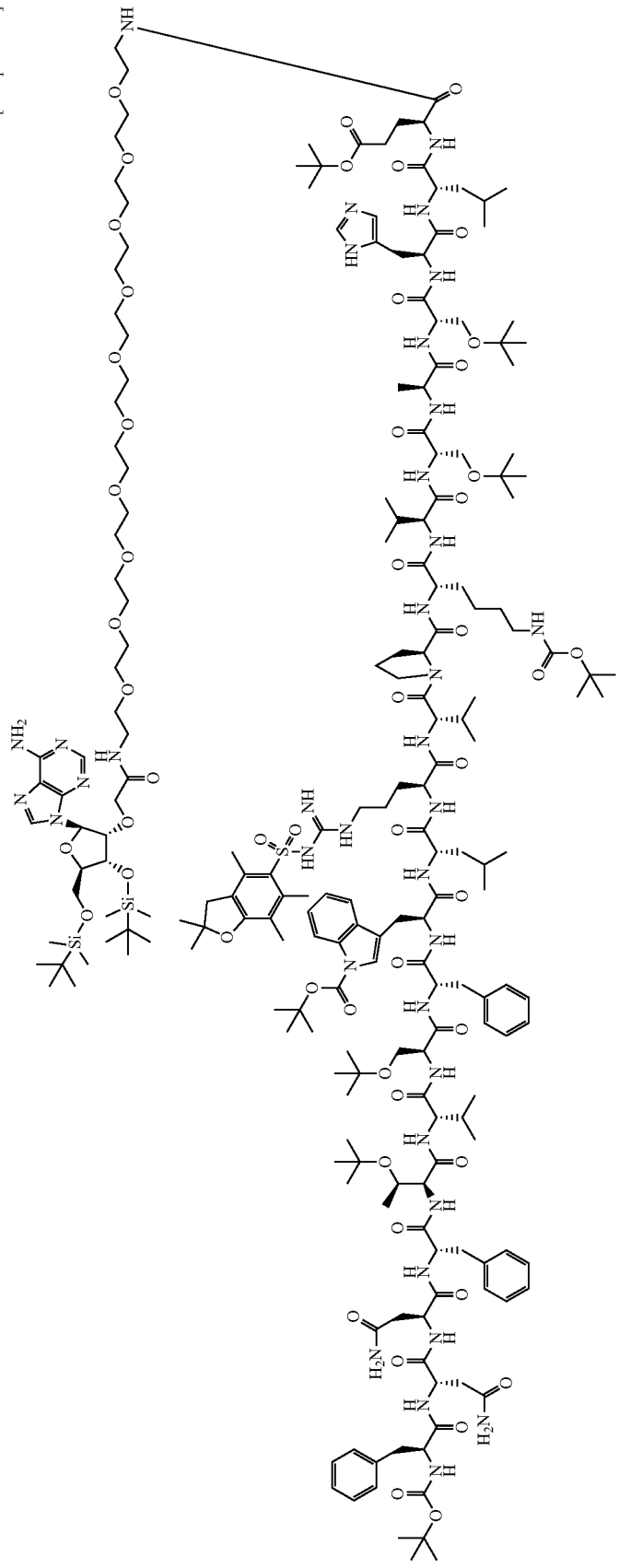

Compound 006 (354 mg, 0.110 mmol), 1-hydroxybenzotriazole (13 mg, 0.100 mol), and 1-ethyl-3-(3-dimethylaminopropyl) carbodiimide hydrochloride (19 mg, 0.100 mol) were added to a solution of compound 012 (86 mg, 0.083 mmol) in N,N-dimethylformamide (1.5 ml), and it was stirred for two hours at room temperature. The filtrate of the reaction mixture was purified by preparative condition A described in Table 6. A mixture of compounds 013 and 014 (72 mg) was obtained.

Compound 013

LCMS (ESI) m/z=1525 (M+3H)3+, 1144 (M+4H)4+

Retention time: 1.13 minute (Analysis condition, SQDAA50)

Compound 014

LCMS (ESI) m/z=1444 (M+3H)3+, 1083 (M+4H)4+

Retention time: 1.02 minute (Analysis condition, SQDAA50)

(5-2-8) Synthesis of 2'-Adenosine-PEG-Peptide (Adenosine 2'-PEG-Peptide Conjugate or 2'-(PEG-Peptide)Adenosine) (Compound 015)

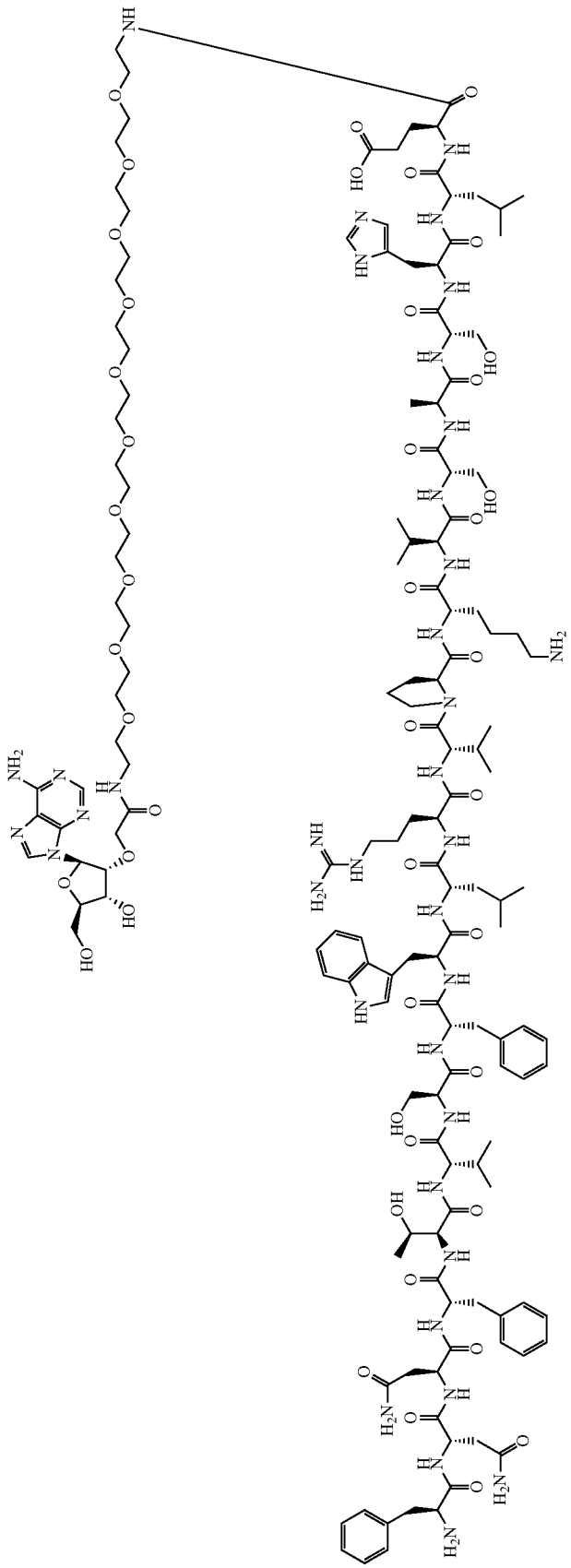
[Compound 15]

Trifluoroacetic acid (16 ml), dichloromethane (8 ml), water (1.3 ml), and tetraisopropylsilane (1.3 ml) were added to the mixture of compounds 013 and 014 (42 mg), and it was stirred for six hours at room temperature. The residue obtained by concentrating the reaction mixture under reduced pressure was purified by preparative condition B described in Table 6. Thus, compound 015 (10 mg) was obtained.

LCMS (ESI) m/z=1090 (M+3H)3+, 818 (M+4H)4+

Retention time: 0.52 minute (Analysis condition, SQDAA50)

(5-2-9) Synthesis of Compound 016

[Compound 16]

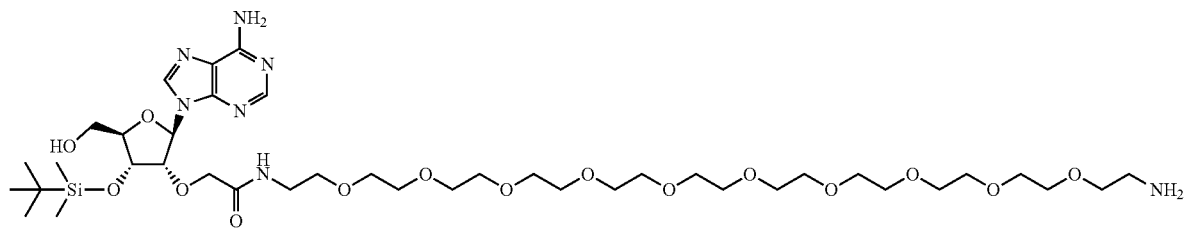

10% palladium carbon (34 mg) was added to a solution of compound 011 (70 mg, 0.074 mmol) in ethanol (1 ml), and the reaction mixture was stirred for five hours under hydrogen atmosphere. The filtrate of the reaction mixture was concentrated under reduced pressure. Thus, compound 016 (58 mg, 85%) was obtained.

LCMS (ESI) m/z=923 (M+H)+

Retention time: 0.50 minute (Analysis condition, SQDFA05)

(5-2-10) Synthesis of Compound 017

[Compound 17]

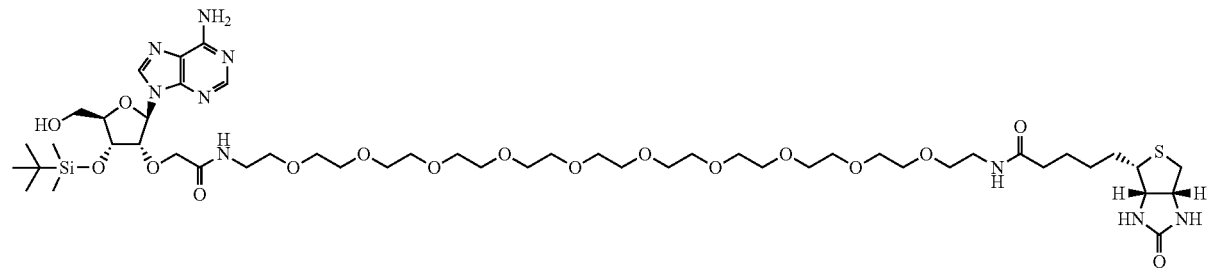

D-biotin N-succinimidyl (24 mg, 0.069 mmol) and triethylamine (13 μl, 0.094 mol) were added to a solution of compound 016 (58 mg, 0.063 mmol) in N,N-dimethylformamide (1 ml), and it was stirred for two hours at room temperature. Then, after D-biotin N-succinimidyl (5 mg, 0.015 mmol) was added, the reaction was completed upon 1.5 hours of stirring at room temperature. The reaction mixture was purified by reverse phase silica gel column chromatography (aqueous 10 mM ammonium acetate solution/methanol. Compound 017 (50 mg, 69%) was obtained.

LCMS (ESI) m/z=1149 (M+H)+

Retention time: 1.04 minute (Analysis condition, SQDFA05)

(5-2-11) Synthesis of 2'-Adenosine-PEG-Biotin (Adenosine 2'-PEG-Biotin Conjugate or 2'-(PEG-Biotin)Adenosine) (Compound 018)

[Compound 18]

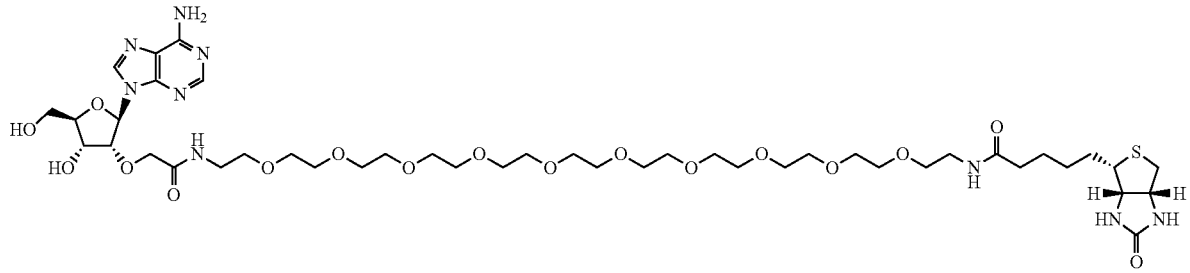

A solution of 1 M tetra-n-butylammonium fluoride in tetrahydrofuran (65 μl, 0.065 mmol) was added to a solution of compound 017 (62 mg, 0.054 mmol) in tetrahydrofuran (2 ml), and it was stirred at room temperature for one hour. Then, 1 M tetra-n-butylammonium fluoride in tetrahydrofuran solution (20 μl, 0.020 mmol) was added, and the reaction was completed by stirring at room temperature for one hour. The reaction mixture was concentrated under a reduced pressure, and the residue was purified by reverse phase silica gel column chromatography (aqueous 0.1% formic acid solution/0.1% formic acid in acetonitrile). Compound 018 (12 mg, 21%) was obtained.

LCMS (ESI) m/z=1035 (M+H)+

Retention time: 0.71 minute (Analysis condition, SQDAA05)

Furthermore, 5'-Adenosine-PEG-peptide and 5'-Adenosine-PEG-biotin were also synthesized by the same reaction.

(5-3) Production of Adenosine-Binding Antibodies in Animals and Antibody Screening Rabbits were immunized with 2'-Adenosine-PEG-peptide and/or 5'-Adenosine-PEG-peptide by a conventional method. Candidates for cells with adenosine-binding activity were selected from suspensions of cells collected from blood of the immunized rabbits, by using autoMACS Pro Separator and FACSAria (BD) which uses Adenosine-PEG-biotin-binding activity and rabbit IgG expression as indicators. Then, screening was carried out with antibodies secreted in the culture supernatants of the selected cells. In the screening, ELISA was performed to assess the presence of binding activity to Adenosine-PEG-biotin. ELISA was also performed to assess whether adenosine, when added in combination with Adenosine-PEG-biotin at a level 1000 times or more of that of Adenosine-PEG-biotin, suppresses the binding to Adenosine-PEG-biotin. The H-chain and L-chain variable regions were isolated by PCR from cells selected using as an indicator the presence of the Adenosine-PEG-biotin-binding activity as well as suppression of the binding to Adenosine-PEG-biotin by adenosine added in combination with Adenosine-PEG-biotin. The obtained variable regions were expressed in combination with a human IgG1 heavy chain constant region and a human light chain constant region.

(5-4) Acquisition of B Cells to Prepare Adenosine-Binding Immune Library

Cells were collected from the spleens of rabbits immunized with the 2'-Adenosine-PEG-Tetanus toxin peptide and 5'-Adenosine-PEG-Tetanus toxin peptide. From the cell suspensions, candidates for cells with adenosine-binding activity were selected using autoMACS Pro Separator and FACSAria (BD) with the presence of binding to Adenosine-PEG-biotin as well as the expression of rabbit IgG or IgM as indicators. The selected cells were washed with PBS(−), and the prepared cell pellets were used to construct immune libraries.

[Example 6] Assessment of Clones Obtained by Rabbit B Cell Cloning (6-1) Assessment of Clones Obtained by Rabbit B Cell Cloning for their Binding Activity to 2'-Adenosine-PEG-Biotin Clones obtained by rabbit B cell cloning were assessed for their binding activity to adenosine by the SPR method. Antigen-antibody reaction between the clones and 2'-Adenosine-PEG-Biotin was kinetically analyzed using Biacore 4000 (GE Healthcare). Sensor chip CM5 (GE Healthcare) was immobilized with an appropriate amount of protein A/G (Invitrogen) by amine coupling. Antibodies of interest were captured by the chip. Then, after 100 nmol/l 2'-adenosine-PEG-Biotin was interacted as an analyte for 60 seconds, the dissociation of the analyte was monitored and measured for 60 seconds. The running buffer used was HBS-P+ (GE Healthcare). All measurements were carried out at 25° C. The analyte was diluted using the running buffer.

Figure 14:
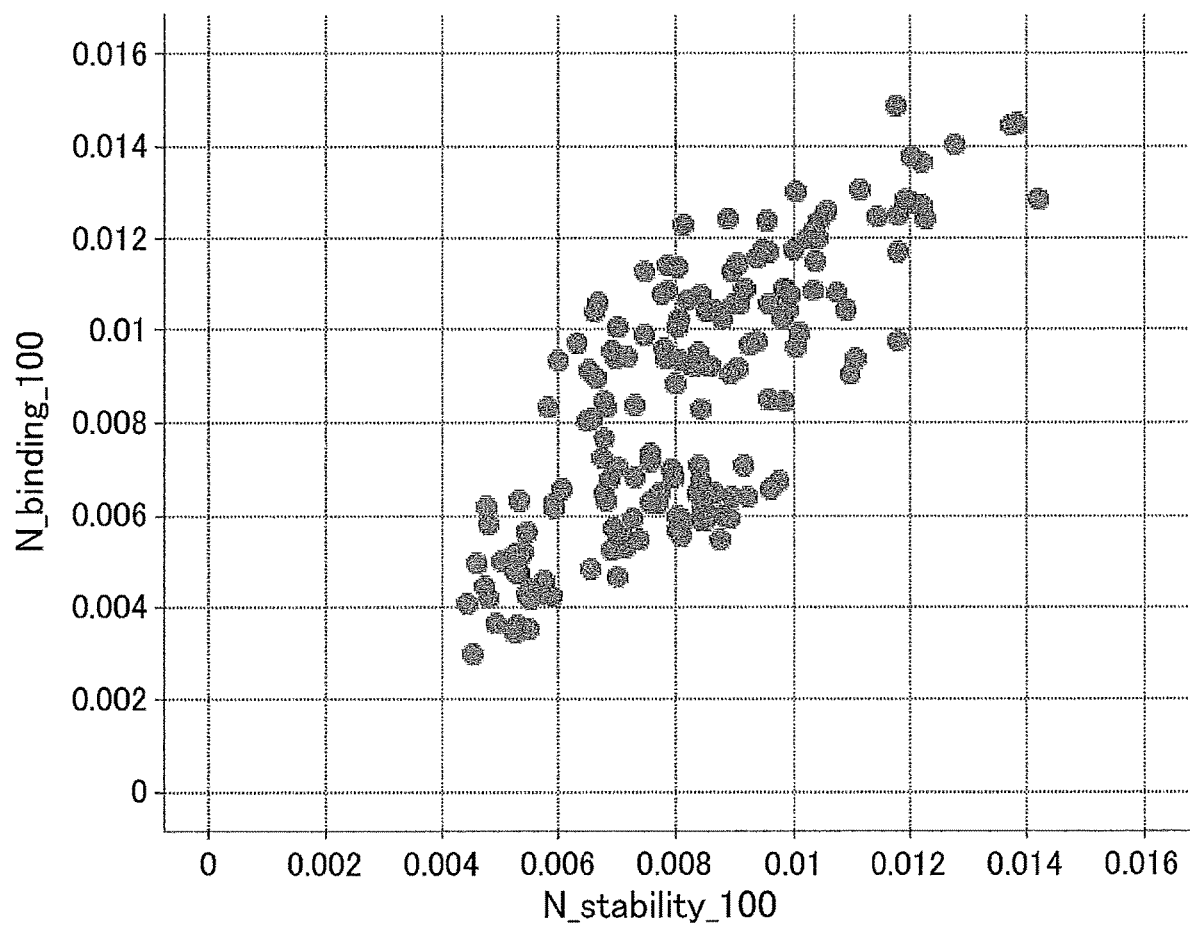
FIG. 14 is a graph where the vertical axis shows the value (N_binding_100) obtained by dividing the amount of binding in the interaction of each antibody with 2'-Adenosine-PEG-biotin by the capture level (RU) of each antibody, and the horizontal axis shows the value (N_stability_100) obtained by dividing the value obtained 60 seconds after dissociation of 2'-Adenosine-PEG-biotin from each antibody after interaction with 2'-Adenosine-PEG-biotin by the capture level (RU) of each antibody.
Figure 15A:
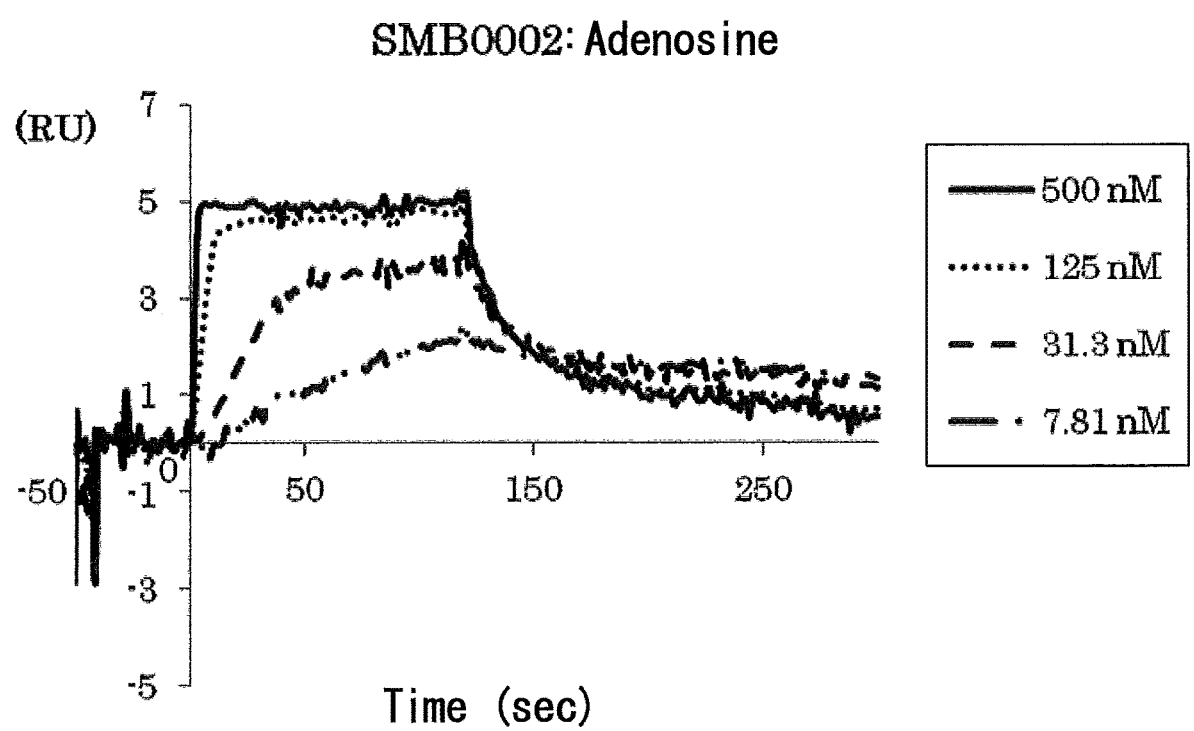
FIG. 15A indicates sensorgrams of surface plasmon resonance-based analyses which show that clone SMB0002 binds to (interacts with) adenosine. The sensorgrams show the interactions between SMB0002 and the antigen at 7.81, 31.3, 125, and 500 nM in order from the bottom.
Figure 15B:
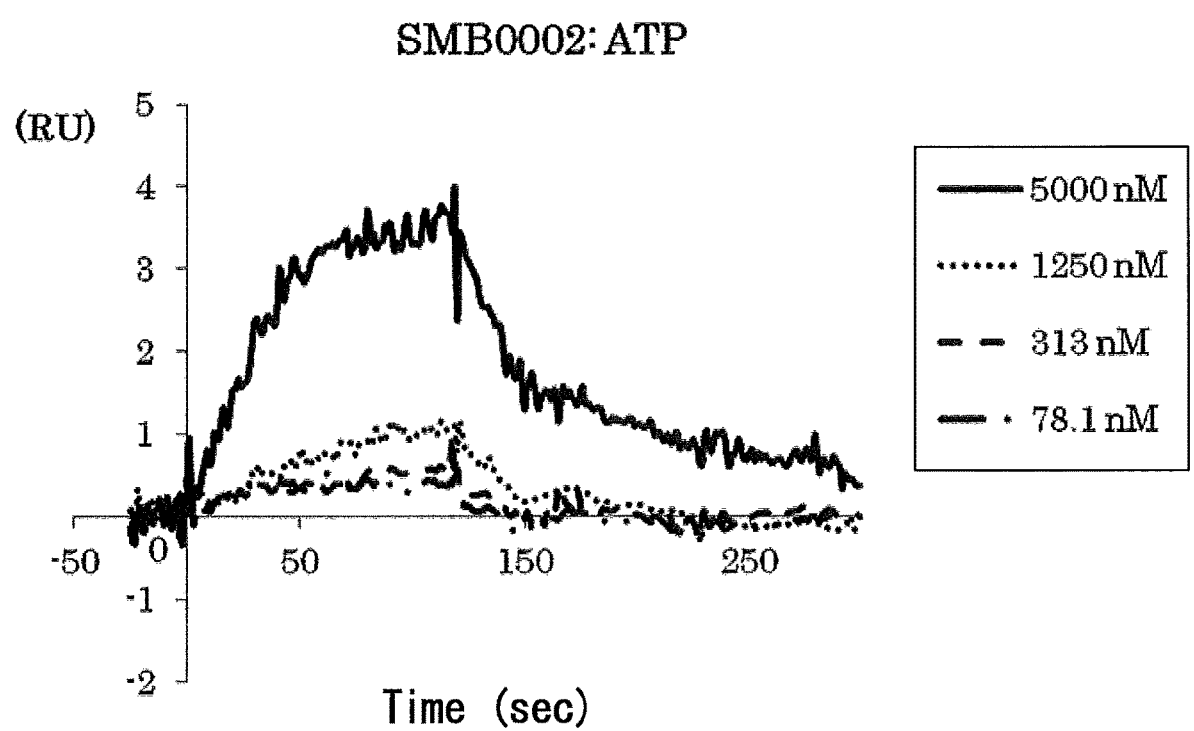
FIG. 15B indicates sensorgrams of surface plasmon resonance-based analyses which show that clone SMB0002 binds to (interacts with) ATP. The sensorgrams show the interactions between SMB0002 and the antigen at 78.1, 313, 1250, and 5000 nM in order from the bottom.
Figure 15C:
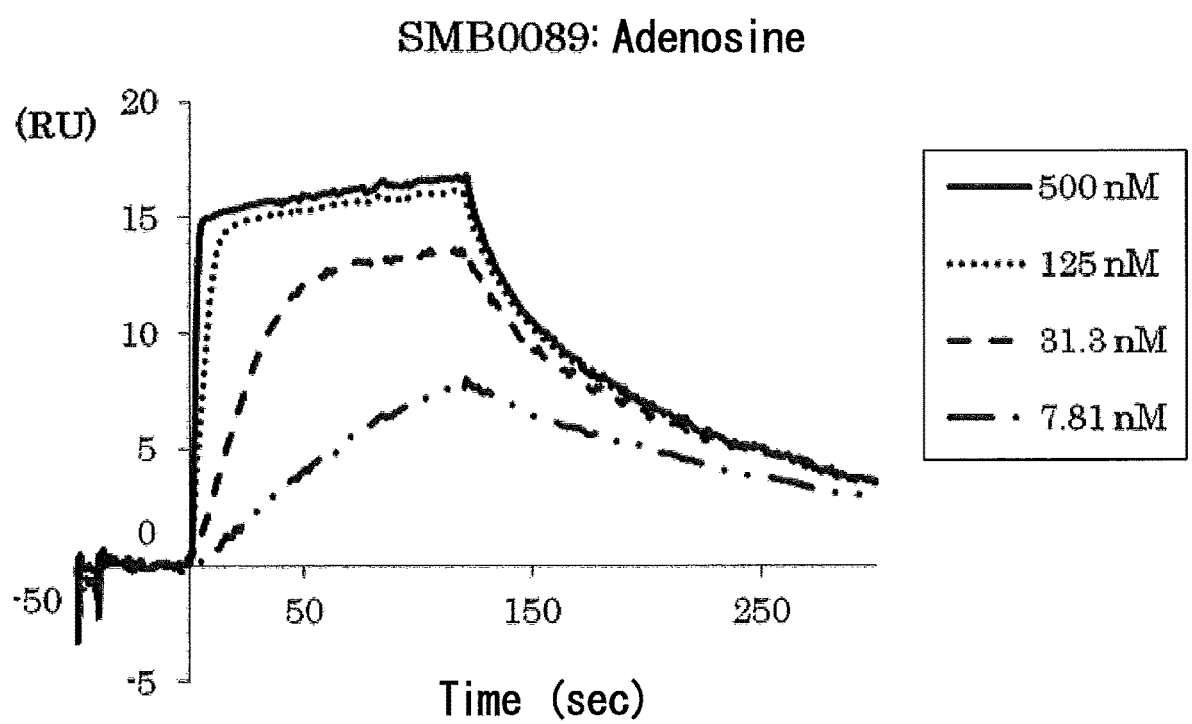
FIG. 15C indicates sensorgrams of surface plasmon resonance-based analyses which show that clone SMB0089 binds to (interacts with) adenosine. The sensorgrams show the interactions between SMB0089 and the antigen at 7.81, 31.3, 125, and 500 nM in order from the bottom.
Figure 15D:
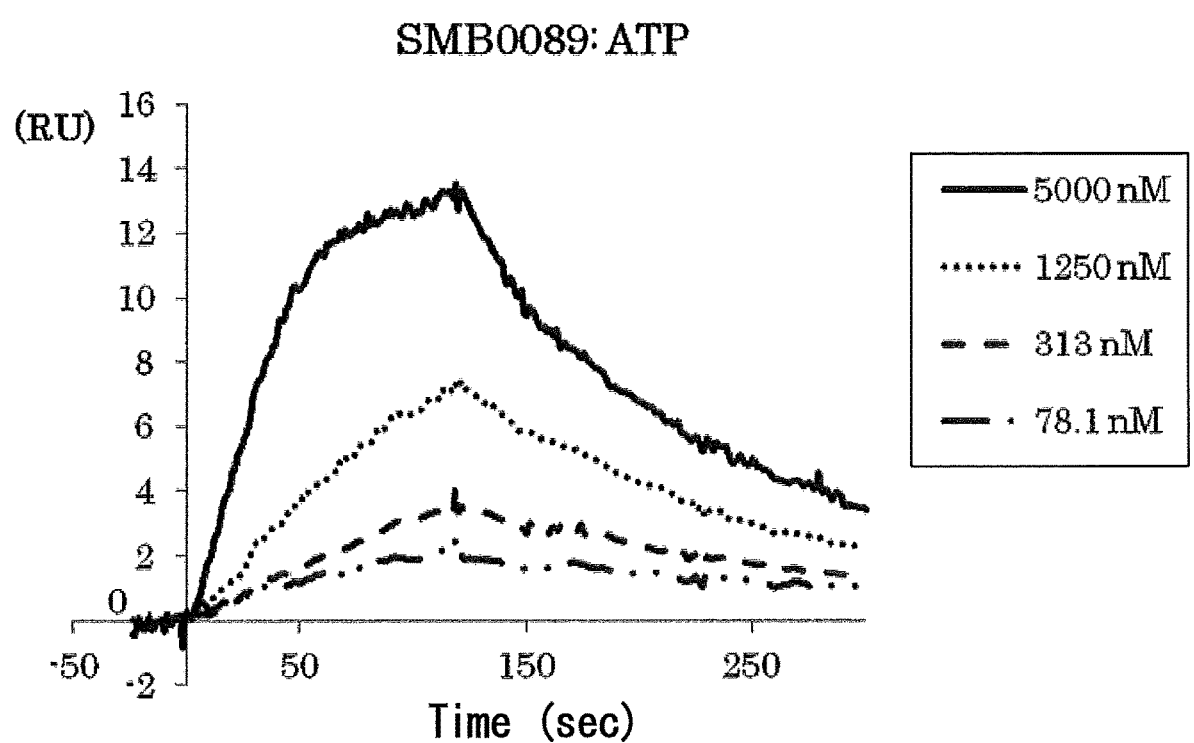
FIG. 15D indicates sensorgrams of surface plasmon resonance-based analyses which show that clone SMB0089 binds to (interacts with) ATP. The sensorgrams show the interactions between SMB00089 and the antigen at 78.1, 313, 1250, and 5000 nM in order from the bottom.
Figure 15E:
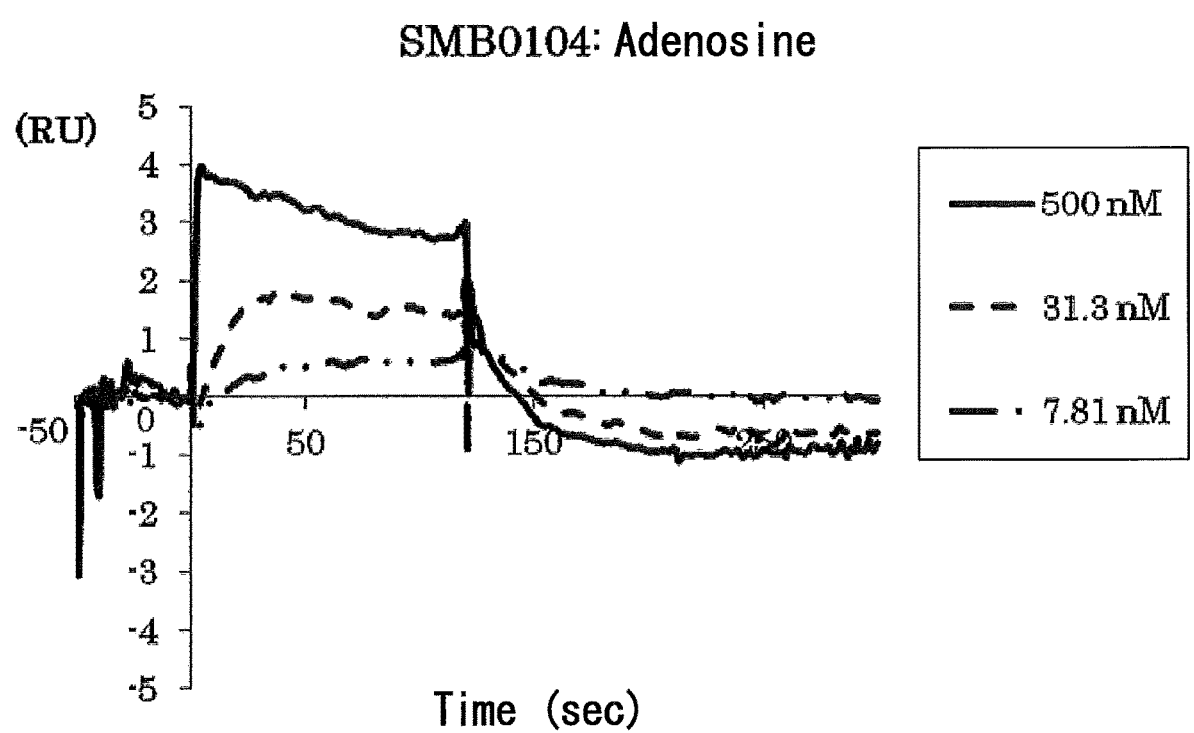
FIG. 15E indicates sensorgrams of surface plasmon resonance-based analyses which show that clone SMB0104 binds to (interacts with) adenosine. The sensorgrams show the interactions between SMB0104 and the antigen at 7.81, 31.3, and 500 nM in order from the bottom.
Figure 15F:
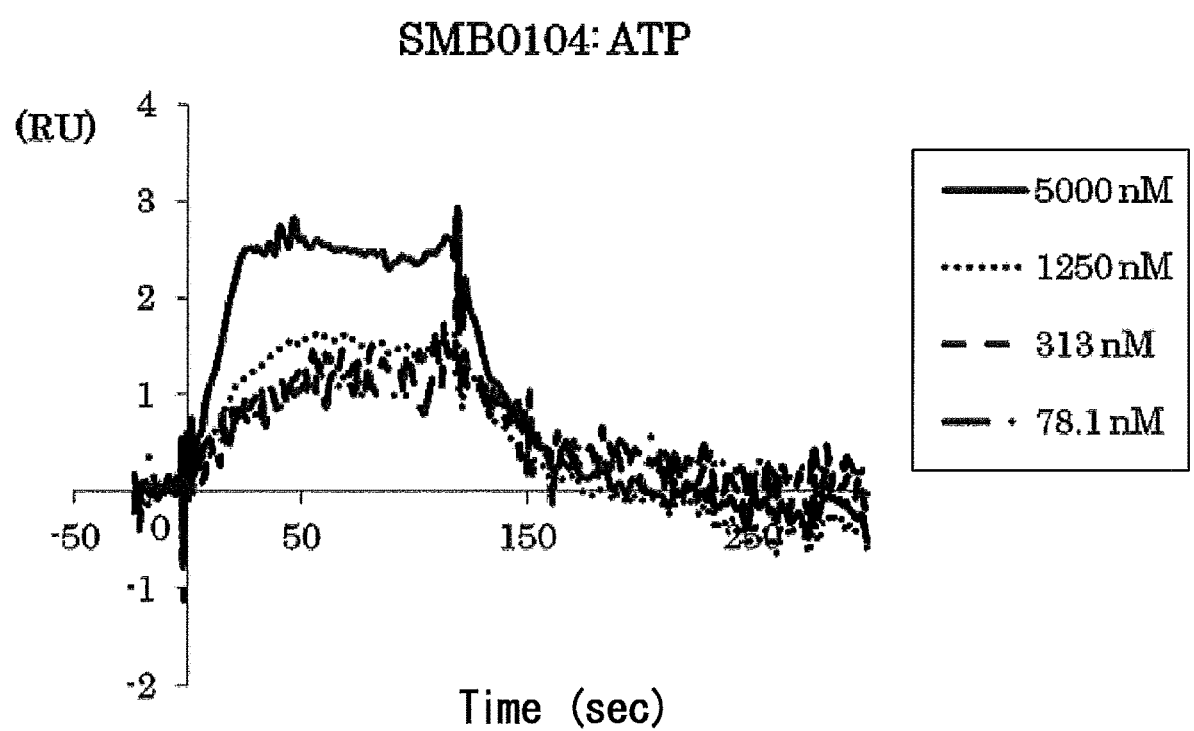
FIG. 15F indicates sensorgrams of surface plasmon resonance-based analyses which show that clone SMB0104 binds to (interacts with) ATP. The sensorgrams show the interactions between SMB0104 and the antigen at 78.1, 313, 1250, and 5000 nM in order from the bottom.

The respective antibodies were compared for their binding activity to 2'-Adenosine-PEG-Biotin using as an indicator the value (N_binding_100) of dividing the amount of binding upon interaction with 2'-Adenosine-PEG-Biotin by the amount of capture (RU) for each antibody, and the value (N_stability_100) of dividing the amount of dissociation of 2'-Adenosine-PEG-Biotin from each antibody for 60 seconds after interaction with 2'-Adenosine-PEG-Biotin by the amount of capture (RU) for each antibody. Regarding antibodies for which the amount of capture was 1500 RU or less, their binding was not sufficiently detectable and thus they were excluded from the subjects to be tested. The result is shown in FIG. 14. The result shown in FIG. 14 demonstrates that the B cell cloning method yielded adenosine-binding clones with various affinity.

(6-2) Assessment of 2'-Adenosine-PEG-Biotin-Binding Clones for their Binding Activity to Adenosine and ATP, and Sequence Analysis of the Clones Clones which were demonstrated to bind to 2'-Adenosine-PEG-Biotin were assessed for their binding to adenosine and ATP by SPR and competitive ELISA.

(6-2-1) Assessment by SPR of 2'-Adenosine-PEG-Biotin-Binding Clones for their Binding to Adenosine and ATP Using Biacore T200 (GE Healthcare), antibodies SMB0002, SMB0089, and SMB0104 obtained by the B cell cloning method were analyzed for their interaction with adenosine and ATP in antigen-antibody reaction. Sensor chip CM5 (GE Healthcare) was immobilized with an appropriate amount of protein A/G (Invitrogen) by amine coupling. Antibodies of interest were captured by the chip to allow interaction to adenosine or ATP as an antigen. The running buffer used was 10 mmol/l ACES, 150 mmol/l NaCl, 0.05% (w/v) Tween20, pH 7.4. All measurements were carried out at 25° C. The antigens were diluted using the running buffer.

Regarding SMB0002, SMB0089, and SMB0104, the diluted antigen solutions and the running buffer as a blank were injected at a flow rate of 20 µl/min for two minutes to allow interaction of each antigen with the antibodies captured on the sensor chip. Then, the running buffer was injected at a flow rate of 20 µl/min for three minutes, and dissociation of the antigens from the antibodies was observed. Next, 10 mmol/l glycine-HCl (pH 1.5) was injected at a flow rate of 30 µl/min for 30 seconds to regenerate the sensor chip. The association rate constant ka (1/Ms) and dissociation rate constant kd (1/s), both of which are kinetic parameters, were calculated from the sensorgrams obtained by the measurement. The dissociation constant KD (M) was calculated based on these constants. Each parameter was calculated using the Biacore T200 Evaluation Software (GE Healthcare).

The result showed that multiple clones including SMB0002, SMB0089, and SMB0104 bound to both adenosine and ATP. The sensorgrams observed to assess each clone for its binding at adenosine concentrations of 500, 125, 31.3, and 7.81 nM or at ATP concentrations of 5000, 1250, 313, and 78.1 nM are shown in FIG. 15. As shown in FIG. 15, SMB0002, SMB0089, and SMB0104 were demonstrated to bind to both adenosine and ATP. KDs of SMB0002, SMB0089, and SMB0104 were $9.3E^{-9}$, $6.9E^{-9}$, and $4.1E^{-8}$ (mol/l) for adenosine, and $1.0E^{-5}$, $8.8E^{-7}$, and $1.4E^{-7}$ (mol/l) for ATP, respectively.

In the same manner using Biacore 4000 (GE Healthcare), antibody SMB0171 obtained by B cell cloning was analyzed for its interaction with adenosine and ATP in antigen-antibody reaction. Sensor chip CM5 (GE Healthcare) was immobilized with an appropriate amount of protein A/G (Invitrogen) by amine coupling. Antibodies of interest were captured by the chip to allow interaction with adenosine or ATP as an antigen. The running buffer used was HBS-P+(GE Healthcare). All measurements were carried out at 25° C. The antigens were diluted using the running buffer.

Regarding SMB0171, diluted antigen solutions and the running buffer as a blank were injected at a flow rate of 10 µl/min for one minute to allow interaction of each antigen with antibodies captured on the sensor chip. Then, the running buffer was injected at a flow rate of 10 µl/min for three minutes, and dissociation of the antibody from the antigens was observed. Then, 10 mmol/l glycine-HCl (pH 1.5) was injected at a flow rate of 30 µl/min for 30 seconds to regenerate the sensor chip. The association rate constant ka (1/Ms) and dissociation rate constant kd (1/s), both of which are kinetic parameters, were calculated from the sensorgrams obtained by measurement. The dissociation constant KD (M) was calculated based on these constants. Each parameter was calculated using the Biacore 4000 Evaluation Software (GE Healthcare).

Figure 16:
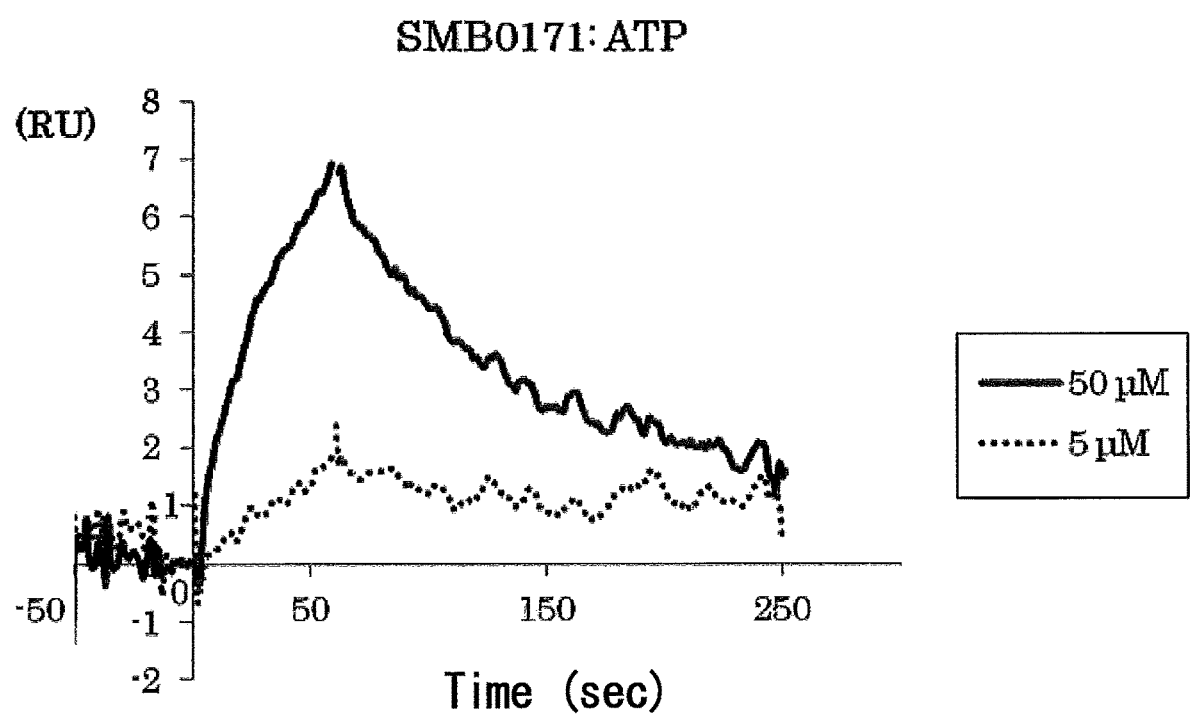
FIG. 16 indicates sensorgrams of surface plasmon resonance-based analyses which show that clone SMB0171 binds to (interacts with) ATP. The sensorgrams show the interactions between SMB0171 and the antigen at 5 and 50 µM in order from the bottom.

The result showed that SMB0171 binds to ATP. The sensorgrams observed in assessing each clone for its binding at ATP concentrations of 50 and 5 µM are shown in FIG. 16. As shown in FIG. 16, SMB0171 was demonstrated to bind to ATP. KD of SMB0171 for ATP was $5.9E^{-6}$ (mol/l).

(6-2-2) Assessment of 2'-Adenosine-PEG-Biotin-Binding Clones for their Binding to Adenosine and ATP by Competitive ELISA Antibodies demonstrated to bind to 2'-Adenosine-PEG-Biotin were diluted to 1 µg/ml with PBS, and added to each well of a 384-well MAXISorp (Nunc). To immobilize the antibodies, the plate was allowed to stand for one hour or more at room temperature. After the antibodies diluted with PBS were removed from each well, TBS containing 1% BSA was added thereto and the plate was allowed to stand for one hour or more. Then, the TBS (pH 7.4) containing 1% BSA was removed from the plate. 2'-Adenosine-PEG-Biotin diluted to 50 nM with PBS, a mixture of 2'-Adenosine-PEG-Biotin and adenosine diluted to 50 nM and 500 µM respectively with PBS, a mixture of 2'-Adenosine-PEG-Biotin and ATP diluted to 50 nM and 500 µM respectively with PBS, or PBS alone was added to the plate. The plate was allowed to stand at room temperature for one hour, and then washed three times with 80 µl of PBS containing 0.05% Tween-20. Then, Streptavidin-HRP (Thermo fisher scientific) diluted 20000 times with PBS was added to each well, and the plate was allowed to stand for one hour or more at room temperature. After the plate was washed three times with 80 µl of PBS containing 0.05% Tween-20, a chromogenic substrate (ABTS peroxidase substrate) was added to each well. After the plate was incubated for one hour, color development in the solution of each well was assessed by measuring absorbance at 405 nm using SpectraMax from Molecular Device.

Figure 17:
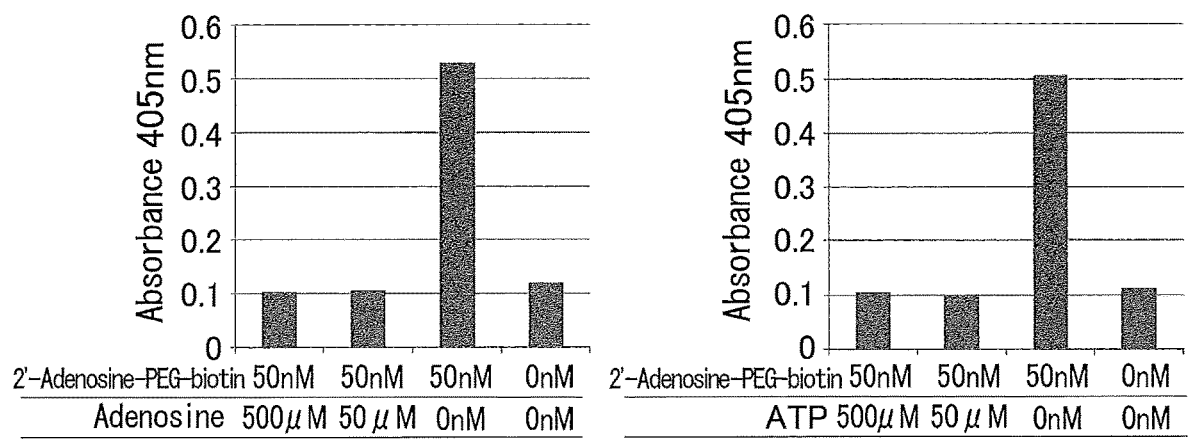
FIG. 17 indicates the results of competitive ELISA which shows that clone SMB0002 binds to adenosine and ATP.

As shown in FIG. 17, the result showed that the binding of SMB0002 to 2'-Adenosine-PEG-Biotin was inhibited by adding excess amounts of adenosine and ATP. Thus, the antibody clones were demonstrated to bind not only to 2'-Adenosine-PEG-Biotin but also to both adenosine and ATP.

(6-2-3) Sequence Analysis of Clones Identified as Adenosine and ATP Binders by SPR The amino acid sequences of clones demonstrated to bind to both adenosine and ATP are shown in Table 7.

TABLE 7

| Clone name | Heavy chain SEQ ID NO | Light chain SEQ ID NO |
|---|---|---|
| SMB0002 | SEQ ID NO: 38 | SEQ ID NO: 39 |
| SMB0089 | SEQ ID NO: 40 | SEQ ID NO: 41 |
| SMB0104 | SEQ ID NO: 42 | SEQ ID NO: 43 |
| SMB0171 | SEQ ID NO: 44 | SEQ ID NO: 45 |

[Example 7] Acquisition of Antibodies that Bind to Adenosine and/or ATP from Human Antibody Library Using Phage Display Techniques (7-1) Construction of Phage-Display Library of Naïve Human Antibodies A phage-display library of human antibodies consisting of multiple phages that present the Fab domains of human antibodies whose sequences were different from one another was constructed using, as a template, polyA RNA prepared from human PBMC, commercially available human polyA RNA, or such according to a method known to those skilled in the art.

(7-2) Acquisition of Antibodies that Bind to Adenosine and/or ATP from Library by Bead Panning The phage-display library of naïve human antibodies constructed as described in (7-1) was screened for antibodies that exhibit antigen-binding activity, specifically, by collecting phages that display antibodies with binding activity to antigens captured by beads. Biotinylated ATP, 2'-adenosine-PEG-Biotin, and 5'-adenosine-PEG-Biotin were used as antigens.

Phages produced in *E. coli* containing the phagemid vector constructed for phage display were purified by a conventional method, and then dialyzed against TBS to prepare a phage library suspension. Then, BSA was added at a final concentration of 4% to the suspension. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

Next, 250 pmol of biotinylated ATP, 2'-adenosine-PEG-Biotin, and 5'-adenosine-PEG-Biotin were added to the prepared phage library suspension. Thus, the phage library suspension was contacted with adenosine and ATP for 60 minutes at room temperature. Then, BSA-blocked magnetic beads were added to the phage library suspension, and the complex of phage with adenosine and/or ATP was allowed to bind to the magnetic beads at room temperature for 15 minutes. The beads were washed once with TBS. Then, the beads were combined with 0.5 ml of 1 mg/ml trypsin solution. Immediately after the beads were suspended at room temperature for 15 minutes, a phage suspension was collected from the isolated beads using a magnetic stand. The collected phage suspension was added to 10 ml of *E. coli* cells of strain ER2738 at the logarithmic growth phase (OD600=0.4 to 0.7). The *E. coli* was incubated at 37° C. for one hour under gentle stirring to be infected by phage. The infected *E. coli* was seeded in a 225 mm×225 mm plate. Then, phages were collected from the culture medium of the seeded *E. coli* to prepare a liquid stock of phage library.

A second round of panning was performed to also enrich phages that are capable of binding to adenosine and/or ATP. The prepared phage library suspension was contacted with adenosine and ATP for 60 minutes at room temperature by adding 50 pmol each of biotinylated ATP, 2'-Adenosine-PEG-Biotin, and 5'-Adenosine-PEG-Biotin. Then, the BSA-blocked magnetic beads were added to the phage library suspension, and the complex of phage with adenosine and/or ATP was allowed to bind to the magnetic beads at room temperature for 15 minutes. The beads were washed three times with TBST and twice with TBS. Then, the beads were combined with 0.5 ml of 1 mg/ml trypsin solution. Immediately after the beads were suspended at room temperature for 15 minutes, a phage suspension was collected from the isolated beads using a magnetic stand. The collected phage suspension was added to 10 ml of *E. coli* cells of strain ER2738 at the logarithmic growth phase (OD600=0.4 to 0.7). The *E. coli* was incubated at 37° C. for one hour with gentle stirring to be infected by phage. The infected *E. coli* was seeded in a 225 mm×225 mm plate. Then, phages were collected from the culture medium of the seeded *E. coli* to prepare a liquid stock of phage library.

By the same procedure, panning was performed three times to obtain antibodies that are capable of binding to adenosine and/or ATP. In the fourth round of panning, TBST wash and TBS wash were each performed five times.

(7-3) Assessment of Adenosine- and ATP-Binding Activity by Phage ELISA

From single colonies of *E. coli* obtained by panning as described in the Example above, culture supernatants containing phages were collected according to a conventional method (Method Mol. Biol. (2002) 178, 133-145). The collected culture supernatants were treated by ultrafiltration using NucleoFast 96 (MACHERY-NAGEL). 100 µl of the culture supernatants were added to each well of NucleoFast 96 and centrifuged at 4500 g for 45 minutes to remove flow through. After addition of 100 µl of $H_2O$, the NucleoFast 96 was washed by centrifugation at 4500 g for 30 minutes. After addition of 100 µl of TBS, the NucleoFast 96 was allowed to stand for five minutes at room temperature. Then, phage suspensions were collected from the supernatants.

Purified phages, to which TBS was added, were subjected to ELISA by the following procedure. A StreptaWell 96 microtiter plate (Roche) was coated at room temperature for one hour with 100 µl of TBS containing biotin-labeled antigens (a mixture of equal amounts of 2'-adenosine-PEG-biotin, 5'-adenosine-PEG-biotin, and ATP-PEG-biotin). After antigens were removed from each well of the plate by washing with TBST (TBS containing 0.1% Tween20), the wells were blocked with 250 µl of 2% skim milk/TBS for one hour or more. 2% skim milk/TBS was removed, and then the prepared, purified phages were added to each well. The plate was allowed to stand at room temperature for one hour to allow the phage-displayed antibody to bind antigens in each well. After washing with TBST, an HRP-conjugated anti-M13 antibody (Amersham Pharmacia Biotech) diluted with TBS was added to each well. The plate was incubated for one hour. Following TBST wash, the TMB single solution (ZYMED) was added to each well. The chromogenic reaction in the solution of each well was terminated by adding sulfuric acid. Then, the developed color was assessed by measuring absorbance at 450 nm.

From the 192 clones subjected to phage ELISA, 106 clones that have the ability to bind to any one or two, or all three of 2'-Adenosine-PEG-biotin, 5'-Adenosine-PEG-biotin, and ATP-PEG-biotin were obtained.

Next, for the purpose of confirming to which antigen of 2'-adenosine-PEG-biotin, 5'-adenosine-PEG-biotin, and ATP-PEG-biotin these clones have binding ability, the purified phages diluted with TBS were subjected to ELISA by the following procedure. A StreptaWell 96 microtiter plate (Roche) was coated at room temperature for one hour with 100 µl of TBS containing a biotin-labeled antigen (2'-adenosine-PEG-biotin, 5'-adenosine-PEG-biotin, or ATP-PEG-biotin). After the antigens were removed by washing each well of the plate with TBST, the wells were blocked with 250 µl of 2% skim milk/TBS for one hour or more. 2% skim milk/TBS was removed, and then the prepared, purified phages were added to each well. The plate was allowed to stand at room temperature for one hour to allow binding of antibody-displaying phages to antigens in each well. After TBST wash, an HRP-conjugated anti-M13 antibody (Amersham Pharmacia Biotech) diluted with TBS was added to each well. The plate was incubated for one hour. Following TBST wash, the TMB single solution (ZYMED) was added to each well. The chromogenic reaction in the solution of each well was terminated by adding sulfuric acid. Then, the developed color was assessed by measuring absorbance at 450 nm. The result of phage ELISA is shown in Table 8 below.

TABLE 8

| Enrichment indicator | Antigen binding ability (S/N ratio > 1.5) |
|---|---|
| Number of panning | 4 |
| Number of clones subjected to ELISA | 192 |
| Number of ELISA-positive Combination of 2'-Adenosine-PEG-biotin, 5'-Adenosine-PEG-biotin, and ATP-PEG-biotin | 106 |

TABLE 8-continued

| | Enrichment indicator | Antigen binding ability (S/N ratio > 1.5) |
|---|---|---|
| clones | 2'-Adenosine-PEG-biotin | 0 |
| | 5'-Adenosine-PEG-biotin | 6 |
| | ATP-PEG-biotin | 76 |
| | Bind to two or more of 2'-Adenosine-PEG-biotin, 5'-Adenosine-PEG-biotin, and ATP-PEG-biotin | 1 |

Among the clones subjected to phage ELISA, a clone was demonstrated to bind to two or more types of antigens. Its gene was amplified with specific primers using the antibody fragment as a template. The nucleotide sequence of the gene was analyzed. This clone had the ability to bind to both 5'-Adenosine-PEG-biotin and ATP-PEG-biotin, and was named ATNLSA1-4_D12. The heavy-chain variable region sequence of antibody ATNLSA1-4_D12 is shown in SEQ ID NO: 46, and its light-chain variable region sequence is shown in SEQ ID NO: 47.

(7-4) Assessment of Adenosine- and ATP-Binding Activity by Competitive Phage ELISA Based on the structures of 5'-Adenosine-PEG-biotin and ATP-PEG-biotin, there remained the possibility that clone ATNLSA1-4_D12 (heavy chain variable region, SEQ ID NO: 46; light chain, SEQ ID NO: 47), which was demonstrated by the result of phage ELISA to have the ability to bind to both 5'-Adenosine-PEG-biotin and ATP-biotin, recognizes the biotin tag or PEG moiety. Thus, to demonstrate that ATNLSA1-4_D12 is not an antibody that recognizes the biotin tag or PEG, whether the antigen binding is inhibited by adenosine or ATP was tested by phage ELISA using ATNLSA1-4_D12, and IL-6R-binding clone PF1 (heavy chain, SEQ ID NO: 48; light chain, SEQ ID NO: 49) prepared as a negative control. ATNLSA1-4_D12 and PF1 were each diluted with TBS and subjected to ELISA by the following procedure.

A StreptaWell 96 microtiter plate (Roche) was coated at room temperature for one hour with 100 µl of TBS containing biotin-labeled antigens (a mixture of 5'-adenosine-PEG-biotin and ATP-PEG-biotin). After the antigens were removed by washing each well of the plate with TBST, the wells were blocked with 250 µl of 2% skim milk/TBS for one hour or more. 2% skim milk/TBS was removed, and then the prepared, purified phages were added to each well. The plate was allowed to stand at room temperature for one hour to allow binding of the antibody-displaying phages to the antigens in each well. Then, TBS that does not contain antigen or that contains serial dilutions of ATP from an equal amount up to 10000 times that of the antigen was added to the wells. For the competition of the immobilized antigen with ATP, the plate was allowed to stand at room temperature for one hour. Then, after TBST wash, an HRP-conjugated anti-M13 antibody (Amersham Pharmacia Biotech) diluted with TBS was added to each well. The plate was incubated for one hour. Following TBST wash, the TMB single solution (ZYMED) was added to each well. The chromogenic reaction in the solution of each well was terminated by adding sulfuric acid. Then, the developed color was assessed by measuring absorbance at 450 nm.

Figure 18:
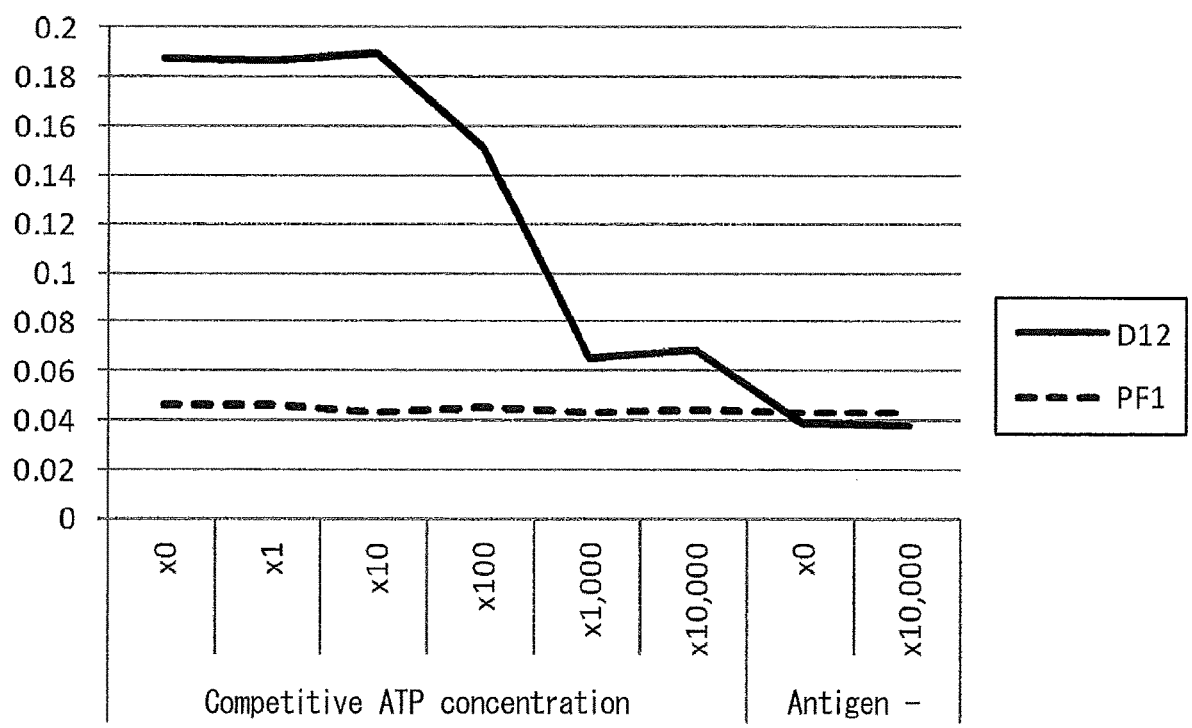
FIG. 18 shows a graph that assesses the inhibitive ability of ATP towards binding of biotin-labeled antigens (a mixture of 5'-Adenosine-PEG-biotin and ATP-PEG-biotin) by ATNLSA1-4_D12.

The measurement result is shown in FIG. 18. It was demonstrated that the higher the ATP concentration, the smaller the degree of color development for ATNLSA1-4_D12 in the presence of an excess amount of ATP. Thus, the binding between ATNLSA1-4_D12 and its antigen was demonstrated to be inhibited in an ATP concentration-dependent manner. Meanwhile, in a control experiment with PF1 as a negative control, its antigen binding was not detected regardless of the ATP concentration. The above finding demonstrates that ATNLSA1-4_D12 is an antibody that has the ability to bind to ATP but does not recognize the biotin tag or PEG.

(7-5) Expression and Purification of Antibodies that Bind to ATP and Adenosine

Using specific primers, genes were amplified from clone ATNLSA1-4_D12 that had been assessed to have binding activity to ATP and adenosine by the phage ELISA described in Example 7. The nucleotide sequences of the genes were analyzed (the heavy-chain and light-chain sequences are shown in SEQ ID NOs: 46 and 47, respectively). The gene encoding the variable region of ATNLSA1-4_D12 was inserted into an animal expression plasmid for human IgG1/Lambda. The antibody was expressed using the method described below. Cells of human fetal kidney cell-derived FreeStyle 293-F (Invitrogen) were suspended at a cell density of $1.33 \times 10^6$ cells/ml in FreeStyle 293 Expression Medium (Invitrogen) and aliquoted at 3 ml into each well of a 6-well plate. The constructed plasmid was introduced into the cells by lipofection. After four days of culture in a $CO_2$ incubator (37° C., 8% $CO_2$, 90 rpm), the antibody was purified from the culture supernatants by a method known to those skilled in the art using rProtein A Sepharose™ Fast Flow (Amersham Biosciences). Absorbance of the purified antibody solutions was measured at 280 nm using a spectrophotometer. From the values obtained by the measurement, the concentration of the purified antibody was calculated using an extinction coefficient determined by the PACE method (Protein Science (1995) 4, 2411-2423).

(7-6) Assessment of the ATP- and Adenosine-Binding Antibody for its ATP and Adenosine Binding by Surface Plasmon Resonance Biacore T200 (GE Healthcare) was used to analyze the interaction of D12, in which the constant region of IgG is linked to the variable region of clone ATNLSA1-4_D12 with ATP- and adenosine-binding activity, in antigen-antibody reaction. Sensor chip CM5 or CM4 (GE Healthcare) was immobilized with an appropriate amount of protein A (Life technologies) by amine coupling. The antibody of interest was captured by the chip to allow interaction with ATP (Wako), adenosine (Wako), or ADP (adenosine diphosphate) (Wako) as an antigen. The running buffer used was 50 mM Tris-HCl (Takara, T903), 500 mM NaCl, 0.01% (w/v) Tween20. The antigen was allowed to interact for 30 seconds at a flow rate of 30 µl/min, and was dissociated for 30 seconds. The interaction with the antigen was assessed at 15° C. The antigen was diluted using the same running buffer.

The dissociation constant $K_D$ (M) was calculated based on the association rate constant ka (1/Ms) and dissociation rate constant kd (1/s), both of which are kinetic parameters calculated from the sensorgram obtained by the measurement. Alternatively, the dissociation constant $K_D$ (M) was calculated using steady state analysis. Each parameter was calculated using the Biacore T200 Evaluation Software (GE Healthcare).

To calculate the $K_D$ for adenosine, the binding response was assessed at various concentrations of adenosine in the presence or absence of 20 µmol/l ADP. In addition, the binding response was separately assessed in the presence of 20 µmol/l ADP. The response (R) for specific adenosine binding was obtained by subtracting the value of binding response in the presence of ADP alone from the binding response to various concentrations of adenosine in the presence of ADP, and then subtracting the resultant value, which is assumed to correspond to the non-specific binding components, from the value of binding response to adenosine in the absence of ADP. From a curve in which adenosine concentration is plotted on the X axis and R calculated according to Formula 2 is plotted on the Y axis, the value of $K_D$ for adenosine was determined by the least squares method using the Solver function of Office Excel 2007 (Microsoft).

$$R = R\text{max} \times \text{conc}/(K_D + \text{conc}) \quad \text{(Formula 2)}$$

In Formula 2, conc represents adenosine concentration (mol/l) while Rmax represents the value of response expected for the maximal binding of adenosine to antibody. Measured response values were extracted by using Scrubber2 (BioLogics. Inc).

The KD of D12 determined by the measurement described above was 8.5 µmol/l for ATP, 0.25 µmol/l for ADP, or 1100 µmol/l for adenosine. This result demonstrates that D12 has binding activity to ATP, ADP, and adenosine; and it also suggests that D12 has binding activity to AMP (adenosine monophosphate) and cAMP (cyclic adenosine monophosphate).

Figure 19:
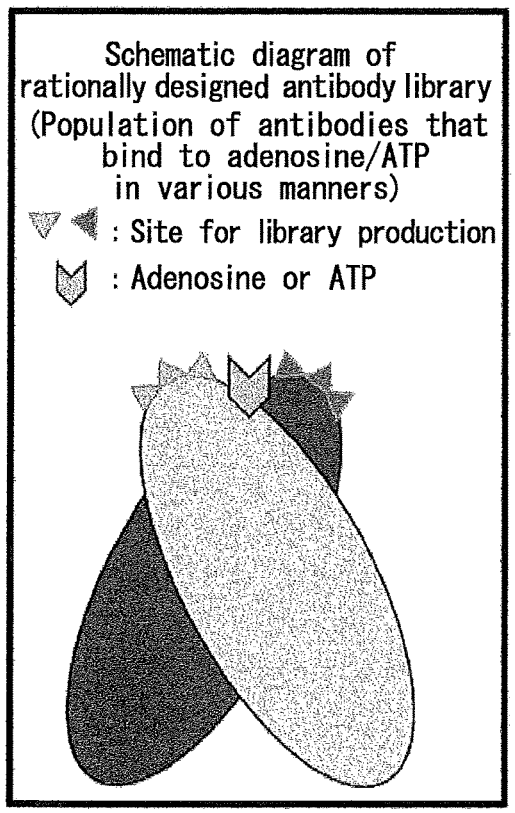
FIG. 19 shows the concept of a rationally designed antibody library that can obtain adenosine/ATP-switch antibodies against any antigen, wherein the library is made from antibody variable region portions that contact with the antigens such that adenosine or ATP is positioned between the antibody and antigen.
Figure 19:
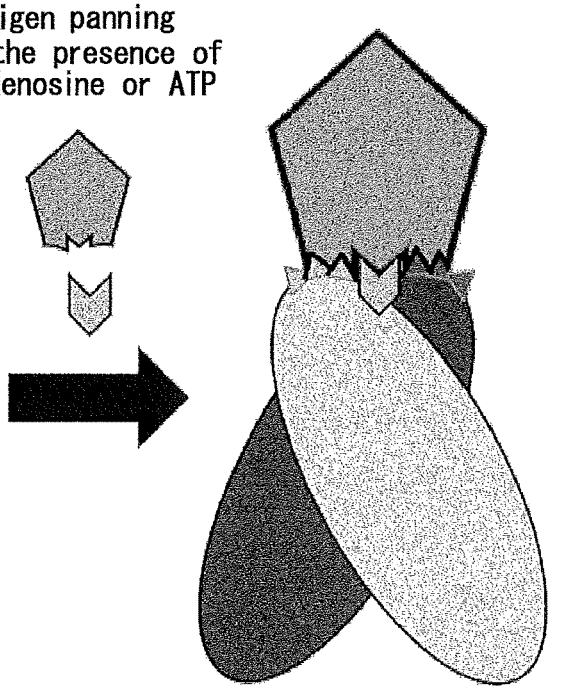

[Example 8] Design of Library Using Anti-ATP/Adenosine Antibodies to Prepare ATP/Adenosine Switch Antibodies In cancer tissues and inflamed tissues, not only the adenosine but also the ATP concentration is known to be high. Thus, it is beneficial to use antibodies for which both adenosine and ATP (referred to as ATP/adenosine in this Example) can serve as a switch (specifically, antibodies that can bind to antigens when adenosine or ATP is present at a high concentration) as well as antibodies for which either adenosine or ATP alone serves as a switch. ATNLSA1-4_D12 described in Example 7-4 is an antibody that binds to ATP/adenosine. As shown in FIG. 19, ATP/adenosine is thought to be fit between the antibody and its target antigen, and thus the antibody comprises an antibody variable region that comes in contact with the target antigen. Thus, the present inventors conceived that synthetic antibody libraries that can isolate ATP/adenosine switch antibodies whose binding activity to arbitrary antigens is altered depending on the presence of ATP/adenosine could be constructed by collecting, as a library, antibody variable region segments that are capable of establishing contact with a target antigen and maintaining ATP/adenosine binding.

The crystal structure of the complex between ATP and ATP/adenosine antibody ATNLSA1-4_D12 obtained from a human antibody library as described in Example 7-4 was analyzed. The result of crystal structure analysis revealed the mode of adenosine (or ATP) recognition by the antibody as well as identification of amino acid residues that are considered not to be substantially involved in adenosine (or ATP) binding in the antibody variable region. Amino acid residues that have been identified to be closely involved in the adenosine (ATP) binding are Ser52, Ser52a, Arg53, Gly96, Leu100a, and Trp100c (Kabat numbering) in the heavy chain.

In designing such a library, positions that meet at least one of the conditions described below were selected as suitable for the library construction.

Condition 1: a position that is not closely involved in ATP binding, or if involved in the binding, a position having an amino acid other than the wild-type sequence that does not inhibit the ATP binding;

Condition 2: a position that is polymorphic to a certain extent in terms of amino acid occurrence frequency; and Condition 3: a position that is not essential for the formation of canonical structure.

In regions contained in both heavy chain and light chain of the ATNLSA1-4_D12 sequence and that meet the conditions described above, amino acids in the CDR1 and CDR2 regions that have an occurrence frequency of 2% or more in the germ line, as well as amino acids in the CDR3 region that have an occurrence frequency of 1% or more in the germ line were comprehensively substituted. These substitutions were combined to construct multiple variants of ATNLSA1-4_D12.

Alteration sites in the heavy chain (in the Table, positions indicated by "Kabat" according to Kabat numbering), as well as amino acids before alteration (in the table, amino acids referred to as "natural sequence") at the sites and amino acids after alteration (in the table, amino acids referred to as "altered amino acids") are shown in Table 9.

TABLE 9

|  | HCDR1 | | | HCDR2 | | | HCDR3 | | | | |
| --- | --- | --- | --- | --- | --- | --- | --- | --- | --- | --- | --- |
| Kabat | 31 | 32 | 35 | 55 | 57 | 58 | 96 | 97 | 99 | 100 | 100a |
| Wild type sequence | T | Y | N | N | I | N | G | R | G | D | L |
| Altered amino acid | A | | | A | A | A | | A | A | A | A | A |
| | C | | | | | | | | | | | |
| | E | | | | | | | | | | | |
| | D | | | D | | D | | D | D | D | | |
| | G | | | G | | G | G | | | | | |
| | F | | | F | | | F | | | | | F |
| | I | | | | | | | | | | | I |
| | H | | | H | H | | H | | | | | |
| | K | | | | | | K | | | | K | K | K |
| | M | | | | | | | | | | | M |
| | L | | | | | L | | | | | | |

TABLE 9-continued

|  | HCDR1 | | | HCDR2 | | | HCDR3 | | | | |
|---|---|---|---|---|---|---|---|---|---|---|---|
| Kabat | 31 | 32 | 35 | 55 | 57 | 58 | 96 | 97 | 99 | 100 | 100a |
| Wild type sequence | T | Y | N | N | I | N | G | R | G | D | L |
| N | N | N |   |   |   |   | N | N | N | N |   |
| Q |   |   |   |   |   |   |   |   |   |   |   |
| P |   |   |   |   |   |   |   |   |   |   |   |
| S | S | S | S | S | S |   | S | S | S | S |   |
| R | R |   |   | R | R |   |   |   |   |   | R |
| T |   |   | T | T | T | T |   |   |   |   |   |
| W | W |   |   |   |   |   |   |   |   |   | W |
| V | V |   |   |   |   |   |   | V | V | V | V |
| Y | Y |   |   |   | Y |   |   | Y | Y | Y | Y |

Alteration sites in the light chain (in the Table, positions indicated by "Kabat" according to Kabat numbering), as well as amino acids before alteration (in the table, amino acids referred to as "natural sequence") at the sites and amino acids after alteration (in the table, amino acids referred to as "altered amino acids") are shown in Table 10.

TABLE 10

|  | LCDR1 | | | | | | | | | LCDR2 | | | | | | LCDR3 | | | | | | | | |
|---|---|---|---|---|---|---|---|---|---|---|---|---|---|---|---|---|---|---|---|---|---|---|---|---|
| Kabat | 26 | 27 | 27a | 27b | 27c | 28 | 29 | 31 | 32 | 50 | 51 | 52 | 53 | 54 | 55 | 89 | 90 | 91 | 92 | 93 | 94 | 95a | 96 | 97 |
| Wild type sequence | T | S | S | D | V | G | G | N | Y | E | V | S | K | R | P | S | S | Y | A | G | S | N | V | V |
| Altered amino acid A | A |   |   |   |   |   |   | A | A |   |   | A |   |   |   | A | A | A |   | A | A | A | A | A |
| C | C |   |   |   |   |   |   |   |   |   |   |   |   |   |   |   |   |   |   |   |   |   |   |   |
| E |   |   |   |   |   |   |   |   | E |   |   | E |   |   |   |   |   | E |   |   | E |   |   |   |
| D |   |   |   |   |   | D | D | D | D | D | D | D | D |   |   |   | D | D |   | D | D | D | D | D |
| G |   |   | G |   |   |   |   |   |   |   | G | G |   |   |   | G |   |   |   |   | G | G | G | G |
| F |   |   |   |   |   | F |   |   |   |   |   |   |   |   |   | F | F |   |   |   |   |   | F |   |
| I |   |   |   |   | I |   |   |   |   |   |   |   |   |   |   |   |   |   |   | I | I | I |   | I |
| H |   |   |   |   |   |   |   |   |   |   |   |   | H |   |   |   | H |   |   |   |   | H | H |   |
| K |   |   |   |   |   |   |   | K |   | K | K |   |   | K |   |   | K |   |   |   |   |   | K | K |
| M |   |   |   |   |   |   |   |   |   |   |   |   |   |   |   |   |   |   |   |   |   |   |   | M |
| L |   |   |   |   |   |   |   |   |   |   |   |   |   | L | L | L |   |   |   |   | L | L | L |   |
| N |   |   | N | N |   |   |   |   |   | N | N | N |   |   |   | N |   | N | N |   |   | N |   |   |
| Q |   |   |   |   |   |   |   |   |   |   | Q |   | Q |   |   | Q |   |   |   |   |   | Q | Q |   |
| P |   |   |   |   |   |   |   |   |   |   |   |   |   |   |   |   |   |   |   |   |   | P | P |   |
| S | S | S |   |   |   |   |   | S | S | S |   | S |   |   |   | S | S | S |   |   |   | S | S | S |
| R |   |   |   |   |   |   |   | R |   | R |   |   |   |   |   | R | R | R | R |   |   |   |   |   |
| T |   | T | T |   |   |   |   | T |   | T |   | T | T |   |   | T | T | T | T | T |   | T |   |   |
| W |   |   |   |   |   |   |   |   |   |   |   |   |   |   |   |   |   | W |   |   |   |   |   | W |

TABLE 10-continued

| | LCDR1 | | | | | | | | | LCDR2 | | | | | | LCDR3 | | | | | | | | |
|---|---|---|---|---|---|---|---|---|---|---|---|---|---|---|---|---|---|---|---|---|---|---|---|---|
| Kabat | 26 | 27 | 27a | 27b | 27c | 28 | 29 | 31 | 32 | 50 | 51 | 52 | 53 | 54 | 55 | 89 | 90 | 91 | 92 | 93 | 94 | 95a | 96 | 97 |
| Wild type sequence | T | S | S | D | V | G | G | N | Y | E | V | S | K | R | P | S | S | Y | A | G | S | N | V | V |
| | V | | | | | | | | | | | | | | | V | V | V | V | V | | | | |
| | Y | | | | | Y | | | | Y | | Y | | Y | | Y | | | Y | Y | | | Y | Y |

Each variant expressed and purified by the method described in Example 7-1 was assayed for its ATP and adenosine binding by the same method as described in Example 7-6 using Biacore. Based on the assay result, the affinity of each variant for ATP was calculated as a KD value. Sites in the heavy chain, where alteration does not reduce the ATP-binding ability to less than 1/5 of the binding ability of ATNLSA1-4_D12 (specifically, where the KD value is lower than 42.5 pmol/l), and sites in the light chain where the ATP-binding ability is larger than that of ATNLSA1-4_D12 (specifically, where the KD value is smaller than 8.5 pmol/l), were assessed to be plausible for alteration. Amino acids substituted at those sites were judged to be appropriate for inclusion in the library (flexible residues to be introduced into library).

Based on the assessment result on the ATP-binding ability of each variant, the ATP-binding ability was predicted to be reduced by collecting each site to construct a library. Thus, substitutions were introduced at sites close to positions that are expected to be involved in ATP binding, and various variants resulting from combination of these substitutions were comprehensively assessed to test whether it is possible to identify alterations which are expected to have effect of augmenting the ATP-binding ability. Such alteration sites (positions indicated by "Kabat" according to Kabat numbering in the Table), and amino acids before alteration (amino acids referred to as "wild type sequence" in the table) and amino acids after alteration (amino acids referred to as "altered amino acids" in the table) at the sites are shown in Table 11.

TABLE 11

| | HCDR1 | HCDR2 | | HCDR3 | | | LCDR3 |
|---|---|---|---|---|---|---|---|
| Kabat | 33 | 50 | 56 | 95 | 98 | 100b | 95 |
| Wild type sequence | T | S | Y | F | K | N | N |
| Altered amino acid | A | A | A | A | A | A | A |
| | C | | | | | | |
| | E | E | E | E | | E | E |
| | D | D | D | D | |

TABLE 12

| | Kabat Wild type sequence | HCDR1 | | | HCDR2 | | | | | HCDR3 | | | | | | |
|---|---|---|---|---|---|---|---|---|---|---|---|---|---|---|---|---|
| | | 31 | 32 | 35 | 55 | 56 | 57 | 58 | 59 | 95 | 97 | 98 | 99 | 100 | 100a | 100b |
| | | T | Y | N | N | Y | I | N | Y | F | R | K | G | D | L | N |
| Altered amino acid | A | | | | 17% | | 25% | | | | 11% | | | 5% | | |
| | C | | | | | | | | | | | | | | | |
| | E | | | | | | | | | | | | 9% | 5% | | |
| | D | | | | | | | 13% | | | | | 9% | 5% | | |
| | G | 33% | | | 17% | | | 13% | | | 11% | | 9% | 5% | | |
| | F | | 33% | | | | | 13% | | 50% | | | 9% | 5% | | |
| | I | | | | | | 25% | | | | 11% | | | 5% | | |
| | H | | 33% | 50% | | 50% | | 13% | | | 11% | | 9% | 5% | 17% | |
| | K | | | | | | 25% | | | | 11% | 33% | 9% | 5% | | |
| | M | | | | | | | | | | 11% | | | 5% | 17% | |
| | L | | | | | | | | 50% | | 11% | 33% | | 5% | 17% | 50% |
| | N | | | 50% | 17% | | | 13% | | | | | 9% | 5% | | 50% |
| | Q | | | | | | | | | | | | 9% | 5% | | |
| | P | | | | | | | | | | | | | 5% | | |
| | S | 33% | | | 17% | | | 13% | | | | | | 5% | | |
| | R | | | | 17% | | 25% | | | | 11% | 33% | 9% | 5% | 17% | |
| | T | 33% | | | 17% | | | 13% | | | | | | 5% | | |
| | W | | | | | | | | | | | | 9% | 5% | 17% | |
| | V | | | | | | | | | | 11% | | | 5% | | |
| | Y | | 33% | | | 50% | | 13% | 50% | 50% | | | 9% | 5% | 17% | |

TABLE 13

| | Kabat Wild type sequence | LCDR1 | | LCDR2 | | | LCDR3 | | | | | | | | |
|---|---|---|---|---|---|---|---|---|---|---|---|---|---|---|---|
| | | 27a | 29 | 50 | 51 | 54 | 90 | 91 | 92 | 93 | 94 | 95 | 95a | 96 | 97 |
| | | S | S | E | V | R | S | Y | A | G | S | N | N | V | V |
| Altered amino acid | A | | 17% | | | | | | 17% | 14% | 13% | 6% | | | 17% |
| | C | | | | | | | | | | | | | | |
| | E | | | | 14% | | | | 17% | | | 6% | | | |
| | D | | 17% | | 14% | | | | | 14% | 13% | 6% | 11% | | |
| | G | | 17% | | 14% | 25% | | | | 14% | 13% | 6% | 11% | | 17% |
| | F | | 17% | | | | | | | | | 6% | | | |
| | I | | | | | | | | | 14% | 13% | 6% | 11% | | |
| | H | | | | | | | | | | | 6% | 11% | | |
| | K | | | | 14% | 50% | | 14% | | | | 6% | | | |
| | M | | | | | | | | | | | 6% | | | 17% |
| | L | | | | | | 25% | | | | | 6% | 11% | 33% | 17% |

TABLE 13-continued

| | LCDR1 | | LCDR2 | | | LCDR3 | | | | | | | | |
|---|---|---|---|---|---|---|---|---|---|---|---|---|---|---|
| Kabat | 27a | 29 | 50 | 51 | 54 | 90 | 91 | 92 | 93 | 94 | 95 | 95a | 96 | 97 |
| Wild type sequence | S | S | E | V | R | S | Y | A | G | S | N | N | V | V |
| N | | | | 25% | | | 14% | | | 13% | 6% | 11% | | |
| Q | | | 14% | | | | | | | | 6% | 11% | | |
| P | | | | | | | | | | | 6% | | 33% | |
| S | 50% | 17% | 14% | | | 25% | | 17% | 14% | 13% | 6% | 11% | | 17% |
| R | | | | | 50% | | 14% | 17% | | 13% | 6% | | | |
| T | 50% | 17% | | 25% | | 25% | 14% | 17% | 14% | 13% | 6% | | | |
| W | | | | | | | 14% | | | | 6% | | | |
| V | | | | 25% | | 25% | 14% | | | | | | 33% | 17% |
| Y | | | | | 14% | | 14% | 17% | 14% | | 6% | 11% | | |

The result of sequence analysis suggests that the framework of ATNLSA1-4_D12 was derived from germ line VH3-21. Then, for the purpose of improving antibody stability, the framework sequence of ATNLSA1-4_D12 was restored to the germ line sequence VH3-21 by introducing into the framework sequence of ATNLSA1-4_D12, alterations Gln01Glu, Gln05Val, Asp10Gly, Asn30Ser, Leu48Val, and Asn58Tyr (numerals represent Kabat numbers). ATNLSA1-4_D12 variants expressed and purified by the method described in Example 7-1 were measured for their Tm by DSC. DSC measurement was carried out by a method known to those skilled in the art. Tm of the variant which results from adding these alterations to ATNLSA1-4_D12 was markedly improved from 74.37° C. to 81.44° C., and stabilization of the structure was observed. It is sometimes preferable to use highly stable frameworks for antibody libraries, and thus a framework sequence to which alterations described above had been added was used as the framework sequence of a library. The framework used for the library is shown in Table 14.

TABLE 14

| Framework | SEQ ID NO: | Sequence |
|---|---|---|
| Heavy chain framework1 | 56 | EVQLVESGGGLVKPGGFLRLSCAASGFTFS |
| Heavy chain framework2 | 57 | WVRQAPGKGLEWVS |
| Heavy chain framework3 | 58 | RFTISRDNAKNSLYLQMNSLRAEDTAVYYCAR |
| Heavy chain framework4 | 59 | WGQGTLVTVSS |
| Light chain framework 1 | 60 | QSALTQPPSASGSPGQTVTISC |
| Light chain framework 2 | 61 | SWYQQHPGKAPKLMIY |
| Light chain framework 3 | 62 | GVPDRFSGSKSGNTASLTVSGLQAEDEADYFC |
| Light chain framework 4 | 63 | FGGGTKLTVL |

Genes were synthesized to comprise respective sequences in a library designed as described above (DNA2.0), and the gene library was amplified with primers that are capable of amplifying VH and VL respectively, by using a collection (library) of the respective genes as a template. The sequences of primers used for VL amplification are shown in SEQ ID NOs: 102 and 103, while the sequences of primers used for VH amplification are shown in SEQ ID NOs: 104 and 105. The amplified rationally designed gene library of the heavy-chain and light-chain variable regions of human antibody was inserted into an appropriate phagemid vector carrying both a human IgG-derived CH1 sequence and a human IgG-derived light chain constant region sequence. The phagemid vector was introduced into E. coli by electroporation to construct a rationally designed library which presents Fab domains containing a human antibody variable region-constant region, and from which one can isolate antibodies that are capable of binding to antigens via adenosine or ATP as a switch. Such a rationally designed library which is constituted with various H chains and L chains that have adenosine- or ATP-binding activity is expected to be useful as a library containing human antibodies that, with the adenosine (or ATP) is fit in between antibody and antigen as shown in FIG. 19, can efficiently obtain adenosine/ATP switch antibodies against any arbitrary antigen. Furthermore, as described above, since ATNLSA1-4_D12 binds not only to adenosine and ATP but also to ADP, it was predicted to have binding activity to AMP and cAMP which are structurally similar to ATP, ADP, and adenosine. This suggests that such libraries are useful for isolating switch antibodies whose binding activity to arbitrary target antigens is altered depending on the presence of any one or more small molecules of ATP, ADP, AMP, cAMP, and adenosine.

[Example 9] Construction of an Immune Library to Obtain Adenosine/ATP Switch Antibodies Containing Anti-ATP/Adenosine Antibody Repertoires Multiple phage-display libraries of rabbit antibodies which present Fab domains comprising rabbit antibody sequences were constructed using as a template mRNA collected from a B cell population selected using MACS and FACS as described in Example 5-4, which expresses adenosine-PEG-biotin-binding antibodies. The construction method was carried out by referring to Rader (Methods Mol. Biol. (2009) 525, 101-28).

More specifically, cDNA was prepared by reverse transcription using as a template mRNA collected from 600,000 cells of the above-described B cells which were selected from nine immunized rabbits. Using the cDNA as a template, the heavy chain variable region sequence and the light chain variable region-constant region sequence were amplified by PCR using the primers shown in Table 15 under adequate conditions.

TABLE 15

| Primer name | SEQ ID NO: | Sequence |
|---|---|---|
| primer 1 | 64 | TATTACTCGCGGCCCAGCCGGCCATGGCAGCC WTCGANWTGACCCAGACT |
| primer 2 | 65 | TATTACTCGCGGCCCAGCCGGCCATGGCAGCC TATGATNTGACCCAGACT |
| primer 3 | 66 | TATTACTCGCGGCCCAGCCGGCCATGGCAGCB CAAGTGCTGACCCAGACT |
| primer 4 | 67 | TATTACTCGCGGCCCAGCCGGCCATGGCAGCC MTYGTGATGACCCAGACT |
| primer 5 | 68 | TATTACTCGCGGCCCAGCCGGCCATGGCAGCC GCCGTGCTGACCCAGACT |
| primer 6 | 69 | TATTACTCGCGGCCCAGCCGGCCATGGCGGCT GACATTGTGATGACCCAG |
| primer 7 | 70 | TATTACTCGCGGCCCAGCCGGCCATGGCCGCC GAYRTYGTGATGACCCAG |
| primer 8 | 71 | CTOTTCTAGAACGCGTCTAAGOGICACCCCTA TTGAAGCTC |
| primer 9 | 72 | TATTACTCGCGGCCCAGCCGGCCATGGCGCAG CYYGTGCTGACTCAGTCGCCCTC |
| primer 10 | 73 | CTCTTCTAGAACGCGTCTAAGCTTCTGCAGGG GCCAGGCTCTTC |
| primer 11 | 74 | TTCCGCCTCGGCGCTAGCCCAGGAGCAGSTGG WGGAGTCC |
| primer 12 | 75 | TTCCGCCTCGGCGCTAGCCCAGTCNNTGGAGG AGTCCGGG |
| primer 13 | 76 | TTCCGCCTCGGCGCTAGOCCAGTOGNNGGAGG AGTCCGGG |
| primer 14 | 77 | TTCCGCCTCGGCGCTAGCCCAGCAGCAGCTGG WGGAGTCC |

Figure 20:
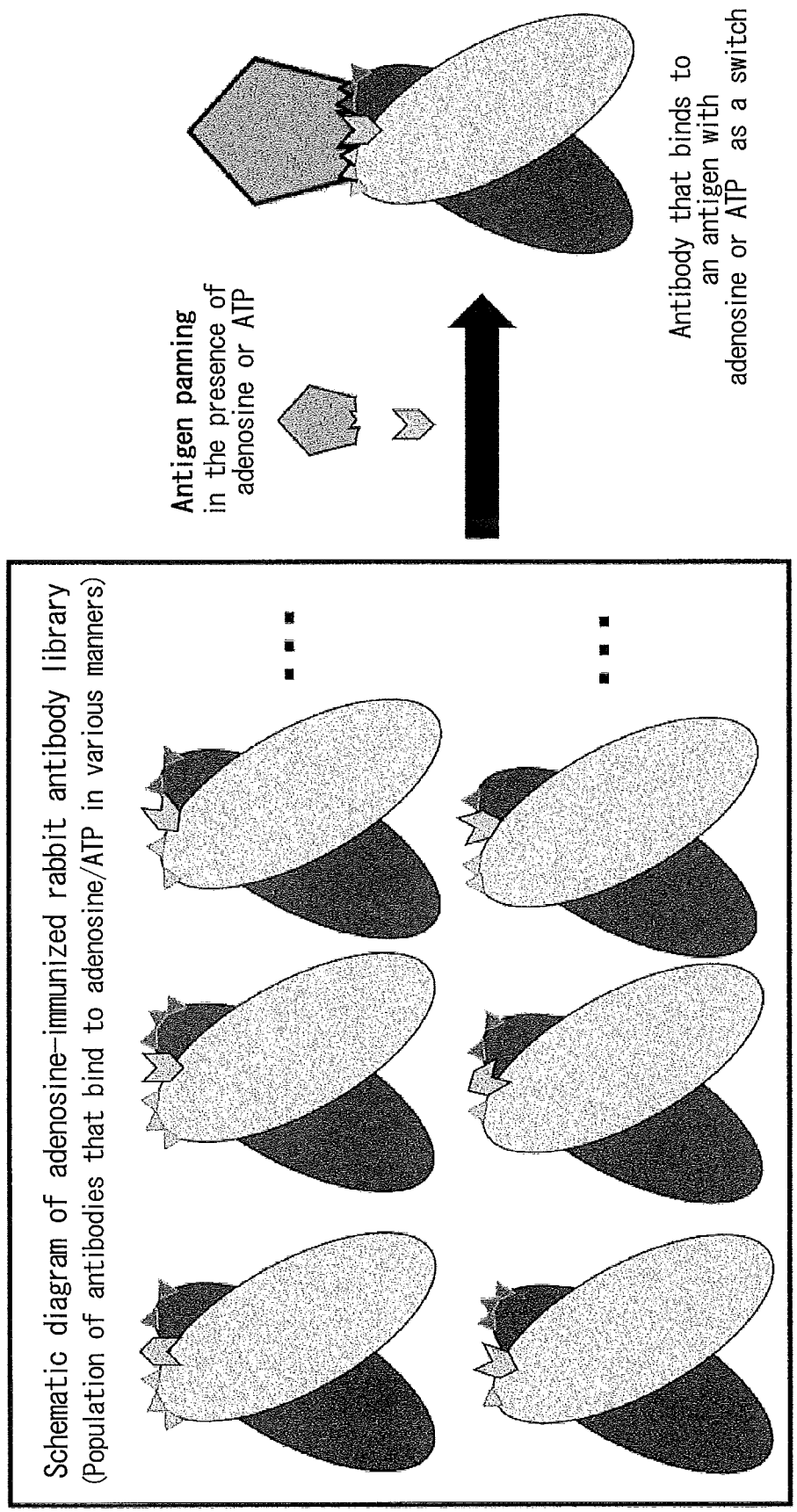
FIG. 20 shows the concept of an adenosine-immunized rabbit antibody library which yields adenosine/ATP-switch antibodies against any antigen and in which adenosine or ATP is sandwiched between the antibody and the antigen.

A combination of an amplified library of rabbit antibody heavy chain variable region genes and a library of rabbit antibody light chain variable region-constant region genes was inserted into an appropriate phagemid vector carrying a rabbit IgG-derived CH1 sequence. The phagemid vector was introduced into *E. coli* by electroporation to construct a phage-display library of rabbit antibodies (hereinafter, an antibody library from adenosine-immunized rabbits) which presents Fab domains containing a rabbit antibody variable region-constant region, and from which one can isolate antibodies that are capable of binding to antigens via adenosine or ATP as a switch. Such an adenosine immune library which is constituted by various H chains and L chains that exhibit adenosine binding property is expected to be useful as an immune library, with adenosine (or ATP) is sandwiched in between antibody and antigen as shown in FIG. 20, that can isolate adenosine/ATP switch antibodies against any arbitrary antigen.

[Example 10] Acquisition of Antibodies that Bind to Antigens in the Presence of Adenosine and ATP from Antibody Library Using Phage Display Techniques (10-1) Acquisition of Antibodies that Bind to Antigens in the Presence of Small Molecules from Library Using a Mixture of Adenosine and ATP Antibodies that exhibit antigen-binding activity in the presence of adenosine and/or ATP were obtained from the constructed phage-display library of antibodies from adenosine-immunized rabbits and the phage-display library of rationally designed antibodies. To obtain antibodies, phages displaying antibodies that exhibit the ability to bind to antigens captured by beads in the presence of adenosine and ATP were collected, and then the phages were collected in eluate from the beads in the absence of adenosine and ATP.

Phages were produced in *E. coli* containing the phagemid vector constructed for phage display. To the culture medium of *E. coli* in which phage production was carried out, 2.5 M NaCl/10% PEG was added to precipitate phages. The precipitated phage fraction was diluted with TBS to prepare a library suspension. Then, BSA was added at a final concentration of 4% to the phage library suspension. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

500 pmol of biotin-labeled antigen and a final concentration of 1 mM ATP-Na and adenosine were each added to the prepared phage library suspension. The phage library suspension was contacted with the antigen, adenosine, and ATP at room temperature for 60 minutes. The BSA-blocked magnetic beads were added to the phage library suspension, and the antigen-phage complex was allowed to bind to the magnetic beads at room temperature for 15 minutes. The beads were washed once with ATP- and adenosine-dissolved TBS. Then, the beads were combined with 0.5 ml of 1 mg/ml trypsin. Immediately after the beads at room temperature were suspended for 15 minutes, a phage suspension was collected from the isolated beads using a magnetic stand. The collected phage suspension was added to 10 ml of *E. coli* cells of strain ER2738 at the logarithmic growth phase (OD600=0.4 to 0.7). The *E. coli* was incubated at 37° C. with gentle stirring for one hour to be infected by phage. The infected *E. coli* was seeded in a 225 mm×225 mm plate. Then, phages were collected from the culture medium of the seeded *E. coli* to prepare a liquid stock of phage library.

The first round of panning was carried out to collect phages that are capable of antigen binding in the presence of adenosine and ATP, while the second and subsequent rounds of panning were performed to enrich phages that are capable of antigen binding only in the presence of adenosine and ATP. Specifically, 40 pmol of biotin-labeled antigen and a final concentration of 1 mM adenosine and ATP were each added to the prepared phage library suspension. Thus, the phage library was contacted with antigen, adenosine, and ATP for 60 minutes at room temperature. BSA-blocked magnetic beads were added, and the antigen-phage complex was allowed to bind to the magnetic beads for 15 minutes at room temperature. The beads were washed with 1 ml of adenosine and ATP-dissolved TBST (hereinafter referred to as (adenosine+ATP)/TBST), adenosine, and adenosine and ATP-dissolved TBS (hereinafter referred to as (adenosine+ATP)/TBS). Then, the beads were combined with 0.5 ml of TBS. Immediately after the beads were suspended at room temperature, a phage suspension was collected from the isolated beads using a magnetic stand. After this treatment was repeated, the two separately eluted phage suspensions were combined together. The pIII protein (helper phage-derived protein pIII) that does not display Fab was cleaved off from phages by adding 5 μl of 100 mg/ml trypsin to the collected phage suspension to eliminate the ability of phages that do not display Fab to infect E. coli. The phages collected from the trypsinized phage suspension were added to 10 ml of E. coli cells of strain ER2738 at the logarithmic growth phase (OD600=0.4 to 0.7). The E. coli was incubated at 37° C. with gentle stirring for one hour to be infected by phage. The infected E. coli was seeded in a 225 mm×225 mm plate. Then, phages were collected from the culture medium of the seeded E. coli to prepare a phage library suspension. Panning was performed three times to isolate antibodies that have antigen-binding activity in the presence of adenosine and ATP.

(10-2) Acquisition of Antibodies that Bind to Antigens in the Presence of Adenosine and ATP from Antibody Library Using a Negative Selection Method A phage-display library of antibodies constructed from rabbits immunized with adenosine or a phage-display library of rationally designed antibodies was screened for antibodies that exhibit antigen-binding activity in the presence of adenosine and/or ATP. As a first step of screening, the phage-display antibody library was contacted with biotin-labeled antigen-streptavidin in the absence of adenosine and ATP to eliminate phages displaying antibodies that have antigen-binding activity even in the absence of adenosine and ATP. Then, panning was performed in the same manner in the presence of adenosine and ATP to screen for antibodies that exhibit antigen-binding activity in the presence of adenosine and ATP.

Phages were produced in E. coli containing the constructed phage-display phagemid. To the culture medium of E. coli in which phage production took place, 2.5 M NaCl/10% PEG was added to precipitate phages. The precipitated phage fraction was diluted with TBS to prepare a library suspension. Then, BSA was added at a final concentration of 4% to the phage library suspension. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

Together with 250 pmol of biotin-labeled antigen, a mixture of adenosine and ATP was added at a final concentration of 1 mM to the prepared phage library suspension. Thus, the phage library suspension was contacted with the antigen, adenosine, and ATP for 60 minutes at room temperature. Then, BSA-blocked magnetic beads were added to the phage library suspension, and allowed to bind to the antigen-phage complex at room temperature for 15 minutes. The beads were washed once with (adenosine+ATP)/TBS. Then, the beads were combined with 0.5 ml of 1 mg/ml trypsin solution. Immediately after the beads were suspended at room temperature for 15 minutes, a phage suspension was collected from the isolated beads using a magnetic stand. The collected phage suspension was added to 10 ml of E. coli cells of strain ER2738 at the logarithmic growth phase (OD600=0.4 to 0.7). The E. coli was incubated at 37° C. with gentle stirring for one hour to be infected by phage. The infected E. coli was seeded in a 225 mm×225 mm plate. Then, phages were collected from the culture medium of the seeded E. coli to prepare a liquid stock of phage library.

The first round of panning was carried out to collect phages that are capable of binding in the presence of adenosine and ATP, while the second and subsequent rounds of panning were performed to enrich phages that are capable of antigen binding only in the presence of adenosine and ATP. Specifically, 250 pmol of biotinylated antigen was added to BSA-blocked Sera-Mag NeutrAvidin beads, and allowed to bind at room temperature for 15 minutes. The beads were washed three times with TBS. The phage library suspension subjected to BSA blocking was added to the washed beads, and allowed to bind at room temperature for one hour. Phages that did not bind to the antigens or beads were collected by isolating the beads using a magnetic stand. Forty pmol of biotin-labeled antigen, and a final concentration of 1 mM adenosine and ATP were each added to the collected phages. Thus, the phage library was contacted with the antigen, adenosine, and ATP for 60 minutes at room temperature. Then, BSA-blocked magnetic beads were added to the mixture of the labeled antigen, adenosine, ATP, and phage library, and allowed to bind to the antigen-phage complex for 15 minutes at room temperature. The beads were washed with 1 ml of (adenosine+ATP)/TBST and (adenosine+ATP)/TBS. Then, 0.5 ml of 1 mg/ml trypsin solution was added to the mixture. After the mixed suspension was stirred at room temperature for 20 minutes, phages were collected from the beads that had been separated using a magnetic stand. The collected phages were added to 10 ml of E. coli cells of strain ER2738 at the logarithmic growth phase (OD600=0.4 to 0.7). The E. coli was incubated at 37° C. with gentle stirring for one hour to be infected by phage. The infected E. coli was seeded in a 225 mm×225 mm plate. Panning was performed three times to isolate antibodies that have antigen-binding activity in the presence of adenosine and ATP.

(10-3) Acquisition of Antibodies that Bind to Antigens in the Presence of Adenosine and ATP from Antibody Library Using an Alternating Panning Method A phage-display antibody library constructed from rabbits immunized with adenosine or a phage-display library of rationally designed antibodies is screened for antibodies that exhibit antigen-binding activity in the presence of adenosine and/or ATP. As a first step of screening, the phage-display antibody library is contacted with biotinylated adenosine and ATP-NeutrAvidin in the presence of non-labeled antigens to collect a phage-display library of antibodies that bind to adenosine and/or ATP in the presence of the antigen. Then, the phage-display antibody library is contacted with biotinylated antigen-streptavidin in the presence of adenosine and ATP to collect antibodies that bind to the antigen in the presence of adenosine and ATP. Thus, screening is carried out for antibodies that have antigen-binding activity in the presence of adenosine and ATP by performing panning in the alternating manner described above.

Phages are produced in E. coli containing the phagemid vector constructed for phage display. To the culture medium of E. coli in which phage production is took place, 2.5 M NaCl/10% PEG is added to precipitate phages. The precipitated phage fraction is diluted with TBS to prepare a library suspension. Then, BSA is added at a final concentration of 4% to the phage library suspension. Panning is performed using antigen-immobilized magnetic beads. The magnetic beads used are NeutrAvidin coated beads (Sera-Mag Speed-Beads NeutrAvidin-coated) and Streptavidin coated beads (Dynabeads M-280 Streptavidin).

Together with 1000 pmol of non-labeled antigen, 250 pmol of biotinylated ATP, 2'-Adenosine-PEG-Biotin, and 5'-Adenosine-PEG-Biotin are added to the prepared phage library suspension. Thus, the phage library suspension is contacted with the antigen, adenosine, and ATP at room temperature for 60 minutes. Then, BSA-blocked magnetic beads are added to the phage library suspension, and the complex of phage with the antigen, and adenosine and/or ATP is allowed to bind to the magnetic beads at room temperature for 15 minutes. The beads are washed once with TBS containing 1000 pmol of the antigen. Then, the beads are combined with 0.5 ml of 1 mg/ml trypsin solution. Immediately after the beads are suspended at room temperature for 15 minutes, a phage suspension is collected from the isolated beads using a magnetic stand. The collected phage suspension is added to 10 ml of $E.$ $coli$ cells of strain ER2738 at the logarithmic growth phase (OD600=0.4 to 0.7). The $E.$ $coli$ is incubated at 37° C. with gentle stirring for one hour to be infected by phage. The infected $E.$ $coli$ are plated onto a 225 mm×225 mm plate. Then, phages are collected from the culture medium of the seeded $E.$ $coli$ to prepare a phage library suspension.

A second round of panning is performed to enrich phages that are capable of binding to the biotinylated antigen in the presence of adenosine and ATP. Specifically, 40 pmol of biotinylated antigen and a final concentration of 1 mM adenosine and ATP are added to the prepared phage library solution. Thus, the phage library suspension is contacted with the antigen, as well as adenosine and ATP for 60 minutes at room temperature. Then, BSA-blocked magnetic beads are added to the phage library solution, and the complex of phage with the antigen as well as adenosine and/or ATP is allowed to bind to the magnetic beads at room temperature for 15 minutes. The beads are washed three times with TBST containing adenosine and ATP at a final concentration of 1 mM, and twice with TBS containing adenosine and ATP at a final concentration of 1 mM. Then, the beads are combined with 0.5 ml of 1 mg/ml trypsin solution. Immediately after the beads are suspended at room temperature for 15 minutes, a phage solution is collected from the isolated beads using a magnetic stand. The collected phage solution is added to 10 ml of $E.$ $coli$ cells of strain ER2738 at the logarithmic growth phase (OD600=0.4 to 0.7). The $E.$ $coli$ is incubated at 37° C. with gentle stirring for one hour to be infected by phage. The infected $E.$ $coli$ is seeded in a 225 mm×225 mm plate. Then, phages are collected from the culture medium of the seeded $E.$ $coli$ to prepare a phage library solution.

At subsequent even-numbered rounds, panning is performed in the same manner as the second-round panning. However, in the fourth and subsequent rounds of panning, the number of bead washes with (adenosine+ATP)/TBST and (adenosine+ATP)/TBS are both increased to five times.

A third round of panning is performed to also enrich phages that are capable of binding to biotinylated adenosine and ATP in the presence of the antigen. Specifically, together with 250 pmol of biotinylated ATP, 2'-adenosine-PEG-Biotin and 5'-adenosine-PEG-Biotin, 1000 pmol of non-labeled antigen is added to the prepared phage library solution. Thus, the phage library solution is contacted with the antigen, as well as adenosine and ATP for 60 minutes at room temperature. Then, BSA-blocked magnetic beads are added to the phage library solution, and the complex of phage with the antigen as well as adenosine and/or ATP is allowed to bind to the magnetic beads at room temperature for 15 minutes. The beads are washed three times with TBST containing 1000 pmol of the antigen, and twice with TBS containing 1000 pmol of the antigen. Then, the beads are combined with 0.5 ml of a 1 mg/ml trypsin solution. Immediately after the beads are suspended at room temperature for 15 minutes, a phage solution is collected from the isolated beads using a magnetic stand. The collected phage solution is added to 10 ml of $E.$ $coli$ cells of strain ER2738 at the logarithmic growth phase (OD600=0.4 to 0.7). The $E.$ $coli$ is incubated at 37° C. with gentle stirring for one hour to be infected by phage. The infected $E.$ $coli$ is seeded in a 225 mm×225 mm plate. Then, phages are collected from the culture medium of the seeded $E.$ $coli$ to prepare a phage library solution.

At subsequent odd-numbered rounds, panning is performed in the same manner as the third-round panning. However, in the fourth and subsequent rounds of panning, the number of bead washes with TBST containing the antigen and TBS containing the antigen is both increased to five times. Alternatively, regardless of whether it is an odd- or even-numbered round, panning in the third and subsequent rounds is always performed in the same manner as the third-round panning. However, in the fourth and subsequent rounds of panning, the number of bead washes with TBST containing antigen and TBS containing antigen is both increased to five times.

(10-4) Assessment of Binding Activity in the Presence or Absence of Adenosine and/or ATP by Phage ELISA Phage-containing culture supernatants were collected according to a conventional method (Methods Mol. Biol. (2002) 178, 133-145) from single colonies of $E.$ $coli$ obtained by the method described above. The collected culture supernatants were treated by ultrafiltration using NucleoFast 96 (MACHERY-NAGEL). 100 µl of the culture supernatants were added to each well of NucleoFast 96, and it was centrifuged (4500 g for 45 minutes) to remove flow through. After addition of 100 µl of $H_2O$, the NucleoFast 96 was washed by centrifugation (4500 g for 30 minutes). Finally, 100 µl of TBS was added, and the NucleoFast 96 was allowed to stand for five minutes at room temperature. A phage suspension was collected from the supernatant in each well of the NucleoFast 96.

The purified phages, to which TBS or (adenosine+ATP)/TBS was added, were subjected to ELISA by the following procedure. A StreptaWell 96 microtiter plate (Roche) was coated overnight with 100 µl of TBS containing biotin-labeled antigen. After the antigen was removed by washing each well of the plate with TBST, the wells were blocked with 250 µl of 2% skim milk/TBS for one hour or more. 2% skim milk/TBS was removed, and then the prepared, purified phages were added to each well. The plate was allowed to stand at 37° C. for one hour to allow binding of antibody-displaying phages to the antigen in each well in the presence or absence of adenosine and/or ATP. After washing with TBST or (adenosine+ATP)/TBST, HRP-conjugated anti-M13 antibody (Amersham Pharmacia Biotech) diluted with TBS or (adenosine+ATP)/TBS was added to each well. The plate was incubated for one hour. Following washes with TBST or (adenosine+ATP)/TBST, the TMB single solution (ZYMED) was added to each well. The chromogenic reaction in the solution of each well was terminated by adding sulfuric acid. Then, the developed color was assessed by measuring absorbance at 450 nm. The result revealed that for three types of antigens: human IL6, human IL6 receptor, and HSA (human serum albumin), there were multiple types of antibodies bound in the presence of small molecules. Antibodies that bind in the presence of ATP were also obtained from the human naïve antibody library. Meanwhile, switch antibodies to human IL6, human IL6 receptor, and HSA could be obtained with greater efficiency. The result of phage ELISA is shown in Table 16.

TABLE 16

|  | human IL6 | human IL6R | HSA |
| --- | --- | --- | --- |
| Number of panning | 4 | 3 | 4 | 4 |
| Number of clones subjected to ELISA | 96 | 96 | 96 | 96 |
| Number of positive clones (S/N ratio > 10) | 35 | 23 | 64 | 52 |
| Number of dependent clones (SM +/− ratio > 2) | 18 | 22 | 64 | 50 |
| Number of dependent clone sequences | 2 | 17 | 35 | 5 |

(10-5) Assessment for Binding Ability of Switch Antibodies Whose Antigen-Binding Activity is Altered Depending on the Presence of Adenosine and ATP, and Sequence Analysis Genes were amplified using specific primers (SEQ ID NOs: 111 and 112) from clones that had been assessed to have antigen-binding activity in the presence of adenosine or ATP based on the phage ELISA result described in (10-4). The nucleotide sequences of the genes were analyzed, and the result showed that multiple antibodies that bind to antigens, human IL6, HSA, and human IL6R, and have sequences different from one another were obtained. The amino acid sequences of I6DL2C1-4_076 (antibody to human IL6), HSDL3C5-4_015 (antibody to HSA), and 6RAD2C1-4_011 and 6RAD2C1-4_076 (antibodies to human IL-6R) are shown in Table 17.

TABLE 17

| Clone name | Heavy chain SEQ ID NO | Light chain SEQ ID NO |
| --- | --- | --- |
| I6DL2C1-4_076 | SEQ ID NO: 78 | SEQ ID NO: 79 |
| HSDL3C5-4_015 | SEQ ID NO: 80 | SEQ ID NO: 81 |
| 6RAD2C1-4_011 | SEQ ID NO: 82 | SEQ ID NO: 83 |
| 6RAD2C1-4_076 | SEQ ID NO: 84 | SEQ ID NO: 85 |

(10-6) Identification of Small Molecules Required for Antigen Binding of the Obtained Antibodies Each of the obtained antibodies I6DL2C1-4_076, HSDL3C5-4_015, 6RAD2C1-4_011, and 6RAD2C1-4_076 was subjected to ELISA. The small molecules used were 1 mM ATP, adenosine, and a mixture thereof. The antigens used were biotin-labeled human IL6, human IL6R, and HSA.

Figure 25:
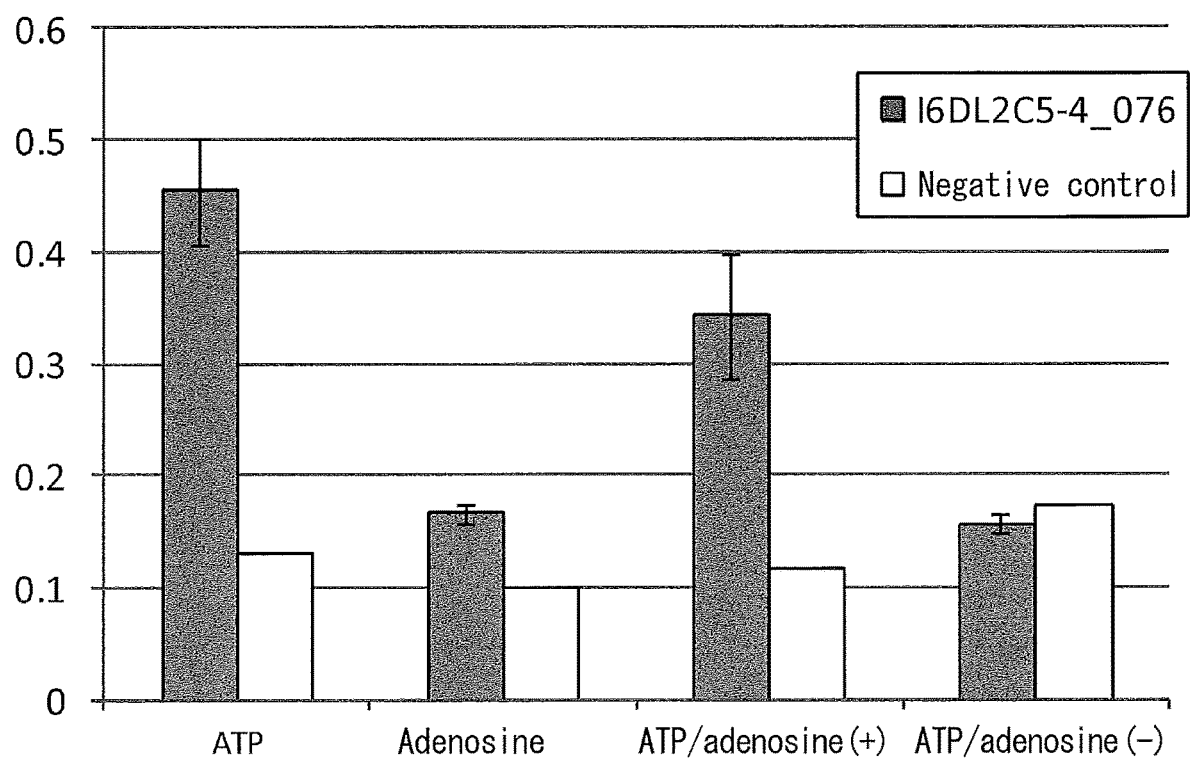
FIG. 25 is a figure showing the result of ELISA performed on clone 16DL2C5-4_076, which was obtained from the rationally designed antibody library against human IL-6 in the presence or absence of ATP and/or adenosine at 1 mM. The vertical axis shows the absorbance value which evaluates binding activity of the antibody to human IL-6. Results obtained when using M13KO7 Helper Phage are presented as the negative control.
Figure 26:
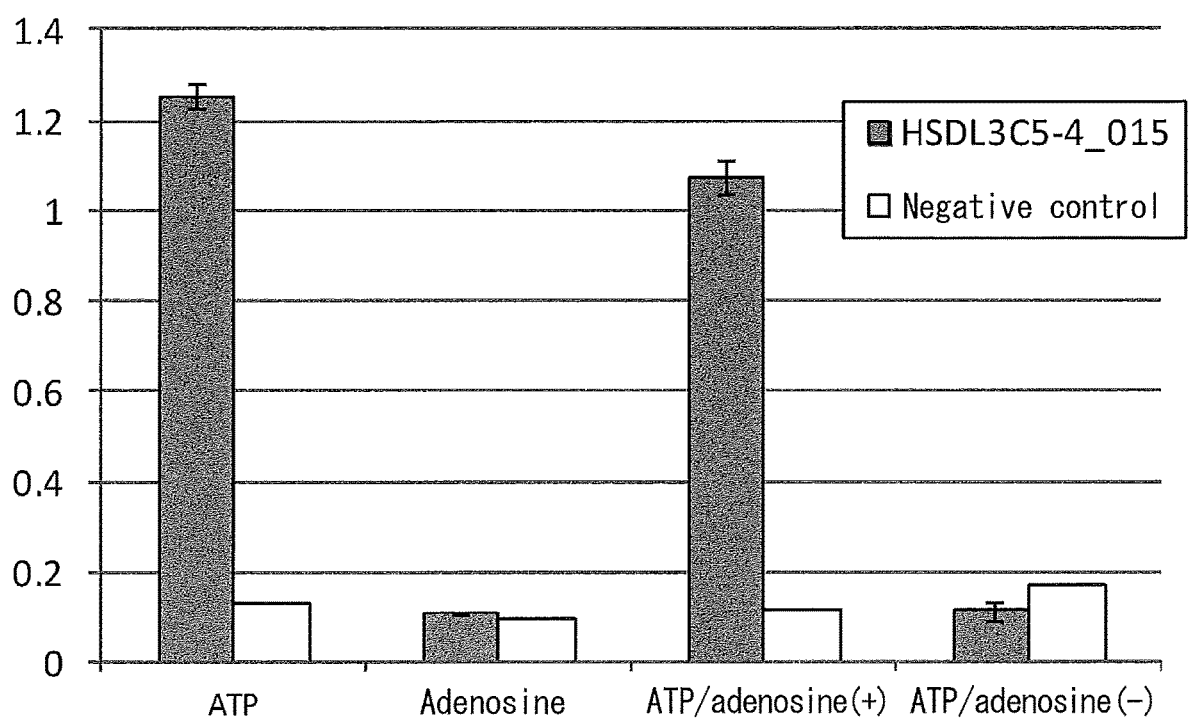
FIG. 26 is a figure showing the result of ELISA performed on clone HSDL3C5-4_015, which was obtained from the rationally designed antibody library against human serum albumin in the presence or absence of ATP and/or adenosine at 1 mM. The vertical axis shows the absorbance value which assesses binding activity of the antibody to human serum albumin. Results obtained when using M13KO7 Helper Phage are presented as the negative control.
Figure 27:
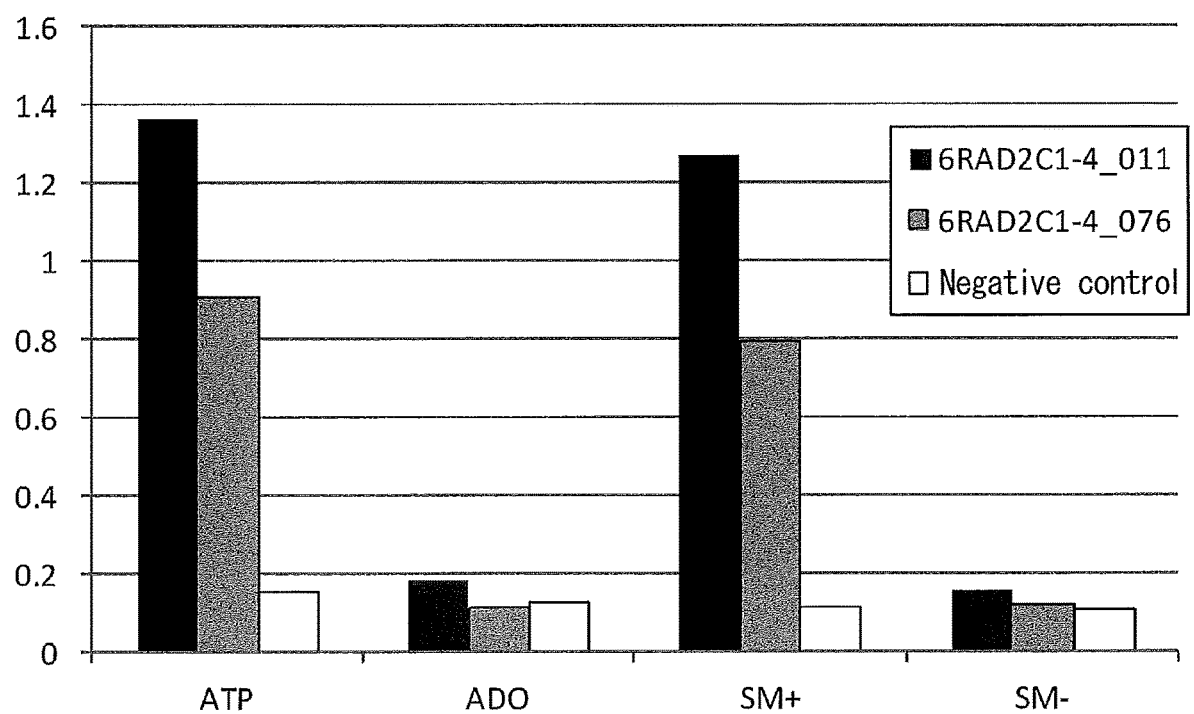
FIG. 27 is a figure showing the result of ELISA performed on clone 6RAD2C1-4_011 and 6RAD2C1-4_076, which were obtained from the rationally designed antibody library against human IL-6 receptor in the presence or absence of ATP and/or adenosine (written as ADO) at 1 mM, and in the presence or absence of a small-molecule cocktail (SC). The vertical axis shows absorbance values which assess the binding activity of the antibody to the human IL-6 receptor. Results obtained when using M13KO7 Helper Phage are presented as the negative control.

First, a StreptaWell 96 microtiter plate (Roche) was coated at room temperature for one hour or more with 100 µl of TBS containing a biotin-labeled antigen. Following TBST wash to remove the unbound biotin-labeled antigen from the plate, each well was blocked with 250 µl of 2% skim milk/TBS for one hour or more. After 2% skim milk/TBS was removed from each well, 50 µl of the antibody-displaying phage was added to the plate. The plate was allowed to stand at room temperature for one hour to allow binding of each phage to the biotin-labeled antigen in each well in the presence or absence of ATP and/or adenosine. After washing with TBST with or without ATP and/or adenosine, an HRP-conjugated anti-M13 antibody (Amersham Pharmacia Biotech) diluted with TBS or (adenosine and/or ATP)/TBS was added to each well. The plate was incubated for one hour. Following wash with TBST with or without each small molecule, the TMB single solution (ZYMED) was added to each well. The chromogenic reaction in the solution of each well was terminated by adding sulfuric acid. Then, the developed color was assessed by measuring absorbance at 450 nm (FIGS. 25, 26, and 27).

[Example 11] Binding Activity of Antibodies Obtained as Described in Example 2 to Human IL-6 in the Presence of Amino Acid Metabolites Other than Kynurenine Antibody I6NMSC1-3_A11 obtained as described in Example 2-4, which binds to human IL-6 in the presence of small molecules, is an antibody that binds to human IL-6 in the presence of kynurenine as described in Example 3-2. Kynurenine is a tryptophan metabolite, which is converted to anthranilic acid by kynureninase; to 3-hydroxykynurenine by kynurenine 3-hydroxylase; and to kynurenic acid by kynurenine aminotransferase (Stefan Lob et. al., Nat Rev Cancer. (2009) 9 (6), 445-452). Amino acid metabolites such as tryptophan metabolites were assessed as to whether they are appropriate as a non-limiting embodiment of cancer tissue-specific compounds of the present invention, particularly cancer cells-specific metabolites of the present invention.

I6NMSC1-3_A11 described in Example 3-2 which has antigen-binding activity in the presence of kynurenine, a known anti-human IL-6 antibody CLB8-F1, and GC413 as a negative control were subjected to ELISA under the seven conditions described Table 18. Meanwhile, each amino acid and metabolites thereof were appropriately prepared at the concentrations shown in Table 18 using the buffers indicated in Table 4. The antigen used was biotin-labeled human IL-6.

TABLE 18

| Condition | Small molecule | Concentration |
| --- | --- | --- |
| 1 | Kynurenine | 100 µM |
| 2 | Tryptophan | 100 µM |
| 3 | Phenylalanine | 100 µM |
| 4 | Anthranilic acid | 100 µM |
| 5 | 3-Hydroxykynurenine | 100 µM |
| 6 | Kynurenic acid | 100 µM |
| 7 | — | — |

First, a StreptaWell 96 microtiter plate (Roche) was coated at room temperature for one hour or more with 100 µl of PBS containing a biotin-labeled antigen. After washing with Wash buffer to remove the unbound antigen from the plate, each well was blocked for one hour or more with 250 µl of Blocking Buffer. After Blocking Buffer was removed from each well, the purified IgGs were prepared to 2.5 µg/ml in Sample Buffer containing small molecules at the final concentrations shown in Table 18, and each was aliquoted at 100 µl into the plate. The plate was allowed to stand at room temperature for one hour to allow binding of each IgG to the antigen in each well. After washing with Wash Buffer containing amino acids or amino acid metabolites at the final concentrations shown in Table 18, an HRP-conjugated anti-human IgG antibody (BIOSOURCE) diluted with Sample Buffer containing the same amino acids and amino acid metabolites was added to each well. The plate was incubated for one hour. Following wash with Wash Buffer containing each amino acid or amino acid metabolite, the TMB single solution (ZYMED) was added to each well. The chromogenic reaction in the solution of each well was terminated by adding sulfuric acid. Then, the developed color was assessed by measuring absorbance at 450 nm. The compositions of buffers used are shown in Table 4.

Figure 21:
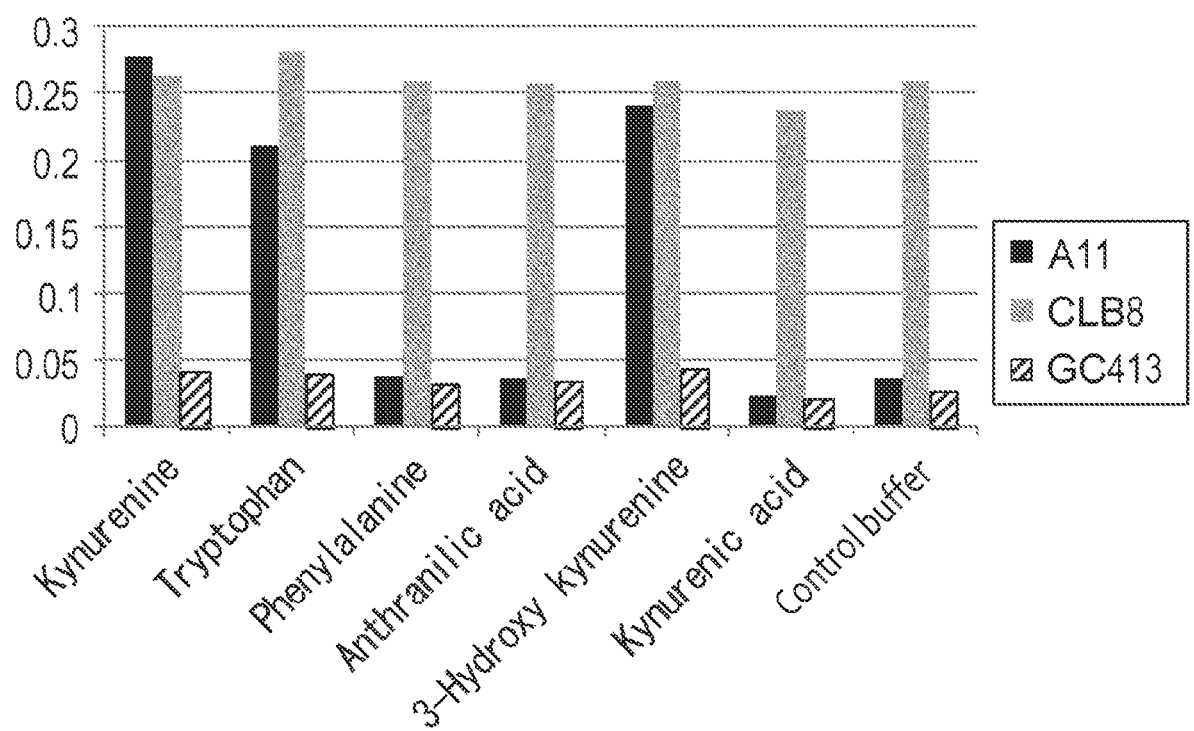
FIG. 21 is a figure showing the result of ELISA for binding of the antibody to human IL-6. The vertical axis shows the binding activity of each antibody to human IL-6 depending on the presence or absence of amino acids or amino acid metabolites (kynurenine, tryptophan, phenylalanine, anthranilic acid, 3-hydroxykynurenine, and kynurenic acid), presented as absorbance values at wavelength of 450 nm.

The measurement result is shown in FIG. 21. The absorbance for CLB8-F1 was constant regardless of the type and presence of small molecules. Meanwhile, the absorbance for I6NMSC1-3_A11 was markedly lower under condition 7 (in the absence of small molecules) as compared to under condition 1 (kynurenine solution). Furthermore, the absorbance for I6NMSC1-3_A11 was high under condition 2 (tryptophan solution) and condition 5 (3-hydroxykynurenine solution) as well as under condition 1. This shows that I6NMSC1-3_A11 is an antibody that binds to human IL-6 as an antigen not only in the presence of kynurenine, but also in the presence of an amino acid (tryptophan) as a kynurenine precursor or in the presence of a kynurenine metabolite.

This finding suggests that the same method can be used to obtain antibodies that bind to an antigen of interest not only in the presence of a single type of amino acid metabolite but also in the presence of multiple different types of amino acids or amino acid metabolites.

[Example 12] Acquisition of Antibodies that Bind to Human IL-6 in the Presence of Small Molecules from Human Antibody Library Using Phage-Display Technique (12-1) Acquisition of Antibodies that Bind to Human IL-6 in the Presence of Small Molecules from the Library Using Bead Panning or a Negative Selection Method By the same method described in 2-2 and 2-3, the phage-display library of naïve human antibodies constructed as described in Example 2-1 was screened for antibodies that exhibit antigen-binding activity in the presence of small molecules.

(12-2) Assessment of Binding Activity in the Presence of Small Molecules by Phage ELISA Culture supernatants containing phages were obtained from single colonies of E. coli obtained by the same method described in Example 2-4. The phages were subjected to ELISA. By carrying out phage ELISA using the 768 isolated clones, clones "I6NMSC1-3_#03" and "I6NMSC1-3_#17", which exhibited binding activity to human IL-6 as an antigen in the presence of small molecule cocktail, were newly obtained.

(12-3) Expression and Purification of Antibodies that Bind to Human IL-6

Genes were amplified from clones I6NMSC1-3_#03 and I6NMSC1-3_#17 that had been assessed to have antigen-binding activity in the presence of SC by phage ELISA, using specific primers (SEQ ID NOs: 110 and 112); and their nucleotide sequences were analyzed. The heavy-chain and light-chain sequences of I6NMSC1-3_#03 are the sequences of SEQ ID NOs: 50 and 51, respectively. Meanwhile, the heavy-chain and light-chain sequences of I6NMSC1-3_#17 are the sequences of SEQ ID NOs: 52 and 53, respectively. The gene sequence encoding the variable region of I6NMSC1-3_#17 was inserted into an animal expression plasmid for human IgG1/Lambda, while the gene sequence encoding the variable region of I6NMSC1-3_#03, a known anti-human IL-6 antibody CLB8-F1 (the heavy chain and light chain sequences are shown in SEQ ID NOs: 32 and 33, respectively), or an anti-human glypican-3 antibody GC413 (the heavy chain and light chain sequences are shown in SEQ ID NOs: 34 and 35, respectively) as a negative control was inserted into an animal expression plasmid for human IgG1/Kappa. The expressed antibodies were purified by the method described in Example 3.

(12-4) Identification of Small Molecules Necessary for the Binding of Antibody I6NMSC1-3_#03 to Human IL-6

I6NMSC1-3_#03 was subjected to ELISA under the nine conditions described in Table 3. Meanwhile, each small molecule was appropriately prepared at the concentrations shown in Table 3 using the buffers indicated in Table 4. The antigen used was biotin-labeled human IL-6.

First, a StreptaWell 96 microtiter plate (Roche) was coated at room temperature for one hour or more with 100 µl of PBS containing the biotin-labeled antigen. After washing with Wash buffer to remove the unbound antigen from the plate, each well was blocked for one hour or more with 250 µl of Blocking Buffer. After removing Blocking Buffer from each well, the purified IgGs were prepared to 2.5 µg/ml in Sample Buffer containing small molecules at the final concentrations shown in Table 3, and each was aliquoted at 100 µl into the plate. The plate was allowed to stand at room temperature for one hour to allow binding of each IgG to the antigen in each well. After washing with Wash Buffer containing small molecules at the final concentrations shown in Table 3, an HRP-conjugated anti-human IgG antibody (BIOSOURCE) diluted with Sample Buffer containing the same small molecules was added to each well. The plate was incubated for one hour. Following wash with Wash Buffer containing each small molecule, the TMB single solution (ZYMED) was added to each well. The chromogenic reaction in the solution of each well was terminated by adding sulfuric acid. Then, the developed color was assessed by measuring absorbance at 450 nm. The composition of the buffer used is shown in Table 4.

Figure 22:
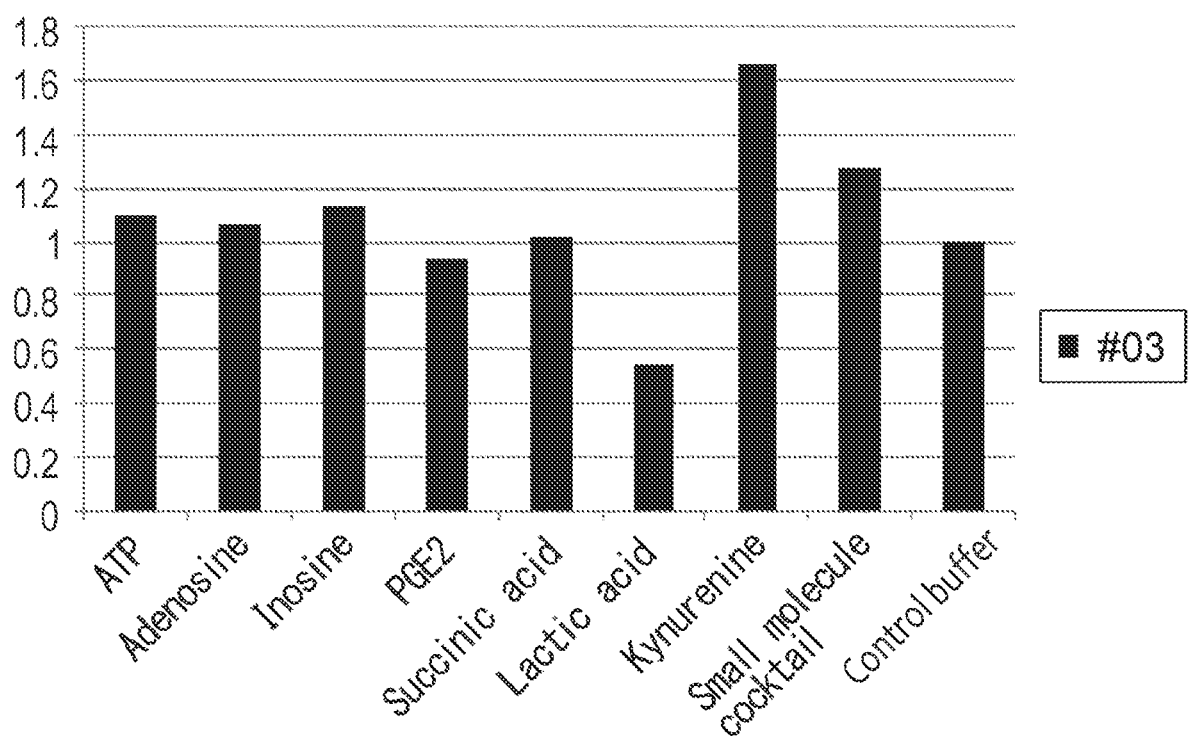
FIG. 22 is a figure showing the result of ELISA for binding of the antibody to human IL-6. The vertical axis shows the binding activity of the I6NMSC1-3_#03 antibody to human IL-6 depending on the presence or absence of each small molecule (ATP, adenosine, inosine, PGE2, succinic acid, lactic acid, kynurenine, and a small-molecule cocktail), presented as specific activity values calculated from absorbance values at wavelength of 450 nm.

The measurement result is shown in FIG. 22. The result showed that the absorbance for I6NMSC1-3_#03 was markedly lower under condition 9 (without small molecules) as compared to that under condition 8 (the complete small molecule cocktail solution). Similar to the result of phage ELISA, this result confirmed that I6NMSC1-3_#03 has the property that its antigen binding is altered depending on the presence or absence of small molecules. Furthermore, the absorbance for I6NMSC1-3_#03 was comparable between condition 7 (100 µM kynurenine) and condition 8; however, the absorbance was lower under other conditions. This demonstrated that, like I6NMSC1-3_A11 described in Example 3, I6NMSC1-3_#03 was an antibody that binds to human IL-6 as an antigen in the presence of kynurenine. I6NMSC1-3_#03 has an amino acid sequence different from I6NMSC1-3_A111, which demonstrates that the method described above can be used to isolate different types of antibodies that bind to antigens in the presence of small molecules.

(12-5) Identification of Small Molecules Necessary for the Binding of Antibody I6NMSC1-3_#17 to Human IL-6

Three types of antibodies: obtained I6NMSC1-3_#17, control CLB8-F1, and negative control GC413 were subjected to ELISA under the nine conditions described in Table 3. Each small molecule was prepared to an appropriate concentration shown in Table 3 using the buffers shown in Table 4. The antigen used was biotin-labeled human IL-6.

First, a StreptaWell 96 microtiter plate (Roche) was coated at room temperature for one hour or more with 100 µl of PBS containing the biotin-labeled antigen. After washing with Wash buffer to remove the unbound antigen from the plate, each well was blocked for one hour or more with 250 µl of Blocking Buffer. After Blocking Buffer was removed from each well, the purified IgGs were prepared to 0.15 µg/ml in Sample Buffer containing small molecules at the final concentrations shown in Table 3, and each was aliquoted at 100 µl into the plate. The plate was allowed to stand at room temperature for one hour to allow binding of each IgG to the antigen in each well. After washing with Wash Buffer containing small molecules at the final concentrations shown in Table 3, an HRP-conjugated anti-human IgG antibody (BIOSOURCE) diluted with Sample Buffer containing the same small molecules was added to each well. The plate was incubated for one hour. Following wash with Wash Buffer containing each small molecule, the TMB single solution (ZYMED) was added to each well. The chromogenic reaction in the solution of each well was terminated by adding sulfuric acid. Then, the developed color was assessed by measuring absorbance at 450 nm. The composition of the buffer used is shown in Table 4.

Figure 23:
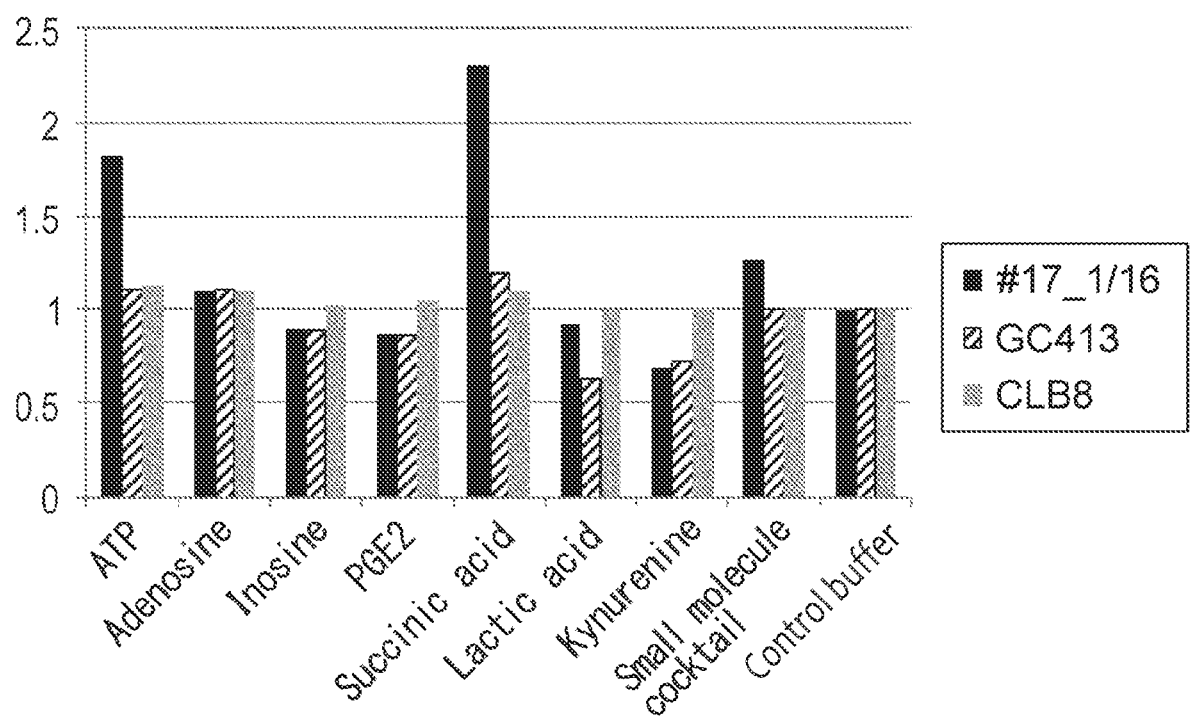
FIG. 23 is a figure showing the result of ELISA for binding of the antibody to human IL-6. The vertical axis shows the binding activity of the I6NMSC1-3_#17 antibody to human IL-6 depending on the presence or absence of each small molecule (ATP, adenosine, inosine, PGE2, succinic acid, lactic acid, kynurenine, and a small-molecule cocktail), presented as specific activity values calculated from absorbance values at wavelength of 450 nm.

The measurement result is shown in FIG. 23. The result showed that the absorbance for CLB8-F1 was the same regardless of the type and presence or absence of small molecule, whereas the absorbance for I6NMSC1-3_#17 was markedly lower under condition 9 (without small molecules) as compared to that under condition 8 (the complete small molecule cocktail solution). Similar to the result of phage ELISA, this result confirmed that I6NMSC1-3_#17 has the property that its antigen binding is altered depending on the presence or absence of small molecules. Furthermore, the absorbance for I6NMSC1-3_#17 under condition 1 (1 mM ATP-Na) and condition 5 (1 mM succinic acid) was comparable to that under condition 8; however, the absorbance was lower under other conditions. This result suggests that I6NMSC1-3_#17 is an antibody that binds to human IL-6 as an antigen in the presence of either ATP-Na or succinic acid. ATP is known to be released from cancer cells. Succinic acid is also known to be accumulated inside and outside of cells in a cancer cell-specific manner. The phenomenon that even in aerobic environments cancer cells metabolize in a glycolysis-dependent manner rather than by oxidative phosphorylation is known as Warburg effect. Both glycolysis and oxidative phosphorylation are chronically limited in ischemic-type cancers because of chronic insufficiency of blood flow, and thus such cancers acquire energy in poorer conditions. Ischemic-type cancers are known to perform energy metabolism depending on fumarate respiration, resulting in accumulation of succinic acid as a fumarate metabolite (Cancer Res. (2009) 69 (11), 4918-4925).

This demonstrated that by using such method, it is possible to obtain antibodies that bind to antigens in the presence of a small molecule other than kynurenine. Also, this showed that it is possible to obtain antibodies that bind to antigens in the presence of small molecules such as ATP-Na and succinic acid which share a common feature that they have multiple negative charges but are structurally different from each other.

[Example 13] Acquisition of Antibodies that Bind to Human Serum Albumin (Hereinafter Also Referred to as HSA) in the Presence of Small Molecules by Phage-Display Techniques from Human Antibody Library (13-1) Acquisition of Antibodies that Bind to HSA in the Presence of Small Molecules from Library by Bead Panning The phage-display library of naïve human antibodies constructed as described in Example 2 was screened for antibodies that exhibit HSA-binding activity in the presence of small molecules, specifically, by collecting phages displaying antibodies that in the presence of small molecules exhibit binding activity to HSA captured by beads. Phages were collected from a phage suspension eluted from the beads in the absence of small molecules. In this preparation method, biotin-labeled HSA was used as the antigen.

Phages produced in E. coli containing the phagemid vector constructed for phage display were purified by a conventional method. Then, a phage library suspension was prepared through dialysis against TBS. Next, skim milk was added to the phage library suspension at a final concentration of 3%. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

For efficient acquisition of small-molecule switch antibodies that are dependent on small molecules which can serve as a switch in cancer tissues, panning was performed to enrich antibodies that bind to antigens in the presence of a mixture of such small molecules (adenosine, adenosine triphosphate (adenosine 5'-triphosphate (ATP)), inosine, kynurenine, prostaglandin E2 (PGE2), succinic acid, and lactic acid (hereinafter referred to as small molecule cocktail (SC)) but do not bind to antigens in the absence of SC.

Specifically, together with 250 pmol of the biotin-labeled antigen, SC containing adenosine triphosphate sodium salt (ATP-Na), adenosine, inosine, succinic acid, and lactic acid at a final concentration of 1 mM, prostaglandin E2 (PGE2) at a final concentration of 1 µM, and kynurenine at a final concentration of 100 µM, which had been adjusted to be pH 7.4 with NaOH, was added and contacted with the prepared phage library suspension for 60 minutes at room temperature. Then, skim milk-blocked magnetic beads were added to the phage library suspension, and the antigen-phage complex was allowed to bind to the magnetic beads at room temperature for 15 minutes. The beads were washed once with SC/TBS (TBS containing SC). Then, the beads were combined with 0.5 ml of a 1 mg/ml trypsin solution. Immediately after the beads were suspended at room temperature for 15 minutes, a phage suspension was collected from the isolated beads using a magnetic stand. The collected phage suspension was added to 10 ml of E. coli cells of strain ER2738 at the logarithmic growth phase (OD600=0.4 to 0.7). The E. coli was incubated at 37° C. for one hour under gentle stirring to be infected by phage. The infected E. coli was seeded in a 225 mm×225 mm plate. Then, phages were collected from the culture medium of the seeded E. coli to prepare a liquid stock of phage library.

The first round of panning was carried out to collect phages that are capable of binding in the presence of small molecules, while the second and subsequent rounds of panning were performed to enrich phages that are capable of antigen binding in the presence of small molecules. Specifically, 40 pmol of the biotin-labeled antigen, SC, and NaOH were added to the prepared phage library suspension. Thus, the phage library was contacted with the antigen and small molecules for 60 minutes at room temperature. Skim milk-blocked magnetic beads were added and allowed to bind the antigen-phage complex for 15 minutes at room temperature. The beads were washed with 1 ml of SC/TBST and SC/TBS. Then, the beads were combined with 0.5 ml of TBS. Immediately after the beads were suspended at room temperature, a phage suspension was collected from the isolated beads using a magnetic stand. After repeating this treatment, the two separately eluted phage suspensions were combined together. Then, the resultant beads were combined with 0.5 ml of TBS, and stirred at room temperature for five minutes. A phage suspension was collected from the isolated beads using a magnetic stand. The pIII protein (helper phage-derived protein pIII) that does not display Fab was cleaved off from phages by adding 5 µl of 100 mg/ml trypsin to the collected phage suspension to eliminate the ability of phages that do not display Fab to infect *E. coli*. The phages collected from the trypsinized phage suspension were added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. The two types of infected *E. coli* obtained through two rounds of panning were mixed in equal amount at this time point. Then, phages were collected from the culture medium of the seeded *E. coli* to prepare a phage library suspension. Panning was performed three times to obtain antibodies that have antigen-binding activity in the presence of small molecules.

(13-2) Acquisition of Antibodies that Bind to HSA in the Presence of Small Molecules from the Library Using a Negative Selection Method The constructed phage-display library of naïve human antibodies was screened for antibodies that exhibit HSA-binding activity in the presence of small molecules. As a first step of screening, the phage-display library of naïve human antibodies was contacted with biotin-labeled antigen-streptavidin in the absence of small molecules to eliminate phages displaying antibodies that have HSA-binding activity even in the absence of small molecules. Then, panning was performed in the presence of small molecules in the same manner. Thus, screening was carried out for antibodies that have HSA-binding activity in the presence of small molecules. Biotin-labeled HSA was used as the antigen.

Phages were produced in *E. coli* containing the phagemid vector constructed for phage display. The produced phages were purified by a conventional method, and then a phage library suspension was prepared by dialyzing the phages against TBS. Then, skim milk was added at a final concentration of 3% to the phage library suspension. The magnetic beads used were NeutrAvidin coated beads (Sera-Mag SpeedBeads NeutrAvidin-coated) and Streptavidin coated beads (Dynabeads M-280 Streptavidin). Panning was performed using biotin-labeled HSA immobilized on magnetic beads.

Together with 250 pmol of biotin-labeled HSA, SC containing ATP-Na, adenosine, inosine, succinic acid, and lactic acid at a final concentration of 1 mM, PGE2 at a final concentration of 1 μM, and kynurenine at a final concentration of 100 μM, which had been adjusted to be pH 7.4 with NaOH, was added and contacted with the prepared phage library solution for 60 minutes at room temperature. Then, skim milk-blocked magnetic beads were added to the phage library solution, and allowed to bind to the complex of phage with biotin-labeled HSA for 15 minutes at room temperature. The beads were washed once with SC/TBS. Then, the beads were combined with 0.5 ml of a 1 mg/ml trypsin solution. Immediately after the beads were suspended at room temperature for 15 minutes, a phage suspension was collected from the isolated beads using a magnetic stand. The collected phage suspension was added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. Then, phages were collected from the culture medium of the seeded *E. coli* to prepare a phage library solution.

The first round of panning was carried out to collect phages that are capable of binding in the presence of small molecules, while the second and subsequent rounds of panning were performed to enrich phages that are capable of binding to biotin-labeled HSA in the presence of small molecules. Specifically, 250 pmol of biotin-labeled HSA was added to skim milk-blocked Sera-Mag NeutrAvidin beads and allowed to bind for 15 minutes at room temperature. The beads were washed three times with TBS; and a skim milk-blocked phage library solution was added to the beads, and allowed to bind at room temperature for one hour. The beads were isolated using a magnetic stand to collect phages that did not bind to biotin-labeled HSA or the beads. Forty pmol of biotin-labeled HSA, SC, and NaOH were added to the collected phages. Thus, the phage library was contacted with biotin-labeled HSA and small molecules in SC for 60 minutes at room temperature. Then, skim milk-blocked magnetic beads were added to the mixture of biotin-labeled HSA, SC, and phage library, and the complex of biotin-labeled HSA and phage was allowed to bind to the magnetic beads for 15 minutes at room temperature. The beads were washed with 1 ml of SC/TBST and SC/TBS. Then, 0.5 ml of a 1 mg/ml trypsin solution was added to the mixture. After the mixed solution was stirred for 20 minutes at room temperature, phages were collected from the beads separated using a magnetic stand. The collected phages were added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. Panning was performed three times to obtain antibodies that have binding activity to biotin-labeled HSA in the presence of small molecules.

(13-3) Assessment of Binding Activity in the Presence of Small Molecules by Phage ELISA Culture supernatants containing phages were collected according to a conventional method (Methods Mol. Biol. (2002) 178, 133-145) from single colonies of *E. coli* obtained by the method described above. The collected culture supernatants were treated by ultrafiltration using NucleoFast 96 (MACHEREY-NAGEL). 100 μl of the culture supernatants were added to each well, and the NucleoFast 96 was centrifuged (4500 g for 45 minutes) to remove flow-through. One hundred μl of $H_2O$ was added to each well, and again the NucleoFast 96 was centrifuged (4500 g for 30 minutes) for washing. After 100 μl of TBS was added, the NucleoFast 96 was allowed to stand for five minutes at room temperature. Finally, phage solution contained in the supernatant of each well was collected.

The purified phages, to which TBS or SC/TBS was added, were subjected to ELISA by the following procedure. A StreptaWell 96 microtiter plate (Roche) was coated overnight with 100 μl of TBS containing biotin-labeled HSA. After biotin-labeled HSA was removed by washing each well of the plate with TBST, the wells were blocked with 250 μl of 2% skim milk/TBS for one hour or more. 2% skim milk/TBS was removed, and then the prepared, purified phages were added to each well. The plate was allowed to stand at room temperature for one hour to allow binding of antibody-displaying phages to biotin-labeled HSA in each well in the presence or absence of SC. After washing with TBST or SC/TBST, an HRP-conjugated anti-M13 antibody (Amersham Pharmacia Biotech) diluted with TBS or SC/TBS was added to each well. The plate was incubated for one hour. Following wash with TBST or SC/TBST, the TMB single solution (ZYMED) was added to each well. The chromogenic reaction in the solution of each well was terminated by adding sulfuric acid. Then, the developed color was assessed by measuring absorbance at 450 nm.

Clone HSNMSC1-4_#22, which has binding activity to HSA as antigen in the presence of the small molecule cocktail, was obtained by carrying out phage ELISA using the 782 isolated clones.

(13-4) Expression and Purification of HSA-Binding Antibodies

Genes were amplified from clone HSNMSC1-4_#22 which had been assessed to have binding activity to biotin-labeled HSA in the presence of SC by the phage ELISA described in (13-3), using specific primers (SEQ ID NOs: 110 and 112). The nucleotide sequences of the genes were analyzed (the heavy chain and light chain sequences are represented by SEQ ID NOs: 54 and 55, respectively). Genes encoding the variable regions of HSNMSC1-4_#22 were inserted into an animal expression plasmid for human IgG1/Lambda. Meanwhile, genes encoding the variable regions of the negative control anti-human glypican-3 antibody GC413 (the heavy chain and light chain are represented by SEQ ID NOs: 34 and 35, respectively) were inserted into an animal expression plasmid for human IgG1/Kappa. The expressed antibodies were purified by the method described in Example 3.

(13-5) Identification of Small Molecules Necessary for Binding of the Obtained Antibodies to HSA Two types of antibodies obtained: HSNMSC1-4_#22 and GC413, were subjected to ELISA under the nine conditions described in Table 3. Meanwhile, each small molecule was appropriately prepared at the concentrations shown in Table 3 using the buffers indicated in Table 19. Biotin-labeled HSA was used as the antigen.

TABLE 19

| | |
|---|---|
| Wash buffer | 10 mM ACES, 150 mM NaCl, 0.05% Tween20, pH 7.4 |
| Blocking Buffer | 10 mM ACES, 150 mM NaCl, 2% SkimMilk, pH 7.4 |
| Sample Buffer | 10 mM ACES, 150 mM NaCl, Small molecule, pH 7.4 |

First, a StreptaWell 96 microtiter plate (Roche) was coated at room temperature for one hour or more with 100 µl of PBS containing biotin-labeled HSA. After washing with Wash buffer to remove unbound biotin-labeled HSA from the plate, each well was blocked for one hour or more with 250 µl of Blocking Buffer. After Blocking Buffer was removed from each well, the purified IgGs were prepared to 2.5 µg/ml in Sample Buffer containing small molecules at the final concentrations shown in Table 3, and each was aliquoted at 100 µl into the plate. The plate was allowed to stand at room temperature for one hour to allow binding of each IgG to biotin-labeled HSA in each well. After washing with Wash Buffer containing small molecules at the final concentrations shown in Table 3, an HRP-conjugated anti-human IgG antibody (BIOSOURCE) diluted with Sample Buffer containing the same small molecules was added to each well. The plate was incubated for one hour. Following wash with Wash Buffer containing each small molecule, the TMB single solution (ZYMED) was added to each well. The chromogenic reaction in the solution of each well was terminated by adding sulfuric acid. Then, the developed color was assessed by measuring absorbance at 450 nm. The composition of the buffer used is shown in Table 19.

Figure 24:
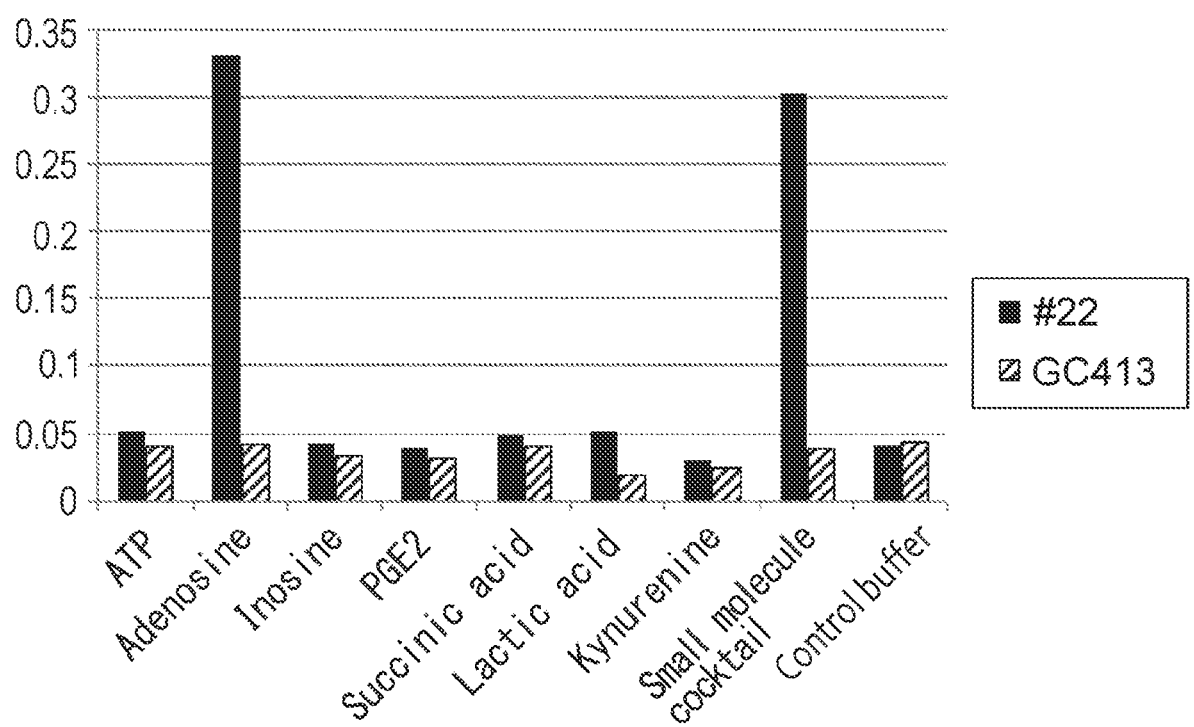
FIG. 24 is a figure showing the result of ELISA for binding of the antibody to HSA. The vertical axis shows the binding activity of the HSNMSC1-4_#22 antibody to HSA depending on the presence or absence of each small molecule (ATP, adenosine, inosine, PGE2, succinic acid, lactic acid, kynurenine, and a small-molecule cocktail), presented as absorbance values at wavelength of 450 nm.

The measurement result is shown in FIG. 24. The result showed that the absorbance for HSNMSC1-4_#22 was markedly lower under condition 9 (without small molecules) as compared to that under condition 8 (the complete small molecule cocktail solution). Similar to phage ELISA, this result confirmed that HSNMSC1-4_#22 has the property that its antigen binding is altered depending on the presence or absence of small molecules. Meanwhile, the absorbance for HSNMSC1-4_#22 was the same between condition 2 (1 mM adenosine) and condition 8, but it was markedly lower under other conditions. This result demonstrated that HSNMSC1-4_#22 is an antibody that binds to HSA as an antigen in the presence of adenosine. Thus, it was demonstrated that such method can be used to isolate antibodies that bind to antigens in the presence of small molecules other than kynurenine.

[Example 14] Acquisition of Antibodies that Bind to Human IL-6 Receptor (hIL-6R) in the Presence of Small Molecules from Human Antibody Library Using Phage Display Techniques (14-1) Acquisition of Antibodies that Bind to hIL-6R in the Presence of Small Molecules from the Library of Naïve Human Antibodies by Bead Panning The phage-display library of naïve human antibodies constructed as described in Example 2 was screened for antibodies that exhibit hIL-6R-binding activity in the presence of small molecules, specifically, by collecting phages displaying antibodies that in the presence of small molecules exhibit binding activity to hIL-6R captured by beads. Phages were collected from a phage eluate eluted from the beads in the absence of small molecules. In this preparation method, biotin-labeled hIL-6R was used as the antigen.

Phages produced in *E. coli* containing the phagemid vector constructed for phage display were purified by a conventional method. Then, a phage library solution was prepared by dialyzing the phages against TBS. Next, BSA was added at a final concentration of 4% to the phage library solution. Panning was performed using antigen-immobilized magnetic beads. The magnetic beads used were NeutrAvidin coated beads (Sera-Mag SpeedBeads NeutrAvidin-coated) and Streptavidin coated beads (Dynabeads M-280 Streptavidin).

For efficient acquisition of small molecule switch antibodies that are dependent on small molecules which can serve as a switch in cancer tissues, panning described in (2-2) was performed to enrich antibodies that bind to antigens in the presence of SC but do not bind to antigens in the absence of SC.

Specifically, together with 250 pmol of biotin-labeled antigen, SC prepared as described in (2-2) was added and contacted with the prepared phage library solution at room temperature for 60 minutes. Then, the phage library solution was added to BSA-blocked magnetic beads, and the antigen-phage complex was allowed to bind to the magnetic beads for 15 minutes at room temperature. The beads were washed once with SC/TBS (TBS containing SC). Then, the beads were combined with 0.5 ml of a 1 mg/ml trypsin solution. Immediately after the beads were suspended at room temperature for 15 minutes, the phage solution was collected from the isolated beads using a magnetic stand. The collected phage solution was added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. Then, phages were collected from the culture medium of the seeded *E. coli* to prepare a liquid stock of phage library.

Panning was performed as described in (2-2), except adding 10 µl of 100 mg/ml trypsin to cleave the pIII protein (helper phage-derived pIII protein) from phages that do not display Fab in order to eliminate the ability of the phages that do not display Fab to infect *E. coli*.

(14-2) Acquisition of Antibodies that Bind to hIL-6R in the Presence of Small Molecules from the Naïve Human Antibody Library Using a Negative Selection Method The constructed phage-display library of naïve human antibodies was screened for antibodies that exhibit hIL-6R-binding activity in the presence of small molecules. As a first step of screening, the phage-display library of naïve human antibodies was contacted with biotin-labeled antigen-streptavidin in the absence of small molecules to eliminate phages displaying antibodies that have hIL-6R-binding activity even in the absence of small molecules. Then, panning was performed in the presence of small molecules in the same manner to screen for antibodies that have hIL-6R-binding activity in the presence of small molecules. The antigen used was biotin-labeled hIL-6R. Then, a phage library solution was prepared by the method described in (2-3) using biotin-labeled hIL-6R as an antigen.

(14-3) Assessment of Binding Activity in the Presence of Small Molecules by Phage ELISA Culture supernatants containing phages were collected according to a conventional method (Methods Mol. Biol. (2002) 178, 133-145) from single colonies of *E. coli* obtained as described in (14-2). Phages purified by the method described in (2-4) were subjected to ELISA by the following procedure. A StreptaWell 96 microtiter plate (Roche) was coated overnight with 100 μl of TBS containing biotin-labeled hIL-6R. After biotin-labeled hIL-6R was removed by washing each well of the plate with TBST, the wells were blocked with 250 μl of 2% skim milk/TBS for one hour or more. 2% skim milk/TBS was removed, and then the prepared, purified phages were added to each well. The plate was allowed to stand at room temperature for one hour to allow binding of antibody-displaying phages to biotin-labeled hIL-6R in each well in the presence or absence of SC. After washing with TBST or SC/TBST, an HRP-conjugated anti-M13 antibody (Amersham Pharmacia Biotech) diluted with TBS or SC/TBS was added to each well. The plate was incubated for one hour. Following wash with TBST or SC/TBST, the TMB single solution (ZYMED) was added to each well. The chromogenic reaction in the solution of each well was terminated by adding sulfuric acid. Then, the developed color was assessed by measuring absorbance at 450 nm.

Clones 6RNMSC1-2_F02 and 6RNMSC1-3_G02, which have binding activity to hIL-6R as an antigen in the presence of a small molecule cocktail, were obtained by carrying out phage ELISA using 960 isolated clones.

(14-4) Expression and Purification of Antibodies that Bind to hIL-6R

Genes were amplified using specific primers (SEQ ID NOs: 110 and 112) from clones 6RNMSC1-2_F02 and 6RNMSC1-3_G02, which had been assessed to have binding activity to biotin-labeled hIL-6R in the presence of SC by the phage ELISA described in (14-3). The nucleotide sequences of the genes were analyzed (6RNMSC1-2_F02: the heavy chain and light chain sequences are shown in SEQ ID NOs: 86 and 87, respectively; 6RNMSC1-3_G02: the heavy chain and light chain sequences are shown in SEQ ID NOs: 88 and 89, respectively). Genes encoding the variable regions of 6RNMSC1-2_F02 and 6RNMSC1-3_G02, and those of the negative control anti-human glypican-3 antibody GC413 (the heavy chain and light chain are SEQ ID NOs: 34 and 35, respectively) were inserted into an animal expression plasmid for human IgG1/Kappa. The expressed antibodies were purified by the method described in Example 3.

(14-5) Identification of Small Molecules Necessary for Binding of the Obtained Antibodies to hIL-6R Three types of antibodies obtained: 6RNMSC1-2_F02 and 6RNMSC1-3_G02, and GC413 were subjected to ELISA under the nine conditions described in Table 3. Meanwhile, each small molecule was appropriately prepared at the concentrations shown in Table 3 using the buffers indicated in Table 19. The antigen used was biotin-labeled hIL-6R.

First, a StreptaWell 96 microtiter plate (Roche) was coated at room temperature for one hour or more with 100 μl of PBS containing biotin-labeled hIL-6R. After washing with Wash buffer to remove unbound biotin-labeled hIL-6R from the plate, each well was blocked for one hour or more with 250 μl of Blocking Buffer. After Blocking Buffer was removed from each well, the purified IgGs were prepared to 2.5 μg/ml in Sample Buffer containing small molecules at the final concentrations shown in Table 3, and each was aliquoted at 100 μl into the plate. The plate was allowed to stand at room temperature for one hour to allow binding of each IgG to biotin-labeled hIL-6R in each well. After washing with Wash Buffer containing small molecules at the final concentrations shown in Table 3, an HRP-conjugated anti-human IgG antibody (BIOSOURCE) diluted with Sample Buffer containing the same small molecules was added to each well. The plate was incubated for one hour. Following wash with Wash Buffer containing each small molecule, the TMB single solution (ZYMED) was added to each well. The chromogenic reaction in the solution of each well was terminated by adding sulfuric acid. Then, the developed color was assessed by measuring absorbance at 450 nm. The composition of the buffer used is shown in Table 19.

Figure 28:
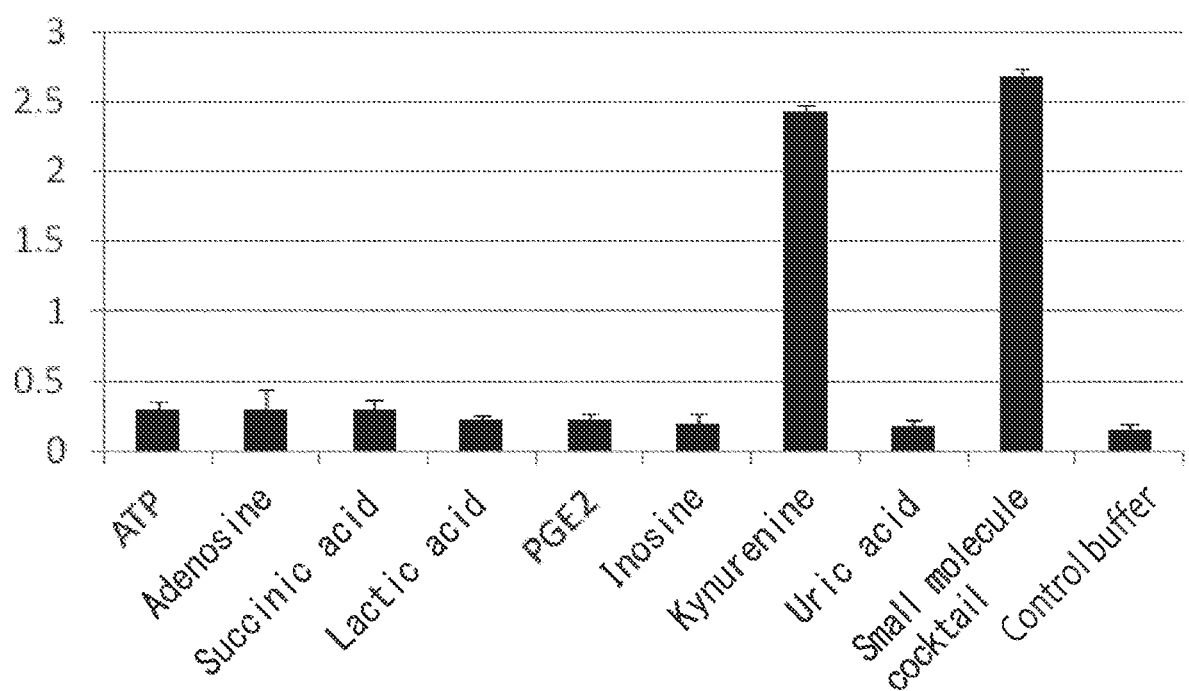
FIG. 28 is a figure showing the result of ELISA for binding of clone 6RNMSC1-2_F02 to human IL-6R. The vertical axis shows the absorbance values which assess the binding activity of the antibody to human IL-6R in the presence or absence of each small molecule.
Figure 29:
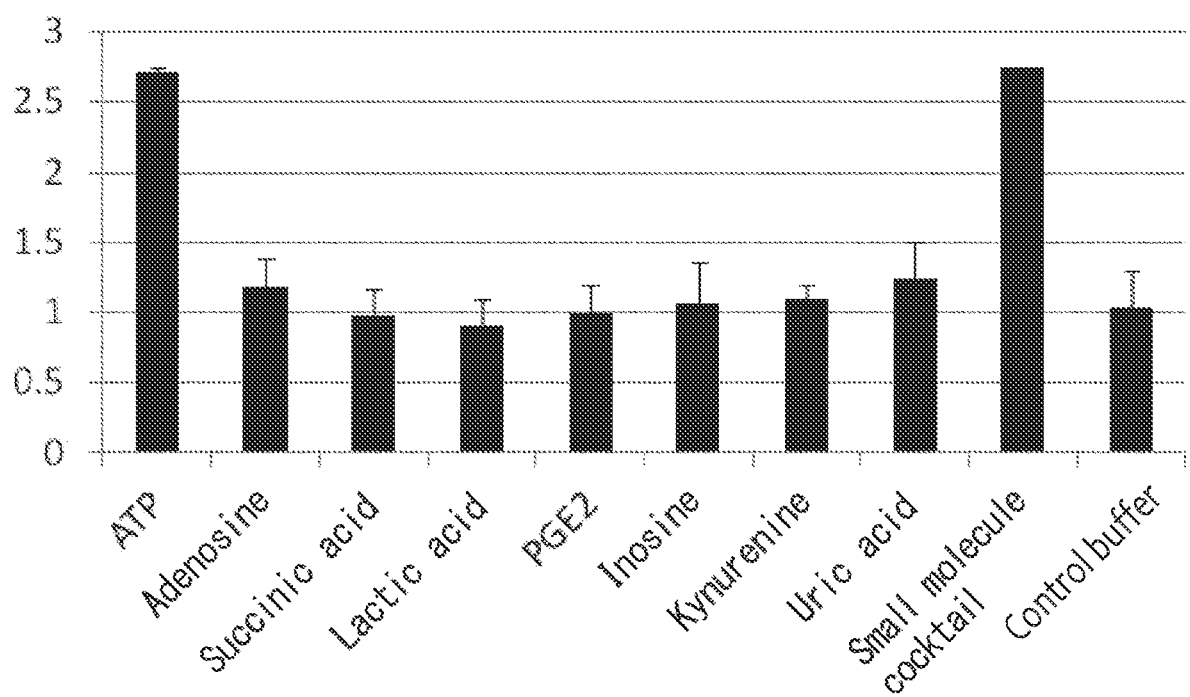
FIG. 29 is a figure showing the result of ELISA for binding of clone 6RNMSC1-3_G02 to human IL-6R. The vertical axis shows the absorbance values which assess the binding activity of the antibody to human IL-6R in the presence or absence of each small molecule.

The measurement result is shown in FIGS. 28 and 29. When 6RNMSC1-2_F02 or 6RNMSC1-3_G02 was used, the absorbance was markedly lower under condition 9 (in the absence of small molecules) as compared to under condition 8 (the complete small molecule cocktail solution). This result confirmed that 6RNMSC1-2_F02 and 6RNMSC1-3_G02 have the property that their antigen binding is altered depending on the presence or absence of small molecules. Meanwhile, when 6RNMSC1-2_F02 was used, the absorbance was the same between condition 7 (100 μM kynurenine) and condition 8, but the absorbance was markedly lower under other conditions, which shows that 6RNMSC1-2_F02 is an antibody that binds to hIL-6R as an antigen in the presence of kynurenine (FIG. 28). Furthermore, when 6RNMSC1-3_G02 was used, the absorbance was the same between condition 1 (1 mM ATP-Na) and condition 8, but the absorbance was markedly lower under other conditions, showing that 6RNMSC1-3_G02 is an antibody that binds to hIL-6R as an antigen in the presence of ATP (FIG. 29). It was thus demonstrated that the method described above can be used to isolate at one time multiple antibodies whose antigen-binding activity is altered in the presence of a different small molecule.

[Example 15] Characterization of Antibody 6RNMSC1-2_F02

(15-1) ELISA Assessment of hIL6R-Binding Activity in the Presence of Amino Acids and Amino Acid Metabolites Other than Kynurenine Antibody 6RNMSC1-2_F02 obtained as described in Example 14, which binds to hIL-6R in the presence of small molecules, is an antibody that binds to hIL-6R in the presence of kynurenine. Amino acid metabolites such as tryptophan metabolites described in Example 11 were assessed as to whether they are preferable as a non-limiting embodiment of cancer tissue-specific compounds, particularly cancer cell-specific metabolites, for use in the present invention.

6RNMSC1-2_F02 described in Example 14, which has antigen-binding activity in the presence of kynurenine, and negative control GC413 were subjected to ELISA under the seven conditions described in Table 18. Meanwhile, each small molecule was appropriately prepared at the concentrations shown in Table 18 using the buffers indicated in Table 4. The antigen used was biotin-labeled hIL-6R. ELISA was carried out using the method described in Example 11.

Figure 30:
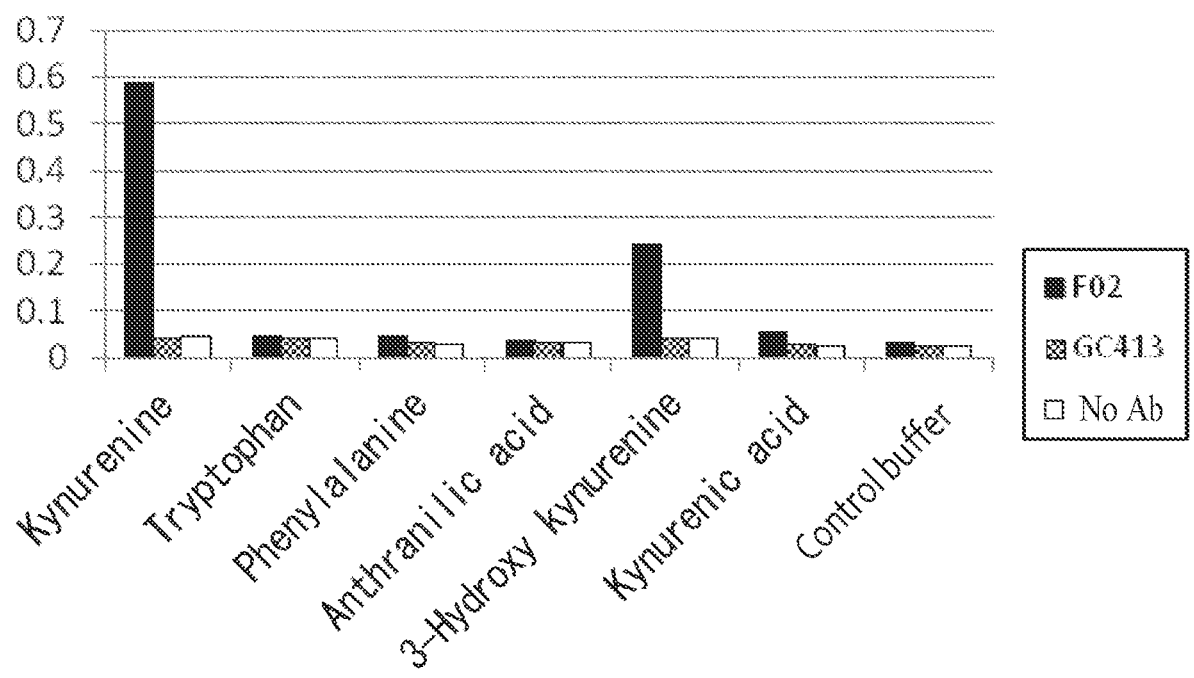
FIG. 30 is a figure showing the result of ELISA for binding of an antibody to human IL-6R. The vertical axis shows the absorbance values which assess the binding activity of the antibody to human IL-6R in the presence or absence of each amino acid or amino acid metabolite.

The measurement result is shown in FIG. 30. When 6RNMSC1-2_F02 was used, the absorbance was markedly lower under condition 7 (in the absence of small molecules) as compared to under condition 1 (kynurenine solution). Similarly, 6RNMSC1-2_F02 showed the same high absorbance under condition 5 (3-hydroxykynurenine solution) as under condition 1, suggesting that it is an antibody that binds to hIL-6R as an antigen not only in the presence of kynurenine but also in the presence of a kynurenine metabolite. Furthermore, the absorbance for 6RNMSC1-2_F02 was markedly lower under other conditions, suggesting that 6RNMSC1-2_F02 is an antibody that does not bind to hIL-6R as an antigen in the presence of tryptophan, a kynurenine precursor. The expression level of IDO, an enzyme that metabolizes tryptophan to produce kynurenine, is elevated in cancer microenvironment. Thus, antibodies that bind to antigens in the presence of kynurenine or its metabolite but not in the presence of tryptophan are expected to be important as antibodies that bind to antigens only in cancer microenvironment. This suggests that the same method can be used to obtain antibodies that bind to an antigen of interest not only in the presence of a single amino acid metabolite but also in the presence of multiple, structurally different amino acid metabolites.

(15-2) Assessment of Kynurenine for its Effect on Human IL6 Receptor Binding by Surface Plasmon Resonance Biacore T200 (GE Healthcare) was used to analyze the interaction of 6RNMSC1-2_F02 with human IL6 receptor (IL-6R) in antigen-antibody reaction. Sensor chip CM5 (GE Healthcare) was immobilized with an appropriate amount of protein A (Invitrogen) by amine coupling. The antibody of interest was captured by the chip to allow interaction with IL-6R as an antigen. The running buffer used was 20 mmol/l ACES, 150 mmol/l NaCl, 0.05% (w/v) Tween20, pH 7.4. The interaction with the antigen IL-6R was assayed at 25° C. The buffers used to dilute IL-6R were the running buffer itself, and a buffer prepared by adding 100 μmol/l kynurenine to the running buffer, and in addition a buffer prepared as a control by adding 10 mmol/l ATP to the running buffer.

A diluted IL-6R solution and a running buffer as a blank were injected at a flow rate of μl/min for one minute to allow interaction of IL-6R with 6RNMSC1-2_F02 captured on the sensor chip. Then, the running buffer was injected at a flow rate of 10 μl/min for one minute. After observation of IL-6R dissociation from the antibody, 10 mmol/l glycine-HCl (pH 1.5) was injected at a flow rate of 30 μl/min for 30 seconds to regenerate the sensor chip. The dissociation constant $K_D$ (M) of 6RNMSC1-2_F02 was calculated for IL-6R based on the association rate constant ka (1/Ms) and dissociation rate constant kd (1/s), both of which are kinetic parameters calculated from the sensorgram obtained by the measurement. Each parameter was calculated using the Biacore T200 Evaluation Software (GE Healthcare).

Figure 31:
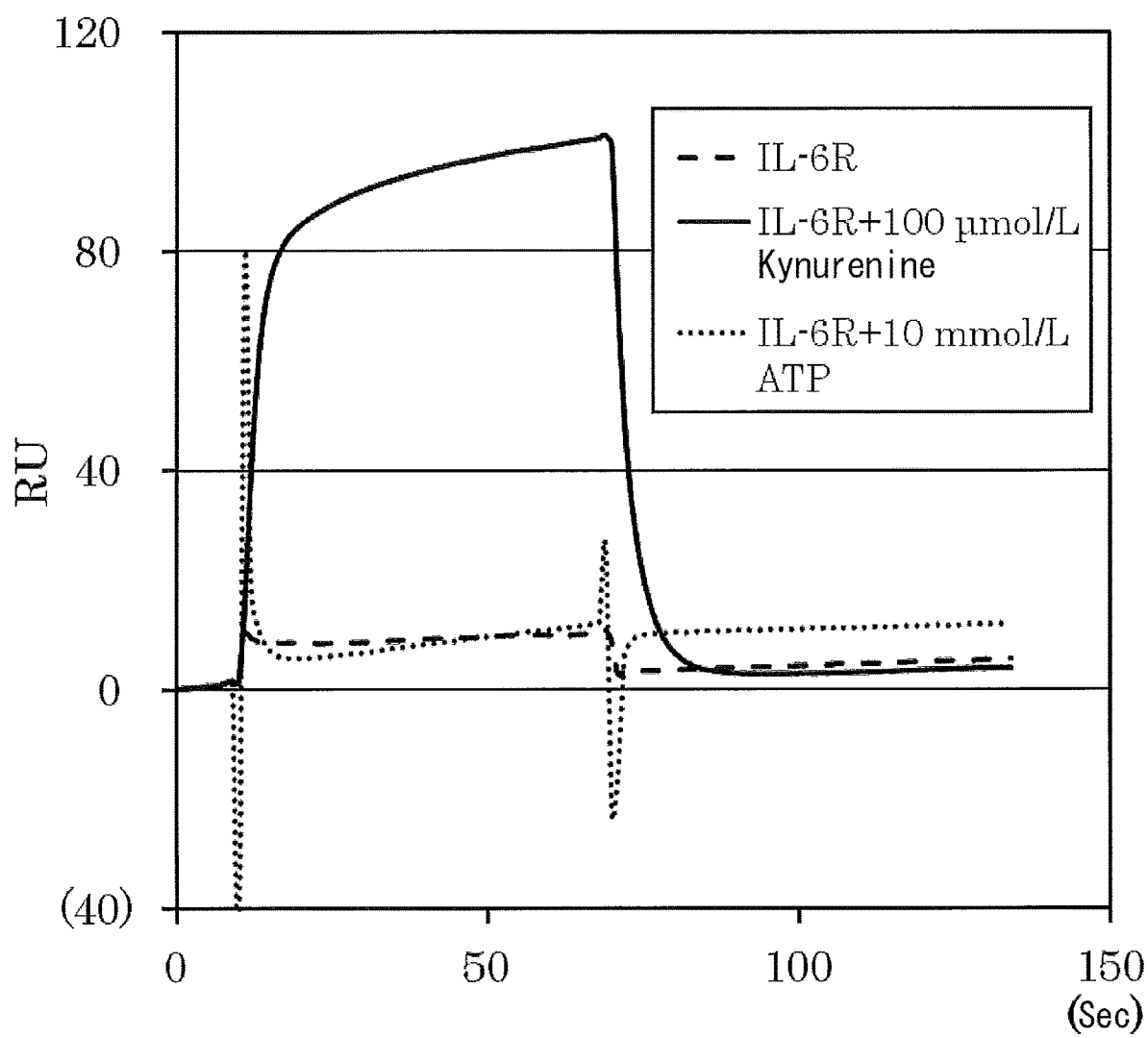
FIG. 31 presents sensorgrams showing the interaction between 6RNMSC1-2_F02 and 1 μmol/L IL-6R in the presence of 100 μmol/L kynurenine, in the presence of 10 mmol/L ATP, and in the absence of kynurenine and ATP. The solid line indicates the interaction in the presence of kynurenine, the dotted line indicates the interaction in the presence of ATP, and the dashed line indicates the interaction in their absence.

Sensorgrams obtained by this measurement for the interaction between 6RNMSC1-2_F02 and 1 μmol/l IL-6R in the presence of 100 μmol/l kynurenine and in the presence or absence of 10 mmol/l ATP are shown in FIG. 31. As shown in FIG. 31, 6RNMSC1-2_F02 binds to IL-6R in the presence of 100 μmol/l kynurenine; however, its IL-6R binding was not detectable in the absence of kynurenine. This demonstrates that 6RNMSC1-2_F02 has the property that it binds to IL-6R via kynurenine as a switch. Meanwhile, the dissociation constant $K_D$ of 6RNMSC1-2_F02 was 1.5 μmol/l in the presence of 100 μmol/l kynurenine.

Figure 32:
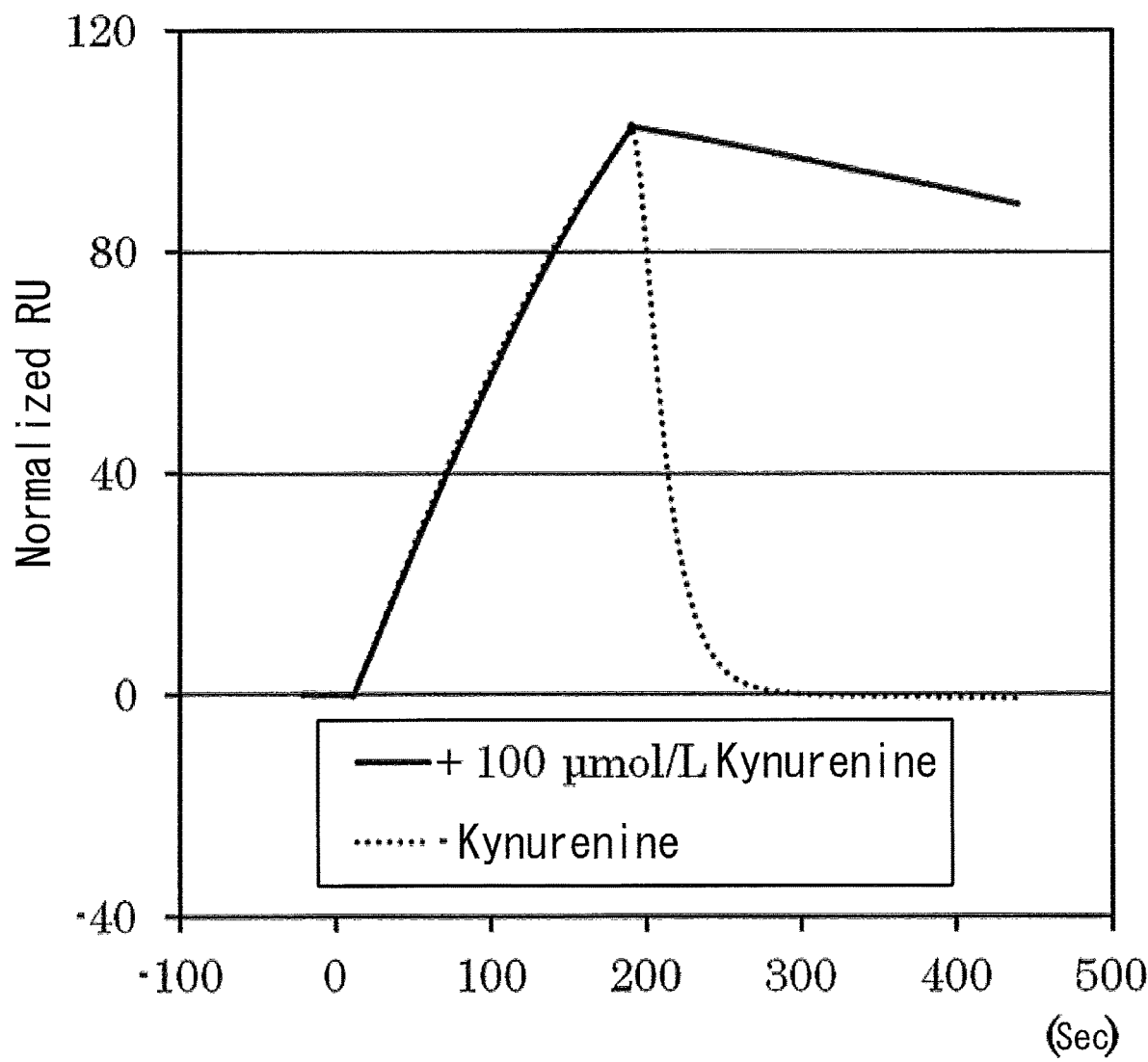
FIG. 32 is a graph obtained by allowing 6RNMSC1-2_F02 to interact with IL-6R immobilized on Sensorchip CM5 in the presence of 100 μmol/L kynurenine, and then observing the dissociation of 6RNMSC1-2_F02 from IL-6R in the presence of a buffer containing 100 μmol/L kynurenine or in the presence of a buffer that does not contain kynurenine. In the figure, the vertical axis shows values normalized by defining the amount of 6RNMSC1-2_F02 bound in the presence of 100 μmol/L kynurenine as 100, and the horizontal axis shows the passage of time (in seconds) from the start of the interaction. The solid line shows the dissociation of 6RNMSC1-2_F02 from IL-6R in the presence of kynurenine, and the dotted line shows the dissociation of 6RNMSC1-2_F02 from IL-6R in the absence of kynurenine.

(15-3) Effect of Kynurenine as a Switch on Dissociation of Antibodies from IL-6R Biacore T200 (GE Healthcare) was used to evaluate whether 6RNMSC1-2_F02 which binds to IL-6R in the presence of kynurenine dissociates in a kynurenine concentration-dependent manner in the presence of kynurenine. The running buffers used were 20 mmol/l ACES, 150 mmol/l NaCl, 0.05% (w/v) Tween20, pH 7.4, and 20 mmol/l ACES, 150 mmol/l NaCl, 0.05% (w/v) Tween20, pH 7.4, 100 μmol/l kynurenine, and assay was carried out at 25° C. IL-6R was immobilized onto Sensor chip CM5 by amine coupling; and 6RNMSC1-2_F02 was diluted to 5 μg/ml with 20 mmol/l ACES, 150 mmol/l NaCl, 0.05% (w/v) Tween20, pH 7.4, containing 100 μmol/l kynurenine, and it was interacted as an analyte for 180 seconds. Then, the dissociation of IL-6R was monitored under each running buffer condition. In order to compare the degree of dissociation between the respective running buffer conditions, the values were normalized by taking as 100 the amount of 6RNMSC1-2_F02 bound to IL-6R in the presence of 100 μmol/l kynurenine and compared. A sensorgram that represents the interaction between 6RNMSC1-2_F02 and IL-6R after normalization is shown in FIG. 32. The result shown in FIG. 32 demonstrates that 6RNMSC1-2_F02 has the property that it binds to IL-6R in the presence of kynurenine and then rapidly dissociates from IL-6R in the absence of kynurenine. Specifically, the kynurenine-mediated regulation on binding of the antibody to IL-6R was demonstrated to be reversible.

(15-4) Assessment of Kynurenine Concentration Effect on IL-6R Binding

Figure 33:
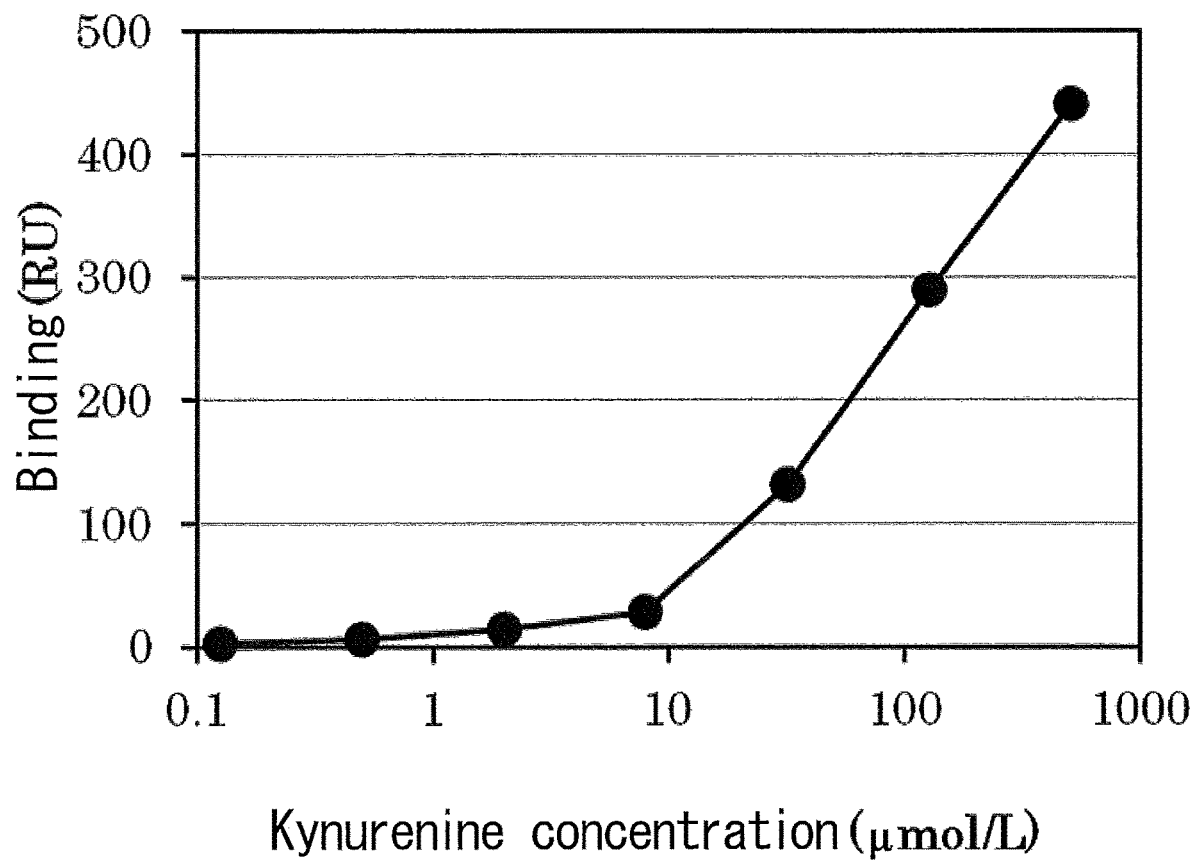
FIG. 33 is a graph produced by allowing 5 μg/L of 6RNMSC1-2_F02 to interact as an analyte for 180 seconds, and assessing the response to IL-6R immobilized onto Sensorchip CM5. The vertical axis shows change in the response (RU) before and after 6RNMSC1-2_F02 interaction, and the horizontal axis shows the concentration (μmol/L) of kynurenine contained in the solution.

Next, Biacore T200 (GE Healthcare) was used to assess the effect of kynurenine concentration on the antigen-antibody reaction between 6RNMSC1-2_F02 and IL-6R. The running buffer used was 20 mmol/l ACES, 150 mmol/l NaCl, 0.05% (w/v) Tween20, pH 7.4. The antigen-antibody reaction between 6RNMSC1-2_F02 and human IL-6R was assayed at 25° C. IL-6R was immobilized onto sensor chip CM5 by amine coupling; and 6RNMSC1-2_F02 was diluted to 1 μg/ml with 20 mmol/l ACES, 150 mmol/l NaCl, 0.05% (w/v) Tween20, pH 7.4 containing various concentrations of kynurenine, and it was allowed to interact as an analyte for 180 seconds to observe changes in the amount of binding. The result is shown in FIG. 33. This result demonstrated that the higher the concentration of kynurenine serving as a switch, the greater the amount of 6RNMSC1-2_F02 bound to IL-6R.

Meanwhile, since IL-6R is immobilized on a sensor chip in this assay system, 6RNMSC1-2_F02 is thought to bind in a divalent manner. In such an assay system where 6RNMSC1-2_F02 recognizes IL-6R in a divalent manner, the amount of 6RNMSC1-2_F02 bound to IL-6R was also observed to increase with a higher kynurenine concentration. This result demonstrated that 6RNMSC1-2_F02 has the property that it binds to IL-6R via kynurenine as a switch also in divalent binding.

These results demonstrated that 6RNMSC1-2_F02 is an antibody that binds to IL-6R in the presence of kynurenine with kynurenine as a switch, but is dissociated from IL-6R in the absence of kynurenine. Furthermore, it was confirmed that it is possible to have full ON/OFF control of 6RNMSC1-2_F02 so that it does not demonstrate IL-6R-binding activity in the absence of kynurenine. The switch function was expected to be achieved in the manner such as shown in FIG. 2.

(15-5) Effect of Kynurenine on the ADCC Activity of 6RNMSC1-2_F02

The genes encoding the variable regions of 6RNMSC1-2_F02 determined as described in Example 14 were inserted into an animal expression plasmid for human IgG1/Kappa, which comprises an antibody heavy-chain constant region comprising the sequence of SEQ ID NO: 90 and a light-chain kappa constant region sequence comprising the sequence of SEQ ID NO: 91. The respective genes encoding the variable regions of a known anti-human IL-6R antibody, MRA (the heavy chain and light chain sequences are shown in SEQ ID NOs: 92 and 93, respectively), were also inserted into the animal expression plasmid for human IgG1/Kappa, which has the above-described constant regions (SEQ ID NOs: 90 and 91). Antibodies were expressed using the method described below. FreeStyle 293-F (Invitrogen) which was derived from human fetal kidney cells were suspended at a cell density of $1.33 \times 10^6$ cells/ml in the FreeStyle 293 Expression Medium (Invitrogen), and aliquoted at 3 ml into each well of a 6-well plate. The plasmid DNA was transfected into the cells by lipofection. From the culture supernatants after four days of culture in a $CO_2$ incubator (37° C., 8% $CO_2$, 90 rpm), antibodies were purified by a method known to those skilled in the art using rProtein A Sepharose™ Fast Flow (Amersham Biosciences). Absorbance of the purified antibody solutions was measured at 280 nm using a spectrophotometer. From values obtained by the measurement, the concentrations of purified antibodies were calculated using an extinction coefficient determined by the PACE method (Protein Science (1995) 4, 2411-2423).

6RNMSC1-2_F02 antibody which has an antigen-binding activity in the presence of kynurenine as described in Example 14 was assessed for its binding to soluble hIL-6R. As a first step in assessing the ADCC activity of 6RNMSC1-2_F02 to hIL-6R-expressing cells, 6RNMSC1-2_F02 was evaluated as to whether it has the ability to bind to membrane-type hIL-6R expressed in hIL-6R-expressing cells. Specifically, the binding of 6RNMSC1-2_F02 to cells of the BaF/hIL-6R line (WO2012/073992) was assayed and analyzed using a flow cytometer. An appropriate number of BaF/hIL-6R cells were prepared and blocked with PBS containing 2% FBS on ice for one hour or more. Supernatant was removed from the blocked cells by centrifugation, and 100 μl of 6RNMSC1-2_F02 or the control antibody MRA (the heavy chain and light chain sequences are shown in SEQ ID NOs: 92 and 93, respectively) was added under two conditions: in the presence or absence of a final concentration of kynurenine at 100 μM. In this step, the antibodies were contacted with cell-membrane hIL-6R on ice for 30 minutes. The antibody-cell complex was washed with Wash Buffer containing kynurenine or with Wash Buffer that does not contain kynurenine. Then, in the presence or absence of kynurenine, the complex was contacted with a secondary antibody (Beckman Coulter IM1627) that recognizes the antibody constant region. After 30 minutes of incubation with the antibody on ice, the cells were again washed with Wash Buffer and then re-suspended in PBS/2% FBS. The binding of 6RNMSC1-2_F02 to the prepared cells was assayed and analyzed using the BD FACS cant II Flow Cytometer (BD).

Figure 34:
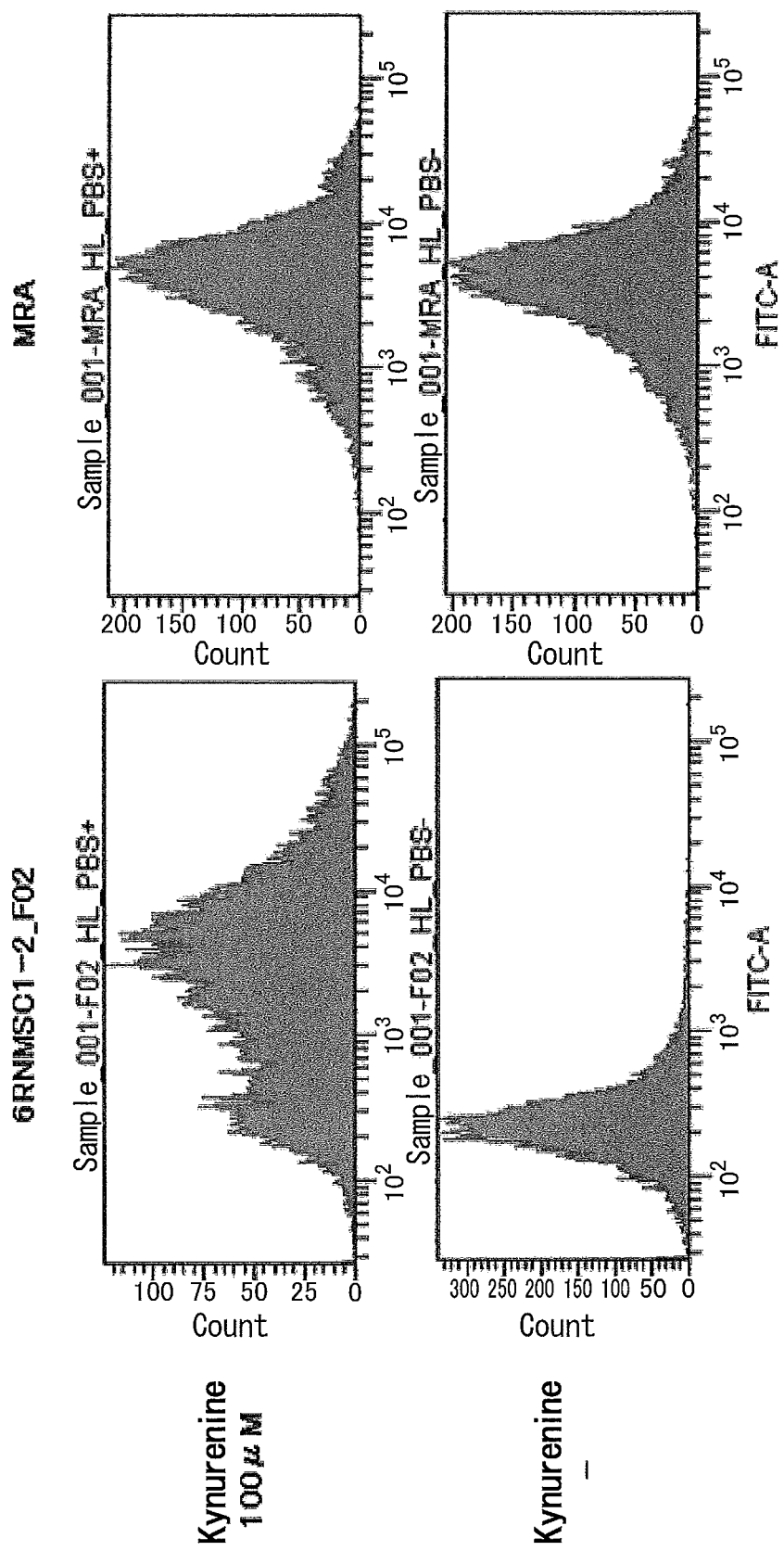
FIG. 34 is a figure showing assessment of the binding of antibodies to membrane-type human IL-6R by FCM. The top panel shows results obtained in the presence of Kynurenine, and the bottom panel shows results obtained in the absence of Kynurenine. The horizontal axis shows the fluorescence intensity and the vertical axis shows the cell count.

The assay result was shown in FIG. 34. With the control antibody MRA, fluorescence was detectable regardless of the presence or absence of kynurenine. In contrast, for 6RNMSC1-2_F02, fluorescence shift was observed for the first time in the presence of 100 μM kynurenine; however, fluoresce was not detectable in the absence of kynurenine. This demonstrates that 6RNMSC1-2_F02 is an antibody that has the ability to bind to hIL-6R expressed on cell membrane in the presence of kynurenine.

In general, natural antibodies bind at their Fab directly to antigens on target cells and their Fc binds to FcγR on effector cells, resulting in induction of cytotoxic activity (ADCC activity) of effector cells against the target cells. In this context, whether ADCC activity is exerted against hIL-6R-expressing cells upon binding of 6RNMSC1-2_F02 to hIL-6R in the presence of kynurenine was assessed by the method described below.

Figure 35A:
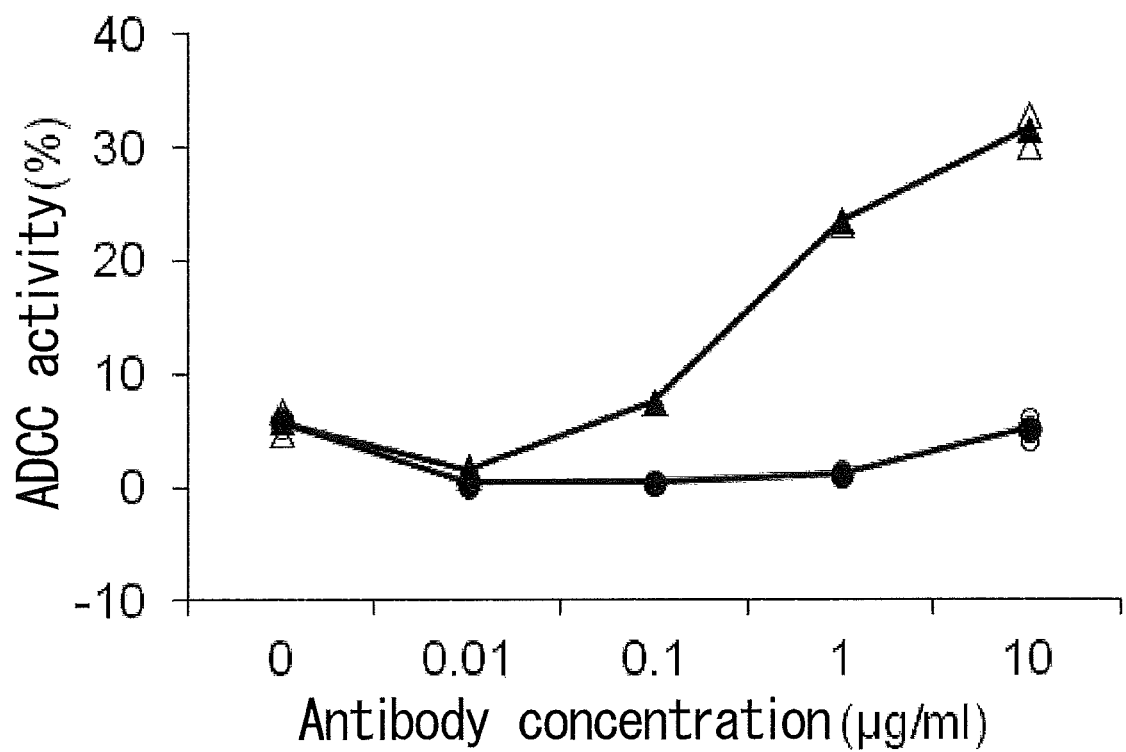
FIG. 35A shows the ADCC activity of antibodies that bind to antigens in the presence of small molecules toward cells expressing the antigens. It shows the ADCC activity of clone 6RNMSC1-2_F02, which binds to hIL-6R in the presence of kynurenine, toward BaF cells expressing hIL-6R in the presence (triangles) or absence (circles) of kynurenine. The open triangles and circles show the measured values, and the filled triangles and circles show the mean values.
Figure 35B:
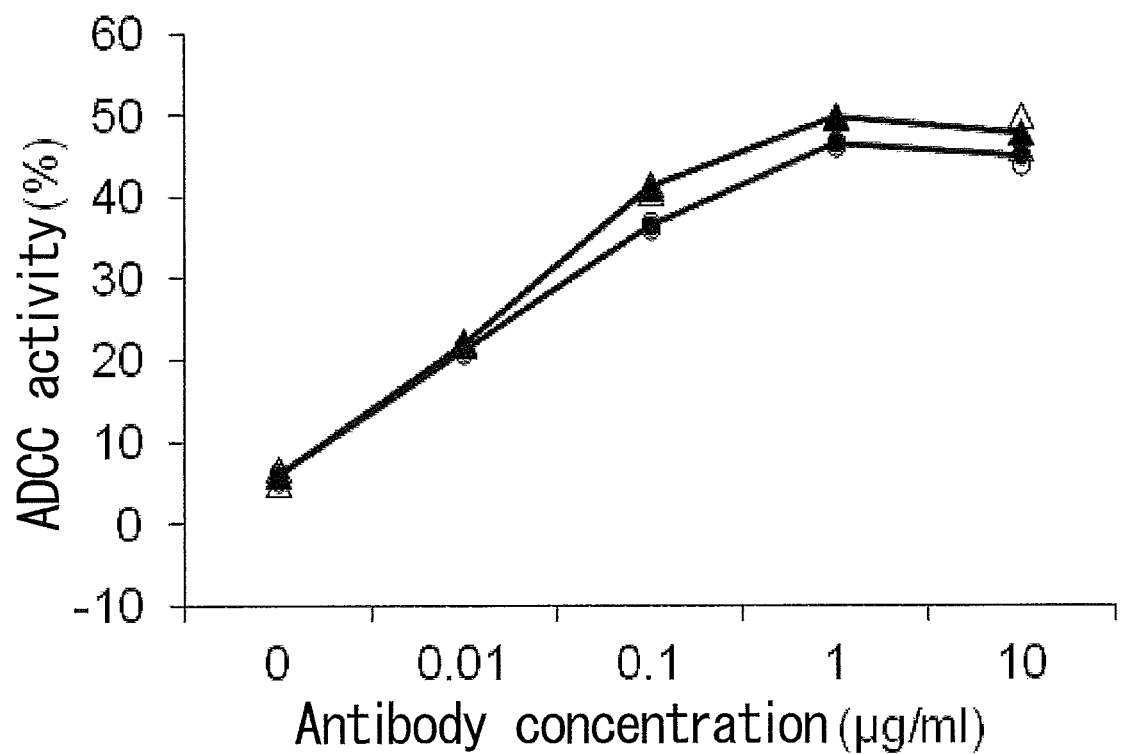
FIG. 35B shows the ADCC activity of antibodies that bind to antigens in the presence of small molecules toward cells that express the antigen. It shows the ADCC activity of MRA, which binds to hIL-6R regardless of the presence of kynurenine, toward BaF cells expressing hIL-6R in the presence (triangles) or absence (circles) of kynurenine. The open triangles and circles show the measured values, and the filled triangles and circles show the mean values.

Variant 6RNMSC1-2_F02 with increased effector activity (the heavy chain and light chain sequences are shown in SEQ ID NOs: 94 and 91, respectively) was used. At various concentrations of 6RNMSC1-2_F02, ADCC activity against hIL-6R-expressing cells was assayed in the presence or absence of kynurenine according to the method described in Reference Example 1. The assay result is shown in FIG. 35.

The assay result confirmed that in the presence of kynurenine, ADCC activity against hIL-6R-expressing cells was induced by 6RNMSC1-2_F02 in an antibody concentration-dependent manner. The finding demonstrates that the antigen binding of the antibody via kynurenine induces ADCC activity against antigen-expressing cells and, in terms of the function via antitumor activity such as ADCC activity, antibodies that bind to antigens in the presence of small molecules as a switch can also be regulated by the presence of small molecules serving as a switch.

Figure 36:
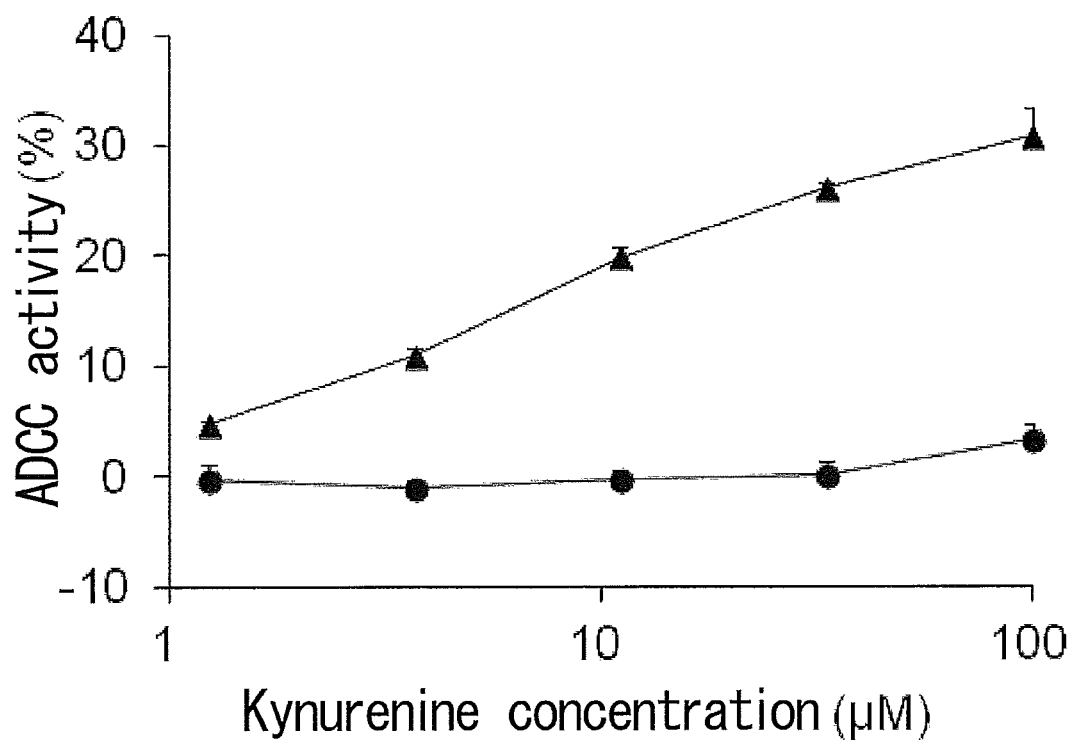
FIG. 36 shows the ADCC activity of antibodies that bind to antigens in the presence of small molecules toward cells expressing the antigen. It shows the ADCC activity of clone 6RNMSC1-2_F02 toward BaF cells expressing hIL-6R in the presence (triangles) or absence (circles) of clone 6RNMSC1-2_F02 which binds to hIL-6R in the presence of kynurenine. The horizontal axis shows the kynurenine concentration and the vertical axis shows the ADCC activity (%). The mean values and standard deviations of ADCC activity are shown.

Furthermore, there is a difference in the kynurenine concentration between normal and tumor tissues, and thus it is preferable that the ADCC activity of an antibody is exerted against antigen-expressing tumor cells only at the kynurenine concentration in tumor tissues, while at the normal-tissue kynurenine concentration, the ADCC activity is impaired or not exerted. Then, 6RNMSC1-2_F02 was assessed for ADCC activity against hIL-6R-expressing cells at various kynurenine concentrations according to the method described in Reference Example 2. The assay result is shown in FIG. 36. The assay result demonstrated that ADCC activity against hIL-6R-expressing cells was included with 6RNMSC1-2_F02 in a kynurenine concentration-dependent manner. Furthermore, in contrast to the approximately 10% ADCC activity at 4 to 6 μM which is considered to be the kynurenine concentration in normal tissues, the ADCC activity at 30 to 40 μM which is considered to be the kynurenine concentration in tumor tissues was about 25%.

Based on these results, with 6RNMSC1-2_F02, the ADCC activity against hIL-6R-expressing cells was weak in normal tissues where the kynurenine concentration is low; and in tumor tissues where the concentration is high, the ADCC activity of 6RNMSC1-2_F02 against hIL-6R-expressing cells was greater. This suggests that by administering an antibody that uses kynurenine as a switch, the cytotoxicity to normal tissues expressing a target antigen can be reduced without impairing the pharmaceutical effect against tumor tissues expressing the target antigen.

(15-6) Assessment of the Obtained Antibody for its Binding Activity to hIL-6R in Mouse Serum by IgG ELISA Antibody 6RNMSC1-2_F02 obtained as described in Example 14, which binds to hIL-6R in the presence of small molecules, is an antibody that binds to hIL-6R in the presence of kynurenine. So far, 6RNMSC1-2_F02 has been assessed for its antigen-binding ability in buffers such as PBS and TBS. Many unknown small molecules including amino acids are considered to exist in mouse serum, and one cannot rule out the possibility that such small molecules affect the antigen binding of 6RNMSC1-2_F02. Thus, 6RNMSC1-2_F02 was assessed for its antigen-binding ability in mouse serum.

As described in Example 14, antibody 6RNMSC1-2_F02 which has antigen-binding activity in the presence of kynurenine, and the known anti-hIL-6R antibody MRA were subjected to ELISA under the two conditions described in Table 20. The antigen used was biotin-labeled hIL-6R.

TABLE 20

| Condition | Buffer composition |
|---|---|
| 1 | Mouse serum |
| 2 | Mouse serum, 100 µM Kynurenine |

First, a StreptaWell 96 microtiter plate (Roche) was coated at room temperature for one hour or more with 100 µl of PBS containing the biotin-labeled antigen. After washing with Wash buffer to remove unbound antigen from the plate, each well was blocked for one hour or more with 250 µl of Blocking Buffer. After Blocking Buffer was removed from each well, each of the purified IgGs was prepared to 2.5 µg/ml under condition 2 shown in Table 20, and aliquoted at 100 µl into the plate. The plate was allowed to stand at room temperature for one hour to allow binding of each IgG to the antigen in each well. After washing with Wash Buffer containing 100 µM kynurenine, an HRP-conjugated anti-human IgG antibody (BIOSOURCE) diluted with Sample Buffer containing kynurenine was added to each well. The plate was incubated for one hour. Following wash with Wash Buffer containing kynurenine, the TMB single solution (ZYMED) was added to each well. The chromogenic reaction in the solution of each well was terminated by adding sulfuric acid. Then, the developed color was assessed by measuring absorbance at 450 nm.

Figure 37:
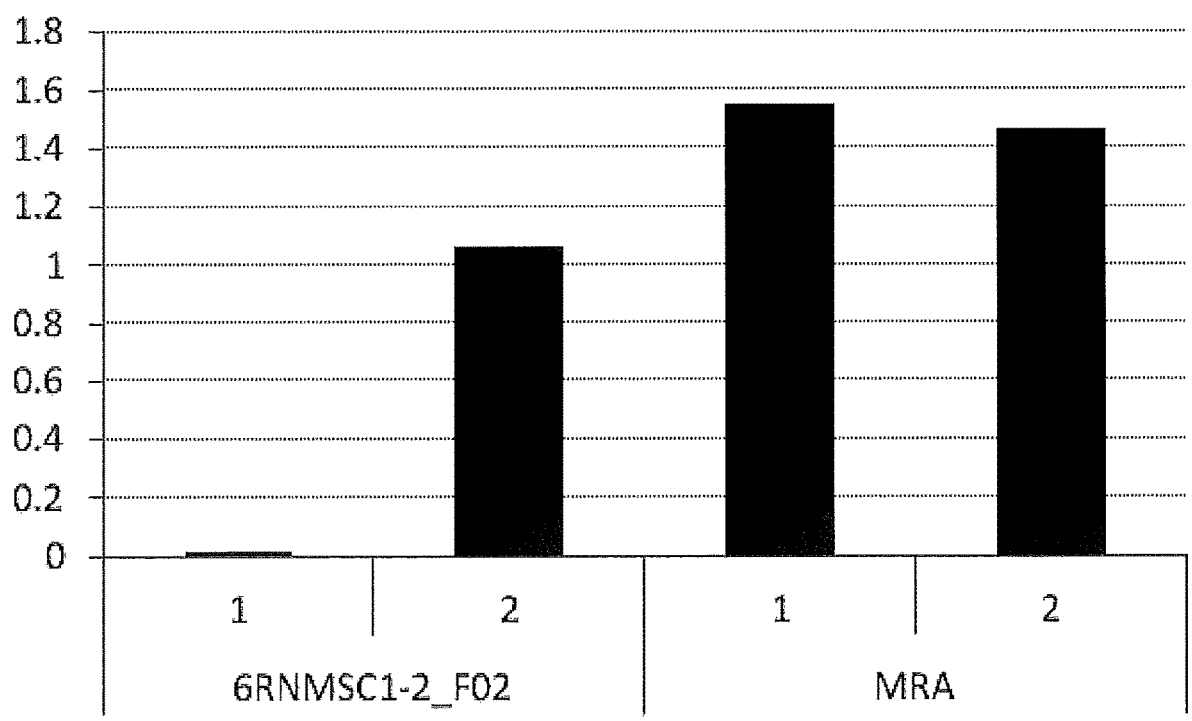
FIG. 37 is a figure showing the result of ELISA for the binding of clone 6RNMSC1-2_F02 in mouse serum to human IL-6R. The vertical axis shows the absorbance values which evaluate the binding activities of the antibody to human IL-6R in the presence or absence of kynurenine.

The measurement result is shown in FIG. 37. With MRA, the absorbance was the same regardless of the presence or absence of kynurenine. In contrast, when 6RNMSC1-2_F02 was used, the absorbance was markedly lower under condition 1 (mouse serum without kynurenine) as compared to under condition 2 (mouse serum in the presence of kynurenine) shown in Table 20. This suggests that 6RNMSC1-2_F02 is an antibody that binds to hIL-6R as an antigen in the presence of kynurenine without being affected by unknown small molecules in mouse serum.

[Example 16] Acquisition of Antibodies that Bind to Antigens in the Absence of Adenosine or ATP from Antibody Library Using Phage-Display Techniques (16-1) Acquisition of Antibodies Whose Antigen Binding is Inhibited in the Presence of Small Molecules from a Library Using a Mixture of Adenosine and ATP Antibodies that bind to target antigens in the presence of small molecules serving as a switch were obtained as described in Examples above. In the experiment described in this Example, the present inventors attempted to obtain antibodies that bind to target antigens in the absence of small molecules.

Antibodies that exhibit antigen-binding activity in the absence of adenosine and/or ATP but whose binding ability is impaired in the presence of adenosine and/or ATP were obtained from a constructed phage-display library of rationally designed antibodies. As a first step to isolate antibodies, a phage-display library of antibodies was contacted with biotinylated adenosine and ATP-NeutrAvidin to collect a phage-display library of antibodies that bind to adenosine and/or ATP. Then, the phage-display antibody library was contacted with biotinylated antigen-streptavidin in the absence of adenosine and ATP to collect antibodies that bind to antigens in the absence of adenosine and ATP. Panning was performed in the alternating manner described above to screen for antibodies that have binding activity to both antigen and adenosine and/or ATP. In the presence of adenosine and ATP, the antigen binding of antibodies with such properties was expected to be inhibited by binding of adenosine and/or ATP to the antibodies.

Phages were produced in E. coli containing the phagemid vector constructed for phage display. To the culture medium of E. coli in which phage production was carried out, 2.5 M NaCl/10% PEG was added to precipitate phages. The precipitated phage fraction was diluted with TBS to prepare a phage library solution. Then, BSA was added at a final concentration of 4% to the phage library solution. Panning was performed using antigen-immobilized magnetic beads. The magnetic beads used were NeutrAvidin-coated beads (Sera-Mag SpeedBeads NeutrAvidin-coated) and Streptavidin-coated beads (Dynabeads M-280 Streptavidin).

500 pmol of biotinylated ATP, 2'-adenosine-PEG-Biotin, and 5'-adenosine-PEG-Biotin were added to the prepared phage library solution. Thus, the phage library solution was contacted with adenosine and ATP for 60 minutes at room temperature. Then, BSA-blocked magnetic beads were added to the phage library solution and the complex of phage with adenosine and/or ATP was allowed to bind to the magnetic beads at room temperature for 15 minutes. The beads were washed once with TBS, and then 0.5 ml of a 1 mg/ml trypsin solution was added to the beads.

Immediately after the beads were suspended at room temperature for 15 minutes, a phage solution was collected from the isolated beads using a magnetic stand. The collected phage solution was added to 10 ml of E. coli cells of strain ER2738 at the logarithmic growth phase (OD600=0.4 to 0.7). The E. coli was incubated with gentle stirring at 37° C. for one hour to be infected by phage. The infected E. coli was seeded in a 225 mm×225 mm plate. Then, phages were collected from the culture medium of the seeded E. coli to prepare a phage library solution.

The second round of panning was performed to enrich phages capable of binding to the biotinylated antigen in the absence of adenosine and ATP. Specifically, 250 pmol of biotinylated antigen was added to the prepared phage library solution. Thus, the phage library solution was contacted with the antigen for 60 minutes at room temperature. Then, BSA-blocked magnetic beads were added to the phage library solution, and the antigen-phage complex was allowed to bind to the magnetic beads at room temperature for 15 minutes. The beads were washed twice with TBST and once with TBS. Then, 0.5 ml of a 1 mg/ml trypsin solution was added to the beads. Immediately after the beads were suspended at room temperature for 15 minutes, a phage solution was collected from the isolated beads using a magnetic stand. The collected phage solution was added to 10 ml of *E. coli* cells of strain ER2738 at the logarithmic growth phase (OD600=0.4 to 0.7). The *E. coli* was incubated with gentle stirring at 37° C. for one hour to be infected by phage. The infected *E. coli* was seeded in a 225 mm×225 mm plate. Then, phages were collected from the culture medium of the seeded *E. coli* to prepare a phage library solution.

At subsequent odd-numbered rounds, panning was performed in the same manner as the first-round panning. However, the number of bead washes with TBST and TBS was increased to three times and twice, respectively.

At subsequent even-numbered rounds, panning was performed in the same manner as the second-round panning. However, in the fourth and subsequent rounds of panning, the biotinylated antigen was reduced to 40 pmol, and the number of bead washes with TBST and TBS was increased to three times and twice, respectively.

(16-2) Assessment of Binding Activity in the Presence of Small Molecules by Phage ELISA Culture supernatants containing phages were collected according to a conventional method (Methods Mol. Biol. (2002) 178, 133-145) from single colonies of *E. coli* obtained by the method described above. The collected culture supernatants were ultrafiltrated using NucleoFast 96 (MACHEREY-NAGEL). 100 µl of the culture supernatants were added to each well, and the NucleoFast 96 was centrifuged (4500 g for 45 minutes) to remove flow-through. 100 µl of $H_2O$ was added to each well, and again the NucleoFast 96 was washed by centrifugation (4500 g for 30 minutes). After 100 µl of TBS was added, the NucleoFast 96 was allowed to stand at room temperature for five minutes. Finally, a phage solution was collected from the supernatant in each well.

Purified phages, to which TBS, or ATP and adenosine/TBS had been added, were subjected to ELISA by the following procedure. A StreptaWell 96 microtiter plate (Roche) was coated overnight with 100 µl of TBS containing a biotin-labeled antigen. After the antigen was removed from each well of the plate by washing with TBST, the wells were blocked with 250 µl of 2% skim milk/TBS for one hour or more. 2% skim milk/TBS was removed, and then the plate prepared, purified phages were added to each well. The plate was allowed to stand at 37° C. for one hour to allow binding of antibody-displaying phages to antigens in each well in the presence or absence of 10 mM adenosine and ATP. After washing with TBST or 10 mM (ATP and adenosine)/TBST, an HRP-conjugated anti-M13 antibody (Amersham Pharmacia Biotech) diluted with TBS or 10 mM (ATP and adenosine)/TBS was added to each well. The plate was incubated for one hour. Following wash with TBST or 10 mM (ATP and adenosine)/TBST, the TMB single solution (ZYMED) was added to each well. The chromogenic reaction in the solution of each well was terminated by adding sulfuric acid. Then, the developed color was assessed by measuring absorbance at 450 nm.

Figure 38:
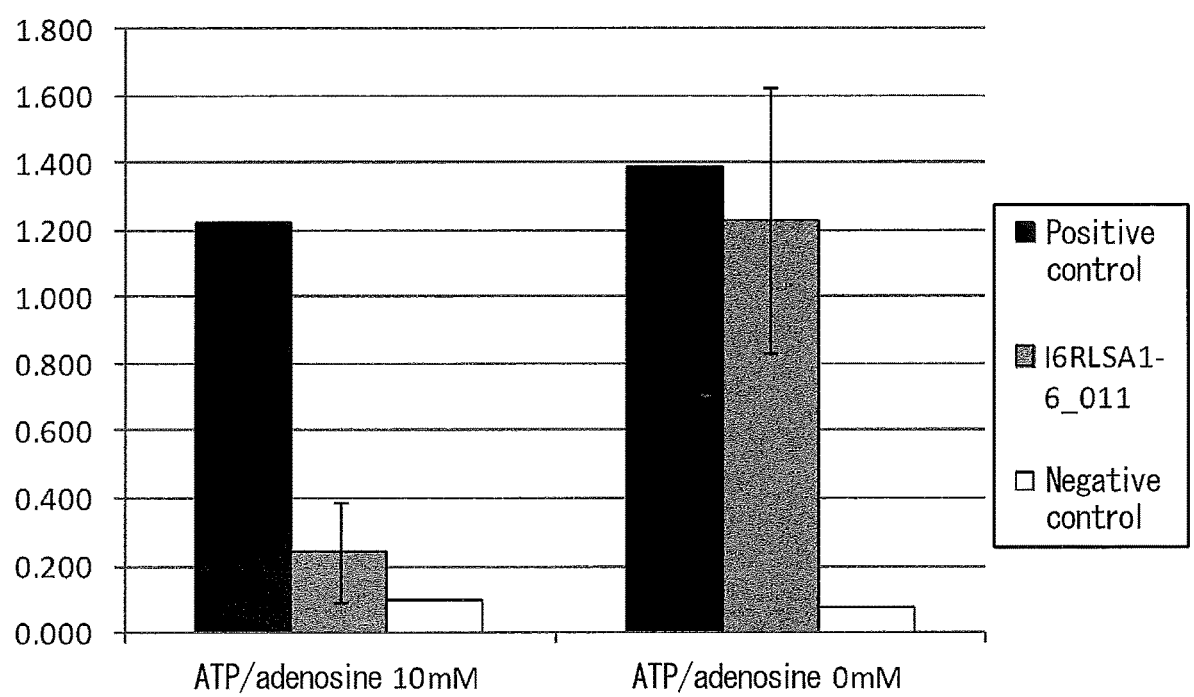
FIG. 38 is a figure showing the result of ELISA performed with clone I6RLSA1-6_011, which was obtained from the rationally designed antibody library, against human IL-6 in the presence or absence of ATP and adenosine at 10 mM. The vertical axis shows the absorbance value which evaluates binding activity of the antibody to human IL-6. Results obtained when using a clone obtained from the rationally designed antibody library and showing binding activity toward human IL-6 regardless of the presence of small molecules are presented as the positive control. Results obtained when using the M13KO7 Helper Phage are presented as the negative control.
Figure 39:
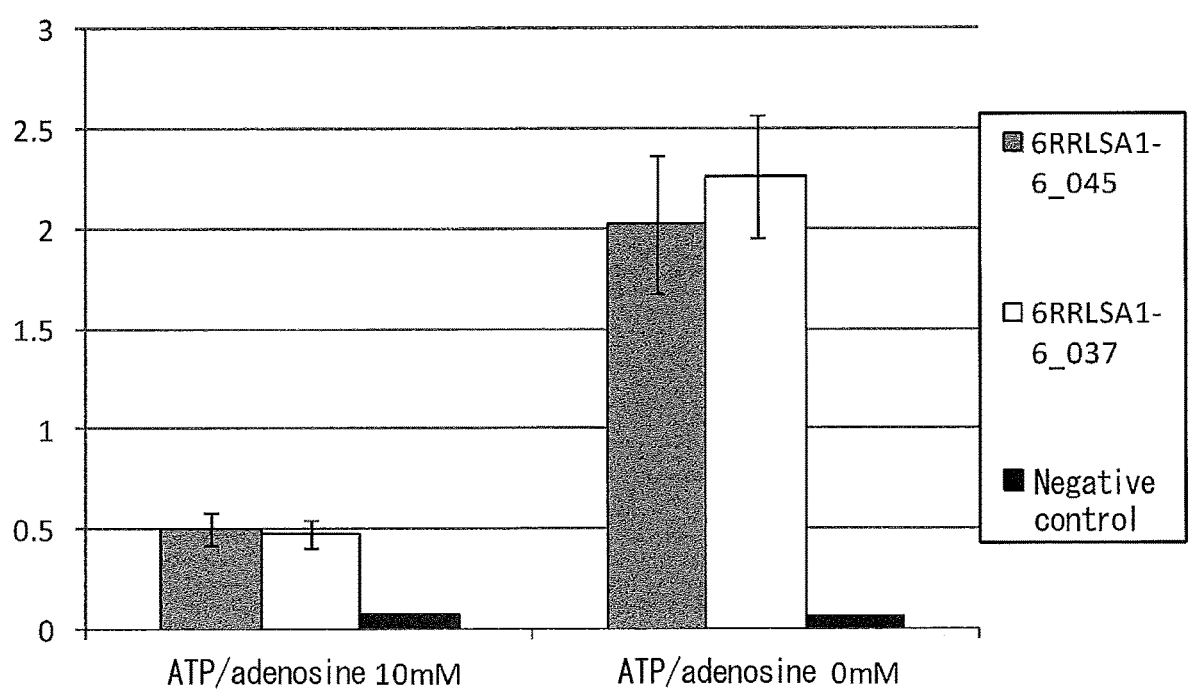
FIG. 39 is a figure showing the result of ELISA performed with clone 6RRLSA1-6_037 and 6RRLSA1-6_045, which were obtained from the rationally designed antibody library, against the human IL-6 receptor in the presence or absence of ATP and adenosine at 10 mM. The vertical axis shows the absorbance value which evaluates the binding activity of the antibodies to the human IL-6 receptor. Results obtained when using the M13KO7 Helper Phage are presented as the negative control.
Figure 45:
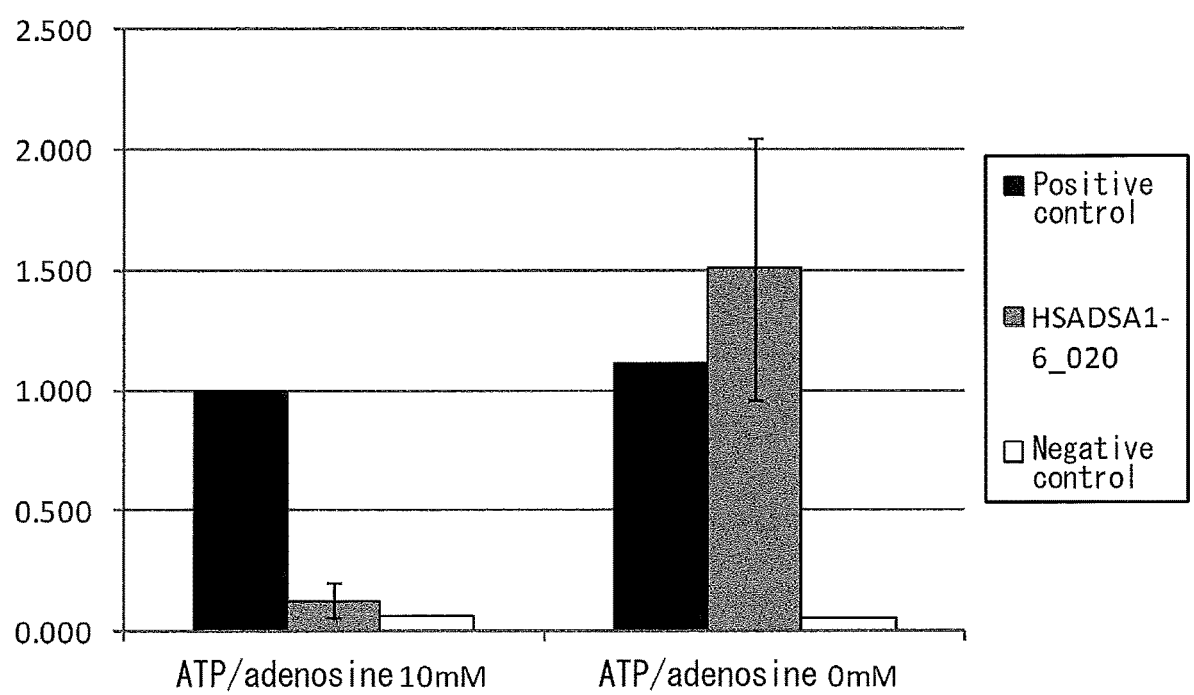
FIG. 45 is a figure showing the result of ELISA performed on clone HSADSA1-6_020 obtained from the rationally designed antibody library against HSA in the presence or absence of ATP and adenosine at 10 mM. The vertical axis shows the absorbance value which evaluates binding activity of the antibody to HSA. Results obtained when using a clone obtained from the rationally designed antibody library and showing binding activity toward HSA regardless of the presence of small molecules are presented as the positive control. Results obtained when using the M13KO7 Helper Phage are presented as the negative control.

Phage ELISA was carried out using 96 isolated clones to obtain from the library of rationally designed antibodies, clone "I6RLSA1-6_011", which had an antigen-binding activity to human IL-6 in the absence of ATP and adenosine, clone "HSADSA1-6_020", which had antigen-binding activity to human serum albumin (HSA) in the absence of ATP and adenosine, as well as clones "6RRLSA1-6_037" and "6RRLSA1-6_045", which had an antigen-binding activity to human IL-6 receptor in the absence of ATP and adenosine (FIGS. 38, 39, and 45).

(16-3) Sequence Analysis of Antibodies for which Adenosine and ATP Serve as a Switch Genes were amplified using specific primers (SEQ ID NOs: 111 and 112) from clones that had been assessed to have antigen-binding activity in the absence of adenosine and ATP based on the result of phage ELISA described in (16-2). The nucleotide sequences of the genes were analyzed. Based on the analysis result, the amino acid sequences are shown in Table 21 below.

TABLE 21

| Clone name | Heavy chain SEQ ID NO | Light chain SEQ ID NO |
| --- | --- | --- |
| I6RLSA1-6_011 | SEQ ID NO: 95 | SEQ ID NO: 96 |
| HSADSA1-6_020 | SEQ ID NO: 97 | SEQ ID NO: 98 |
| 6RRLSA1-6_037 | SEQ ID NO: 106 | SEQ ID NO: 107 |
| 6RRLSA1-6_045 | SEQ ID NO: 108 | SEQ ID NO: 109 |

[Example 17] Acquisition of Antibodies that Bind to Antigens in the Presence of Adenosine and ATP from Antibody Library Using Multivalent Phage-Display Technique (17-1) Acquisition of Antibodies that Bind to Antigens in the Presence of Small Molecules from Library Using Multivalent Display Multivalent display of antibodies on phage was used to obtain antibodies that have an antigen-binding activity in the presence of adenosine and/or ATP from a phage-display library of rationally designed antibodies. In obtaining antibodies from a library, the acquisition probability increases when the ratio of the antigen-binding ability between in the presence and absence of small molecules is greater. Thus, panning based on augmentation of the apparent binding ability was performed to efficiently collect antibodies with binding ability in the presence of small molecules. More specifically, the apparent binding ability was augmented through an avidity effect (effect of multivalent antigen binding) by allowing phages to display antibodies in a multivalent manner. First, a phage-display library of rationally designed antibodies was contacted with biotinylated antigens in the presence of adenosine and ATP to collect a phage-display library of antibodies that bind to the antigens in the presence of adenosine and ATP. Then, according to the method described in Rondot (Nat. Biotechnol. (2001) 19, 75-78), *E. coli* was infected with the collected phage-display library of antibodies, and then infected with helper phages that are deficient in the gene encoding pIII to prepare a multivalent phage-display library of antibodies where antibodies are presented at all pIIIs. The multivalent phage-display library of antibodies was contacted with biotinylated antigen-streptavidin in the presence of adenosine and ATP. After the library was collected, phages were eluted from the beads in the absence of adenosine and ATP, and collected in the eluate. This cycle of phage preparation and panning was carried out several times to screen for antibodies that have antigen-binding activity only in the presence of adenosine and/or ATP.

*E. coli* containing the constructed phage-display phagemid were infected with helper phage M13KO7 and cultured overnight at 30° C. to produce a monovalent phage-display library of antibodies. After phage production, 2.5 M NaCl/10% PEG was added to the culture medium of *E. coli* to precipitate phages. The precipitated phage fraction was diluted with TBS to prepare a phage library solution. Then, BSA was added at a final concentration of 4% to the phage library solution. Panning was performed using antigen-immobilized magnetic beads. The magnetic beads used were NeutrAvidin-coated beads (Sera-Mag SpeedBeads NeutrAvidin-coated) and Streptavidin-coated beads (Dynabeads M-280 Streptavidin).

The phage library solution was contacted with an antigen, adenosine, and ATP at room temperature for 60 minutes by adding 500 pmol of biotin-labeled human IgA-Fc (SEQ ID NO: 99) as the antigen, and a final concentration of 1 mM ATP-Na and adenosine to the prepared phage library solution. BSA-blocked magnetic beads were added to the phage library solution, and the antigen-phage complex was allowed to bind to the magnetic beads at room temperature for 15 minutes. The beads were washed once with TBS dissolved with ATP and adenosine. Then, 0.5 ml of a 1 mg/ml trypsin solution was added to the beads. Immediately after the beads were suspended at room temperature for 15 minutes, a phage solution was collected from the isolated beads using a magnetic stand. The collected phage solution was added to 10 ml of E. coli cells of strain ER2738 at the logarithmic growth phase (OD600=0.4 to 0.7). The E. coli was incubated with gentle stirring at 37° C. for one hour to be infected by phage. The infected E. coli was seeded in a 225 mm×225 mm plate. Then, helper phage M13KO7 or M13KO7ΔpIII (referred to as hyperphage) (PROGEN Biotechnik) was allowed to infect the culture medium of the seeded E. coli, and phages were collected from the supernatant of the culture incubated overnight at 30° C. to prepare a monovalent phage-display antibody library or a multivalent phage-display antibody library solution, respectively.

The first round of panning was carried out to collect phages that are capable of antigen binding in the presence of adenosine and ATP, while the second and subsequent rounds of panning were performed to enrich phages that are capable of antigen binding only in the presence of adenosine and ATP. Specifically, 250 pmol of the biotin-labeled antigen, and a final concentration of 1 mM adenosine and ATP were each added to the prepared phage library solution. Thus, the phage library was contacted with the antigen, adenosine, and ATP at room temperature for 60 minutes. BSA-blocked magnetic beads were added, and allowed to bind to the phage-antigen complex for 15 minutes at room temperature. The beads were washed with 1 ml of TBST dissolved with adenosine and ATP (hereinafter referred to as (adenosine+ATP)/TBST) and with TBS dissolved with adenosine and ATP (hereinafter referred to as (adenosine+ATP)/TBS). Then, the 0.5 ml of TBS was added to the beads. Immediately after the beads were suspended at room temperature, a phage solution was collected from the isolated beads using a magnetic stand. After this treatment was repeated, the two separately eluted phage solutions were combined. The pIII protein (helper phage-derived protein pIII) that does not display Fab was cleaved off from phages by adding 5 μl of 100 mg/ml trypsin to the collected phage solution to eliminate the E. coli-infecting ability of the phages that do not display Fab. The phages collected from the trypsinized phage solution were added to 10 ml of E. coli cells of strain ER2738 at the logarithmic growth phase (OD600=0.4 to 0.7). The E. coli was incubated with gentle stirring at 37° C. for one hour to be infected with phage. The infected E. coli was seeded in a 225 mm×225 mm plate. Then, in the same manner as used in the first round panning, phages were collected from the culture medium of the seeded E. coli to obtain a monovalent phage-display antibody library and a multivalent phage-display antibody library solution. Panning was performed three times to obtain antibodies that have antigen-binding activity in the presence of adenosine and ATP. Meanwhile, in the third and subsequent rounds of panning, the biotinylated antigen was used at 40 pmol.

(17-2) Assessment of Binding Activity in the Presence of Adenosine and/or ATP by Phage ELISA Culture supernatants containing phages were collected according to a conventional method (Methods Mol. Biol. (2002) 178, 133-145) from single colonies of E. coli obtained by the method described above. The collected culture supernatants were ultrafiltrated using NucleoFast 96 (MACHERY-NAGEL). 100 μl of the culture supernatants were added to each well of NucleoFast 96 and centrifuged (4500 g for 45 minutes) to remove flow-through. After 100 μl of H$_2$O was added, the NucleoFast 96 was washed by centrifugation (4500 g for 30 minutes). Finally, 100 μl of TBS was added, and the NucleoFast 96 was allowed to stand for five minutes at room temperature. A phage solution contained in the supernatant in each well was collected.

Figure 40:
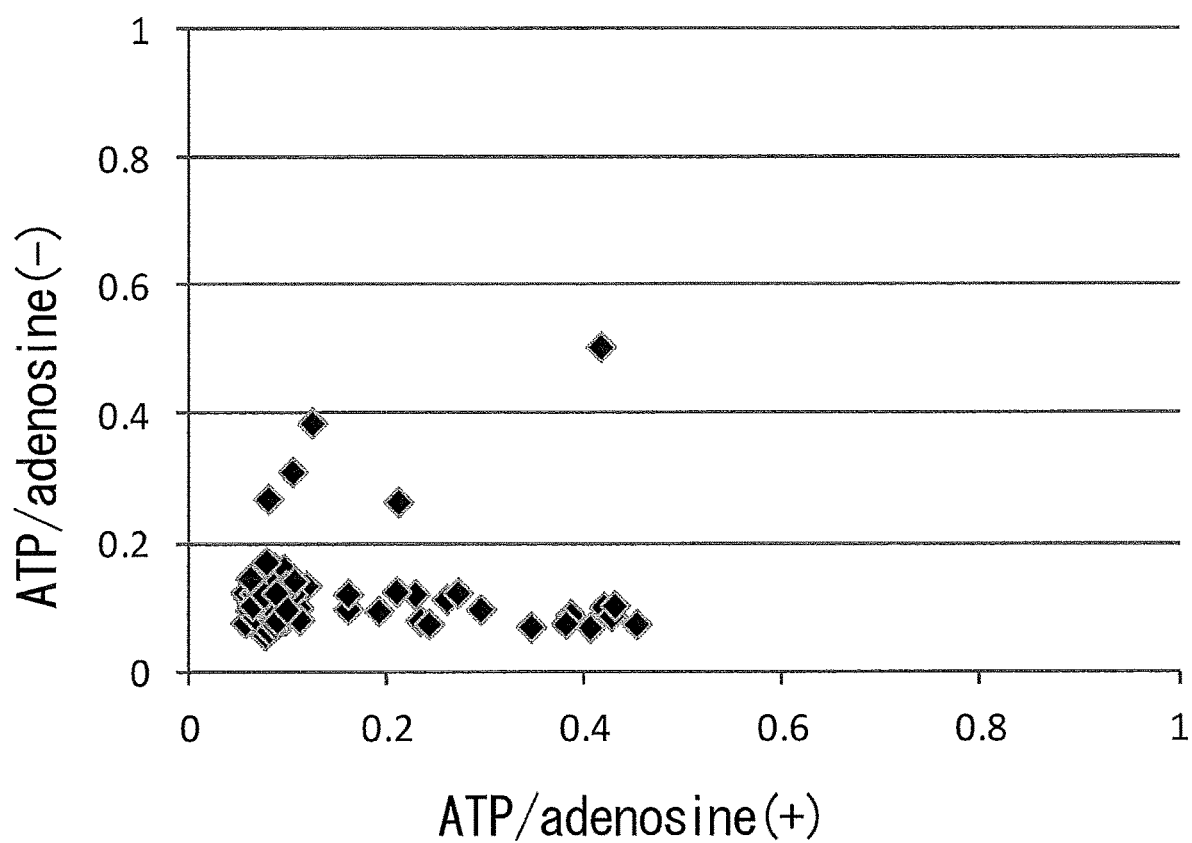
FIG. 40 is a figure showing the result of ELISA performed on 96 clones obtained by panning the rationally designed antibody library four times against human IgA-Fc using a multivalent antibody phage display. The absorbance values which evaluate the binding activity of the antibodies to human IgA-Fc in the absence of ATP and adenosine are shown on the vertical axis, and absorbance values which evaluate the binding activity of the antibodies to human IgA-Fc in the presence of ATP and adenosine are shown on the horizontal axis.
Figure 41:
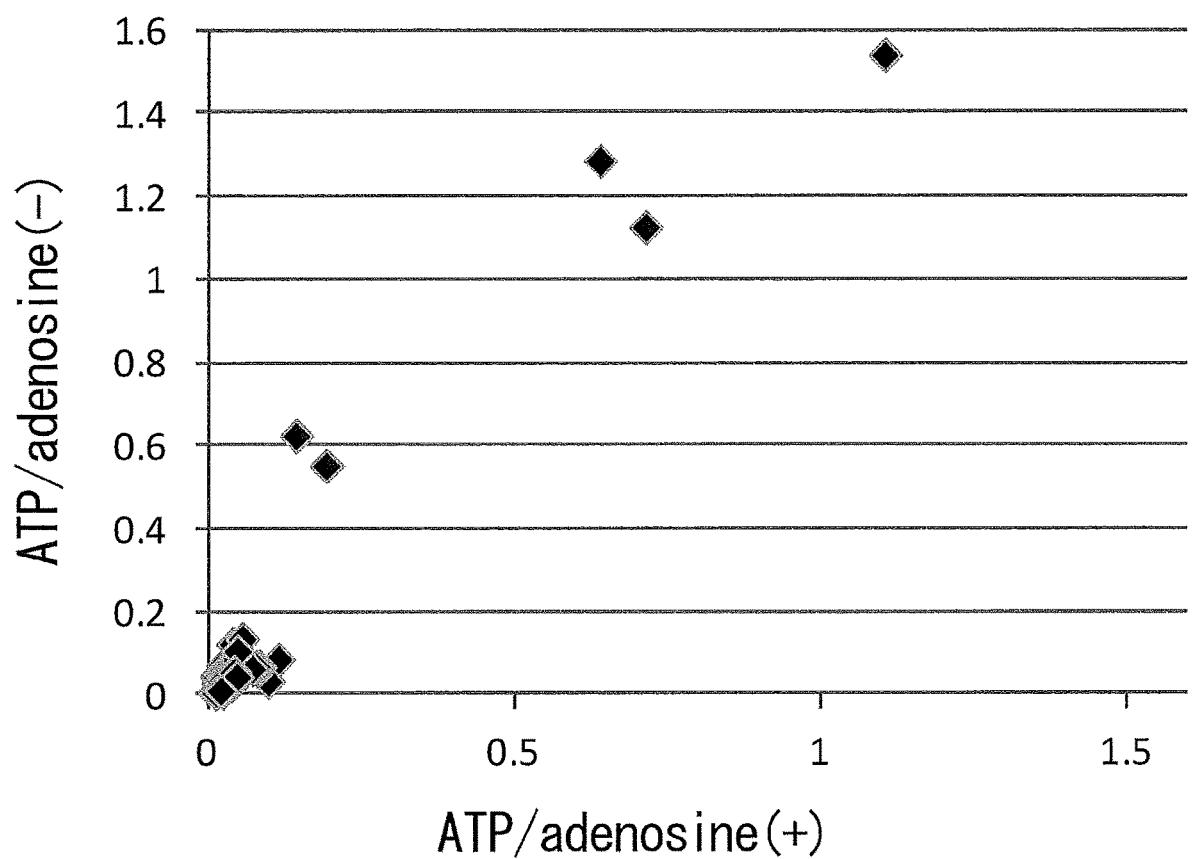
FIG. 41 is a figure showing the result of ELISA performed on 96 clones obtained by panning the rationally designed antibody library four times against human IgA-Fc using a monovalent antibody phage display. The absorbance values which evaluate the binding activity of the antibodies to human IgA-Fc in the absence of ATP and adenosine are shown on the vertical axis, and the absorbance values which evaluate the binding activity of the antibodies to human IgA-Fc in the presence of ATP and adenosine are shown on the horizontal axis.

Purified phages, to which TBS or (adenosine+ATP)/TBS was added, were subjected to ELISA by the following procedure. A StreptaWell 96 microtiter plate (Roche) was coated overnight with 100 μl of TBS containing a biotin-labeled antigen. After the antigen was removed from each well of the plate by washing with TBST, the wells were blocked with 250 μl of 2% skim milk/TBS for one hour or more. 2% skim milk/TBS was removed, and then the prepared, purified phages were added to each well. The plate was allowed to stand for one hour to allow binding of antibody-displaying phages to the antigen in each well in the presence or absence of adenosine and ATP. After washing with TBST or (adenosine+ATP)/TBST, an HRP-conjugated anti-M13 antibody (Amersham Pharmacia Biotech) diluted with TBS or (adenosine+ATP)/TBS was added to each well. The plate was incubated for one hour. Following wash with TBST or (adenosine+ATP)/TBST, the TMB single solution (ZYMED) was added to each well. The chromogenic reaction in the solution of each well was terminated by adding sulfuric acid. Then, the developed color was assessed by measuring absorbance at 450 nm. The result shows that a greater number of antibodies that have binding activity in the presence of small molecules were obtained from the multivalent phage-display antibody library (FIGS. 40 and 41). This finding suggests that antibodies that have binding activity in the presence of small molecules can be obtained more efficiently by using the multivalent phage-display antibody library method. The result of phage ELISA is shown in Table 22 below.

TABLE 22

|  | Monovalent presentation | Multivalent presentation |
| --- | --- | --- |
| Number of panning | 4 | 4 |
| Number of clones subjected to ELISA | 96 | 96 |
| Number of positive clones (Absorbance > 0.1) | 6 | 28 |
| Number of dependent clones (SM+/− ratio > 1.3) | 1 | 19 |
| Number of dependent clone sequences | 1 | 5 |

Figure 42:
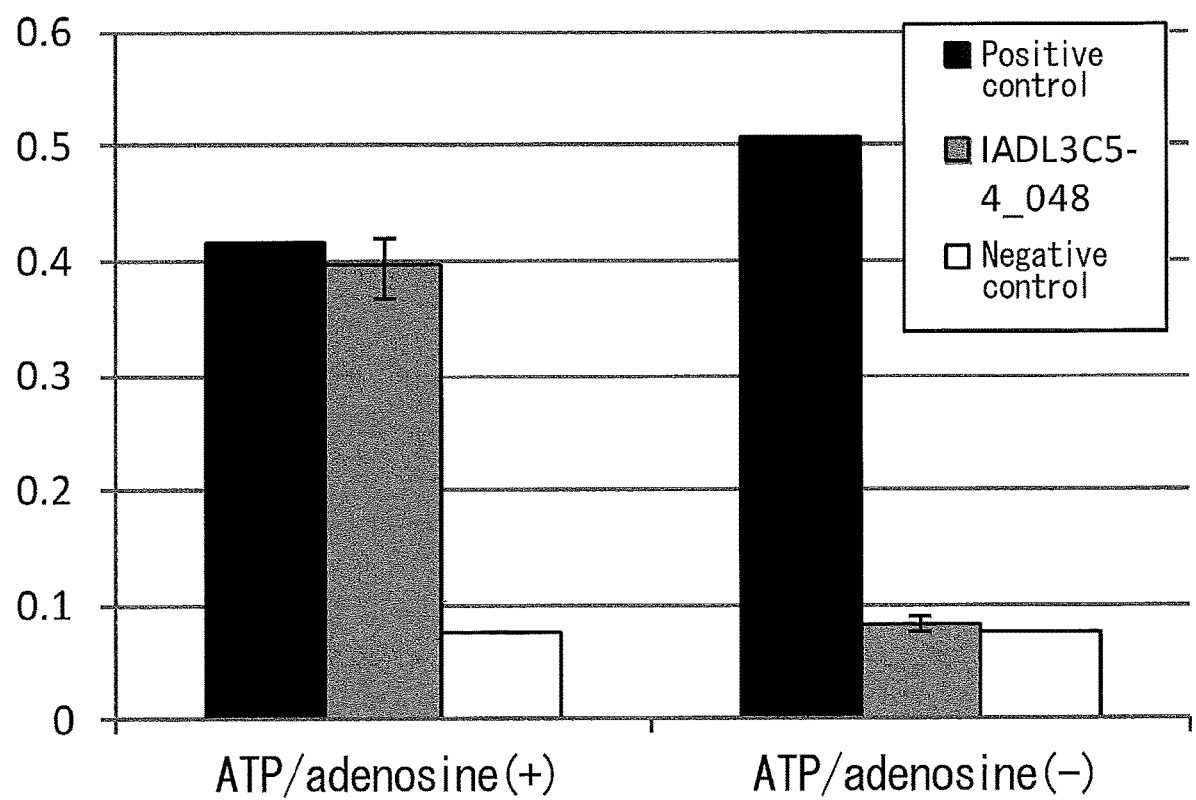
FIG. 42 is a figure showing the result of ELISA performed on clone IADL3C5-4_048 obtained from the rationally designed antibody library against human IgA-Fc in the presence or absence of ATP and adenosine at 1 mM. The vertical axis shows the absorbance value which evaluates binding activity of the antibody to human IgA-Fc. Results obtained when using a clone obtained from the rationally designed antibody library and showing binding activity toward human IgA-Fc regardless of the presence of small molecules are presented as the positive control. Results obtained when using the M13KO7 Helper Phage are presented as the negative control.

(17-3) Assessment of the Binding Ability of Antibodies that Use Adenosine and ATP as a Switch, and Sequence Analysis Genes were amplified using specific primers (SEQ ID NOs: 111 and 112) from clones that had been assessed to have antigen-binding activity in the presence of adenosine and ATP based on the result of phage ELISA described in (17-2). The nucleotide sequences of the genes were analyzed. As a result, clone "IADL3C5-4_048 (heavy chain, SEQ ID NOs: 100; light chain, SEQ ID NO: 101)," which exhibits antigen-binding activity in the presence of adenosine and ATP, was obtained (FIG. 42).

[Example 18] Characterization of ATP/Adenosine-Dependent Antibodies Obtained from Library (18-1) Preparation of ATP/Adenosine-Dependent Antibodies Obtained from Library Genes were amplified using specific primers from clones 6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011, which were obtained as described in Example 10 and were assessed to have binding activity to biotin-labeled hIL-6R in the presence of ATP or adenosine; and their nucleotide sequences were analyzed (Table 23).

TABLE 23

| Clone name | Heavy chain SEQ ID NO | Light chain SEQ ID NO |
| --- | --- | --- |
| 6RAD2C1-4_001 | SEQ ID NO: 113 | SEQ ID NO: 114 |
| 6RAD2C1-4_005 | SEQ ID NO: 115 | SEQ ID NO: 116 |
| 6RAD2C1-4_011 | SEQ ID NO: 82 | SEQ ID NO: 83 |
| 6RAD2C1-4_026 | SEQ ID NO: 117 | SEQ ID NO: 118 |
| 6RAD2C1-4_030 | SEQ ID NO: 119 | SEQ ID NO: 120 |
| 6RAD2C1-4_042 | SEQ ID NO: 121 | SEQ ID NO: 122 |
| 6RAD2C1-4_076 | SEQ ID NO: 84 | SEQ ID NO: 85 |
| 6RDL3C1-4_085 | SEQ ID NO: 123 | SEQ ID NO: 124 |
| 6RDL3C5-4_011 | SEQ ID NO: 125 | SEQ ID NO: 126 |

The variable regions of 6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011 were inserted into an animal expression plasmid for human IgG1/Kappa that has the antibody heavy chain constant region of SEQ ID NO: 90 and the light chain kappa constant region sequence of SEQ ID NO: 91. Antibodies were expressed using the method described below. FreeStyle 293-F (Invitrogen) which was derived from human fetal kidney cells were suspended at a cell density of $1.33 \times 10^6$ cells/ml in the FreeStyle 293 Expression Medium (Invitrogen), and aliquoted at 3 ml into each well of a 6-well plate. The plasmid DNA was transfected into the cells by lipofection. From the culture supernatants after four days of culture in a $CO_2$ incubator (37° C., 8% $CO_2$, 90 rpm), antibodies were purified by a method known to those skilled in the art using rProtein A Sepharose™ Fast Flow (Amersham Biosciences). Absorbance of the purified antibody solutions was measured at 280 nm using a spectrophotometer. From values obtained by the measurement, concentrations of purified antibodies were calculated using an extinction coefficient determined by the PACE method (Protein Science (1995) 4, 2411-2423).

(18-2) Assessment of the Effect of Various Small Molecules on Human IL6 Receptor Binding by Surface Plasmon Resonance Biacore T200 (GE Healthcare) was used to evaluate the effect of various small molecules on the antigen-antibody reaction of IL-6R with 9 ATP/adenosine-dependent antibodies (6RAD2C1-4_001, 6RAD2C1-4_005, 6RAD2C1-4_011, 6RAD2C1-4_026, 6RAD2C1-4_030, 6RAD2C1-4_042, 6RAD2C1-4_076, 6RDL3C1-4_085, and 6RDL3C5-4_011) obtained from the library. The running buffer was used: 20 mmol/l ACES, 150 mmol/l NaCl, 0.05% (w/v) Tween20, pH 7.4. Assay was carried out at 25° C. IL-6R was immobilized onto sensor chip CM5 by amine coupling; and the antibodies were allowed to interact as analyte for 120 seconds, and changes in the amount of binding were observed. For dilution of the antibodies, the running buffer or the running buffer containing any one of ATP, ADP, AMP, cAMP, and adenosine (ADO) were used. The final concentration of each small molecule and the final concentration of each antibody were adjusted to 1 mM and 1 µM, respectively. Meanwhile, under the 1 mM ATP condition, assay was carried out with a series of stepwise antibody concentrations. The dissociation constant $K_D$ (mol/L) of each clone for IL-6R was calculated from a plot of equilibrium value against antibody concentration. The parameters were calculated using the Biacore T200 Evaluation Software (GE Healthcare). The dissociation constant $K_D$ of each clone in the presence of 1 mM ATP is shown in Table 24.

TABLE 24

| Clone name | Dissociation constant $K_D$ (mol/L) |
| --- | --- |
| 6RAD2C1-4_01 | 3.0E−07 |
| 6RAD2C1-4_05 | 3.4E−07 |
| 6RAD2C1-4_11 | 2.3E−07 |
| 6RAD2C1-4_26 | 2.1E−07 |
| 6RAD2C1-4_30 | 3.3E−07 |
| 6RAD2C1-4_42 | 2.5E−07 |
| 6RAD2C1-4_76 | 2.5E−07 |
| 6RDL3C1-4_85 | 3.9E−07 |
| 6RDL3C5-4_11 | 1.3E−07 |

Figure 43:
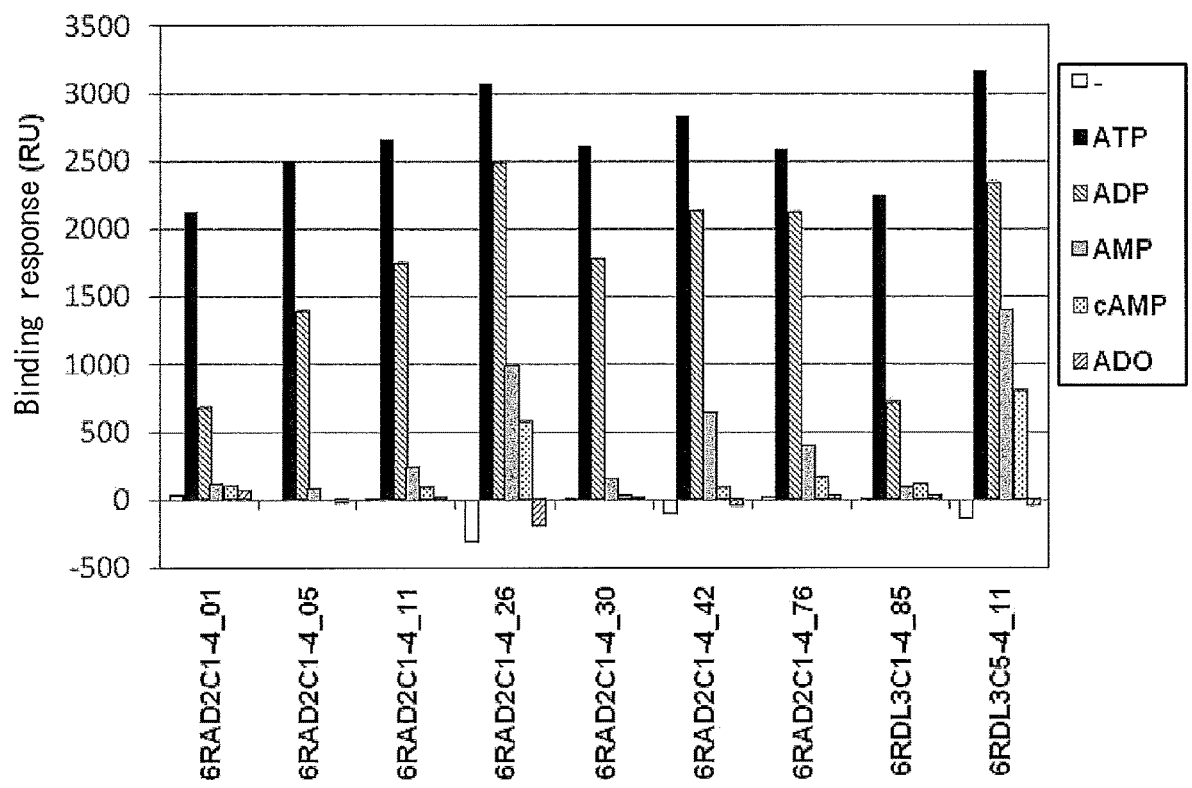
FIG. 43 is a graph showing the binding level (binding response (RU)) when each clone at 1 μM was made to interact for 120 seconds with IL-6R immobilized on Sensorchip CM5 in the presence or absence of each of the small molecules at 1 mM.

The amount of each clone that binds to IL-6R as determined by this assay in the presence or absence of 1 mM small molecules is shown in FIG. 43. As shown in FIG. 43, each clone binds to IL-6R in the presence of 1 mM ATP, but their IL-6R binding was not detectable in the absence of ATP. This demonstrates that each clone has the property that it binds to IL-6R via ATP as a switch. In small molecules besides ATP, binding of all clones was observed in the presence of ADP, and some clones were shown to bind in the presence of AMP and cAMP. IL-6R binding was not detectable in the presence of ADO.

This demonstrates that antibodies that bind to target antigens in the presence of any one or more of ATP, ADP, AMP, and cAMP can be obtained by using rationally designed libraries. As described in this Example, panning was carried out in the presence of both ATP and ADO which bind to antibody ATNLSA1-4_D12 used as a reference in designing the design libraries. The result showed that antibodies that strongly bind to target antigens were isolated in the presence of ATP which strongly binds to ATNLSA1-4_D12 but not in the presence of ADO which binds more weakly to ATNLSA1-4_D12 than ATP. Antibodies that bind to antigens in a manner depending on a desired small molecule alone can be obtained by isolating antigen-binding antibodies by contacting antigens with libraries in the presence of the small molecule alone. For example, antibodies that bind in the presence of ADO can be efficiently obtained from libraries by performing panning in the presence of ADO alone.

(18-3) Effect of ATP on the ADCC Activity of Obtained Antibodies

Figure 44A:
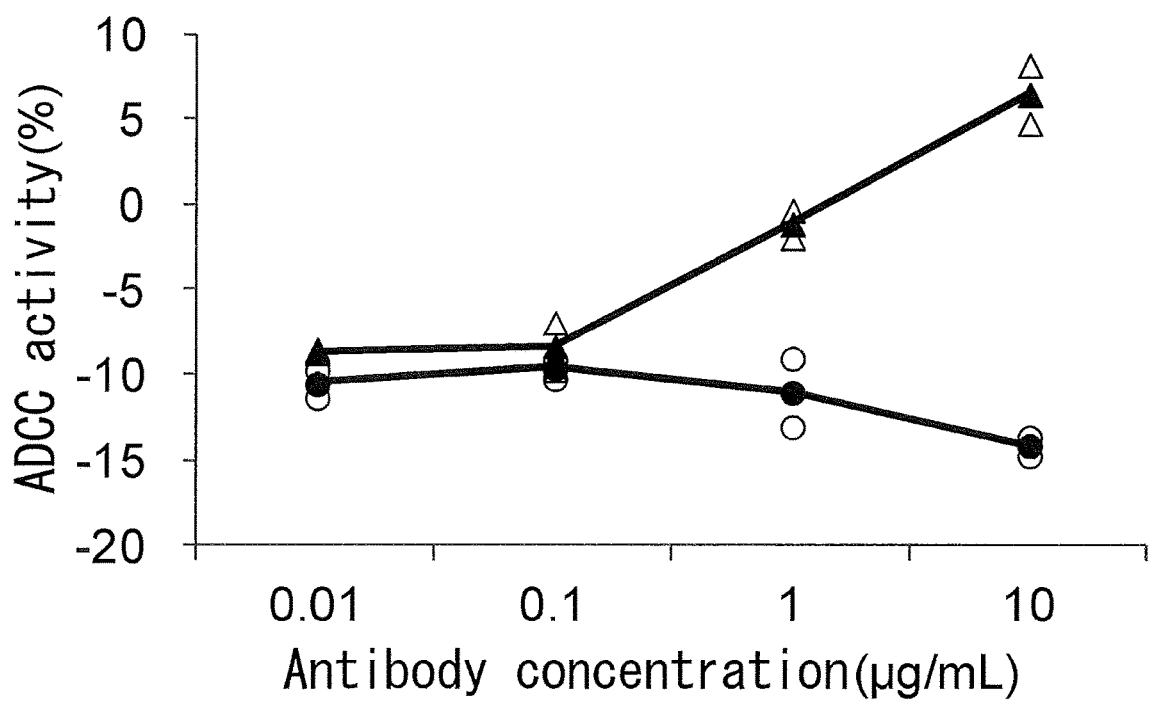
FIG. 44A shows the ADCC activity of antibodies that bind to antigens in the presence of small molecules toward cells expressing the antigen. It is a figure showing the ADCC activity of clone 6RAD2C1-4_030, which binds to hIL-6R in the presence of ATP, toward CHO cells expressing hIL-6R in the presence (triangles) or absence (circles) of ATP. The open triangles and circles show the measured values, and the filled triangles and circles show the mean values.
Figure 44B:
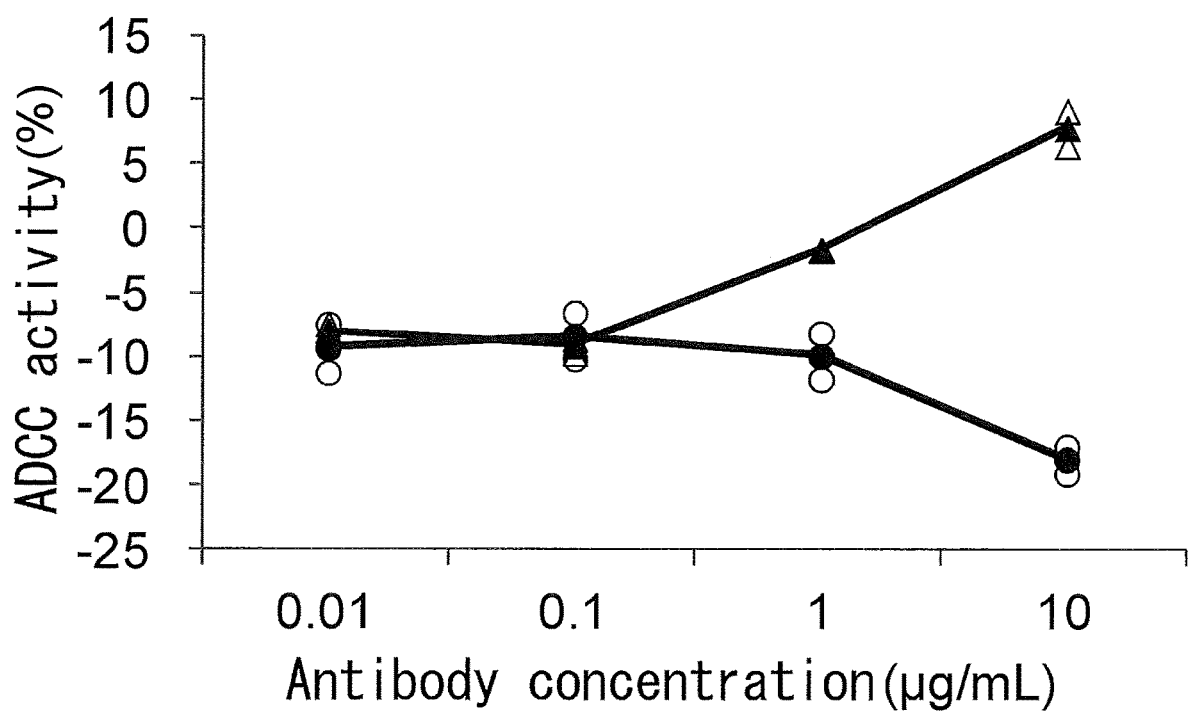
FIG. 44B shows the ADCC activity of antibodies that bind to antigens in the presence of small molecules toward cells expressing the antigen. It is a figure showing the ADCC activity of clone 6RAD2C1-4_011, which binds to hIL-6R in the presence of ATP, toward CHO cells expressing hIL-6R in the presence (triangles) or absence (circles) of ATP. The open triangles and circles show the measured values, and the filled triangles and circles show the mean values.
Figure 44C:
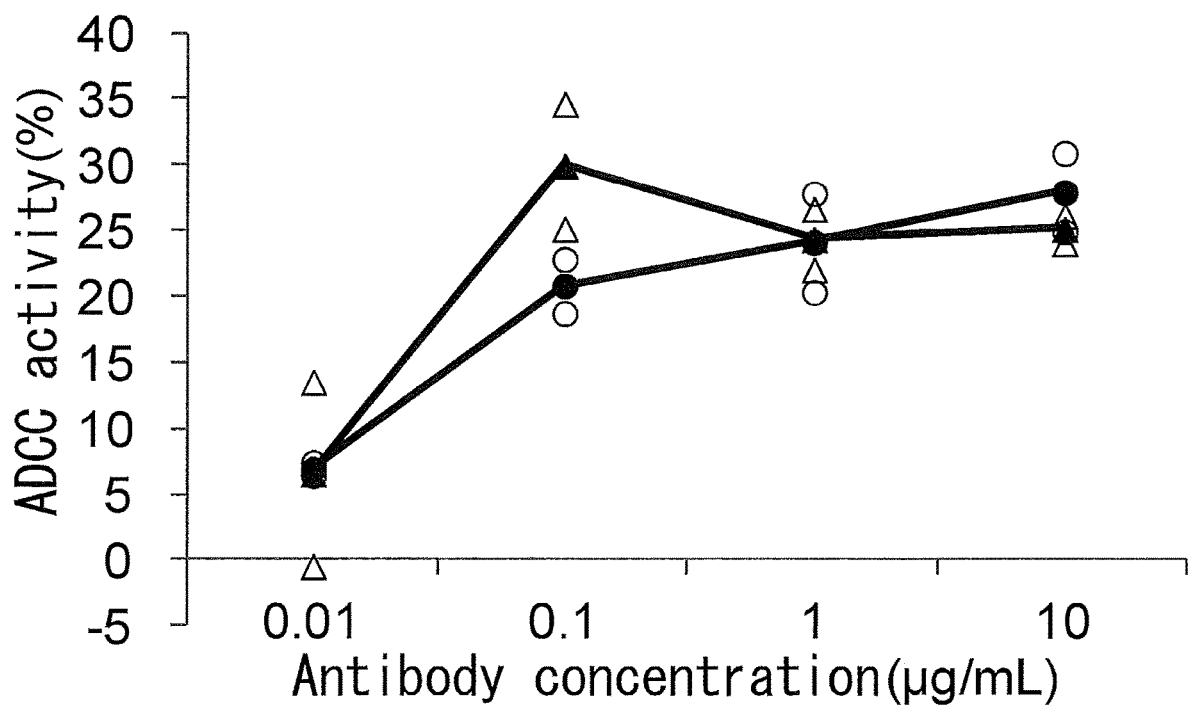
FIG. 44C shows the ADCC activity of antibodies that bind to antigens in the presence of small molecules toward cells expressing the antigen. It is a figure showing the ADCC activity of MRA, which binds to hIL-6R regardless of the presence or absence of ATP, toward CHO cells expressing in the presence (triangles) or absence (circles) of ATP. The open triangles and circles show the measured values, and the filled triangles and circles show the mean values.

The obtained antibodies 6RAD2C1-4_030 and 6RAD2C1-4_011 were assessed by the method described below to test whether ADCC activity against hIL-6R-expressing cells is mediated via hIL-6R binding of the antibodies in the presence of adenosine triphosphate (ATP). This assessment was carried out using variant 6RAD2C1-4_030 with increased effector activity (antibody heavy chain variable region, SEQ ID NO: 119; antibody light chain variable region, SEQ ID NO: 120; antibody heavy chain constant region, SEQ ID NO: 90, antibody light chain constant region, SEQ ID NO: 91) and variant 6RAD2C1-4_011 with increased effector activity (antibody heavy chain variable region, SEQ ID NO: 82; antibody light chain variable region, SEQ ID NO: 83; antibody heavy chain constant region, SEQ ID NO: 90; antibody light chain constant region, SEQ ID NO: 91) prepared as described in Example 18-1, as well as a known anti-human IL-6R antibody MRA (antibody heavy chain variable region, SEQ ID NO: 92; antibody light chain variable region, SEQ ID NO: 92; antibody heavy chain constant region, SEQ ID NO: 90; antibody light chain constant region, SEQ ID NO: 91) prepared as described in Example 15-5. At various antibody concentrations in the presence or absence of ATP, 6RAD2C1-4_030, 6RAD2C1-4_011, and MRA were assessed for the ADCC activity to hIL-6R-expressing cells according to the method described in Reference Example 3. The assay result is shown in FIG. 44.

The assay result confirmed antibody concentration-dependent ADCC activity by 6RAD2C1-4_030 and 6RAD2C1-4_011 in the presence of ATP. This finding shows that ADCC activity is induced against antigen-expressing cells by antigen-antibody binding mediated by not only kynurenine but also ATP; and thus it is revealed that for antibodies that bind to antigens in the presence of small molecules as a switch, their function of antitumor activity such as ADCC activity can also be regulated by the presence of small molecules serving as a switch.

These results suggest strong induction of ADCC activity against hIL-6R-expressing cells is expected in tumor tissues where ATP concentration is high, and weak induction of ADCC activity in normal tissues where ATP concentration is low. Based on the above, by administering antibodies for which ATP serves as a switch, the cytotoxicity against normal tissues expressing a target antigen can be reduced without impairing the pharmaceutical effect on tumor tissues expressing the target antigen.

[Reference Example 1] ADCC Activity of Test Antibodies Using Human Peripheral Blood Mononuclear Cells as Effector Cells Antibodies that bind antigens in a kynurenine-dependent manner were assessed for their ADCC activity against antigen-expressing cells at different antibody concentrations according to the method described below. Human peripheral blood mononuclear cells (hereinafter referred to as human PBMC) were used as effector cells to measure the ADCC activity of each test antibody as follows.

(1) Preparation of Human PBMC Solution

Syringes pre-filled with 200 µl of 1000 units/ml heparin solution (Novo-Heparin 5000 units for Injection; Novo Nordisk) were used to collect 50 ml of peripheral blood from healthy volunteers (male adult) affiliated with Chugai Pharmaceutical Co. Ltd. The peripheral blood was diluted two-fold with PBS(−), and divided into four equal parts, each of which was transferred into a pre-centrifuged leukocyte separation tube Leucosep (Greiner Bio-One) containing 15 ml of Ficoll-Paque PLUS. The separation tubes containing an aliquot of the peripheral blood were centrifuged at 2150 rpm for ten minutes at room temperature. Then, the resulting mononuclear cell fractions were collected from the tubes. The cells in each fraction were washed once with RPMI-1640 (nacalai tesque) supplemented with 10% FBS (hereinafter referred to as 10% FBS/RPMI), and then suspended at a cell density of $1\times10^7$ cells/ml in 10% FBS/RPMI. The cell suspensions were used as the human PBMC solution in subsequent experiments.

(2) Preparation of Target Cells 0.74 MBq of Cr-51 was added to $3\times10^6$ cells of BaF/hIL6R (Mihara et al., (Int. Immunopharmacol. (2005) 5, 1731-40) which is Ba/F3 cells expressing human IL-6 receptor. Then, the cells were incubated in 5% $CO_2$ incubator at 37° C. for 1 hour. After washing 3 times with 10% FBS/RPMI, the cells were suspended at a cell density of $2\times10^5$ cells/ml in 10% FBS/RPMI. The cell suspension was used as the target cells in subsequent experiments.

(3) Preparation of Kynurenine Solution

L-Kynurenine (sigma) was diluted to 5 mM with PBS(−), and then its concentration was adjusted to 400 µM using 10% FBS/RPMI. The solution was used as the kynurenine solution in subsequent experiments.

(4) Chrome Release Assay (ADCC)

ADCC activity was assessed based on specific chrome release rate determined by chrome release assay. First, antibody solutions prepared at various concentrations (0, 0.04, 0.4, 4, and 40 µg/ml) were added at 50 µl to each well of a round-bottomed 96-well plate. Then, the target cells prepared as described in (2) were seeded at 50 µl ($1\times10^4$ cells/well) to the wells. Furthermore, the kynurenine solution prepared as described in (3) was added at 50 µl to the wells, and the plate was allowed to stand at room temperature for 15 minutes. Then, the human PBMC solution prepared as described in (1) was added at 50 µl to each well ($5\times10^5$ cells/well). The plate was allowed to stand in 5% $CO_2$ incubator at 37° C. for 4 hours, followed by centrifugation. 100 µl of culture supernatant from each well of the plate was measured for radioactivity using a gamma counter. The specific chrome release rate was determined based on the equation below.

$$\text{Chrome release rate (\%)}=(A-C)\times100/(B-C)$$

In this equation, "A" represents mean radioactivity (cpm) of 100 µl of culture supernatant in each well. "B" represents mean radioactivity (cpm) of 100 µl of culture supernatant in a well containing target cells, 50 µl of 4% NP-40 aqueous solution (Nonidet P-40; Nacalai Tesques), and 100 µl of 10% FBS/RPMI. Furthermore, "C" represents mean radioactivity (cpm) of 100 µl of culture supernatant in a well containing target cells, 150 µl of 10% FBS/RPMI or 100 µl of 10% FBS/RPMI, and 50 µl of kynurenine solution. The test was carried out in duplicate. The mean specific chrome release rate (%) that reflects the ADCC activity of each test antibody was calculated based on the assay described above.

[Reference Example 2] ADCC Activity of Each Test Antibody Using Human Peripheral Blood Mononuclear Cells as Effector Cells Antibodies that bind to antigens in a kynurenine-dependent manner were assessed for their ADCC activity against antigen-expressing cells at various kynurenine concentrations according to the method described below. Using human peripheral blood mononuclear cells as effector cells, the ADCC activity of each test antibody was assayed as follows. Human PBMC solution and target cells were prepared by the same method as described in Reference Example 1.

(1) Preparation of Kynurenine Solutions

L-Kynurenine (sigma) was diluted to 5 mM with PBS(−), and then its concentration was adjusted to 400, 133, 44, 14.8, and 4.9 μM using 10% FBS/RPMI. The solutions were used as kynurenine solutions in subsequent experiments.

(2) Chrome Release Assay (ADCC)

ADCC activity was assessed based on specific chrome release rate determined by chrome release assay. First, an antibody solution prepared to 200 μg/ml was added at 50 μl to each well of a round-bottomed 96-well plate. Then, the target cells prepared as described above were seeded at 50 μl ($1 \times 10^4$ cells/well) to the wells. Furthermore, the kynurenine solution prepared at each concentration as described in (1) was added at 50 μl to the wells, and the plate was allowed to stand at room temperature for 15 minutes. Then, the human PBMC solution prepared as described above was added at 50 μl to each well ($5 \times 10^5$ cells/well). The plate was allowed to stand in 5% $CO_2$ incubator at 37° C. for 4 hours, followed by centrifugation. 100 μl of culture supernatant from each well of the plate was measured for radioactivity using a gamma counter. The specific chrome release rate was determined based on the equation described in Reference Example 1.

[Reference Example 3] ADCC Activity of Test Antibodies Using Human NK Cell Line NK92 as Effector Cells Antibodies that bind to antigens in an ATP-dependent manner were assessed for their ADCC activity against antigen-expressing cells at various antibody concentrations according to the method described below. The ADCC activity of each test antibody was assayed by using as effector cells NK92-CD16(V) resulting from forced expression of human FcgRIIIa in human NK cell line NK92 as follows.

(1) Preparation of NK92-CD16(V)

NK92-CD16(V) was suspended at a cell density of $1 \times 10^5$ cells/ml in RPMI/10% FBS. The cell suspension was used as an NK92-CD16(V) solution in subsequent experiments.

(2) Preparation of Target Cells 0.74 MBq of Cr-51 was added to $3 \times 10^6$ cells of CHO/hIL6R which is CHO cells expressing human IL-6 receptor. Then, the cells were incubated in 5% $CO_2$ incubator at 37° C. for 1 hour. After washing 3 times with 10% FBS/RPMI, the cells were suspended at a cell density of $2 \times 10^5$ cells/ml in 10% FBS/RPMI. The cell suspension was used as target cells in subsequent experiments.

(3) Preparation of ATP Solution

ATP (sigma) was diluted to 100 mM with 10% FBS/RPMI, and then its concentration was adjusted to 4 mM. The solution was used as an ATP solution in subsequent experiments.

(4) Chrome Release Assay (ADCC)

ADCC activity was assessed based on the specific chrome release rate determined by chrome release assay. First, antibody solutions prepared to various concentrations (0, 0.04, 0.4, 4, or 40 μg/ml) were each added at 50 μl to a well of a round-bottomed 96-well plate. Then, the target cells prepared as described in (2) were seeded at 50 μl ($1 \times 10^4$ cells/well) to the wells. Furthermore, the ATP solution prepared as described in (3) was added at 50 μl to the wells, and the plate was allowed to stand at room temperature for 15 minutes. Then, the NK92-CD16(V) solution prepared as described in (1) was added at 50 μl to each well ($5 \times 10^5$ cells/well). The plate was allowed to stand in 5% $CO_2$ incubator at 37° C. for 4 hours, followed by centrifugation. 100 μl of culture supernatant from each well of the plate was measured for radioactivity using a gamma counter. The specific chrome release rate was determined based on the equation described in Reference Example 1.

The invention claimed is:

1. An antigen-binding molecule comprising an antigen-binding domain whose antigen-binding activity varies depending on the concentration of a compound that is present at a higher concentration in a target tissue than in a non-target tissue in a subject, wherein the compound is not the antigen or a fragment thereof and is selected from adenosine, inosine, adenosine monophosphate, cyclic adenosine monophosphate, adenosine diphosphate, and adenosine triphosphate;
   wherein the antigen-binding domain comprises an antibody heavy-chain variable region and an antibody light-chain variable region;
   wherein at least one of the following amino acid residues is in the antibody heavy-chain variable region and binds to the compound: Ser at position 52, Ser at position 52a, Arg at position 53, Gly at position 96, Leu at position 100a, and Trp at position 100c, with all positions by Kabat numbering; and
   wherein that binding to the compound increases the antigen-binding activity of the antigen-binding domain.

2. The antigen-binding molecule of claim 1, wherein the target tissue is a cancer tissue.

3. The antigen-binding molecule of claim 1, wherein the target tissue is an inflamed tissue.

4. The antigen-binding molecule of claim 1, wherein the antigen is a molecule expressed on a cell membrane.

5. The antigen-binding molecule of claim 1, wherein, when the antigen-binding molecule binds to the antigen, the antigen is neutralized.

6. The antigen-binding molecule of claim 1, wherein the antigen-binding molecule has cytotoxic activity.

7. The antigen-binding molecule of claim 1, wherein the antigen-binding molecule comprises an Fc region.

8. The antigen-binding molecule of claim 7, wherein the amino acid sequence of the Fc region is identical to the sequence of an Fc region included within the constant region sequence of one of SEQ ID NO: 5, 6, 7, or 8.

9. The antigen-binding molecule of claim 7, wherein the Fc region is a modified Fc region whose binding affinity for an Fcγ receptor is increased compared to the binding affinity of a native human IgG Fc region for the Fcγ receptor, wherein the native human IgG Fc region is of the same IgG subclass as the modified Fc region.

10. The antigen-binding molecule of claim 9, wherein the modified Fc region differs from the native human IgG Fc region at one or more of the following EU numbering positions: 221, 222, 223, 224, 225, 227, 228, 230, 231, 232, 233, 234, 235, 236, 237, 238, 239, 240, 241, 243, 244, 245, 246, 247, 249, 250, 251, 254, 255, 256, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 311, 313, 315, 317, 318, 320, 322, 323, 324, 325, 326, 327, 328, 329, 330, 331, 332, 333, 334, 335, 336, 337, 339, 376, 377, 378, 379, 380, 382, 385, 392, 396, 421, 427, 428, 429, 434, 436, 440.

11. The antigen-binding molecule of claim 10, wherein at least one of the following EU numbering positions in the modified Fc region is occupied by the indicated amino acid:
   either Lys or Tyr at position 221;
   any one of Phe, Trp, Glu, or Tyr at position 222;
   any one of Phe, Trp, Glu, or Lys at position 223;
   any one of Phe, Trp, Glu, or Tyr at position 224;
   any one of Glu, Lys, or Trp at position 225;
   any one of Glu, Gly, Lys, or Tyr at position 227;
   any one of Glu, Gly, Lys, or Tyr at position 228;
   any one of Ala, Glu, Gly, or Tyr at position 230;
   any one of Glu, Gly, Lys, Pro, or Tyr at position 231;
   any one of Glu, Gly, Lys, or Tyr at position 232;
   any one of Ala, Asp, Phe, Gly, His, Ile, Lys, Leu, Met, Asn, Gln, Arg, Ser, Thr, Val, Trp, or Tyr at position 233;
   any one of Ala, Asp, Glu, Phe, Gly, His, Ile, Lys, Met, Asn, Pro, Gln, Arg, Ser, Thr, Val, Trp, or Tyr at position 234;
   any one of Ala, Asp, Glu, Phe, Gly, His, Ile, Lys, Met, Asn, Pro, Gln, Arg, Ser, Thr, Val, Trp, or Tyr at position 235;
   any one of Ala, Asp, Glu, Phe, His, Ile, Lys, Leu, Met, Asn, Pro, Gln, Arg, Ser, Thr, Val, Trp, or Tyr at position 236;
   any one of Asp, Glu, Phe, His, Ile, Lys, Leu, Met, Asn, Pro, Gln, Arg, Ser, Thr, Val, Trp, or Tyr at position 237;
   any one of Asp, Glu, Phe, Gly, His, Ile, Lys, Leu, Met, Asn, Gln, Arg, Ser, Thr, Val, Trp, or Tyr at position 238;
   any one of Asp, Glu, Phe, Gly, His, Ile, Lys, Leu, Met, Asn, Pro, Gln, Arg, Thr, Val, Trp, or Tyr at position 239;
   any one of Ala, Ile, Met, or Thr at position 240;
   any one of Asp, Glu, Leu, Arg, Trp, or Tyr at position 241;
   any one of Leu, Glu, Leu, Gln, Arg, Trp, or Tyr at position 243;
   His at position 244;
   Ala at position 245;
   any one of Asp, Glu, His, or Tyr at position 246;
   any one of Ala, Phe, Gly, His, Ile, Leu, Met, Thr, Val, or Tyr at position 247;
   any one of Glu, His, Gln, or Tyr at position 249;
   either Glu or Gln at position 250;
   Phe at position 251;
   any one of Phe, Met, or Tyr at position 254;
   any one of Glu, Leu, or Tyr at position 255;
   any one of Ala, Met, or Pro at position 256;
   any one of Asp, Glu, His, Ser, or Tyr at position 258;
   any one of Asp, Glu, His, or Tyr at position 260;
   any one of Ala, Glu, Phe, Ile, or Thr at position 262;
   any one of Ala, Ile, Met, or Thr at position 263;

any one of Asp, Glu, Phe, Gly, His, Ile, Lys, Leu, Met, Asn, Pro, Gln, Arg, Ser, Thr, Trp, or Tyr at position 264;
any one of Ala, Leu, Phe, Gly, His, Ile, Lys, Leu, Met, Asn, Pro, Gln, Arg, Ser, Thr, Val, Trp, or Tyr at position 265;
any one of Ala, Ile, Met, or Thr at position 266;
any one of Asp, Glu, Phe, His, Ile, Lys, Leu, Met, Asn, Pro, Gln, Arg, Thr, Val, Trp, or Tyr at position 267;
any one of Asp, Glu, Phe, Gly, Ile, Lys, Leu, Met, Pro, Gln, Arg, Thr, Val, or Trp at position 268;
any one of Phe, Gly, His, Ile, Lys, Leu, Met, Asn, Pro, Arg, Ser, Thr, Val, Trp, or Tyr at position 269;
any one of Glu, Phe, Gly, His, Ile, Leu, Met, Pro, Gln, Arg, Ser, Thr, Trp, or Tyr at position 270;
any one of Ala, Asp, Glu, Phe, Gly, His, Ile, Lys, Leu, Met, Asn, Gln, Arg, Ser, Thr, Val, Trp, or Tyr at position 271;
any one of Asp, Phe, Gly, His, Ile, Lys, Leu, Met, Pro, Arg, Ser, Thr, Val, Trp, or Tyr at position 272;
either Phe or Ile at position 273;
any one of Asp, Glu, Phe, Gly, His, Ile, Leu, Met, Asn, Pro, Arg, Ser, Thr, Val, Trp, or Tyr at position 274;
either Leu or Trp at position 275;
any one of Asp, Glu, Phe, Gly, His, Ile, Leu, Met, Pro, Arg, Ser, Thr, Val, Trp, or Tyr at position 276;
any one of Asp, Glu, Gly, His, Ile, Lys, Leu, Met, Asn, Pro, Gln, Arg, Ser, Thr, Val, or Trp at position 278;
Ala at position 279;
any one of Ala, Gly, His, Lys, Leu, Pro, Gln, Trp, or Tyr at position 280;
any one of Asp, Lys, Pro, or Tyr at position 281;
any one of Glu, Gly, Lys, Pro, or Tyr at position 282;
any one of Ala, Gly, His, Ile, Lys, Leu, Met, Pro, Arg, or Tyr at position 283;
any one of Asp, Glu, Leu, Asn, Thr, or Tyr at position 284;
any one of Asp, Glu, Lys, Gln, Trp, or Tyr at position 285;
any one of Glu, Gly, Pro, or Tyr at position 286;
any one of Asn, Asp, Glu, or Tyr at position 288;
any one of Asp, Gly, His, Leu, Asn, Ser, Thr, Trp, or Tyr at position 290;
any one of Asp, Glu, Gly, His, Ile, Gln, or Thr at position 291;
any one of Ala, Asp, Glu, Pro, Thr, or Tyr at position 292;
any one of Phe, Gly, His, Ile, Leu, Met, Asn, Pro, Arg, Ser, Thr, Val, Trp, or Tyr at position 293;
any one of Phe, Gly, His, Ile, Lys, Leu, Met, Asn, Pro, Arg, Ser, Thr, Val, Trp, or Tyr at position 294;
any one of Asp, Glu, Phe, Gly, His, Ile, Lys, Met, Asn, Pro, Arg, Ser, Thr, Val, Trp, or Tyr at position 295;
any one of Ala, Asp, Glu, Gly, His, Ile, Lys, Leu, Met, Asn, Gln, Arg, Ser, Thr, or Val at position 296;
any one of Asp, Glu, Phe, Gly, His, Ile, Lys, Leu, Met, Pro, Gln, Arg, Ser, Thr, Val, Trp, or Tyr at position 297;
any one of Ala, Asp, Glu, Phe, His, Ile, Lys, Met, Asn, Gln, Arg, Thr, Val, Trp, or Tyr at position 298;
any one of Ala, Asp, Glu, Phe, Gly, His, Ile, Lys, Leu, Met, Asn, Pro, Gln, Arg, Ser, Val, Trp, or Tyr at position 299;
any one of Ala, Asp, Glu, Gly, His, Ile, Lys, Leu, Met, Asn, Pro, Gln, Arg, Ser, Thr, Val, or Trp at position 300;
any one of Asp, Glu, His, or Tyr at position 301;
Ile at position 302;
any one of Asp, Gly, or Tyr at position 303;
any one of Asp, His, Leu, Asn, or Thr at position 304;
any one of Glu, Ile, Thr, or Tyr at position 305;
any one of Ala, Asp, Asn, Thr, or Tyr at position 311;
Phe at position 313;
Leu at position 315;
either Glu or Gln at position 317;
any one of His, Leu, Asn, Pro, Gln, Arg, Thr, Val, or Tyr at position 318;
any one of Asp, Phe, Gly, His, Ile, Leu, Asn, Pro, Ser, Thr, Val, Trp, or Tyr at position 320;
any one of Ala, Asp, Phe, Gly, His, Ile, Pro, Ser, Thr, Val, Trp, or Tyr at position 322;
Ile at position 323;
any one of Asp, Phe, Gly, His, Ile, Leu, Met, Pro, Arg, Thr, Val, Trp, or Tyr at position 324;
any one of Ala, Asp, Glu, Phe, Gly, His, Ile, Lys, Leu, Met, Pro, Gln, Arg, Ser, Thr, Val, Trp, or Tyr at position 325;
any one of Ala, Asp, Glu, Gly, Ile, Leu, Met, Asn, Pro, Gln, Ser, Thr, Val, Trp, or Tyr at position 326;
any one of Ala, Asp, Glu, Phe, Gly, His, Ile, Lys, Leu, Met, Asn, Pro, Arg, Thr, Val, Trp, or Tyr at position 327;
any one of Ala, Asp, Glu, Phe, Gly, His, Ile, Lys, Met, Asn, Pro, Gln, Arg, Ser, Thr, Val, Trp, or Tyr at position 328;
any one of Asp, Glu, Phe, Gly, His, Ile, Lys, Leu, Met, Asn, Gln, Arg, Ser, Thr, Val, Trp, or Tyr at position 329;
any one of Cys, Glu, Phe, Gly, His, Ile, Lys, Leu, Met, Asn, Pro, Arg, Ser, Thr, Val, Trp, or Tyr at position 330;
any one of Asp, Phe, His, Ile, Leu, Met, Gln, Arg, Thr, Val, Trp, or Tyr at position 331;
any one of Ala, Asp, Glu, Phe, Gly, His, Lys, Leu, Met, Asn, Pro, Gln, Arg, Ser, Thr, Val, Trp, or Tyr at position 332;
any one of Ala, Asp, Glu, Phe, Gly, His, Ile, Leu, Met, Pro, Ser, Thr, Val, or Tyr at position 333;
any one of Ala, Glu, Phe, Ile, Leu, Pro, or Thr at position 334;
any one of Asp, Phe, Gly, His, Ile, Leu, Met, Asn, Pro, Arg, Ser, Val, Trp, or Tyr at position 335;
any one of Glu, Lys, or Tyr at position 336;
any one of Glu, His, or Asn at position 337;
any one of Asp, Phe, Gly, Ile, Lys, Met, Asn, Gln, Arg, Ser, or Thr at position 339;
either Ala or Val at position 376;
either Gly or Lys at position 377;
Asp at position 378;
Asn at position 379;
any one of Ala, Asn, or Ser at position 380;
either Ala or Ile at position 382;
Glu at position 385;
Thr at position 392;
Leu at position 396;
Lys at position 421;
Asn at position 427;
either Phe or Leu at position 428;
Met at position 429;
Trp at position 434;
Ile at position 436;
any one of Gly, His, Ile, Leu, or Tyr at position 440.

12. The antigen-binding molecule of claim 9, wherein the modified Fc region binds, at a pH between 5.8 and 6.0, to FcRn with an affinity that is increased compared to the binding affinity of the native human IgG Fc region for the FcRn receptor at the same pH.

13. The antigen-binding molecule of claim 12, wherein the modified Fc region differs from the native human IgG Fc region at one or more of the following EU numbering positions: 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447.

14. The antigen-binding molecule of claim 13, wherein at least one of the following EU numbering positions in the modified Fc region is occupied by the indicated amino acid:
Leu at position 238;
    Leu at position 244;
    Arg at position 245;
    Pro at position 249;
    either Gln or Glu at position 250;
    any one of Arg, Asp, Glu, or Leu at position 251;
    any one of Phe, Ser, Thr, or Tyr at position 252;
    either Ser or Thr at position 254;
    any one of Arg, Gly, Ile, or Leu at position 255;
    any one of Ala, Arg, Asn, Asp, Gln, Glu, Pro, or Thr at position 256;
    any one of Ala, Ile, Met, Asn, Ser, or Val at position 257;
    Asp at position 258;
    Ser at position 260;
    Leu at position 262;
    Lys at position 270;
    either Leu or Arg at position 272;
    any one of Ala, Asp, Gly, His, Met, Asn, Gln, Arg, Ser, Thr, Trp, or Tyr at position 279;
    any one of Ala, Asp, Phe, Gly, His, Ile, Lys, Leu, Asn, Pro, Gln, Arg, Ser, Thr, Trp, or Tyr at position 283;
    Asn at position 285;
    Phe at position 286;
    either Asn or Pro at position 288;
    Val at position 293,
    any one of Ala, Glu, Gln, or Met at position 307;
    any one of Ala, Glu, Ile, Lys, Leu, Met, Ser, Val, or Trp at position 311;
    Pro at position 309;
    any one of Ala, Asp, or Pro at position 312;
    either Ala or Leu at position 314;
    Lys at position 316;
    Pro at position 317;
    either Asn or Thr at position 318;
    any one of Phe, His, Lys, Leu, Met, Arg, Ser, or Trp at position 332;
    any one of Asn, Thr, or Trp at position 339;
    Pro at position 341;
    any one of Glu, His, Lys, Gln, Arg, Thr, or Tyr at position 343;
    Arg at position 375;
    any one of Gly, Ile, Met, Pro, Thr, or Val at position 376;
    Lys at position 377;
    any one of Asp, Asn, or Val at position 378;
    any one of Ala, Asn, Ser, or Thr at position 380;
    any one of Phe, His, Ile, Lys, Leu, Met, Asn, Gln, Arg, Ser, Thr, Val, Trp, or Tyr at position 382;
    any one of Ala, Arg, Asp, Gly, His, Lys, Ser, or Thr at position 385;
    any one of Arg, Asp, Ile, Lys, Met, Pro, Ser, or Thr at position 386;
    any one of Ala, Arg, His, Pro, Ser, or Thr at position 387;
    any one of Asn, Pro, or Ser at position 389;
    Asn at position 423;
    Asn at position 427;
    any one of Leu, Met, Phe, Ser, or Thr at position 428;
    any one of Ala, Phe, Gly, His, Ile, Lys, Leu, Met, Asn, Gln, Arg, Ser, Thr, Val, or Tyr at position 430;
    either His or Asn at position 431;
    any one of Arg, Gln, His, Ile, Lys, Pro, or Ser at position 433;
    any one of Ala, Gly, His, Phe, Ser, Trp, or Tyr at position 434;
    any one of Arg, Asn, His, Ile, Leu, Lys, Met, or Thr at position 436;
    any one of Lys, Leu, Thr, or Trp at position 438;
    Lys at position 440;
    Lys at position 442; and
    any one of Ile, Pro, or Thr at position 308.

15. The antigen-binding molecule of claim 1, wherein the antigen-binding molecule is a multispecific or a multi-paratopic antigen-binding molecule comprising at least two different antigen-binding domains, wherein each of the antigen-binding domains binds to a different epitope.

16. The antigen-binding molecule of claim 15, wherein the antigen-binding activity of each of the antigen-binding domains varies depending on the concentration of the compound.

17. The antigen-binding molecule of claim 15, wherein at least one of the antigen-binding domains binds to an antigen expressed on a cancer cell membrane, and at least one of the antigen-binding domains binds to an antigen expressed on an effector cell membrane.

18. The antigen-binding molecule of claim 17, wherein the effector cell is an NK cell, a macrophage, or a T cell.

19. The antigen-binding molecule of claim 17, wherein the antigen expressed on an effector cell membrane is CD2, CD3, CD28, CD44, CD16, CD32, CD64, NKG2D, or a polypeptide that constitutes part of the T cell receptor (TCR).

20. The antigen-binding molecule of claim 15, wherein at least one of the antigen-binding domains binds to an antigen expressed on a cancer cell membrane, and at least one of the antigen-binding domains binds to an antigen that is a cytotoxic substance.

21. The antigen-binding molecule of claim 15, wherein the antigen-binding molecule is an antibody fragment.

22. The antigen-binding molecule of claim 1, wherein the antigen-binding molecule is an antibody.

23. The antigen-binding molecule of claim 1, wherein the antigen is a soluble molecule.

24. The antigen-binding molecule of claim 23, wherein, when the antigen-binding molecule binds to the antigen, the antigen is neutralized.

25. The antigen-binding molecule of claim 23, wherein the antigen-binding molecule comprises an Fc region.

26. The antigen-binding molecule of claim 25, wherein the amino acid sequence of the Fc region is identical to the sequence of an Fc region included within the constant region sequence of one of SEQ ID NO: 5, 6, 7, or 8.

27. The antigen-binding molecule of claim 25, wherein the Fc region is a modified Fc region that, at a pH between 5.8 and 6.0, binds to FcRn with an affinity that is increased compared to the binding affinity of a native human IgG Fc region to FcRn at the same pH, wherein the native human IgG Fc region is of the same IgG subclass as the modified Fc region.

28. The antigen-binding molecule of claim 27, wherein the modified Fc region differs from the native human IgG Fc region at one or more of the following EU numbering positions: 238, 244, 245, 249, 250, 251, 252, 253, 254, 255, 256, 257, 258, 260, 262, 265, 270, 272, 279, 283, 285, 286, 288, 293, 303, 305, 307, 308, 309, 311, 312, 314, 316, 317, 318, 332, 339, 340, 341, 343, 356, 360, 362, 375, 376, 377, 378, 380, 382, 385, 386, 387, 388, 389, 400, 413, 415, 423, 424, 427, 428, 430, 431, 433, 434, 435, 436, 438, 439, 440, 442, and 447.

29. The antigen-binding molecule of claim 28, wherein at least one of the following EU numbering positions in the modified Fc region is occupied by the indicated amino acid:
   Leu at position 238;
   Leu at position 244;
   Arg at position 245;
   Pro at position 249;
   either Gln or Glu at position 250;
   any one of Arg, Asp, Glu, or Leu at position 251;
   any one of Phe, Ser, Thr, or Tyr at position 252;
   either Ser or Thr at position 254;
   any one of Arg, Gly, Ile, or Leu at position 255;
   any one of Ala, Arg, Asn, Asp, Gln, Glu, Pro, or Thr at position 256;
   any one of Ala, Ile, Met, Asn, Ser, or Val at position 257;
   Asp at position 258;
   Ser at position 260;
   Leu at position 262;
   Lys at position 270;
   either Leu or Arg at position 272;
   any one of Ala, Asp, Gly, His, Met, Asn, Gln, Arg, Ser, Thr, Trp, or Tyr at position 279;
   any one of Ala, Asp, Phe, Gly, His, Ile, Lys, Leu, Asn, Pro, Gln, Arg, Ser, Thr, Trp, or Tyr at position 283;
   Asn at position 285;
   Phe at position 286;
   either Asn or Pro at position 288;
   Val at position 293,
   any one of Ala, Glu, Gln, or Met at position 307;
   any one of Ile, Pro, or Thr at position 308;
   Pro at position 309;
   any one of Ala, Glu, Ile, Lys, Leu, Met, Ser, Val, or Trp at position 311;
   any one of Ala, Asp, or Pro at position 312;
   either Ala or Leu at position 314;
   Lys at position 316;
   Pro at position 317;
   either Asn or Thr at position 318;
   any one of Phe, His, Lys, Leu, Met, Arg, Ser, or Trp at position 332;
   any one of Asn, Thr, or Trp at position 339;
   Pro at position 341;
   any one of Glu, His, Lys, Gln, Arg, Thr, or Tyr at position 343;
   Arg at position 375;
   any one of Gly, Ile, Met, Pro, Thr, or Val at position 376;
   Lys at position 377;
   any one of Asp, Asn, or Val at position 378;
   any one of Ala, Asn, Ser, or Thr at position 380;
   any one of Phe, His, Ile, Lys, Leu, Met, Asn, Gln, Arg, Ser, Thr, Val, Trp, or Tyr at position 382;
   any one of Ala, Arg, Asp, Gly, His, Lys, Ser, or Thr at position 385;
   any one of Arg, Asp, Ile, Lys, Met, Pro, Ser, or Thr at position 386;
   any one of Ala, Arg, His, Pro, Ser, or Thr at position 387;
   any one of Asn, Pro, or Ser at position 389;
   Asn at position 423;
   Asn at position 427;
   any one of Leu, Met, Phe, Ser, or Thr at position 428;
   any one of Ala, Phe, Gly, His, Ile, Lys, Leu, Met, Asn, Gln, Arg, Ser, Thr, Val, or Tyr at position 430;
   either His or Asn at position 431;
   any one of Arg, Gln, His, Ile, Lys, Pro, or Ser at position 433;
   any one of Ala, Gly, His, Phe, Ser, Trp, or Tyr at position 434;
   any one of Arg, Asn, His, Ile, Leu, Lys, Met, or Thr at position 436;
   any one of Lys, Leu, Thr, or Trp at position 438;
   Lys at position 440;
   Lys at position 442.

30. The antigen-binding molecule of claim 25, wherein the Fc region is a modified Fc region that, at a pH between 7.0 and 8.0, binds to FcRn with an affinity that is increased compared to the binding affinity of a native human IgG Fc region to FcRn at the same pH, wherein the native human IgG Fc region is of the same IgG subclass as the modified Fc region.

31. The antigen-binding molecule of claim 30, wherein the modified Fc region differs from the native human IgG Fc region at one or more of the following EU numbering positions: 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436.

32. The antigen-binding molecule of claim 31, wherein at least one of the following EU numbering positions in the modified Fc region is occupied by the indicated amino acid:
   Met at position 237;
   Ile at position 248;
   any one of Ala, Phe, Ile, Met, Gln, Ser, Val, Trp, or Tyr at position 250;
   any one of Phe, Trp, or Tyr at position 252;
   Thr at position 254;
   Glu at position 255;
   any one of Asp, Asn, Glu, or Gln at position 256;
   any one of Ala, Gly, Ile, Leu, Met, Asn, Ser, Thr, or Val at position 257;
   His at position 258;
   Ala at position 265;
   either Ala or Glu at position 286;
   His at position 289;
   Ala at position 297;
   Ala at position 303;
   Ala at position 305;
   any one of Ala, Asp, Phe, Gly, His, Ile, Lys, Leu, Met, Asn, Pro, Gln, Arg, Ser, Val, Trp, or Tyr at position 307;
   any one of Ala, Phe, Ile, Leu, Met, Pro, Gln, or Thr at position 308;
   any one of Ala, Asp, Glu, Pro, or Arg at position 309;
   any one of Ala, His, or Ile at position 311;
   either Ala or His at position 312;
   either Lys or Arg at position 314;
   any one of Ala, Asp, or His at position 315;
   Ala at position 317;
   Val at position 332;
   Leu at position 334;
   His at position 360;
   Ala at position 376;
   Ala at position 380;
   Ala at position 382;
   Ala at position 384;
   either Asp or His at position 385;
   Pro at position 386;
   Glu at position 387;
   either Ala or Ser at position 389;
   Ala at position 424;
   any one of Ala, Asp, Phe, Gly, His, Ile, Lys, Leu, Asn, Pro, Gln, Ser, Thr, Val, Trp, or Tyr at position 428;

Lys at position 433;

any one of Ala, Phe, His, Ser, Trp, or Tyr at position 434; and any one of His, Ile, Leu, Phe, Thr, or Val at position 436.

33. The antigen-binding molecule of claim 25, wherein the binding affinity of the Fc region for an inhibitory Fcγ receptor is higher than the binding affinity of the Fc region for an activating Fcγ receptor.

34. The antigen-binding molecule of claim 33, wherein the inhibitory Fcγ receptor is human FcγRIIb.

35. The antigen-binding molecule of claim 33, wherein the activating Fcγ receptor is human FcγRIa, human FcγRIIa$^{R131}$, human FcγRIIa$^{H131}$, human FcγRIIIa$^{V158}$ or human FcγRIIIa$^{F158}$.

36. The antigen-binding molecule of claim 33, wherein the Fc region is a modified Fc region that differs from a native human IgG Fc region at either EU numbering position 238 or EU numbering position 328, wherein the native human IgG Fc region is of the same IgG subclass as the modified Fc region.

37. The antigen-binding molecule of claim 36, wherein the modified Fc region has either Asp at EU numbering position 238 or Glu at EU numbering position 328.

38. The antigen-binding molecule of claim 37, wherein at least one of the following EU numbering positions in the modified Fc region is occupied by the indicated amino acid:

Asp at position 233;

either Trp or Tyr at position 234;

any one of Ala, Asp, Glu, Leu, Met, Phe, Trp, or Tyr at position 237;

Asp at position 239;

any one of Ala, Gln, or Val at position 267;

any one of Asn, Asp, or Glu at position 268;

Gly at position 271;

Asp at position 296;

any one of Ala, Asn, Asp, Gln, Glu, Leu, Met, Ser, or Thr at position 326;

any one of Arg, Lys, or Met at position 330;

any one of Ile, Leu, or Met at position 323.

39. The antigen-binding molecule of claim 23, wherein the antigen-binding molecule is an antibody.

40. A pharmaceutical composition comprising the antigen-binding molecule of claim 1.

41. The pharmaceutical composition of claim 40, wherein the percentage of the antigen-binding molecule that has a fucose-deficient sugar chain bound at EU numbering position 297 in the composition is higher than the percentage of the antigen-binding molecule that has a fucose-containing sugar chain bound at EU numbering position 297 in the composition.

42. The pharmaceutical composition of claim 40, wherein the percentage of the antigen-binding molecule that has a bisecting N-acetylglucosamine sugar chain bound at EU numbering position 297 in the composition is higher than the percentage of the antigen-binding molecule that has a fucose-containing sugar chain bound at EU numbering position 297 in the composition.

43. A method for producing an antigen-binding molecule, the method comprising:

providing a cell containing DNA encoding the antigen-binding molecule of claim 1;

expressing the DNA, thereby producing the antigen-binding molecule; and collecting the antigen-binding molecule.

44. The antigen-binding molecule of claim 1, wherein the antigen-binding molecule is an IgG antibody.

45. The antigen-binding molecule of claim 1, wherein the antigen-binding domain is capable of binding to the compound in the presence or absence of the antigen.

46. The antigen-binding molecule of claim 1, wherein the antibody heavy-chain variable region comprises Ser at Kabat numbering position 52.

47. The antigen-binding molecule of claim 1, wherein the antibody heavy-chain variable region comprises Gly at Kabat numbering position 96.

48. The antigen-binding molecule of claim 1, wherein the antibody heavy-chain variable region comprises Ser at position 52, Ser at position 52a, Arg at position 53, Gly at position 96, and Trp at position 100c, wherein all positions are by Kabat numbering.

49. The antigen-binding molecule of claim 1, wherein the compound is adenosine.

50. The antigen-binding molecule of claim 1, wherein the compound is selected from adenosine monophosphate, cyclic adenosine monophosphate, and adenosine diphosphate.

51. The antigen-binding molecule of claim 1, wherein the compound is adenosine triphosphate.

\* \* \* \* \*

UNITED STATES PATENT AND TRADEMARK OFFICE
CERTIFICATE OF CORRECTION

PATENT NO. : 11,673,947 B2
APPLICATION NO. : 16/539765
DATED : June 13, 2023
INVENTOR(S) : Tomoyuki Igawa et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 376 days.

Signed and Sealed this
Twelfth Day of November, 2024

Katherine Kelly Vidal
*Director of the United States Patent and Trademark Office*